United States Patent
McCarthy et al.

(10) Patent No.: US 10,941,149 B2
(45) Date of Patent: Mar. 9, 2021

(54) SUBSTITUTED BENZODIAZOLIUMS AS ENAC INHIBITORS

(71) Applicant: ENTERPRISE THERAPEUTICS LIMITED, Brighton (GB)

(72) Inventors: Clive McCarthy, Abingdon (GB); Jonathan David Hargrave, Abingdon (GB); Duncan Alexander Hay, Abingdon (GB); Thomas Beauregard Schofield, Abingdon (GB); Naomi Went, Abingdon (GB)

(73) Assignee: Enterprise Therapeutics Limited, Falmer (GB)

(*) Notice: Subject to any disclaimer, the term of this patent is extended or adjusted under 35 U.S.C. 154(b) by 0 days.

(21) Appl. No.: 16/462,794

(22) PCT Filed: Nov. 22, 2017

(86) PCT No.: PCT/GB2017/053499
§ 371 (c)(1),
(2) Date: May 21, 2019

(87) PCT Pub. No.: WO2018/096325
PCT Pub. Date: May 31, 2018

(65) Prior Publication Data
US 2019/0315757 A1 Oct. 17, 2019

(30) Foreign Application Priority Data

Nov. 22, 2016 (GB) .................................. 1619694

(51) Int. Cl.
| | | |
|---|---|---|
| A61K 31/4985 | (2006.01) | |
| C07D 487/04 | (2006.01) | |
| A61P 11/12 | (2006.01) | |
| A61K 9/00 | (2006.01) | |
| A61K 45/06 | (2006.01) | |

(52) U.S. Cl.
CPC ............ *C07D 487/04* (2013.01); *A61K 9/007* (2013.01); *A61P 11/12* (2018.01); *A61K 45/06* (2013.01)

(58) Field of Classification Search
CPC .......................... A61K 31/4985; C07D 487/04
USPC .......................................... 514/249; 544/350
See application file for complete search history.

(56) References Cited

U.S. PATENT DOCUMENTS

| | | | |
|---|---|---|---|
| 2015/0018313 A1 | 1/2015 | Kley et al. | |
| 2015/0018314 A1 | 1/2015 | Kley et al. | |

FOREIGN PATENT DOCUMENTS

| | | |
|---|---|---|
| WO | WO 2003/070182 | 8/2003 |
| WO | WO 2003/070184 | 8/2003 |
| WO | WO 2004/073629 | 9/2004 |
| WO | WO 2005/016879 | 2/2005 |
| WO | WO 2005/018644 | 3/2005 |
| WO | WO 2005/025496 | 3/2005 |
| WO | WO 2005/034847 | 4/2005 |
| WO | WO 2005/044180 | 5/2005 |
| WO | WO 2006/022935 | 3/2006 |
| WO | WO 2007/018640 | 2/2007 |
| WO | WO 2007/071396 | 6/2007 |
| WO | WO 2007/071400 | 6/2007 |
| WO | WO 2008/124491 | 10/2008 |
| WO | WO 2008/135557 | 11/2008 |
| WO | WO 2009/019506 | 2/2009 |
| WO | WO 2009/074575 | 6/2009 |
| WO | WO 2009/138378 | 11/2009 |
| WO | WO 2009/139948 | 11/2009 |
| WO | WO 2009/150137 | 12/2009 |
| WO | WO 2011/028740 | 3/2011 |
| WO | WO 2011/079087 | 6/2011 |
| WO | WO 2011/113894 | 9/2011 |
| WO | WO 2012/035158 | 3/2012 |
| WO | WO 2013/003386 | 1/2013 |
| WO | WO 2013/064450 | 5/2013 |
| WO | WO 2013/092674 | 6/2013 |
| WO | WO 2013/181232 | 12/2013 |
| WO | WO 2014/044849 | 3/2014 |
| WO | WO 2014/099673 | 6/2014 |
| WO | WO 2014/099676 | 6/2014 |
| WO | WO 2014/099705 | 6/2014 |
| WO | WO 2014/177469 | 11/2014 |

(Continued)

OTHER PUBLICATIONS

Jordan, V. C. Nature Reviews: Drug Discovery, 2, 2003, 205.*
Dorwald, F. Zaragoza. Side Reactions in Organic Synthesis: A Guide to Successful Synthesis Design, Weinheim: WILEY-VCH Verlag GmbH & Co. KGaA, 2005, Preface.*
App et al., "Acute and Long-term Amiloride Inhalation in Cystic Fibrosis Lung Disease. A Rational Approach to Cystic Fibrosis Therapy," *Am Rev Respir Dis.*, 1990, 141(3):605-12.
Botero-Velez et al., "Brief Report: Liddle's Syndrome Revisited—A Disorder of Sodium Reabsorption in the Distal Tubule," *The New England Journal of Medicine*, 1994, 330(3):178-81.

(Continued)

*Primary Examiner* — Douglas M Willis
(74) *Attorney, Agent, or Firm* — Bookoff McAndrews, PLLC

(57) ABSTRACT

(I)

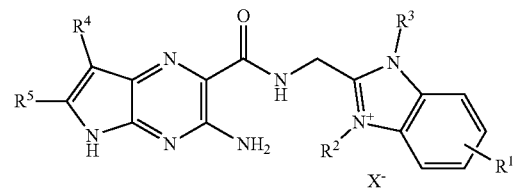

Compounds of general formula (I) wherein $R^1$, $R^2$, $R^3$, $R^4$, $R^5$ and X are as defined herein are inhibitors of the epithelial sodium channel (ENaC) and are useful for the treatment or prevention respiratory diseases and conditions, skin conditions and ocular conditions.

21 Claims, 7 Drawing Sheets

(56) References Cited

FOREIGN PATENT DOCUMENTS

| WO | WO 2015/003083 | 1/2015 |
|---|---|---|
| WO | WO 2015/003958 | 1/2015 |
| WO | WO 2015/007516 | 1/2015 |
| WO | WO 2015/007517 | 1/2015 |
| WO | WO 2015/007519 | 1/2015 |
| WO | WO 2015/018754 | 2/2015 |
| WO | WO 2016/113167 | 7/2016 |
| WO | WO 2016/113168 | 7/2016 |
| WO | WO 2016/113169 | 7/2016 |
| WO | WO 2016/113170 | 7/2016 |
| WO | WO 2017/028926 | 2/2017 |
| WO | WO 2017/028927 | 2/2017 |
| WO | WO 2017/221008 | 12/2017 |
| WO | WO 18/096325 | * 5/2018 |

OTHER PUBLICATIONS

Boucher, "Evidence for Airway Surface Dehydration as the Initiating Event in CF Airway Disease," *Journal of Internal Medicine*, 2007, 261(1):5-16.
Bowler et al., "Nebulised Amiloride in Respiratory Exacerbations of Cystic Fibrosis: A Randomised Controlled Trial," *Archives of Disease in Childhood*, 1995, 73(3):427-30.
Chang et al., "Mutations in Subunits of the Epithelial Sodium Channel Cause Salt Wasting With Hyperkalaemic Acidosis, Pseudohypoaldosteronism Type 1," *The Nature Publishing Group, Nature Genetics*, 1996, 12(3):248-53.
Coote et al., "Camostat Attenuates Airway Epithelial Sodium Channel Function in Vivo Through the Inhibition of a Channel-Activating Protease," *The Journal of Pharmacology and Experimental Therapeutics*, 2009, 329(2):764-74.
Coote et al., "The Guinea-Pig Tracheal Potential Difference as an In Vivo Model for the Study of Epithelial Sodium Channel Function in the Airways," *British Journal of Pharmacology*, 2008, 155(7):1025-33.
Fajac et al., "Nasal Airway Ion Transport is Linked to the Cystic Fibrosis Phenotype in Adult Patients," *Thorax*, 2004, 59(11):971-76.
Frateschi et al., "The Epithelial Sodium Channel ENaC and Its Regulators in The Epidermal Permeability Barrier Function," *The Open Dermatology Journal*, 2010, 4: 27-35.
Graham et al., "No Added Benefit From Nebulized Amiloride in Patients With Cystic Fibrosis," *Eur Respir J.*, 1993, 6(9):1243-48.
Hirsh et al., "Pharmacological Properties of N-(3,5-diamino-6-chloropyrazine-2-carbonyl)-N'-4-[4-(2,3-dihydroxypropoxy)phenyl]butyl-guanidine Methanesulfonate (552-02), A Novel Epithelial Sodium Channel Blocker With Potential Clinical Efficacy for Cystic Fibrosis Lung Disease," *The Journal of Pharmacology and Experimental Therapeutics*, Apr. 2008; 325(1):77-88.
Kellenberger, "Epithelial Sodium Channel/Degenerin Family of Ion Channels: A Variety of Functions for a Shared Structure," *Physiol Rev.*, 2002 82(3):735-67.
Kerem et al., "Pulmonary Epithelial Sodium-Channel Dysfunction and Excess Airway Liquid in Pseudohypoaldosteronism," *The New England Journal of Medicine*, 1999, 341(3):156-62.
Knowles et al., "Abnormal Ion Permeation Through Cystic Fibrosis Respiratory Epithelium," *Science*, 1983, 221(4615):1067-70.
Knowles et al., "A Pilot Study of Aerosolized Amiloride for the Treatment of Lung Disease in Cystic Fibrosis," *The New England Journal of Medicine*, 1990, 322(17):1189-94.
Leal et al., "Airway Ion Transport Impacts on Disease Presentation and Severity in Cystic Fibrosis," *Science Direct, Clinical Biochemistry*, 2008, 41(10-11):764-72.
Matsui et al., "Evidence for Periciliary Liquid Layer Depletion, Not Abnormal Ion Composition, in the Pathogenesis of Cystic Fibrosis Airways Disease," *Cell*, 1998, 95(7):1005-15.
Middleton et al., "Effect of Amiloride and Saline on Nasal Mucociliary Clearance and Potential Difference in Cystic Fibrosis and Normal Subjects," *Thorax*, 1993, 48(8):812-6.
Noone et al., "Airway Deposition and Clearance and Systemic Pharmacokinetics of Amiloride Following Aerosolization With an Ultrasonic Nebulizer to Normal Airways," *Chest*, 1997, 112(5):1283-90.
Paulekuhn et al., "Trends in Active Pharmaceutical Ingredient Salt Selection based on Analysis of the Orange Book Database," *J. Med. Chem.*, 2007, 50: 6665-6672.
Perazella, "Drug-Induced Hyperkalemia: Old Culprits and New Offenders," *Am J Med.*, 2000, 109(4):307-14.
Pons et al., "French Multicenter Randomized Double-Blind Placebo-Controlled Trial on Nebulized Amiloride in Cystic Fibrosis Patients," *Pediatric Pulmonology*, 2000, 30(1):25-31.
Schoenberger et al., "Novel Small Molecule Epithelial Sodium Channel Inhibitors as Potential Therapeutics in Cystic Fibrosis—A Patent Evaluation," *Expert Opinion Ther. Patents*, 2013, 23(10), 1383-89.
Thelin et al., "Effect of Topically Applied Epithelial Sodium Channel Inhibitors on Tear Production in Normal Mice and in Mice With Induced Aqueous Tear Deficiency," *Journal of Ocular Pharmacology and Therapeutics*, 2012, 28(4): 433-38.
International Search Report for PCT/GB2017/053499 dated Jan. 25, 2018 (4 pages).
Howsham et al., "The discovery of novel inhaled ENaC blockers for the treatment of cystic fibrosis lung disease," Ch. 7 in *Ion Channel Drug Discovery*, published by Royal Society of Chemistry, Sep. 18, 2014 (26 pages).

* cited by examiner

A.

B.

SUBSTITUTED BENZODIAZOLIUMS AS ENAC INHIBITORS

CROSS-REFERENCE TO RELATED APPLICATIONS

This application is a U.S. National Stage filing under 35 U.S.C. § 371 of International Application No. PCT/GB2017/053499, filed on Nov. 22, 2017, which claims priority to United Kingdom Application No. GB 1619694.1, filed on Nov. 22, 2016.

TECHNICAL FIELD

The present invention relates to novel compounds which have activity as inhibitors of the epithelial sodium channel (ENaC). The invention also relates to the use of these compounds in treating diseases and conditions modulated by ENaC, particularly respiratory diseases and conditions, methods of preparing the compounds and pharmaceutical compositions containing them.

BACKGROUND

Humans can inhale up to 12,000 L of air each day and with it comes the potertial for airborne pathogens (bacteria, viruses, fungal spores). To protect against these airborne pathogens, the lung has evolved innate defence mechanisms to minimise the potertial for infection and colonisation of the airways. One such mechanism is the mucus clearance system, whereby secreted mucus is propelled up and out of the airways by the coordinated beating of cilia together with cough clearance. This ongoing 'cleansing' of the lung constantly removes inhaled particles and microbes thereby reducing the risk of infection.

In recent years it has become clear that the hydration of the mucus gel is critical to enable mucus clearance (Boucher 2007; Matsui et al, 1998). In a normal, healthy airway, the mucus gel is typically 97% water and 3% solids under which conditions the mucus is cleared by mucociliary action. The hydration of the airway mucosa is regulated by the coordinated activity of a number of ion channels and transporters. The balance of anion ($Cl^-/HCO_3^-$) secretion mediated via the Cystic Fibrosis Transmembrane Conductance Regulator (CFTR) and the Calcium Activated Chloride Conductance (CaCC; TMEM16A, also known as Ano1) and $Na^+$ absorption through the epithelial $Na^+$ channel (ENaC) determine the hydration status of the airway mucosa. As ions are transported across the epithelium, water is osmotically obliged to follow and thus fluid is either secreted or absorbed. As ions are transported across the epithelium, water is osmotically obliged to follow and thus fluid is either secreted or absorbed.

In respiratory diseases such as chronic bronchitis and cystic fibrosis, the % solids of the mucus gel is increased as the hydration is reduced and mucus clearance is reduced (Boucher, 2007). In cystic fibrosis, where loss of function mutations in CFTR attenuates ability of the airway to secrete fluid, the % solids can be increased to 15% which is believed to contribute towards the plugging of small airways and failure of mucus clearance. Furthermore, in cystic fibrosis an increase in ENaC activity has been reported by several groups (Knowles et al, 1983; Middleton et al, 1993) and this increase in ENaC function has been shown to correlate with disease severity (Fajac et al, 2004; Leal et al, 2008). Strategies to increase the hydration of the airway mucus include either the stimulation of anion and thereby fluid secretion or the inhibition of $Na^+$ absorption. To this end, blocking the activity of ENaC will inhibit $Na^+$ absorption and therefore increase fluid accumulation in the airway mucosa, hydrate mucus and enhance mucus clearance mechanisms.

ENaC is expressed in renal, colonic, corneal, sweat duct and respiratory epithelia where it forms a low conductance channel (~4 pS) with a selectivity for $Na^+$ over $K^+$ of approximately 10-fold (Kellenberger 2002). Loss and gain of function mutations in the channel can cause human disease including pseudohypoaldosteronism type 1 (PHA1), a salt wasting disease (Chang et al, 1996), and Liddles's syndrome, a disease associated with salt retention and hypertension (Botero-Velez et al, 1994). Of particular note to lung physiology is the observation that patients with PHA1 loss-of-function mutations in ENaC have an enhanced rate of airway mucociliary clearance (MCC) compared with the normal healthy population, typically 3-4 fold faster (Kerem et al, 1999). Furthermore, the upper airways of these patients appear to be 'wet' and have extra-hydration compared to normal. These observations further support the salient role that ENaC plays in the human airway in the regulation of hydration and the therapeutic benefit that blocking ENaC in the airway could deliver in terms of enhancing MCC and innate defence.

Amiloride, a small compound blocker of ENaC, has been demonstrated to increase MCC in both healthy controls and also patients with CF, further supporting the physiological significance of this mechanism (App et al, 1990). However, the lack of a robust effect of inhaled amiloride on clinical endpoints (Bowler et al, 1995; Graham et al, 1993; Knowles et al, 1990; Pons et al, 2000) was ascribed to the short duration of action of this compound in the lungs (Noone et al., 1997). Novel ENaC blockers, specifically designed for a long duration of action in the airway are therefore predicted to acutely provide an extended enhancement of MCC with resulting clinical benefit in the longer term.

A challenge with the design of inhaled ENaC blockers for the treatment of respiratory diseases has been the potertial for the renal-based side effect of hyperkalaemia (Perazela et al., 2000). ENaC is expressed in the cortical collecting duct of the kidney epithelium and block of the channel here can lead to a systemic accumulation of $K^+$. For this reason, it is desirable that an inhaled ENaC blocker avoids renal exposure following absorption from the lung. This could be achieved through either a high lung retention of ENaC blocker therefore enabling only a low dose to be administered or through the design of a compound that will be rapidly transformed to an inactive metabolite before it reaches the kidney.

ENaC blockers have also been implicated in the hydration of skin and the surface of the eye (Frateschi et al, 2010; Thelin et al, 2012).

Several ENaC blockers are known. For example, WO 2011/113894 relates to compounds which are said to be of use for treating inflammatory or obstructive diseases of the airways or for promoting mucosal hydration. The compounds are of the formula:

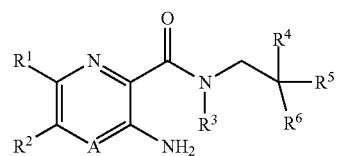

where A is N or CR$^{4a}$ and R$^2$ is haloalkyl. None of the compounds exemplified in this document contain a benzimidazole moiety.

WO 2011/079087 relates to compounds of the formula:

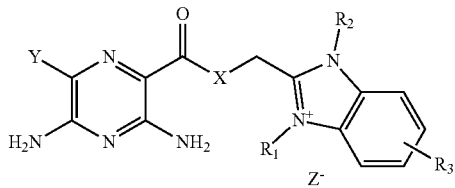

WO 2015/007516, WO 2015/007517 and WO 2015/007519 all relate to compounds of the formula:

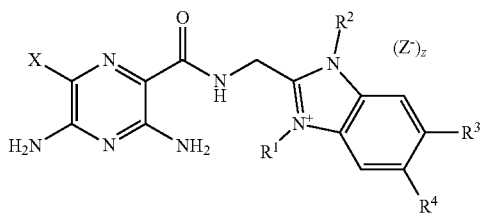

WO 2016/113168, WO 2016/113167 and WO 2016/113169 relate to compounds of the formula:

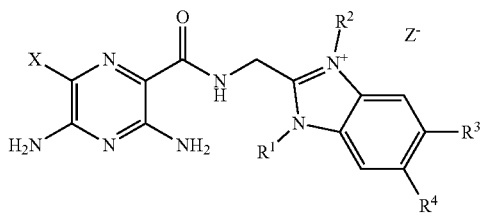

WO 2016/113170 relates to compounds of the formula:

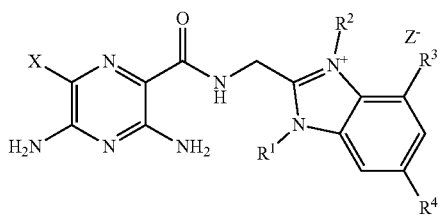

The compounds described in these documents all contain a 6-halo-3,5-diaminopyrazine group and this group is also a structural feature of the ENaC inhibitors disclosed in numerous other documents including WO2013/0664450, WO2013/092674, WO2014/044849, WO 2014/177469, WO 2015/003958, WO2015/018754, WO 2011/028740, WO 2007/071396, WO 2007/071400, WO 2008/135557, WO 2009/074575, WO 2009/138378, WO 2009/150137 and WO 2012/035158 Other documents relating to pyrazine derivatives with ENaC inhibitor activity include WO 2015/003083, WO 2004/073629, WO 03/070184, WO 03/070182, WO 2006/022935, WO 2007/018640, WO 2008/124491, WO 2009/139948, WO 2005/044180, WO 2005/016879, WO 2005/018644, WO 2005/025496, WO 2005/034847 and WO 2013/181232. However, every compound exemplified in these documents contains a 6-halo-3,5-diaminopyrazine group and it is therefore clear that a pyrazine ring with amino substituents at the 3- and 5-positions and 6-halo substituent was, until recently, considered essential for ENaC blocking activity.

Some more recent documents relate to ENaC blocking compounds in which the 5-amino group is not present. For example, WO 2017/028926 relates to ENaC inhibiting compounds of the formula:

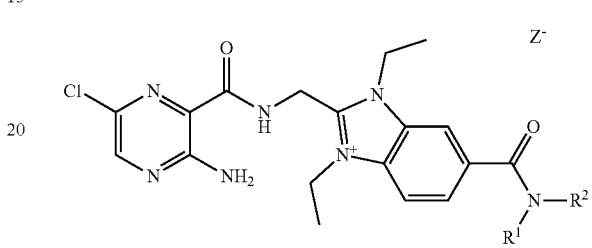

and WO 2017/028927 relates to ENaC inhibiting compounds of the formula:

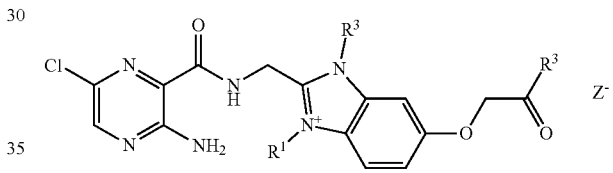

Our earlier application PCT/GB2017/051815 also relates to compounds comprising a pyrazine group with a single amino substituent at the 3-position, with most of these compounds also having a substituent at the pyrazine 6-position.

SUMMARY

The present inventors have surprisingly discovered that compounds with alternative structures to the 6-halo-3,5-diamino pyrazine or 6-substituted-3-aminopyrazine also have ENaC blocking activity and may have beneficial properties compared with the known compounds, particularly in relation to the ADME (Absorption, Excretion, Distribution and Metabolism) properties.

In the present invention there is provided a compound of general formula (I) including all tautomeric forms, all enantiomers and isotopic variants and salts thereof:

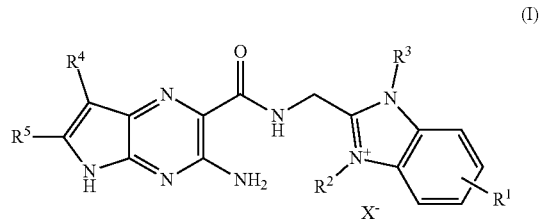

wherein
X⁻ is an anion;
$R^1$ is:
  i. H or halo; or
  ii. —$L^1R^{10}$, wherein
  $L^1$ is:
    —$Z^1$—, —$Q^1$—, —$Z^1Q^1$—, —$Q^1Z^1$—, —$Z^1Q^1Z^2$—, —$Q^1Q^2$—, —$Q^1Q^2Z^1$—, —$Q^1Q^2Z^1Q^3Z^2$—, —$Z^1Q^1OQ^2OQ^3$—;
    —$OZ^1$—, —$OQ^1$—, —$OZ^1Q^1$—, —$OQ^1Z^1$—, —$OZ^1Q^1Z^2$—, —$OQ^1Q^2$—, —$OQ^1Q^2Z^1$—, —$OQ^1Q^2Z^1Q^3Z^2$—, —$OZ^1Q^1OQ^2OQ^3$—;
    —$Z^1N(R^7)Z^2$—, —$Q^1Z^1N(R^7)Z^2$—, —$Z^1N(R^7)Z^2Q^1$—, —$Q^1Z^1N(R^7)Z^2Q^2Z^3$—;
    —$Z^1O(CH_2CH_2O)_nZ^2$—, —$Z^1O(CH_2CH_2O)_nQ^1$—, —$Z^1O(CH_2CH_2O)_nZ^2Q^1$—, —$Z^1O(CH_2CH_2O)_nQ^1Z^2$—, —$Q^1Z^1O(CH_2CH_2O)_nZ^2$—, —$Q^1Z^1O(CH_2CH_2O)_nQ^1$—, —$Q^1Z^1O(CH_2CH_2O)_nZ^2Q^1$—, —$Z^1O(CH_2CH_2O)_nZ^2Q^1Z^3$—;
    —$C(O)Z^1$—, —$C(O)Q^1$—, —$C(O)Z^1Q^1$—, —$C(O)Z^1Q^1Z^2$—, —$C(O)Q^1Z^1$—, —$C(O)Q^1Q^2$—, —$C(O)Q^1Q^2Z^1$—, —$C(O)Q^1N(R^7)C(O)Z^1$—, —$C(O)Q^1N(R^7)C(O)Z^1Q^2$—, —$C(O)Q^1N(R^7)C(O)Z^1Q^2Q^3$—, —$C(O)Q^1N(R^7)C(O)Z^1Q^2Z^2$—, —$C(O)Z^1Q^1OQ^2OQ^3$—;
    —$C(O)N(R^7)Z^1$—, —$C(O)N(R^7)Q^1$—, —$C(O)N(R^7)Z^1Q^1$—, —$C(O)N(R^7)Z^1Q^1Z^2$—, —$C(O)N(R^7)Q^1Z^1$—, —$C(O)N(R^7)Q^1Q^2$—, —$C(O)N(R^7)Q^1Q^2Z^1$—, —$C(O)N(R^7)Z^1Q^1Q^2Z^2$—, —$C(O)N(R^7)Z^1O(CH_2CH_2O)_nZ^2$—, —$C(O)N(R^7)Z^1O(CH_2O)_nZ^2$—, —$C(O)N(R^7)Z^1Q^1Z^2N(R^8)Z^3$—, —$C(O)N(R^7)Z^1N(R^8)Z^2$—, —$C(O)N(R^7)Q^1Z^1N(R^8)Z^2$—, —$C(O)N(R^7)Z^1Q^1OQ^2OQ^3$—, —$C(O)N(R^7)Z^1Q^1OQ^2OQ^3Z^2$—;
    —$Z^1C(O)N(R^7)Z^2$—, —$Z^1C(O)N(R^7)Q^1$—, —$Z^1C(O)N(R^7)Z^2Q^1$—, —$Z^1C(O)N(R^7)Q^1Z^2$—, —$Z^1C(O)N(R^7)Q^1Q^2$—, —$Z^1C(O)Q^1$—, —$Z^1C(O)Q^1Z^2$—, —$Z^1C(O)Q^1Q^2$—, —$Z^1C(O)N(R^7)Q^1Q^2Z^2$—;
    —$C(O)OZ^1$—, —$C(O)OQ^1$—, —$C(O)OZ^1Q^1$—, —$C(O)OZ^1Q^1Z^2$—, —$C(O)OQ^1Z^1$—, —$C(O)OQ^1Q^2$—, —$C(O)OQ^1Q^2Z^1$—;
    —$Q^1C(O)Q^2$—, $Q^1C(O)Z^1$—, —$Q^1C(O)Q^2Z^1$—, $Q^1C(O)Q^2Q^3$—, $Q^1C(O)Z^1Q^2$—, $Q^1C(O)Q^2Q^3Z^1$—;
    —$C(=NR^9)N(R^7)Z^1$—, —$C(=NR^9)N(R^7)Q^1$—, —$C(=NR^9)N(R^7)Z^1Q^1$—, —$C(=NR^9)N(R^7)Z^1Q^1Z^2$—, —$C(=NR^9)N(R^7)Q^1Z^1$—, —$C(=NR^9)N(R^7)Q^1Q^2$— or $C(=NR^9)N(R^7)Q^1Q^2Z^1$—; wherein each of $Z^1$, $Z^2$ and $Z^3$ is independently $C_{1-12}$ alkylene, $C_{2-12}$ alkenylene, $C_{2-12}$ alkynylene any of which is optionally substituted by one or more substituents selected from halo, OH, $C(O)NR^{15}R^{16}$, $C(O)OR^{15}$ and $NR^{15}R^{16}$;

each $R^{15}$ and $R^{16}$ is independently H or $C_{1-6}$ alkyl or $R^{15}$ and $R^{16}$ together with the nitrogen atom to which they are attached may form a 5- or 6-membered heterocyclic ring optionally containing one or more further heteroatoms selected from N, O and S;

each of $Q^1$, $Q^2$ and $Q^3$ is independently carbocyclyl, heterocyclyl, aryl or heteroaryl any of which is optionally substituted with one or more substituents selected from halo, OH, $C_{1-4}$ alkyl, $C_{1-4}$ haloalkyl, $C(O)NR^{15}R^{16}$, $C(O)OR^{15}$ and $NR^{15}R^{16}$, and, for cycloalkyl and heterocyclyl groups, oxo, wherein $R^{15}$ and $R^{16}$ are as defined above;

n is 1 to 6;

each $R^7$ and $R^8$ is independently selected from H and $C_{1-12}$ alkyl optionally substituted with one or more halo or OH groups, or when an $R^7$ and an $R^8$ or two $R^8$ groups are attached to a nitrogen atom they may, together with the nitrogen atom combine to form a 5- or 6-membered heterocyclic ring optionally comprising one or more further heteroatoms selected from N, O and S;

$R^9$ is H or $C_{1-6}$ alkyl;

$R^{10}$ is H, —$N(R^7)R^8$, —$N(R^7)C(=NR^9)N(R^8)_2$, —$N(R^7)$—$C(O)OR^8$, $OR^7$ or —$C(O)OR^7$; or a cationic group selected from —$N(R^7)$—$C(O)$—$(C_{1-3}$ alkylene)—$N^+(R^8)_3$ and —$N^+(R^8)_3$, in which case, an additional anion X⁻ will be required; and $R^7$, $R^8$ and $R^9$ are as defined above; or iii. —$R^{12}$, —$OR^{12}$ —$SO_2R^{12}$, —$C(O)OR^{12}$, —$C(O)NR^{12}R^{13}$, —$C(=NR^9)NR^{12}R^{13}$, —$Q^1R^{12}$—, —$Q^1OR^{12}$ —$Q^1SO_2R^{12}$, —$Q^1C(O)OR^{12}$, —$Q^1C(O)NR^{12}R^{13}$, —$Q^1C(=NR^7)NR^{12}R^{13}$, —$Q^1Q^2OR^{12}$, —$Q^1SO_2R^{12}$, —$Q^1Q^2C(O)OR^{12}$, —$Q^1Q^2C(O)NR^{12}R^{13}$ or —$Q^1Q^2C(=NR^9)NR^{12}R^{13}$; wherein $Q^1$ and $Q^2$ are defined as above; and each $R^{12}$ and $R^{13}$ is independently H, $C_{1-6}$ alkyl, $C_{2-6}$ alkenyl, $C_{2-6}$ alkynyl, $C_{3-8}$ cycloalkyl or $C_{3-8}$ heterocyclyl, any of which is optionally substituted by one or more substituents selected from halo, $OR^7$, $C(O)OR^7$, —$N(R^7)R^8$ and $C(O)N(R^7)R^8$ and, in the case of cycloalkyl or heterocyclyl groups, oxo; wherein $R^7$, $R^8$ and $R^9$ are as defined above;

each of $R^2$ and $R^3$ is independently $C_{1-10}$ alkyl, wherein one or more —$CH_2$— groups is optionally replaced by —O—, —S— or —$NR^7$— provided that adjacent —$CH_2$— groups are not so replaced and which is optionally substituted with one or more substituents selected from halo, OH, SH, $N(R^7)R^8$, aryl, heteroaryl, cycloalkyl, heterocyclyl, —$C(O)OR^7$, —$C(O)N(R^7)R^8$, $OR^7$ and —$N(R^7)R^8$, wherein $R^7$ and $R^8$ are as defined above;

$R^4$ is H, halo, cyano, $C_{1-6}$ alkyl, $C(O)OR^{16}$ or $C(O)N(R^{16})R^{17}$;

wherein alkyl groups are optionally substituted with one or more substituents selected from halo, —$OR^7$ and —$N(R^7)R^8$, wherein $R^7$ and $R^8$ are as defined above;

each $R^{16}$ and $R^{17}$ is independently H or $C_{1-6}$ alkyl or $R^{16}$ and $R^{17}$ together with the nitrogen atom to which they are attached may form a 5- or 6-membered heterocyclic ring optionally containing one or more further heteroatoms selected from O, N and S; and $R^5$ is H or methyl.

The compounds of general formula (I) have ENaC blocking activity and, furthermore, are expected to have one or both of the following advantageous properties.

Effective mucocilliary clearance in vivo.

Prolonged lung retention so reducing the dose required to give adequate inhibition of ENaC commensurate with b.i.d. or q.d. dosing without leading to hyperkalaemia.

DESCRIPTION

In the present specification, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

In the present specification, references to "pharmaceutical use" refer to use for administration to a human or an animal, in particular a human or a mammal, for example a domesticated or livestock mammal, for the treatment or prophylaxis of a disease or medical condition. The term "pharmaceutical composition" refers to to a composition which is suitable for pharmaceutical use and "pharmaceutically acceptable" refers to an agent which is suitable for use in a pharmaceutical composition. Other similar terms should be construed accordingly.

In the context of the present specification, the term "plurality" refers to two or more.

The anion $X^-$ can have any negative charge and will be balanced by the appropriate number of cations. Thus, for example, a compound of general formula (I) in which $X^-$ is an anion having a single negative charge will have a 1:1 ratio of cation:anion whereas if the anion $X^-$ has a charge of $-2$, the ratio of cation:anion in the compound of general formula (I) will be 2:1. The anion $X^-$ is suitably a pharmacologically acceptable anion, although other anions may also be useful, particularly in synthetic precursors to the compounds of general formula (I). Suitable anions, $X^-$ include halide, sulfate, nitrate, phosphate, formate, acetate, trifluoroacetate, fumarate, citrate, tartrate, oxalate, succinate, mandelate, methane sulfonate and p-toluene sulfonate. An additional anion $X^-$ or an anion with additional negative charge, e.g. a charge of $-2$, will be required if the $R^1$ substituent contains a moiety $R^{10}$ which is cationic such that the charge in the compound of general formula (I) is balanced.

All of the compounds of general formula (I) are salts. In the present specification, references to salts of the compounds of formula (I) may refer to salts of an additional basic nitrogen atom, for example a nitrogen atom to which $R^7$ and $R^8$ moieties are attached. Counter ions for such salts are as defined for $X^-$.

Alternatively, when $R^1$, $R^2$ or $R^3$ comprises a carboxyl group C(O)OH, salts may be formed. Suitable counter ions for such salts include sodium, potassium, calcium, aluminium, zinc, magnesium and other metal ions as well as choline, diethanolamine, ethanolamine, ethyl diamine, megulmine and other well-known basic addition salts as summarised in Paulekuhn et al., (2007) *J. Med. Chem.* 50: 6665-6672 and/or known to those skilled in the art. In some cases, $R^2$ or $R^3$ may comprise an anionic group, for example $C(O)O^-$, which may act as counter ion to the $N^+$ moiety in the benzimidazolium ring.

In the present specification, the term "$C_{1-6}$" alkyl refers to a straight or branched fully saturated hydrocarbon group having from 1 to 6 carbon atoms. The term encompasses methyl, ethyl, n-propyl, isopropyl, n-butyl, isobutyl and t-butyl. Other alkyl groups, for example $C_{1-12}$ alkyl and $C_{1-4}$ alkyl are as defined above but contain different numbers of carbon atoms.

The term "$C_{2-6}$ alkenyl" refers to a straight or branched hydrocarbon group having from 2 to 6 carbon atoms and at least one carbon-carbon double bond. Examples include ethenyl, prop-1-enyl, hex-2-enyl etc. Other alkenyl groups, for example $C_{1-12}$ alkenyl are as defined above except that they contain the specified number (e.g. 1 to 12) carbon atoms.

The term "$C_{2-6}$ alkynyl" refers to a straight or branched hydrocarbon group having from 2 to 6 carbon atoms and at least one carbon-carbon triple bond. Examples include ethynyl, prop-1-ynyl, hex-2-ynyl etc. Other alkynyl groups, for example $C_{2-12}$ alkynyl are as defined above except that they contain the specified number (e.g. 2 to 12) carbon atoms.

The term "$C_{1-6}$ alkylene" refers to a straight or branched fully saturated hydrocarbon chain having from 1 to 6 carbon atoms. Examples of alkylene groups include —$CH_2$—, —$CH_2CH_2$—, $CH(CH_3)$—$CH_2$—, $CH_2CH(CH_3)$—, —$CH_2CH_2CH_2$—, —$CH_2CH(CH_2CH_3)$— and —$CH_2CH(CH_2CH_3)CH_2$—. Other alkylene groups, for example $C_{1-12}$ alkylene are as defined above except that they contain the specified number (e.g. 1 to 12) carbon atoms.

The term "$C_{2-6}$ alkenylene" refers to a straight or branched hydrocarbon chain containing from 2 to 6 carbon atoms and at least one carbon-carbon double bond. Examples of alkenylene groups include —CH=CH—, —CH=C(CH_3)—, —$CH_2$CH=CH—, —CH=CHCH_2—, $CH_2CH_2$CH=CH—, $CH_2$CH=C($CH_3$)— and —$CH_2$CH=C($CH_2CH_3$)—. Other alkenylene groups, for example $C_{2-12}$ alkenylene, are as defined above except that they contain the specified number (e.g. 2 to 12) carbon atoms.

The term "$C_{2-6}$ alkynylene" refers to a straight or branched hydrocarbon chain containing from 2 to 6 carbon atoms and at least one carbon-carbon triple bond. Examples of alkenylene groups include —C≡C—, —$CH_2$C≡C—, —C≡C—$CH_2$—, $CH_2CH_2$C≡C—, $CH_2$C≡C$CH_2$— and —$CH_2$CH≡C—$CH_2CH_2$—.)—. Other alkynylene groups, for example $C_{2-12}$ alkynylene, are as defined above except that they contain the specified number (e.g. 2 to 12) carbon atoms.

The terms "carbocyclic" and "carbocyclyl" refer to a non-aromatic hydrocarbon ring system containing from 3 to 10 ring carbon atoms, unless otherwise indicated, and optionally one or more double bond. The carbocyclic group may be a single ring or may contain two or three rings which may be fused or bridged. Examples include cyclopropyl, cyclobutyl, cyclopentyl, cyclohexyl, cyclopentenyl and cyclohexenyl.

In the context of the present specification, the terms "heterocyclic" and "heterocyclyl" refer to a non-aromatic ring system containing 3 to 10 ring atoms including at least one heteroatom selected from N, O and S. The heterocyclic group may be a single ring or may contain two or three rings which may be fused or bridged. Examples include tetrahydrofuranyl, tetrahydroypranyl, pyrrolidine, piperidinyl, morpholinyl, piperazinyl and thiomorpholinyl.

The terms "aryl" and "aromatic" in the context of the present specification refer to a ring system with aromatic character having from 5 to 14 ring carbon atoms and containing up to three rings. Where an aryl group contains more than one ring, not all rings must be fully aromatic in character. Examples of aromatic moieties are benzene, naphthalene, fluorene, indane and indene.

The terms "heteroaryl" and "heteroaromatic" in the context of the specification refer to a ring system with aromatic character having from 5 to 14 ring atoms, at least one of which is a heteroatom selected from N, O and S, and containing up to three rings. Where a heteroaryl group contains more than one ring, not all rings must be fully aromatic in character. Examples of heteroaryl groups include pyridine, pyrimidine, indole, benzofuran, benzimidazole and indolene.

The term "halogen" refers to fluorine, chlorine, bromine or iodine, the term "halo" to fluoro, chloro, bromo or iodo groups and "halide" to fluoride, chloride, bromide or iodide.

The term "$C_{1-6}$ haloalkyl" as used herein refers to a $C_{1-6}$ alkyl group as defined above in which one or more of the hydrogen atoms is replaced by a halo group. Any number of hydrogen atoms may be replaced, up to perhalo substitution. Examples include trifluoromethyl, chloroethyl and 1,1-difluoroethyl. Other haloalkyl groups, for example $C_{1-12}$ haloalkyl are as defined above except that they contain the specified number (e.g. 1 to 12) carbon atoms.

The term "isotopic variant" refers to isotopically-labelled compounds which are identical to those recited in formula (I) but for the fact that one or more atoms are replaced by an atom having an atomic mass or mass number different from the atomic mass or mass number most commonly found in nature, or in which the proportion of an atom having an atomic mass or mass number found less commonly in nature has been increased (the latter concept being referred to as "isotopic enrichment"). Examples of isotopes that can be incorporated into compounds of the invention include isotopes of hydrogen, carbon, nitrogen, oxygen, fluorine, iodine and chlorine such as 2H (deuterium), 3H, 11C, 13C, 14C, 18F, 123I or 125I (e.g. 3H, 11C, 14C, 18F, 123I or 125I), which may be naturally occurring or non-naturally occurring isotopes.

The concept of canonical forms is well understood by the person of skill in the art. Thus, a compound of general formula (I) can have canonical forms as follows:

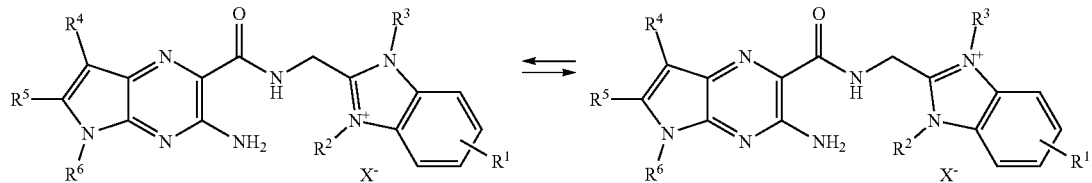
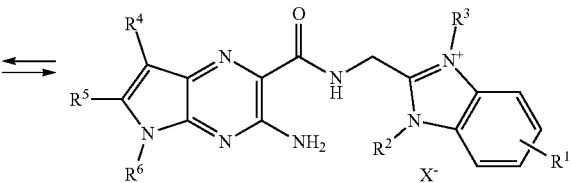

Both of these canonical forms are included within the scope of the invention.

The $R^1$ substituent is suitably at the 5- or the 6-position and thus the compound of general formula (I) can be a compound of general formula (IA):

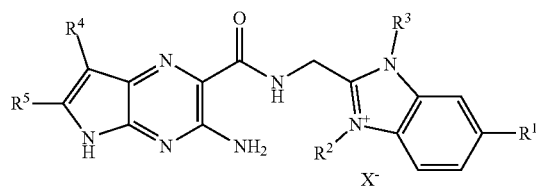

(IA)

wherein $R^1$, $R^2$, $R^3$, $R^4$ $R^5$ and $X^-$ are as defined for general formula (I);

or a compound of general formula (IB):

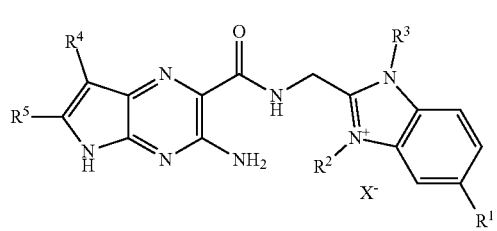

(IB)

wherein $R^1$, $R^2$, $R^3$, $R^4$ $R^5$ and $X^-$ are as defined for general formula (I).

It should be noted that, because the compound of general formula (I) can have different canonical forms as discussed above, if $R^2$ and $R^3$ are the same then the 5- and 6-positions are equivalent.

In some suitable compounds of general formula (I), $R^1$ is: H, halo, —$R^{12}$, —C(O)O$R^{12}$ or —O$R^{12}$; in particular, H, halo, or $C_{1-6}$ alkyl, $C_{2-6}$ alkenyl, $C_{2-6}$ alkynyl, —O($C_{1-6}$ alkyl), —O($C_{2-6}$ alkenyl) or —O($C_{2-6}$ alkynyl), any of which is optionally substituted by one or more halo substituents.

More suitably in these compounds, $R^1$ is H, halo, $C_{1-6}$ alkyl, $C_{1-6}$ haloalkyl, $C_{1-6}$ alkoxy or $C_{1-6}$ haloalkoxy.

Examples of such $R^1$ groups include H, chloro, methyl, trifluoromethyl, methoxy and trifluoromethoxy.

In other suitable compounds of general formula (I), $R^1$ is —$L^1R^{10}$.

Suitably in such compounds, $L^1$ is:
—$Z^1$—, —$Q^1$—, —$Z^1Q^1$—, —$Q^1Z^1$—, —$Z^1Q^1Z^2$—, —$Q^1Q^2$—, —$Q^1Q^2Z^1$—, —$Q^1Q^2Z^1Q^3Z^2$—;
—O$Z^1$—, —O$Z^1Q^1$—, —O$Z^1Q^1Z^2$—;

—$Z^1$N($R^7$)$Z^2$—, —$Q^1Z^1$N($R^7$)$Z^2$—;
—C(O)$Q^1$—, —C(O)$Q^1Z^1$—, —C(O)$Q^1Q^2$—, —C(O)$Q^1Q^2Z^1$—, —C(O)$Q^1$N($R^7$)C(O)$Z^1$—, —C(O)$Q^1$N($R^7$)C(O)$Z^1Q^2$—;
—C(O)N($R^7$)$Z^1$—, —C(O)N($R^7$)$Q^1$—, —C(O)N($R^7$)$Z^1Q^1$—, —C(O)N($R^7$)$Z^1Q^1Z^2$—, —C(O)N($R^7$)$Q^1Z^1$—, —C(O)N($R^7$)$Q^1Q^2$—, —C(O)N($R^7$)$Q^1Q^2Z^1$—, —C(O)N($R^7$)$Z^1Q^1Q^2Z^2$—, —C(O)N($R^7$)$Z^1$O(CH$_2$CH$_2$O)$_n$$Z^2$—, —C(O)N($R^7$)$Z^1$O(CH$_2$)$_n$$Z^2$—, —C(O)N($R^7$)$Z^1Q^1Z^2$N($R^8$)$Z^3$—, —C(O)N($R^7$)$Z^1$N($R^8$)$Z^2$—, —C(O)N($R^7$)$Q^1Z^1$N($R^8$)$Z^2$—, —C(O)N($R^7$)$Z^1Q^1$O$Q^2$O$Q^3$—, —C(O)N($R^7$)$Z^1Q^1$O$Q^2$O$Q^3Z^2$—;
—C(O)O$Z^1$—, —C(O)O$Z^1Q^1$—, —C(O)O$Z^1Q^1Z^2$—;
—$Q^1$C(O)$Q^2$—, $Q^1$C(O)$Z^1$—, —$Q^1$C(O)$Q^2Z^1$—, $Q^1$C(O)$Q^2Q^3$—, $Q^1$C(O)$Z^1Q^2$— or $Q^1$C(O)$Q^2Q^3Z^1$—.

In some more suitable compounds, $L^1$ is:
—$Z^1$—, —$Q^1$—, —$Q^1Z^1$—, —$Q^1Q^2$—, —$Q^1Q^2Z^1$—, —$Q^1Q^2Z^1Q^3Z^2$—,
—O$Z^1$—;
—$Z^1$N($R^7$)$Z^2$—, —$Q^1Z^1$N($R^7$)$Z^2$—;
—C(O)$Q^1$—, —C(O)$Q^1Z^1$—, —C(O)$Q^1Q^2$—, —C(O)$Q^1$N($R^7$)C(O)$Z^1$—;
—C(O)N($R^7$)$Z^1$—, —C(O)N($R^7$)$Q^1$—, —C(O)N($R^7$)$Z^1Q^1$—, —C(O)N($R^7$)$Z^1Q^1Z^2$—, —C(O)N($R^7$)$Q^1Z^1$—, —C(O)N($R^7$)$Q^1Q^2$—, —C(O)N($R^7$)$Q^1Q^2Z^1$—, —C(O)N($R^7$)$Z^1Q^1Q^2Z^2$—, —C(O)N($R^7$)$Z^1$O(CH$_2$CH$_2$O)$_n$$Z^2$—, —C(O)N($R^7$)$Z^1$N($R^8$)$Z^2$—, —C(O)N($R^7$)$Z^1Q^1$O$Q^2$O$Q^3Z^2$—; or —$Q^1$C(O)$Q^2$—.

In other more suitable compounds, $L^1$ is:
—$Z^1$—, —$Q^1$—, —$Q^1Z^1$—, —$Q^1Q^2$—, —$Q^1Q^2Z^1$—,
—O$Z^1$;
—C(O)$Q^1$—, —C(O)$Q^1Z^1$—;
—C(O)N($R^7$)$Z^1$—, C(O)N($R^7$)$Q^1$—, —C(O)N($R^7$)$Z^1Q^1$—, —C(O)N($R^7$)$Q^1Z^1$—, —C(O)N($R^7$)$Z^1Q^1Q^2Z^2$—, —C(O)N($R^7$)$Z^1$O(CH$_2$CH$_2$O)$_n$$Z^2$— or —C(O)N($R^7$)$Z^1Q^1Z^2$N($R^8$)$Z^3$—.

In some suitable compounds where $R^1$ is —L$R^{10}$, the cyclic groups $Q^1$, $Q^2$ and $Q^3$ are independently selected from 5- and 6-membered aryl and heteroaryl groups and 4 to 8-membered carbocyclyl and heterocyclyl groups.

More suitably, $Q^1$, $Q^2$ and $Q^3$ are selected from phenyl, 5- and 6-membered heteroaryl groups and 4- to 7-membered and heterocyclyl groups, still more suitably phenyl, 5- and 6-membered nitrogen-containing heteroaryl and 4- to 7-membered nitrogen-containing heterocyclyl groups.

Examples of such heteroaryl $Q^1$, $Q^2$ and $Q^3$ groups include pyridyl, pyrimidinyl, pyrazolyl, imidazolyl and oxazolyl groups, with 5-membered rings such as imidazolyl and oxazolyl and especially pyrazolyl being particularly suitable. When $Q^1$, $Q^2$ or $Q^3$ is pyrazolyl, it may have the following regiochemistry:

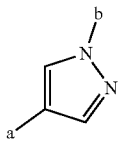

Where a and b show the links to the remainder of the molecule.

Examples of heterocyclyl $Q^1$, $Q^2$ and $Q^3$ groups include azetidinyl, piperidinyl, piperazinyl, and aziridinyl, with 6-membered rings such as piperazinyl and piperidinyl being more suitable. Piperidinyl is a particularly suitable heterocyclyl group, especially 1,4-piperidinyl.

Other more suitable $Q^1$, $Q^2$ and $Q^3$ groups include cyclohexyl and tetrohydropyran groups, either or which may be substituted with one or more substituents selected from OH, or $NR^{15}R^{16}$, especially OH, $NH_2$ or $NHCH_3$.

When $L^1$ comprises a C(O) moiety linked to a Q moiety, the Q moiety may be a nitrogen containing heterocyclyl ring in which C(O) is linked to the nitrogen atom.

For example, in —C(O)$Q^1$—, —C(O)$Q^1Z^1$—, —C(O)$Q^1Q^2$—, —C(O)$Q^1Q^2Z^1$—, —C(O)$Q^1N(R^7)C(O)Z^1$—, —C(O)$Q^1N(R^7)C(O)Z^1Q^2$—, —C(O)$Q^1N(R^7)C(O)Z^1Q^2Q^3$—, —C(O)$Q^1N(R^7)C(O)Z^1Q^2Z^2$—, $Q^1$ is suitably a 5- or 6-membered heterocyclyl ring which is linked to the —C(O) moiety via a ring nitrogen atom. Suitably, $Q^1$ is a 5- or 6-membered nitrogen-containing heterocyclyl ring such as piperidin-1-yl or pyrrolidine-1-yl, more suitably piperidin-1yl. Suitably, when $Q^1$ is piperidin-1-yl the remainder of the molecule is linked to the 4-position of the piperidine ring.

When $Q^1$ is pyrrolidine-1-yl, the remainder of the molecule may be linked to the 3-position of the pyrrolidine ring.

When $L^1$ is —$Q^1$C(O)$Q^2$—, —$Q^1$C(O)$Q^2Z^1$—, $Q^1$C(O)$Q^2Q^3$—, $Q^1$C(O)$Q^2Q^3Z^1$—, $Q^2$ is suitably a 5- or 6-membered heterocyclyl ring which is linked to the —C(O) moiety via a ring nitrogen atom. Suitably, $Q^2$ is piperidin-1-yl or pyrrolidine-1-yl, more suitably piperidin-1yl. Suitably, when $Q^1$ is piperidin-1-yl the remainder of the molecule is linked to the 4-position of the piperidine ring. When $Q^1$ is pyrrolidine-1-yl, the remainder of the molecule may be linked to the 3-position of the pyrrolidine ring.

In other cases, however, when $L^1$ comprises a C(O) moiety linked to a Q moiety, the Q moiety may be a heterocyclyl group which is linked to the C(O) moiety via a ring carbon atom. Examples of heterocyclyl groups include 5- and 6-membered rings, suitably nitrogen-containing rings such as piperidinyl or pyrrolidinyl. Suitably, in this case, when $Q^1$ is a piperidine ring it is a piperidin-4-yl group such that the piperidine 4-position is linked to the C(O) moiety. Suitably, the piperidine nitrogen atom is linked to the remainder of the molecule. Examples of $L^1$ moieties of this type include C(O)$Q^1Z^1$, in which $Q^1$ may be a piperidine ring in which the 4-position is linked to C(O) and the 1-position is linked to $Z^1$.

When $L^1$ comprises a —C(O)N($R^7$)— moiety linked to a Q moiety, the Q moiety is suitably a heterocyclyl ring, e.g. a 5- or 6-membered nitrogen-containing heterocyclyl ring, which is linked to the —C(O)N($R^7$)— moiety via a ring carbon atom.

For example, when $L^1$ is —C(O)N($R^7$)$Q^1$—, —C(O)N($R^7$)$Q^1Z^1$—, —C(O)N($R^7$)$Q^1Q^2$—, —C(O)N($R^7$)$Q^1Q^2Z^1$—, —C(O)N($R^7$)$Q^1Z^1N(R^8)Z^2$—, —$Z^1$C(O)N($R^7$)$Q^1$—, —$Z^1$C(O)N($R^7$)$Q^1Z^2$— or —$Z^1$C(O)N($R^7$)$Q^1Q^2$—, $Q^1$ is suitably a 5- or 6-membered heterocyclyl ring which is linked to the —C(O)N($R^7$)— moiety via a ring carbon atom, with the remainder of the molecule being linked to a ring nitrogen atom. Suitably, $Q^1$ is piperidin-4-yl or pyrrolidinyl. When $Q^1$ is piperidin-4-yl, the remainder of the molecule is suitably linked to the 1-position of the piperidine ring.

For other $L^1$ groups in which $Q^1$ and/or $Q^2$ and/or $Q^2$ is piperidinyl, they are suitably either piperidin-1-yl or piperidin-4-yl.

When the $L^1$ comprises a —$Q^1Q^2$— or —$Q^2Q^3$— moiety, this may be, for example:

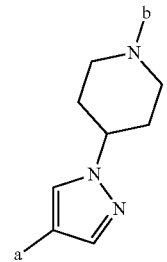

Where a and b show the links to the remainder of the molecule.

Other examples of —$Q^1Q^2$— and —$Q^2Q^3$— moieties include biphenyl, suitably a 1,1'-biphenyl-4-yl moiety. This type of —$Q^1Q^2$— or —$Q^2Q^3$— moiety is suitably linked at each side to a Z moiety, for example as in —C(O)N($R^7$)$Z^1Q^1Q^2Z^2$—

In some suitable compounds where $R^1$ is —$L^1R^{10}$, and $L^1$ contains $Z^1$ and optionally $Z^2$ and $Z^3$, each of $Z^1$, $Z^2$ and $Z^3$ is independently $C_{1-12}$ alkylene, optionally substituted by one or more halo or OH groups.

In some compounds of the invention, $R^1$ is $L^1R^{10}$ and $L^1$ comprises a $Z^1$, and optionally a $Z^2$ and optionally a $Z^3$ moiety.

In compounds where $L^1$ is:

—$Z^1$—, —$Z^1Q^1$—, —$Q^1Z^1$—, —$Z^1Q^1Z^2$—, —$Q^1Q^2Z^1$—, —$Q^1Q^2Z^1Q^3Z^2$—, —$Z^1Q^1OQ^2OQ^3$—;

—$OZ^1$—, —$OZ^1Q^1$—, —$OQ^1Z^1$—, —$OZ^1Q^1Z^2$—, —$OQ^1Q^2Z^1$—, —$OQ^1Q^2Z^1Q^3Z^2$—, —$OZ^1Q^1OQ^2OQ^3$—;

—$Z^1N(R^7)Z^2$—, —$Q^1Z^1N(R^7)Z^2$—, —$Z^1N(R^7)Z^2Q^1$—, —$Q^1Z^1N(R^7)Z^2Q^2Z^3$—;

—$Z^1O(CH_2CH_2O)_nZ^2$—, —$Z^1O(CH_2CH_2O)_nQ^1$—, —$Z^1O(CH_2CH_2O)_nZ^2Q^1$, —$Z^1O(CH_2CH_2O)_nQ^1Z^2$—, —$Q^1Z^1O(CH_2CH_2O)_nZ^2$—, —$Q^1Z^1O(CH_2CH_2O)_nQ^1$—, —$Q^1Z^1O(CH_2CH_2O)_nZ^2Q^1$, —$Z^1O(CH_2CH_2O)_nZ^2Q^1Z^3$—;

—C(O)$Z^1$—, —C(O)$Z^1Q^1$—, —C(O)$Z^1Q^1Z^2$—, —C(O)$Q^1Z^1$—, —C(O)$Q^1Q^2Z^1$—, —C(O)$Q^1N(R^7)C(O)Z^1$—, —C(O)$Q^1N(R^7)C(O)Z^1Q^2$—, —C(O)$Q^1N(R^7)C(O)Z^1Q^2Q^3$—, —C(O)$Q^1N(R^7)C(O)Z^1Q^2Z^2$—, —C(O)$Z^1Q^1OQ^2OQ^3$—;

—C(O)N(R$^7$)Z$^1$—, —C(O)N(R$^7$)Z$^1$Q$^1$—, —C(O)N(R$^7$)Z$^1$Q$^1$Z$^2$—, —C(O)N(R$^7$)Q$^1$Z$^1$—, —C(O)N(R$^7$)Q$^1$Q$^2$Z$^1$—, —C(O)N(R$^7$)Z$^1$Q$^1$Q$^2$Z$^2$—, —C(O)N(R$^7$)Z$^1$O(CH$_2$CH$_2$O)$_n$Z$^2$—, —C(O)N(R$^7$)Z$^1$O(CH$_2$O)$_n$Z$^2$—, —C(O)N(R$^7$)Z$^1$Q$^1$Z$^2$N(R$^8$)Z$^3$—, —C(O)N(R$^7$)Z$^1$N(R$^8$)Z$^2$—, —C(O)N(R$^7$)Q$^1$Z$^1$N(R$^8$)Z$^2$—, —C(O)N(R$^7$)Z$^1$Q$^1$OQ$^2$OQ$^3$—, —C(O)N(R$^7$)Z$^1$Q$^1$OQ$^2$OQ$^3$Z$^2$—;

—Z$^1$C(O)N(R$^7$)Z$^2$—, —Z$^1$C(O)N(R$^7$)Q$^1$—, —Z$^1$C(O)N(R$^7$)Z$^2$Q$^1$—, —Z$^1$C(O)N(R$^7$)Q$^1$Z$^2$—, —Z$^1$C(O)N(R$^7$)Q$^1$Q$^2$—, —Z$^1$C(O)Q$^1$—, —Z$^1$C(O)Q$^1$Z$^2$—, —Z$^1$C(O)Q$^1$Q$^2$—, —Z$^1$C(O)N(R$^7$)Q$^1$Q$^2$Z$^2$—;

—C(O)OZ$^1$—, —C(O)OZ$^1$Q$^1$—, —C(O)OZ$^1$Q$^1$Z$^2$—, —C(O)OQ$^1$Z$^1$—, —C(O)OQ$^1$Q$^2$—, —C(O)OQ$^1$Q$^2$Z$^1$—; —Q$^1$C(O)Z$^1$—, —Q$^1$C(O)Q$^2$Z$^1$—, —Q$^1$C(O)Z$^1$Q$^2$—, Q$^1$C(O)Q$^2$Q$^3$Z$^1$—;

—C(=NR$^9$)N(R$^7$)Z$^1$—, —C(=NR$^9$)N(R$^7$)Q$^1$—, —C(=NR$^9$)N(R$^7$)Z$^1$Q$^1$—, —C(=NR$^9$)N(R$^7$)Z$^1$Q$^1$Z$^2$—, —C(=NR$^9$)N(R$^7$)Q$^1$Z$^1$—, —C(=NR$^9$)N(R$^7$)Q$^1$Q$^2$—, C(=NR$^9$)N(R$^7$)Q$^1$Q$^2$Z$^1$—;

the groups Z$^1$ and, where present, Z$^2$ and Z$^3$ suitably comprise C$_{1-8}$ alkylene, C$_{2-8}$ alkenylene, C$_{2-8}$ alkynylene any of which is optionally substituted by one or more halo, OH, C(O)NR$^{15}$R$^{16}$, C(O)OR$^{15}$ or NR$^{15}$R$^{16}$, wherein R$^{15}$ and R$^{16}$ are as defined above.

In some more suitable compounds, the groups Z$^1$ and, where present, Z$^2$ and Z$^3$ comprise C$_{1-6}$ alkylene optionally substituted by one or more halo, OH, C(O)NR$^{15}$R$^{16}$, C(O)OR$^{15}$ or NR$^{15}$R$^{16}$; wherein R$^{15}$ and R$^{16}$ are as defined above.

Still more suitably, the groups Z$^1$ and, where present, Z$^2$ and Z$^3$ comprise C$_{1-4}$ alkylene which is unsubstituted or substituted by one or more halo, OH, C(O)NR$^{15}$R$^{16}$, C(O)OR$^{15}$ or NR$^{15}$R$^{16}$, wherein each R$^{15}$ and R$^{16}$ is H. Typically, Z$^1$ and where present, Z$^2$ and Z$^3$ comprise C$_{1-4}$ alkylene which is unsubstituted or substituted with one or more OH, halo, C(O)NH$_2$ or C(O)OH.

In some particularly suitable compounds, Z$^1$ and, where present, Z$^2$ and Z$^3$ are unsubstituted C$_{1-4}$ alkylene.

In other particularly suitable compounds, Z$^1$ is C$_{1-4}$ alkylene substituted with one or more halo, C(O)NH$_2$ or C(O)OH.

These Z$^1$, Z$^2$ and Z$^3$ moieties are particularly suitable when L$^1$ is:

—Z$^1$—, —Q$^1$Z$^1$— where Q$^1$ is linked via a ring carbon atom to Z$^1$, —Q$^1$Q$^2$Z$^1$— where Q$^2$ is linked via a ring carbon atom to Z$^1$;

—OZ$^1$—;

—C(O)Q$^1$Z$^1$—, where Q$^1$ is linked via a ring nitrogen atom to C(O) and via a ring carbon atom to Z$^1$;

—C(O)N(R$^7$)Z$^1$—, —C(O)N(R$^7$)Q$^1$Z$^1$—, —C(O)N(R$^7$)Z$^1$Q$^1$Q$^2$Z$^2$—, —C(O)N(R$^7$)Z$^1$O(CH$_2$CH$_2$O)$_n$Z$^2$— —C(O)N(R$^7$)Z$^1$Q$^1$Z$^2$N(R$^8$)Z$^3$—.

In some compounds of general formula (I), Z$^1$, Z$^2$ or Z$^3$ may be directly linked to a cyclic group via a ring nitrogen atom. This may occur, for example, in compounds where R$^1$ is L$^1$R$^{10}$ and L$^1$ is:

—Q$^1$Z$^1$—, —Z$^1$Q$^1$Z$^2$—, —Q$^1$Q$^2$Z$^1$—, —OQ$^1$Z$^1$—, —OZ$^1$Q$^1$Z$^2$—, —OQ$^1$Q$^2$Z$^1$—, —Z$^1$O(CH$_2$CH$_2$O)$_n$Q$^1$Z$^2$—, —Q$^1$Z$^1$O(CH$_2$CH$_2$O)$_n$Z$^2$—, —Z$^1$O(CH$_2$CH$_2$O)$_n$Z$^2$Q$^1$Z$^3$—, —C(O)Z$^1$Q$^1$Z$^2$—, —C(O)Q$^1$Z$^1$—, —C(O)Q$^1$Q$_2$Z$^1$—, —C(O)Q$^1$N(R$^7$)C(O)Z$^1$Q$^2$Z$^2$—, —(O)N(R$^7$)Z$^1$Q$^1$Z$^2$—, —C(O)N(R$^7$)Q$^1$Z$^1$—, —C(O)N(R$^7$)Q$^1$Q$^2$Z$^1$—, —C(O)N(R$^7$)Z$^1$Q$^1$Q$^2$Z$^2$—, —C(O)N(R$^7$)Z$^1$Q$^1$OQ$^2$OQ$^3$Z$^2$—, Z$^1$C(O)N(R$^7$)Q$^1$Z$^1$—, —Z$^1$C(O)Q$^1$Z$^2$—, Z$^1$C(O)N(R$^7$)Q$^1$Q$^2$Z$^2$—, —C(O)OZ$^1$Q$^1$Z$^2$—, —C(O)OQ$^1$Z$^1$—, —C(O)OQ$^1$Q$^2$Z$^1$—; Q$^1$C(O)Q$^2$Z$^1$—, Q$^1$C(O)Q$^2$Q$^3$Z$^1$—, —C(=NR$^9$)N(R$^7$)Z$^1$Q$^1$Z$^2$—, —C(=NR$^9$)N(R$^7$)Q$^1$Z$^1$—.

In some such compounds, the Z$^1$ or Z$^2$ or Z$^3$ group is also linked to R$^{10}$. Where this is the case, the Z$^1$ or Z$^2$ or Z$^3$ group may be C$_{1-12}$ alkylene substituted with one or more OH group, suitably by a plurality of OH groups, for example 2-11 OH groups. Typically, the number of OH groups will be one less than the number of carbon atoms in the alkylene group;

More suitably in this case, Z$^1$ is a C$_{1-8}$ alkylene group substituted with 2-7 OH groups, for example 5-7 OH groups.

Examples of suitable Z$^1$ or Z$^2$ or Z$^3$ groups of this type include —CH$_2$[CH(OH)]$_n$—, where n is suitably 3-7. Most suitably, Z$^1$ or Z$^2$ or Z$^3$ where appropriate is —CH$_2$—CH(OH)—CH(OH)—CH(OH)—CH(OH)—CH(OH)—.

In such compounds, R$^{10}$ is suitably H such that the Z$^1$R$^{10}$, Z$^2$R$^{10}$ or Z$^3$R$^{10}$ moiety is —CH$_2$[CH(OH)]$_n$—H, where n is suitably 3-7, for example —CH$_2$—[CH(OH)]$_4$—CH$_2$OH.

In compounds where R$^1$ is —L$^1$R$^{10}$, suitable R$^{10}$ groups include H, —N(R$^7$)R$^8$, —N(R$^7$)C(=NR$^9$)N(R$^8$)$_2$, —N(R$^7$)—C(O)OR$^8$, —N(R$^7$)—C(O)—(C$_{1-3}$ alkylene)-N$^+$(R$^8$)$_3$, —N$^+$(R$^8$)$_3$, OR$^7$ or —C(O)OR$^7$.

More suitably, R$^{10}$ is H, —N(R$^7$)R$^8$, —N(R$^7$)C(=NR$^9$)N(R$^8$)$_2$, —N(R$^7$)C(O)OR$^8$ or —C(O)OR$^7$.

When R$^{10}$ is H, L$^1$ is suitably —Z$^1$—, Q$^1$, —Q$^1$Z$^1$—, —Z$^1$Q$^1$Z$^2$—, —Q$^1$Q$^2$, —Q$^1$Q$^2$Z$^1$—;

—OZ$^1$—, —OQ$^1$Z$^1$—, —OZ$^1$Q$^1$Z$^2$—, —OOQ$^1$Q$^2$Z$^1$—; —Z$^1$O(CH$_2$CH$_2$O)$_n$Q$^1$Z$^2$—, —Q$^1$Z$^1$O(CH$_2$CH$_2$O)$_n$Z$^2$—, —Z$^1$O(CH$_2$CH$_2$O)$_n$Z$^2$Q$^1$Z$^3$—; —C(O)Z$^1$—, —C(O)Z$^1$Q$^1$Z$^2$—, —C(O)Q$^1$Z$^1$—, —C(O)Q$^1$Q$^2$Z$^1$—;

—C(O)N(R$^7$)Z$^1$—, —C(O)N(R$^7$)Q$^1$—, —C(O)Q$^1$N(R$^7$)C(O)Z$^1$Q$^2$Z$^2$—, —C(O)N(R$^7$)Z$^1$Q$^1$Z$^2$—, —C(O)N(R$^7$)Q$^1$Z$^1$—, —C(O)N(R$^7$)Q$^1$Z$^2$Z$^1$—, —C(O)N(R$^7$)Z$^1$Q$^1$Q$^2$Z$^2$—; —C(O)N(R$^7$)Z$^1$Q$^1$OQ$^2$OQ$^3$Z$^2$—, Z$^1$C(O)N(R$^7$)Q$^1$Z$^2$—;

—C(O)N(R$^7$)Q$^1$Q$^2$Z$^1$—, —Z$^1$C(O)Q$^1$Z$^2$—, Z$^1$C(O)N(R$^7$)Q$^1$Q$^2$Z$^2$—;

—C(O)OZ$^1$—, —C(O)OZ$^1$Q$^1$Z$^2$—, —C(O)OQ$^1$Z$^1$—, —C(O)OQ$^1$Q$^2$—, C(O)OQ$^1$Q$^2$Z$^1$—;

—C(O)OQ$^1$Z$^1$—, —C(O)OQ$^1$Q$^2$Z$^1$—; Q$^1$C(O)Q$^2$Z$^1$—, Q$^1$C(O)Q$^2$Q$^3$Z$^1$—, —C(=NR$^9$)N(R$^7$)Z$^1$—, C(=NR$^9$)N(R$^7$)Z$^1$Q$^1$Z$^2$—, —C(=NR$^9$)N(R$^7$)Q$^1$Z$^1$—, C(=NR$^9$)N(R$^7$)Q$^1$Q$^2$Z$^1$—.

In some more suitable compounds, when R$^{10}$ is H, L$^1$ is —OZ$^1$, where Z$^1$ is as defined above but is suitably C$_{1-8}$ alkylene optionally substituted as described above. More suitably in these compounds, Z$^1$ is C$_{1-4}$ alkylene such that the group —OZ$^1$R$^{10}$ is —O(C$_{1-4}$ alkyl), for example methoxy, ethyoxy isopropoxy or t-butyloxy. In one embodiment (e.g. as used in Examples 4, 7-14 and 19), R$^1$ is methoxy.

In other more suitable compounds, when R$^{10}$ is H, L$^1$ is —Q$^1$—, —Q$^1$Q$^2$— or —C(O)N(R$^7$)Q$^1$—, where the Q$^1$ group or, for —Q$^1$Q$^2$—, the Q$^2$ group, is a nitrogen-containing heterocyclyl group which is linked to the R$^{10}$ group via a ring nitrogen atom. Examples of such groups Q$^1$R$^{10}$ or Q$^2$R$^{10}$ groups include:

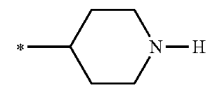

where * indicates the point at which the group is joined to the remainder of the molecule.

In an embodiment (e.g. as used in Example 30), R$^1$ is —Q$^1$—H.

In an embodiment (e.g. as used in Example 31), $R^1$ is $-Q^1Q^2Z^1-H$.

In an embodiment (e.g. as used in Example 40), $R^1$ is $-C(O)N(R^7)Q^1-H$.

In still other more suitable compounds, when $R^{10}$ is H, $L^1$ is:
- $-Z^1-$, $-Q^1-$, $-Q^1Z^1-$, $-Q^1Q^2-$, $-Q^1Q^2Z^1-$;
- $-OZ^1-$, $-OQ^1Z^1-$, $OQ^1Q^2Z^1-$;
- $-C(O)Z^1-$, $-C(O)Q^1Z^1-$, $-C(O)Q^1Q^2Z^1-$;
- $-C(O)N(R^7)Z^1-$, $-C(O)N(R^7)Q^1Z^1-$, $-C(O)N(R^7)Q^1Q^2Z^1-$;
- $-C(O)OZ^1-$, $-C(O)OQ^1Z^1-$, $-C(O)OQ^1Q^2-$, $C(O)OQ^1Q^2Z^1$;
- $-C(=NR^9)N(R^7)Z^1-$, $-C(=NR^9)N(R^7)Q^1Z^1-$ or $C(=NR^9)N(R^7)Q^1Q^2Z^1-$.

In still other more suitable compounds, when $R^{10}$ is H, and which contain a cyclic group $Q^1$, $Q^2$ or $Q^3$ linked to $Z^1$ or $Z^2$ or $Z^3$, the cylic group may be a nitrogen containing heterocyclyl group linked to $Z^1$ or $Z^2$ or $Z^3$ via a ring nitrogen atom. This may occur, for example, in compounds where $R^1$ is $L^1R^{10}$ and $L^1$ is:
- $-Q^1Z^1-$, $-Z^1Q^1Z^2-$, $-Q^1Q^2Z^1-$;
- $-OQ^1Z^1-$, $-OZ^1Q^1Z^2-$, $-OQ^1Q^2Z^1-$;
- $-Z^1O(CH_2CH_2O)_nQ^1Z^2-$, $-Q^1Z^1O(CH_2CH_2O)_nZ^2-$, $-Z^1O(CH_2CH_2O)_nZ^2Q^1Z^3-$;
- $-C(O)Z^1Q^1Z^2-$, $-C(O)Q^1Z^1-$, $-C(O)Q^1Q^2Z^1-$, $-C(O)Q^1N(R^7)C(O)Z^1Q^2Z^2-$, $-C(O)N(R^7)Z^1Q^1Z^2-$, $-C(O)N(R^7)Q^1Z^1-$;
- $-C(O)N(R^7)Q^1Q^2Z^1-$, $-C(O)N(R^7)Z^1Q^1Q^2Z^2-$, $-C(O)N(R^7)Z^1Q^1OQ^2OQ^3Z^2-$;
- $Z^1C(O)N(R^7)Q^1Z^2-$, $-Z^1C(O)Q^1Z^2-$, $Z^1C(O)N(R^7)^7Q^1Q^2Z^2-$;
- $-C(O)OZ^1Q^1Z^2-$, $-C(O)OQ^1Z^1-$, $-C(O)OQ^1Q^2Z^1-$;
- $Q^1C(O)Q^2Z^1-$, $Q^1C(O)Q^2Q^3Z^1-$;
- $-C(=NR^9)N(R^7)Z^1Q^1Z^2-$, $-C(=NR^9)N(R^7)Q^1Z^1-$ or $-C(=NR^9)N(R^7)Q^1Q^2Z^1-$.

Particularly suitable compounds of this type are those in which $R^{10}$ is H and $L^1$ is $-Q^1Z^1-$, $-Q^1Q^2Z^1-$, $-C(O)N(R^7)Q^1Z^1-$, or $-C(O)Q^1Z^1-$; or, still more suitably, $-Q^1Z^1-$, $-Q^1Q^2Z^1-$ or $-C(O)N(R^7)Q^1Z^1-$.

In compounds where $R^{10}$ is H and in which $L^1$ contains a moiety $Z^1$, $Z^2$ or $Z^3$ linked directly to $R^{10}$, the $Z^1$, $Z^2$ or $Z^3$ moiety is suitably a $C_{1-12}$ alkylene group substituted by a plurality of OH groups, for example 2 to 11 OH groups. Typically, the number of OH groups will be one less than the number of carbon atoms in the alkylene group;

More suitably in this case, $Z^1$ is a $C_{1-8}$ alkylene group substituted with 2-7 OH groups, for example 5-7 OH groups.

Examples of suitable $Z^1$ groups of this type include $-CH_2[CH(OH)]_n-$, where n is suitably 3-7. Most suitably, n is 5 and in this case, $Z^1$ is $-CH_2[CH(OH)]_4-CH(OH)-$ such that the group $Z^1R^{10}$, $Z^2R^{10}$ or $Z^3R^{10}$ is a moiety $-CH_2[CH(OH)]_4-CH_2OH$.

Examples of compounds where the group $Z^1R^{10}$ is a moiety $-CH_2[CH(OH)]_4-CH_2OH$ include those in which $R^1$ is:
- $-$piperidinyl-4-yl-$CH_2-CH(OH)-CH(OH)-CH(OH)-CH(OH)-CH_2(OH)$.
- $-$pyrazol-4-yl-piperidin-4-yl-$CH_2-CH(OH)-CH(OH)-CH(OH)-CH(OH)-CH_2(OH)$.
- $-C(O)NH$-piperidin-4-yl-$CH_2-CH(OH)-CH(OH)-CH(OH)-CH(OH)-CH_2(OH)$.

In an embodiment (e.g. as used in Example 46), $R^1$ is $-Q^1Z^1-H$.

In an embodiment (e.g. as used in Example 47), $R^1$ is $-Q^1Q^2Z^1-H$.

In an embodiment (e.g. as used in Example 49), $R^1$ is $C(O)N(R^7)Q^1Z^1-H$.

Other suitable compounds in which $R^{10}$ is H include those in which $R^{10}$ is attached to a ring nitrogen atom of a moiety $Q^1$, $Q^2$ or $Q^3$ or the $L^1$ group.

When $R^{10}$ is other than H, $Z^1$, $Z^2$ and $Z^3$, where present, may be $-(CH_2)_n-$ where n is 1 to 6 or $-O(CH_2)_m-$, where m is 1 to 5.

In compounds where $R^{10}$ is $-C(O)OR^7$, $L^1$ is suitably:
- $-Q^1-$ or $-Q^1Q^2-$ where $Q^1$ or, for $-Q^1Q^2-$, $Q^2$ is a carbocyclyl or heterocyclyl group and is linked to $R^{10}$ via a ring carbon atom; or
- $C(O)N(R^7)Q^1$, where $Q^1$ is a is a carbocyclyl or heterocyclyl group and is linked to $R^{10}$ via a ring nitrogen atom.

In these compounds, $R^7$ is suitably $C_{1-6}$ alkyl, still more suitably $C_{1-4}$ alkyl, for example t-butyl.

In an embodiment (e.g. as used in Example 25), $R^1$ is $-Q^1C(O)OR^7$, where $Q^1$ is piperidin-4-yl and $R^7$ is t-butyl.

In an embodiment (e.g. as used in Example 26), $R^1$ is $-Q^1Q^2C(O)OR^7$, where $Q^1$ is pyrazol-4-yl, $Q^2$ is piperidin-4-yl and $R^7$ is t-butyl.

In an embodiment (e.g. as used in Example 36), $R^1$ is $C(O)NHQ^1C(O)OR^7$, where $Q^1$ is piperidin-1-yl and $R^7$ is When $R^{10}$ is $-N(R^7)R^8$, $-N(R^7)C(=NR^9)N(R^8)_2$ or $-N(R^7)C(O)OR^8-$, $L^1$ is suitably:
- $-Z^1-$,
- $-OZ^1-$;
- $-C(O)N(R^7)Z^1-$, $-C(O)N(R^7)Z^1Q^1Q^2Z^2-$, $-C(O)N(R^7)Z^1Q^1Z^2N(R^8)Z^3$, $-C(O)N(R^7)Z^1O(CH_2CH_2O)_nZ^2$;
- $-C(O)N(R^7)Q^1-$, $-C(O)N(R^7)Z^1Q^1-$ or $-C(O)Q^1-$, where $Q^1$ is a carbocyclyl or heterocyclyl group and is linked to $R^{10}$ via a ring carbon atom; or $C(O)Q^1Z^1-$.

Compounds in which $R^{10}$ is $-N(R^7)R^8$ are particularly suitable.

Typically, when $R^{10}$ is $-N(R^7)R^8$, each of $R^7$ and $R^8$ is independently either H or $C_{1-8}$ alkyl optionally substituted with one or more OH groups. In some cases, both $R^7$ and $R^8$ are H.

In the case where either or both of $R^7$ and $R^9$ is $C_{1-8}$ alkyl, it may be substituted with a plurality of OH groups, for example 2-7 OH groups. Typically, the number of OH groups will be one less than the number of carbon atoms in the alkyl group. More suitably in compounds of this type, one or preferably both, of $R^7$ and $R^8$ may be $-CH_2[CH(OH)]_mCH_2OH$, where m is suitably 2-6. Most suitably, m is 4 and in this case, the $R^7$ and/or $R^8$ group is a moiety $-CH_2[CH(OH)]_4-CH_2OH$.

In particularly suitable compounds $R^{10}$ is $-N\{CH_2[CH(OH)]_4-CH_2OH\}_2$.

In an embodiment (e.g. as used in Example 29), $L^1$ is $-Z^1-$ and $R^{19}$ is $NH_2$ In an embodiment (e.g. as used in Examples 27 and 28), $L^1$ is $-OZ^1-$ and $R^{10}$ is $NH_2$.

In an embodiment (e.g. as used in Example 39), $L^1$ is $-C(O)N(R^7)Z^1-$ and $R^{10}$ is $NH_2$.

In an embodiment (e.g. as used in Example 41), $L^1$ is $-C(O)Q^1$ and and $R^{10}$ is $NH_2$.

In an embodiment (e.g. as used in Example 42), $L^1$ is $-C(O)N(R^7)Z^1Q^1$ and $R^{10}$ is $NH_2$.

In an embodiment (e.g. as used in Examples 43 and 44), $L^1$ is $-OZ^1-$ and $R^{10}$ is $-N\{CH_2[CH(OH)]_4-CH_2OH\}_2$.

In an embodiment (e.g. as used in Example 45), $L^1$ is $-Z^1-$ and $R^{10}$ is $-N\{CH2[CH(OH)]_4-CH_2OH\}_2$.

In an embodiment (e.g. as used in Examples 48, 57, 58 and 61), $L^1$ is $-C(O)N(R^7)Z^1-$ and $R^{10}$ is $-N\{CH_2[CH(OH)]_4-CH_2OH\}_2$.

In an embodiment (e.g. as used in Examples 50, 53, 54, 65 and 66), $L^1$ is —C(O)$Q^1$ and $R^{10}$ is —N{CH$_2$[CH(OH)]$_4$—CH$_2$OH}$_2$.

In an embodiment (e.g. as used in Example 51), $L^1$ is —C(O)N($R^7$)$Z^1Q^1$ and $R^{10}$ is —N{CH$_2$[CH(OH)]$_4$—CH$_2$OH}$_2$.

In an embodiment (e.g. as used in Examples 55 and 56), $L^1$ is —C(O)N($R^7$)$Q^1$ and $R^{10}$ is —N{CH$_2$[CH(OH)]$_4$—CH$_2$OH}$_2$.

In an embodiment (e.g. as used in Example 59), $L^1$ is —C(O)N($R^7$)$Z^1$O(CH$_2$CH$_2$O)$_n$$Z^2$— and $R^{10}$ is —N{CH$_2$[CH(OH)]$_4$—CH$_2$OH}$_2$.

In an embodiment (e.g. as used in Example 60), $L^1$ is —C(O)N($R^7$)$Z^1Q^1Q^2Z^2$— and $R^{10}$ is —N{CH$_2$[CH(OH)]$_4$—CH$_2$OH}$_2$.

In an embodiment (e.g. as used in Example 62), $L^1$ is —C(O)N($R^7$)$Z^1Q^1Z^2$N($R^9$)$Z^3$— and $R^{10}$ is —N{CH$_2$[CH(OH)]$_4$—CH$_2$OH}$_2$.

When $R^{10}$ is —N($R^7$)C(=N$R^9$)N($R^8$)$_2$, each of $R^7$ and $R^9$ is suitably H or $C_{1-4}$ alkyl, particularly H or methyl and especially H; and each $R^8$ is independently either H or $C_{1-8}$ alkyl optionally substituted with one or more OH groups. In the case where either or both $R^8$ groups is a $C_{1-8}$ alkyl group, it may be substituted with a plurality of OH groups, for example 2-7 OH groups. Typically, the number of OH groups will be one less than the number of carbon atoms in the alkyl group. More suitably in compounds of this type, one or preferably both, $R^8$ groups may be —CH$_2$[CH(OH)]$_m$CH$_2$OH, where m is suitably 2-6. Most suitably, m is 4 and in this case, one or preferably both the $R^8$ groups is a moiety —CH$_2$[CH(OH)]$_4$—CH$_2$OH.

In particularly suitable compounds —N($R^7$)C(=N$R^9$)N($R^8$)$_2$ is:

—NHC(=NH)—N{CH$_2$[CH(OH)]$_4$—CH$_2$OH}$_2$.

When $R^{10}$ is —N($R^7$)C(O)O$R^8$, each of $R^7$ and $R^8$ is suitably H or $C_{1-6}$ alkyl. More suitably, $R^7$ is H and $R^8$ is $C_{1-6}$ alkyl, still more suitably $C_{1-4}$ alkyl, for example t-butyl.

In still other compounds of general formula (I), $R^1$ is —O$R^{12}$ —SO$_2R^{12}$, —C(O)O$R^{12}$, —C(O)$_{NR}{}^{12}R^{13}$, —(=N$R^9$)N$R^{12}R^{13}$, —$Q^1$O$R^{12}$ —$Q^1$SO$_2R^{12}$, —$Q^1$C(O)O$R^{12}$, —$Q^1$C(O)N$R^{12}R^{13}$, —$Q^1$C(=N$R^7$)N$R^{12}R^{14}$, —$Q^1Q^2$O$R^{12}$, —$Q^1Q^2$SO$_2R^{12}$, —$Q^1Q^2$C(O)O$R^{12}$, —$Q^1Q^2$C(O)N$R^{12}R^{13}$ or —$Q^1Q^2$C(=N$R^9$)N$R^{12}R^{13}$;

Suitable groups $Q^1$ and $Q^2$ are as set out above.

Suitable $R^{12}$ and $R^{13}$ groups include H and $C_{1-6}$ alkyl optionally substituted with one or more substituents selected from halo and O$R^7$.

As mentioned above, each of $R^2$ and $R^3$ is independently $C_{1-10}$ alkyl in which one or more —CH$_2$— groups is optionally replaced by —O—, —S— or —N$R^7$— and which is optionally substituted as defined above. There may, for example, be no such substituents or a single substituent.

Suitably, each of $R^2$ and $R^3$ is independently $C_{1-10}$ alkyl in which one or more —CH$_2$— groups is optionally replaced by —O— or —S— and which is optionally substituted as defined above.

Examples of $R^2$ and $R^3$ groups include —(CH$_2$)$_s$CH$_3$ or (CH$_2$CH$_2$O)$_t$—H, either of which is optionally substituted as defined above; and wherein s is 0-9, more suitably 0-6 and still more suitably 0-3; and t is 1-3, especially 2 or 3.

Particularly suitable compounds of general formula (I) are those in which $R^2$ and $R^3$ are the same or different and are both unsubstituted $C_{1-4}$ alkyl, for example methyl or ethyl. In some such compounds $R^2$ and $R^3$ are the same and are both methyl or both ethyl. In other such compounds, one of $R^2$ and $R^3$ is methyl and the other of $R^2$ and $R^3$ is ethyl.

Suitable substituents for $R^2$ and $R^3$ include OH, SH, halo, N($R^7$)$R^8$, C(O)O$R^7$, C(O)N($R^7$)$R^8$, phenyl or pyridyl, where $R^7$ and $R^8$ are as defined above. Particularly suitable substituents for $R^2$ include OH, SH, phenyl or pyridyl, particularly OH, phenyl, pyridyl, C(O)O—$C_{1-6}$ alkyl, C(O)OH, C(O)NH$_2$ or C(O)N($R^7$)$R^8$, where each of $R^7$ and $R^8$ is $C_{1-3}$ alkyl or $R^7$ and $R^8$ together with the nitrogen atom to which they are attached form a pyrrolidine, piperidine, piperazine or morpholine ring.

In some compounds of general formula (I), at least one of $R^2$ and $R^3$ is —(CH$_2$)$_s$CH$_3$, wherein s is as defined above, and is optionally substituted with a single substituent as defined above.

In some such compounds of general formula (I) at least one of $R^2$ and $R^3$ is methyl, ethyl, benzyl, pyridylmethyl, —CH$_2$OH, —CH$_2$NH$_2$, —CH$_2$CH$_2$OH or CH$_2$CH$_2$NH$_2$.

In other particularly suitable compounds, at least one of $R^2$ and $R^3$ is —CH$_2$CH$_2$OCH$_2$CH$_2$OH or —CH$_2$CH$_2$OCH$_2$CH$_2$OCH$_2$CH$_2$OH In suitable compounds of general formula (I), $R^4$ is H, halo, cyano or $C_{1-3}$ alkyl. In more suitable compounds of general formula (I), $R^4$ is H, chloro, bromo, cyano or methyl. In particularly suitable compounds of general formula (I), $R^4$ is H, chloro or methyl and especially H.

As set out above, $R^5$ is H or methyl, more suitably H.

In some compounds of general formula (I), both $R^4$ and $R^5$ are H.

In other compounds of general formula (I), $R^4$ is H and $R^5$ is methyl.

In other compounds of general formula (I), $R^4$ is methyl and $R^5$ is H.

In other compounds of general formula (I), $R^4$ is halo (e.g. chloro or bromo) and $R^5$ is H.

In other compounds of general formula (I), $R^4$ is cyano and $R^5$ is H.

Some particularly suitable compounds of the present invention include those having a cation selected from:

1. 2-[({3-amino-5H-pyrrolo[2,3-b]pyrazin-2-yl}formamido)methyl]-1-ethyl-3-methyl -1H-1,3-benzodiazol-3-ium;

2. 2-[({3-amino-5H-pyrrolo[2,3-b]pyrazin-2-yl}formamido)methyl]-1-ethyl-6-fluoro-3-methyl-1H-1,3-benzodiazol-3-ium;

3. 2-[({3-amino-5H-pyrrolo[2,3-b]pyrazin-2-yl}formamido)methyl]-6-chloro-1-ethyl-3-methyl-1H-1,3-benzodiazol-3-ium;

4. 2-[({3-amino-5H-pyrrolo[2,3-b]pyrazin-2-yl}formamido)methyl]-1-ethyl-6-methoxy -3-methyl-1H-1,3-benzodiazol-3-ium;

5. 2-[({3-amino-5H-pyrrolo[2,3-b]pyrazin-2-yl}formamido)methyl]-1-ethyl-3-methyl-6-(trifluoromethyl)-1H-1,3-benzodiazol-3-ium;

6. 2-[({3-amino-5H-pyrrolo[2,3-b]pyrazin-2-yl}formamido)methyl]-1-ethyl-3-methyl-6-(trifluoromethoxy)-1H-1,3-benzodiazol-3-ium;

7. 2-[({3-amino-5H-pyrrolo[2,3-b]pyrazin-2-yl}formamido)methyl]-1,3-diethyl-6-methoxy-1H-1,3-benzodiazol-3-ium;

8. 2-[({3-amino-5H-pyrrolo[2,3-b]pyrazin-2-yl}formamido)methyl]-3-benzyl-1-ethyl-6-methoxy-1H-1,3-benzodiazol-3-ium;

9. 2-[({3-amino-5H-pyrrolo[2,3-b]pyrazin-2-yl}formamido)methyl]-1-ethyl-6-methoxy -3-(2-methoxy-2-oxoethyl)-1H-1,3-benzodiazol-3-ium;

10. 2-[({3-amino-5H-pyrrolo[2,3-b]pyrazin-2-yl}formamido)methyl]-3-(carboxylatomethyl)-1-ethyl-6-methoxy-1H-1,3-benzodiazol-3-ium 11. 2-[({3-amino-5H-pyrrolo[2,3-b]pyrazin-2-yl}formamido)methyl]-3-(carbamoylmethyl)-1-ethyl-6-methoxy-1H-1,3-benzodiazol-3-ium;

12. 2-[({3-amino-5H-pyrrolo[2,3-b]pyrazin-2-yl}formamido)methyl]-1-ethyl-6-methoxy -3-[2-(methylsulfanyl)ethyl]-1H-1,3-benzodiazol-3-ium;

13. 2-[({3-amino-5H-pyrrolo[2,3-b]pyrazin-2-yl}formamido)methyl]-1-ethyl-3-(2-hydroxyethyl)-6-methoxy-1H-1,3-benzodiazol-3-ium;

14. 2-[({3-amino-5H-pyrrolo[2,3-b]pyrazin-2-yl}formamido)methyl]-1-ethyl-3-{2-[2-(2-hydroxyethoxy)ethoxy]ethyl}-6-methoxy-1H-1,3-benzodiazol-3-ium;

15. 2-[({3-amino-5H-pyrrolo[2,3-b]pyrazin-2-yl}formamido)methyl]-1-benzyl-3-methyl -1H-1,3-benzodiazol-3-ium;

16. 2-[({3-amino-5H-pyrrolo[2,3-b]pyrazin-2-yl}formamido)methyl]-3-benzyl-6-chloro -1-ethyl-1H-1,3-benzodiazol-3-ium;

17. 2-[({3-amino-5H-pyrrolo[2,3-b]pyrazin-2-yl}formamido)methyl]-3-benzyl-1-ethyl-6-(trifluoromethyl)-1H-1,3-benzodiazol-3-ium;

18. 2-[({3-amino-5H-pyrrolo[2,3-b]pyrazin-2-yl}formamido)methyl]-3-benzyl-1-[2-oxo -2-(piperidin-1-yl)ethyl]-1H-1,3-benzodiazol-3-ium;

19. 2-[({3-amino-6-methyl-5H-pyrrolo[2,3-b]pyrazin-2-yl}formamido)methyl]-1-ethyl-6-methoxy-3-methyl-1H-1,3-benzodiazol-3-ium;

20. 2-[({3-amino-7-methyl-5H-pyrrolo[2,3-b]pyrazin-2-yl}formamido) methyl]-6-chloro -1,3-diethyl-1H-1,3-benzodiazol-3-ium;

21. 2-[({3-amino-7-chloro-5H-pyrrolo[2,3-b]pyrazin-2-yl}formamido)methyl]-6-chloro -1,3-diethyl-1H-1,3-benzodiazol-3-ium;

22. 2-[({3-amino-5H-pyrrolo[2,3-b]pyrazin-2-yl}formamido)methyl]-6-(2-{[(tert -butoxy)carbonyl]amino}ethoxy)-1,3-diethyl-1H-1,3-benzodiazol-3-ium;

23. 2-[({3-amino-5H-pyrrolo[2,3-b]pyrazin-2-yl}formamido)methyl]-6-(3-{[(tert -butoxy)carbonyl]amino}propoxy)-1,3-diethyl-1H-1,3-benzodiazol-3-ium;

24. 2-[({3-amino-5H-pyrrolo[2,3-b]pyrazin-2-yl}formamido)methyl]-6-(3-{[(tert -butoxy)carbonyl]amino}propyl)-1,3-diethyl-1H-1,3-benzodiazol-3-ium;

25. 2-[({3-amino-5H-pyrrolo[2,3-b]pyrazin-2-yl}formamido)methyl]-6-{1-[(tert -butoxy)carbonyl]piperidin-4-yl}-1,3-diethyl-1H-1,3-benzodiazol-3-ium;

26. 2-[({3-amino-5H-pyrrolo[2,3-b]pyrazin-2-yl}formamido)methyl]-6-(1-{1-[(tert -butoxy)carbonyl]piperidin-4-yl}-1H-pyrazol-4-yl)-1,3-diethyl-1H-1,3-benzodiazol-3-ium;

27. 2-[({3-amino-5H-pyrrolo[2,3-b]pyrazin-2-yl}formamido)methyl]-6-(2-aminoethoxy) -1,3-diethyl-1H-1,3-benzodiazol-3-ium;

28. 2-[({3-amino-5H-pyrrolo[2,3-b]pyrazin-2-yl}formamido)methyl]-6-(3-aminopropoxy)-1,3-diethyl-1H-1,3-benzodiazol-3-ium;

29. 2-[({3-amino-5H-pyrrolo[2,3-b]pyrazin-2-yl}formamido)methyl]-6-(3-aminopropyl) -1,3-diethyl-1H-1,3-benzodiazol-3-ium;

30. 2-[({3-amino-5H-pyrrolo[2,3-b]pyrazin-2-yl}formamido)methyl]-1,3-diethyl-6-(piperidin-4-yl)-1H-1,3-benzodiazol-3-ium;

31. 2-[({3-amino-5H-pyrrolo[2,3-b]pyrazin-2-yl}formamido)methyl]-1,3-diethyl-6-[1-(piperidin-4-yl)-1H-pyrazol-4-yl]-1H-1,3-benzodiazol-3-ium;

32. 2-[({3-amino-5H-pyrrolo[2,3-b]pyrazin-2-yl}formamido)methyl]-6-(2-carbamimidamidoethoxy)-1,3-diethyl-1H-1,3-benzodiazol-3-ium;

33. 2-[({3-amino-5H-pyrrolo[2,3-b]pyrazin-2-yl}formamido)methyl]-6-(3-carbamimidamidopropyl)-1,3-diethyl-1H-1,3-benzodiazol-3-ium;

34. 2-[({3-amino-5H-pyrrolo[2,3-b]pyrazin-2-yl}formamido)methyl]-6-carboxy-1,3-diethyl-1H-1,3-benzodiazol-3-ium;

35. 2-[({3-amino-5H-pyrrolo[2,3-b]pyrazin-2-yl}formamido) methyl]-6-[(3-{[(tert -butoxy)carbonyl]amino}propyl)carbamoyl]-1,3-diethyl-1H-1,3-benzodiazol-3-ium formic acid;

36. 2-[({3-amino-5H-pyrrolo[2,3-b]pyrazin-2-yl}formamido) methyl]-6-({1-[(tert -butoxy)carbonyl]piperidin-4-yl}carbamoyl)-1,3-diethyl-1H-1,3-benzodiazol-3-ium;

37. 2-[({3-amino-5H-pyrrolo[2,3-b]pyrazin-2-yl}formamido) methyl]-6-(4-{[(tert -butoxy)carbonyl]amino}piperidine-1-carbonyl)-1,3-diethyl-1H-1,3-benzodiazol-3-ium;

38. 2-[({3-amino-5H-pyrrolo[2,3-b]pyrazin-2-yl}formamido)methyl]-6-{[2-(4-{[(tert -butoxy)carbonyl]amino}piperidin-1-yl)ethyl]carbamoyl}-1,3-diethyl-1H-1,3-benzodiazol-3-ium;

39. 2-[({3-amino-5H-pyrrolo[2,3-b]pyrazin-2-yl}formamido)methyl]-6-[(3-aminopropyl)carbamoyl]-1,3-diethyl-1H-1,3-benzodiazol-3-ium;

40. 2-[({3-amino-5H-pyrrolo[2,3-b]pyrazin-2-yl}formamido)methyl]-1,3-diethyl-6-[(piperidin-4-yl)carbamoyl]-1H-1,3-benzodiazol-3-ium;

41. 2-[({3-amino-5H-pyrrolo[2,3-b]pyrazin-2-yl}formamido)methyl]-6-(4-aminopiperidine-1-carbonyl)-1,3-diethyl-1H-1,3-benzodiazol-3-ium;

42. 2-[({3-amino-5H-pyrrolo[2,3-b]pyrazin-2-yl}formamido)methyl]-6-{[2-(4-aminopiperidin-1-yl)ethyl]carbamoyl}-1,3-diethyl-1H-1,3-benzodiazol-3-ium;

43. 2-[({3-amino-5H-pyrrolo[2,3-b]pyrazin-2-yl}formamido)methyl]-5-(2-{bis[(2S,3R,4R,5R)-2,3,4,5,6-pentahydroxyhexyl]amino}ethoxy)-1,3-diethyl-1H -1,3-benzodiazol-3-ium;

44. 2-[({3-amino-5H-pyrrolo[2,3-b]pyrazin-2-yl}formamido)methyl]-5-(3-{bis[(2S,3R,4R,5R)-2,3,4,5,6-pentahydroxyhexyl]amino}propoxy)-1,3-diethyl-1H -1,3-benzodiazol-3-ium;

45. 2-[({3-amino-5H-pyrrolo[2,3-b]pyrazin-2-yl}formamido)methyl]-5-(3-{bis[(2S,3R,4R,5R)-2,3,4,5,6-pentahydroxyhexyl]amino}propyl)-1,3-diethyl-1H -1,3-benzodiazol-3-ium;

46. 2-[({3-amino-5H-pyrrolo[2,3-b]pyrazin-2-yl}formamido)methyl]-1,3-diethyl-6-{1-[(2S,3R,4R,5R)-2,3,4,5,6-pentahydroxyhexyl]piperidin-4-yl}-1H-1,3-benzodiazol -3-ium;

47. 2-[({3-amino-5H-pyrrolo[2,3-b]pyrazin-2-yl}formamido)methyl]-1,3-diethyl-6-(1-{1-[(2S,3R,4R,5R)-2,3,4,5,6-pentahydroxyhexyl]piperidin-4-yl}-1H-pyrazol-4-yl)-1H -1,3-benzodiazol-3-ium;

48. 2-[({3-amino-5H-pyrrolo[2,3-b]pyrazin-2-yl}formamido)methyl]-6-[(3-{bis[(2S,3R,4R,5R)-2,3,4,5,6-pentahydroxyhexyl]amino}propyl)carbamoyl]-1,3-diethyl-1H-1,3-benzodiazol-3-ium;

49. 2-[({3-amino-5H-pyrrolo[2,3-b]pyrazin-2-yl}formamido)methyl]-1,3-diethyl-6-({1-[(2S,3R,4R,5R)-2,3,4,5,6-pentahydroxyhexyl]piperidin-4-yl}carbamoyl)-1H-1,3-benzodiazol-3-ium;

50. 2-[({3-amino-5H-pyrrolo[2,3-b]pyrazin-2-yl}formamido)methyl]-6-(4-{bis[(2S,3R,4R,5R)-2,3,4,5,6-pentahydroxyhexyl]amino}piperidine-1-carbonyl) -1,3-diethyl-1H-1,3-benzodiazol-3-ium;

51. 2-[({3-amino-5H-pyrrolo[2,3-b]pyrazin-2-yl}formamido)methyl]-6-{[2-(4-{bis[(2S,3R,4R,5R)-2,3,4,5,6-pentahydroxyhexyl]amino}piperidin-1-yl)ethyl]carbamoyl}-1,3-diethyl-1H-1,3-benzodiazol-3-ium;

52. 2-[({3-amino-5H-pyrrolo[2,3-b]pyrazin-2-yl}formamido)methyl]-5-[4-({bis[(2S,3R,4R,5R)-2,3,4,5,6-pentahydroxyhexyl]amino}methyl)piperidine-1-carbonyl]-1,3-diethyl-1H-1,3-benzodiazol-3-ium;

53. 2-[({3-amino-5H-pyrrolo[2,3-b]pyrazin-2-yl}formamido)methyl]-6-[(3R)-3-{bis[(2S,3R,4R,5R)-2,3,4,5,6-pentahydroxyhexyl]amino}pyrrolidine-1-carbonyl]-1,3-diethyl-1H-1,3-benzodiazol-3-ium;

54. 2-[({3-amino-5H-pyrrolo[2,3-b]pyrazin-2-yl}formamido)methyl]-6-[(3S)-3-{bis[(2S,3R,4R,5R)-2,3,4,5,6-pentahydroxyhexyl]amino}pyrrolidine-1-carbonyl]-1,3-diethyl-1H-1,3-benzodiazol-3-ium;

55. 2-[({3-amino-5H-pyrrolo[2,3-b]pyrazin-2-yl}formamido)methyl]-1,3-diethyl-6-{[(1r,4r)-4-{bis[(2S,3R,4R,5R)-2,3,4,5,6-pentahydroxyhexyl]amino}cyclohexyl]carbamoyl}-1H-1,3-benzodiazol-3-ium;

56. 2-[({3-amino-5H-pyrrolo[2,3-b]pyrazin-2-yl}formamido)methyl]-1,3-diethyl-6-{[(1s,4s)-4-{bis[(2S,3R,4R,5R)-2,3,4,5,6-pentahydroxyhexyl]amino}cyclohexyl]carbamoyl}-1H-1,3-benzodiazol-3-ium;

57. 2-[({3-amino-5H-pyrrolo[2,3-b]pyrazin-2-yl}formamido)methyl]-6-[(3-{bis[(2S,3R,4R,5R)-2,3,4,5,6-pentahydroxyhexyl]amino}propyl)(methyl)carbamoyl]-1,3-diethyl-1H-1,3-benzodiazol-3-ium;

58. 2-[({3-amino-5H-pyrrolo[2,3-b]pyrazin-2-yl}formamido)methyl]-6-[(2-{bis[(2S,3R,4R,5R)-2,3,4,5,6-pentahydroxyhexyl]amino}ethyl)carbamoyl]-1,3-diethyl-1H-1,3-benzodiazol-3-ium;

59. 2-[({3-amino-5H-pyrrolo[2,3-b]pyrazin-2-yl}formamido)methyl]-1,3-diethyl-5-{[(14S,15R,16R,17R)-14,15,16,17,18-pentahydroxy-12-[(2S,3R,4R,5R)-2,3,4,5,6-pentahydroxyhexyl]-3,6,9-trioxa-12-azaoctadecan-1-yl]carbamoyl}-1H-1,3-benzodiazol-3-ium;

60. 2-[({3-amino-5H-pyrrolo[2,3-b]pyrazin-2-yl}formamido)methyl]-6-({2-[4'-(2-{bis[(2S,3R,4R,5R)-2,3,4,5,6-pentahydroxyhexyl]amino}ethyl)-[1,1'-biphenyl]-4-yl]ethyl}carbamoyl)-1,3-diethyl-1H-1,3-benzodiazol-3-ium;

61. 2-[({3-amino-5H-pyrrolo[2,3-b]pyrazin-2-yl}formamido) methyl]-6-{[(3S)-3-[(3-{bis[(2S,3R,4R,5R)-2,3,4,5,6-pentahydroxyhexyl]amino}propyl)amino]-3-carbamoylpropyl]carbamoyl}-1,3-diethyl-1H-1,3-benzodiazol-3-ium;

62. 2-[({3-amino-5H-pyrrolo[2,3-b]pyrazin-2-yl}formamido)methyl]-6-{[4-(4-{3-[(3-{bis[(2S,3R,4R,5R)-2,3,4,5,6-pentahydroxyhexyl]amino}propyl)amino]-3-carbamoylpropyl}phenyl)butyl]carbamoyl}-1,3-diethyl-1H-1,3-benzodiazol-3-ium;

63. 2-[({3-amino-7-chloro-5H-pyrrolo[2,3-b]pyrazin-2-yl}formamido)methyl]-6-carboxy -1,3-diethyl-1H-1,3-benzodiazol-3-ium;

64. 2-[({3-amino-7-bromo-5H-pyrrolo[2,3-b]pyrazin-2-yl}formamido)methyl]-6carboxy-1,3-diethyl-1H-1,3-benzodiazol-3-ium;

65. 2-[({3-amino-7-chloro-5H-pyrrolo[2,3-b]pyrazin-2-yl}formamido)methyl]-6-(4-{bis[(2S,3R,4R,5R)-2,3,4,5,6-pentahydroxyhexyl]amino}piperidine-1-carbonyl) -1,3-diethyl-1H-1,3-benzodiazol-3-ium;

66. 2-[({3-amino-7-bromo-5H-pyrrolo[2,3-b]pyrazin-2-yl}formamido)methyl]-6-(4-{bis[(2S,3R,4R,5R)-2,3,4,5,6-pentahydroxyhexyl]amino}piperidine-1-carbonyl) -1,3-diethyl-1H-1,3-benzodiazol-3-ium;

67. 2-[({3-amino-7-cyano-5H-pyrrolo[2,3-b]pyrazin-2-yl}formamido)methyl]-1,3-diethyl-6-methoxy-1H-1,3-benzodiazol-3-ium;

and an anion X⁻ as defined for general formula (I).

Compounds of general formula (I) may be prepared by reacting a compound of general formula (II) or a salt or activated derivative thereof:

(II)

wherein R⁴ and R⁵ are as defined for general formula (I); with a salt of general formula (III):

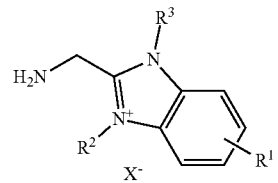

(III)

wherein R¹, R² and R³ are as defined for general formula (I); and X⁻ is as defined for general formula (I) and which may be the same or different from the X⁻ of the product of general formula (I).

Suitably the reaction is carried out under basic conditions in the presence of a coupling reagent, which may generate an activated acid as an intermediate. The basic conditions may be supplied by a non-nucleophilic base such as N,N-diisopropylethylamine (DIPEA) or trimethylamine. Suitable coupling reagents include O-(7-Azabenzotriazol-1-yl) -N,N,N',N'-tetramethyluronium hexafluorophosphate (HATU), 0-(Benzotriazol-1-yl) -N,N,N',N'-tetramethyluronium tetrafluoroborate (TBTU), N,N,N',N'-tetramethyl-O-(1H -benzotriazol-1-yl)uronium hexafluorophosphate (HBTU) or a combination of 1-ethyl-3-(3-dimethylaminopropyl)carbodiimide (EDC) with 1-hydroxy-7-azabenzotriazole (HOAt) or hydroxybenzotriazole (HOBt).

In some cases, carbonyldiimidazole (CDI) may be used as a coupling agent.

In other cases, imidazole or a salt thereof (e.g. imidazole hydrochloride) may be used.

The reaction may be conducted at a temperature of about 10 to 50° C., more usually at 15 to 30° C., or room temperature and in an organic solvent such as N,N-dimethylformamide.

When a CDI coupling agent is used, a compound of general formula (I) may be prepared by reacting a compound of general formula (III) as defined above with an activated compound of general formula (IV):

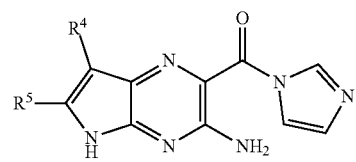

(IV)

wherein R⁴ and R⁵ are as defined for general formula (I).

As discussed above, the reaction is suitably conducted at a temperature of about 10 to 50° C., more usually at 15 to 30° C., or room temperature and in an organic solvent such as N,N-dimethylformamide.

The activated compounds of general formula (IV) are prepared by reacting a compound of general formula (II) as defined above or a salt thereof with carbonyl diimidazole (CDI). Suitably the reaction takes place in an organic solvent such as N,N-dimethylformamide and at a temperature of from about 10 to 30° C., more usually 15 to 25° C. or room temperature.

In cases where the target compound of general formula (I) has an $R^1$, $R^2$, $R^3$, $R^4$ and/or $R^5$ substituent which is sensitive to the conditions used when the compound of general formula (III) is reacted with a compound of general formula (II) or an activated derivative thereof, for example a compound of general formula (IV), the compounds of general formulae (III) may comprise a protected $R^1$, $R^2$ and/or $R^3$ substituent and/or the compounds of general formulae (II) and (IV) may comprise a protected $R^4$ and/or $R^5$ substituent. This is illustrated in Example 46, where a compound of general formula (IV) is reacted with a protected derivative of a compound of general formula (III) in which $R^1$ is a group $LR^{10}$, where L is a group —$Q^1$-$Z^1$—, where $Z^1$ is —$CH_2$[CH(OH)]$_5$— and $R^{10}$ is H (Intermediate 98) to give a protected derivative of general formula (I) (Intermediate 99). In Intermediates 98 and 99, two of the OH groups are protected by forming a substituted 1,3-dioxanyl group. This protecting group may be removed by treatment with aqueous acid, e.g. aqueous hydrochloric acid (see Example 46). Similarly, Intermediates 89 and 93, which are compounds of general formula (III) are prepared by deprotecting Intermediates 88 and 92 respectively.

Compounds of general formula (II) may be prepared by hydrolysis of a compound of general formula (V):

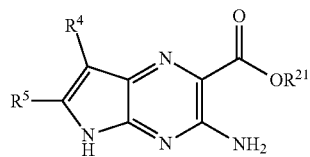

(V)

wherein $R^4$ and $R^5$ are as defined for general formula (I) and $R^{21}$ is $C_{1-6}$ alkyl or benzyl.

Suitably, the hydrolysis is base hydrolysis such that the compound of general formula (V) is reacted with a base, suitably a strong aqueous base such as lithium hydroxide, potassium hydroxide or sodium hydroxide.

Compounds of general formula (V) wherein $R^4$ and $R^5$ are H and $R^{21}$ is $C_{1-6}$ alkyl or benzyl. may be prepared by cyclising a compound of general formula (XX):

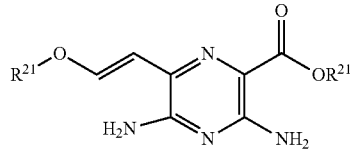

(XX)

wherein each $R^{21}$ is independently $C_{1-6}$ alkyl or benzyl.

Suitably, the cyclisation is acid mediated, suitably the acid is acetic acid at elevated temperature such as 80° C.

Compounds of general formula (XX) may be prepared by palladium mediated coupling of a vinyl boronate ester with a compound of formula (XXI):

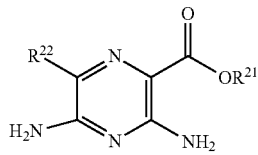

(XXI)

wherein $R^{21}$ is as defined above and $R^{22}$ is halo, particularly Cl, Br or I.

Compounds of general formula (XXI) are well known and are commercially available or may be prepared by methods familiar to those of skill in the art.

Some compounds of general formula (V) may be converted to other compounds of general formula (V). For example, compounds of general formula (V) in which $R^4$ is halo may be prepared from compounds of general formula (V) in which $R^4$ is H by reaction with a halogenating agent such as N-chlorosuccinimide, N-bromosuccinimide or N-iodosuccinimide. Suitable reaction conditions are described in the preparation of Intermediates 10, 14 and 161. In some cases, for example as shown in the synthesis of Intermediate 161, the nitrogen at the 5-position of the pyrrolopyrazine ring may be protected with a trimethylsilylethoxymethyl protecting group.

Compounds of general formula (V) in which $R^4$ is halo may be converted into compounds of general formula (V) in which $R^4$ is alkyl or cyano. Compounds in which $R^4$ is alkyl may be prepared from compounds in which $R^4$ is halo by reaction with an organometallic reagent, for example dialkyl zinc, as described for the preparation of Intermediate 11 below.

Compounds of general formula (V) in which $R^4$ is cyano may be prepared from compounds of general formula (V) in which $R^4$ is halo by reaction with potassium ferrocyanide, as described for the preparation of Intermediate 166. For this reaction, the nitrogen at the 5-position of the pyrrolopyrazine ring should be protected, for example with a trimethylsilylethoxymethyl protecting group.

Compounds of general formula (V) in which $R^4$ is $C_{1-6}$ alkyl and $R^5$ is H may be prepared by transition metal mediated coupling of the appropriate dialkyl zinc to a compound of general formula (V) in which $R^4$ is halo. Suitably, the transition metal is a Palladium (0) complex.

Compounds of general formula (V) in which $R^4$ is H and $R^5$ is methyl may be prepared by transition metal mediated cyclisation of a compound of general formula (XXII).

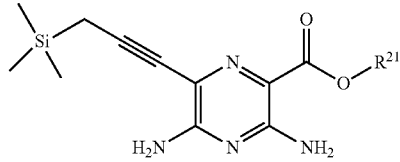

(XXII)

wherein $R^{21}$ is as defined above.

Suitably, the transition metal is a Palladium (0) complex. Suitably the cyclisation is carried out in the presence of copper (I) iodide and a base.

Compounds of general formula (XXII) may be prepared by transition metal mediated coupling of a compound of general formula (XXI) with a propargyl silane.

Compounds of general formula (III) may be prepared from compounds of general formula (VII)

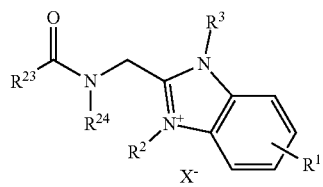

(VII)

wherein $R^1$, $R^2$ and $R^3$ are as defined for general formula (I) and $X^-$ is as defined for general formula (I) and which may be the same or different from the $X^-$ of the product of general formula (III);

$R^{23}$ is $O(C_{1-6})$ alkyl optionally substituted with aryl; or aryl optionally substituted with C(O)OH; and $R^{24}$ is H; or $R^{23}$ and $R^{24}$ together with the carbon and nitrogen atoms to which they are attached form a heterocyclic ring, optionally fused to an aryl or heteroaryl ring and optionally containing a further =O substituent.

In some cases, the removal of the protecting group $R^{23}$ may be achieved by reaction with an acid. This is appropriate for alkyloxycarbonyl protecting groups, for example when $R^{23}$ is $^t$butyloxy. Reaction with an acid may result in a change in the anion $X^-$. Furthermore, following reaction with an acid, the compound of formula (III) will usually be present in the form of its acid addition salt.

Other protecting groups, for example Fmoc (i.e. when $R^{23}$ is fluorenylmethyloxy), can be removed by treatment with a base, for example piperidine or morpholine.

In some suitable compounds of general formula (VII), $R^{23}$ is benzyloxy or fluoren-9-ylmethyloxy and $R^1$ comprises another protecting group, for example $^t$butyloxycarbonyl (Boc), such that the two protecting groups are stable under different conditions.

Examples of cyclic $N(R^{24})C(O)R^{23}$ groups include 1,3-dioxo-2,3-dihydro-1H-isoindol-2-yl. Examples of individual $R^{23}$ groups include methoxy, ethoxy, $^n$propoxy, $^i$propoxy, $^n$butyloxy, $^s$butyloxy, $^t$butyloxy, benzyloxy, fluorenylmethyloxy and phenyl optionally substituted with C(O)OH.

When $R^{23}$ and $R^{24}$ together with the carbon and nitrogen atoms to which they are attached form a heterocyclic ring of this type, the compound of general formula (IIIA) may be synthesised by reacting the compound of general formula (VII) with hydrazine hydrate. Suitably, this reaction is carried out in an alcoholic solvent such as methanol and at elevated temperature, for example about 60-90° C., typically about 75° C.

Some compounds of general formula (VII) are known. For example, Intermediate 58 may be synthesised according to the procedure described in US 2015/0018313)

Other compounds of general formula (VII) may be prepared from compounds of general formula (VIII):

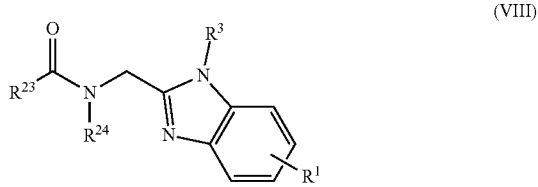

(VIII)

wherein $R^1$ and $R^3$ are as defined for general formula (I) and $R^{23}$ and $R^{24}$ are as defined for general formula (VII);

by reaction with a compound of general formula (IX):

wherein $R^2$ is as defined for general formula (I) and $X^1$ is a leaving group such as halo; or with a compound of general formula (IXA):

wherein $X^1$ is as defined above for general formula (IX) and $R^{2a}$ is a protected $R^2$ group. For example, when the desired $R^2$ group contains one or more OH moieties, these may be protected using standard protecting groups, for example silyl protecting groups such as trimethylsilyl (TMS), $^t$butyldimethylsilyl (TBDMS) etc.

When the route via the compound of general formula (IXA) is used, the compound of general formula (VIII) is suitably one in which $R^{23}$ is $-O(C_{1-6})$ alkyl optionally substituted with aryl, or $R^{23}$ is aryl optionally substituted with C(O)OH; and $R^{24}$ is H; because, in this case, the silyl and carbonyloxy protecting groups can be removed using an acid such as hydrogen chloride solution.

In some cases, when a compound of general formula (IX) is reacted with a compound of general formula (VIII) in which $N(R^{24})C(O)R^{23}$ is a cyclic group such as 1,3-dioxo-2,3-dihydro-1H-isoindol-2-yl, the reaction may be accompanied by ring opening. Thus a compound of general formula (VIII) in which $N(R^{24})C(O)R^{23}$ is 1,3-dioxo-2,3-dihydro-1H-isoindol-2-yl may give rise to a product of general formula (VII) in which $N(R^{24})C(O)R^{23}$ is:

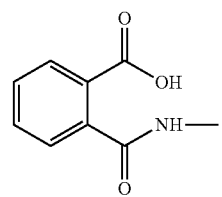

Some compounds of general formula (VIII) are known. For example, Intermediate 23 (see examples below) may be synthesised by the route set out in US 2015/0018314 A1.

Some compounds of general formulae (VII) and (VIII) may be synthesised from other compounds of general formulae (VII) and (VIII). For example, a compound of general formula (VIII) in which $R^1$ is $C(O)OR^5$, where $R^5$ is other than H may be converted to a compound of general formula (VIII) in which $R^1$ is C(O)OH by hydrolysis, for example with a base, suitably an alkali metal hydroxide such as lithium hydroxide. The compound in which $R^1$ is C(O)OH may then be converted to a compound in which $R^1$ is $C(O)OR^{12}$, where $R^{12}$ is other than H by reaction with a compound of general formula (X):

wherein $R^{12}$ is as defined for general formula (I) except that it is not H and $R^{25}$ is $C_{1-4}$ alkyl.

This type of conversion is exemplified below in the synthesis of Intermediate 81.

Compounds of general formula (VIII) can also be converted to other compounds of general formula (VIII) with a different $R^{23}$ and/or $R^{24}$ groups. For example, when $R^{23}$ is $O(C_{1-6})$ alkyl optionally substituted with aryl, or $R^{23}$ is aryl optionally substituted with C(O)OH; and $R^{24}$ is H, the compound of general formula (VIII) may be hydrolysed, for example by reaction with HCl in a solvent such as dioxane, to give a compound of general formula (XI):

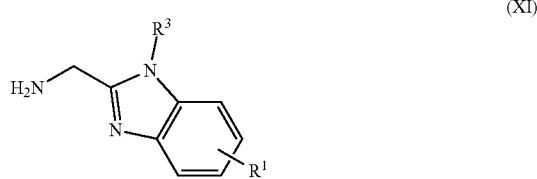

wherein $R^1$ and $R^3$ are as defined in general formula (I). This is exemplified by the synthesis of Intermediate 79 from Intermediate 78.

The compound of general formula (XI) may be re-protected to obtain a new compound of general formula (VIII), for example by reaction with a compound of general formula (XII):

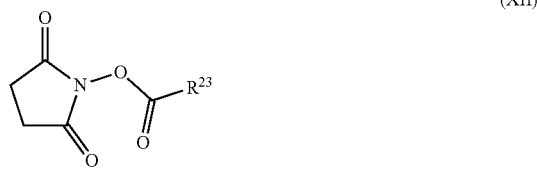

wherein $R^{23}$ is as defined above for general formula (VII). The reaction may be conducted in the presence of a base such as trimethylamine in a polar organic solvent, for example dichloromethane and at a temperature of from 10 to 30° C., more usually 15 to 25° C., typically at room temperature. An example of this type of process is the synthesis of Intermediate 80 from Intermediate 79

Compounds of general formula (VII) and (VIII) may also be synthesised from other compounds of general formula (VII) and (VIII) using the methods described for the preparation of Intermediates 66, 67, 70, 71, 74, 81, 86, 87, 90, 91, 96, 97, 157 and 159 below.

Thus, for example a compound of general formula (VII) or (VIII) in which $R^1$ is halo, particularly bromo, may be reacted with an alkyne to give a compound of general formula (VII) in which $R^1$ is —$L^1R^{10}$, where $L^1$ comprises an alkynylene group. The reaction may be catalysed with a copper (I) salt, for example copper (I) iodide. This is illustrated in the synthesis of Intermediate 66.

A compound of general formula (VII) or (VIII) in which $R^1$ is halo, particularly bromo, may also be reacted with a compound of general formula (XX):

$$R^{1a}\text{-}X^2 \quad (XX)$$

where $R^{1a}$ is as defined above for $R^1$ except that it is not halo and $X^2$ is an organoborane group, for example 4,4,5,5-tetramethyl-1,3,2-dioxaborolan-2-yl. A reaction of this type is used in the preparation of Intermediates 70 and 74.

Compounds of general formulae (VII) and (VIII) in which $R^1$ is —$L^1R^{10}$, where $L^1$ comprises an alkenylene, alkynylene or partially saturated carbocyclyl or heterocyclyl moiety may be reduced, suitably by catalytic hydrogenation, to give compounds of formula (VII) in which $L^1$ comprises an alkylene or saturated carbocyclyl or heterocyclyl moiety. Examples of this are shown in the synthesis of Intermediates 67 and 71 below.

Compounds of general formulae (VII) and (VIII) in which $R^1$ is C(O)OH may be esterified to give compounds of general formulae (VII) and (VIII) in which $R^1$ is $C(O)OR^{12}$, where $R^{12}$ is as defined above except that it is not H. An example of this is the preparation of Intermediate 81, in which the carboxylic acid derivative Intermediate 80 is reacted with 1,1-di-tert-butoxy-N,N-dimethylmethanamine.

Compounds of general formulae (VII) and (VIII) in which $R^1$ or $R^3$ (for compounds of general formula (VIII)) comprises a —$C(O)OR^{12}$ or —$C(O)OR^7$ group in which $R^{12}$ or $R^7$ is other than H; or a —$C(O)N(R^7)R^8$ group can be converted to compounds in which $R^1$ or $R^3$ comprises a —C(O)OH group by hydrolysis. In some cases, base hydrolysis may be used, for example using a base such as lithium hydroxide, sodium hydroxide or potassium hydroxide. Alternatively, the hydrolysis may be acid hydrolysis using an acid such as hydrochloric acid. This is particularly suitable when the $R^{12}$ or $R^7$ group is an alkyl group such as tert-butyl.

Compounds of general formulae (VII) and (VIII) in which $R^1$ is C(O)OH may be converted to compounds in which $R^1$ is —$C(O)NR^{12}R^{13}$, wherein $R^{12}$ and $R^{13}$ are as defined above, or in which $R^1$ is —$L^1R^{10}$, wherein $L^1$ is —C(O)N($R^7$)$Z^1$—, —C(O)N($R^7$)$Q^1$—, —C(O)N($R^7$)$Z^1Q^1$—, —C(O)N($R^7$)$Z^1Q^1Z^2$—, —C(O)N($R^7Q^1Z^1$—, —C(O)N($R^7$)$Q^1Q^2$—, —C(O)N($R^7$)$Q^1Q^2Z^1$—, —C(O)N($R^7$)$Z^1Q^1Q^2Z^2$—, —C(O)N($R^7$)$Z^1O(CH_2CH_2O)_nZ^2$—, —C(O)N($R^7Z^1O(CH_2O)_nZ^2$—, —C(O)N($R^7$)$Z^1Q^1Z^2N(R^8)Z^3$—, —C(O)N($R^7$)$Z^1N(R^8)Z^2$—, —C(O)N($R^7$)$Q^1Z^1N(R^8)Z^2$—, —C(O)N($R^7$)$Z^1Q^1OQ^2OQ^3$— or —C(O)N($R^7$)$Z^1Q^1OQ^2OQ^3Z^2$—;

especially

—C(O)N($R^7$)$Z^1$—, —C(O)N($R^7$)$Q^1$—, —C(O)N($R^7$)$Z^1Q^1$—, —C(O)N($R^7$)$Z^1Q^1Z^2$—, —C(O)N($R^7$)$Q^1Z^1$—, —C(O)N($R^7$)$Q^1Q^2$— or —C(O)N($R^7$)$Q^1Q^2Z^1$—;

by reaction with an appropriate amine or ammonium salt.

Compounds of general formulae (VII) and (VIII) in which $R^1$ is $L^1R^{10}$ where $R^{10}$ —N($R^7$)—$C(O)OR^8$ can be converted to compounds of general formulae (VII) and (VIII) in which $R^1$ is $L^1R^{10}$ where $R^{10}$ —$NH_2$ by hydrolysis, for example acid hydrolysis using hydrochloric acid in a solvent such as dioxane. An example of this is the synthesis of Intermediate 86.

These compounds can in turn be converted to compounds of general formulae (VII) and (VIII) in which $R^{10}$ is N(H)$R^7$ or N($R^7$)$R^8$ where $R^7$ is $CH_2$-$R^{7a}$ and $R^8$ is $CH_2$-$R^{8a}$ and each $R^{7a}$ and $R^{8a}$ is independently selected from H and $C_{1-11}$ alkyl optionally substituted with one or more halo or OH groups or protected OH groups. The conversion can be achieved by reductive amination using a reducing agent such as a hydride, for example sodium cyanoborohydride, with an aldehyde or acetal as shown below:

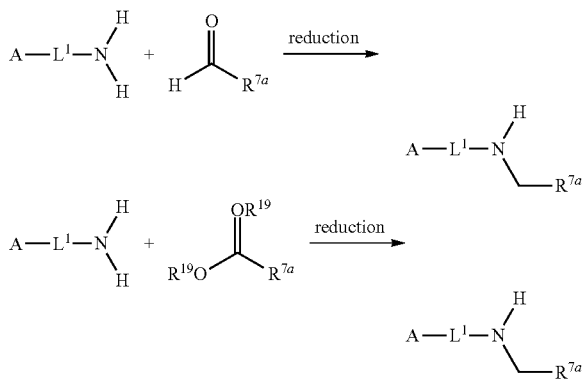

where $L^1$ is as defined for general formula (I);
$R^7$ is —$CH_2R^{7a}$, where $R^{7a}$ is H or $C_{1-11}$ alkyl optionally substituted with one or more halo or OH groups; and
$R^{19}$ is $C_{1-12}$ alkyl; and
A is a fragment of a compound of general formula (VII) or (VIII) not including $R^1$ as follows:

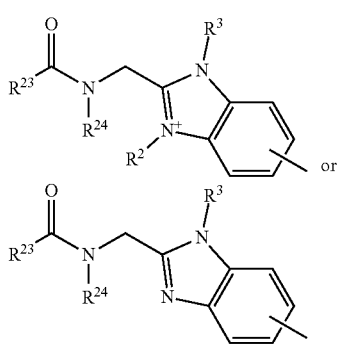

In other cases, a cyclic hemiacetal can be used in place of the aldehyde or acetal. The scheme below shows an example where a 6-membered hemiacetal is used to give a compound in which $R^1$ is $L^1$-$NHR^7$ where $R^7$ is $(CH_2)_4CH_2OH$:

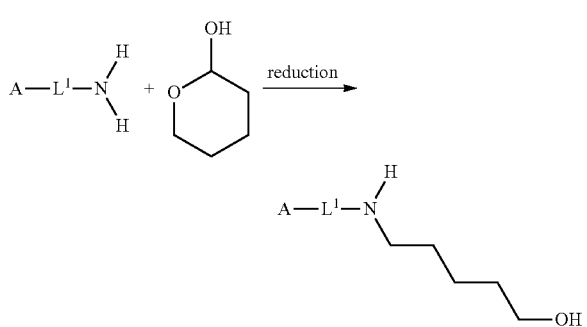

wherein A and $L^1$ are as defined above.
If a large excess of the aldehyde, acetal or cyclic hemiacetal is used, both of the amine hydrogen atoms will be replaced. In some cases, it may be possible to react successively with different aldehydes, acetals or hemicacetals to yield compounds in which $R^7$ and $R^8$ are different.

More suitably in these product compounds of general formulae (VII) or (VIII) both $R^{7a}$ and $R^{8a}$ are $C_{1-11}$ alkyl optionally substituted with one or more halo or OH or protected OH groups; and most suitably each $R^7$ and $R^8$ is $CH_2[CH(OH)]_4CH_2OH$, wherein OH groups are optionally protected, for example as acetals, such as benzylidene acetals.

Examples of this type of reaction include the conversion of Intermediate 86 to Intermediate 87 and the conversion of Intermediate 90 to Intermediate 91.

Similarly, compounds of general formulae (VII) and (VIII) in which $R^1$ is $L^1R^{10}$ where:

Similarly, compounds of general formulae (VII) and (VIII) in which $L^1$ comprises a moiety $Q^1$, $Q^2$ or $Q^3$ linked to $R^{10}$ via a ring nitrogen atom and in which $R^{10}$ is C(O) $OR^7$;

may be converted to compounds in which $R^{10}$ is H by hydrolysis, for example acid hydrolysis using hydrochloric acid in a solvent such as dioxane.

An example of a reaction of this type is the preparation of Intermediate 96 from Intermediate 95.

Compounds of general formulae (VII) and (VIII) in which $L^1$ comprises a moiety $Q^1$, $Q^2$ or $Q^3$ linked to $R^{10}$ via a ring nitrogen atom and in which $R^{10}$ is H can be converted to compounds of general formula (I) in which the $Q^1$, $Q^2$ or $Q^3$ moiety is linked is linked to a $Z^1$, $Z^2$ or $Z^3$ moiety, wherein $Z^1$, $Z^2$ or $Z^3$ is:

$CH_2$-$C_{1-11}$ alkylene, $CH_2$-$C_{2-11}$ alkenylene, $CH_2$-$C_{2-11}$ alkynylene any of which is optionally substituted by one or more halo, OH, C(O)$NR^{15}R^{16}$, C(O)$OR^{15}$ or $NR^{15}R^{16}$; and each $R^{15}$ and $R^{16}$ is independently H or $C_{1-6}$ alkyl; and $R^{10}$ is H;

by reductive amination with an aldehyde, acetal or cyclic hemiacetal equivalent compound using a method similar to that described above for the conversion of compounds of general formulae (VII) and (VIII) in which $R^1$ is $L^1NH_2$ to compounds of general formulae (VII) and (VIII) in which $R^1$ is $L^1N(R^7)R^8$ where $R^7$ is $CH_2$-$R^{7a}$ and $R^8$ is $CH_2$-$R^{8a}$ and each each $R^{7a}$ and $R^{8a}$ is independently selected from H and $C_{1-11}$ alkyl optionally substituted with one or more halo or OH groups.

More suitably in these product compounds of general formulae (VII) or (VIII) $Z^1$, $Z^2$ or $Z^3$ is $CH_2$-$C_{1-11}$ alkyl optionally substituted with one or more halo or OH groups; and most suitably is $CH_2[CH(OH)]_4CH_2OH$, wherein OH groups are optionally protected, for example as acetals, such as benzylidene acetals.

An example of this process is shown in the preparation of Intermediate 97.

Compounds of general formulae (VII) and (VIII) in which $R^1$ is $L^1R^{10}$ and $R^{10}$ is $NH_2$ can be converted into compounds in which $R^{10}$ is —NHC(=$NR^9$)N($R^8$)$_2$ by reaction with a carboximidamide or a salt thereof, for example 1,2,4-triazole carboximidamide hydrochloride.

Compounds of general formula (VIII) may also be prepared from compounds of general formula (XIII):

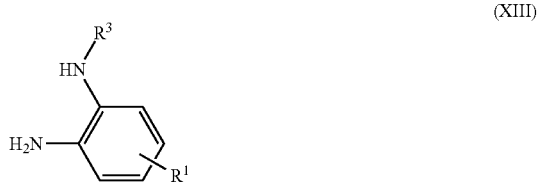

wherein $R^1$ and $R^3$ are as defined for general formula (I); by reaction with a compound of general formula (XIV):

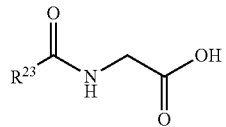
(XIV)

wherein $R^{23}$ is as defined above for general formula (VII).

The reaction suitably takes place in the presence of a base, typically a non-nucleophilic base, for example an amine such as N,N-diisopropylethylamine (DIPEA) or triethylamine and a peptide coupling agent, for example HATU, TBTU, HBTU or a combination of EDC with HOAt or HOBt. The reaction is suitably conducted at a temperature of about 10 to 30° C., usually 15 to 25° C., for example at room temperature. Suitable reaction solvents include organic solvents such as N,N-dimethylformamide (DMF).

Compounds of general formulae (XIII) and (XIV) are known and are readily available or may be prepared by methods known to those of skill in the art.

Alternatively, compounds of general formula (XIII) may be prepared from compounds of general formula (XV):

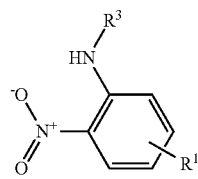
(XV)

wherein $R^1$ and $R^3$ are as defined for general formula (I); by catalytic hydrogenation, suitably using a palladium catalyst.

The hydrogenation is suitably carried out at 1 atmosphere pressure and at a temperature of about 10 to 30° C., usually 15 to 25° C., for example at room temperature.

The product of general formula (XIII) can be reacted directly with a compound of general formula (XIV) as described above without further isolation or purification steps.

Compounds of general formula (XV) may be prepared from compounds of general formula (XVI):

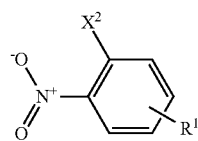
(XVI)

wherein $R^1$ is as defined for general formula (I) and $X^2$ is a leaving group, particularly a halo group such as chloro or fluoro;
by reaction with a compound of general formula (XVII):

$R^3$-$NH_2$ (XVII)

wherein $R^3$ is as defined for general formula (I).

The reaction is suitably carried out under pressure, at a temperature of about 30-70° C., more usually about 40-60° C., typically about 50° C. and in an organic solvent such as tetrahydrofuran.

Compounds of general formulae (XVI) and (XVII) are known and are readily available or may be prepared by methods known to those of skill in the art.

An alternative method for the preparation of a compound of general formula (I) is by reaction of a compound of general formula (XVIII):

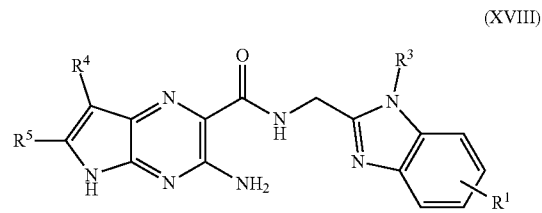
(XVIII)

wherein $R^1$, $R^3$, $R^4$ and $R^5$ are as defined for general formula (I);
with a compound of general formula (IX) or (IXA) as defined above under conditions similar to those described above for the reaction of the compound of general formula (VIII) with the compound of general formula (IX) or (IXA).

Compounds of general formula (I) may also be synthesised from other compounds of general formula (I), for example using the methods described in Examples 10, 27-33, 35-42 and 47-62 below. In general, methods of converting compounds of general formulae (VI) and (VIII) to other compounds of general formulae (VI) and (VIII) may also be applied to compound of general formula (I) and vice versa.

Thus, for example, compounds of general formula (I) in which $R^3$ comprises a —C(O)OR$^7$ group in which $R^7$ is other than H or a —C(O)N(R$^7$)R$^8$ group can be converted to compounds in which $R^3$ comprises a —C(O)OH or C(O)O$^-$ group by hydrolysis. In some cases the hydrolysis may be base hydrolysis, for example using a base such as lithium hydroxide, sodium hydroxide or potassium hydroxide as shown in Example 10. Alternatively, acid hydrolysis may be employed, for example using hydrochloric acid.

Compounds of general formula (I) in which $R^1$ is $L^1R^{10}$ where $R^{10}$ is —N(R$^7$)—C(O)OR$^8$ can be converted to compounds of general formula (I) in which $R^1$ is $L^1R^{10}$ where $R^{10}$ is —NHR$^7$ by hydrolysis, for example acid hydrolysis using hydrochloric acid in a solvent such as dioxane. Suitably R$^7$ is H such that in the product compound of general formula (I) $R^{10}$ is NH$_2$. This is illustrated in Examples 27-29, 39, 41 and 42.

Compounds of general formula (I) in which $R^1$ is $LR^{10}$, wherein $L^1$ comprises a moiety $Q^1$, $Q^2$ or $Q^3$ which is linked to $R^{10}$ via a ring nitrogen atom and in which $R^{10}$ is C(O)OR$^7$ can be converted to compounds of formula (I) in which $R^{10}$ is H by a similar method, i.e. by hydrolysis, for example acid hydrolysis using hydrochloric acid in a solvent such as dioxane. This is illustrated in Examples 30, 31 and 40.

The compounds of formula (I) in which $R^1$ is $LR^{10}$, and $R^{10}$ is NH$_2$ can in turn be converted to compounds of general formula (I) in which $R^{10}$ is N(R$^7$)R$^8$ where $R^7$ is CH$_2$-R$^{7a}$ and $R^8$ is CH$_2$-R$^{8a}$ and one of R$^{7a}$ and R$^{8a}$ is $C_{1-11}$ alkyl optionally substituted with one or more halo or OH groups; and the other of R$^{7a}$ and R$^{8a}$ is H or $C_{1-11}$ alkyl optionally substituted with one or more halo or OH groups. Similarly, the compounds of general formula (I) in which $R^1$ is $LR^{10}$, and $L^1$ comprises a moiety $Q^1$, $Q^2$ or $Q^3$ linked to $R^{10}$ via a ring nitrogen atom and in which $R^{10}$ is H can be converted to compounds of general formula (I) in which $Q^1$, $Q^2$ or $Q^3$ is linked to a $Z^1$, $Z^2$ or $Z^3$ moiety via a ring nitrogen atom, wherein $Z^1$, $Z^2$ or $Z^3$ is $CH_2$-$C_{1-11}$ alkyl optionally substituted with one or more halo or OH groups; and $R^{10}$ is H. These conversions can be achieved by reductive amination with an aldehyde, acetal or cyclic hemiacetal equivalent compound using a similar method to that described above for the compounds of general formulae (VII) and (VIII). Examples of this type of reaction include the methods of:

Example 45, where the compound of Example 29, in which $L^1$ is a moiety —$Z^1$— and $R^{10}$ is $NH_2$ is reacted with 4,6-O-benzylidene-D-glucopyranose to give a product where $R^{10}$ is —$N\{CH_2[CH(OH)]_4$—$CH_2OH\}_2$; and Example 47, where the compound of Example 31, where $L^1$ is a moiety —$Q^1Q^2$— in which $Q^2$ is linked to $R^{10}$ via a ring nitrogen atom and $R^{10}$ is H is reacted with 4,6-O-benzylidene-D-glucopyranose to give a product in which $L^1$ is $Q^1Q^2Z^1$, where $Z^1$ is $CH_2[CH(OH)]_4CH_2O$—; and $R^{10}$ is H.

Compounds in which $R^1$ is $L^1R^{10}$ and $R^{10}$ is $NH_2$ can be converted into compounds in which $R^{10}$ is —$NHC(=NR^9)N(R^8)_2$ by reaction with a carboximidamide or a salt thereof, for example 1,2,4-triazole carboximidamide hydrochloride. This process is shown in Examples 32 and 33.

Compounds in which $R^1$ is C(O)OH may be converted to compounds in which $R^1$ is —$C(O)NR^{12}R^{13}$, wherein $R^{12}$ and $R^{13}$ are as defined above, or in which $R^1$ is —$L^1R^{10}$, wherein $L^1$ is —$C(O)N(R^7)Z^1$—, —$C(O)N(R^7)Q^1$—, —$C(O)N(R^7)Z^1Q^1$—, —$C(O)N(R^7)Z^1Q^1Z^2$—, —$C(O)N(R^7)Q^1Z^1$—, —$C(O)N(R^7)Q^1Q^2$—, —$C(O)N(R^7)Q^1Q^2Z^1$—, —$C(O)N(R^7)Z^1Q^1Q^2Z^2$—, —$C(O)N(R^7)Z^1O(CH_2CH_2O)_nZ^2$— —$C(O)N(R^7)Z^1O(CH_2O)_nZ^2$—, —$C(O)N(R^7)Z^1Q^1Z^2N(R^8)Z^3$—, —$C(O)N(R^7)Z^1N(R^8)Z^2$—, —$C(O)N(R^7)Q^1Z^1N(R^8)Z^2$—, —$C(O)N(R^7)Z^1Q^1OQ^2OQ^3$—, —$C(O)N(R^7)Z^1Q^1OQ^2OQ^3Z^2$—; or $L^1$ is —$C(O)Q^1$—, —$C(O)Q^1Z^1$—, —$C(O)Q^1Q^2$—, —$C(O)Q^1Q^2Z^1$—, —$C(O)Q^1N(R^7)C(O)Z^1$—, —$C(O)Q^1N(R^7)C(O)Z^1Q^2$—, —$C(O)Q^1N(R^7)C(O)Z^1Q^2Q^3$— or —$C(O)Q^1NR(R^7)C(O)Z^1Q^2Z^2$—, wherein $Q^1$ is a heterocyclyl ring linked to the —C(O) moiety via a ring nitrogen atom;

by reaction with an appropriate amine or ammonium salt.

Suitably the reaction is carried out under basic conditions in the presence of a coupling reagent. The basic conditions may be supplied by a non-nucleophilic base such as N,N-diisopropylethylamine (DIPEA) or trimethylamine. Suitable coupling reagents include O-(7-Azabenzotriazol-1-yl)-N,N,N',N'-tetramethyluronium hexafluorophosphate (HATU), O-(Benzotriazol-1-yl)-N,N,N',N'-tetramethyluronium tetrafluoroborate (TBTU), N,N,N',N'-tetramethyl-O-(1H-benzotriazol-1-yl)uronium hexafluorophosphate (HBTU) or a combination of 1-ethyl-3-(3-dimethylaminopropyl)carbodiimide (EDC) with 1-hydroxy-7-azabenzotriazole (HOAt) or hydroxybenzotriazole (HOBt).

This type of reaction is illustrated in Examples 35 to 38, 48-60, 65 and 66.

In some compounds of the invention, such as Example 35, $L^1$ is —$C(O)N(R^7)Z^1$— where $R^7$ is H and $Z^1$ is as defined above; $R^{10}$ is —$N(R^7)$—$C(O)OR^8$; $R^7$ is H and $R^8$ is as defined above.

In some compounds of the invention, such as Example 36, $L^1$ is —$C(O)N(R^7)Q^1$— where $R^7$ is H and $Q^1$ is heterocyclyl linked to $R^{10}$ via a ring nitrogen atom; $R^{10}$ is —C(O)OR^7$ where $R^7$ is as defined above.

In some compounds of the invention, such as Example 37, $L^1$ is —$C(O)Q^1$— where $Q^1$ is heterocyclyl linked to C(O) via a ring nitrogen atom and to $R^{10}$ via a ring carbon atom; $R^{10}$ is —$N(R^7)$—$C(O)OR^8$; $R^7$ is H and $R^8$ is as defined above.

In some compounds of the invention, such as Example 38, $L^1$ is —$C(O)N(R^7)Z^1Q^1$— where $R^7$ is H, $Z^1$ is as defined above, $Q^1$ is heterocyclyl linked to $R^{10}$ via a ring carbon atom; $R^{10}$ is —$N(R^7)$—$C(O)OR^8$; $R^7$ is H and $R^8$ is as defined above.

In some compounds of the invention, such as Examples 48, 57 and 58, $L^1$ is $C(O)N(R^7)Z^1$ where $R^7$ is H or methyl and $Z^1$ is as defined above; $R^{10}$ is $N(R^7)R^8$, where $R^7$ and $R^8$ are both $C_{1-12}$ alkyl substituted with one or more OH groups.

In some compounds of the invention, such as Example 49, $L^1$ is $C(O)N(R^7)Q^1Z^1$ where $R^7$ is H, $Q^1$ is linked to —C(O)N(R^7)$— via a ring carbon atom and to $Z^1$ via a ring nitrogen, $Z^1$ is $C_{1-12}$ alkylene substituted with one or more OH; $R^{10}$ is H.

In some compounds of the invention, such as Examples 50, 53, 54, 65 and 66, $L^1$ is $C(O)Q^1$, where $Q^1$ is linked to C(O) via a ring nitrogen atom; $R^{10}$ is $N(R^7)R^8$, where $R^7$ and $R^8$ are both $C_{1-12}$ alkyl substituted with one or more OH groups.

In some compounds of the invention, such as Example 51, $L^1$ is —$C(O)N(R^7)Z^1Q^1$— where $R^7$ is H; $Z^1$ is as defined above, $Q^1$ is linked to $R^{10}$ via a ring carbon atom, $R^{10}$ is $N(R^7)R^8$, where $R^7$ and $R^8$ are both $C_{1-12}$ alkyl substituted with one or more OH groups.

In some compounds of the invention, such as Example 52, $L^1$ is —$C(O)Q^1Z^1$— where $Q^1$ is linked to the C(O) moiety via a ring nitrogen atom and $Z^1$ as defined above; $R^{10}$ is $N(R^7)R^8$, where $R^7$ and $R^8$ are both $C_{1-12}$ alkyl substituted with one or more OH groups.

In some compounds of the invention, such as Examples 55 and 56, $L^1$ is —$C(O)N(R^7)Q^1$— where $R^7$ is H, $Q^1$ is linked to —$C(O)N(R^7)$— via a ring carbon atom and to $R^{10}$ via a ring nitrogen atom; $R^{10}$ is $N(R^7)R^8$, where $R^7$ and $R^8$ are both $C_{1-12}$ alkyl substituted with one or more OH groups.

In some compounds of the invention, such as Example 59, $L^1$ is —$C(O)N(R^7)Z^1O(CH_2CH_2O)_nZ^2$—, where $R^7$ is H, $Z^1$, n and $Z^2$ are as defined above; $R^{10}$ is $N(R^7)R^8$, where $R^7$ and $R^8$ are both $C_{1-12}$ alkyl substituted with one or more OH groups.

In some compounds of the invention, such as Example 60, $L^1$ is —$C(O)N(R^7)Z^1Q^1Q^2Z^2$—, where $R^7$ is H, $Z^1$, $Q^1$, $Q^2$ and $Z^2$ are as defined above; $R^{10}$ is $N(R^7)R^8$, where $R^7$ and $R^8$ are both $C_{1-12}$ alkyl substituted with one or more OH groups.

The amines or ammonium salts which react with the compounds of general formulae (I), (VII) or (VIII) in which $R^1$ is C(O)OH are described below. For example, an amine of general formula (XXX):

(XXX)

wherein $R^7$ and $R^8$ are as defined for general formula (I); $L^1$ is as defined for general formula (I) and is linked to H via an amine of a $Z^1$ moiety or a ring nitrogen atom of a $Q^1$ moiety;

may be prepared from a protected compound of general formula (XXXI):

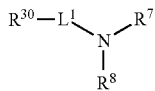

(XXXI)

wherein $R^7$ and $R^8$ are as defined for general formula (I), $L^1$ is as defined for general formula (XXX) and $R^{30}$ is an amine protecting group such as fluorenylmethyloxycarbonyl (Fmoc), butyloxycarbonyl (Boc) or benzyloxycarbonyl (Cbz). Deprotection may be by hydrogenation for compounds where $R^{30}$ is Cbz or by reaction with an acid such as hydrochloric or hydrobromic acid in the case where $R^{30}$ is a protecting group such as Boc or Cbz or with a weak base such as morpholine or piperidine when $R^{30}$ is a protecting group such as Fmoc.

When $R^7$ and/or $R^8$ is a group —$CH_2[CH(OH)]_4CH_2OH$, this may be protected in the compound of general formula (XXXI), for example as a benzylidene acetal.

An amine of general formula (XXXI) in which $R^7$ and/or $R^8$ is a group —$CH_2[CH(OH)]_4CH_2OH$, protected as a benzylidene acetal may be reacted with a compound of general formula (VII) or (VIII). In the resulting product, when the protecting group $R^{23}$ is an acid labile group such as Boc, the protecting group $R^{23}$ and the benzylidene acetal protecting groups can be removed simultaneously using an acid. In some cases, however, a two step deprotection process may be used wherein the $R^{23}$ group is removed by hydrogenation and the benzylidene acetal is subsequently removed by treatment with an acid. When the protecting group $R^{23}$ is a group such as Fmoc it may be removed by treatment with a base as described above. Treatment with an acid will then be required to remove the benzylidene acetal protection.

The preparation of other intermediates which can be used to react with compounds of general formulae (I), (VII) or (VIII) to convert them to other compounds of general formulae (I), (VII) or (VIII) is described below.

The compounds of general formula (I) are ENaC blockers and are therefore useful in the treatment or prevention of respiratory diseases and conditions.

Therefore in a further aspect of the invention there is provided a compound of general formula (I) for use in medicine.

Suitably, the compound of general formula (I) is for use in the treatment or prophylaxis of a disease or condition mediated by ENaC.

There is also provided:
A compound of general formula (I) for use in the treatment or prophylaxis of respiratory diseases and conditions.
A compound of general formula (I) for use in the treatment or prophylaxis of skin conditions or ocular conditions.
The invention further provides:
The use of a compound of general formula (I) in the preparation of a medicament for the treatment or prophylaxis of respiratory diseases and conditions.
The use of a compound of general formula (I) in the preparation of a medicament for the treatment or prophylaxis of skin conditions or ocular conditions There is also provided:
A method for the treatment or prophylaxis of respiratory diseases and conditions, the method comprising administering to a patient in need of such treatment an effective amount of a compound of general formula (I).
A method for the treatment or prophylaxis of skin conditions and ocular conditions, the method comprising administering to a patient in need of such treatment an effective amount of a compound of general formula (I).

Respiratory diseases and conditions which may be treated by the compounds of general formula (I) include cystic fibrosis, chronic obstructive pulmonary disease (COPD), chronic bronchitis, emphysema, bronchiectasis, including non-cystic fibrosis bronchiectasis, asthma and primary ciliary dyskinesia.

Skin conditions which may be treated by the compounds of the present invention include psoriasis, atopic dermatitis and ichthyosis.

Ocular conditions which may be treated by the compounds of the present invention included dry eye disease.

Compounds of the present invention have good ENaC blocking activity. They are particularly suitable for treating respiratory diseases because they have a prolonged retention time in the lungs. Furthermore, in vivo experiments have shown that treatment with compounds of the present invention significantly increases mucocilliary clearance.

The patient to be treated is suitably a mammal and more suitably a human.

The compounds of general formula (I) may be administered in a pharmaceutical composition and therefore in a further aspect of the invention there is provided a pharmaceutical composition comprising a compound of general formula (I) and a pharmaceutically acceptable excipient. Other pharmacologically active materials may also be present, as considered appropriate or advisable for the disease or condition being treated or prevented.

The carrier, or, if more than one be present, each of the carriers, must be acceptable in the sense of being compatible with the other ingredients of the formulation and not deleterious to the recipient.

The formulations include those suitable for oral, rectal, nasal, bronchial (inhaled), topical (including dermal, transdermal, eye drops, buccal and sublingual), vaginal or parenteral (including subcutaneous, intramuscular, intravenous and intradermal) administration and may be prepared by any methods well known in the art of pharmacy.

The route of administration will depend upon the condition to be treated but preferred compositions are formulated for oral, nasal, bronchial or topical administration.

The composition may be prepared by bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formula (I) in conjunction or association with a pharmaceutically acceptable carrier or vehicle.

Formulations for oral administration in the present invention may be presented as: discrete units such as capsules, sachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate, stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

More suitably a compound of formula (I) is administered topically to the lung, eye or skin. Hence there is provided according to the invention a pharmaceutical composition comprising a compound of the general formula (I) optionally in combination with one or more topically acceptable diluents or carriers.

For topical application to the skin, compounds of general formula (I) may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12). Suitable HFC propellants include tetrafluoroethane (HFC-134a) and heptafluoropropane (HFC-227). The propellant typically comprises 40%-99.5% e.g. 40%-90% by weight of the total inhalation composition. The formulation may comprise excipients including co-solvents (e.g. ethanol) and surfactants (e.g. lecithin, sorbitan trioleate and the like). Other possible excipients include polyethylene glycol, polyvinylpyrrolidone, glycerine and the like. Aerosol formulations are packaged in canisters and a suitable dose is delivered by means of a metering valve (e.g. as supplied by Bespak, Valois or 3M or alternatively by Aptar, Coster or Vari).

Topical administration to the lung may also be achieved by use of a non-pressurised formulation such as an aqueous solution or suspension. These may be administered by means of a nebuliser e.g. one that can be hand-held and portable or for home or hospital use (ie non-portable). The formulation may comprise excipients such as water, buffers, tonicity adjusting agents, pH adjusting agents, surfactants and co-solvents. Suspension liquid and aerosol formulations (whether pressurised or unpressurised) will typically contain the compound of the invention in finely divided form, for example with a $D_{50}$ of 0.5-10 μm e.g. around 1-5 82 m. Particle size distributions may be represented using $D_{10}$, $D_{50}$ and $D_{90}$ values. The $D_{50}$ median value of particle size distributions is defined as the particle size in microns that divides the distribution in half. The measurement derived from laser diffraction is more accurately described as a volume distribution, and consequently the $D_{50}$ value obtained using this procedure is more meaningfully referred to as a $Dv_{50}$ value (median for a volume distribution). As used herein Dv values refer to particle size distributions measured using laser diffraction. Similarly, $D_{10}$ and $D_{90}$ values, used in the context of laser diffraction, are taken to mean $Dv_{10}$ and $Dv_{90}$ values and refer to the particle size whereby 10% of the distribution lies below the $D_{10}$ value, and 90% of the distribution lies below the $D_{90}$ value, respectively.

Topical administration to the lung may also be achieved by use of a dry-powder formulation. A dry powder formulation will contain the compound of the disclosure in finely divided form, typically with a mass mean diameter (MMAD) of 1-10 μm or a $D_{50}$ of 0.5-10 μm e.g. around 1-5 μm. Powders of the compound of the invention in finely divided form may be prepared by a micronization process or similar size reduction process. Micronization may be performed using a jet mill such as those manufactured by Hosokawa Alpine. The resultant particle size distribution may be measured using laser diffraction (e.g. with a Malvern Mastersizer 2000S instrument). The formulation will typically contain a topically acceptable diluent such as lactose, glucose or mannitol (preferably lactose), usually of comparatively large particle size e.g. a mass mean diameter (MMAD) of 50 μm or more, e.g. 100 μm or more or a $D_{50}$ of 40-150 μm. As used herein, the term "lactose" refers to a lactose-containing component, including α-lactose monohydrate, β-lactose monohydrate, α-lactose anhydrous, β-lactose anhydrous and amorphous lactose. Lactose components may be processed by micronization, sieving, milling, compression, agglomeration or spray drying. Commercially available forms of lactose in various forms are also encompassed, for example Lactohale® (inhalation grade lactose; DFE Pharma), InhaLac®70 (sieved lactose for dry powder inhaler; Meggle), Pharmatose® (DFE Pharma) and Respitose® (sieved inhalation grade lactose; DFE Pharma) products. In one embodiment, the lactose component is selected from the group consisting of α-lactose monohydrate, α-lactose anhydrous and amorphous lactose. Preferably, the lactose is α-lactose monohydrate.

Dry powder formulations may also contain other excipients. Thus in one embodiment a dry powder formulation according the present disclosure comprises magnesium or calcium stearate. Such formulations may have superior chemical and/or physical stability especially when such formulations also contain lactose.

A dry powder formulation is typically delivered using a dry powder inhaler (DPI) device. Example dry powder delivery systems include SPINHALER®, DISKHALER®, TURBOHALER®, DISKUS®, SKYEHALER®, ACCUHALER® and CLICKHALER®. Further examples of dry powder delivery systems include ECLIPSE, NEXT, ROTAHALER, HANDIHALER, AEROLISER, CYCLO- HALER, BREEZHALER/NEOHALER, MONODOSE, FLOWCAPS, TWINCAPS, X-CAPS, TURBOSPIN, ELPENHALER, MIATHALER, TWISTHALER, NOVOLIZER, PRESSAIR, ELLIPTA, ORIEL dry powder inhaler, MICRODOSE, PULVINAL, EASYHALER, ULTRAHALER, TAIFUN, PULMOJET, OMNIHALER, GYROHALER, TAPER, CONIX, XCELOVAIR and PROHALER.

In one embodiment a compound of general formula (I) is provided as a micronized dry powder formulation, for example comprising lactose of a suitable grade.

Thus, as an aspect of the invention there is provided a pharmaceutical composition comprising a compound of general formula (I) in particulate form in combination with particulate lactose, said composition optionally comprising magnesium stearate.

In one embodiment a compound of general formula (I) is provided as a micronized dry powder formulation, comprising lactose of a suitable grade and magnesium stearate, filled into a device such as DISKUS. Suitably, such a device is a multidose device, for example the formulation is filled into blisters for use in a multi-unit dose device such as DISKUS.

In another embodiment a compound of general formula (I) is provided as a micronized dry powder formulation, for example comprising lactose of a suitable grade, filled into hard shell capsules for use in a single dose device such as AEROLISER.

In another embodiment a compound of general formula (I) is provided as a micronized dry powder formulation, comprising lactose of a suitable grade and magnesium stearate, filled into hard shell capsules for use in a single dose device such as AEROLISER.

In another embodiment a compound of general formula (I) is provided as a fine powder for use in an inhalation dosage form wherein the powder is in fine particles with a $D_{50}$ of 0.5-10 µm e.g. around 1-5 µm, that have been produced by a size reduction process other than jet mill micronisation e.g. spray drying, spray freezing, microfluidisation, high pressure homogenisation, super critical fluid crystallisation, ultrasonic crystallisation or combinations of these methods thereof, or other suitable particle formation methods known in the art that are used to produce fine particles with an aerodynamic particle size of 0.5-10 µm. The resultant particle size distribution may be measured using laser diffraction (e.g. with a Malvern Mastersizer 2000S instrument). The particles may either comprise the compound alone or in combination with suitable other excipients that may aid the processing. The resultant fine particles may form the final formulation for delivery to humans or may optionally be further formulated with other suitable excipients to facilitate delivery in an acceptable dosage form.

The compound of the invention may also be administered rectally, for example in the form of suppositories or enemas, which include aqueous or oily solutions as well as suspensions and emulsions and foams. Such compositions are prepared following standard procedures, well known by those skilled in the art. For example, suppositories can be prepared by mixing the active ingredient with a conventional suppository base such as cocoa butter or other glycerides. In this case, the drug is mixed with a suitable non-irritating excipient which is solid at ordinary temperatures but liquid at the rectal temperature and will therefore melt in the rectum to release the drug. Such materials are cocoa butter and polyethylene glycols.

Generally, for compositions intended to be administered topically to the eye in the form of eye drops or eye ointments, the total amount of the compound of general formula (I) will be about 0.0001 to less than 4.0% (w/w).

Preferably, for topical ocular administration, the compositions administered according to general formula (I) will be formulated as solutions, suspensions, emulsions and other dosage forms. Aqueous solutions are generally preferred, based on ease of formulation, as well as a patient's ability to administer such compositions easily by means of instilling one to two drops of the solutions in the affected eyes. However, the compositions may also be suspensions, viscous or semi-viscous gels, or other types of solid or semi-solid compositions. Suspensions may be preferred for compounds that are sparingly soluble in water.

An alternative for administration to the eye is intravitreal injection of a solution or suspension of the compound of general formula (I). In addition, the compound of general formula (I) may also be introduced by means of ocular implants or inserts.

The compositions administered according to general formula (I) may also include various other ingredients, including, but not limited to, tonicity agents, buffers, surfactants, stabilizing polymer, preservatives, co-solvents and viscosity building agents. Suitable pharmaceutical compositions of general formula (I) include a compound of the invention formulated with a tonicity agent and a buffer. The pharmaceutical compositions of general formula (I) may further optionally include a surfactant and/or a palliative agent and/or a stabilizing polymer.

Various tonicity agents may be employed to adjust the tonicity of the composition, preferably to that of natural tears for ophthalmic compositions. For example, sodium chloride, potassium chloride, magnesium chloride, calcium chloride, simple sugars such as dextrose, fructose, galactose, and/or simply polyols such as the sugar alcohols mannitol, sorbitol, xylitol, lactitol, isomaltitol, maltitol, and hydrogenated starch hydrolysates may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm and most preferably at approximately 290 mOsm). In general, the tonicity agents of the invention will be present in the range of 2 to 4% w/w. Preferred tonicity agents of the invention include the simple sugars or the sugar alcohols, such as D-mannitol.

An appropriate buffer system (e.g. sodium phosphate, sodium acetate, sodium citrate, sodium borate or boric acid) may be added to the compositions to prevent pH drift under storage conditions. The particular concentration will vary, depending on the agent employed. Preferably however, the buffer will be chosen to maintain a target pH within the range of pH 5 to 8, and more preferably to a target pH of pH 5 to 7.

Surfactants may optionally be employed to deliver higher concentrations of compound of general formula (I). The surfactants function to solubilise the compound and stabilise colloid dispersion, such as micellar solution, microemulsion, emulsion and suspension. Examples of surfactants which may optionally be used include polysorbate, poloxamer, polyosyl 40 stearate, polyoxyl castor oil, tyloxapol, Triton, and sorbitan monolaurate. Preferred surfactants to be employed in the invention have a hydrophile/lipophile/balance "HLB" in the range of 12.4 to 13.2 and are acceptable for ophthalmic use, such as TritonX114 and tyloxapol.

Additional agents that may be added to the ophthalmic compositions of compounds of general formula (I) are demulcents which function as a stabilising polymer. The stabilizing polymer should be an ionic/charged example with precedence for topical ocular use, more specifically, a polymer that carries negative charge on its surface that can exhibit a zeta -potential of (−) 10-50 mV for physical stability and capable of making a dispersion in water (i.e. water soluble). A preferred stabilising polymer of the invention would be polyelectrolyte, or polyelectrolytes if more than one, from the family of cross-linked polyacrylates, such as carbomers and Pemulen(R), specifically Carbomer 974p (polyacrylic acid), at 0.1-0.5% w/w.

Other compounds may also be added to the ophthalmic compositions of the compound of general formula (I) to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edentate disodium, sorbic acid, polyquaternium-1, or other agents known to those skilled in the art. Such preservatives are typically employed at a level of from 0.001 to 1.0% w/v. Unit dose compositions of general formula (I) will be sterile, but typically unpreserved. Such compositions, therefore, generally will not contain preservatives.

The medical practitioner, or other skilled person, will be able to determine a suitable dosage for the compound of general formula (I), and hence the amount of the compound of the invention that should be included in any particular pharmaceutical formulation (whether in unit dosage form or otherwise).

Compounds of general formula (I) may be used in combination with one or more other active agents which are useful in the treatment or prophylaxis of respiratory diseases and conditions.

An additional active agent of this type may be included in the pharmaceutical composition described above but alternatively it may be administered separately, either at the same time as the compound of general formula (I) or at an earlier or later time.

Therefore, in a further aspect of the present invention there is provided a product comprising a compound of general formula (I) and an additional agent useful in the treatment or prevention of respiratory conditions as a combined preparation for simultaneous, sequential or separate use in the treatment of a disease or condition mediated by ENaC and especially a respiratory disease or condition, for example one of the diseases and conditions mentioned above.

There is also provided a compound of general formula (I) in combination with an additional agent useful in the treatment or prevention of respiratory conditions as a combined preparation for simultaneous, sequential or separate use in the treatment of a disease or condition mediated by ENaC and especially a respiratory disease or condition, for example one of the diseases and conditions mentioned above.

Suitable additional active agents which may be included in a pharmaceutical composition or a combined preparation with the compounds of general formula (I) include:

β2 adrenoreceptor agonists such as metaproterenol, isoproterenol, isoprenaline, albuterol, salbutamol, formoterol, salmeterol, indacaterol, terbutaline, orciprenaline, bitolterol mesylate and pirbuterol;

antihistamines, for example histamine $H_1$ receptor antagonists such as loratadine, cetirizine, desloratadine, levocetirizine, fexofenadine, astemizole, azelastine and chlorpheniramine or $H_4$ receptor antagonists; dornase alpha;

corticosteroids such as prednisone, prednisolone, flunisolide, triamcinolone acetonide, beclomethasone dipropionate, budesonide, fluticasone propionate mometasone furoate and fluticasone furoate;

leukotriene antagonists such as montelukast and zafirlukast;

CFTR repair therapies e.g. CFTR potertiators such as Ivacaftor and CFTR correctors such as Lumacaftor and Tezacaftor;

TMEM16A modulators, particularly TMEM16A potertiators; antibiotics.

BRIEF DESCRIPTION OF THE DRAWINGS

The invention will now be described in greater detail with reference to the non-limiting examples and to the drawings in which.

EXAMPLES

Figure 1:
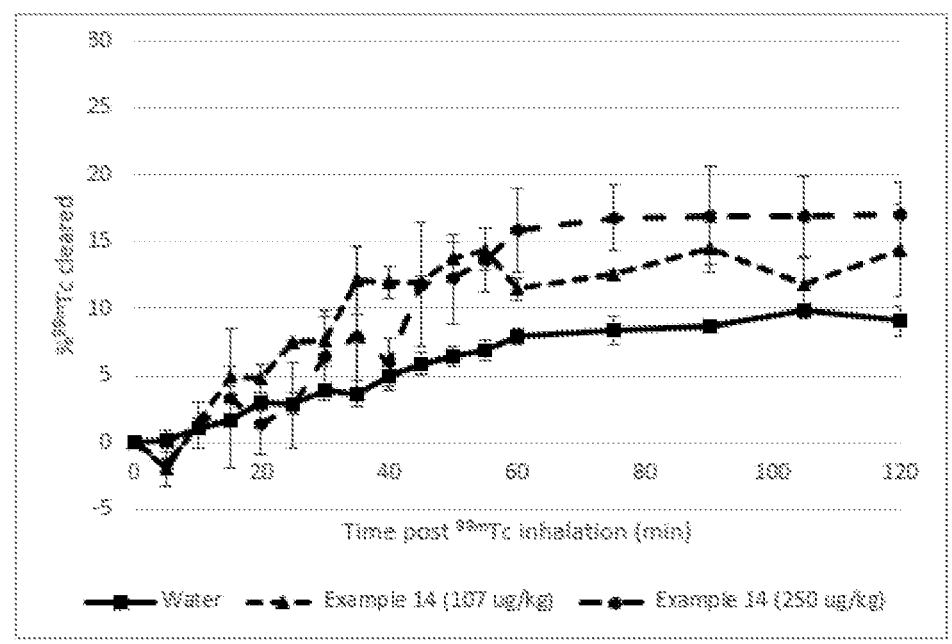
FIG. 1 is a plot showing the results of the sheep MCC experiment of Example 70 showing clearance of 99mTc-SC from the lungs of sheep treated with the compound of Example 14 at doses of 107 μg/kg (▲) and 250 μg/kg (●) and water (■).

All reactions involving moisture-sensitive reagents were carried out under a nitrogen atmosphere using standard vacuum line techniques and oven-dried glassware. Commercial anhydrous solvents were used in reactions and HPLC grade solvents were employed for work-up and chromatography. Water was purified using an Elix UV-5 system. All other reagents were used as supplied without prior purification. Reported yields are corrected for LC/MS purity (determined by UV (215 nm) or ELS detection) unless otherwise stated. Sealed tube reactions were carried out in heavy wall Ace pressure tubes. Microwave experiments were carried out using a Biotage Initiator+in crimp-sealed Biotage microwave vials. Flash column chromatography was carried out using a Biotage Isolera 4 using Biotage SNAP KP or SNAP Ultra columns. NMR spectra were recorded on a Bruker Avance III HD 500 MHz or a Bruker Avance III HD 250 MHz using the solvent as internal deuterium lock. Spectra were recorded at room temperature unless otherwise stated.

Analytical LC/MS were carried out on the following systems:

System A: stationary phase: Kinetex Core-Shell C18 2.1×50 mm, 5 μm, 40° C.; detection UV 215 nm-ELS-MS; mobile phase: A, water+0.1% formic acid; B, MeCN+0.1% formic acid; gradient (A:B ratio, time): 95:5-0:100, 1.20 min; 100:0, 0.10 min; 100:0-5:95, 0.01 min; flowrate: 1.2 ml/min;

System B: stationary phase: Phenomenex Gemini-NX C18 2.0×50 mm, 3 μm, 60° C.; detection UV 215 nm-ELS-MS; mobile phase: A, 2 mM ammonium bicarbonate pH 10; B, MeCN; gradient (A:B ratio, time): 99:1-0:100, 1.80 min; 100:0, 0.30 min; 100:0-1:99, 0.20 min; 1:99, 1.20 min; flowrate: 1.0 ml/min;

System C: stationary phase: Phenomenex Kinetex-XB C18 2.1×100 mm, 1.7 μm, 40° C.; detection UV 215 nm-ELS-MS; mobile phase: A, water+0.1% formic acid; B, MeCN+0.1% formic acid; gradient (A:B ratio, time): 95:5-0:100, 5.30 min; 100:0, 0.50 min; 100:0-5:95, 0.02 min; 5:95, 1.18 min; flowrate: 0.6 ml/min;

System D: stationary phase: Waters CSH C18 2.1×100 mm, 1.7 μm, 40° C.; detection UV 215 nm-ELS-MS; mobile phase: A, 5 mM ammonium acetate pH 7; B, MeCN; gradient (A:B ratio, time): 95:5-0:100, 5.30 min; 100:0, 0.50 min; 100:0-5:95, 0.02 min; 5:95, 1.18 min; flowrate: 0.6 ml/min.

Preparative HPLC purification was carried out using the following conditions:

Method A: stationary phase: Waters Sunfire 30×100 mm, 10 μm; detection UV 215 and 254 nm; mobile phase A: water+0.1% formic acid; B: MeCN+0.1% formic acid; gradient: 5-95% solvent B over 14 min; flowrate: 40 ml/min;

Method B: stationary phase: Waters Sunfire 30×100 mm, 5 μm; detection UV 215 and 254 nm; mobile phase A: water+0.1% formic acid; B: MeCN+0.1% formic acid; gradient: 2-12% solvent B over 12 min; flowrate: 40 ml/min;

Method C: stationary phase: XSelect CSH C18 30×100 mm, 5 μm; detection UV 220 nm; mobile phase A: water+0.1% TFA; B: MeCN+0.1% TFA; gradient: 5-15% solvent B over 21 min; flowrate: 42 ml/min;

Method D: stationary phase: XSelect CSH C18 30×100 mm, 5 μm; detection UV 220 nm; mobile phase A: water+0.1% TFA; B: MeCN+0.1% TFA; gradient: 2-15% solvent B over 12 min; flowrate: 42 ml/min;

Method E: stationary phase: XSelect CSH C18 30×100 mm, 5 μm; detection UV 220 nm; mobile phase A: water+0.1% TFA; B: MeCN+0.1% TFA; gradient: 10-35% solvent B over 10 min; flowrate: 42 ml/min.

The following abbreviations and terms have the indicated meanings throughout:

AcOH glacial acetic acid
br broad
CDI 1,1'-carbonyldiimidazole
CV column volumes
dd doublet of doublets
DIPEA N,N-diisopropylethylamine
DMF N,N-dimethylformamide
DMSO dimethyl sulfoxide
dppf 1,1'-bis(diphenylphosphino)ferrocene
EDC.HCl N-(3-dimethylaminopropyl)-N'-ethylcarbodiimide hydrochloride
ELS evaporative light scattering
ESI electrospray ionisation
EtOAc ethyl acetate
FMOC fluorenylmethyloxycarbonyl
HATU 1-[bis(dimethylamino)methylene]-1H-1,2,3-triazolo[4,5-b]pyridinium 3-oxide hexafluorophosphate
HBTU 3-[bis(dimethylamino)methyliumyl]-3H-benzotriazol-1-oxide hexafluorophosphate
HOAt 1-hydroxy-7-azabenzotriazole
HPLC high-performance liquid chromatography
LC/MS liquid chromatography—mass spectrometry
m multiplet
MeCN acetonitrile
MeOH methanol
NCS N-chlorosuccinimide
NMR nuclear magnetic resonance
Ph phenyl
q quartet
RT room temperature
Rt retention time
s singlet
SCX strong cation exchange
SPhos 2-dicyclohexylphosphino-2',6'-dimethoxybiphenyl t triplet
t-Bu tert-butyl
TBTU O-(Benzotriazol-1-yl)-N,N,N',N'-tetramethyluronium tetrafluoroborate
TFA trifluoroacetic acid
THF tetrahydrofuran
XPhos-Pd-G2 chloro(2-dicyclohexylphosphino-2',4',6'-triisopropyl-1,1'-biphenyl)[2-(2'-amino-1,1'-biphenyl)]palladium(II)

A. SYNTHESIS OF INTERMEDIATES

Intermediate 1-Synthesis of methyl 3,5-diamino-6-[(E)-2-ethoxyethenyl]pyrazine-2-carboxylate

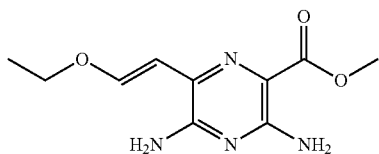 [SMILES: CCO/C=C/c1nc(C(=O)OC)c(N)nc1N]

A mixture of methyl 3,5-diamino-6-chloropyrazine-2-carboxylate (40.0 g, 197 mmol), 2-[(E)-2-ethoxyethenyl]-4,4,5,5-tetramethyl-1,3,2-dioxaborolane (84 ml, 400 mmol), SPhos (8.11 g, 19.7 mmol), palladium(II) acetate (2.22 g, 9.87 mmol) and K$_3$PO$_4$ (83.8 g, 395 mmol) in water:MeCN (2:3, 350 ml) was stirred at 80° C. for 2 h then allowed to cool to RT. The solid was collected by filtration then washed with EtOAc (100 ml) and water (100 ml) then dried in vacuo to afford the product as a brown solid (36.7 g, 76%).

$^1$H NMR (500 MHz, DMSO-d$_6$) δ 7.15 (d, J=12.2 Hz, 1H), 6.79 (s, 4H), 5.97 (d, J=12.2 Hz, 1H), 3.91 (q, J=7.0 Hz, 2H), 3.72 (s, 3H), 1.25 (t, J=7.0 Hz, 3H).

LC/MS (System A): m/z (ESI+)=239 [MH$^+$], Rt=0.88 min, UV purity=98%.

Intermediate 2-Synthesis of methyl 3-amino-5H-pyrrolo[2,3-b]pyrazine-2-carboxylate

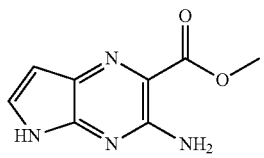

A solution of methyl 3,5-diamino-6-[(E)-2-ethoxyethenyl]pyrazine-2-carboxylate, Intermediate 1 (98%, 36.6 g, 151 mmol) in AcOH (360 ml) was heated at 80° C. for 16 h. The reaction was allowed to cool to RT then concentrated in vacuo. The residue was azeotroped with toluene (2×100 ml). The resulting residue was dissolved in CH$_2$Cl$_2$:MeOH (4:1, 600 ml) then warmed at 50° C. Activated charcoal (5 g) was added then the resultant mixture was stirred at 50° C. for 0.5 h. The mixture was allowed to cool then filtered through a Celite pad. The filtrate was concentrated in vacuo to afford the product as a brown solid (20.2 g, 68%).

$^1$H NMR (500 MHz, DMSO-d$_6$) δ 11.48 (s, 1H), 7.50 (d, J=3.8 Hz, 1H), 7.05 (s, 2H), 6.42 (d, J=3.7 Hz, 1H), 3.84 (s, 3H).

LC/MS (System A): m/z (ESI+)=193 [MH$^+$], Rt=0.76 min, UV purity=98%.

Intermediate 3-Synthesis of lithium(1$^+$) ion 3-amino-5H-pyrrolo[2,3-b]pyrazine-2-carboxylate

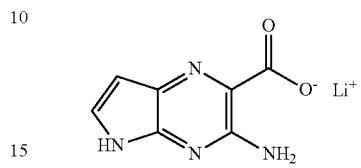

Aqueous LiOH solution (1.0 M, 210 ml, 210 mmol) was added to a mixture of methyl 3-amino-5H-pyrrolo[2,3-b]pyrazine-2-carboxylate, Intermediate 2 (20.2 g, 105 mmol) in MeOH (300 ml). The resulting mixture was heated at 50° C. for 16 h then allowed to cool to RT. The solid was collected by filtration then washed with water and MeOH and then dried under vacuum to afford the product as a yellow solid (15.6 g, 79%).

$^1$H NMR (500 MHz, DMSO-d$_6$) δ 11.17 (s, 1H), 8.62-6.43 (m, 3H), 6.18 (d, J=3.6 Hz, 1H).

LC/MS (System C): m/z (ESI+)=179 [MH$^+$], Rt=0.96 min, UV purity=97%.

Intermediate 4-Synthesis of 2-(1H-imidazole-1-carbonyl)-5H-pyrrolo[2,3-b]pyrazin-3-amine

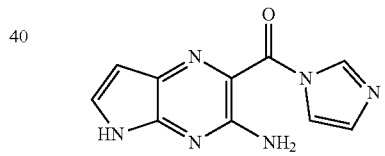

A mixture of lithium(1$^+$) ion 3-amino-5H-pyrrolo[2,3-b]pyrazine-2-carboxylate, Intermediate 3 (5.00 g, 27.2 mmol), CDI (6.61 g, 40.7 mmol) and 1H-imidazole hydrochloride (1:1) (3.12 g, 29.9 mmol) in DMF (80 ml) was stirred at RT for 16 h. Additional CDI (2.00 g, 12.3 mmol) was added and the reaction was left to stir for a further 1 h at RT. The reaction mixture was diluted with water (350 ml) then stirred at RT for 5 min then left to stand at RT for 0.5 h. The resultant mixture was filtered then the collected solid was washed with water then dried under vacuum to afford the product as a yellow/orange solid (3.30 g, 52%).

$^1$H NMR (500 MHz, DMSO-d$_6$) δ 11.69 (s, 1H), 8.74 (t, J=0.9 Hz, 1H), 7.94 (t, J=1.4 Hz, 1H), 7.63 (dd, J=3.8, 2.3 Hz, 1H), 7.44 (s, 2H), 7.08 (dd, J=1.5, 0.8 Hz, 1H), 6.52 (dd, J=3.8, 1.3 Hz, 1H).

LC/MS (System A): m/z (ESI+)=229 [MH$^+$], Rt=0.65 min, UV purity=97%.

Intermediate 7-Synthesis of methyl 3,5-diamino-6-[3-(trimethylsilyl)prop-1-yn-1-yl]pyrazine-2-carboxylate

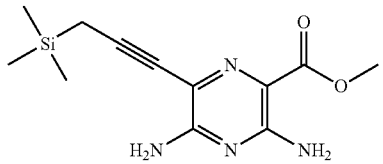

Trimethyl(prop-2-yn-1-yl)silane (332 mg, 2.96 mmol) was added to a solution of methyl 3,5-diamino-6-chloropyrazine-2-carboxylate (500 mg, 2.47 mmol), $PdCl_2(PPh3)_2$ (170 mg, 0.25 mmol), CuI (47 mg, 0.25 mmol) and triethylamine (520 µl, 3.7 mmol) in DMSO (5 ml) in a pressure tube. The tube was sealed then heated at 60° C. for 2 h. The reaction was allowed to cool to RT then left to stir at RT for 16 h, then at 60° C. again for a further 2 h. The reaction mixture was diluted with EtOAc (20 ml) and water (20 ml) then filtered through a Celite pad. The phases of the filtrate were separated then the organic phase was extracted with water (2×50 ml) and brine (100 ml), then dried over $Na_2SO_4$ and concentrated in vacuo to a viscous orange/brown oil. The crude material was purified by flash column chromatography on a silica column (50 g). The column was eluted with EtOAc:heptane, using the following gradient (% EtOAc, column volumes): 0%, 1 CV; 0-46%, 6 CV; 46-67%, 2 CV; 67%, 1 CV; 67-100%, 3 CV. The desired fractions were combined and concentrated in vacuo to afford the product as a yellow solid (330 mg, 44%).

$^1$H NMR (500 MHz, DMSO-$d_6$) δ 7.12 (s, 4H), 3.72 (s, 3H), 1.84 (s, 2H), 0.13 (s, 9H).

LC/MS (System A): m/z (ESI+)=279 [MH$^+$], Rt=1.11 min, UV purity=92%.

Intermediate 8-Synthesis of methyl 3-amino-6-methyl-5H-pyrrolo[2,3-b]pyrazine-2-carboxylate

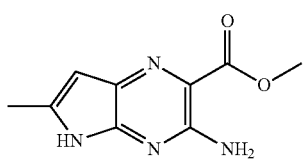

Potassium tert-butoxide (141 mg, 1.26 mmol) was added to a solution of methyl 3,5-diamino-6-[3-(trimethylsilyh-prop-1-yn-1-yl]pyrazine-2-carboxylate, Intermediate 7 (92%, 318 mg, 1.05 mmol) in THF (25 ml). The reaction mixture was stirred under reflux for 1 h. Potassium tert-butoxide (141 mg, 1.26 mmol) was added then the reaction was heated under reflux for a further 1 h. The reaction mixture was diluted with EtOAc (100 ml) then extracted with saturated aqueous $NH_4Cl$ (50 ml), water (50 ml) and brine (50 ml). The organic phase was dried over $Na_2SO_4$ and concentrated in vacuo. The crude material was purified by flash column chromatography on C18 (30 g). The column was eluted with MeCN:water+0.1% formic acid using the following gradient (% MeCN, column volumes): 0%, 1 CV; 0-7%, 2 CV; 7-9%, 1 CV; 9-41%, 4 CV; 41-83%, 3 CV; 100% 1 CV. The desired fractions were combined and concentrated in vacuo to afford the product as a yellow solid (105 mg, 40%).

$^1$H NMR (250 MHz, DMSO-$d_6$) δ 11.35 (s, 1H), 6.97 (s, 2H), 6.22-6.02 (m, 1H), 3.81 (s, 3H), 2.35 (d, J=1.0 Hz, 3H).

LC/MS (System A): m/z (ESI+)=207 [MH$^+$], Rt=0.82 min, UV purity=82%.

Intermediate 9-Synthesis of 3-amino-6-methyl-5H-pyrrolo[2,3-b]pyrazine-2-carboxylic acid

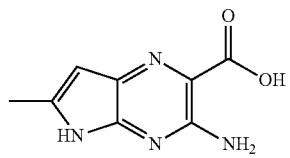

Aqueous LiOH solution (1.0 M, 1.0 ml, 1.0 mmol) was added to a solution of methyl 3-amino-6-methyl-5H-pyrrolo[2,3-b]pyrazine-2-carboxylate, Intermediate 8 (82%, 100 mg, 0.40 mmol) in MeOH (4 ml). The reaction mixture was stirred at 50° C. for 1 h. Aqueous LiOH solution (1.0 M, 1.0 ml, 1.0 mmol) was added then the reaction mixture was stirred at 65° C. for a further 1 h. The reaction mixture was allowed to cool then concentrated in vacuo. The resulting residue was dissolved in water (5 ml) then acidified to pH 3 using dilute aqueous HCl solution. The mixture was left to stand at RT for 64 h then filtered. The resulting solid was washed with water (2 ml) then dried under vacuum to afford the product as a brown solid (85 mg, >99%). $^1$H NMR (250 MHz, DMSO-$d_6$) δ 11.39 (s, 1H), 6.91 (br. s, 2H), 6.14 (s, 1H), 2.36 (s, 3H).

LC/MS (System A): m/z (ESI+)=193 [MH$^+$], Rt=0.64 min, UV purity=90%.

Intermediate 10-Synthesis of methyl 3-amino-7-iodo-5H-pyrrolo[2,3-b]pyrazine-2-carboxylate

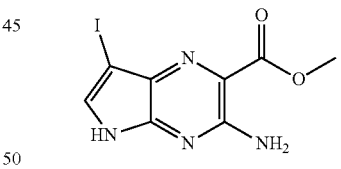

A mixture of methyl 3-amino-5H-pyrrolo[2,3-b]pyrazine-2-carboxylate, Intermediate 2 (98%, 1.50 g, 7.65 mmol) and NIS (1.84 g, 8.16 mmol) in acetone (30 ml) was stirred at RT for 2 h. Additional NIS (350 mg, 1.56 mmol) was added and the reaction was stirred at RT for a further 0.5 h. The reaction mixture was concentrated in vacuo to a black solid. The crude material was purified by flash column chromatography on a silica column (100 g). The column was eluted with $CH_2Cl_2$:MeOH, using the following gradient (% MeOH, column volumes): 0%, 1 CV; 0-3.5%, 4 CV; 3.5%, 2 CV; 3.5-4.4%, 1 CV. The desired fractions were combined and concentrated in vacuo. The material thus obtained was further purified by preparative HPLC (Method A). The desired fractions were combined and concentrated in vacuo to afford the product as a yellow/orange solid (591 mg, 24%).

$^1$H NMR (500 MHz, DMSO-d$_6$) δ 11.89 (s, 1H), 7.72 (s, 1H), 7.21 (s, 2H), 3.88 (s, 3H).

LC/MS (System A): m/z (ESI+)=319 [MH$^+$], Rt=0.94 min, UV purity=100%.

Intermediate 11-Synthesis of methyl 3-amino-7-methyl-5H-pyrrolo[2,3-b]pyrazine -2-carboxylate

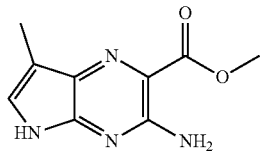

Dimethylzinc solution in toluene (2.0 M, 0.88 ml, 1.8 mmol) was added dropwise over 2 min to a cooled (0° C.) suspension of methyl 3-amino-7-iodo-5H-pyrrolo[2,3-b]pyrazine-2-carboxylate, Intermediate 10 (280 mg, 0.88 mmol) and Pd(Pt-Bu$_3$)$_2$ (45 mg, 0.09 mmol) in THF (5 ml). The reaction mixture was stirred at 0° C. for 30 min then allowed to warm to RT. Additional dimethylzinc solution in toluene (2.0 M, 0.88 ml, 1.8 mmol) and a solution of Pd(Pt-Bu$_3$)$_2$ (45 mg, 0.09 mmol) in THF (2 ml) were added then the resulting mixture was stirred at RT for 10 min. Saturated aqueous NaHCO$_3$ solution (10 ml) was added followed by EtOAc (30 ml). The mixture was filtered through a Celite pad then the phases were separated. The organic phase was extracted with water (3×80 ml) and brine (80 ml) then dried over Na$_2$SO$_4$ and concentrated in vacuo. The crude material was purified by flash column chromatography on a silica column (100 g). The column was eluted with EtOAc:heptane, increasing the gradient linearly from 0-100% EtOAc over 10 CV. The desired fractions were combined and concentrated in vacuo to afford the product as a yellow solid (85 mg, 46%).

$^1$H NMR (500 MHz, DMSO-d$_6$) δ 11.13 (s, 1H), 7.25 (dd, J=2.3, 1.2 Hz, 1H), 7.03 (s, 2H), 3.85 (s, 3H), 2.17 (d, J=1.2 Hz, 3H).

LC/MS (System A): m/z (ESI+)=207 [MH$^+$], Rt=0.85 min, UV purity=99%.

Intermediate 12-Synthesis of lithium (1l ion 3-amino-7-methyl-5H-pyrrolo[2,3-b]pyrazine-2-carboxylate

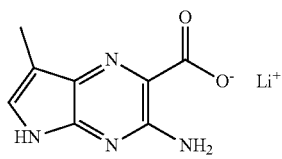

Aqueous LiOH solution (1.0 M, 1.0 ml, 1.0 mmol) was added to a mixture of methyl 3 -amino-7-methyl-5H-pyrrolo[2,3-b]pyrazine-2-carboxylate, Intermediate 11 (110 mg, 0.53 mmol) in MeOH (1 ml). The reaction was heated at 50° C. for 1 h then allowed to cool to RT. The resultant mixture was filtered then the solid was washed with water and dried under vacuum to afford the product as a yellow solid (91 mg, 84%).

$^1$H NMR (500 MHz, DMSO-d$_6$) δ 10.80 (s, 1H), 8.68-6.32 (m, 3H), 2.12 (s, 3H).

LC/MS (System A): m/z (ESI+)=193 [MH$^+$], Rt=0.77 min, UV purity=98%.

Intermediate 13-Synthesis of 2-(1H-imidazole-1-carbonyl)-7-methyl-5H -pyrrolo[2,3-b]pyrazin-3-amine

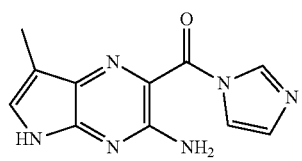

A mixture of lithium(1$^+$) ion 3-amino-7-chloro-5H-pyrrolo[2,3-b]pyrazine-2-carboxylate, Intermediate 12 (90 mg, 0.45 mmol), CDI (110 mg, 0.67 mmol) and 1H-imidazole hydrochloride (1:1) (56 mg, 0.53 mmol) in DMF (2 ml) was stirred at RT for 1 h. Additional CDI (50 mg, 0.31 mmol) was added and the reaction was allowed to continue for a further 1 h. The reaction mixture was diluted with water (4 ml) then filtered. The solid was washed with water then dried under vacuum to afford the product as a yellow solid (83 mg, 75%).

$^1$H NMR (500 MHz, DMSO-d$_6$) δ 11.37 (s, 1H), 8.84 (s, 1H), 8.00 (t, J=1.4 Hz, 1H), 7.45 (s, 2H), 7.41-7.37 (m, 1H), 7.12-7.08 (m, 1H), 2.22 (d, J=1.1 Hz, 3H).

LC/MS (System A): m/z (ESI+)=243 [MH$^+$], Rt=0.78 min, UV purity=98%.

Intermediate 14-Synthesis of methyl 3-amino-7-chloro-5H-pyrrolo[2,3-b]pyrazine -2-carboxylate

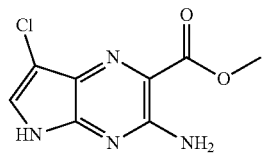

A mixture of methyl 3-amino-5H-pyrrolo[2,3-b]pyrazine-2-carboxylate, Intermediate 2 (98%, 1.00 g, 5.10 mmol) and NCS (0.561 g, 4.20 mmol) in DMF (15 ml) was stirred at 40° C. for 2 h. Additional NCS (50 mg, 0.37 mmol) was added and the reaction was stirred at 40° C. for an additional 2 h. The reaction mixture was partitioned between water (100 ml) and EtOAc (100 ml). The phases were separated then the organic phase was washed with water (2×100 ml) then dried over Na$_2$SO$_4$ and concentrated in vacuo. The crude material was purified by flash column chromatography on a silica column (100 g). The column was eluted with CH$_2$Cl$_2$:MeOH, increasing the gradient linearly from 100:0 to 90:10 over 8 column volumes then isocratic at 90:10 for 5 column volumes. The desired fractions were combined and evaporated. The residue thus obtained was suspended in CH$_2$Cl$_2$:MeOH (9:1, 20 ml) then filtered. The filtrate was further purified by flash column chromatography on C18 (60 g). The column was eluted with MeCN:water+0.1% formic acid using the following gradient (% MeCN, column volumes): 10%, 2 CV; 10-20%, 8 CVs; 20-37%, 8 CV; 37-100%, 5 CV;

100%, 1 CV. The solid from the filtration was dissolved in DMSO:MeCN (2:1) then purified by preparative HPLC (Method A). The desired fractions from both columns were combined and evaporated to afford the product as a yellow solid (222 mg, 19%).

$^1$H NMR (500 MHz, DMSO-$d_6$) δ 11.76 (s, 1H), 7.68 (s, 1H), 7.24 (s, 2H), 3.87 (s, 3H).

LC/MS (System A): m/z (ESI+)=227 [MH$^+$], Rt=0.88 min, UV purity=100%.

Intermediate 15-Synthesis of lithium(1$^+$) ion 3-amino-7-chloro-5H-pyrrolo[2,3b]-pyrazine-2-carboxylate

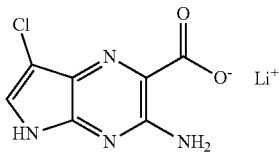

Aqueous LiOH solution (1.0 M, 1.9 ml, 1.9 mmol) was added to a mixture of methyl 3-amino-7-chloro-5H-pyrrolo[2,3-b]pyrazine-2-carboxylate, Intermediate 14 (220 mg, 0.97 mmol) in MeOH (3 ml). The reaction mixture was heated to 50° C. for 2 h then allowed to cool to RT. The resulting suspension was filtered then the collected solid was washed with the minimum of MeOH and water. The resulting solid was dried under vacuum to afford the product as a yellow solid (191 mg, 87%).

$^1$H NMR (500 MHz, DMSO-$d_6$) δ 11.37 (s, 1H), 8.39-7.10 (m, 3H).

LC/MS (System A): m/z (ESI+)=213 [MH$^+$], Rt=0.81 min, UV purity=97%.

Intermediate 16-Synthesis of 7-chloro-2-(1H-imidazole-1-carbonyl)-5H-pyrrolo[2,3-b]pyrazin-3-amine

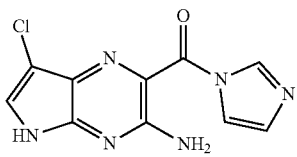 [SMILES: Nc1nc2[nH]cc(Cl)c2nc1C(=O)n1ccnc1]

A mixture of lithium(1$^+$) ion 3-amino-7-chloro-5H-pyrrolo[2,3-b]pyrazine-2-carboxylate, Intermediate 15 (190 mg, 0.869 mmol), CDI (211 g, 1.30 mmol) and 1H-imidazole hydrochloride (1:1) (100 mg, 0.956 mmol) in DMF (4 ml) was stirred at RT for 0.5 h. Additional CDI (50 mg, 0.31 mmol) was added and the reaction was left to stir at RT for a further 0.5 h. The reaction mixture was diluted with water (6 ml) then left to stir at RT for 20 min. The resulting suspension was filtered then the collected solid was washed with water then dried under vacuum to afford the product as a yellow/orange solid (164 mg, 72%).

$^1$H NMR (500 MHz, DMSO-$d_6$) δ 11.98 (s, 1H), 8.80 (s, 1H), 7.99 (t, J=1.4 Hz, 1H), 7.84 (s, 1H), 7.58 (s, 2H), 7.12 (dd, J=1.5, 0.8 Hz, 1H).

LC/MS (System A): m/z (ESI+)=263 [MH$^+$], Rt=0.82 min, ELS purity=100%.

Intermediate 17-Synthesis of tert-butyl N-[(1-ethyl-6-fluoro-1H-1,3-benzodiazol-2-yl)methyl]carbamate

A solution of 2-{[(tert-butoxy)carbonyl]amino}acetic acid (1.70 g, 9.73 mmol), HATU (4.07 g, 10.7 mmol) and DIPEA (3.39 ml, 19.5 mmol) in DMF (20 ml) was stirred at RT for 20 min. A solution of 1-N-ethyl-5-fluorobenzene-1,2-diamine (1.05 g, 9.73 mmol) in THF (10 ml) was added and the resulting mixture was stirred at RT for 16 h. The reaction mixture was poured onto saturated aqueous NaHCO$_3$ solution (80 ml). EtOAc (100 ml) and water (50 ml) were added then the phases were separated. The aqueous phase was extracted with EtOAc (2×50 ml) then the combined organic phases were washed with water (4×50 ml) and brine (50 ml), then dried over Na$_2$SO$_4$, filtered and evaporated to afford the intermediate as a black oil (4 g). The intermediate was dissolved in acetic acid (30 ml) then heated at 60° C. for 4 h. The reaction mixture was allowed to cool to RT then stirred at RT for 16 h. The resulting mixture was evaporated then the resulting residue was partitioned between EtOAc (150 ml) and water (100 ml). The aqueous phase was extracted with EtOAc (50 ml) then the combined organic phases were washed with water (4×50 ml) and brine (50 ml), then dried over Na$_2$SO$_4$, filtered and evaporated to a black solid (4 g). The solid was dissolved in the minimum of CH$_2$Cl$_2$/MeOH then evaporated onto silica (9 g). The crude material was purified by flash column chromatography on a silica column (120 g). The column was eluted with CH$_2$Cl$_2$:MeOH, increasing the gradient linearly from 100:0 to 95:5 over 10 column volumes. The desired fractions were combined and evaporated to a black solid (2.9 g). The solid thus obtained was dissolved in EtOAc (100 ml) and extracted with saturated aqueous sodium bicarbonate solution (3×50 ml) and water (50 ml) then dried over Na$_2$SO$_4$, filtered and evaporated to a black soli d (2.5 g). The solid was dissolved in the minimum of CH$_2$Cl$_2$/MeOH then evaporated onto silica (10 g). The material was further purified by flash column chromatography on a silica column (120 g). The column was eluted with EtOAc:heptane, increasing the gradient linearly from 0:100 to 100:0 over 10 column volumes. The desired fractions were combined and evaporated to afford the product as a pink solid (1.78 g, 62%).

$^1$H NMR (500 MHz, DMSO-$d_6$) δ 7.56 (dd, J=8.8, 4.9 Hz, 1H), 7.50-7.41 (m, 2H), 7.01 (ddd, J=9.9, 8.9, 2.5 Hz, 1H), 4.42 (d, J=5.9 Hz, 2H), 4.24 (q, J=7.2 Hz, 2H), 1.45-1.20 (m, 12H).

LC/MS (System A): m/z (ESI$^+$)=294 [MH$^+$], R$_t$=0.92 min, UV purity=100%.

Intermediate 18-Synthesis of 2-({[(tert-butoxy)carbonyl]amino}methyl)-1-ethyl-6-fluoro-3-methyl-1H-1,3-benzodiazol-3-ium iodide

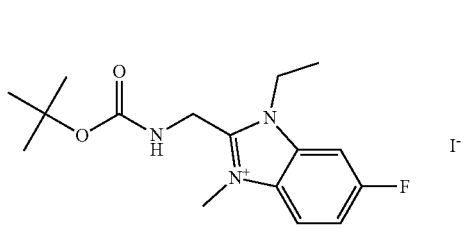 [SMILES: CCn1c(CNC(=O)OC(C)(C)C)[n+](C)c2ccc(F)cc21 ; [I-]]

Iodomethane (497 µl, 7.98 mmol) was added to a suspension of tert-butyl N-[(1-ethyl-6-fluoro-1H-1,3-benzodiazol-2-yl)methyl]carbamate, Intermediate 17 (780 mg, 2.66 mmol) in MeCN (12 ml) in a pressure tube. The tube was sealed then heated at 75° C. for 4 h. The reaction mixture was allowed to cool to RT then concentrated in vacuo to afford the product as a pale yellow solid (1.16 g, 99%).

$^1$H NMR (500 MHz, DMSO-d$_6$) δ 8.14-8.04 (m, 2H), 7.94 (t, J=5.2 Hz, 1H), 7.68-7.56 (m, 1H), 4.73 (d, J=5.4 Hz, 2H), 4.58 (q, J=7.2 Hz, 2H), 4.08 (s, 3H), 1.38 (d, J=11.2 Hz, 12H).

LC/MS (System A): m/z (ESI$^+$)=308 [M$^+$], R$_t$=0.87 min, UV purity=99%.

Intermediate 19-Synthesis of 2-(aminomethyl)-1-ethyl-6-fluoro-3-methyl-1H-1,3-benzodiazol-3-ium hydrochloride iodide

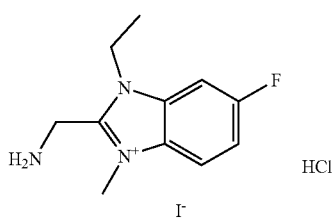

HCl solution in dioxane (4.0 M, 3.3 ml, 13.2 mmol) was added to a solution of 2-({[(tert-butoxy)carbonyl]amino}methyl)-1-ethyl-6-fluoro-3-methyl-1H-1,3-benzodiazol-3-ium iodide, Intermediate 18 (1.16 g, 2.66 mmol) in MeCN (5 ml). The reaction was stirred at RT for 0.5 h then concentrated in vacuo. The solid was azeotroped with MeCN (10 ml) then dried under vacuum to yield the product as a yellow/green solid (870 mg, 88%).

$^1$H NMR (500 MHz, DMSO-d$_6$) δ 9.21 (s, 3H), 8.25-8.14 (m, 2H), 7.69 (td, J=9.3, 2.4 Hz, 1H), 4.76 (s, 2H), 4.70 (q, J=7.2 Hz, 2H), 4.19 (s, 3H), 1.42 (t, J=7.2 Hz, 3H).

LC/MS (System A): m/z (ESI$^+$)=208 [M$^+$], R$_t$=0.14 min, ELS purity=100%.

Intermediate 20-Synthesis of 2-[(6-chloro-1-ethyl-1H-1,3-benzodiazol-2-yl)methyl]-2,3-dihydro-1H-isoindole-1,3-dione

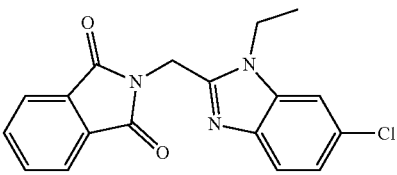 [SMILES: CCn1c(CN2C(=O)c3ccccc3C2=O)nc2ccc(Cl)cc21]

A mixture of N-phthaloylglycine (2.15 g, 10.5 mmol), TBTU (3.52 g, 11.0 mmol) and triethylamine (2.31 ml, 13.0 mmol) in DMF (30 ml) was stirred at RT for 45 min. A solution of 5-chloro-1-N-ethylbenzene-1,2-diamine (1.70 g, 9.96 mmol) in THF (20 ml) was added and the resulting mixture was stirred at RT for 18 h. The reaction mixture was added to saturated aqueous NaHCO3 solution (100 ml) which caused a pale brown solid to precipitate from solution. The solid was filtered, washed with water and dried under vacuum. The solid thus obtained was triturated in MeCN then filtered and dried under vacuum to afford the intermediate as a pale pink solid (5.4 g). The solid thus obtained was added portion-wise to acetic acid (30 ml). The resulting suspension was heated at 100° C. for 45 min then allowed to cool to RT over 16 h. The resulting suspension was filtered and washed with EtOAc then dried under vacuum to afford the product as a pale pink solid (585 mg). The solid was suspended in MeCN (5 ml) then MeCN:water (1:1, 1 ml) was added. The resulting suspension was filtered then the solid was dried under vacuum to afford the product as a pale pink solid (430 mg, 13%). The filtrate was again filtered, then the solid was washed with EtOAc and dried under vacuum to afford a second batch of product as a pale pink solid (2.00 g). The solid was suspended in MeCN (20 ml) then MeCN:water (1:1, 5 ml) was added. The resulting suspension was filtered then the solid was dried under vacuum to afford second batch of the product as a pale pink solid (1.33 g, 38%). The two batches of product were as a suspension in MeCN then concentrated in vacuo and dried under vacuum to afford the product as a pale pink solid (1.76 g, 51%).

$^1$H NMR (250 MHz, DMSO-d$_6$) δ 8.02-7.85 (m, 4H), 7.76 (d, J=1.9 Hz, 1H), 7.49 (d, J=8.6 Hz, 1H), 7.15 (dd, J=8.6, 2.0 Hz, 1H), 5.13 (s, 2H), 4.39 (q, J=7.1 Hz, 2H), 1.37 (t, J=7.2 Hz, 3H).

LC/MS (System A): m/z (ESI$^+$)=340 [M($^{35}$Cl)H$^+$], 342 [M($^{37}$Cl)H$^+$], R$_t$=1.12 min, UV purity=99%.

Intermediate 21-Synthesis of 6-chloro-2-[(1,3-dioxo-2,3-dihydro-1H-isoindol-2-yl)methyl]-1-ethyl-3-methyl-1H-1,3-benzodiazol-3-ium iodide

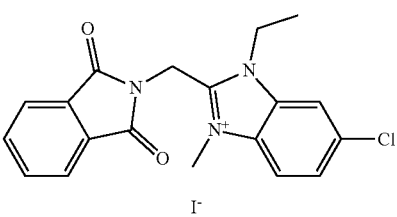 [SMILES: CCn1c(CN2C(=O)c3ccccc3C2=O)[n+](C)c2ccc(Cl)cc21 ; [I-]]

A mixture of 2-[(6-chloro-1-ethyl-1H-1,3-benzodiazol-2-yl)methyl]-2,3-dihydro-1H-isoindole-1,3-dione, Intermediate 20 (600 mg, 1.77 mmol) and iodomethane (330 µl, 5.30 mmol) in MeCN (6 ml) was heated at 75° C. in a sealed tube for 1.5 h then allowed to cool to RT. Iodomethane (165 µl, 2.65 mmol) was added then the reaction was heated at 80° C. for 5 h. The reaction was allowed to cool to RT then filtered to afford a solid which was washed with MeCN and dried under vacuum to afford the product as a yellow solid (644 mg, 73%).

$^1$H NMR (500 MHz, DMSO-$d_6$) δ 8.40 (d, J=1.8 Hz, 1H), 8.13 (d, J=8.9 Hz, 1H), 7.91 (ddt, J=18.3, 5.8, 3.1 Hz, 4H), 7.79 (dd, J=8.9, 1.9 Hz, 1H), 5.40 (s, 2H), 4.74 (q, J=7.2 Hz, 2H), 4.14 (s, 3H), 1.43 (t, J=7.2 Hz, 3H).

LC/MS (System A): m/z (ESI$^+$)=354 [M($^{35}$Cl)$^+$], 356 [M($^{37}$Cl)$^+$], $R_t$=0.90 min, UV purity=97%.

Intermediate 22-Synthesis of 2-(aminomethyl)-6-chloro-1-ethyl-3-methyl-1H-1,3-benzodiazol-3-ium iodide

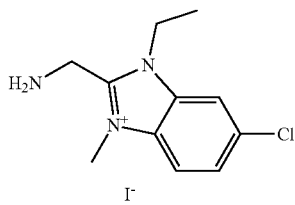

Hydrazine hydrate (446 µl, 9.17 mmol) was added to a suspension of 6-chloro-2-[(1,3-dioxo-2,3-dihydro-1H-isoindol-2-yl)methyl]-1-ethyl-3-methyl-1H-1,3-benzodiazol-3-ium iodide, Intermediate 21 (640 mg, 1.33 mmol) in MeOH (8 ml) in a pressure tube. The tube was sealed and heated at 75° C. for 3 h then allowed to cool to RT. The resulting suspension was filtered and the solid was washed with MeOH (10 ml). The filtrate was concentrated in vacuo to afford an orange solid, which was suspended in CH$_2$Cl$_2$ (10 ml) then filtered and washed through with CH$_2$Cl$_2$. The solid thus obtained was suspended in CH$_2$Cl$_2$ (10 ml). A few drops of MeOH were added and the suspension was sonicated. The resulting suspension was filtered then the solid was dried under vacuum to afford the product as an off-white solid (360 mg, 77%).

$^1$H NMR (500 MHz, DMSO-$d_6$) δ 8.31 (d, J=1.9 Hz, 1H), 8.06 (d, J=8.9 Hz, 1H), 7.73 (dd, J=8.8, 1.9 Hz, 1H), 4.60 (q, J=7.2 Hz, 2H), 4.25 (s, 2H), 4.06 (s, 3H), 2.52-2.10 (s, 2H+DMSO), 1.41 (t, J=7.2 Hz, 3H).

LC/MS (System A): m/z (ESI$^+$)=224 [M($^{35}$Cl)$^+$], 226 [M($^{37}$Cl)$^+$], $R_t$=0.16 min, ELS purity=100%.

Intermediate 23-Synthesis of 2-[(1-ethyl-6-methoxy-1H-1,3-benzodiazol-2-yl)methyl]-2,3-dihydro-1H-isoindole-1,3-dione

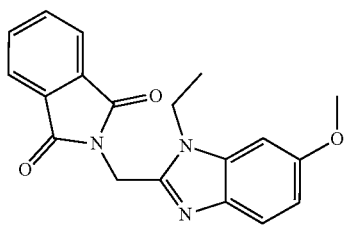 [SMILES: CCn1c(CN2C(=O)c3ccccc3C2=O)nc2ccc(OC)cc21]

Intermediate 23 was synthesised according to literature procedures (US 2015/0018314 A1).

Intermediate 24-Synthesis of 2-[(1,3-dioxo-2,3-dihydro-1H-isoindol-2-yl)methyl]-1-ethyl-6-methoxy-3-methyl-1H-1,3-benzodiazol-3-ium iodide

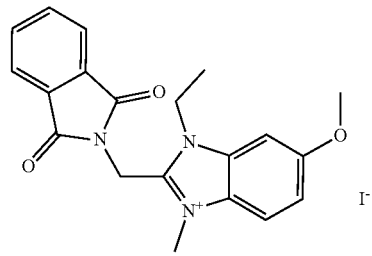 [SMILES: CCn1c(CN2C(=O)c3ccccc3C2=O)[n+](C)c2ccc(OC)cc21 ; [I-]]

Iodomethane (590 µl, 9.47 mmol) was added to a suspension of 2-[(1-ethyl-6-methoxy-1H-1,3-benzodiazol-2-yl)methyl]-2,3-dihydro-1H-isoindole-1,3-dione, Intermediate 23 (1.59 g, 4.74 mmol) in MeCN (13 ml) in a pressure tube. The mixture was heated at 80° C. for 4 h then allowed to cool to RT. The resulting suspension was reduced to approximately half of the original volume under a stream of nitrogen. The solid was collected by filtration then washed with further MeCN (3 ml) to yield the product as a white solid (1.99 g, 87%).

$^1$H NMR (500 MHz, DMSO-$d_6$) δ 8.01-7.84 (m, 5H), 7.62 (d, J=2.2 Hz, 1H), 7.32 (dd, J=9.2, 2.3 Hz, 1H), 5.37 (s, 2H), 4.71 (q, J=7.1 Hz, 2H), 4.11 (s, 3H), 3.92 (s, 3H), 1.42 (t, J=7.2 Hz, 3H).

LC/MS (System A): m/z (ESI$^+$)=350 [M$^+$], $R_t$=0.87 min, UV purity=99%.

Intermediate 25-Synthesis of 2-(aminomethyl)-1-ethyl-6-methoxy-3-methyl-1H-1,3-benzodiazol-3-ium iodide

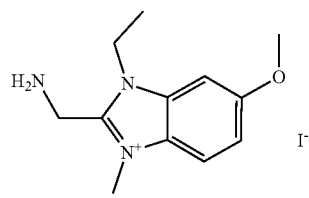 [SMILES: CCn1c(CN)[n+](C)c2ccc(OC)cc21 ; [I-]]

Hydrazine hydrate (1.17 ml, 24.0 mmol) was added to a suspension of 2-[(1,3-dioxo-2,3-dihydro-1H-isoindol-2-yl)methyl]-1-ethyl-6-methoxy-3-methyl-1H-1,3-benzodiazol-3-ium iodide, Intermediate 24 (2.29 g, 4.80 mmol) in MeOH (25 ml). The mixture was heated at 75° C. for 1 h. The reaction was concentrated in vacuo and the resulting solid was suspended in CH$_2$Cl$_2$:MeOH (10:1). The solid was collected by filtration and washed with CH$_2$Cl$_2$. The filtrate was concentrated in vacuo to afford the product as a pale brown solid (1.60 g, 96%).

$^1$H NMR (500 MHz, DMSO-$d_6$) δ 7.91 (d, J=9.1 Hz, 1H), 7.57 (d, J=2.3 Hz, 1H), 7.26 (dd, J=9.1, 2.3 Hz, 1H), 4.58 (q, J=7.2 Hz, 2H), 4.23 (s, 2H), 4.03 (s, 3H), 3.91 (s, 3H), 1.42 (t, J=7.2 Hz, 3H).

LC/MS (System A): m/z (ESI⁺)=220 [M⁺], $R_t$=0.14 min, ELS purity=100%.

Intermediate 26-Synthesis of tert-butyl N-{[1-ethyl-6-(trifluoromethyl)-1H-1,3-benzodiazol-2-yl]methyl}carbamate

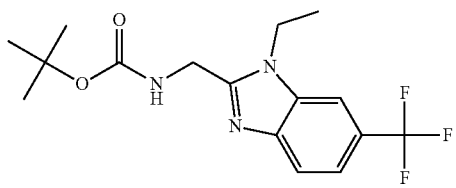 [SMILES: CCn1c(CNC(=O)OC(C)(C)C)nc2ccc(C(F)(F)F)cc21]

Intermediate 26 was synthesised according to literature procedures (WO 2009019506 A1).

Intermediate 27-Synthesis of 2-({[(tert-butoxy)carbonyl]amino}methyl)-1-ethyl-3-methyl-6-(trifluoromethyl)-1H-1,3-benzodiazol-3-ium iodide

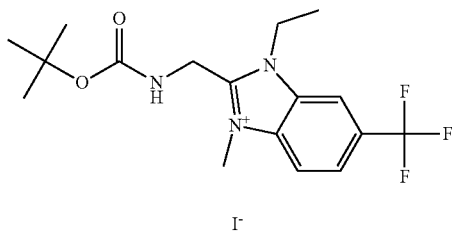 [SMILES: CCn1c(CNC(=O)OC(C)(C)C)[n+](C)c2ccc(C(F)(F)F)cc21 ; [I-]]

Iodomethane (381 μl, 6.12 mmol) was added to a suspension of tert-butyl N-{[1-ethyl-6-(trifluoromethyl)-1H-1,3-benzodiazol-2-yl]methyl}carbamate, Intermediate 26 (700 mg, 2.04 mmol) in MeCN (10 ml) in a pressure tube. The tube was sealed and heated at 75° C. for 8 h then allowed to cool to RT. The reaction mixture was concentrated in vacuo to afford the product as a pale yellow solid (1.01 g, >99%).

¹H NMR (500 MHz, DMSO-d₆) δ 8.64 (s, 1H), 8.29 (d, J=8.7 Hz, 1H), 8.08 (d, J=8.7 Hz, 1H), 7.98 (t, J=5.2 Hz, 1H), 4.80 (d, J=5.6 Hz, 2H), 4.73 (q, J=7.2 Hz, 2H), 4.14 (s, 3H), 1.40 (m, 12H).

LC/MS (System A): m/z (ESI⁺)=358 [M⁺], $R_t$=0.91 min, UV purity=98%.

Intermediate 28-Synthesis of 2-(aminomethyl)-1-ethyl-3-methyl-6-(trifluoromethyl)-1H-1,3-benzodiazol-3-ium hydrochloride iodide

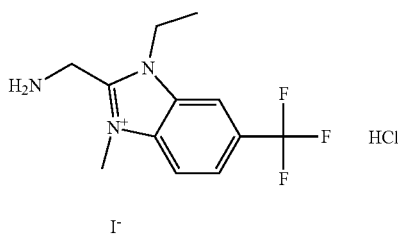 [SMILES: CCn1c(CN)[n+](C)c2ccc(C(F)(F)F)cc21 ; Cl ; [I-]]

HCl solution in dioxane (4.0 M, 2.8 ml, 11 mmol) was added to a solution of 2-({[(tert-butoxy)carbonyl]amino}methyl)-1-ethyl-3-methyl-6-(trifluoromethyl)-1H-1,3-benzodiazol-3-ium iodide, Intermediate 27 (1.07 g, 2.21 mmol) in MeCN (5 ml). The reaction was stirred at RT for 16 h then concentrated in vacuo to yield the product as an off-white solid (875 mg, 94%).

¹H NMR (500 MHz, DMSO-d₆) δ 9.14 (s, 3H), 8.74 (s, 1H), 8.38 (d, J=8.8 Hz, 1H), 8.14 (dd, J=8.8, 1.3 Hz, 1H), 4.84 (d, J=5.5 Hz, 4H), 4.24 (s, 3H), 1.45 (t, J=7.2 Hz, 3H).

LC/MS (System A): m/z (ESI⁺)=258 [M⁺], $R_t$=0.17 min, ELS purity=100%.

Intermediate 29-Synthesis of N-ethyl-2-nitro-5-(trifluoromethoxy)aniline

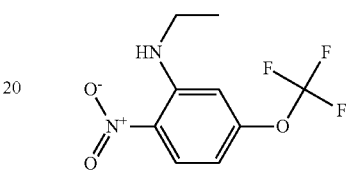

Two identical reactions were carried out in parallel as follows then combined for work-up. Ethylamine solution in THF (2.0 M, 4.1 ml, 8.2 mmol) was added to a suspension of 2-chloro-1-nitro-4-(trifluoromethoxy)benzene (1.00 g, 4.14 mmol) and K₂CO₃ (1.71 g, 6.21 mmol) in THF (12 ml) in a pressure tube. The tube was sealed then heated at 50° C. for 16 h then allowed to cool to RT. Additional ethylamine solution in THF (2.0 M, 2.1 ml, 4.2 mmol) was added then the reaction was heated at 50° C. for 24 h. The combined reactions were filtered then the solid thus obtained was rinsed with EtOAc (100 ml). The combined filtrates were extracted with saturated aqueous NaHCO₃ solution (2×100 ml), water (50 ml) and brine (50 ml) then dried over Na₂SO₄, then filtered and evaporated to an orange oil. The crude material was purified by flash column chromatography on C18 (120 g). The column was eluted with MeCN:water using the following gradient (% MeCN, column volumes): 10%, 2 CV; 10-100%, 20 CVs; 100%, 2 CV. The desired fractions were combined and concentrated in vacuo to remove most of the MeCN. The residual aqueous mixture was extracted with EtOAc (100 ml). The organic phase was separated, then dried over Na₂SO₄ and evaporated to afford the product as a bright orange oil (1.42 g, 69%).

¹H NMR (500 MHz, CDCl₃) δ 8.23 (d, J=9.4 Hz, 1H), 8.04 (s, 1H), 6.61 (d, J=2.0 Hz, 1H), 6.48 (ddd, J=9.4, 2.4, 1.2 Hz, 1H), 3.33 (qd, J=7.2, 5.1 Hz, 2H), 1.39 (t, J=7.2 Hz, 3H).

LC/MS (System A): m/z (ESI⁺)=251 [MH⁺], $R_t$=1.32 min, UV purity=100%.

Intermediate 30-Synthesis of tert-butyl N-{[1-ethyl-6-(trifluoromethoxy)-1H-1,3-benzodiazol-2-yl]methyl} carbamate

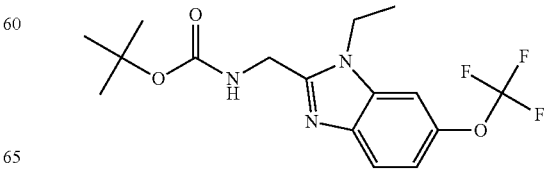

A suspension of palladium on carbon (10 wt %, 0.3 g) and N-ethyl-2-nitro-5-(trifluoromethoxy)aniline, Intermediate 29 (1.42 g, 5.68 mmol) solution in EtOH (40 ml) was stirred under a hydrogen atmosphere at RT for 16 h. The reaction mixture was filtered through glass fibre filter paper and washed through with EtOAc. The filtrate was concentrated in vacuo and then diluted with THF (10 ml). The resulting solution was added to a pre-mixed solution of 2-{[(tert-butoxy)carbonyl]amino}acetic acid (994 mg, 5.68 mmol), HATU (2.37 g, 6.24 mmol) and DIPEA (1.98 ml, 11.4 mmol) in DMF (20 ml). The reaction mixture was stirred at RT for 68 h then poured onto saturated aqueous NaHCO$_3$ (80 ml). EtOAc (50 ml) and water (50 ml) were added and the phases were separated. The aqueous phase was extracted with EtOAc (2×50 ml) then the combined organic phases were washed with water (4×50 ml) and brine (50 ml) then dried over Na$_2$SO$_4$, filtered and evaporated to a black oil. The oil thus obtained was dissolved in acetic acid (10 ml) and the resulting solution was heated at 70° C. for 1.5 h. The reaction solution was concentrated in vacuo then the residue was partitioned between EtOAc (50 ml) and saturated aqueous NaHCO$_3$ solution (50 ml). The organic phase was washed with saturated aqueous NaHCO$_3$ solution (4×50 ml), water (50 ml) and brine (10 ml) then dried over Na$_2$SO$_4$, filtered and evaporated to a brown solid (1.95 g). The crude material was dissolved in CH$_2$Cl$_2$/MeOH then evaporated onto silica (10 g) and purified by flash column chromatography on a silica column (120 g). The column was eluted with EtOAc:heptane, increasing the gradient linearly from 0:100 to 100:0 over 10 column volumes. The desired fractions were combined and evaporated to yield the product as a pink solid (1.04 g, 47%).

$^1$H NMR (500 MHz, DMSO-d$_6$) δ 7.70-7.61 (m, 2H), 7.49 (d, J=5.1 Hz, 1H), 7.19-7.10 (m, 1H), 4.44 (d, J=5.9 Hz, 2H), 4.29 (q, J=7.1 Hz, 2H), 1.45-1.23 (m, 12H).

LC/MS (System A): m/z (ESI$^+$)=360 [MH$^+$], R$_t$=1.11 min, UV purity=92%.

Intermediate 31-Synthesis of 2-({[(tert-butoxy)carbonyl]amino}methyl)-1-ethyl-3-methyl-6-(trifluoromethoxy)-1H-1,3-benzodiazol-3-ium iodide

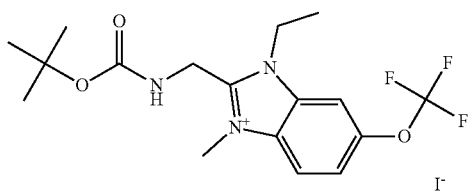 [SMILES: CCn1c(CNC(=O)OC(C)(C)C)[n+](C)c2ccc(OC(F)(F)F)cc21 ; [I-]]

Iodomethane (208 µl, 3.34 mmol) was added to a suspension of tert-butyl N-{[1-ethyl-6-(trifluoromethoxy)-1H-1,3-benzodiazol-2-yl]methyl} carbamate, Intermediate 30 (92%, 400 mg, 1.02 mmol) in MeCN (5 ml) in a pressure tube. The tube was sealed then heated at 75° C. for 5 h then allowed to cool to RT. The reaction mixture was concentrated in vacuo to yield the product as a dark green solid (552 mg, >99%).

$^1$H NMR (500 MHz, DMSO-d$_6$) δ 8.30 (s, 1H), 8.18 (d, J=9.1 Hz, 1H), 7.95 (t, J=5.2 Hz, 1H), 7.76 (d, J=9.1 Hz, 1H), 4.75 (d, J=5.4 Hz, 2H), 4.64 (q, J=7.1 Hz, 2H), 4.10 (s, 3H), 1.44-1.25 (m 12H).

LC/MS (System A): m/z (ESI$^+$)=374 [M$^+$], R$_t$=0.96 min, UV purity=93%.

Intermediate 32-Synthesis of 2-(aminomethyl)-1-ethyl-3-methyl-6-(trifluoromethoxy)-1H-1,3-benzodiazol-3-ium hydrochloride iodide

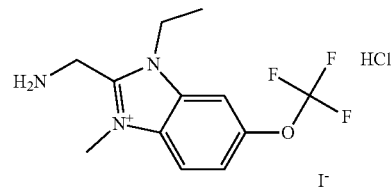 [SMILES: CCn1c(CN)[n+](C)c2ccc(OC(F)(F)F)cc21 ; Cl ; [I-]]

HCl solution in dioxane (4.0 M, 1.4 ml, 5.6 mmol) was added to a solution of 2-({[(tert-butoxy)carbonyl]amino}methyl)-1-ethyl-3-methyl-6-(trifluoromethoxy)-1H-1,3-benzodiazol-3-ium iodide, Intermediate 31 (93%, 550 mg, 1.02 mmol) in MeCN (5 ml). The reaction was left to stir at RT for 16 h then concentrated in vacuo. The solid was azeotroped with MeCN (10 ml) then dried under vacuum to yield the product as a brown solid (480 mg, 94%).

$^1$H NMR (500 MHz, DMSO-d$_6$) δ 9.11 (s, 3H), 8.40 (d, J=1.6 Hz, 1H), 8.28 (d, J=9.1 Hz, 1H), 7.83 (dd, J=9.1, 1.2 Hz, 1H), 4.80 (s, 2H), 4.75 (q, J=7.2 Hz, 2H), 4.21 (s, 3H), 1.42 (t, J=7.2 Hz, 3H).

LC/MS (System A): m/z (ESI$^+$)=274 [M$^+$], R$_t$=0.37 min, ELS purity=87%.

Intermediate 33-Synthesis of 6-chloro-2-[(1,3-dioxo-2,3-dihydro-1H-isoindol-2-yl)methyl]-1,3-diethyl-1H-1,3-benzodiazol-3-ium iodide

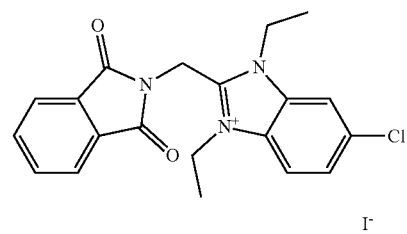 [SMILES: CCn1c(CN2C(=O)c3ccccc3C2=O)[n+](CC)c2ccc(Cl)cc21 ; [I-]]

A mixture of 2-[(6-chloro-1-ethyl-1H-1,3-benzodiazol-2-yl)methyl]-2,3-dihydro-1H-isoindole-1,3-dione, Intermediate 20 (850 mg, 2.50 mmol) and iodomethane (2.0 ml, 25 mmol) in MeCN (12 ml) was heated under microwave irradiation for 3 h at 120° C. The resulting solution was left to stand at RT for 64 h, resulting in precipitation of a solid. The solid was collected by filtration then washed with MeCN and dried under vacuum to afford the product as a pale yellow solid (850 mg, 67%).

$^1$H NMR (500 MHz, DMSO-d$_6$) δ 8.41 (d, J=1.8 Hz, 1H), 8.18 (d, J=8.9 Hz, 1H), 7.98-7.94 (m, 2H), 7.93-7.89 (m, 2H), 7.79 (dd, J=8.9, 1.9 Hz, 1H), 5.43 (s, 2H), 4.74-4.66 (m, 4H), 1.46-1.38 (m, 6H).

LC/MS (System A): m/z (ESI$^+$)=368 [M($^{35}$Cl)$^+$], 370 [M($^{37}$Cl)$^+$], R$_t$=0.93 min, UV purity=98%.

Intermediate 34-Synthesis of 2-(aminomethyl)-6-chloro-1,3-diethyl-1H-1,3-benzodiazol-3-ium iodide

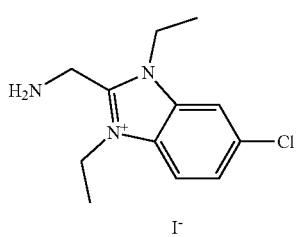 [SMILES: CCn1c(CN)[n+](CC)c2ccc(Cl)cc21 ; [I-]]

Hydrazine hydrate (787 μl, 16.2 mmol) was added to a suspension of 6-chloro-2-[(1,3-dioxo-2,3-dihydro-1H-isoindol-2-yhmethyl]-1,3-diethyl-1H-1,3-benzodiazol-3-ium iodide, Intermediate 33 (845 mg, 1.62 mmol) in MeOH (6 ml) in a pressure tube. The tube was sealed and heated at 80° C. for 4 h then allowed to cool to RT. The reaction mixture was concentrated in vacuo. The resultant residue was suspended in CH$_2$Cl$_2$:MeOH (9:1, 20 ml) then filtered. The filtrate was concentrated in vacuo to afford the product as a yellow solid (301 mg, 49%).

$^1$H NMR (500 MHz, DMSO-d$_6$) δ 7 8.32 (d, J=1.8 Hz, 1H), 8.11 (d, J=8.9 Hz, 1H), 7.73 (dd, J=8.8, 1.9 Hz, 1H), 4.65-4.56 (m, 4H), 4.29 (s, 2H), 1.46-1.40 (m, 6H).

LC/MS (System B): m/z (ESI$^+$)=238 [M($^{35}$Cl)$^+$], 240 [M($^{37}$Cl)$^+$], R$_t$=2.00 min, UV purity=97%.

Intermediate 35-Synthesis of 2-[(1,3-dioxo-2,3-dihydro-1H-isoindol-2-yl)methyl]-1,3-diethyl-6-methoxy-1H-1,3-benzodiazol-3-ium iodide

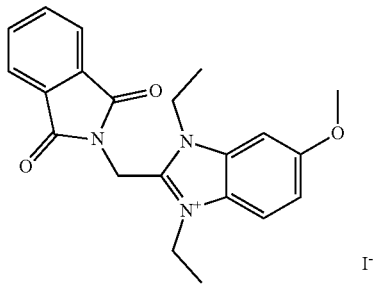 [SMILES: CCn1c(CN2C(=O)c3ccccc3C2=O)[n+](CC)c2ccc(OC)cc21 ; [I-]]

Iodoethane (715 μl, 8.95 mmol) was added to a suspension of 2-[(1-ethyl-6-methoxy-1H -1,3-benzodiazol-2-yl)methyl]-2,3-dihydro-1H-isoindole-1,3-dione, Intermediate 23 (3.00 g, 8.95 mmol) in MeCN (20 ml). The mixture was heated at 80° C. for 4 h. Iodoethane (715 μl, 8.95 mmol) was added and mixture was stirred at 80° C. for 16 h. Iodoethane (715 μl, 8.95 mmol) was added and mixture was stirred at 80° C. for a further 24 h the allowed to cool to RT. The mixture was concentrated in vacuo to approximately one third of the original volume. The precipitate was collected by filtration then washed with MeCN to afford a grey solid (2.6 g). The filtrate was concentrated to afford a dark grey solid. The two batches of solid thus obtained were combined and suspended in MeCN (20 ml). Iodoethane (715 μl, 8.95 mmol) was added then the reaction mixture was stirred at 80° C. for 18 h then at 100° C. for 4 h. The reaction mixture was split into two equal portions in pressure tubes. Iodoethane (300 μl, 3.75 mmol) was added to both reaction mixtures then the pressure tubes were sealed and left to heat at 100° C. for 16 h. The reaction mixtures were allowed to cool to RT then combined. The resultant mixture was concentrated in vacuo to ~5 ml then filtered. The collected solid was washed with the minimum of MeCN (0.5 ml) to yield the product as a grey solid (2.37 g). The filtrate was concentrated under reduced pressure to afford a dark brown solid, which was triturated with EtOAc (~10 ml) and filtered. The filtrate was left to stand for 16 h then it was filtered again. The solids obtained from the EtOAc filtrations were combined and dried to yield an additional batch of the product as a grey solid (1.24 g). The two batches of product obtained were combined as an EtOAc suspension then evaporated and dried under vacuum to afford the product as a grey solid (3.61 g, 81%).

$^1$H NMR (250 MHz, DMSO-d$_6$) δ 8.02 (d, J=9.2 Hz, 1H), 7.98-7.86 (m, 4H), 7.63 (d, J=2.2 Hz, 1H), 7.31 (dd, J=9.1, 2.3 Hz, 1H), 5.40 (s, 2H), 4.74-4.60 (m, 4H), 3.92 (s, 3H), 1.49-1.33 (m, 6H).

LC/MS (System A): m/z (ESI$^+$)=364 [M$^+$], R$_t$=0.93 min, UV purity=99%.

Intermediate 36-Synthesis of 2-(aminomethyl)-1,3-diethyl-6-methoxy-1H-1,3-iodide:

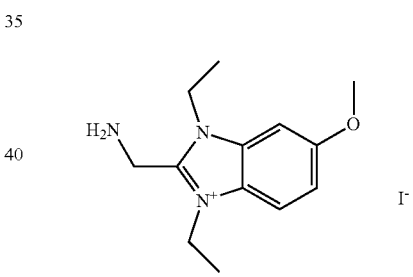

Hydrazine hydrate (1.18 ml, 24.1 mmol) was added to a suspension of 2-[(1,3-dioxo-2,3-dihydro-1H-isoindol-2-yl)methyl]-1,3-diethyl-6-methoxy-1H-1,3-benzodiazol-3-ium iodide, Intermediate 35 (2.37 g, 4.82 mmol) in MeOH (25 ml). The mixture was then heated at 75° C. for 2.5 h then left to cool to RT over 16 h. The reaction mixture was concentrated in vacuo and the resulting solid was suspended in CH$_2$Cl$_2$:MeOH (10:1) then filtered. The collected solid was washed with CH$_2$Cl$_2$. The filtrate was concentrated in vacuo to afford the product as a grey solid (1.89 g, >99%).

$^1$H NMR (250 MHz, DMSO-d$_6$) δ 7.95 (d, J=9.1 Hz, 1H), 7.58 (d, J=2.3 Hz, 1H), 7.25 (dd, J=9.1, 2.3 Hz, 1H), 4.65-4.50 (m, 4H), 4.25 (s, 2H), 3.91 (s, 3H), 1.50-1.39 (m, 6H).

LC/MS (System A): m/z (ESI$^+$)=234 [M$^+$], R$_t$=0.16 min, ELS purity=92%.

Intermediate 37-Synthesis of 3-benzyl-2-[(1,3-dioxo-2,3-dihydro-1H-isoindol-2-yl)methyl]-1-ethyl-6-methoxy-1H-1,3-benzodiazol-3-ium bromide

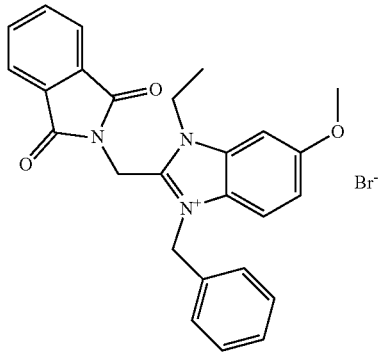 [SMILES: CCn1c(CN2C(=O)c3ccccc3C2=O)[n+](Cc2ccccc2)c2ccc(OC)cc21 ; [Br-]]

A mixture of 2-[(1-ethyl-6-methoxy-1H-1,3-benzodiazol-2-yl)methyl]-2,3-dihydro-1H-isoindole-1,3-dione, Intermediate 23 (500 mg, 1.49 mmol) and (bromomethyl)benzene (531 µl, 4.47 mmol) in MeCN (5 ml) was heated at 80° C. in a sealed tube for 16 h. The reaction mixture allowed to cool to RT then filtered. The solid was washed with MeCN then dried under vacuum to afford the product as a white solid (665 mg, 87%).

$^1$H NMR (500 MHz, DMSO-$d_6$) δ 7.84-7.79 (m, 3H), 7.78-7.74 (m, 2H), 7.71 (d, J=2.3 Hz, 1 H), 7.29 (dd, J=9.2, 2.3 Hz, 1H), 7.09 (t, J=7.7 Hz, 2H), 7.00-6.94 (m, 3H), 5.85 (s, 2H), 5.50 (s, 2H), 4.79 (q, J=7.2 Hz, 2H), 3.94 (s, 3H), 1.51 (t, J=7.2 Hz, 3H).

LC/MS (System A): m/z (ESI$^+$)=426 [M$^+$], R$_t$=1.02 min, UV purity=99%.

Intermediate 38-Synthesis of 2-(aminomethyl)-3-benzyl-1-ethyl-6-methoxy-1H-1,3-benzodiazol-3-ium bromide

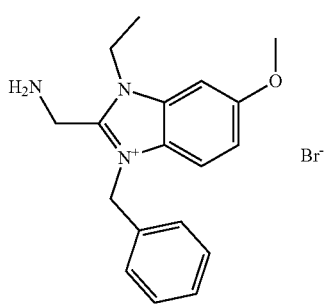 [SMILES: CCn1c(CN)[n+](Cc2ccccc2)c2ccc(OC)cc21 ; [Br-]]

A mixture of 3-benzyl-2-[(1,3-dioxo-2,3-dihydro-1H-isoindol-2-yl)methyl]-1-ethyl-6-methoxy-1H-1,3-benzodiazol-3-ium bromide, Intermediate 37 (665 mg, 1.31 mmol) and hydrazine hydrate (638 µl, 13.1 mmol) in MeOH (5 ml) was stirred at 80° C. for 2 h in a sealed tube. The reaction mixture was allowed to cool then concentrated in vacuo to a yellow solid. The residue was suspended in CH$_2$Cl$_2$ (20 ml) with sonication. The resultant suspension was filtered then the solid was re-suspended in CH$_2$Cl$_2$:MeOH (1:1, 30 ml) with sonication. The resultant suspension was filtered then the combined filtrates were concentrated in vacuo to afford the product as a yellow solid (526 mg, 60%).

$^1$H NMR (500 MHz, DMSO-$d_6$) δ 7.71 (d, J=9.1 Hz, 1H), 7.62 (d, J=2.3 Hz, 1H), 7.41-7.31 (m, 5H), 7.20 (dd, J=9.1, 2.3 Hz, 1H), 5.86 (s, 2H), 4.63 (q, J=7.2 Hz, 2H), 4.34 (s, 2H), 3.90 (s, 3H), 1.48 (t, J=7.2 Hz, 3H).

LC/MS (System A): m/z (ESI$^+$)=296 [M$^+$], R$_t$=0.76 min, UV purity=56%.

Intermediate 39-Synthesis of tert-butyl N-[(1-ethyl-6-methoxy-1H-1,3-benzodiazol-2-yl)methyl]carbamate

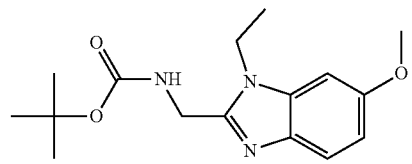 [SMILES: CCn1c(CNC(=O)OC(C)(C)C)nc2ccc(OC)cc21]

HATU (8.53 g, 22.3 mmol) and DIPEA (7.1 ml, 41 mmol) were added to a solution of N-(tert-butoxycarbonyl)glycine (3.93 g, 22.4 mmol) in DMF (40 ml). The resulting solution was stirred at RT for 0.5 h then a solution of 1-N-ethyl-5-methoxybenzene-1,2-diamine (3.39 g, 20.4 mmol) in THF (20 ml) was added. The reaction was left to stir at RT for 80 min then the reaction mixture was diluted with EtOAc (200 ml) and water (150 ml). The phases were separated then the organic phase was washed with water (3×150 ml) and brine (150 ml). The combined organic phases were dried over Na$_2$SO$_4$ then concentrated in vacuo to afford the crude intermediate as a dark red viscous oil. The intermediate was taken up in AcOH (40 ml) and the resulting solution was stirred at 60° C. for 18 h. The reaction mixture was allowed to cool then concentrated in vacuo. The residue was then dissolved in EtOAc (200 ml) then the pH was adjusted to 9 by the addition of saturated aqueous NaHCO3 solution. The phases were separated and the organic phase was washed with water (2×150 ml) and brine (150 ml), then dried over Na$_2$SO$_4$ and concentrated in vacuo to afford the crude product as a dark red oil. The crude material was purified by flash column chromatography on a silica column (340 g). The column was eluted with CH$_2$Cl$_2$:MeOH, increasing the gradient linearly from 100:0 to 92:8 over 10 column volumes. The desired fractions were combined and evaporated to a viscous dark red oil which solidified on standing to yield the product as a dark red solid (5.02 g, 77%).

$^1$H NMR (500 MHz, DMSO-$d_6$) δ 7.47-7.39 (m, 2H), 7.06 (d, J=2.4 Hz, 1H), 6.78 (dd, J=8.7, 2.4 Hz, 1H), 4.39 (d, J=5.9 Hz, 2H), 4.22 (q, J=7.1 Hz, 2H), 3.81 (s, 3H), 1.39 (s, 9H), 1.28 (t, J=7.2 Hz, 3H).

LC/MS (System A): m/z (ESI$^+$)=306 [MH$^+$], R$_t$=0.88 min, UV purity=96%.

Intermediate 40-Synthesis of 2-({[(tert-butoxy)carbonyl]amino}methyl)-1-ethyl-6-methoxy-3-(2-methoxy-2-oxoethyl)-1H-1,3-benzodiazol-3-ium bromide

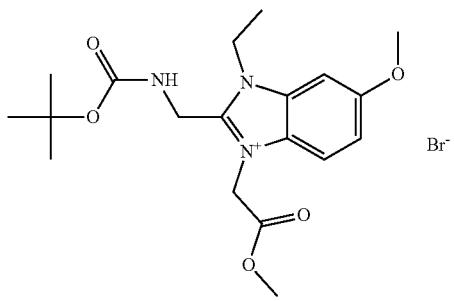 [SMILES: CCn1c(CNC(=O)OC(C)(C)C)[n+](CC(=O)OC)c2ccc(OC)cc21 ; [Br-]]

Methyl bromoacetate (395 µl, 4.18 mmol) was added to a suspension of tert-butyl N-[(1-ethyl-6-methoxy-1H-1,3-benzodiazol-2-yl)methyl]carbamate, Intermediate 39 (85%, 500 mg, 1.39 mmol) in MeCN (4 ml) in a pressure tube. The tube was sealed and the resulting mixture was stirred at 75° C. for 4 h then allowed to cool to RT. The resultant suspension was filtered then the solid was washed with cold MeCN and dried under vacuum to afford the product as a white solid (454 mg, 71%).

$^1$H NMR (500 MHz, DMSO-$d_6$) δ 7.90 (d, J=9.2 Hz, 1H), 7.86 (t, J=5.3 Hz, 1H), 7.62 (d, J=2.2 Hz, 1H), 7.29 (dd, J=9.1, 2.3 Hz, 1H), 5.58 (s, 2H), 4.75 (d, J=5.4 Hz, 2H), 4.65 (q, J=7.2 Hz, 2H), 3.92 (s, 3H), 3.75 (s, 3H), 1.43 (t, J=7.2 Hz, 3H), 1.35 (s, 9H).

LC/MS (System A): m/z (ESI$^+$)=378 [M$^+$], $R_t$=0.88 min, UV purity=100%.

Intermediate 41-Synthesis of 2-(aminomethyl)-1-ethyl-6-methoxy-3-(2-methoxy-2-oxoethyl)-1H-1,3-benzodiazol-3-ium hydrochloride bromide

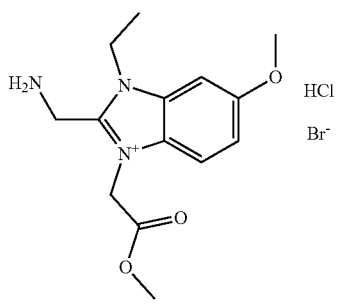 [SMILES: CCn1c(CN)[n+](CC(=O)OC)c2ccc(OC)cc21 ; Cl ; [Br-]]

A mixture of 2-({[(tert-butoxy)carbonyl]amino}methyl)-1-ethyl-6-methoxy-3-(2-methoxy-2-oxoethyl)-1H-1,3-benzodiazol-3-ium bromide, Intermediate 40 (454 mg, 0.990 mmol) and HCl solution in dioxane (4.0 M, 2.5 ml, 10 mmol) was stirred at RT for 0.5 h. The reaction mixture was concentrated in vacuo to afford the product as a pale orange foam (580 mg, 96%-yield corrected for 35 wt % residual dioxane observed in NMR).

$^1$H NMR (500 MHz, DMSO-$d_6$) $^1$H NMR (500 MHz, DMSO-$d_6$) δ 8.86 (s, 3H), 7.97 (d, J=9.2 Hz, 1H), 7.68 (d, J=2.3 Hz, 1H), 7.35 (dd, J=9.2, 2.3 Hz, 1H), 5.77 (s, 2H), 4.79 (s, 2H), 4.72 (q, J=7.2 Hz, 2H), 3.94 (s, 3H), 3.77 (s, 3H), 1.47 (t, J=7.2 Hz, 3H).

LC/MS (System A): m/z (ESI$^+$)=278 [M$^+$], $R_t$=0.14 min, ELS purity=95%.

Intermediate 42-Synthesis of 2-({[(tert-butoxy)carbonyl]amino}methyl)-3-(carbamoylmethyl)-1-ethyl-6-methoxy-1H-1,3-benzodiazol-3-ium bromide

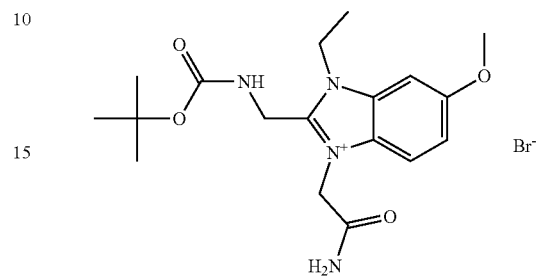

2-Bromoacetamide (691 mg, 5.01 mmol) was added to a suspension of tert-butyl N-[(1-ethyl-6-methoxy-1H-1,3-benzodiazol-2-yl)methyl]carbamate, Intermediate 39 (85%, 600 mg, 1.67 mmol) in MeCN (6 ml) in a pressure tube. The tube was sealed then the reaction mixture was stirred at 80° C. for 5 h. The reaction was allowed to cool to RT then stirred at RT for 64 h. The reaction mixture was heated to 80° C. for a further 2 h then allowed to cool to RT. The resultant mixture was concentrated in vacuo to a viscous red oil. The crude material was purified by flash column chromatography on a silica column (50 g). The column was eluted with $CH_2Cl_2$:MeOH, using the following gradient (% MeOH, column volumes): 0%, 1 CV; 0-9%, 8 CV; 9%, 3 CV; 9-14%, 2 CV, 14%, 1 CV; 14-20%, 2 CV. The desired fractions were combined and evaporated to afford the product as a pale magenta foam (638 mg, 84%).

$^1$H NMR (500 MHz, DMSO-$d_6$) δ 7.90 (s, 1H), 7.86-7.77 (m, 2H), 7.63 (s, 1H), 7.60 (d, J =2.2 Hz, 1H), 7.29 (dd, J=9.1, 2.3 Hz, 1H), 5.30 (s, 2H), 4.70 (d, J=5.4 Hz, 2H), 4.62 (q, J=7.2 Hz, 2H), 3.92 (s, 3H), 1.42 (t, J=7.2 Hz, 3H), 1.36 (s, 9H).

LC/MS (System A): m/z (ESI$^+$)=363 [M$^+$], $R_t$=0.83 min, UV purity=98%.

Intermediate 43-Synthesis of 2-(aminomethyl)-3-(carbamoylmethyl)-1-ethyl-6-methoxy-1H-1,3-benzodiazol-3-ium hydrochloride bromide

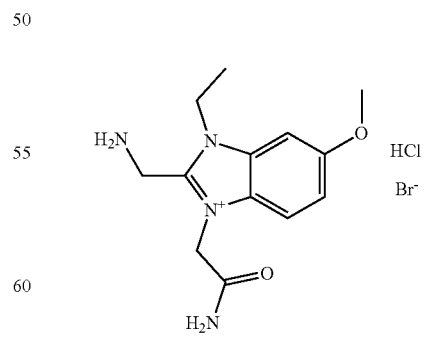

A mixture of 2-({[(tert-butoxy)carbonyl]amino}methyl)-3-(carbamoylmethyl)-1-ethyl-6-methoxy-1H-1,3-benzodiazol-3-ium bromide, Intermediate 42 (98%, 638 mg, 1.41 mmol) and HCl solution in dioxane (4.0 M, 3.5 ml, 14 mmol) was stirred at RT for 0.5 h. The reaction mixture was concentrated in vacuo to afford the product as a purple solid (719 mg, 97%-yield corrected for 28 wt % residual dioxane observed in NMR).

$^1$H NMR (500 MHz, DMSO-d$_6$) δ 8.91 (s, 3H), 8.35 (s, 1H), 7.98-7.89 (m, 2H), 7.68 (d, J=2.3 Hz, 1H), 7.38 (dd, J=9.2, 2.3 Hz, 1H), 5.45 (s, 2H), 4.77 (s, 2H), 4.71 (q, J=7.2 Hz, 2H), 3.94 (s, 3H), 1.46 (t, J=7.2 Hz, 3H).

LC/MS (System A): m/z (ESI$^+$)=263 [M$^+$], R$_t$=0.15 min, ELS purity=100%.

Intermediate 44-Synthesis of 2-[(1,3-dioxo-2,3-dihydro-1H-isoindol-2-yl)methyl]-1-ethyl-6-methoxy-3-[2-(methylsulfanyl)ethyl]-1H-1,3-benzodiazol-3-ium iodide

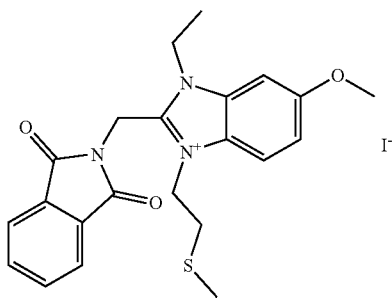 [SMILES: CCn1c(CN2C(=O)c3ccccc3C2=O)[n+](CCSC)c2ccc(OC)cc21 ; [I-]]

A mixture of 2-[(1-ethyl-6-methoxy-1H-1,3-benzodiazol-2-yl)methyl]-2,3-dihydro-1H-isoindole-1,3-dione, Intermediate 23 (500 mg, 1.49 mmol), 1-chloro-2-(methylsulfanyl)ethane (730 μl, 7.45 mmol) and NaI (1.12 g, 7.45 mmol) in MeCN (8 ml) was heated to 100° C. in a sealed tube for 5 h then allowed to cool to RT. The reaction mixture was concentrated in vacuo to a brown solid. The solid thus obtained was suspended in MeOH (8 ml) with sonication. The resultant suspension was filtered then the solid was washed with MeOH and dried under vacuum to afford the product as a brown solid (1.13 g, 50%)

$^1$H NMR (500 MHz, DMSO-d$_6$) δ 8.04 (d, J=9.2 Hz, 1H), 7.99-7.88 (m, 4H), 7.64 (t, J=2.6 Hz, 1H), 7.32 (dd, J=9.2, 2.3 Hz, 1H), 5.47-5.37 (m, 2H), 4.90-4.68 (m, 4H), 4.11 (s, 1H), 3.92 (d, J=1.4 Hz, 3H), 3.03 (t, J=7.1 Hz, 2H), 2.15 (s, 2H), 1.42 (q, J=6.9 Hz, 3H).

LC/MS (System A): m/z (ESI$^+$)=410 [M$^+$], R$_t$=0.99 min, UV purity=66%.

Intermediate 45-Synthesis of 2-(aminomethyl)-1-ethyl-6-methoxy-3-[2-(methylsulfanyl)ethyl]-1H-1,3-benzodiazol-3-ium iodide

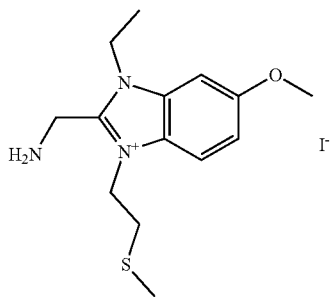 [SMILES: CCn1c(CN)[n+](CCSC)c2ccc(OC)cc21 ; [I-]]

A mixture of 2-[(1,3-dioxo-2,3-dihydro-1H-isoindol-2-yl)methyl]-1-ethyl-6-methoxy-3-[2-(methylsulfanyl)ethyl]-1H-1,3-benzodiazol-3-ium iodide, Intermediate 44 (66%, 1.00 g, 1.62 mmol) and hydrazine hydrate (226 μl, 4.65 mmol) in MeOH (5 ml) was heated to 80° C. in a sealed tube for 80 min. The reaction mixture was concentrated in vacuo to an orange solid. The solid thus obtained was suspended in CH$_2$Cl$_2$ (50 ml) with sonication. The suspension was filtered then the filtrate was concentrated in vacuo to afford the product as a pale orange solid (395 mg, 48%).

$^1$H NMR (500 MHz, DMSO-d$_6$) δ 7.96 (d, J=9.1 Hz, 1H), 7.60-7.56 (m, 1H), 7.27 (dt, J=9.1, 2.1 Hz, 1H), 4.76 (t, J=6.9 Hz, 2H), 4.61 (q, J=6.1, 4.9 Hz, 2H), 4.30 (s, 2H), 3.92 (d, J=1.4 Hz, 3H), 3.01 (t, J=6.9 Hz, 2H), 2.41-2.30 (m, 2H), 2.13 (s, 3H), 1.45 (t, J=7.3 Hz, 3H).

LC/MS (System A): m/z (ESI$^+$)=280 [M$^+$], R$_t$=0.65 min, UV purity=80%.

Intermediate 46-Synthesis of 2-ntert-butoxy)carbonyl{amino}methyl)-1-ethyl-3-(2-hydroxyethyl)-6-methoxy-1H-1,3-benzodiazol-3-ium bromide

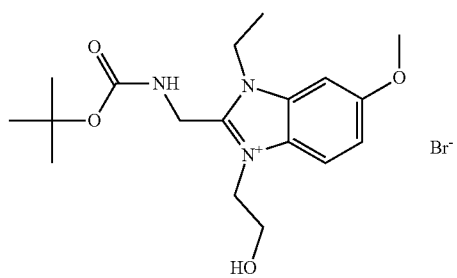 [SMILES: CCn1c(CNC(=O)OC(C)(C)C)[n+](CCO)c2ccc(OC)cc21 ; [Br-]]

(2-Bromoethoxy)(tert-butyl)dimethylsilane (1.66 g, 6.96 mmol) was added to a suspension of tert-butyl N-[(1-ethyl-6-methoxy-1H-1,3-benzodiazol-2-yl)methyl]carbamate, Intermediate 39 (85%, 500 mg, 1.39 mmol) in MeCN (5 ml) in a pressure tube. The tube was sealed then the reaction mixture was stirred at 80° C. for 0.5 h then at 100° C. for 16 h. The reaction was allowed to cool to RT then additional (2-bromoethoxy)(tert-butyl)dimethylsilane (1.00 g, 4.18 mmol) was added. The tube was sealed then the reaction was left to stir at 100° C. for a further 24 h. The reaction mixture was allowed to cool then concentrated in vacuo to a red oil. The crude material was purified by flash column chromatography on a silica column (25 g). The column was eluted with CH$_2$Cl$_2$:MeOH, increasing the gradient linearly from 100:0 to 90:10 over 10 column volumes. The desired fractions were combined and evaporated to yield a viscous dark red oil (615 mg). The material was further purified by flash column chromatography on C18 (30 g). The column was eluted with MeCN:water+0.1% formic acid using the following gradient (% MeCN, column volumes): 10%, 2 CV; 10-36%; 36%, 2 CV; 36-50%, 4 CV; 50-100%, 3 CV; 100%, 3 CV. The desired fractions were combined and evaporated to yield the product as a viscous dark red oil (278 mg, 43%).

$^1$H NMR (500 MHz, DMSO-d$_6$) δ 8.28 (s, 1H), 7.99-7.84 (m, 2H), 7.57 (d, J=2.2 Hz, 1H), 7.28 (dd, J=9.1, 2.3 Hz, 1H), 4.76 (d, J=5.5 Hz, 2H), 4.71-4.65 (m, 2H), 4.59 (q, J=7.1 Hz, 2H), 3.92 (s, 3H), 3.77 (t, J=4.7 Hz, 2H), 1.41 (t, J=7.2 Hz, 3H), 1.38 (d, J=2.8 Hz, 9H).

LC/MS (System A): m/z (ESI$^+$)=350 [MH$^+$], R$_t$=0.88 min, UV purity=92%.

Intermediate 47-Synthesis of 2-(aminomethyl)-1-ethyl-3-(2-hydroxyethyl)-6-methoxy-1H-1,3-benzodiazol-3-ium hydrochloride bromide

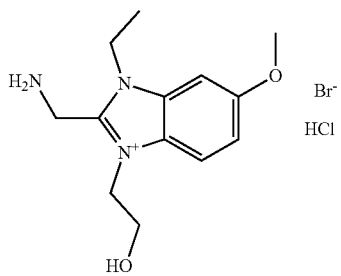 [SMILES: CCn1c(CN)[n+](CCO)c2ccc(OC)cc21 ; Cl ; [Br-]]

Hydrogen chloride solution in dioxane (4.0 M, 1.2 ml, 4.8 mmol) was added to a solution of 2-({[(tert-butoxy)carbonyl]amino}methyl)-1-ethyl-3-(2-hydroxyethyl)-6-methoxy-1H-1,3-benzodiazol-3-ium bromide, Intermediate 46 (92%, 227 mg, 0.49 mmol) in MeCN (3 ml). The resulting mixture was stirred at RT for 1 h. The reaction mixture was concentrated in vacuo to afford the product as a dark purple solid (174 mg, 97%).

$^1$H NMR (500 MHz, DMSO-$d_6$) δ 8.89 (s, 3H), 8.03 (d, J=9.2 Hz, 1H), 7.66 (d, J=2.3 Hz, 1H), 7.35 (dd, J=9.2, 2.3 Hz, 1H), 4.82-4.73 (m, 4H), 4.69 (q, J=7.2 Hz, 2H), 3.94 (s, 3H), 3.80 (t, J=4.6 Hz, 2H), 1.45 (t, J=7.2 Hz, 3H).

LC/MS (System B): m/z (ESI$^+$)=250 [MH$^+$], $R_t$=1.58 min, UV purity=99%.

Intermediate 48-Synthesis of 2-{[(2-carboxyphenyl)formamido]methyl}-1-ethyl-3-{2-[2-(2-hydroxyethoxy)ethoxy]ethyl}-6-methoxy-1H-1,3-benzodiazol-3-ium iodide

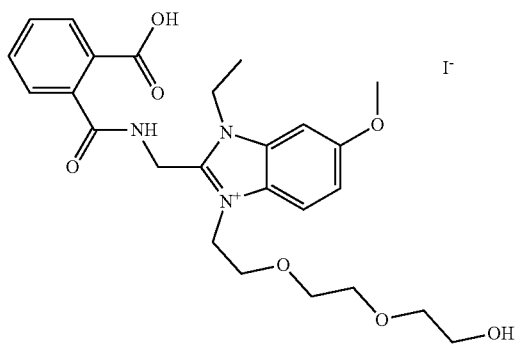 [SMILES: CCn1c(CNC(=O)c2ccccc2C(=O)O)[n+](CCOCCOCCO)c2ccc(OC)cc21 ; [I-]]

A mixture of 2-[(1-ethyl-6-methoxy-1H-1,3-benzodiazol-2-yl)methyl]-2,3-dihydro-1H-isoindole-1,3-dione, Intermediate 23 (2.00 g, 5.96 mmol) and 2-[2-(2-iodoethoxy)ethoxy]ethan-1-ol (90%, 8.62 g, 29.8 mmol) in MeCN (15 ml) was heated at 130° C. in a sealed tube for 16 h then allowed to cool to RT. The reaction mixture was concentrated in vacuo then the crude material was purified by flash column chromatography on C18 (12 g). The column was eluted with MeCN:water+0.1% formic acid using the following gradient (% MeCN, column volumes): 10%, 2 CV; 10-14%, 2 CV; 14-18%, 1 CV; 18-27%, 2 CV; 27-31%, 0.5 CV; 31-60%, 0.5 CV; 60-100%, 1 CV; 100%, 1 CV. The desired fractions were combined and evaporated to yield the product as a yellow amorphous solid (1.72 g, 47%).

$^1$H NMR (500 MHz, DMSO-$d_6$) δ 12.97-12.91 (m, 1H), 7.96 (d, J=9.2 Hz, 1H), 7.72 (dd, J=7.8, 1.2 Hz, 1H), 7.60 (dd, J=7.7, 1.3 Hz, 1H), 7.57 (d, J=2.3 Hz, 1H), 7.37 (td, J=7.5, 1.4 Hz, 1H), 7.30-7.24 (m, 2H), 5.04 (d, J=5.0 Hz, 2H), 4.91 (t, J=4.8 Hz, 2H), 4.77-4.62 (m, 3H), 3.91 (s, 3H), 3.83 (t, J=4.9 Hz, 2H), 3.51-3.46 (m, 2H), 3.43-3.39 (m, 4H), 3.36-3.28 (m, 2H +HDO), 1.41 (t, J=7.2 Hz, 3H).

LC/MS (System A): m/z (ESI$^+$)=486 [M$^+$], $R_t$=0.80 min, UV purity=100%.

Intermediate 49-Synthesis of 2-(aminomethyl)-1-ethyl-3-{2-[2-(2-hydroxyethoxy)ethoxy]ethyl}-6-methoxy-1H-1,3-benzodiazol-3-ium iodide

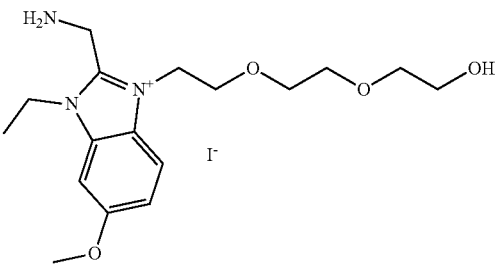 [SMILES: CCn1c(CN)[n+](CCOCCOCCO)c2ccc(OC)cc21 ; [I-]]

Hydrazine hydrate (639 µl, 13.2 mmol) was added to a solution of 2-{[(2-carboxphenyl)formamido]methyl}-1-ethyl-3-{2-[2-(2-hydroxyethoxy)ethoxy]ethyl}-6-methoxy-1H-1,3-benzodiazol-3-ium iodide, Intermediate 48 (1.52 g, 2.48 mmol) in MeOH (12 ml) in a pressure tube. The tube was sealed and the reaction solution was heated at 75° C. for 3.5 h. The reaction was allowed to cool to RT then stirred at RT for 64 h. Additional hydrazine hydrate (639 µl, 13.2 mmol) was added and the reaction was heated at 75° C. for a further 18 h, then at 80° C. for a further 24 h. The reaction mixture was allowed to cool to RT then concentrated in vacuo to an orange solid. The solid thus obtained was suspended in CH$_2$Cl$_2$:MeOH (9:1, 30 ml) then filtered. The filtrate was concentrated in vacuo to afford the product as a viscous orange oil (1.21 g, 88%).

LC/MS (System B): m/z (ESI$^+$)=338 [M$^+$], Rt=1.41 min, UV purity=84%.

Intermediate 50-Synthesis of 3-benzyl-6-chloro-2-[(1,3-dioxo-2,3-dihydro-1H-isoindol-2-yl)methyl]-1-ethyl-1H-1,3-benzodiazol-3-ium bromide

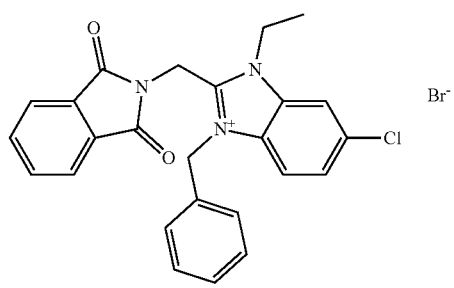 [SMILES: CCn1c(CN2C(=O)c3ccccc3C2=O)[n+](Cc2ccccc2)c2ccc(Cl)cc21 ; [Br-]]

Benzyl bromide (88 µl, 0.74 mmol) was added to a suspension of 2-[(6-chloro-1-ethyl-1H-1,3-benzodiazol-2- yhmethyl]-2,3-dihydro-1H-isoindole-1,3-dione, Intermediate 20 (0.25 g, 0.74 mmol) in MeCN (5 ml) in a pressure tube. The tube was sealed then the reaction was stirred at 80° C. for 16 h then allowed to cool to RT. Benzyl bromide (88 µl, 0.74 mmol) was added then the reaction was stirred at 80° C. for a further 6 h. The reaction was allowed to cool to RT then left to stand at RT for 64 h. Benzyl bromide (88 µl, 0.74 mmol) was added then the reaction was stirred at 80° C. for a further 24 h. The reaction was allowed to cool to RT then filtered. The solid was washed with MeCN then dried under vacuum to afford the product as a white solid (370 mg, 97%).

$^1$H NMR (500 MHz, DMSO-$d_6$) δ 8.50 (d, J=1.8 Hz, 1H), 7.98 (d, J=8.9 Hz, 1H), 7.85 - 7.68 (m, 5H), 7.14-7.05 (m, 2H), 6.99 (t, J=6.5 Hz, 3H), 5.89 (s, 2H), 5.52 (s, 2H), 4.82 (q, J=7.2 Hz, 2H), 1.51 (t, J=7.2 Hz, 3H).

LC/MS (System B): m/z (ESI$^+$)=430 [M$^+$], Rt=0.98 min, UV purity=99%.

Intermediate 51-Synthesis of 2-(aminomethyl)-3-benzyl-6-chloro-1-ethyl-1H-1,3-benzodiazol-3-ium bromide

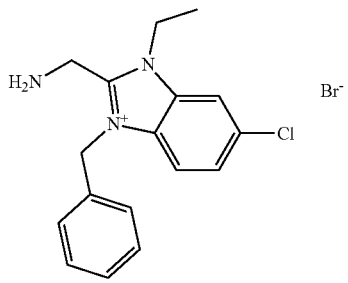 [SMILES: CCn1c(CN)[n+](Cc2ccccc2)c2ccc(Cl)cc21 ; [Br-]]

Hydrazine hydrate (0.18 ml, 3.62 mmol) was added to a suspension of 3-benzyl-6-chloro -2-[(1,3-dioxo-2,3-dihydro-1H-isoindol-2-yl)methyl]-1-ethyl-1H-1,3-benzodiazol-3-ium bromide, Intermediate 50 (370 mg, 0.724 mmol) in MeOH (4 ml) in a pressure tube. The tube was sealed then the reaction was stirred at 75° C. for 3 h. The reaction mixture was allowed to cool to RT then filtered. The filtrate was concentrated in vacuo to afford an orange solid. The solid thus obtained was suspended in CH$_2$Cl$_2$:MeOH (9:1, 10 ml) then filtered. The solid was dried under vacuum then suspended in MeOH. The suspension was filtered then the filtrate was concentrated in vacuo. The resultant residue was suspended in CH$_2$Cl$_2$:MeOH (9:1, 10 ml) with sonication. The resultant suspension was filtered then the filtrate was concentrated in vacuo to afford the product as a pale yellow solid (107 mg, 33%).

$^1$H NMR (500 MHz, DMSO-$d_6$) δ 8.36 (d, J=1.8 Hz, 1H), 7.83 (d, J=8.9 Hz, 1H), 7.66 (dd, J=8.9, 1.9 Hz, 1H), 7.43-7.30 (m, 5H), 5.89 (s, 2H), 4.63 (q, J=7.2 Hz, 2H), 4.35 (s, 2H), 1.46 (t, J=7.2 Hz, 3H).

LC/MS (System B): m/z (ESI$^+$)=300 [M$^+$], Rt=0.81 min, UV purity=85%.

Intermediate 52-Synthesis of 3-benzyl-2-({[(tert-butoxy)carbonyl]amino}methyl)-1-ethyl-6-(trifluoromethyl)-1H-1,3-benzodiazol-3-ium bromide

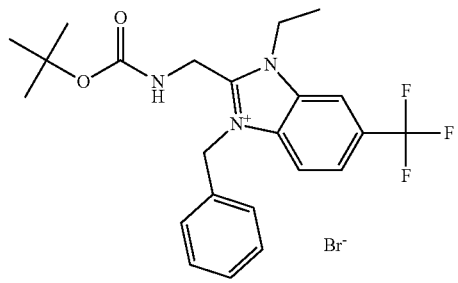 [SMILES: CCn1c(CNC(=O)OC(C)(C)C)[n+](Cc2ccccc2)c2ccc(C(F)(F)F)cc21 ; [Br-]]

Benzyl bromide (173 µl, 1.46 mmol) was added to a suspension of tert-butyl N-{[1-ethyl-6-(trifluoromethyl)-1H-1,3-benzodiazol-2-yl]methyl}carbamate, Intermediate 26 (250 mg, 0.73 mmol) in MeCN (3 ml) in a pressure tube. The tube was sealed and heated at 80° C. for 16 h then the reaction mixture was concentrated in vacuo to afford an orange oil which solidified on standing. The resulting solid was suspended in MeCN (2 ml). The solid was collected by filtration then dried under vacuum to afford the product as a white solid (160 mg). The filtrate was concentrated in vacuo. The residue was suspended in the minimum volume of MeCN then filtered. The solid thus obtained was dried under vacuum to yield a second batch of product as an off-white solid (90 mg). The 2 batches of product were combined in MeCN then evaporated to afford the product as an off-white solid (250 mg, 64%).

$^1$H NMR (500 MHz, DMSO-$d_6$) δ 8.69 (s, 1H), 8.03-7.87 (m, 3H), 7.43-7.36 (m, 3H), 7.31-7.23 (m, 2H), 5.92 (s, 2H), 4.97-4.85 (m, 2H), 4.78 (q, J=7.1 Hz, 2H), 1.49 (t, J=7.1 Hz, 3H), 1.30 (s, 9H).

LC/MS (System A): m/z (ESI$^+$)=435 [M$^+$], R$_t$=1.05 min, UV purity=96%.

Intermediate 53-Synthesis of 2-(aminomethyl)-3-benzyl-1-ethyl-6-(trifluoromethyl) -1H-1,3-benzodiazol-3-ium hydrochloride bromide

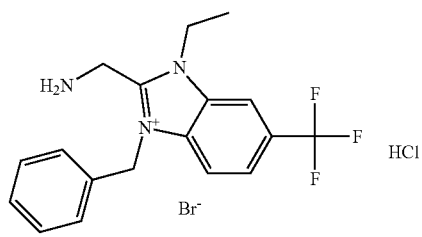 [SMILES: CCn1c(CN)[n+](Cc2ccccc2)c2ccc(C(F)(F)F)cc21 ; [Br-] ; Cl]

HCl solution in dioxane (4.0 M, 0.61 ml, 2.4 mmol) was added to a solution of 3-benzyl-2-({[(tert-butoxy)carbonyl]amino}methyl)-1-ethyl-6-(trifluoromethyl)-1H-1,3-benzodiazol-3-ium bromide, Intermediate 52 (250 mg, 0.49 mmol) in MeCN (2.5 ml). The reaction was stirred at RT for 18 h then concentrated in vacuo. The residue was azeotroped with MeCN then dried under vacuum to afford the product as a pale yellow solid (209 mg, 95%).

$^1$H NMR (500 MHz, DMSO-$d_6$) δ 9.18 (s, 3H), 8.77 (s, 1H), 8.10-7.99 (m, 2H), 7.51-7.46 (m, 2H), 7.44-7.34 (m, 3H), 6.05 (s, 2H), 4.94-4.79 (m, 4H), 1.53 (t, J=7.2 Hz, 3H).

LC/MS (System A): m/z (ESI$^+$)=334 [M$^+$], R$_t$=0.86 min, UV purity=100%.

Intermediate 54-Synthesis of tert-butyl N-[(1-benzyl-1H-1,3-benzodiazol-2-yl)methyl]carbamate

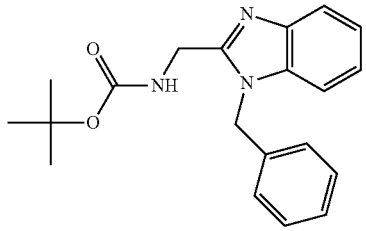 [SMILES: CC(C)(C)OC(=O)NCc1nc2ccccc2n1Cc1ccccc1]

Benzyl bromide (1.29 ml, 10.8 mmol) was added to a mixture of tert-butyl N-(1H-1,3-benzodiazol-2-ylmethyl)carbamate (85%, 3.15 g, 10.8 mmol) and K$_2$CO$_3$ (2.25 g, 16.3 mmol) in DMF (25 ml). The resulting mixture was stirred at RT for 16 h. The reaction mixture was partitioned between water (150 ml) and EtOAc (150 ml). The phases were separated then the aqueous phase was extracted with EtOAc (5×150 ml). The combined organics were dried over Na$_2$SO$_4$ then concentrated in vacuo to approximately 50 ml. The resultant slurry was recrystallized from the minimum volume of refluxing EtOAc to afford the product as white solid (2.22 g, 61%).

$^1$H NMR (500 MHz, DMSO-d$_6$) δ 7.64-7.58 (m, 1H), 7.51-7.45 (m, 1H), 7.40-7.34 (m, 1H), 7.34-7.24 (m, 3H), 7.20-7.11 (m, 4H), 5.51 (s, 2H), 4.44 (d, J=5.8 Hz, 2H), 1.32 (s, 9H).

LC/MS (System A): m/z (ESI$^+$)=338 [MH$^+$], R$_t$=1.02 min, UV purity=100%.

Intermediate 55-Synthesis of 1-benzyl-2-({[(tert-butoxy)carbonyl]amino}methyl)-3-(2-methoxy-2-oxoethyl)-1H-1,3-benzodiazol-3-ium bromide

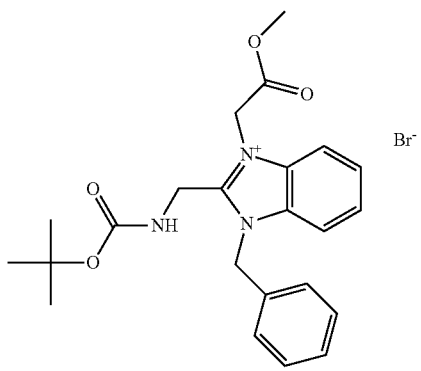 [SMILES: COC(=O)C[n+]1c(CNC(=O)OC(C)(C)C)n(Cc2ccccc2)c2ccccc21 ; [Br-]]

A mixture of tert-butyl N-[(1-benzyl-1H-1,3-benzodiazol-2-yl)methyl]carbamate, Intermediate 54 (500 mg, 1.48 mmol) and methyl bromoacetate (421 µl, 4.45 mmol) in MeCN (5 ml) was stirred at 70° C. in a sealed tube for 16 h. The reaction mixture was allowed to cool then concentrated in vacuo to afford the product as a white solid (717 mg, 96%).

$^1$H NMR (500 MHz, DMSO-d$_6$) δ 8.06 (d, J=8.3 Hz, 1H), 7.89 (t, J=5.4 Hz, 1H), 7.81 (d, J=8.2 Hz, 1H), 7.73-7.60 (m, 2H), 7.42-7.32 (m, 3H), 7.28 (d, J=6.8 Hz, 2H), 5.97 (s, 2H), 5.69 (s, 2H), 4.89 (d, J=5.4 Hz, 2H), 3.77 (s, 3H), 1.32 (s, 9H).

LC/MS (System A): m/z (ESI$^+$)=410 [M$^+$], R$_t$=0.94 min, UV purity=97%.

Intermediate 56-Synthesis of 1-benzyl-2-({[(tert-butoxy)carbonyl]amino}methyl)-3-[2-oxo-2-(piperidin-1-yl)ethyl]-1H-1,3-benzodiazol-3-ium bromide

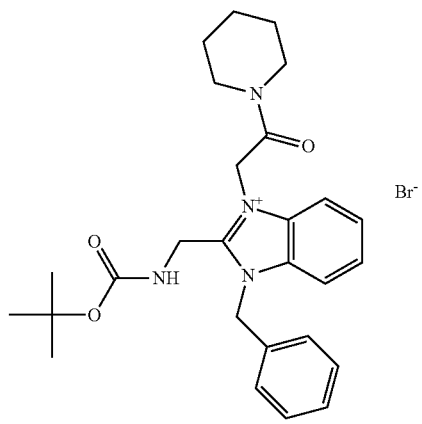 [SMILES: CC(C)(C)OC(=O)NCc1n(Cc2ccccc2)c2ccccc2[n+]1CC(=O)N1CCCCC1 ; [Br-]]

A mixture of 1-benzyl-2-({[(tert-butoxy)carbonyl]amino}methyl)-3-(2-methoxy-2-oxoethyl)-1H-1,3-benzodiazol-3-ium bromide, Intermediate 55 (350 mg, 0.71 mmol) in aqueous LiOH solution (1.0 M, 1.4 ml, 1.4 mmol) and MeOH (1.5 ml) was stirred at RT for 16 h. The reaction mixture was acidified to pH 3 by dropwise addition of aqueous HCl solution (1 M) then concentrated in vacuo to afford the crude intermediate as a beige solid (469 mg). The crude intermediate thus obtained was dissolved in DMF (4 ml) then HATU (340 mg, 0.89 mmol) and DIPEA (206 µl, 1.18 mmol) were added. Piperidine (88 µl, 0.89 mmol) was added to the reaction solution then the resulting mixture was stirred at RT for 45 min. Additional piperidine (150 µl, 1.52 mmol) and HATU (300 mg, 0.89 mmol) were added and the reaction was left to stir at RT for an additional 64 h. The reaction mixture was concentrated in vacuo then the crude material was purified by flash column chromatography on C18 (30 g). The column was eluted with MeCN:water+0.1% formic acid using the following gradient (% MeCN, column volumes): 10-45%, 12 CV; 45%, 2 CV; 45-53%, 3 CV; 53-100%, 3 CV; 100%, 1 CV. The desired fractions were combined and evaporated to afford the product as a pale orange foam (209 mg, 53%).

$^1$H NMR (500 MHz, DMSO-d$_6$) δ 7.98 (d, J=8.3 Hz, 1H), 7.83-7.76 (m, 2H), 7.70-7.58 (m, 2H), 7.43-7.32 (m, 3H), 7.25 (d, J=6.8 Hz, 2H), 5.97 (s, 2H), 5.76 (s, 2H), 4.78 (d, J=5.4 Hz, 2H), 3.58-3.51 (m, 2H), 3.47-3.42 (m, 2H), 1.76-1.62 (m, 4H), 1.51 (s (br), 2H), 1.32 (s, 9H).

LC/MS (System A): m/z (ESI$^+$)=463 [M$^+$], R$_t$=1.00 min, UV purity=99%.

Intermediate 57-Synthesis of 2-(aminomethyl)-1-benzyl-3-[2-oxo-2-(piperidin-1-yl)ethyl]-1H-1,3-benzodiazol-3-ium hydrochloride bromide

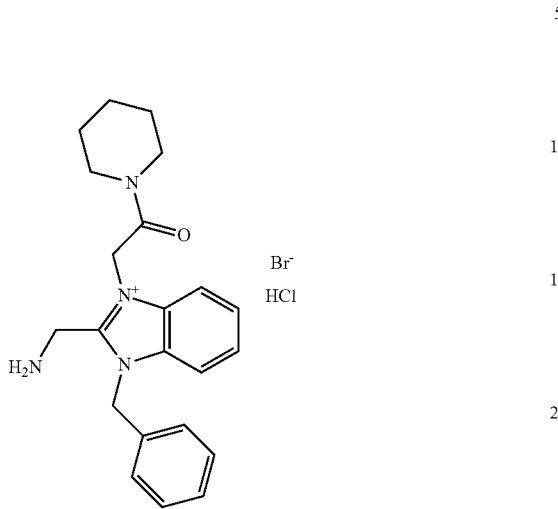

A mixture of 1-benzyl-2-({[(tert-butoxy)carbonyl]amino}methyl)-3-[2-oxo-2-(piperidin-1-yl)ethyl]-1H-1,3-benzodiazol-3-ium bromide, Intermediate 56 (205 mg, 0.377 mmol) and HCl solution in dioxane (4.0 M, 1.1 ml, 4.4 mmol) was stirred at RT for 0.5 h. The reaction mixture was concentrated in vacuo to afford the product as a viscous orange oil (219 mg, 92%-yield corrected for 24 wt % residual dioxane observed in NMR).

$^1$H NMR (500 MHz, DMSO-$d_6$) δ 8.15-8.09 (m, 1H), 7.91 (d, J=8.3 Hz, 1H), 7.74 (t, J=7.7 Hz, 1H), 7.68 (t, J=7.8 Hz, 1H), 7.44-7.33 (m, 3H), 7.32 (d, J=7.0 Hz, 2H), 6.05 (s, 2H), 5.97 (s, 2H), 4.74 (s, 2H), 3.63-3.58 (m, 2H), 3.48-3.45 (m, 2H), 1.79-1.71 (m, 2H), 1.71-1.63 (m, 2H), 1.57-1.46 (m, 2H).

LC/MS (System A): m/z (ESI$^+$)=363 [M$^+$], R$_t$=0.82 min, UV purity=93%.

Intermediate 58-Synthesis of 6-(2-{[(tert-butoxy)carbonyl]amino}ethoxy)-1,3-diethyl-2-({[(9H-fluoren-9-ylmethoxy)carbonyl]amino}methyl)-1H-1,3-benzodiazol-3-ium iodide

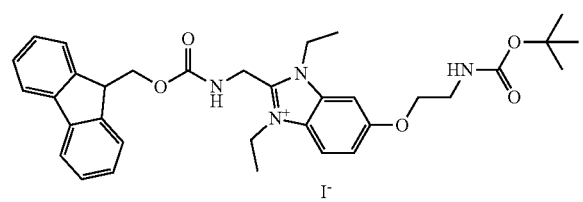 [SMILES: CCn1c(CNC(=O)OCC2c3ccccc3-c3ccccc32)[n+](CC)c2ccc(OCCNC(=O)OC(C)(C)C)cc21 ; [I-]]

Intermediate 58 was synthesised by according to literature procedures (US 2015/0018313 A1).

Intermediate 59-Synthesis of 2-(aminomethyl)-6-(2-{[(tert-butoxy)carbonyl]amino}ethoxy)-1,3-diethyl-1H-1,3-benzodiazol-3-ium iodide

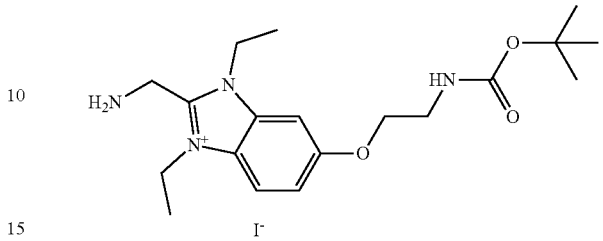

Morpholine (3.46 ml, 40.0 mmol) was added to a solution of 6-(2-{[(tert-butoxy)carbonyl]amino}ethoxy)-1,3-diethyl-2-({[(9H-fluoren-9-ylmethoxy)carbonyl]amino}methyl)-1H-1,3-benzodiazol-3-ium iodide, Intermediate 58 (95%, 3.00 g, 4.00 mmol) in THF (50 ml). The reaction mixture was stirred at RT for 25 min then diluted with diethyl ether (150 ml). The resulting mixture was agitated then the supernatant was decanted off. The residual gum was washed further with ether (2×60 ml) then dried under vacuum. The residue was dissolved in THF then concentrated in vacuo afford the product as a pale orange solid (1.99 g, 83%).

$^1$H NMR (500 MHz, DMSO-$d_6$) δ 7.95 (d, J=9.1Hz, 1H), 7.65-7.61 (m, 1H), 7.25 (dd, J=9.1, 2.3 Hz, 1H), 7.11-7.05 (m, 1H), 4.61-4.53 (m, 4H), 4.25 (s, 2H), 4.11 (t, J=5.9 Hz, 2H), 3.36 (q, J=5.9 Hz, 2H), 1.45-1.41 (m, 6H), 1.39 (s, 9H).

LC/MS (System A): m/z (ESI$^+$)=363 [M$^+$], R$_t$=0.76 min, UV purity=82%.

Intermediate 60-Synthesis tert-butyl N-[3-(3-fluoro-4-nitrophenoxy)propyl]carbamate

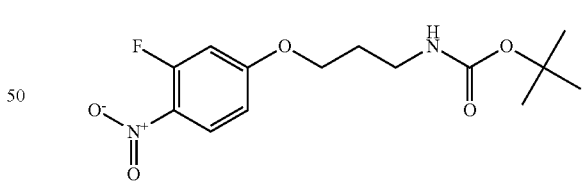

A suspension of 3-fluoro-4-nitrophenol (2.50 g, 15.9 mmol), tert-butyl (3-bromopropyl)carbamate (3.98 g, 16.7 mmol) and K$_2$CO$_3$ (2.64 g, 19.1 mmol) in acetone (15 ml) was stirred at 60° C. for 18 h. The reaction mixture was concentrated in vacuo then the residue was partitioned between EtOAc (50 ml) and water (50 ml). The phases were separated then the organic phase was extracted with water (2×50 ml) and brine (50 ml) then dried over Na$_2$SO$_4$ and concentrated in vacuo to afford the product as a viscous orange oil (4.65 g, 84%).

¹H NMR (500 MHz, Acetone-d6) δ 8.14 (t, J=9.2 Hz, 1H), 7.16 (dd, J=13.7, 2.5 Hz, 1H), 6.96 (dd, J=9.3, 2.6 Hz, 1H), 6.92 (t, J=5.5 Hz, 1H), 4.13 (t, J=6.2 Hz, 2H), 3.07 (q, J =6.6 Hz, 2H), 1.84 (p, J=6.5 Hz, 2H), 1.37 (s, 9H). LC/MS (System A): R$_t$=1.22 min, UV purity=90%.

Intermediate 61-Synthesis of tert-butyl N-{3-[3-(ethylamino)-4-nitrophenoxy]propyl}carbamate

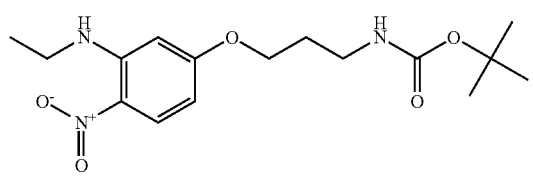 [SMILES: CCNc1cc(OCCCNC(=O)OC(C)(C)C)ccc1[N+](=O)[O-]]

Ethylamine solution in THF (2.0 M, 10 ml, 20 mmol) was added to a mixture of tert-butyl N-[3-(3-fluoro-4-nitrophenoxy)propyl]carbamate, Intermediate 60 (90%, 4.65 g, 13.3 mmol) and K$_2$CO$_3$ (2.20 g, 16.0 mmol) in THF (30 ml). The reaction mixture was stirred at RT for 16 h then additional ethylamine solution in THF (2.0 M, 3.0 ml, 6.0 mmol) was added. The reaction mixture was left to stir at RT for a further 70 h then filtered. The filter pad was rinsed with EtOAc then the combined filtrate was extracted with water (2×150 ml) and brine (150 ml) then dried over Na$_2$SO$_4$ and concentrated in vacuo to afford the product as a viscous yellow/orange oil (4.69 g, 93%).

¹H NMR (500 MHz, DMSO-d$_6$) δ 8.26 (t, J=5.0 Hz, 1H), 8.02 (d, J=10.0 Hz, 1H), 6.92-6.86 (m, 1H), 6.30-6.27 (m, 2H), 4.09 (t, J=6.3 Hz, 2H), 3.40-3.35 (m, 2H), 3.08 (q, J=6.7 Hz, 2H), 1.84 (p, J=6.5 Hz, 2H), 1.37 (s, 9H), 1.24 (t, J=7.1Hz, 3H).

LC/MS (System A): m/z (ESI⁺)=340 [MH⁺], R$_t$=1.30 min, UV purity=90%.

Intermediate 62-Synthesis of (9H-fluoren-9-yl) methyl N-{[6-(3-{[(tert -butoxy)carbonyl] amino}propoxy)-1-ethyl-1H-1,3-benzodiazol-2-yl] methyl}carbamate Palladium on carbon (10 wt %, 662 mg) was added to a solution of tert-butyl N-{3-[3-(ethylamino)-4-nitrophenoxy] propyl}carbamate, Intermediate 61 (90%, 4.69 g, 12.4 mmol) in EtOH (60 ml). The resulting mixture was stirred under a hydrogen atmosphere for 20 h. The reaction mixture was filtered through a Celite pad then the filtrate was concentrated in vacuo. The residue was dissolved in DMF (10 ml) to give a solution of the phenylenediamine intermediate. A solution of FMOC-glycine (3.88 g, 13.1 mmol), HATU (5.20 g, 13.7 mmol) and DIPEA (4.3 ml, 25 mmol) in DMF (20 ml) was stirred at RT for 0.5 h. The phenylenediamine DMF solution was then added and the resulting solution was stirred at RT for 1 h. Additional FMOC-glycine (2.00 g, 6.73 mmol and HATU (2.50 g, 6.57 mmol) were added then the reaction was left to stir at RT for a further 45 min. The reaction mixture was partitioned between EtOAc (100 ml) and water (100 ml). The phases were separated then the organic phase was washed with water (2×100 ml) and brine (100 ml) then dried over Na$_2$SO$_4$ and concentrated in vacuo to afford a red solid. The solid thus obtained was dissolved in AcOH (20 ml) then heated at 60° C. for 16 h. The reaction was allowed to cool to RT then concentrated in vacuo. The residue thus obtained was treated with saturated aqueous NaHCO3 solution until pH 9 then partitioned between EtOAc (250 ml) and water (250 ml). The phases were separated then the organic phase was dried over Na$_2$SO$_4$ and concentrated in vacuo.

The crude material was purified by flash column chromatography on a silica column (340 g). The column was eluted with CH$_2$Cl$_2$:MeOH, using the following gradient (% MeOH, column volumes): 0%, 1 CV; 0-3.3%, 7 CV; 3.3%, 1 CV; 3.3-4.5%, 2 CV. The desired fractions were combined and evaporated to afford the product as a pale orange solid (4.73 g, 53%).

LC/MS (System A): m/z (ESI⁺)=571 [MH⁺], R$_t$=1.18 min, UV purity=80%.

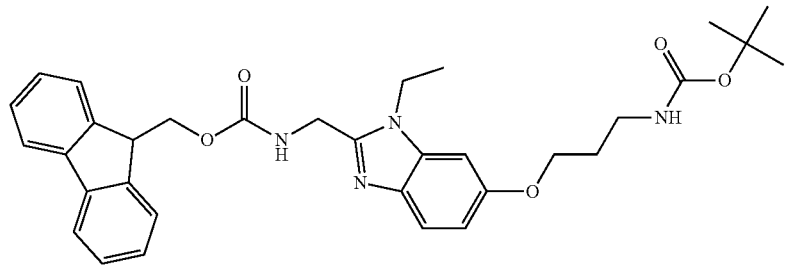 [SMILES: CCn1c(CNC(=O)OCC2c3ccccc3-c3ccccc32)nc2ccc(OCCCNC(=O)OC(C)(C)C)cc21]

Intermediate 63-Synthesis of 6-(3-{[(tert-butoxy)carbonyl]amino}propoxy)-1,3-diethyl-2-[({[(9H-fluoren-9-yl)methoxy]carbonyl}amino)methyl]-1H-1,3-benzodiazol-3-ium iodide

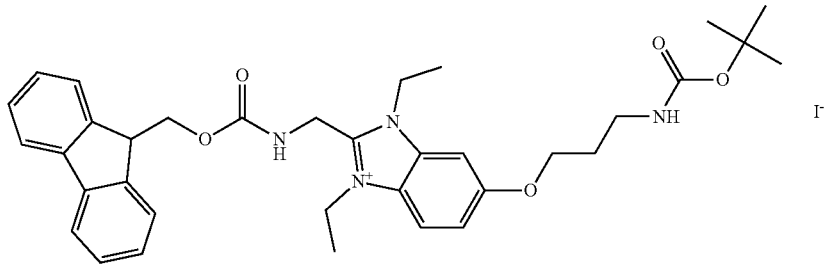 [SMILES: CCn1c(CNC(=O)OCC2c3ccccc3-c3ccccc32)[n+](CC)c2ccc(OCCCNC(=O)OC(C)(C)C)cc21 ; [I-]]

A mixture of 9H-fluoren-9-ylmethyl N-{[6-(3-{[(tert-butoxy)carbonyl]amino}propoxy)-1-ethyl-1H-1,3-benzodiazol-2-yl]methyl}carbamate, Intermediate 62 (80%, 1.50 g, 2.10 mmol) and iodoethane (1.69 ml, 21.0 mmol) in THF (15 ml) was heated under microwave irradiation for 1.5 h at 120° C. The reaction mixture was concentrated in vacuo then the crude material was purified by flash column chromatography on a silica column (100 g). The column was eluted with $CH_2Cl_2$:MeOH, using the following gradient (% MeOH, column volumes): 0%, 1 CV; 0-3.4%, 7 CV; 3.4-4.3%, 2 CV, 4.3-6.0%, 2 CV. The desired fractions were combined and evaporated to afford the product as a pale orange foam (1.03 g, 61%).

$^1$H NMR (500 MHz, DMSO-$d_6$) δ 8.24 (t, J=5.1 Hz, 1H), 7.95 (d, J=9.1 Hz, 1H), 7.86 (d, J=7.5 Hz, 2H), 7.62 (d, J=7.5 Hz, 2H), 7.56 (s, 1H), 7.36 (t, J=7.4 Hz, 2H), 7.30-7.22 (m, 3H), 6.93-6.88 (m, 1H), 4.74 (d, J=5.1 Hz, 2H), 4.55-4.47 (m, 6H), 4.22 (t, J=5.8 Hz, 1H), 4.13 (t, J=6.0 Hz, 2H), 3.12 (q, J=6.4 Hz, 2H), 1.94-1.85 (m, 2H), 1.37-1.31 (m, 15H).

LC/MS (System A): m/z (ESI$^+$)=599 [M$^+$], R$_t$=1.15 min, UV purity=90%.

Intermediate 64-Synthesis of 2-(aminomethyl)-6-(3-{[(tert-butoxy)carbonyl]amino}propoxy)-1,3-diethyl-1H-1,3-benzodiazol-3-ium iodide

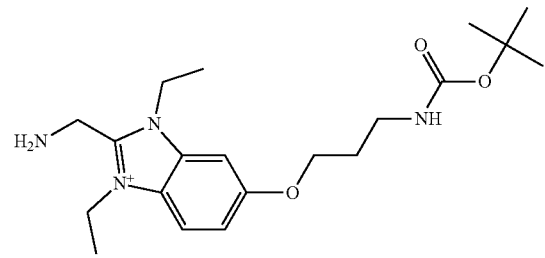

Morpholine (1.10 ml, 12.7 mmol) was added to a solution of 6-(3-{[(tert-butoxy)carbonyl]amino}propoxy)-1,3-diethyl-2-({[(9H-fluoren-9-ylmethoxy)carbonyl]amino}methyl)-1H-1,3-benzodiazol-3-ium iodide, Intermediate 63 (90%, 1.03 g, 1.27 mmol) in THF (10 ml). The reaction mixture was stirred at RT for 2 h then diluted with diethyl ether (40 ml). The mixture was agitated then the supernatant was decanted off. The procedure was repeated with further diethyl ether washes (2×20 ml). The residue thus obtained was dried under vacuum to afford the product as a pale orange foam (700 mg, 99%).

$^1$H NMR (500 MHz, DMSO-$d_6$) δ 7.94 (d, J=9.1Hz, 1H), 7.56 (d, J=2.1Hz, 1H), 7.25 (dd, J=9.1, 2.2 Hz, 1H), 6.99-6.83 (m, 1H), 4.56 (q, J=7.2 Hz, 4H), 4.24 (s, 2H), 4.12 (t, J=6.2 Hz, 2H), 3.12 (q, J=6.6 Hz, 2H), 1.94-1.84 (m, 2H), 1.42 (t, J=7.2 Hz, 6H), 1.37 (s, 9H).

LC/MS (System A): m/z (ESI$^+$)=377 [M$^+$], R$_t$=0.82 min, UV purity=91%.

Intermediate 65-Synthesis of 2-[(6-bromo-1-ethyl-1H-1,3-benzodiazol-2-yl)methyl]-2,3-dihydro-1H-isoindole-1,3-dione

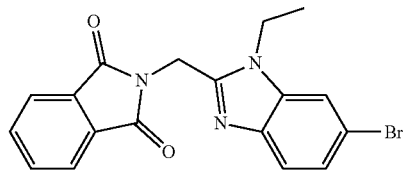 [SMILES: CCn1c(CN2C(=O)c3ccccc3C2=O)nc2ccc(Br)cc21]

A mixture of N-phthaloylglycine (13.1 g, 63.8 mmol), TBTU (21.5 g, 67.0 mmol) and triethylamine (14.1 ml, 79.1 mmol) in DMF (150 ml) was stirred at RT for 45 min. A solution of 5-bromo-1-N-ethylbenzene-1,2-diamine (13.1 g, 60.9 mmol) in THF (50 ml) was added and the resulting mixture was stirred at RT for 18 h. The reaction mixture was added onto saturated aqueous NaHCO3 solution (400 ml). The resulting precipitate was collected by filtration then washed with water and dried under vacuum to afford the intermediate as a light grey solid. The solid thus obtained was added portionwise to acetic acid (150 ml). The resulting suspension was heated at 100° C. for 2.5 h then allowed to cool to RT. The reaction mixture was concentrated in vacuo then the residue was partitioned between EtOAc (300 ml) and water (300 ml). The resulting precipitate was collected by filtration and washed with EtOAc (200 ml) and water (200 ml) then dried under vacuum to afford the product as a pink solid (17.9 g, 76%).

$^1$H NMR (500 MHz, DMSO-$d_6$) δ 7.96 (dd, J=5.6, 3.0 Hz, 2H), 7.93-7.88 (m, 3H), 7.44 (d, J=8.5Hz, 1H), 7.27 (dd, J=8.5, 1.9 Hz, 1H), 5.12 (s, 2H), 4.39 (q, J=7.2 Hz, 2H), 1.37 (t, J=7.2 Hz, 3H).

LC/MS (System A): m/z (ESI$^+$)=384 [M($^{79}$Br)H$^+$], 386 [M($^{81}$Br)H$^+$], R$_t$=1.12 min, UV purity =100%.

Intermediate 66-Synthesis of tert-butyl N-(3-{2-[(1,3-dioxo-2,3-dihydro-1H-isoindol-2-yl)methyl]-1-ethyl-1H-1,3-benzodiazol-6-yl}prop-2-yn-1-yl)carbamate

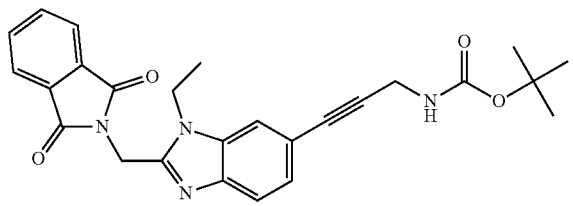 [SMILES: CCn1c(CN2C(=O)c3ccccc3C2=O)nc2ccc(C#CCNC(=O)OC(C)(C)C)cc21]

CuI (0.25 g, 1.29 mmol) was added to a solution of 2-[(6-bromo-1-ethyl-1H-1,3-benzodiazol-2-yl)methyl]-2,3-dihydro-1H-isoindole-1,3-dione, Intermediate 65 (5.00 g, 13.0 mmol) and tert-butyl N-(prop-2-yn-1-yl)carbamate (2.40 g, 15.5 mmol) in DMF (60 ml). Nitrogen was bubbled through the reaction mixture for 5 min then Pd(PPh$_3$)$_4$ (0.74 g, 0.64 mmol) was added, followed by triethylamine (2.92 ml, 19.3 mmol). The reaction mixture was heated at 65° C. for 24 h then concentrated in vacuo. The crude material was purified by flash column chromatography on a silica column (100 g). The column was eluted with EtOAc:heptane, increasing the gradient linearly from 0:100 to 50:50 over 10 column volumes. The desired fractions were combined and evaporated to afford the product as a yellow foam (2.45 g, 39%).

$^1$H NMR (250 MHz, DMSO-d$_6$) δ 7.99-7.88 (m, 4H), 7.71 (s, 1H), 7.46 (d, J=8.3 Hz, 1H), 7.35 (s,1H), 7.16 (dd, J=8.3, 1.3 Hz, 1H), 5.13 (s, 2H), 4.40 (q, J=7.1Hz, 2H), 4.02-3.97 (m, 2H), 1.41 (s,9H), 1.36 (t, J=7.1Hz, 3H).

LC/MS (System A): m/z (ESI$^+$)=459 [MH$^+$], R$_t$=1.17 min, UV purity=95%.

Intermediate 67-Synthesis of tert-butyl N-(3-{2-[(1,3-dioxo-2,3-dihydro-1H-isoindol-2-yl)methyl]-1-ethyl-1H-1,3-benzodiazol-6-yl}propyl)carbamate

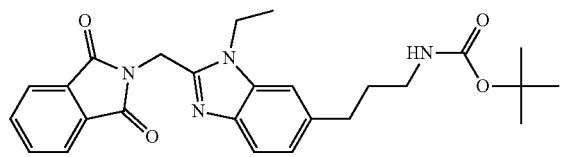 [SMILES: CCn1c(CN2C(=O)c3ccccc3C2=O)nc2ccc(CCCNC(=O)OC(C)(C)C)cc21]

Palladium on carbon (10 wt %, 557 mg) was added to a solution of tert-butyl N-(3-{2-[(1,3-dioxo-2,3-dihydro-1H-isoindol-2-yl)methyl]-1-ethyl-1H-1,3-benzodiazol-6-yl}prop-2-yn-1-yl)carbamate, Intermediate 66 (2.4 g, 5.23 mmol) in EtOH (120 ml). The reaction mixture was stirred at RT under a hydrogen atmosphere for 48 h. The reaction was recharged with palladium on carbon (10 wt %, 278 mg) and stirred at RT under a hydrogen atmosphere for a further 24 h. The reaction was re-charged with palladium on carbon (10 wt %, 278 mg) and stirred at RT under a hydrogen atmosphere for a further 24 h. The reaction mixture was filtered through a Celite pad. The Celite pad was rinsed with EtOH (100 ml), MeOH (100 ml), EtOAc (100 ml), and DMF (5 ml). The combined filtrate was concentrated in vacuo then the crude material was purified by flash column chromatography on a silica column (25 g). The column was eluted with EtOAc:heptane, increasing the gradient linearly from 0:100 to 75:25 over 10 column volumes. The desired fractions were combined and evaporated to afford the product as a light yellow solid (1.20 g, 43%).

$^1$H NMR (500 MHz, DMSO-d$_6$) δ 7.98-7.93 (m, 2H), 7.92-7.88 (m, 2H), 7.37-7.34 (m, 2H), 6.97 (dd, J=8.2, 1.5 Hz, 1H), 6.84 (t, J=5.3 Hz, 1H), 5.09 (s, 2H), 4.35 (q, J=7.2 Hz, 2H), 2.96-2.90 (m, 2H), 2.69- 2.63 (m, 2H), 1.71 (p, J=7.3 Hz, 2H), 1.40-1.35 (m, 12H).

LC/MS (System A): m/z (ESI$^+$)=463 [MH$^+$], R$_t$=1.07 min, UV purity=86%.

Intermediate 68-Synthesis of 6-(3-{[(tert-butoxy)carbonyl]amino}propyl)-2-[(1,3-dioxo-2,3-dihydro-1H-isoindol-2-yl)methyl]-1,3-diethyl-1H-1,3-benzodiazol-3-ium iodide

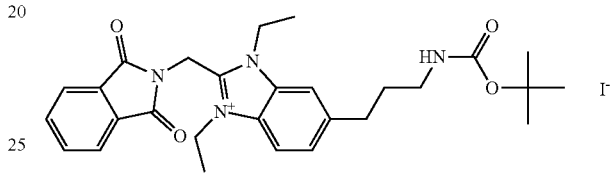

Iodoethane (1.04 ml, 13.0 mmol) was added to a solution of tert-butyl N-(3-{2-[(1,3-dioxo -2,3-dihydro-1H-isoindol-2-yhmethyl]-1-ethyl-1H-1,3-benzodiazol-6-yl}propyhcarbamate, Intermediate 67 (86%, 1.20 g, 2.23 mmol) in MeCN (18 ml) in a pressure tube. The tube was sealed and heated at 110° C. for 4 h. The reaction was allowed to cool to RT then iodoethane (1.04 ml, 13.0 mmol) was added then the reaction was heated at 110° C. for a further 4 h. The reaction mixture was allowed to cool to RT then concentrated in vacuo to afford the product as a brown solid (1.52 g, >99%).

$^1$H NMR (500 MHz, DMSO-d$_6$) δ 8.02 (d, J=8.6 Hz, 1H), 7.97-7.93 (m, 3H), 7.92-7.88 (m, 2H), 7.58(d, J=8.6 Hz, 1H), 6.89 (s, 1H), 5.42 (s, 2H), 4.70-4.66 (m, 4H), 2.93 (q, J=6.2 Hz, 2H), 2.79 (t, J=7.4Hz, 2H), 1.81-1.72 (m, 2H), 1.44-1.40 (m, 6H), 1.37 (s, 9H).

LC/MS (System A): m/z (ESI$^+$)=491 [M$^+$], R$_t$=1.08 min, UV purity=91%.

Intermediate 69-Synthesis of 2-(aminomethyl)-6-(3-{[(tert -butoxy)carbonyl]amino}propyl)-1,3-diethyl-1H-1,3-benzodiazol-3-ium iodide

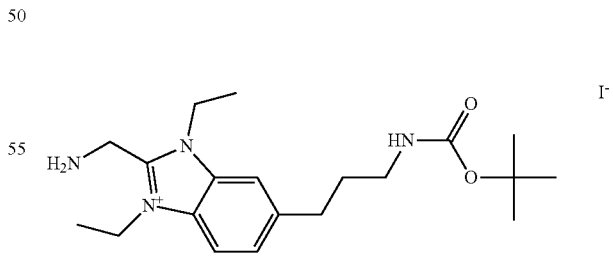

Hydrazine hydrate (609 μl, 12.5 mmol) was added to a solution of 6-(3-{[(tert -butoxy)carbonyl]amino}propyl)-2-[(1,3-dioxo-2,3-dihydro-1H-isoindol-2-yl)methyl]-1,3-diethyl-1H-1,3-benzodiazol-3-ium iodide, Intermediate 68 (91%, 1.52 g, 2.23 mmol) in MeOH (20 ml) in a pressure tube. The tube was sealed then heated at 75° C. for 3 h. The reaction mixture was allowed to cool to RT then concentrated in vacuo. The residue was suspended in CH₂Cl₂:MeOH (9:1, 20 ml) then filtered. The filtrate was concentrated in vacuo to afford the product as a yellow foam (1.21 g, 89%).

¹H NMR (500 MHz, DMSO-d₆) δ 7.95 (d, J=8.5 Hz, 1H), 7.88 (s, 1H), 7.51 (dd, J=8.5, 1.3 Hz, 1H), 6.91 (t, J=5.5 Hz, 1H), 4.60-4.52 (m, 4H), 4.26 (s, 2H), 2.93 (app. q, J=6.6 Hz, 2H), 2.78 (t, J=7.5 Hz, 2H), 1.80-1.70 (m, 2H), 1.46-1.40 (m, 6H), 1.37 (s, 9H).

LC/MS (System A): m/z (ESI⁺)=361 [M⁺], R$_t$=0.81 min, UV purity=80%.

Intermediate 70-Synthesis of tert-butyl 4-{2-[(1,3-dioxo-2,3-dihydro-1H-isoindol-2-yl)methyl]-1-ethyl-1H-1,3-benzodiazol-6-yl}-1,2,3,6-tetrahydropyridine-1-carboxylate

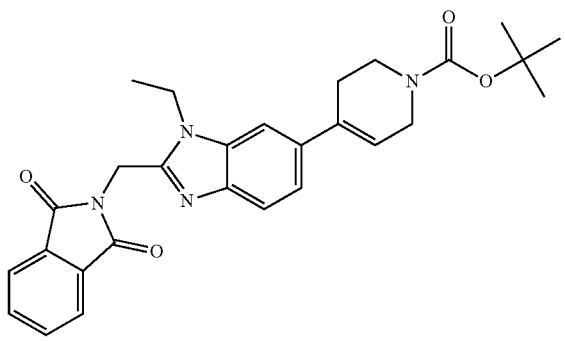 [SMILES: CCn1c(CN2C(=O)c3ccccc3C2=O)nc2ccc(C3=CCN(C(=O)OC(C)(C)C)CC3)cc21]

tert-Butyl 4-(4,4,5,5-tetramethyl-1,3,2-dioxaborolan-2-yl)-3,6-dihydropyridine-1(2H)-carboxylate (966 mg, 3.12 mmol) was added to a solution of 2-[(6-bromo-1-ethyl-1H-1,3-benzodiazol-2-yl)methyl]-2,3-dihydro-1H-isoindole-1,3-dione, Intermediate 65 (1.00 g, 2.60 mmol) in dioxane (10 ml) and water (2 ml). K₂CO₃ (1.08 g, 7.81 mmol) was added then nitrogen was bubbled through the resulting suspension for 10 min. Pd(dppf)₂Cl₂ (190 mg, 0.26 mmol) was added then the reaction mixture was heated under microwave irradiation for 2 h at 85° C. The reaction mixture was partitioned between EtOAc (100 ml) and water (50 ml). The phases were separated then the organic phase was washed with brine (50 ml) then dried over Na₂SO₄, filtered and concentrated in vacuo. The crude material was purified by flash column chromatography on a silica column (50 g). The column was eluted with EtOAc:heptane, using the following gradient (% EtOAc, column volumes): 0%, 1 CV; 0-50%, 7 CV; 50-79%, 3 CV; 79%, 2 CV; 79-92%, 2 CV, 100%, 2 CV. The desired fractions were combined and concentrated in vacuo to afford the product as a white solid (670 mg, 50%).

¹H NMR (250 MHz, DMSO-d₆) δ 7.99-7.87 (m, 4H), 7.60 (s, 1H), 7.42 (d, J=8.5 Hz, 1H), 7.25 (dd, J=8.5, 1.5 Hz, 1H), 6.16 (s, 1H), 5.11 (s, 2H), 4.49-4.31 (m, 2H), 4.05-3.97 (m, 2H), 3.56 (t, J=5.6 Hz, 2H), 2.54 (s, 2H), 1.43 (s, 9H), 1.37 (t, J=7.1Hz, 3H).

LC/MS (System A): m/z (ESI⁺)=487 [MH⁺], R$_t$=1.18 min, UV purity=95%.

Intermediate 71-Synthesis of tert-butyl 4-{2-[(1,3-dioxo-2,3-dihydro-1H-isoindol-2-yl)methyl]-1-ethyl-1H-1,3-benzodiazol-6-yl}piperidine-1-carboxylate

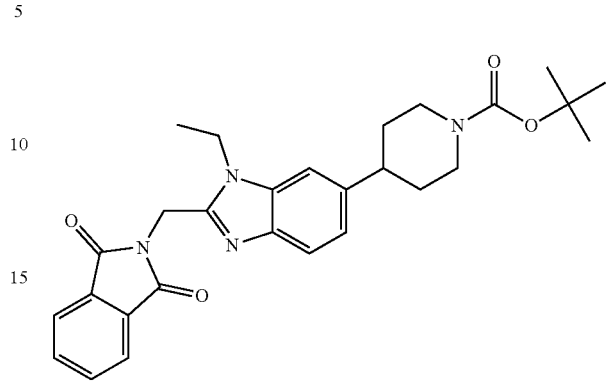

Palladium on carbon (10 wt %, 142 mg) was added to a solution of tert-butyl 4-{2-[(1,3-dioxo-2,3-dihydro-1H-isoindol-2-yl)methyl]-1-ethyl-1H-1,3-benzodiazol-6-yl}-1,2,3,6-tetrahydropyridine-1-carboxylate, Intermediate 70 (95%, 660 mg, 1.29 mmol) in EtOH (40 ml). The reaction mixture was stirred at RT under a hydrogen atmosphere for 16 h. The reaction was recharged with palladium on carbon (10 wt %, 140 mg) and stirred at RT under a hydrogen atmosphere for a further 48 h. The reaction mixture was filtered through Celite pad then concentrated in vacuo to afford the product as a colourless oil (635 mg, 94%).

¹H NMR (500 MHz, DMSO-d₆) δ 7.96 (dd, J=5.6, 2.9 Hz, 2H), 7.91 (dd, J=5.6, 3.0 Hz, 2H), 7.45 (s, 1H), 7.38 (d, J=8.3 Hz, 1H), 7.02 (dd, J=8.4, 1.4 Hz, 1H), 5.09 (s, 2H), 4.37 (q, J=7.2 Hz, 2H), 4.33(t, J=5.1 Hz, 1H), 4.10 (d, J=10.4 Hz, 2H), 2.84-2.75 (m, 2H), 1.78 (d, J=12.8 Hz, 2H), 1.58 (qd, J=12.7, 4.3 Hz, 2H), 1.42 (s, 9H), 1.37 (t, J=7.2 Hz, 3H).

LC/MS (System A): m/z (ESI⁺)=489 [MH⁺], R$_t$=1.13 min, UV purity=93%.

Intermediate 72-Synthesis of 6-{1-[(tert-butoxy)carbonyl]piperidin-4-yl}-2-[(1,3-dioxo-2,3-dihydro-1H-isoindol-2-yl)methyl]-1,3-diethyl-1H-1,3-benzodiazol-3-ium iodide

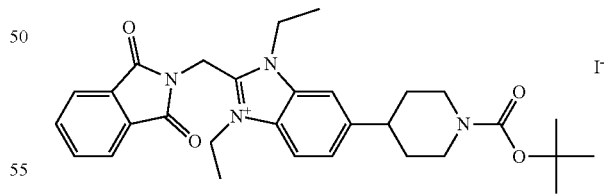

Iodoethane (486 μl, 6.04 mmol) was added to a solution of tert-butyl 4-{2-[(1,3-dioxo-2,3-dihydro-1H-isoindol-2-yl)methyl]-1-ethyl-1H-1,3-benzodiazol-6-yl}piperidine-1-carbon/late, Intermediate 71 (93%, 635 mg, 1.21 mmol) in MeCN (10 ml). The reaction mixture was heated under microwave irradiation for 3 h at 120° C. The reaction mixture was concentrated in vacuo to afford the product as a brown solid (765 mg, 84%).

¹H NMR (250 MHz, DMSO-d₆) δ 8.07-8.01 (m, 2H), 7.98-7.88 (m, 4H), 7.64 (d, J=9.3 Hz, 1H), 5.43 (s, 2H), 4.69

(q, J=7.0 Hz, 4H), 4.20-4.04 (m, 2H), 3.05-2.71 (m, 3H), 1.85-1.75 (m, 2H), 1.67 (td, J=12.3, 3.5 Hz, 2H), 1.46-1.37 (m, 15H).

LC/MS (System A): m/z (ESI$^+$)=517 [M$^+$], R$_t$=1.06 min, UV purity=86%.

Intermediate 73-Synthesis of 2-(aminomethyl)-6-{1-[(tert -butoxy)carbonyl]piperidin-4-yl}-1,3-diethyl-1H-1,3-benzodiazol-3-ium iodide

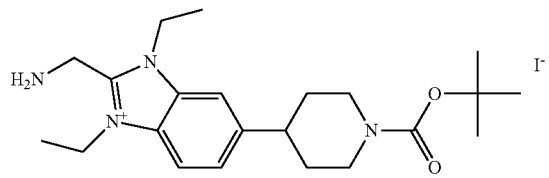 [SMILES: CCn1c(CN)[n+](CC)c2ccc(C3CCN(C(=O)OC(C)(C)C)CC3)cc21 ; [I-]]

Hydrazine hydrate (284 µl, 5.82 mmol) was added to a solution of 6-{1-[(tert -butoxy)carbonyl]piperidin-4-yl}-2-[(1,3-dioxo-2,3-dihydro-1H-isoindol-2-yl)methyl]-1,3-diethyl-1H-1,3-benzodiazol-3-ium iodide, Intermediate 72 (86%, 750 mg, 1.00 mmol) in MeOH (10 ml) in a pressure tube. The tube was sealed then the reaction mixture was heated at 75° C. for 5 h. The reaction mixture was allowed to cool to RT then concentrated in vacuo. The residue was suspended in CH$_2$Cl$_2$:MeOH (9:1, 20 ml) then filtered. The filtrate was concentrated in vacuo to afford the product as a yellow foam (605 mg, 85%).

$^1$H NMR (250 MHz, DMSO-d$_6$) δ 7.96 (d, J=8.7 Hz, 1H), 7.95 (s, 1H), 7.58 (d, J=8.7 Hz, 1H), 4.65-4.51 (m, 4H), 4.27 (s, 2H), 4.13 (d, J=13.3 Hz, 2H), 3.02-2.77 (m, 3H), 1.89-1.76 (m, 2H), 1.72-1.58 (m, 2H), 1.47-1.39 (m, 15H).

LC/MS (System A): m/z (ESI$^+$)=387 [M$^+$], R$_t$=0.89 min, UV purity=72%.

Intermediate 74-Synthesis of tert-butyl 4-(4-{2-[(1,3-dioxo-2,3-dihydro-1H-isoindol -2-yl)methyl]-1-ethyl-1H-1,3-benzodiazol-6-yl}-1H-pyrazol-1-yl)piperidine-1-carboxylate

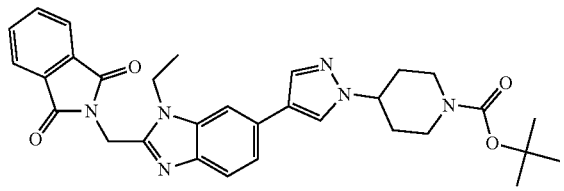 [SMILES: CCn1c(CN2C(=O)c3ccccc3C2=O)nc2ccc(-c3cnn(C4CCN(C(=O)OC(C)(C)C)CC4)c3)cc21]

tert-Butyl 4-[4-(tetramethyl-1,3,2-dioxaborolan-2-yl)-1H-pyrazol-1-yl]piperidine-1-carboxylate (540 mg, 1.43 mmol) was added to a solution of 2-[(6-bromo-1-ethyl-1H-1,3-benzodiazol-2-yl)methyl]-2,3-dihydro-1H-isoindole-1,3-dione, Intermediate 65 (500 mg, 1.30 mmol) in dioxane (10 ml) and water (0.5 ml) in a pressure tube. Cs$_2$CO$_3$ (848 mg, 2.60 mmol) was added then the resulting suspension was de-gassed by bubbling a stream of nitrogen through the reaction mixture for 10 min. XPhos-Pd-G2 (61 mg, 0.078 mmol) was added then the nitrogen bubbling was continued for a further 5 min. The tube was sealed then heated at 100° C. for 16 h. The reaction mixture was concentrated in vacuo then partitioned between EtOAc (100 ml) and water (100 ml). The phases were separated then the organic phase was washed with water (50 ml) and brine (2×50 ml), then dried over MgSO$_4$, filtered and evaporated. The crude material was purified by flash column chromatography on a silica column (50 g). The column was eluted with EtOAc:heptane, increasing the gradient linearly from 0:100 to 100:0 over 10 column volumes. The desired fractions were combined and evaporated to yield the product as a light yellow foam (226 mg, 31%).

$^1$H NMR (500 MHz, DMSO-d$_6$) δ 8.28 (s, 1H), 7.98-7.94 (m, 2H), 7.94-7.89 (m, 3H), 7.81-7.76 (m, 1H), 7.43 (d, J=8.4 Hz, 1H), 7.38 (dd, J=8.4, 1.5 Hz, 1H), 5.11 (s, 2H), 4.43-4.34 (m, 3H), 4.04 (dd, J=15.8, 8.8 Hz, 2H), 2.93 (s, 2H), 2.09-2.02 (m, 2H), 1.81 (qd, J=12.4, 4.3 Hz, 2H), 1.43 (s, 9H), 1.42-1.39 (m, 3H).

LC/MS (System A): m/z (ESI$^+$)=555 [MH$^+$], R$_t$=1.13 min, UV purity=100%.

Intermediate 75-Synthesis of 6-(1-{1-[(tert-butoxy)carbonyl]piperidin-4-yl}-1H -pyrazol-4-yl)-2-[(1,3-dioxo-2,3-dihydro-1H-isoindol-2-yl)methyl]-1,3-diethyl-1H-1,3-benzodiazol-3-ium iodide

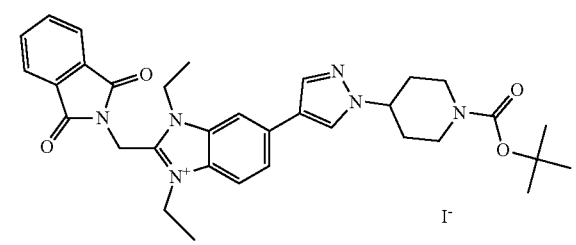 [SMILES: CCn1c(CN2C(=O)c3ccccc3C2=O)[n+](CC)c2ccc(-c3cnn(C4CCN(C(=O)OC(C)(C)C)CC4)c3)cc21 ; [I-]]

Iodoethane (159 µl, 1.98 mmol) was added to a solution of tert-butyl 4-(4-{2-[(1,3-dioxo -2,3-dihydro-1H-isoindol-2-yl)methyl]-1-ethyl-1H-1,3-benzodiazol-6-yl}-1H-pyrazol-1-yl)piperidine-1-carboxylate, Intermediate 74 (220 mg, 0.397 mmol) in MeCN (5 ml). The reaction mixture was heated under microwave irradiation for 2 h at 120° C. Iodoethane (130 µl, 1.62 mmol) was added then the reaction mixture was heated under microwave irradiation for 1 h at 120° C. The reaction mixture was concentrated in vacuo then azeotroped with diethyl ether. The residue was dried under vacuum to afford the product as a light yellow solid (280 mg, 80%).

$^1$H NMR (500 MHz, DMSO-d$_6$) δ 8.50 (s, 1H), 8.29 (s, 1H), 8.12 (s, 1H), 8.10 (d, J=8.8 Hz, 1H), 7.98-7.94 (m, 3H), 7.94-7.89 (m, 2H), 5.42 (s, 2H), 4.74-4.65 (m, 4H), 4.48-4.35 (m, 1H), 4.06 (d, 2H), 2.95 (br. s, 2H), 2.08 (d, J=6.7 Hz, 2H), 1.81 (qd, J=12.7, 4.7 Hz, 2H), 1.49-1.40 (m, 15H).

LC/MS (System A): m/z (ESI$^+$)=583 [M$^+$], R$_t$=1.13 min, UV purity=81%.

Intermediate 76-Synthesis of 2-(aminomethyl)-6-(1-{1-[(tert-butoxy)carbonyl]piperidin-4-yl}-1H-pyrazol-4-yl)-1,3-diethyl-1H-1,3-benzodiazol-3-ium iodide

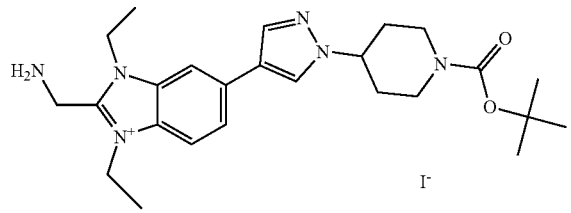 [SMILES: CCn1c(CN)[n+](CC)c2ccc(-c3cnn(C4CCN(C(=O)OC(C)(C)C)CC4)c3)cc21 ; [I-]]

Hydrazine hydrate (96 μl, 2.0 mmol) was added to a solution of 6-(1-{1-[(tert-butoxy)carbonyl]piperidin-4-yl}-1H-pyrazol-4-yl)-2-[(1,3-dioxo-2,3-dihydro-1H-isoindol-2-yl)methyl]-1,3-diethyl-1H-1,3-benzodiazol-3-ium iodide, Intermediate 75 (81%, 280 mg, 0.32 mmol) in MeOH (5 ml) in a pressure tube. The tube was sealed then heated at 75° C. for 1 h. The reaction mixture was allowed to cool to RT then concentrated in vacuo. The residue was suspended in $CH_2Cl_2$ (9:1, 20 ml) then filtered. The solid thus obtained was washed further $CH_2Cl_2$ (20 ml). The filtrates were combined and evaporated to dryness to afford the product as a light yellow solid (224 mg, >99%).

$^1$H NMR (500 MHz, DMSO-$d_6$) δ 8.48 (s, 1H), 8.23 (s, 1H), 8.10 (s, 1H), 8.03 (d, J=8.7 Hz, 1H), 7.90 (dd, J=8.7, 1.3 Hz, 1H), 4.62-4.56 (m, 4H), 4.44-4.36 (m, 1H), 4.28 (s, 2H), 4.07 (d, J=10.4 Hz, 2H), 2.94 (br. s, 2H), 2.08 (d, J=10.4 Hz, 2H), 1.82 (tt, J=12.2, 6.2 Hz, 2H), 1.46-1.40 (m, 15H).

LC/MS (System A): m/z (ESI$^+$)=453 [M$^+$], $R_t$=0.91 min, UV purity=83%.

Intermediate 77-Synthesis of methyl 2-({[(tert-butoxy)carbonyl]amino}methyl)-1-ethyl-1H-1,3-benzodiazole-6-carboxylate

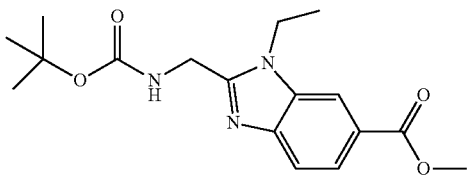 [SMILES: CCn1c(CNC(=O)OC(C)(C)C)nc2ccc(C(=O)OC)cc21]

A mixture of 2-{[(tert-butoxy)carbonyl]amino}acetic acid (8.57 g, 48.9 mmol), HATU (20.5 g, 53.8 mmol) and DIPEA (17.0 ml, 97.8 mmol) in DMF (200 ml) was stirred at RT for 1 h. Methyl 4-amino-3-(ethylamino)benzoate (9.59 g, 48.9 mmol) was added portionwise then rinsed into the reaction with THF (20 ml). The reaction mixture was stirred at RT for 18 h.

A solution of 2-{[(tert-butoxy)carbonyl]amino}acetic acid (0.857 g, 4.89 mmol), HATU (1.86 g, 4.89 mmol) and DIPEA (1.70 ml, 9.78 mmol) in DMF (3 ml) was stirred at RT for 15 min then added to the main reaction. The resulting solution was stirred at RT for 3 h. A solution of 2-{[(tert-butoxy)carbonyl]amino}acetic acid (0.857 g, 4.89 mmol), HATU (1.86 g, 4.89 mmol) and DIPEA (1.70 ml, 9.78 mmol) in DMF (3 ml) was stirred at RT for 15 min then added to the main reaction. The resulting solution was stirred at RT for 64 h. The reaction mixture was added to saturated aqueous NaHCO$_3$ solution (200 ml). EtOAc (150 ml) and water (100 ml) were added then the phases were separated. The aqueous phase was extracted with EtOAc (2×150 ml), then the combined organic phases were washed with water (4×100 ml) and brine (50 ml) then dried over Na$_2$SO$_4$, filtered and evaporated to afford the crude intermediate as a black oil (18 g). The oil thus obtained was dissolved in acetic acid (80 ml) and stirred at 70° C. for 1 h. The reaction was allowed to cool to RT then evaporated to afford a brown solid. The solid was suspended in EtOAc (200 ml) then filtered and was washed with EtOAc, then dried under vacuum to afford a pale pink solid (6.5 g). The solid thus obtained was suspended in EtOAc (200 ml). The resulting suspension was heated at 50° C. for 15 min then allowed to cool to RT. The solid was collected by filtration to afford the product as a white solid (2.43 g). The filtrate was again filtered and the solid was collected by filtration, washed with EtOAc:heptane then dried under vacuum to afford a second batch of the product as a white solid (1.34 g). The filtrate was transferred to a separating funnel then extracted with saturated aqueous NaHCO$_3$ solution (3×100 ml), water (100 ml) and brine (50 ml) then dried over Na$_2$SO$_4$, filtered and evaporated to a yellow solid which was suspended in the minimum volume of EtOAc:heptane (1:4) and filtered then dried under vacuum to afford a third batch of the product as a white solid (1.77 g). The filtrate from the first filtration was transferred to a separating funnel then extracted with saturated aqueous NaHCO$_3$ solution (3×100 ml), water (100 ml) and brine (50 ml) then dried over Na$_2$SO$_4$, filtered and evaporated to a dark brown solid. The solid was suspended in EtOAc (50 ml) then filtered. The solid was dried under vacuum to afford a fourth batch of the product as a white solid (3.4 g). The filtrate was evaporated to afford a dark solid (8 g). The solid thus obtained was dissolved in CH$_2$Cl$_2$ then evaporated onto silica (16 g). The crude material was purified by flash column chromatography on a silica column (100 g). The column was eluted with EtOAc:heptane, increasing the gradient linearly from 0:100 to 100:0 over 10 column volumes. The desired fractions were combined and evaporated to afford a brown solid. The solid thus obtained was suspended in EtOAc:heptane (1:4, 20 ml) then filtered. The solid was washed with EtOAc:heptane then dried under vacuum to afford a fifth batch of the product as a white solid (1.45 g). The filtrate was concentrated in vacuo then the residue was suspended in EtOAc, filtered and dried under vacuum to afford a sixth batch of the product as an off-white solid (0.32 g). The 6 batches of solid were combined as an EtOAc suspension then evaporated and dried under vacuum to yield the product as an off-white solid (10.7 g, 66%).

$^1$H NMR (500 MHz, DMSO-$d_6$) δ 8.16 (d, J=1.1Hz, 1H), 7.82 (dd, J=8.4, 1.6 Hz, 1H), 7.66 (d, J=8.4 Hz, 1H), 7.52 (d, J=5.3 Hz, 1H), 4.47 (d, J=5.8 Hz, 2H), 4.35 (q, J=7.2 Hz, 2H), 3.88 (s, 3H), 1.46-1.22 (m, 12H).

LC/MS (System A): m/z (ESI$^+$)=334 [MH$^+$], $R_t$=0.98 min, UV purity=100%.

Intermediate 78-2-({[(tert-butoxy)carbonyl]amino}methyl)-1-ethyl-1H-1,3-benzodiazole-6-carboxylic acid

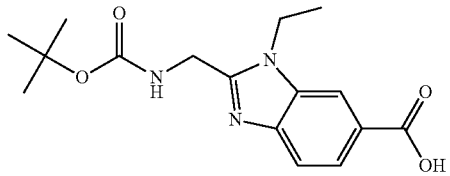 [SMILES: CCn1c(CNC(=O)OC(C)(C)C)nc2ccc(C(=O)O)cc21]

Aqueous LiOH solution (2.0 M, 16 ml, 32 mmol) was added to a suspension of methyl 2-({[(tert-butoxy)carbonyl]amino}methyl)-1-ethyl-1H-1,3-benzodiazole-6-carboxylate, Intermediate 77 (6.91 g, 20.7 mmol) in THF (100 ml). The reaction mixture was stirred at 50° C. for 16 h then allowed to cool to RT. The reaction mixture was concentrated in vacuo then the resulting solid was suspended in water (50 ml). Aqueous HCl solution (2 M) was added dropwise until pH 4 was reached. The resultant suspension was filtered then the solid was washed with the minimum of water and MeCN then dried under vacuum to afford the product as a white solid (6.05 g, 90%).

$^1$H NMR (500 MHz, DMSO-$d_6$) δ 12.77 (s, 1H), 8.18-8.07 (m, 1H), 7.80 (dd, J=8.4, 1.5 Hz, 1H), 7.63 (d, J=8.4 Hz, 1H), 7.52 (s, 1H), 4.47 (d, J=5.8 Hz, 2H), 4.34 (q, J=7.2 Hz, 2H), 1.46-1.21 (m, 12H).

LC/MS (System A): m/z (ESI$^+$)=320 [MH$^+$], $R_t$=0.84 min, UV purity=99%.

Intermediate 79-Synthesis of 2-(aminomethyl)-1-ethyl-1H-1,3-benzodiazole-6-carboxylic acid dihydrochloride

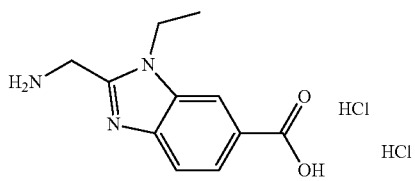 [SMILES: CCn1c(CN)nc2ccc(C(=O)O)cc21 ; Cl ; Cl]

HCl solution in dioxane (4.0 M, 14 ml, 56 mmol) was added to a suspension of 2-({[(tert-butoxy)carbonyl]amino}methyl)-1-ethyl-1H-1,3-benzodiazole-6-carboxylic acid, Intermediate 78 (3.55 g, 11.1 mmol) in MeCN (60 ml). The reaction mixture was stirred at RT for 4 h then filtered. The solid was dried under vacuum to afford the solid as a white solid (3.39 g, 98%).

$^1$H NMR (500 MHz, DMSO-$d_6$) δ 8.78 (s, 3H), 8.25 (s, 1H), 7.88 (dd, J=8.5, 1.2 Hz, 1H), 7.74 (d, J=8.4 Hz, 1H), 4.50 (d, J=4.4 Hz, 2H), 4.38 (q, J=7.2 Hz, 2H), 1.34 (t, J=7.2 Hz, 3H).

LC/MS (System A): m/z (ESI$^+$)=220 [MH$^+$], $R_t$=0.16 min, ELS purity=94%.

Intermediate 80-Synthesis of 2-({[(benzyloxy)carbonyl]amino}methyl)-1-ethyl-1H-1,3-benzodiazole-6-carboxylic acid

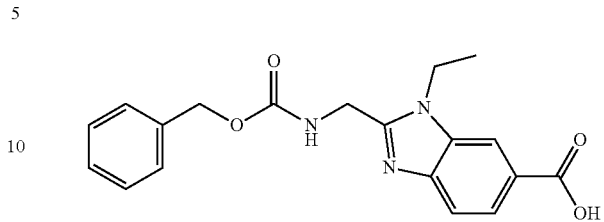

NaHCO$_3$ (4.83 g, 57.5 mmol) was added portionwise to a cooled (0° C.) suspension of 2-(aminomethyl)-1-ethyl-1H-1,3-benzodiazole-6-carboxylic acid dihydrochloride, Intermediate 79 (4.20 g, 14.4 mmol) in water (40 ml). The reaction mixture was allowed to warm to RT then a solution of benzyl 2,5-dioxopyrrolidin-1-yl carbonate (3.94 g, 15.8 mmol) in THF (40 ml) was added dropwise over 15 min. The reaction mixture was left to stir at RT for 16. The resultant mixture was extracted with EtOAc (50 ml). The phases were separated then the organic phase was washed with water (3×10 ml). The combined aqueous phases were acidified to pH 5 by addition of aqueous HCl solution (2 M), resulting in precipitation of a solid. The resultant suspension was filtered then the solid was dried under vacuum to afford the product as a white solid (3.5 g, 69%).

$^1$H NMR (500 MHz, DMSO-$d_6$) δ 8.12 (s, 1H), 7.97 (t, J=5.8 Hz, 1H), 7.80 (dd, J=8.4, 1.4 Hz, 1H), 7.62 (d, J=8.4 Hz, 1H), 7.42-7.09 (m, 5H), 5.06 (s, 2H), 4.54 (d, J=5.9 Hz, 2H), 4.33 (q, J=7.0 Hz, 2H), 1.28 (t, J=7.1Hz, 3H).

LC/MS (System A): m/z (ESI$^+$)=354 [MH$^+$], $R_t$=0.89 min, UV purity=100%.

Intermediate 81-tert-butyl 2-({[(benzyloxy)carbonyl]amino}methyl)-1-ethyl-1H-1,3-benzodiazole-6-carboxylate

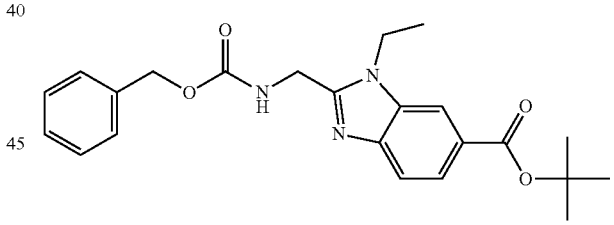

1,1-Di-tert-butoxy-N,N-dimethylmethanamine (6.77 ml, 28.3 mmol) was added to a suspension of 2-({[(benzyloxy)carbonyl]amino}methyl)-1-ethyl-1H-1,3-benzodiazole-6-carboxylic acid, Intermediate 80 (2.50 g, 7.08 mmol) in α,α,α-trifluorotoluene (50 ml). The reaction mixture was heated at 100° C. for 1 h. The reaction mixture was allowed to cool to RT then 1,1-di-tert-butoxy-N,N-dimethylmethanamine (6.77 ml, 28.3 mmol) was added dropwise over 15 min. The resultant mixture was heated at 100° C. for 45 min. The reaction mixture was cooled to 50° C. then 1,1-di-tert-butoxy-N,N-dimethylmethanamine (3.38 ml, 14.15 mmol) was added dropwise over 5 min. The resultant mixture was heated at 100° C. for 0.5 h then allowed to cool to RT. The reaction mixture was partitioned between EtOAc (50 ml) and water (50 ml). The phases were separated then the organic phase was washed with water (2×30 ml), saturated aqueous NaHCO$_3$ solution (20 ml) and brine (10 ml) then dried over Na$_2$SO$_4$, filtered and concentrated in vacuo to afford a beige solid (2.5 g). The solid thus obtained was suspended in MeCN (10 ml). The solid was collected by filtration then dried under vacuum to afford the product as an off-white solid (2.30 g, 79%).

$^1$H NMR (500 MHz, DMSO-d$_6$) δ 8.07 (s, 1H), 7.97 (m, 1H), 7.76 (dd, J=8.4, 1.5 Hz, 1H), 7.64 (d, J=8.4 Hz, 1H), 7.34 (m, 5H), 5.07 (s, 2H), 4.55 (d, J=6.0 Hz, 2H), 4.38-4.25 (m, 2H), 1.57 (s, 9H), 1.29 (m, 3H).

LC/MS (System A): m/z (ESI$^+$)=410 [MH$^+$], R$_t$=1.17 min, UV purity=99%.

Intermediate 82-Synthesis of 2-({[(benzyloxy)carbonyl]amino}methyl)-6-[(tert -butoxy)carbonyl]-1,3-diethyl-1H-1,3-benzodiazol-3-ium iodide

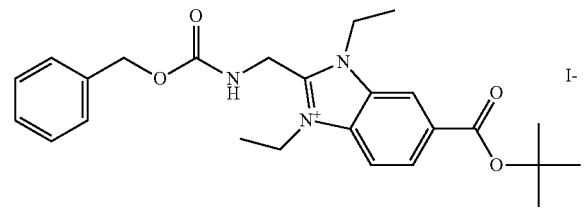 [SMILES: CCn1c(CNC(=O)OCc2ccccc2)[n+](CC)c2ccc(C(=O)OC(C)(C)C)cc21 ; [I-]]

Three reactions were run independently as follows then combined for work-up. Reaction 1: a suspension of tert-butyl 2-({[(benzyloxy)carbonyl]amino}methyl)-1-ethyl-1H-1,3-benzodiazole-6-carboxylate, Intermediate 81 (800 mg, 1.95 mmol) and iodoethane (629 μl, 7.82 mmol) in MeCN (10 ml) was heated under microwave irradiation for 2 h at 120° C. The reaction was retreated with iodoethane (629 μl, 7.82 mmol) then the reaction mixture was heated under microwave irradiation for a further 2 h at 120° C. Reaction 2: a suspension of tert-butyl 2-({[(benzyloxy)carbonyl]amino}methyl)-1-ethyl-1H-1,3-benzodiazole-6-carboxylate, Intermediate 81 (800 mg, 1.95 mmol) and iodoethane (629 μl, 7.82 mmol) in MeCN (10 ml) was heated under microwave irradiation for 1 h 45 min at 120° C. The reaction was retreated with iodoethane (629 μl, 7.82 mmol) then the reaction mixture was heated under microwave irradiation for a further 1.5 h at 120° C. Reaction 3: a suspension of tert-butyl 2-({[(benzyloxy)carbonyl]amino}methyl)-1-ethyl-1H-1,3-benzodiazole-6-carboxylate, Intermediate 81 (700 mg, 1.71 mmol) and iodoethane (591 μl, 6.84 mmol) in MeCN (10 ml) was heated under microwave irradiation for 1.5 h at 120 ° C. The reaction was retreated with iodoethane (629 μl, 7.82 mmol) then the reaction mixture was heated under microwave irradiation for a further 1.5 h at 120° C. The three reactions were combined and concentrated in vacuo. The crude material was purified by flash column chromatography on C18 (60 g). The column was eluted with MeCN:water+0.1% formic acid using the following gradient (% MeCN, column volumes): 5%, 2 CV; 5-31%, 5 CV; 31%, 4 CV; 31-59%, 6 CV; 59-100%, 3 CV; 100% 1 CV. The desired fractions were combined and concentrated in vacuo to afford the product as a white foam (2.13 g, 67%).

$^1$H NMR (500 MHz, DMSO-d$_6$) δ 8.54 (s, 1H), 8.43 (t, J=5.1Hz, 1H), 8.22-8.12 (m, 2H), 7.42-7.27 (m, 5H), 5.06 (s, 2H), 4.90 (d, J=5.3 Hz, 2H), 4.79-4.59 (m, 4H), 1.61 (s, 9H), 1.47-1.36 (m, 6H).

LC/MS (System A): m/z (ESI$^+$)=438 [M$^+$], R$_t$=1.07 min, UV purity=100%.

Intermediate 83-Synthesis of 2-(aminomethyl)-6-carboxy-1,3-diethyl-1H-1,3-benzodiazol-3-ium hydrobromide bromide

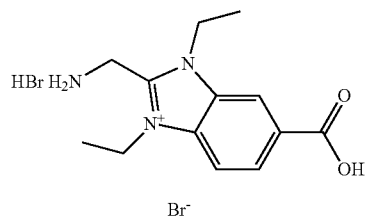

HBr solution in AcOH (33 wt %, 4.28 ml, 18.8 mmol) was added to a solution of 2-({[(benzyloxy)carbonyl]amino}methyl)-6-[(tert-butoxy)carbonyl]-1,3-diethyl-1H-1,3-benzodiazol-3-ium iodide, Intermediate 82 (2.13 g, 3.77 mmol) in AcOH (10 ml). The reaction mixture was stirred at RT for 0.5 h. The resultant suspension was concentrated in vacuo then azeotroped with MeCN. The solid thus obtained was suspended in the minimum volume of MeCN then filtered and dried under vacuum to afford the product as a white solid (1.52 g, 99%).

$^1$H NMR (500 MHz, DMSO-d$_6$) δ 8.69 (s, 1H), 8.31-8.20 (m, 2H), 4.85-4.63 (m, 6H), 1.53 -1.40 (m, 6H).

LC/MS (System A): m/z (ESI$^+$)=248 [M$^+$], R$_t$=0.15 min, ELS purity=100%.

Intermediate 84-Synthesis of 3-amino-N-[(1-ethyl-1H-1,3-benzodiazol-2-yl)methyl]-5H-pyrrolo[2,3-b]pyrazine-2-carboxamide

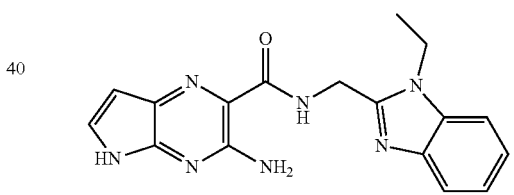

(1-Ethyl-1H-1,3-benzodiazol-2-yl)methanaminium chloride (380 mg, 1.79 mmol) was added to a solution of lithium(1$^+$) ion 3-amino-5H-pyrrolo[2,3-b]pyrazine-2-carboxylate, Intermediate 3 (300 mg, 1.63 mmol), HBTU (927 mg, 2.44 mmol) and DIPEA (852 μl, 4.89 mmol) in DMF (4 ml). The reaction mixture was stirred at RT for 20 h. Additional HBTU (450 mg, 1.18 mmol) was added and the reaction was left to stir at RT for a further 5 h. The reaction mixture was partitioned between water (100 ml) and EtOAc (80 ml). The phases were separated then the aqueous phase was extracted with EtOAc (2×80 ml). The combined organic phases were dried over Na$_2$SO$_4$ then concentrated in vacuo. The crude material was purified by flash column chromatography on C18 (60 g). The column was eluted with MeCN:water+0.1% NH4OH using the following gradient (% MeCN, column volumes): 10%, 2 CV; 10-45%, 15 CV; 45-90%, 4 CV; 90%, 2 CV. The desired fractions were combined and concentrated in vacuo to afford the product as a yellow solid (78 mg, 11%).

1H NMR (500 MHz, DMSO-d$_6$) δ 11.46 (s, 1H), 9.08 (t, J=5.6 Hz, 1H), 7.60 (d, J=7.7 Hz, 1H), 7.55 (d, J=7.9 Hz,

1H), 7.48 (d, J=3.7 Hz, 1H), 7.38-7.10 (m, 4H), 6.44 (d, J=3.7 Hz, 1H), 4.80 (d, J=5.6 Hz, 2H), 4.33 (q, J=7.2 Hz, 2H), 1.32 (t, J=7.2 Hz, 3H).

LC/MS (System A): m/z (ESI$^+$)=336 [MH$^+$], R$_t$=0.87 min, UV purity=79%.

Intermediate 85-Synthesis of 3-amino-N-[(1-benzyl-1H-1,3-benzodiazol-2-yl)methyl]-5H-pyrrolo[2,3-b]pyrazine-2-carboxamide

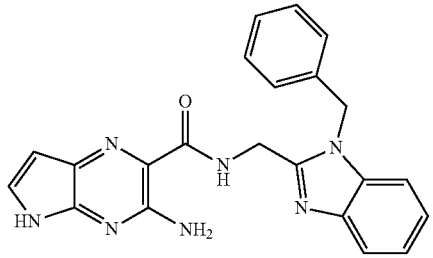 [SMILES: Nc1nc2[nH]ccc2nc1C(=O)NCc1nc2ccccc2n1Cc1ccccc1]

A mixture of lithium(1$^+$) ion 3-amino-5H-pyrrolo[2,3-b]pyrazine-2-carboxylate, Intermediate 3 (50 mg, 0.27 mmol), HBTU (113 mg, 0.272 mmol) and DIPEA (142 µl, 0.815 mmol) in DMF (1 ml) was stirred at RT for 1 h. (1-Benzyl-1H-1,3-benzodiazol-2-yl)methanaminium chloride (82 mg, 0.30 mmol) was added then the resulting mixture was stirred at RT for 4 h. Additional HBTU (60 mg, 0.16 mmol) was added and the reaction was stirred at RT for a further 16 h. The reaction mixture was partitioned between water (10 ml) and EtOAc (10 ml). The phases were separated then the aqueous phase was extracted with EtOAc (2×10 ml). The combined organic phases were dried over Na$_2$SO$_4$ then concentrated in vacuo. The crude material was purified by flash column chromatography on C18 (30 g). The column was eluted with MeCN:water+0.1% NH$_4$OH using the following gradient (% MeCN, column volumes): 10%, 2 CV; 10-33%, 11 CV; 33-58%, 6 CV. The desired fractions were combined and concentrated in vacuo to afford the product as a yellow solid (39 mg, 35%).

$^1$H NMR (500 MHz, DMSO-d$_6$) δ 11.43 (s, 1H), 9.06 (t, J=5.6 Hz, 1H), 7.66-7.59 (m, 1H), 7.51-7.45 (m, 2H), 7.31-7.12 (m, 9H), 6.43 (d, J=3.7 Hz, 1H), 5.60 (s, 2H), 4.77 (d, J=5.6 Hz, 2H).

LC/MS (System A): m/z (ESI$^+$)=398 [MH$^+$], R$_t$=0.97 min, UV purity=96%.

Intermediate 86-Synthesis of 5-(2-aminoethoxy)-1,3-diethyl-2-[({[(9H-fluoren-9-yl)methoxy]carbonyl}amino)methyl]-1H-1,3-benzodiazol-3-ium hydrochloride chloride

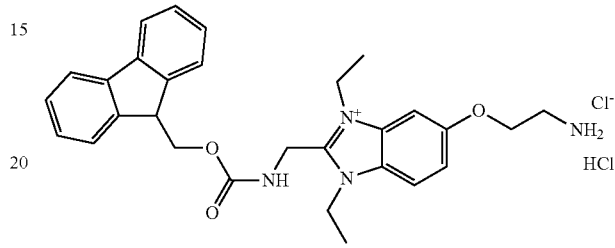

HCl solution in dioxane (4.0 M, 14 ml, 56 mmol) was added to a mixture of 6-(2-{[(tert-butoxy)carbonyl]amino}ethoxy)-1,3-diethyl-2-({[(9H-fluoren-9-ylmethoxy)carbonyl]amino}methyl)-1H-1,3-benzodiazol-3-ium iodide, Intermediate 58 (4.28 g, 6.01 mmol) in MeCN (50 ml). The resulting mixture was stirred at RT for 20 min then concentrated in vacuo to afford the product as a brown/orange foam (3.87 g, 98%).

$^1$H NMR (500 MHz, DMSO-d$_6$) δ 8.30 (t, J=5.3 Hz, 1H), 8.15 (s (br), 3H), 7.99 (d, J=9.1 Hz, 1H), 7.86 (d, J=7.5 Hz, 2H), 7.69-7.60 (m, 3H), 7.38-7.30 (m, 3H), 7.25 (t, J=7.3 Hz, 2H), 4.75 (d, J=5.2 Hz, 2H), 4.58-4.45 (m, 6H), 4.34 (t, J=4.9 Hz, 2H), 4.22 (t, J=6.0 Hz, 1H), 1.37-1.30 (m, 6H).

LC/MS (System A): m/z (ESI$^+$)=485 [M$^+$], R$_t$=0.84 min, UV purity=85%.

Intermediate 87-Synthesis of 5-(2-{bis[(2S,3R)-2,3-dihydroxy-3-[(4R,5R)-5-hydroxy-2-phenyl-1,3-dioxan-4-yl]propyl]amino}ethoxy)-1,3-diethyl-2-[({[(9H-fluoren-9-yl)methoxy]carbonyl}amino)methyl]-1H-1,3-benzodiazol-3-ium chloride

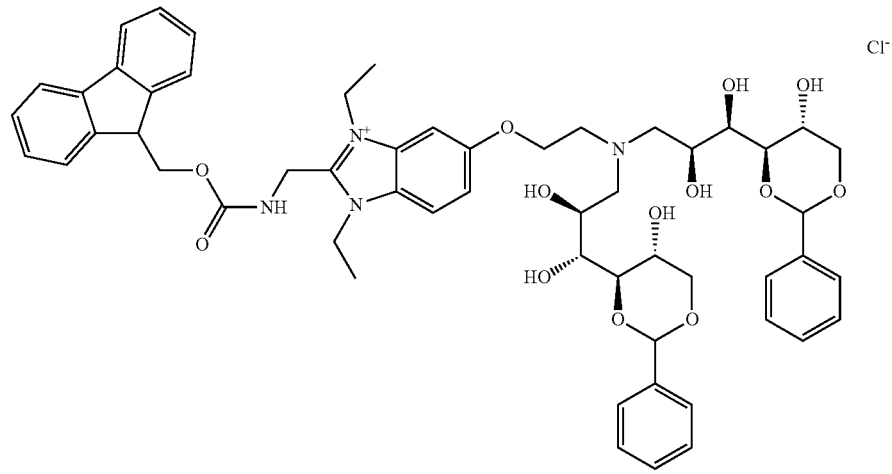

A mixture of 4,6-O-benzylidene-D-glucopyranose (95%, 6.67 g, 23.6 mmol), 5-(2-aminoethoxy)-1,3-diethyl-2-[({[(9H-fluoren-9-yl)methoxy]carbonyl}amino)methyl]-1H-1,3-benzodiazol-3-ium hydrochloride chloride, Intermediate 86 (85%, 3.87 g, 5.91 mmol) and AcOH (1.35 ml, 23.6 mmol) in MeOH (100 ml) was stirred at RT for 0.5 h. NaCNBH$_3$ (1.48 g, 23.6 mmol) was added then the resulting mixture was stirred at RT for 20 h. More MeOH (40 ml) was added then the reaction was left to stir at RT for a further 24 h. More MeOH (80 ml) was added, then the reaction was retreated with 4,6-O-benzylidene-D-glucopyranose (95%, 1.60 g, 5.67 mmol), AcOH (0.34 ml, 5.94 mmol) and NaCNBH$_3$ (0.38 g, 6.05 mmol). The reaction was left to stir at RT for a further 92 h then added to saturated aqueous NaHCO3 solution (250 ml). The resultant suspension was stirred at RT for 20 min. The solid was collected by filtration then washed with water and dried under vacuum to afford the product as a pale pink solid (6.43 g, 89%).

LC/MS (System A): m/z (ESI$^+$)=990 [M$^+$], 496 [(M$^+$)+H$^+$], R$_t$=0.93 min, UV purity=84%.

Intermediate 88-2-(aminomethyl)-5-(2-{bis[(2S,3R)-2,3-dihydroxy-3-[(4R,5R)-5-hydroxy-2-phenyl-1,3-dioxan-4-yl]propyl]amino}ethoxy)-1,3-diethyl-1H-1,3-benzodiazol-3-ium chloride

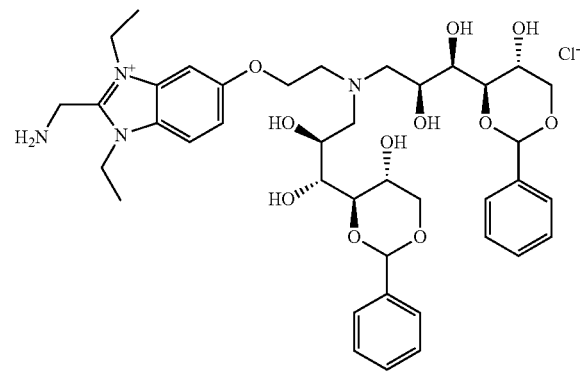

Morpholine (4.77 ml, 55.1 mmol) was added to a stirred mixture of 5-(2-{bis[(2S,3R)-2,3-dihydroxy-3-[(4R,5R)-5-hydroxy-2-phenyl-1,3-dioxan-4-yl]propyl]amino}ethoxy)-1,3-diethyl-2-[({[(9H-fluoren-9-yl)methoxy]carbonyl}amino)methyl]-1H-1,3-benzodiazol-3-ium chloride, Intermediate 87 (84% 6.42 g, 5.26 mmol) in THF (60 ml). The resulting mixture was stirred at RT for 4 h. The reaction mixture was diluted with diethyl ether (150 ml). The resulting suspension was agitated then the suspension was decanted off, leaving behind a viscous oil. More diethyl ether (80 ml) was added to the oil residue then the mixture was sonicated. The resulting suspension was again decanted off to leave behind a viscous oil. The process was repeated once more with diethyl ether (80 ml) then the resulting viscous oil was dried under vacuum to afford the product as a pale purple foam (4.39 g, 85%).

LC/MS (System A): m/z (ESI$^+$)=767 [M$^+$], 384 [(M$^+$)+H$^+$], R$_t$=0.75 min, UV purity=82%.

Intermediate 89-Synthesis of 2-(aminomethyl)-5-(2-{bis[(2S,3R,4R,5R)-2,3,4,5,6-pentahydroxyhexyl]amino}ethoxy)-1,3-diethyl-1H-1,3-benzodiazol-3-ium dihydrochloride chloride

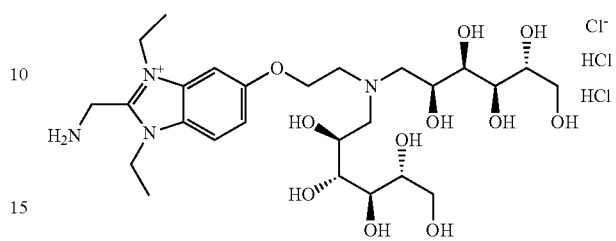

A mixture of 2-(aminomethyl)-5-(2-{bis[(2S,3R)-2,3-dihydroxy-3-[(4R,5R)-5-hydroxy-2-phenyl-1,3-dioxan-4-yl]propyl]amino}ethoxy)-1,3-diethyl-1H-1,3-benzodiazol-3-ium chloride, Intermediate 88 (82%, 1.50 g, 1.53 mmol) and aqueous HCl solution (2.0 M, 25 ml, 50 mmol) was stirred at RT for 1 h. The reaction mixture was concentrated in vacuo then the residue was dissolved in water (10 ml) and lyophilised to afford the product as a pale purple foam (1.53 g, >99%).

LC/MS (System A): m/z (ESI$^+$)=591 [M$^+$], 296 [(M$^+$)+H$^+$], R$_t$=0.13 min, UV purity=70%.

Intermediate 90-Synthesis of 5-(3-aminopropoxy)-1,3-diethyl-2-[({[(9H-fluoren-9-yl)methoxy]carbonyl}amino)methyl]-1H-1,3-benzodiazol-3-ium hydrochloride chloride

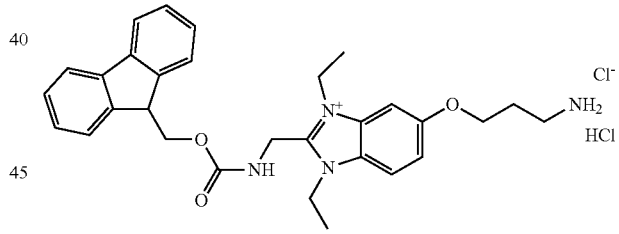

HCl solution in dioxane (4.0 M, 3.3 ml, 13 mmol) was added to a mixture of 6-(3-{[(tert-butoxy)carbonyl]amino}propoxy)-1,3-diethyl-2-({[(9H-fluoren-9-ylmethoxy)carbonyl]amino}methyl)-1H-1,3-benzodiazol-3-ium iodide, Intermediate 63 (95%, 1.00 g, 1.31 mmol) in MeCN (15 ml). The reaction mixture was stirred at RT for 0.5 h then concentrated in vacuo to afford the product as a viscous yellow oil (875 mg, >99% -yield corrected for 15 wt % residual dioxane observed in NMR).

$^1$H NMR (500 MHz, DMSO-d$_6$) δ 8.30 (t, J=5.3 Hz, 1H), 8.00-7.85 (m, 6H), 7.65-7.59 (m, 3H), 7.37 (t, J=7.4 Hz, 2H), 7.31 (dd, J=9.1, 2.1Hz, 1H), 7.27 (t, J=7.4 Hz, 2H), 4.76 (d, J=5.4 Hz, 2H), 4.58-4.46 (m, 6H), 4.27-4.19 (m, 3H), 3.05-2.95 (m, 2H), 2.12-2.06 (m, 2H), 1.34 (t, J=7.1Hz, 6H).

LC/MS (System A): m/z (ESI$^+$)=499 [M$^+$], R$_t$=0.89 min, UV purity=98%.

Intermediate 91-Synthesis of 5-(3-{bis[(2S,3R)-2,3-dihydroxy-3-[(4R,5R)-5-hydroxy -2-phenyl-1,3-dioxan-4-yl]propyl]amino}propoxy)-1,3-diethyl-2-[({[(9H-fluoren-9-yl)methoxy]carbonyl}amino) methyl]-1H-1,3-benzodiazol-3-ium hydrochloride chloride

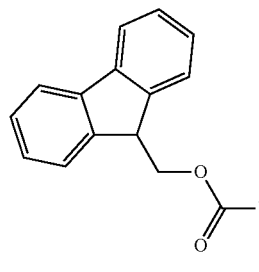
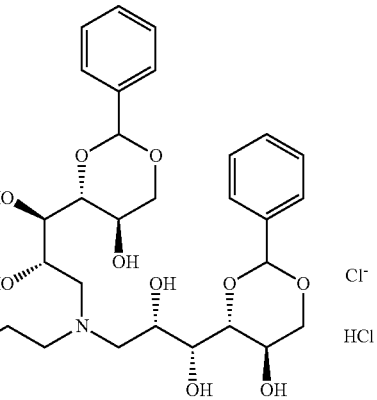

A mixture of 4,6-O-benzylidene-D-glucopyranose (1.43 g, 5.32 mmol), 5-(3- aminopropoxy)-1,3-diethyl-2-[({[(9H-fluoren-9-yl)methoxy]carbonyl}amino)methyl]-1H-1,3- benzodiazol-3-ium hydrochloride chloride, Intermediate 90 (85%, 875 mg, 1.30 mmol) and AcOH (305 µl, 5.32 mmol) in MeOH (25 ml) was stirred at RT for 0.5 h. NaCNBH$_3$ (334 mg, 5.32 mmol) was added then the resulting mixture was stirred at RT for 64 h. Additional 4,6-O-benzylidene-D-glucopyranose (500 mg, 1.86 mmol) and AcOH (110 µl, 1.92 mmol) was added. The mixture was stirred for 0.5 h then NaCNBH$_3$ (115 mg, 1.83 mmol) was added. The resulting mixture was stirred at RT for a further 16 h. Saturated aqueous NaHCO$_3$ solution (40 ml) was added over 5 min whereupon a white precipitate formed. The resultant suspension was filtered and the collected solid was washed with water then dried under vacuum to afford the product as a white solid (1.39 g, 60%).

LC/MS (System A): m/z (ESI$^+$)=503 [(M$^+$)+H$^+$], R$_t$=1.00 min, UV purity=60%.

Intermediate 92-Synthesis of 2-(aminomethyl)-5-(3-{bis[(2S,3R)-2,3-dihydroxy-3-[(4R,5R)-5-hydroxy-2-phenyl-1,3-dioxan-4-yl]propyl]amino}propoxy)-1,3-diethyl-1H -1,3-benzodiazol-3-ium hydrochloride chloride

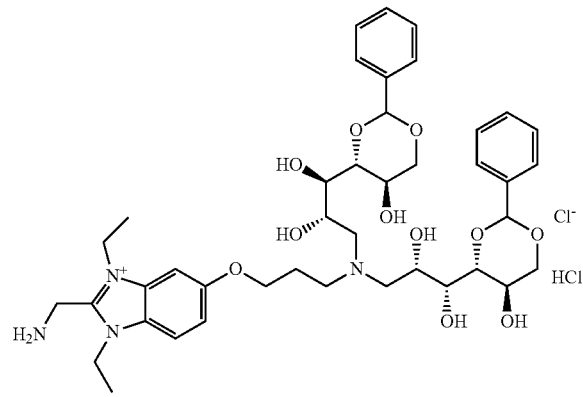

Morpholine (659 µl, 7.62 mmol) was added to a mixture of 5-(3-{bis[(2S,3R)-2,3-dihydroxy -3-[(4R,5R)-5-hydroxy-2-phenyl-1,3-dioxan-4-yl]propyl]amino}propoxy)-1,3-diethyl-2-({[(9H-fluoren-9-ylmethoxy)carbonyl]amino}methyl)-1H-1,3-benzodiazol-3-ium chloride hydrochloride, Intermediate 91 (60%, 1.32 g, 0.762 mmol) in THF (10 ml). The mixture was stirred at RT for 2.5 h. The reaction mixture was diluted with diethyl ether (20 ml). The resulting suspension was sonicated then the suspension was decanted off, leaving behind a viscous oil. More diethyl ether (20 ml) was added to the oil residue then the mixture was sonicated. The resulting suspension was again decanted off to leave behind a viscous oil. The process was repeated once more with diethyl ether (20 ml) then the resulting viscous oil was dried under vacuum to afford the product as a pale orange solid (639 mg, 79%).

LC/MS (System A): m/z (ESI$^+$)=781 [M$^+$], 391 [(M$^+$)+H$^+$], R$_t$=0.78 min, UV purity=80%.

Intermediate 93-Synthesis of 2-(aminomethyl)-5-(3-{bis [(2S,3R,4R,5R)-2,3,4,5,6-pentahydroxyhexyl]amino}propoxy)-1,3-diethyl-1H-1,3-benzodiazol-3-ium hydrochloride chloride

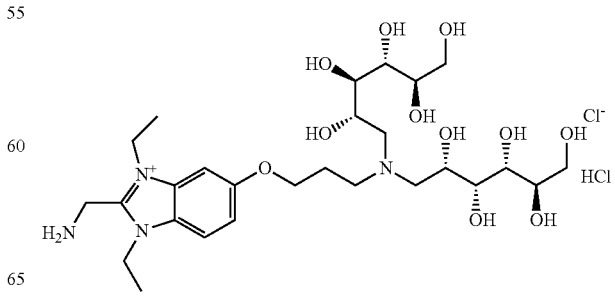

A mixture of 2-(aminomethyl)-5-(3-{bis[(2S,3R)-2,3-dihydroxy-3-[(4R,5R)-5-hydroxy-2-phenyl-1,3-dioxan-4-yl]propyl]amino}propoxy)-1,3-diethyl-1H-1,3-benzodiazol-3-ium hydrochloride chloride, Intermediate 92 (80%, 375 mg, 0.367 mmol) and aqueous HCl solution (2.0 M, 8.0 ml, 16 mmol) was stirred at RT for 40 min. The reaction mixture was concentrated in vacuo then diluted with water and lyophilised to afford the product as a pale orange solid (305 mg, 98%).

LC/MS (System A): m/z (ESI$^+$)=605 [M$^+$], 303 [(M$^+$)+H$^+$], R$_t$=0.13 min, UV purity=80%.

Intermediate 94-Synthesis of tert-butyl 4-{1-ethyl-2-[({[(9H-fluoren-9-yl)methoxy]carbonyl}amino)methyl]-1H-1,3-benzodiazol-6-yl}piperidine-1-carboxylate

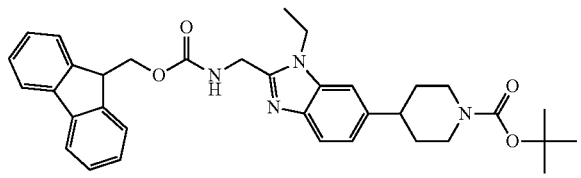 [SMILES: CCn1c(CNC(=O)OCC2c3ccccc3-c3ccccc32)nc2ccc(C3CCN(C(=O)OC(C)(C)C)CC3)cc21]

Step 1: A suspension of hydrazine hydrate (1.27 ml, 1.31 mmol) and tert-butyl 4-{2-[(1,3-dioxo-2,3-dihydro-1H-isoindol-2-ylmethyl]-1-ethyl-1H-1,3-benzodiazol-6-yl}piperidine-1-carboxylate Intermediate 71 (2.56 g, 5.24 mmol) in MeOH (30 ml) was heated under reflux for 2.5 h then allowed to cool to RT. The resultant suspension was left to stand at RT for 16 h then filtered. The collected solid was washed solid with CH$_2$Cl$_2$ then the filtrate was concentrated in vacuo and azeotroped with MeCN to afford the intermediate as a white solid (1.24 g). Step 2: A solution of (2,5-dioxopyrrolidin-1-yl) 9H-fluoren-9-ylmethyl carbonate (1.16 g, 3.43 mmol) in MeCN (20 ml) was added dropwise over 10 min to a mixture of the intermediate from Step 1 and NaHCO$_3$ (576 mg, 6.86 mmol) in MeCN (40 ml) and water (30 ml). The reaction mixture was stirred at RT for 21 h then partitioned between EtOAc (100 ml) and water (100 ml). The phases were separated then the organic phase was washed with water (2×50 ml), brine (50 ml), then dried over Na$_2$SO$_4$, filtered and concentrated in vacuo. The solid thus obtained was suspended in MeCN (150 ml) under reflux, with sonication at various intervals. The resultant suspension was allowed to cool to RT then filtered. The collected solid was dried under vacuum to afford the product as a white solid (1.52 g, 50% over 2 steps).

$^1$H NMR (500 MHz, DMSO-d$_6$) δ 7.99 (s, 1H), 7.88 (d, J=7.5 Hz, 2H), 7.72 (d, J=7.4 Hz, 2H), 7.48 (d, J=8.2 Hz, 1H), 7.44-7.37 (m, 3H), 7.31 (t, J=7.4 Hz, 2H), 7.07 (d, J=8.3 Hz, 1H), 4.48 (d, J=5.7 Hz, 2H), 4.32 (d, J=7.1Hz, 2H), 4.23 (t, J=6.9 Hz, 3H), 4.15-4.05 (m, 2H), 2.95-2.75 (m, 3H), 1.80 (d, J=12.0 Hz, 2H), 1.65-1.52 (m, 2H), 1.42 (s, 9H), 1.26 (t, J=7.1Hz, 3H).

LC/MS (System A): m/z (ESI$^+$)=581 [MH$^+$], R$_t$=1.12 min, UV purity=100%.

Intermediate 95-Synthesis of 6-{1-[(tert-butoxy)carbonyl]piperidin-4-yl}-1,3-diethyl-2-[({[(9H-fluoren-9-yl)methoxy]carbonyl}amino)methyl]-1H-1,3-benzodiazol-3-ium iodide

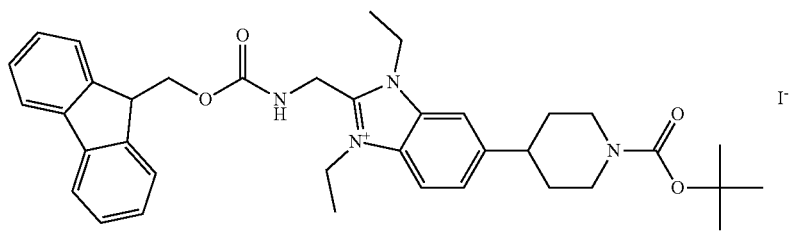 [SMILES: CCn1c(CNC(=O)OCC2c3ccccc3-c3ccccc32)[n+](CC)c2ccc(C3CCN(C(=O)OC(C)(C)C)CC3)cc21 ; [I-]]

A suspension of tert-butyl 4-{1-ethyl-2-[({[(9H-fluoren-9-yl)methoxy]carbonyl}amino)methyl]-1H-1,3-benzodiazol-6-yl}piperidine-1-carboxylate, Intermediate 94 (1.55 g, 2.67 mmol) and iodoethane (1.07 ml, 13.4 mmol) in MeCN (20 ml) was heated under microwave irradiation for 2.5 h at 120° C. The reaction mixture was concentrated in vacuo then the crude material was purified by flash column chromatography on a silica column (25 g). The column was eluted with CH$_2$Cl$_2$:MeOH, using the following gradient (% MeOH, column volumes): 0%, 1 CV; 0-2.3%, 5 CV; 2.3%, 2 CV; 2.3-10%, 7 CV; 10%, 7 CV. The desired fractions were combined and evaporated to afford the product as a light pink foam (1.60 g, 75%).

$^1$H NMR (500 MHz, DMSO-d$_6$) δ 8.26 (t, J=5.2 Hz, 1H), 7.98 (d, J=9.1Hz, 2H), 7.86 (d, J=7.5 Hz, 2H), 7.62 (d, J=7.7 Hz, 3H), 7.35 (t, J=7.4 Hz, 2H), 7.25 (t, J=7.3 Hz, 2H), 4.76 (d, J=5.2 Hz, 2H), 4.59-4.44 (m, 6H), 4.22 (t, J=5.6Hz, 1H), 4.16-4.10 (m, 2H), 3.00-2.80 (m, 3H), 1.83 (d, J=12.1Hz, 2H), 1.66 (qd, J=12.5, 4.0 Hz, 2H), 1.44 (s, 9H), 1.34 (t, J=7.0 Hz, 6H).

LC/MS (System A): m/z (ESI$^+$)=609 [M$^+$], R$_t$=1.11 min, UV purity=92%.

Intermediate 96-Synthesis of 1,3-diethyl-2-[({[(9H-fluoren-9-yl)methoxy]carbonyl}amino)methyl]-6-(piperidin-4-yl)-1H-1,3-benzodiazol-3-ium hydrochloride iodide

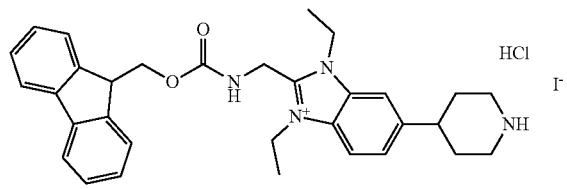 [SMILES: CCn1c(CNC(=O)OCC2c3ccccc3-c3ccccc32)[n+](CC)c2ccc(C3CCNCC3)cc21 ; Cl ; [I-]]

HCl solution in dioxane (4.0 M, 2.0 ml, 8.0 mmol) was added to a solution of 6-{1-[(tert-butoxy)carbonyl]piperidin-4-yl}-1,3-diethyl-2-[({[(9H-fluoren-9-yl)methoxy]carbonyl}amino)methyl]-1H-1,3-benzodiazol-3-ium iodide, Intermediate 95 (1.59 g, 1.99 mmol) in MeCN (50 ml). The reaction mixture was stirred at RT for 2 h then concentrated in vacuo and azeotroped with MeCN (3×25 ml) to afford the product as a yellow solid (1.34 g, >99%).

$^1$H NMR (500 MHz, DMSO-d$_6$) δ 9.00 (br.s, 1H), 8.87 (br.s, 1H), 8.35 (t, J=5.1Hz, 1H), 8.04 (d, J=8.6 Hz, 1H), 7.88 (s, 1H), 7.85 (d, J=7.6 Hz, 2H), 7.62 (d, J=7.5 Hz, 2H), 7.58 (d, J=8.5 Hz, 1H), 7.34 (t, J=7.4 Hz, 2H), 7.24 (t, J=7.4 Hz, 2H), 4.77 (d, J=5.1 Hz, 2H), 4.61-4.50 (m, 4H), 4.48 (d, J=5.9 Hz, 2H), 4.21 (t, J=5.8 Hz, 1H), 3.42 (d, 1H), 3.15-2.96 (m, 4H), 2.04-1.91 (m, 4H), 1.34 (t, J=7.1Hz, 6H).

LC/MS (System A): m/z (ESI$^+$)=509 [M$^+$], R$_t$=0.85 min, UV purity=100%.

Intermediate 97-Synthesis of 6-{1-[(2S,3R)-2,3-dihydroxy-3-[(4R,5R)-5-hydroxy-2-phenyl-1,3-dioxan-4-yl]propyl]piperidin-4-yl}-1,3-diethyl-2-[({[(9H-fluoren-9-yl)methoxy]carbonyl}amino)methyl]-1H-1,3-benzodiazol-3-ium iodide

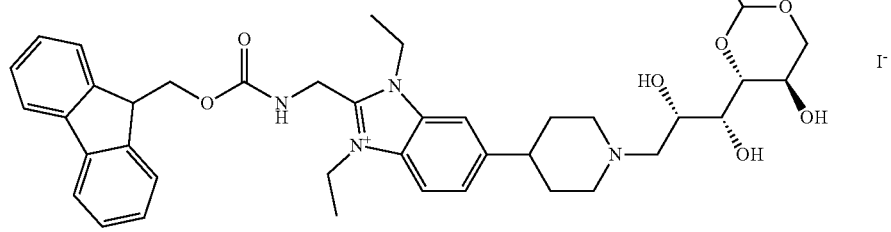

A solution of 1,3-diethyl-2-[({[(9H-fluoren-9-yl)methoxy]carbonyl}amino)methyl]-6-(piperidin-4-yl)-1H-1,3-benzodiazol-3-ium hydrochloride iodide, Intermediate 96 (1.33 g, 1.98 mmol), 4,6-O-benzylidene-D-glucopyranose (1.06 g, 3.95 mmol) and AcOH (226 μl, 3.95 mmol) in MeOH (50 ml) was stirred at RT for 0.5 h. NaCNBH$_3$ (248 mg, 3.95 mmol) was added then the resultant solution was stirred at RT for 24 h. The reaction mixture was recharged with 4,6-O-benzylidene-D-glucopyranose (1.06 g, 3.95 mmol) and AcOH (226 μl, 3.95 mmol) then left to stir at RT for 0.5 h. NaCNBH$_3$ (150 mg, 2.37 mmol) was added then the resultant solution was stirred at RT fora further 16 h. Saturated aqueous NaHCO$_3$ solution (50 ml) was added over 5 min then the resultant suspension was allowed to stand at RT for 0.5 h then filtered. The collected solid was washed with water (100 ml) then dried under vacuum for afford the product as a beige solid (1.24 g, 57%).

LC/MS (System A): m/z (ESI$^+$)=381 [(M$^+$)+H$^+$], R$_t$=0.94 min, UV purity=81%.

Intermediate 98-Synthesis of 2-(aminomethyl)-6-{1-[(2S,3R)-2,3-dihydroxy-3-[(4R,5R)-5-hydroxy-2-phenyl-1,3-dioxan-4-yl]propyl]piperidin-4-yl}-1,3-diethyl-1H -1,3-benzodiazol-3-ium iodide

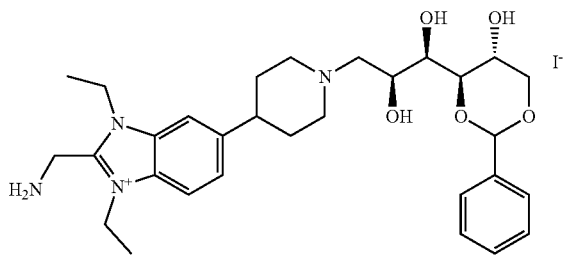

Morpholine (370 μl, 11.3 mmol) was added to a suspension of 6-{1-[(2S,3R)-2,3-dihydroxy -3-[(4R,5R)-5-hydroxy-2-phenyl-1,3-dioxan-4-yl]propyl]piperidin-4-yl}-1,3-diethyl-2-[({[(9H -fluoren-9-yl)methoxy]carbonyl}amino)methyl]-1H-1,3-benzodiazol-3-ium iodide, Intermediate 97 (81% 1.00 g, 0.90 mmol) in THF (10 ml). The resulting suspension was sonicated for 10 min then left to stir at RT for 2.5 h. The reaction mixture was diluted with diethyl ether (25 ml). The resulting white precipitate was filtered and washed with diethyl ether (25 ml) then dried under vacuum to afford the product as a white solid (615 mg, 92%).

LC/MS (System A): m/z (ESI$^+$)=539 [M$^+$], R$_t$=0.73 min, UV purity=90%.

Intermediate 99-Synthesis of 2-[({3-amino-5H-pyrrolo[2,3-b]pyrazin-2-yl}formamido)methyl]-6-{1-[(2S,3R)-2,3-dihydroxy-3-[(4R,5R)-5-hydroxy-2-phenyl -1,3-dioxan-4-yl]propyl]piperidin-4-yl}-1,3-diethyl-1H-1,3-benzodiazol-3-ium iodide

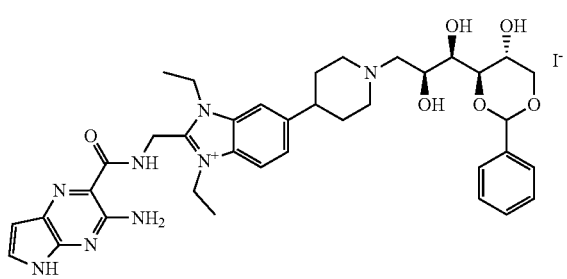

Imidazole hydrochloride (55 mg, 0.53 mmol) was added to a solution of 2-(aminomethyl) -6-{1-[(2S,3R)-2,3-dihydroxy-3-[(4R,5R)-5-hydroxy-2-phenyl-1,3-dioxan-4-yl]propyl]piperidin-4-yl}-1,3-diethyl-1H-1,3-benzodiazol-3-ium iodide, Intermediate 98 (352 mg, 0.475 mmol) and 2-(1H-imidazole-1-carbonyl)-5H-pyrrolo[2,3-b]pyrazin-3-amine, Intermediate 4 (181 mg, 0.790 mmol) in DMF (10 ml). The reaction mixture was stirred at RT for 20 h then concentrated in vacuo. The crude material thus obtained was purified by flash column chromatography on C18 (30 g). The column was eluted with MeCN:water+0.1% TFA using the following gradient (% MeCN, column volumes): 0%, 2 CV; 0-6%, 4 CV; 6-20%, 7 CV; 20-24%, 1 CV; 24-33%, 1 CV; 33%, 1 CV; 33-43%, 1 CV; 43-100%, 2 CV. The desired fractions were combined and concentrated in vacuo to afford the product as a yellow solid (401 mg, 99%).

$^1$H NMR (500 MHz, DMSO-$d_6$) δ 11.54 (s, 1H), 9.72 (t, J=5.3 Hz, 1H), 9.16 (s, 1H), 8.04 (d, J=8.7 Hz, 1H), 7.87 (s, 1H), 7.56 (d, J=8.8 Hz, 1H), 7.52 (dd, J=3.7, 2.6 Hz, 1H), 7.49-7.45 (m, 2H), 7.42-7.35 (m, 3H), 6.42 (dd, J=3.8, 1.7 Hz, 1H), 5.57 (s, 1H), 5.06 (d, J=5.2 Hz, 2H), 4.77-4.63 (m, 4H), 4.23-4.10 (m, 3H), 3.87 (d, J=5.9 Hz, 1H), 3.85 -3.64 (m, 4H), 3.59 (dt, J=20.8, 10.7 Hz, 4H), 3.38 (d, J=12.5 Hz, 1H), 3.25 (d, J=10.2 Hz, 2H), 3.07 (t, J=11.4 Hz, 2H), 2.19-1.85 (m, 4H), 1.41 (td, J=7.2, 2.4 Hz, 6H).

LC/MS (System A): m/z (ESI$^+$)=350 [(M$^+$)+H$^+$], $R_t$=0.81 min, UV purity=97%.

Intermediate 100-Synthesis of tert-butyl N-[3-({[(9H-fluoren-9-yl)methoxy]carbonyl}amino)propyl]carbamate

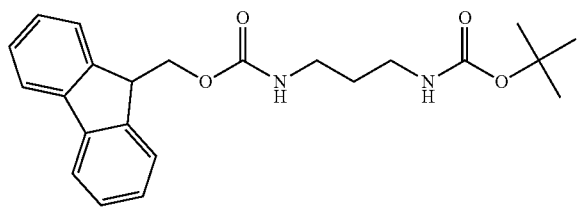 [SMILES: CC(C)(C)OC(=O)NCCCNC(=O)OCC1c2ccccc2-c2ccccc21]

A solution of 2,5-dioxopyrrolidin-1-yl 9H-fluoren-9-ylmethyl carbonate (3.87 g, 11.5 mmol) in MeCN (30 ml) was added dropwise over 20 min to a mixture of NaHCO$_3$ (1.93 g, 23.0 mmol) and tert-butyl N-(3-aminopropyl)carbamate (2.00 g, 11.5 mmol) in MeCN (40 ml) and water (40 ml). The resultant mixture was stirred at RT for 1 h then filtered. The collected solid was washed with water (2×20 ml) then MeCN (2×20 ml), then dried under vacuum to afford a white solid (1.28 g). The solid thus obtained was suspended in EtOAc (10 ml) then filtered. The solid collected was dried under vacuum to afford a first batch of the product as a white solid (1.24 g). The MeCN/water filtrate was concentrated in vacuo then the resulting residue was partitioned between EtOAc (100 ml) and water (50 ml). The phases were separated then the organic phase was washed with water (2×50 ml), brine (20 ml), then dried over Na$_2$SO$_4$, filtered and concentrated in vacuo to afford a white solid (2.30 g). The solid thus obtained was combined with the filtrate from the EtOAc trituration then the combined material was purified by flash column chromatography on a silica column (25 g). The column was eluted with heptane:EtOAc:MeOH using the following gradient: 100:0:0, 3 CV; 100:0:0-81:19:0, 3 CV; 81:19:0%, 2 CV; 81:19:0-61:39:0, 3 CV; 61:39:0, 5 CV; 61:39:0-12:88:0, 8 CV; 12:88:0-0:100:0, 2 CV; 0:100:0, 1 CV; 0:100:0-0:93:7, 4 CV; 0:93:7, 3 CV; 0:93:7-0:91:9, 1 CV. The desired fractions were combined and evaporated to afford a second batch of the product as a white solid (2.60 g), which was analytically identical to the first batch. Overall yield=3.84 g (84%).

$^1$H NMR (500 MHz, DMSO-$d_6$) δ 7.89 (d, J=7.5 Hz, 2H), 7.73-7.59 (m, 2H), 7.41 (t, J=7.4 Hz, 2H), 7.36-7.29 (m, 2H), 7.22 (t, J=5.6 Hz, 1H), 6.74 (s, 1H), 4.29 (d, J=6.9 Hz, 2H), 4.21 (t, J=6.8 Hz, 1H), 3.04-2.78 (m, 4H), 1.56-1.43 (m, 2H), 1.37 (s, 9H).

LC/MS (System A): m/z (ESI$^+$)=419 [(M$^+$Na)$^+$], $R_t$=1.25 min, UV purity=99%.

Intermediate 101-Synthesis of (9H-fluoren-9-yl)methyl N-(3-aminopropyl)carbamate hydrochloride

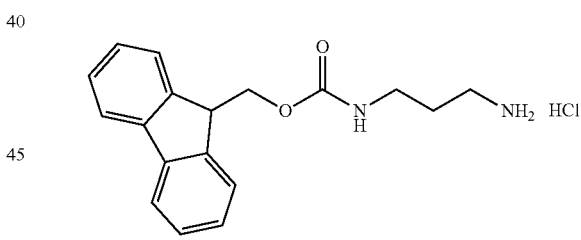

HCl solution in dioxane (4.0 M, 8.0 ml, 32 mmol) was added to a suspension of tert-butyl N-(3-{[(9H-fluoren-9-ylmethoxy)carbonyl]amino}propyl)carbamate, Intermediate 100 (2.60 g, 6.56 mmol) in MeCN (40 ml). The reaction mixture was stirred at RT for 1 h then filtered. The collected solid was rinsed with MeCN then dried under vacuum to afford the product as a white solid (1.89 g, 87%).

$^1$H NMR (500 MHz, DMSO-$d_6$) δ 7.95-7.77 (m, 5H), 7.68 (d, J=7.4 Hz, 2H), 7.48-7.38 (m, 3H), 7.37-7.29 (m, 2H), 4.33 (d, J=6.8 Hz, 2H), 4.26-4.17 (m, 1H), 3.10-2.99 (m, 2H), 2.81-2.71 (m, 2H), 1.76-1.64 (m, 2H).

LC/MS (System A): m/z (ESI$^+$)=297 [MH$^+$], $R_t$=0.91 min, UV purity=100%.

Intermediate 102-Synthesis of (9H-fluoren-9-yl) methyl N-(3-{bis[(2S,3R)-2,3-dihydroxy-3-[(4R,5R)-5-hydroxy-2-phenyl-1,3-dioxan-4-yl]propyl] amino}propyl)carbamate; formic acid

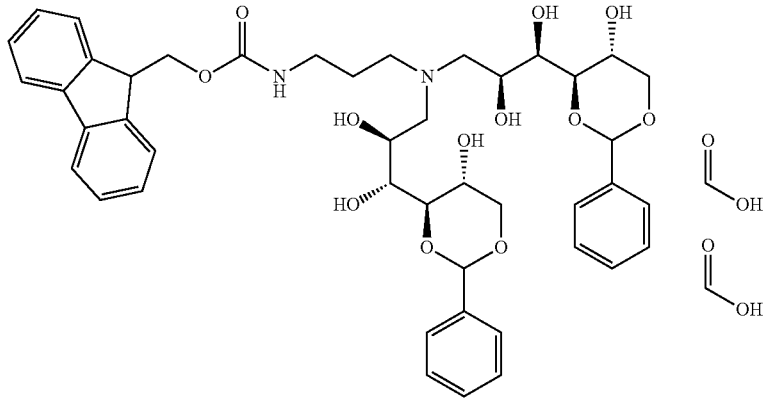

A mixture of 9H-fluoren-9-ylmethyl N-(3-aminopropyl) carbamate hydrochloride, Intermediate 101 (900 mg, 2.70 mmol) and 4,6-O-benzylidene-D-glucopyranose (1.45 g, 5.41 mmol) in MeOH (40 ml) was stirred at RT for 1.5 h. AcOH (0.31 ml, 5.4 mmol) and NaCNBH₃ (340 mg, 5.41 mmol) were added then the reaction was stirred at RT for 18 h. The reaction was recharged with 4,6-O-benzylidene-D-glucopyranose (1.45 g, 5.41 mmol) then the reaction was stirred at RT for 1 h. NaCNBH₃ (340 mg, 5.41 mmol) was added then the reaction was left to stir at RT for a further 114 h. Saturated aqueous NaHCO₃ solution (50 ml) was added dropwise over 10 min then the resultant mixture was partitioned between EtOAc (50 ml) and water (50 ml). The phases were separated then the organic phase was washed with saturated aqueous NaHCO₃ solution (2×50 ml), water (50 ml) and brine (20 ml), then dried using Na₂SO₄, filtered and concentrated in vacuo to afford a white solid (2.25 g). The crude material thus obtained was purified by flash column chromatography on C18 (120 g). The column was eluted with MeCN:water+0.1% formic acid using the following gradient (% MeCN, column volumes): 10%, 2 CV; 10-29%, 4 CV; 29-39%, 2 CV; 39%, 2 CV; 39-47%, 1 CV; 47-73%, 1 CV; 73-100%, 1 CV; 100% 1 CV. The desired fractions were combined and concentrated in vacuo to afford the product as a white solid (1.12 g, 49%).

¹H NMR (500 MHz, DMSO-d₆) δ 8.16 (m, 1H), 7.88 (d, J=7.5 Hz, 2H), 7.67 (d, J=7.4 Hz, 2H), 7.45-7.37 (m, 6H), 7.36-7.25 (m, 8H), 7.24-7.16 (m, 1H), 5.49-5.39 (m, 2H), 5.27 -5.01 (m, 2H), 4.32-4.25 (m, 2H), 4.23-4.16 (m, 1H), 4.16-4.09 (m, 2H), 3.84-3.74 (m, 4H), 3.73-3.66 (m, 2H), 3.64-3.56 (partially obscured m, 2H), 3.53-3.45 (obscured m, 2H), 2.99-2.89 (obscured m, 2H), 2.68-2.54 (obscured m, 6H), 1.60-1.48 (m, 2H).

LC/MS (System A): m/z (ESI⁺)=801 [MH⁺], $R_t$=1.01 min, UV purity=100%.

Intermediate 103-Synthesis of (1R,2S)-3-[(3-aminopropyl)[(2S,3R)-2,3-dihydroxy-3-[(4R,5R)-5-hydroxy-2-phenyl-1,3-dioxan-4-yl]propyl]amino]-1-[(4R,5R)-5-hydroxy-2-phenyl-1,3-dioxan-4-yl] propane-1,2-diol; bis(formic acid)

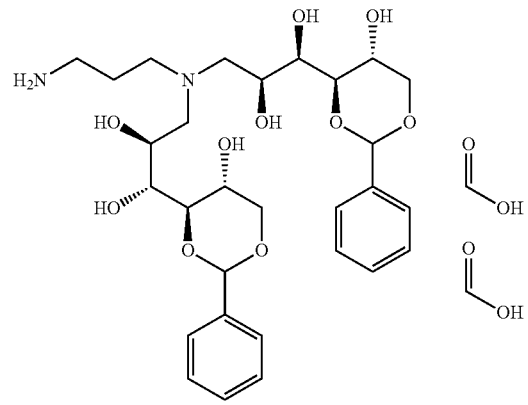

Diethylamine (1.44 ml, 14.0 mmol) was added to a solution of 9H-fluoren-9-ylmethyl N-(3-{bis[(2S,3R)-2,3-dihydroxy-3-[(4R,5R)-5-hydroxy-2-phenyl-1,3-dioxan-4-yl]propyl]amino}propyl)carbamate; formic acid, Intermediate 102 (1.32 g, 1.40 mmol) in THF (20 ml). The reaction mixture was stirred at RT for 16 h then concentrated in vacuo. The crude material thus obtained was purified by flash column chromatography on C18 (60 g). The column was eluted with MeCN:water+0.1% formic acid using the following gradient (% MeCN, column volumes): 5%, 2 CV; 5-18%, 3 CV; 18%, 2 CV; 18-26%, 2 CV; 26-100%, 2 CV; 100% 1 CV. The desired fractions were combined and concentrated in vacuo to afford the product as a white solid (710 mg, 80%).

¹H NMR (500 MHz, DMSO-d₆) δ 8.36-8.24 (m, 2H), 7.44-7.38 (m, 4H), 7.38-7.29 (m, 6H), 5.44 (s, 2H), 4.18-4.08 (obscured m, 2H), 3.87-3.75 (obscured m, 4H), 3.73-3.65 (obscured m, 2H), 3.63-3.56 (obscured m, 2H), 3.53-3.44 (obscured m, 2H), 2.90-2.78 (m, 2H), 2.75-2.55 (obscured m, 6H), 1.78-1.65 (m, 1H), 1.55 (m, 1H).

LC/MS (System A): m/z (ESI⁺)=579 [MH⁺], R$_t$=0.74 min, UV purity=100%.

Intermediate 104-Synthesis of (2R,3R,4R,5S)-6-[(3-aminopropyl)[(2S,3R,4R,5R) -2,3,4,5,6-pentahydroxyhexyl]amino]hexane-1,2,3,4,5-pentol dihydrochioride

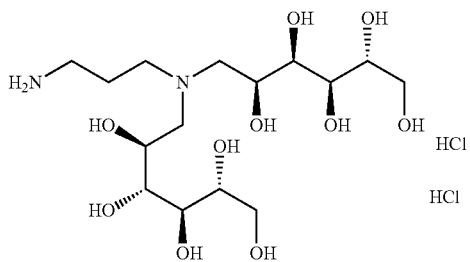 [SMILES: NCCCN(C[C@H](O)[C@@H](O)[C@H](O)[C@H](O)CO)C[C@H](O)[C@@H](O)[C@H](O)[C@H](O)CO ; Cl ; Cl]

A mixture of (1R,2S)-3-[(3-aminopropyl)[(2S,3R)-2,3-dihydroxy-3-[(4R,5R)-5-hydroxy-2-phenyl-1,3-dioxan-4-yl]propyl]amino]-1-[(4R,5R)-5-hydroxy-2-phenyl-1,3-dioxan-4-yl]propane-1,2-diol; bis(formic acid), Intermediate 103 (335 mg, 0.50 mmol) and aqueous HCl solution (2 M, 5 ml, 10 mmol) was stirred at RT for 3 h. The reaction mixture was concentrated in vacuo then the residue was azeotroped with MeCN (3×10 ml) to afford the product as a colourless viscous oil (235 mg, 99%).

¹H NMR (500 MHz, CD$_3$OD) δ 4.25-4.18 (m, 2H), 3.91-3.83 (m, 2H), 3.81-3.76 (m, 2H), 3.74-3.64 (m, 6H), 3.62-3.51 (m, 2H), 3.50-3.39 (m, 4H), 3.10-3.03 (m, 2H), 2.22-2.13 (m, 2H).

LC/MS (System A): m/z (ESI⁺)=403 [MH⁺], R$_t$=0.12 min, ELS purity=100%.

Intermediate 105-Synthesis of tert-butyl 4-({[(9H-fluoren-9-yl)methoxy]carbonyl}amino)piperidine-1-carboxylate

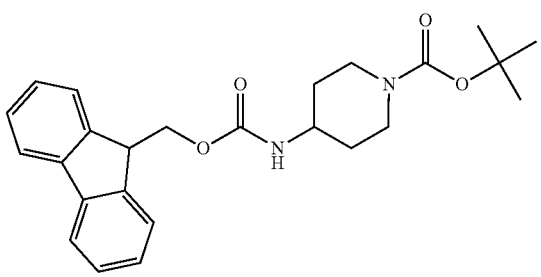 [SMILES: CC(C)(C)OC(=O)N1CCC(NC(=O)OCC2c3ccccc3-c3ccccc32)CC1]

A solution of 2,5-dioxopyrrolidin-1-yl 9H-fluoren-9-ylmethyl carbonate (5.05 g, 15.0 mmol) in MeCN (50 ml) was added dropwise over 20 min to a mixture of tert-butyl 4-aminopiperidine-1-carboxylate (3.00 g, 15.0 mmol) and NaHCO$_3$ (2.52 g, 30.0 mmol) in MeCN (50 ml) and water (50 ml). The resulting mixture was left to stir at RT for 16 h then partitioned between EtOAc (100 ml) and water (100 ml). The phases were separated then the organic phase was washed with water (100 ml) and brine (100 ml) then dried over Na$_2$SO$_4$ and concentrated in vacuo to afford the product as a white foam (6.20 g, 95%).

¹H NMR (500 MHz, DMSO-d$_6$) δ 7.89 (d, J=7.5 Hz, 2H), 7.69 (d, J=7.4 Hz, 2H), 7.41 (t, J=7.4 Hz, 2H), 7.33 (td, J=7.4, 0.9 Hz, 2H), 7.27 (d, J=7.7 Hz, 1H), 4.31 (d, J=6.7 Hz, 2H), 4.21 (t, J=6.6 Hz, 1H), 3.84 (br. d, J=11.7 Hz, 2H), 3.52-3.40 (m, 1H), 2.80 (br. s, 2H), 1.70 (d, J=10.8 Hz, 2H), 1.39 (s, 9H), 1.20-1.29 (m, 2H).

LC/MS (System A): m/z (ESI⁺)=445 [(M+Na)⁺], R$_t$=1.38 min, UV purity=97%.

Intermediate 106-Synthesis of (9H-fluoren-9-yl)methyl N-(piperidin-4-yl)carbamate hydrochloride

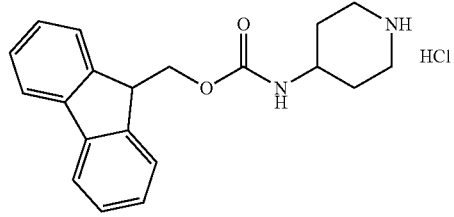 [SMILES: O=C(NC1CCNCC1)OCC1c2ccccc2-c2ccccc21 ; Cl]

HCl solution in dioxane (4.0 M, 11 ml, 44 mmol) was added to a solution of tert-butyl 4-({[(9H-fluoren-9-yl)methoxy]carbonyl}amino)piperidine-1-carboxylate, Intermediate 105 (6.20 g, 14.7 mmol) in MeCN (100 ml). The resulting solution was stirred at RT for 2 h. The reaction was re-dosed with HCl solution in dioxane (4.0 M, 2.0 ml, 8.0 mmol) then the reaction mixture was left to stir at RT for a further 1 h. The reaction mixture was filtered then the collected solid was washed with MeCN then dried under vacuum to afford the product as a white solid (4.60 g, 87%).

¹H NMR (500 MHz, DMSO-d$_6$) δ 8.85 (s, 1H), 8.69 (s, 1H), 7.89 (d, J=7.5 Hz, 2H), 7.69 (d, J=7.4 Hz, 2H), 7.50 (d, J=7.2 Hz, 1H), 7.42 (t, J=7.4 Hz, 2H), 7.36-7.31 (m, 2H), 4.33 (d, J=6.6 Hz, 2H), 4.22 (t, J=6.4 Hz, 1H), 3.62-3.54 (m, 1H), 3.21 (d, J=12.0 Hz, 2H), 2.96-2.88 (m, 2H), 1.88 (d, J=12.1Hz, 2H), 1.67-1.50 (m, 2H).

LC/MS (System A): m/z (ESI⁺)=323 [MH⁺], R$_t$=0.89 min, UV purity=100%.

Intermediate 107-Synthesis of (9H-fluoren-9-yl)methyl N-{1-[(2S,3R)-2,3-dihydroxy -3-[(4R,5R)-5-hydroxy-2-phenyl-1,3-dioxan-4-yl]propyl]piperidin-4-yl}carbamate

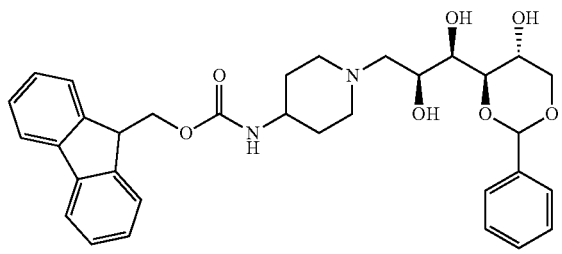

4,6-O-benzylidene-D-glucopyranose (2.99 g, 11.2 mmol) was added to a solution of (9H -fluoren-9-yl)methyl N-(piperidin-4-yl)carbamate hydrochloride, Intermediate 106 (2.00 g, 5.57 mmol) in MeOH (75 ml). The reaction mixture was stirred at RT for 20 min then AcOH (670 µl, 11.7 mmol) and NaCNBH$_3$ (700 mg, 11.2 mmol) were added. The reaction mixture was stirred at RT for 22 h. Saturated aqueous NaHCO₃ solution (50 ml) was added dropwise over 10 min. The resulting mixture was partitioned between EtOAc (200 ml) and water (100 ml). The phases were separated then the organic phase was washed with saturated aqueous NaHCO₃ solution (100 ml), water (2×100 ml) and brine (2×100 ml). The combined organic phases were dried over Na₂SO₄ and concentrated in vacuo to afford the product as a white solid (3.13 g, 92%).

¹H NMR (500 MHz, CD₃OD) δ 7.78 (d, J=7.4 Hz, 2H), 7.63 (d, J=7.1Hz, 2H),7.52-7.45 (m, 2H), 7.39-7.27 (m, 7H), 5.55 (s, 1H), 4.34 (d, J=6.4 Hz, 2H), 4.25 (dd, J=10.7, 5.4 Hz, 1H), 4.21-4.17 (m, 1H), 4.07-4.00 (m, 1H), 3.97-3.92 (m, 1H), 3.90-3.87 (d,J=6.4 Hz, 1H), 3.82 (d, J=9.3 Hz, 1H), 3.61 (t, J=10.5 Hz, 1H), 3.39-3.32 (m, 1H),2.97-2.94 (m, 1H), 2.77-2.64 (m, 2H), 2.47 (dd, J=11.8,6.7 Hz, 1H), 2.14 (t, J=10.5 Hz,1H), 2.06- 2.02 (m, 1H), 1.75 (dd, J=59.2, 11.6 Hz, 2H), 1.53-1.36 (m, 2H).

LC/MS (System A): m/z (ESI⁺)=575 [MH⁺], R$_t$=0.96 min, UV purity=94%.

Intermediate 108-Synthesis of (1R,2S)-3-(4-aminopiperidin-1-yl)-1-[(4R,5R)-5-hydroxy-2-phenyl-1,3-dioxan-4-yl]propane-1,2-diol

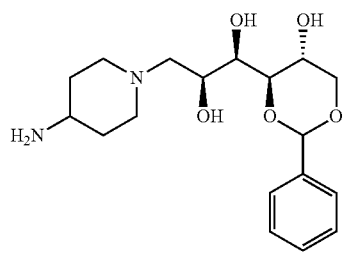

Diethylamine (2.64 ml, 25.6 mmol) was added to a solution of (9H-fluoren-9-yl)methyl N -{1-[(2S,3R)-2,3-dihydroxy-3-[(4R,5R)-5-hydroxy-2-phenyl-1,3-dioxan-4-yl]propyl]piperidin-4-yl}carbamate, Intermediate 107 (94%, 3.13 g, 5.12 mmol) in THF (40 ml). The reaction mixture was left to stir at RT for 1 h. The reaction mixture was re-dosed with diethylamine (2.64 ml, 25.6 mmol) then the reaction was left to stir at RT for a further 20 h. The reaction mixture was concentrated in vacuo then the resultant residue was suspended in EtOAc (10 ml) and water (10 ml). Diethyl ether (50 ml) was added then the mixture was sonicated. The resulting suspension was filtered then the collected solid was rinsed with diethyl ether (20 ml) then dried under vacuum to afford the product as a white solid (1.98 g, >99%).

¹H NMR (500 MHz, DMSO-d₆) δ 7.41 (dd, J=6.5, 3.1Hz, 2H), 7.38-7.31 (m, 3H), 5.49 (5, 1H), 4.11(dd, J=10.5, 4.9 Hz, 1H), 3.81 (q, J=6.2 Hz, 1H), 3.79-3.69 (m, 3H), 3.52-3.48 (m, 1H), 2.83 (d, J=11.3 Hz, 1H), 2.58-2.52 (m, 1H), 2.45 2.45 (m, 2H+DMSO) , 2.24 (dd, J=12.4, 6.1Hz, 1H), 1.93 -1.73 (m, 2H), 1.61 (d, J=12.5 Hz, 1H), 1.49 (d, J=12.1Hz, 1H), 1.17-1.14 (m, 2H).

LC/MS (System A): m/z (ESI⁺)=353 [MH⁺], R$_f$=0.13 min, ELS purity=100%.

Intermediate 109-Synthesis of (2R,3R,4R,5S)-6-(4-aminopiperidin-1-yl)hexane -1,2,3,4,5-pentol dihydrochloride

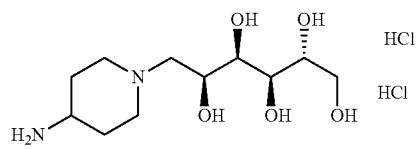 [SMILES: NC1CCN(C[C@H](O)[C@@H](O)[C@H](O)[C@H](O)CO)CC1 ; Cl ; Cl]

Aqueous HCl solution (2.0 M, 11 ml, 22 mmol) was added to a suspension of (1R,2S)-3-(4-aminopiperidin-1-yl)-1-[(4R,5R)-5-hydroxy-2-phenyl-1,3-dioxan-4-yl]propane-1,2-diol, Intermediate 108 (400 mg, 1.13 mmol) in water (5 ml). The reaction mixture was left to stir at RT for 2 h then concentrated in vacuo. The resulting residue was dissolved in water (20 ml) then extracted with EtOAc (20 ml). The aqueous phase was concentrated in vacuo to afford the product as an off-white foam (279 mg, 73%).

¹H NMR (500 MHz, CD₃OD) δ 4.26-4.18 (m, 1H), 3.87-3.74 (m, 4H), 3.74-3.62 (m, 4H), 3.61-3.42 (m, 2H), 3.29-3.12 (m, 2H), 2.28 (t, J=13.2 Hz, 2H), 2.15-1.92 (m, 2H).

LC/MS (System A): m/z (ESI⁺)=265 [MH⁺], R$_t$=0.13 min, ELS purity=100%.

Intermediate 110-Synthesis of benzyl 4-{bis[(2S, 3R)-2,3-dihydroxy-3-[(4R,5R)-5-hydroxy-2-phenyl-1,3-dioxan-4-yl]propyl]amino}piperidine-1-carboxylate

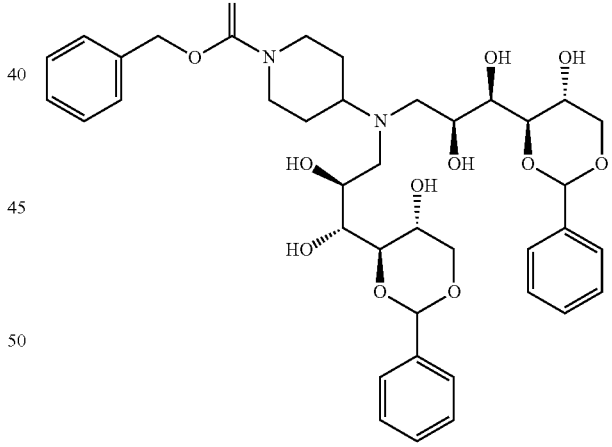

A mixture of benzyl 4-aminopiperidine-1-carboxylate (1.50 g, 6.40 mmol) and 4,6-O -benzylidene-D-glucopyranose (3.44 g, 12.8 mmol) in MeOH (40 ml) was stirred at RT for 2 h. AcOH (733 μl, 12.8 mmol) was added, followed by portionwise addition of NaCNBH₃ (805 mg, 12.8 mmol). The reaction was stirred at RT for 16 h. The reaction was recharged with 4,6-O-benzylidene-D-glucopyranose (3.44 g, 12.8 mmol) then the reaction was stirred at RT for a further 1 h. NaCNBH₃ (805 mg, 12.8 mmol) was added then the reaction mixture was stirred at RT for a further 64 h. The reaction was recharged with AcOH (733 μl, 12.8 mmol) then the reaction was stirred at RT for a further 4 h. 4,6-O-

Benzylidene-D -glucopyranose (3.44 g, 12.8 mmol) was added then the reaction was stirred at RT for 0.5 h. AcOH (733 µl, 12.8 mmol) and NaCNBH$_3$ (805 mg, 12.8 mmol) were added then the reaction was left to stir at RT for a further 16 h. Saturated aqueous NaHCO$_3$ solution (20 ml) was added dropwise over 5 min. The resultant mixture was partitioned between EtOAc (60 ml) and saturated aqueous NaHCO3 solution (50 ml). The phases were separated then the organic phase was washed with saturated aqueous NaHCO$_3$ solution (2×50 ml), water (2×50 ml), brine (20 ml), dried over Na$_2$SO$_4$, filtered and evaporated to afford a white solid (4.8 g). The resultant solid was dissolved in MeOH:MeCN (1:1, 10 ml) then half of the solution was retained crude for future purification whilst the other half was purified by flash column chromatography on C18 (60 g). The column was eluted with MeCN:water+0.1% NH$_4$OH using the following gradient (% MeCN, column volumes): 5%, 2 CV; 5-23%, 4 CV; 23%, 3 CV; 23-49%, 5 CV; 49%, 2 CV; 49-100%, 10 CV; 100%, 2 CV. The desired fractions were combined and concentrated in vacuo to afford a white solid (1.39 g). The material thus obtained was further purified by flash column chromatography on C18 (12 g). The column was eluted with MeCN:water+0.1% formic acid using the following gradient (% MeCN, column volumes): 5%, 2 CV; 5-32%, 5 CV; 32%, 2 CV; 32-59%, 6 CV; 59-81%, 1 CV, 100%, 1 CV. The desired fractions were combined and concentrated in vacuo to afford a white solid (1.12 g). The solid thus obtained was dissolved in EtOAc (50 ml) and extracted with saturated aqueous NaHCO$_3$ solution (2×20 ml) and water (10 ml), then dried over MgSO$_4$, filtered and evaporated to afford the product as a white solid (0.95 g, 20%).

$^1$H NMR (500 MHz, DMSO-d$_6$) δ 7.44-7.24 (m, 15H), 5.49-5.41 (m, 2H), 5.15-5.09 (m, 2H), 5.08-4.99 (m, 2H), 4.47-4.43 (m, 2H), 4.41-4.35 (m, 2H), 4.17-4.08 (m, 2H), 4.01-3.90 (m, 2H), 3.83-3.74 (m, 2H), 3.75-3.66 (m, 4H), 3.64-3.56 (m, 2H), 3.54-3.42 (m, 2H), 2.70-2.33 (m, 7H+DMSO), 1.72-1.59 (m, 2H), 1.39-1.27 (m, 1H), 1.16-1.08 (m, 1H).

LC/MS (System A): m/z (ESI$^+$)=739 [MH$^+$], R$_t$=0.94 min, UV purity=100%.

Intermediate 111-Synthesis of (1R,2S)-3-{[(2S,3R)-2,3-dihydroxy-3-[(4R,5R)-5-hydroxy-2-phenyl-1,3-dioxan-4-yl]propyl]piperidin-4-yl)amino}-1-[(4R,5R)-5-hydroxy-2-phenyl-1,3-dioxan-4-yl]propane-1,2-diol

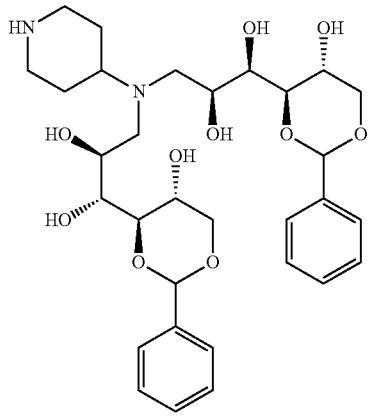

A mixture of benzyl 4-{bis[(2S,3R)-2,3-dihydroxy-3-[(4R,5R)-5-hydroxy-2-phenyl-1,3-dioxan-4-yl]propyl]amino}piperidine-1-carboxylate, Intermediate 110 (950 mg, 1.29 mmol) and palladium on carbon (10 wt % 137 mg) in EtOH (15 ml) and AcOH (1.5 ml) was stirred under an atmosphere of hydrogen for 18 h at RT. The reaction mixture was filtered through a Celite pad then concentrated in vacuo. The residue thus obtained was suspended in MeCN (20 ml) with sonication then concentrated in vacuo. The process was repeated once more with MeCN (20 ml). The residue thus obtained was again suspended in MeCN (20 ml) with sonication then allowed to settle. The supernatant was decanted off using a pipette. The trituration process was repeated with more MeCN (2×20 ml) then the residue was dried under vacuum to afford a white solid (770 mg). The solid thus obtained was dissolved in MeOH then loaded onto a pre-equilibrated SCX cartridge (10 g). The SCX cartridge was eluted with MeOH then basic components were released by elution with a solution of ammonia in MeOH (7 M). The basic eluent was concentrated in vacuo then the resultant oil was suspended in MeCN (15 ml) and concentrated in vacuo. The residue was further azeotroped with MeCN (2×15 ml) then dried under vacuum to afford the product as a white solid (595 mg, 77%).

$^1$H NMR (500 MHz, DMSO-d$_6$) δ 7.48-7.22 (m, 11H), 5.49-5.45 (m, 2H), 5.17-5.06 (m, 2H), 4.52-4.30 (m, 4H), 4.18-4.06 (m, 2H), 3.86-3.76 (m, 2H), 3.73-3.66 (m, 4H), 3.64-3.55 (m, 2H), 3.54-3.44 (m, 2H), 2.96-2.77 (m, 2H), 2.69-2.60 (m, 2H+DMSO), 2.58-2.44 (m, 1H +DMSO), 2.44-2.35 (m, 2H), 2.34-2.26 (m, 1H), 2.21-2.13 (m, 1H), 1.65-1.50 (m, 2H), 1.40-1.27 (m, 1H), 1.22-1.06 (m, 1H).

LC/MS (System A): m/z (ESI$^+$)=605 [MH$^+$], R$_t$=0.75 min, UV purity=100%.

Intermediate 112-Synthesis of (2R,3R,4R,5S)-6-{[(2S,3R,4R,5R)-2,3,4,5,6-pentahydroxyhexyl](piperidin-4-yl)amino}hexane-1,2,3,4,5-pentol dihydrochloride

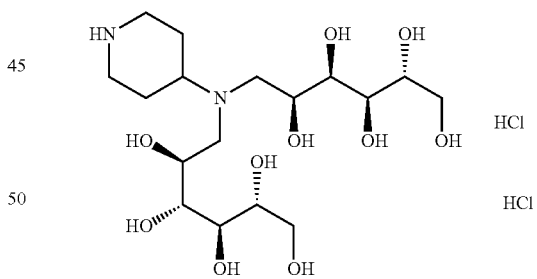

A mixture of (1R,2S)-3-{[(2S,3R)-2,3-dihydroxy-3-[(4R,5R)-5-hydroxy-2-phenyl-1,3-dioxan-4-yl]propyl](piperidin-4-yl)amino}-1-[(4R,5R)-5-hydroxy-2-phenyl-1,3-dioxan-4-yl]propane-1,2-diol, Intermediate 111 (315 mg, 0.520 mmol) and aqueous HCl solution (2 M, 5 ml, 10 mmol) was stirred at RT for 2 h. The reaction mixture was concentrated in vacuo then azeotroped with MeCN to afford the product as a white solid (259 mg, 99%).

$^1$H NMR (500 MHz, D$_2$O) δ 4.35-4.26 (m, 2H), 4.13-3.98 (m, 1H), 3.96-3.41 (m, 16H), 3.30-3.14 (m, 2H), 2.56-2.35 (m, 2H), 2.28-2.15 (m, 1H), 2.10-2.04 (m, 1H).

LC/MS (System A): m/z (ESI$^+$)=429 [MH$^+$], R$_t$=0.75 min, ELS purity=100%.

Intermediate 113-Synthesis of benzyl N-[1-(2-({[(tert -butoxy)carbonyl]amino}ethyl)piperidin-4-yl]carbamate

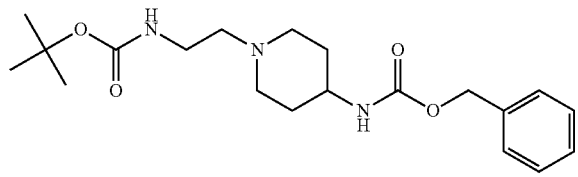 [SMILES: CC(C)(C)OC(=O)NCCN1CCC(NC(=O)OCc2ccccc2)CC1]

Triethylamine (515 µl, 3.69 mmol) was added to a solution of benzyl N-(4-piperidyl)carbamate hydrochloride (500 mg, 1.85 mmol) and tert-butyl N-(2-bromoethyl)carbamate (500 mg, 2.22 mmol) in MeCN (4 ml) in a pressure tube. The tube was sealed then the reaction mixture was heated at 85° C. for 16 h. Additional tert-butyl N -(2-bromoethyl)carbamate (150 mg, 0.67 mmol) was added then the reaction was left to heat at 85° C. for a further 1 h. The reaction mixture was concentrated in vacuo then the solid thus obtained was dissolved in the minimum of refluxing MeCN then allowed to cool to RT. The resultant suspension was filtered then the filtrate was concentrated in vacuo. The crude material was purified by flash column chromatography on a silica column (25 g). The column was eluted with CH$_2$Cl$_2$:MeOH, increasing the gradient linearly from 0-15% MeOH over 10 column volumes. The desired fractions were combined and evaporated to afford a viscous red oil (254 mg). The material thus obtained was partitioned between EtOAc (15 ml) and saturated aqueous NaHCO$_3$ solution (15 ml). The phases were separated then the organic phase was washed with water (2×15 ml) and brine (15 ml) then dried over Na$_2$SO$_4$ and concentrated in vacuo to afford the product as a pale red solid (140 mg, 20%).

$^1$H NMR (500 MHz, DMSO-d$_6$) δ 7.39-7.28 (m, 5H), 7.21 (d, J=7.6 Hz, 1H), 6.59 (t, J=5.3 Hz, 1H), 5.00 (s, 2H), 3.29-3.22 (m, 1H), 3.00 (q, J=6.4 Hz, 2H), 2.76 (d, J=11.5 Hz, 2H), 2.28 (t, J=6.9 Hz, 2H), 1.95 (t, J=11.0 Hz, 2H), 1.69 (d, J=10.5 Hz, 2H), 1.43 -1.32 (m, 11H).

LC/MS (System A): m/z (ESI$^+$)=378 [MH$^+$], R$_t$=0.85 min, UV purity=100%.

Intermediate 114-Synthesis of tert-butyl N-[2-(4-aminopiperidin-1-yl)ethyl]carbamate

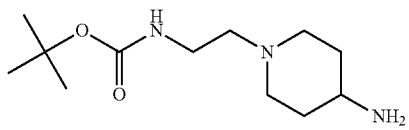 [SMILES: CC(C)(C)OC(=O)NCCN1CCC(N)CC1]

A mixture of benzyl N-[1-(2-{[(tert-butoxy)carbonyl]amino}ethyl)piperidin-4-yl]carbamate, Intermediate 113 (140 mg, 0.370 mmol) and palladium on carbon (10 wt %, 20 mg) in EtOH (5 ml) was stirred under a hydrogen atmosphere at RT for 2 h. The reaction mixture was filtered through a Celite pad then the filtrate was concentrated in vacuo to afford the product as a colourless oil (124 mg, 96%-yield corrected for 70% purity determined by NMR).

$^1$H NMR (500 MHz, DMSO-d$_6$) δ 6.61-6.53 (m, 1H), 4.37 (s, 2H), 3.00 (q, J=6.5 Hz, 2H), 2.76-2.71 (m, 2H), 2.49-2.45 (m, 1H), 2.27 (t, J=7.0 Hz, 2H), 1.91 (t, J=10.6 Hz, 2H), 1.67-1.60 (m, 2H), 1.37 (s, 9H), 1.22-1.15 (m, 2H).

LC/MS (System A): m/z (ESI$^+$)=244 [MH$^+$], R$_t$=0.14 min, ELS purity=100%.

Intermediate 115-Synthesis of bis(formic acid); tert-butyl N[2-(4-{bis[(2S,3R)-2,3-dihydroxy-3-[(4R,5R)-5-hydroxy-2-phenyl-1,3-dioxan-4-yl]propyl]amino}piperidin-1-yl) ethyl]carbamate

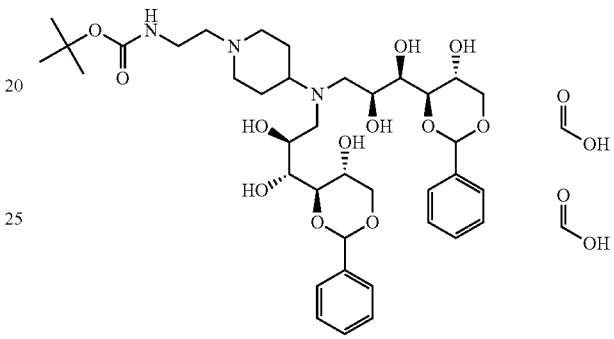

A mixture of tert-butyl N-[2-(4-aminopiperidin-1-yl) ethyl]carbamate, Intermediate 114 (70%, 725 mg, 2.08 mmol), 4,6-O-benzylidene-D-glucopyranose (3.57 g, 12.7 mmol) and AcOH (725 uL, 12.7 mmol) in MeOH (20 ml) was stirred at RT for 0.5 h. NaCNBH$_3$ (795 mg, 12.7 mmol) was added then the resulting mixture was stirred at RT for 5 days. The reaction was retreated with 4,6-O-benzylidene-D-glucopyranose (1.80 g, 6.29 mmol) and AcOH (362 uL, 6.32 mmol) then the reaction was left to stir at RT for 0.5 h. NaCNBH$_3$ (396 mg, 6.30 mmol) was added then the reaction was left to stir at RT for a further 18 h. The reaction was retreated with 4,6-O-benzylidene-D-glucopyranose (1.80 g, 6.29 mmol) and AcOH (362 uL, 6.32 mmol) then the reaction was left to stir at RT for 0.5 h. NaCNBH$_3$ (396 mg, 6.30 mmol) was added then the reaction was left to stir at RT for a further 18 h. The reaction mixture was concentrated under a stream of nitrogen then saturated aqueous NaHCO$_3$ solution was added dropwise until effervescence ceased. The resulting mixture was partitioned between saturated aqueous NaHCO$_3$ solution (150 ml) and EtOAc (150 ml). The phases were separated then the organic phase was washed with NaHCO$_3$ (150 ml), water (2×150 ml) and brine (150 ml), then dried over Na$_2$SO$_4$ and concentrated in vacuo to afford a pale yellow solid. The crude material was purified by flash column chromatography on C18 (120 g). The column was eluted with MeCN:water+0.1% formic acid using the following gradient (% MeCN, column volumes): 10%, 2 CV; 10-16%, 11 CV; 16%-100%, 4 CV; 100%, 1 CV. The desired fractions were combined and concentrated in vacuo to afford the product as a colourless oil (383 mg, 18%).

LC/MS (System A): m/z (ESI$^+$)=375 [(M$^+$)+H$^+$], 748 [MH$^+$], R$_t$=0.82 min, UV purity=83%.

Intermediate 116-Synthesis of (2R,3R,4R,5S)-6-{[1-(2-aminoethyl)piperidin-4-yl][(2S,3R,4R,5R)-2,3,4,5,6-pentahydroxyhexyl]amino}hexane-1,2,3,4,5-pentol trihydrochloride

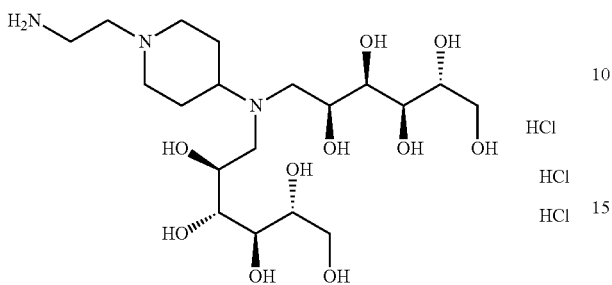

A mixture of tert-butyl N-[2-[4-[bis[(2S,3R)-2,3-dihydroxy-3-[(4R,5R)-5-hydroxy-2-phenyl -1,3-dioxan-4-yl]propyl]amino]-1-piperidyl]ethyl]carbamate, Intermediate 115 (83%, 360 mg, 0.356 mmol) and aqueous HCl solution (4.0 M, 3.6 ml, 14.4 mmol) was stirred at RT for 0.5 h then concentrated in vacuo. The residue was dissolved in water: MeCN (9:1, 12 ml) then lyophilised to afford the product as a white foam (220 mg, 94%).

$^1$H NMR (500 MHz, Deuterium Oxide) δ 4.34-4.26 (m, 2H), 4.16-4.05 (m, 1H), 3.95-3.88 (m, 4H), 3.87 (d, J=2.9 Hz, 1H), 3.84 (d, J=3.0 Hz, 1H), 3.83-3.78 (m, 2H), 3.73-3.67 (m, 4H), 3.64-3.46 (m, 8H), 3.40-3.31 (m, 2H), 2.58 (d, J=14.0 Hz, 1H), 2.51 (d, J=13.7 Hz, 1H), 2.35-2.24 (m, 1H), 2.23-2.12 (m, 1H).

LC/MS (System B): m/z (ESI$^+$)=472 [MH$^+$], R$_t$=0.29 min, ELS purity=88%.

Intermediate 117-Synthesis of (9H-fluoren-9-yl) methyl 4-({[(tert -butoxy)carbonyl]amino}methyl) piperidine-1-carboxylate

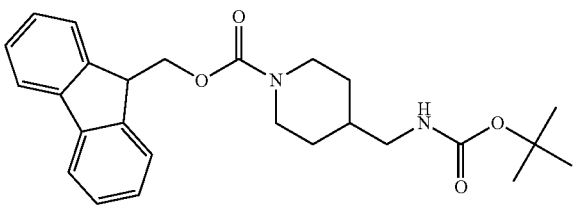 [SMILES: CC(C)(C)OC(=O)NCC1CCN(C(=O)OCC2c3ccccc3-c3ccccc32)CC1]

NaHCO$_3$ (2.35 g, 28.0 mmol) was added portionwise over 1 min to a stirred solution of tert -butyl N-(4-piperidylmethyl)carbamate (3.00 g, 14.0 mmol) in MeCN (50 ml) and water (50 ml). A solution of (2,5-dioxopyrrolidin-1-yl) 9H-fluoren-9-ylmethyl carbonate (4.72 g, 14.0 mmol) in MeCN (50 ml) was added dropwise over 1 h then the reaction was left to stir at RT for 18 h. The reaction mixture was partitioned between EtOAc (100 ml) and water (100 ml). Brine was added to aid separation of phases. The phases were separated then the aqueous phase was extracted with EtOAc (50 ml). The combined organic extracts were washed with brine (70 ml), dried over MgSO$_4$, filtered and concentrated in vacuo to afford the product as an off white solid (7.02 g, 96%).

$^1$H NMR (500 MHz, DMSO-d$_6$) δ 7.89 (d, J=7.5 Hz, 2H), 7.62 (d, J=7.4 Hz, 2H), 7.41 (t, J=7.3 Hz, 2H), 7.33 (td, J=7.4, 0.9 Hz, 2H), 6.85 (t, J=5.8 Hz, 1H), 4.53-4.29 (m, 2H), 4.26 (t, J=6.3 Hz, 1H), 3.97-3.67 (m, 2H), 2.78 (t, J=6.1 Hz, 2H), 2.75-2.61 (m, 2H), 1.60-1.44 (m, 3H), 1.38 (s, 9H), 0.93-0.73 (m, 2H). 5 wt % residual solvent.

LC/MS (System A): m/z (ESI$^+$)=459 [M+N$^+$], R$_t$=1.40 min, UV purity=89%.

Overall purity estimate=84%.

Intermediate 118-Synthesis of (9H-fluoren-9-yl) methyl 4-(aminomethyl)piperidine -1-carboxylate hydrochloride

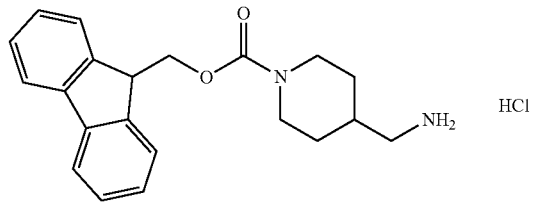 [SMILES: NCC1CCN(C(=O)OCC2c3ccccc3-c3ccccc32)CC1 ; Cl]

HCl solution in dioxane (4.0 M, 12 ml, 48 mmol) was added drop-wise over 8 min to a stirred solution of (9H-fluoren-9-yl)methyl 4-({[(tert -butoxy)carbonyl]amino}methyl)piperidine-1-carboxylate, Intermediate 117 (7.00 g, 16.0 mmol) in MeCN (100 ml). The resulting solution was stirred at RT for 17 h then concentrated in vacuo to afford the product as a white solid (5.56 g, 82%).

$^1$H NMR (500 MHz, DMSO-d$_6$) δ 8.04-7.82 (m, 5H), 7.62 (d, J=7.4 Hz, 2H), 7.42 (t, J=7.4 Hz, 2H), 7.34 (td, J=7.4, 0.9 Hz, 2H), 4.42-4.32 (m, 2H), 4.27 (t, J=6.3 Hz, 1H), 4.04-3.71 (m, 2H), 2.84-2.69 (m, 2H), 2.67 (d, J=6.8 Hz, 2H), 1.80-1.70 (m, 1H), 1.70-1.58 (m, 2H), 1.04-0.87 (m, 2H). 7 wt % residual dioxane.

LC/MS (System A): m/z (ESI$^+$)=337 [MH$^+$], R$_t$=0.86 min, UV purity=95%.

Overall purity estimate=88%.

Intermediate 119-Synthesis of (9H-fluoren-9-yl) methyl 4-({bis[(2S,3R)-2,3-dihydroxy-3-[(4R,5R)-5-hydroxy-2-phenyl-1,3-dioxan-4-yl]propyl] amino}methyl)piperidine-1-carboxylate

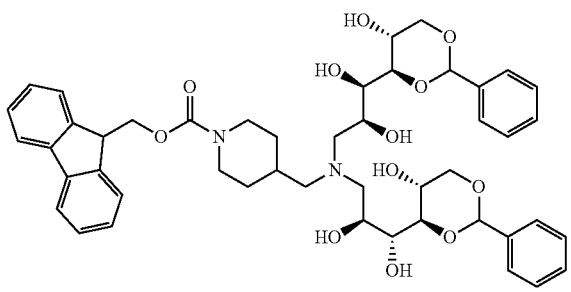

AcOH (3.11 ml, 54.3 mmol) was added to a solution of (9H-fluoren-9-yhmethyl 4-(aminomethyl)piperidine-1-carboxylate hydrochloride, Intermediate 118 (5.56 g, 14.9 mmol) and 4,6-O-benzylidene-D-glucopyranose (14.6 g, 54.3 mmol) in MeOH (100 ml). The reaction was stirred at RT for 40 min then NaCNBH$_3$ (3.41 g, 54.3 mmol) was added in portions over 50 min. The resulting solution was stirred at RT for 17 h. The reaction mixture was re-treated with 4,6-O-benzylidene-D-glucopyranose (7.29 g, 27.2 mmol) and AcOH (1.56 ml, 27.2 mmol) then stirred at RT for 30 min. NaCNBH$_3$ (1.71 g, 27.2 mmol) was added in portions over 1 h. The resulting solution was stirred at RT for a further 70 h then added onto saturated aqueous NaHCO$_3$ solution (200 ml) in portions over 30 min. The resultant suspension was stirred at RT for 1 h then filtered. The solid was washed with water (100 ml) then dried in vacuo to afford a white solid (13.8 g). A portion (5.55 g) of the crude material thus obtained was purified by flash column chromatography on C18 (400 g). The column was eluted with MeCN:H$_2$O+0.1% NH$_4$OH using the following gradient (% MeCN, column volumes): 10%, 2 CV; 10-57%, 16 CV; 57%, 9 CV; 59-63%, 2 CV; 100%, 3 CV. The desired fractions were combined and concentrated in vacuo to afford the product as a beige solid (2.99 g, 23%).

$^1$H NMR (500 MHz, CD$_3$OD-d$_4$) δ 7.86-7.75 (m, 2H), 7.65-7.55 (m, 2H), 7.53-7.44 (m, 4H), 7.43-7.37 (m, 2H), 7.36-7.27 (m, 8H), 5.51 (m, 2H), 4.64-4.36 (m, 5H), 4.27-4.20 (m, 3H), 4.04-3.92 (m, 4H), 3.86 (m, 2H), 3.71 (m, 2H), 3.64-3.57 (m, 2H), 2.73-2.58 (m, 3H), 2.54-2.44 (m, 2H), 2.36-2.23 (m, 2H), 1.81-1.42 (m, 3H), 0.89-0.58 (m, 2H).

LC/MS (System B): m/z (ESI$^+$)=841 [MH$^+$], R$_t$=4.78 min, UV purity=95%.

Intermediate 120-Synthesis of (1R,2S)-3-{[(2S,3R)-2,3-dihydroxy-3-[(4R,5R)-5-hydroxy-2-phenyl-1,3-dioxan-4-yl]propyl][(piperidin-4-yl)methyl]amino}-1-[(4R,5R)-5-hydroxy-2-phenyl-1,3-dioxan-4-yl]propane-1,2-diol; bis(formic acid)

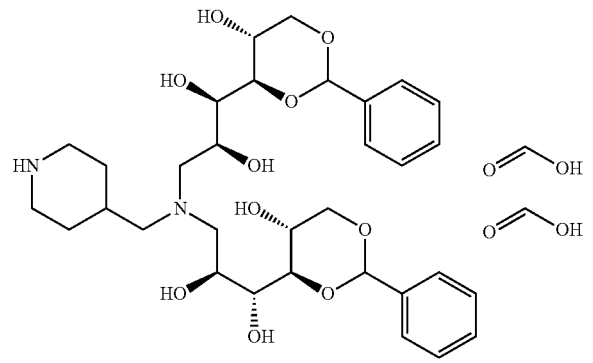

Piperidine (3.30 ml, 33.4 mmol) was added to a stirred solution of (9H-fluoren-9-yl)methyl 4-({bis[(2S,3R)-2,3-dihydroxy-3-[(4R,5R)-5-hydroxy-2-phenyl-1,3-dioxan-4-yl]propyl]amino}methyl)piperidine-1-carboxylate, Intermediate 119 (2.81 g, 3.34 mmol) in THF (40 ml). The reaction mixture was stirred at RT for 18 h then concentrated in vacuo. The residue was suspended in Et$_2$O (30 ml) with sonication then the resultant suspension was filtered. The solid collected was rinsed with Et$_2$O (20 ml) then dried under vacuum to afford a white solid (3.07 g). A sample (1.78 g) of the crude solid was purified by flash column chromatography on C18 (120 g). The column was eluted with MeCN:water+0.1% formic acid using the following gradient (% MeCN, column volumes): 10%, 2 CV; 10-16%, 1.5 CV; 16%, 2.5 CV; 16-39%, 6 CV; 39-100%, 1.5 CV; 100% 2 CV. The remaining crude solid material was purified by flash column chromatography on C18 (120 g). The column was eluted with MeCN:water+0.1% formic acid using the following gradient (% MeCN, column volumes): 10%, 2 CV; 10-14%, 2 CV; 14%, 2 CV; 14-17%, 1 CV; 17-55%, 7 CV; 55-100%, 1 CV; 100% 4 CV. The desired fractions from both columns were combined and concentrated in vacuo to afford the product as an off-white solid (1.58 g, 67%).

$^1$H NMR (500 MHz, CD$_3$OD) δ 8.33 (s, 2H), 7.53-7.45 (m, 4H), 7.41-7.31 (m, 6H), 5.53 (m, 2H), 4.25 (m, 2H), 4.02 (m, 2H), 3.96 (m, 2H), 3.89 (m, 2H), 3.74 (m, 2H), 3.62 (m, 2H), 3.30-3.20 (m, 2H), 2.96-2.80 (m, 4H), 2.78-2.68 (m, 2H), 2.65-2.58 (m, 2H), 2.09-2.00 (m, 1H), 1.92-1.68 (m, 2H), 1.33-1.18 (m, 2H).

LC/MS (System A): m/z (ESI$^+$)=619 [MH$^+$], R$_t$=0.73 min, UV purity=100%.

Intermediate 121-Synthesis of (2R,3R,4R,5S)-6-{[(2S,3R,4R,5R)-2,3,4,5,6-pentahydroxyhexyl][(piperidin-4-yl)methyl]amino}hexane-1,2,3,4,5-pentol dihydrochloride

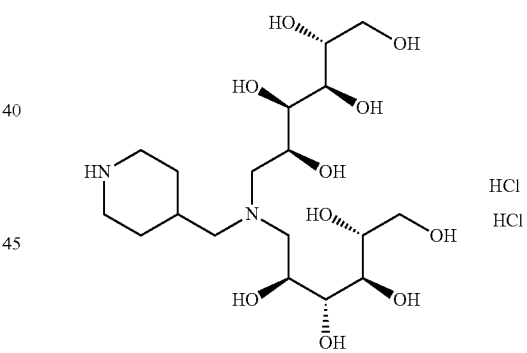

A solution of (1R,2S)-3-{[(2S,3R)-2,3-dihydroxy-3-[(4R,5R)-5-hydroxy-2-phenyl-1,3-dioxan-4-yl]propyl][(piperidin-4-yhmethyl]amino}-1-[(4R,5R)-5-hydroxy-2-phenyl-1,3-dioxan-4-yl]propane-1,2-diol; bis(formic acid), Intermediate 120 (1.52 g, 2.14 mmol) in aqueous HCl solution (2 M, 23 ml, 46 mmol) was stirred at RT for 4.5 h. The reaction was concentrated in vacuo to afford a viscous yellow gum (1.18 g, quantitative based on 93% estimated purity).

$^1$H NMR (500 MHz, D$_2$O) δ 4.32-4.21 (m, 2H), 3.89-3.81 (m, 4H), 3.81-3.75 (m, 2H), 3.72-3.59 (m, 4H), 3.56-3.48 (m, 6H), 3.39 (m, 2H), 3.09 (m, 2H), 2.40-2.27 (m, 1H), 2.21-2.13 (m, 1H), 2.06-1.99 (m, 1H), 1.66-1.53 (m, 2H).

LC/MS (System C): m/z (ESI$^+$)=443 [MH$^+$], R$_t$=0.32 min, ELS purity=100%.

Intermediate 122-Synthesis of formic acid; tert-butyl (3R)-3-{bis[(2S,3R)-2,3-dihydroxy-3-[(4R,5R)-5-hydroxy-2-phenyl-1,3-dioxan-4-yl]propyl]amino}pyrrolidine -1-carboxylate

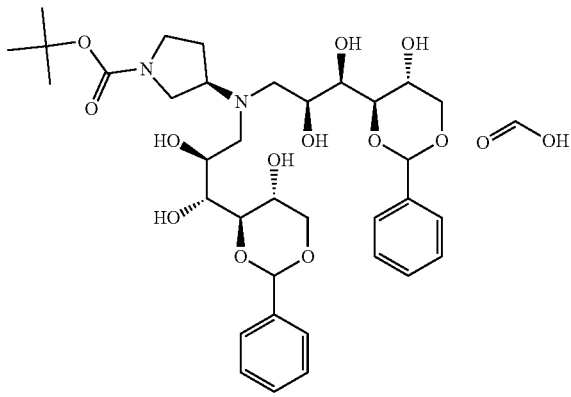

2-Picoline borane complex (0.86 g, 8.05 mmol) was added to a suspension of tert-butyl (3R)-3-aminopyrrolidine-1-carboxylate (500 mg, 2.68 mmol) and 4,6-O-benzylidene-D -glucopyranose (2.88 g, 10.7 mmol) in MeOH (5 ml) . The mixture was heated at 60° C. for 17 h. The reaction mixture was allowed to cool to RT then concentrated in vacuo. The residue was partitioned between EtOAc (15 ml) and water (15 ml). The phases were separated then the organic phase was washed with water (15 ml) and brine (15 ml) then dried over $Na_2SO_4$ and concentrated in vacuo. The crude material was purified by flash column chromatography on C18 (60 g, Ultra). The column was eluted with MeCN:$H_2O$+0.1% formic acid using the following gradient (% MeCN, column volumes): 10%, 2 CV; 10-40%, 10 CV; 40-100%, 2 CV; 100%, 2 CV. The desired fractions were combined and concentrated in vacuo then the residual aqueous solution was lyophilised to afford the product as a white solid (1.39 g, 70%).
$^1$H NMR (500 MHz, $CD_3OD$-$d_4$) δ 8.27 (s, 1H), 7.47 (dd, J=7.2, 2.3 Hz, 4H), 7.34 (qd, J= 4.7, 1.8 Hz, 6H), 5.51 (s, 2H), 4.24 (dd, J=10.6, 5.4 Hz, 2H), 4.04 (s, 2H), 3.95 (td, J= 9.9, 5.4 Hz, 2H), 3.89 (dd, J=5.3, 2.2 Hz, 2H), 3.75 (dd, J=9.4, 2.2 Hz, 2H), 3.69 (d, J= 6.2 Hz, 1H), 3.59 (q, J=11.4, 11.0 Hz, 3H), 3.34-3.29 (m, 1H +$CD_3OD$), 3.24-3.15 (m, 1H), 2.92 (d, J=48.5 Hz, 5H), 1.96 (d, J=31.5 Hz, 1H), 1.75 (s, 1H), 1.45 (s, 9H).
LC/MS (System A): m/z (ESI$^+$)=691 [MH$^+$], R$_t$=0.93 min, UV purity=100%.

Intermediate 123-Synthesis of (2R,3R,4R,5S)-6-{[(2S,3R,4R,5R)-2,3,4,5,6-pentahydroxyhexyl][(3R)-pyrrolidin-3-yl]amino}hexane-1,2,3,4,5-pentol dihydrochloride

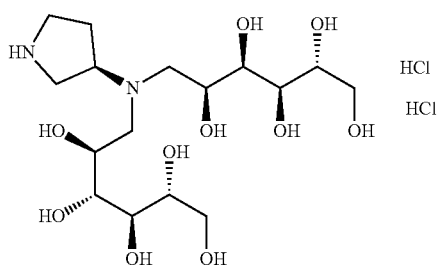 [SMILES: OC[C@@H](O)[C@@H](O)[C@H](O)[C@@H](O)CN(C[C@H](O)[C@@H](O)[C@H](O)[C@H](O)CO)[C@@H]1CCNC1 ; Cl ; Cl]

A suspension of formic acid; tert-butyl (3R)-3-{bis[(2S,3R)-2,3-dihydroxy-3-[(4R,5R)-5-hydroxy-2-phenyl-1,3-dioxan-4-yl]propyl]amino}pyrrolidine-1-carboxylate, Intermediate 122 (1.39 g, 1.89 mmol) in aqueous HCl solution (2 M, 30 ml, 60 mmol) was stirred at RT for 18 h. The reaction mixture was concentrated in vacuo then re-dissolved in water (20 ml) and lyophilised to afford the product as a cream foam (1.11 g, quantitative based on 83% estimated purity).
$^1$H NMR (500 MHz, $D_2O$) δ 4.67 (p, J=8.4 Hz, 1H), 4.33-4.28 (m, 2H), 3.99-3.92 (m, 1H), 3.88 (dd, J=5.0, 2.3 Hz, 2H), 3.83 (dd, J=11.8, 3.0 Hz, 2H), 3.81-3.76 (m, 2H), 3.75-3.64 (m, 6H), 3.63-3.58 (m, 2H), 3.52-3.46 (m, 2H), 3.47-3.39 (m, 1H), 2.75-2.67 (m, 1H), 2.37-2.28 (m, 1H).
LC/MS (System A): m/z (ESI$^+$)=415 [MH$^+$], R$_t$=0.13 min, ELS purity=100%.

Intermediate 124-Synthesis of formic acid; tert-butyl (3S)-3-{bis[(2S,3R)-2,3-dihydroxy-3-[(4R,5R)-5-hydroxy-2-phenyl-1,3-dioxan-4-yl]propyl]amino}pyrrolidine -1-carboxylate

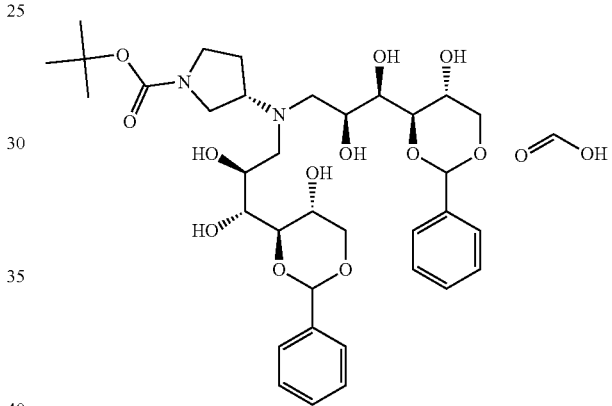

2-Picoline borane complex (861 mg, 8.05 mmol) was added to a suspension of tert-butyl (3S)-3-aminopyrrolidine-1-carboxylate (500 mg, 2.68 mmol) and 4,6-O-benzylidene-D -glucopyranose (2.88 g, 10.7 mmol) in MeOH (5 ml) . The resultant mixture was heated at 60° C. for 16 h. The reaction mixture was allowed to cool to RT partitioned between EtOAc (20 ml) and water (20 ml). The phases were separated then the aqueous phase was extracted with EtOAc (20 ml). The combined organic phases were washed with water (20 ml) and 1:1 water:brine (20 ml) then dried over $Na_2SO_4$ and concentrated in vacuo. The crude material was purified by flash column chromatography on C18 (30 g). The column was eluted with MeCN:$H_2O$+0.1% formic acid using the following gradient (% MeCN, column volumes): 10%, 2 CV; 10-40%, 10 CV; 40-100%, 2 CV; 100%, 2 CV. The desired fractions were combined and concentrated in vacuo to afford the product as a pale yellow foam (1.73 g, 87%).
$^1$H NMR (500 MHz, $CD_3OD$) δ 8.25 (s, 1H), 7.54-7.46 (m, 4H), 7.41-7.30 (m, 6H), 5.54 (s, 2H), 4.30-4.22 (m, 2H), 4.14-4.07 (m, 2H), 4.01-3.92 (m, 2H), 3.91 (dd, J=5.3, 2.2 Hz, 2H), 3.82-3.72 (m, 3H), 3.68-3.53 (m, 3H), 3.41-3.33 (m, 1H), 3.25-3.04 (m, 4H), 3.04-2.89 (m, 2H), 2.17-2.07 (m, 1H), 1.99-1.83 (m, 1H), 1.56-1.36 (m, 9H).
LC/MS (System A): m/z (ESI$^+$)=691 [MH$^+$], R$_t$=0.93 min, ELS purity=100%.

Intermediate 125-Synthesis of (2R,3R,4R,5S)-6-{[(2S,3R,4R,5R)-2,3,4,5,6-pentahydroxyhexyl][(3S)-pyrrolidin-3-yl]amino}hexane-1,2,3,4,5-pentol dihydrochloride

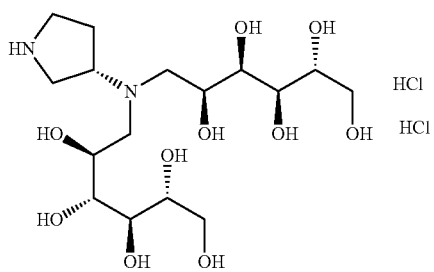 [SMILES: OC[C@@H](O)[C@@H](O)[C@H](O)[C@@H](O)CN(C[C@H](O)[C@@H](O)[C@H](O)[C@H](O)CO)[C@H]1CCNC1 ; Cl ; Cl]

A suspension of formic acid; tert-butyl (3S)-3-{bis[(2S,3R)-2,3-dihydroxy-3-[(4R,5R)-5-hydroxy-2-phenyl-1,3-dioxan-4-yl]propyl]amino}pyrrolidine-1-carboxylate, Intermediate 124 (1.72 g, 2.33 mmol) in aqueous HCl solution (2 M, 30 ml, 60 mmol) and MeOH (1 ml) was stirred at RT for 4 h. The reaction mixture was concentrated in vacuo then re-dissolved in water and lyophilised to afford the product as a cream foam (1.05 g, 92%).

$^1$H NMR (500 MHz, CD$_3$OD) δ 4.72 (p, J=8.2 Hz, 1H), 4.30 (s, 2H), 3.98-3.36 (m, 18H), 2.76-2.66 (m, 1H), 2.48-2.36 (m, 1H).

LC/MS (System A): m/z (ESI$^+$)=415 [MH$^+$], R$_t$=0.13 min, ELS purity=100%.

Intermediate 126-Synthesis of formic acid; tert-butyl N-[(1r,4r)-4-{bis[(2S,3R)-2,3-dihydroxy-3-[(4R,5R)-5-hydroxy-2-phenyl-1,3-dioxan-4-yl]propyl]amino}cyclohexyl]carbamate

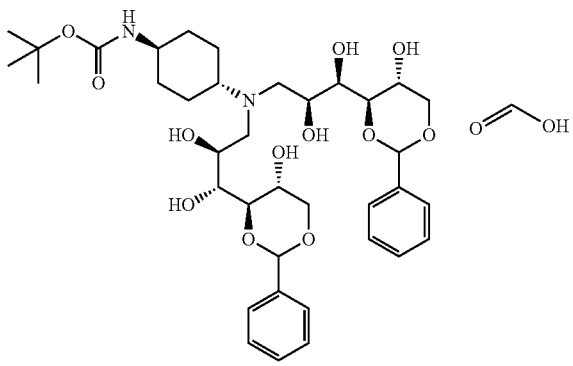

2-Picoline borane complex (939 mg, 8.78 mmol) was added to a suspension of tert-butyl N-(4-aminocyclohexyl)carbamate (627 mg, 2.93 mmol) and 4,6-O-benzylidene-D-glucopyranose (3.14 g, 11.7 mmol) in MeOH (6 ml). The mixture as heated at 60° C. for 16 h then concentrated in vacuo. The residue was partitioned between EtOAc (15 ml) and water (15 ml). The phases were separated then the organic phase was washed with water (10 ml) and brine (10 ml) then dried over Na$_2$SO$_4$ and concentrated in vacuo. The crude material was purified by flash column chromatography on C18 (30 g). The column was eluted with MeCN:H2O+ 0.1% formic acid using the following gradient (% MeCN, column volumes): 10%, 2 CV; 10-40%, 10 CV; 40-100%, 2 CV; 100%, 2 CV. The desired fractions were combined and concentrated in vacuo then the residual aqueous solution was lyophilised to afford the product as a white solid (914 mg, 41% yield)).

$^1$H NMR (500 MHz, CD$_3$OD) δ 8.52 (s, 1H), 7.54-7.48 (m, 4H), 7.44-7.32 (m, 6H), 5.56 (s, 2H), 4.31-4.23 (m, 2H), 4.18-4.06 (m, 2H), 4.02-3.92 (m, 4H), 3.82-3.75 (m, 2H), 3.64 (t, J=10.5 Hz, 2H), 3.30-3.01 (m, 6H), 2.00-1.76 (m, 4H), 1.56-1.39 (m, 10H), 1.36-1.15 (m, 2H), 1.09-0.97 (m, 1H).

LC/MS (System C): m/z (ESI$^+$)=719 [MH$^+$], R$_t$=2.29 min, ELS purity=100%.

Intermediate 127-Synthesis of (2R,3R,4R,5S)-6-{[(2S,3R,4R,5R)-2,3,4,5,6-pentahydroxyhexyl][(1r,4r)-4-aminocyclohexyl]amino}hexane-1,2,3,4,5-pentol dihydrochloride

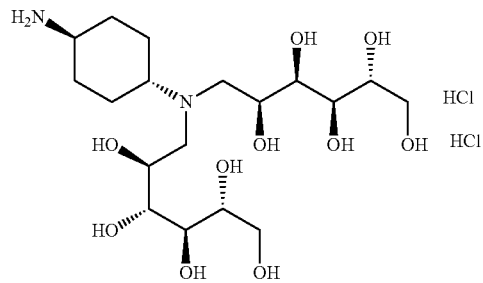 [SMILES: N[C@H]1CC[C@H](N(C[C@H](O)[C@@H](O)[C@H](O)[C@H](O)CO)C[C@H](O)[C@@H](O)[C@H](O)[C@H](O)CO)CC1 ; Cl ; Cl]

A suspension of formic acid; tert-butyl N-[(1r,4r)-4-{bis[(2S,3R)-2,3-dihydroxy-3-[(4R,5R)-5-hydroxy-2-phenyl-1,3-dioxan-4-yl]propyl]amino}cyclohexyl]carbamate, Intermediate 126 (910 mg, 1.19 mmol) in aqueous HCl solution (2 M, 20 ml, 40 mmol) was stirred at RT for 18 h.

The reaction mixture was concentrated in vacuo then the residue was dissolved in water (20 ml) and lyophilised to afford the product as a cream foam (718 mg, quantitative based on 85% estimated purity).

$^1$H NMR (500 MHz, D$_2$O) δ 4.19-4.09 (m, 2H), 3.81-3.66 (m, 6H), 3.63-3.51 (m, 6H), 3.39-3.14 (m, 4H), 2.24-2.13 (m, 3H), 2.11-2.04 (m, 1H), 1.87-1.76 (m, 1H), 1.69-1.45 (m, 3H).

LC/MS (System A): m/z (ESI$^+$)=443 [MH$^+$], R$_t$=0.13 min, ELS purity=100%.

Intermediate 128-Synthesis of (9H-fluoren-9-yl)methyl N-[(1s,4s)-4-{[tert-butoxy)carbonyl]amino}cyclohexyl]carbamate

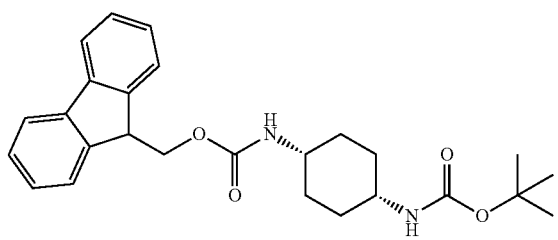 [SMILES: CC(C)(C)OC(=O)N[C@H]1CC[C@@H](NC(=O)OCC2c3ccccc3-c3ccccc32)CC1]

A solution of 9H-fluoren-9-ylmethyl carbonochloridate (4.04 g, 15.6 mmol) in THF (30 ml) was added dropwise over 5 min to a cooled (0° C.) mixture of tert-butyl N-[(1s,4s)-4-aminocyclohexyl]carbamate (3.35 g, 15.6 mmol) and aqueous sodium carbonate solution (1 M, 30 ml, 30 mmol) in THF (60 ml). The reaction was allowed to warm to RT then left to stir at RT for 16 h. The reaction mixture was diluted with water (100 ml) then extracted with EtOAc (100 ml). The organic phase was washed with water (100 ml) and brine (50 ml) then dried over Na₂SO₄ and concentrated in vacuo to afford the product as a pale beige foam (6.71 g, 91%).

$^1$H NMR (500 MHz, DMSO-$d_6$) δ 7.92-7.83 (m, 2H), 7.74-7.56 (m, 2H), 7.45-7.36 (m, 2H), 7.36-7.28 (m, 2H), 7.17 (d, J=5.4 Hz, 1H), 6.70-6.58 (m, 1H), 4.44-4.19 (m, 3H), 3.43-3.33 (m, 2H), 1.65-1.21 (m, 17H).

LC/MS (System A): m/z (ESI⁺)=459 [M+Na⁺], $R_t$=1.35 min, UV purity=93%.

Intermediate 129-Synthesis of (9H-fluoren-9-yl) methyl N-[(1s,4s)-4-aminocyclohexyl]carbamate hydrochloride

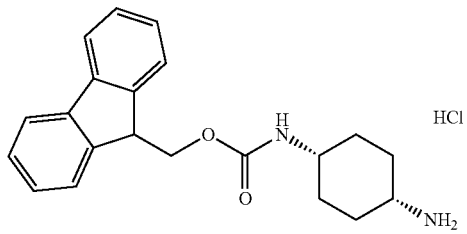 [SMILES: N[C@H]1CC[C@@H](NC(=O)OCC2c3ccccc3-c3ccccc32)CC1 ; Cl]

HCl solution in dioxane (4.0 M, 77 ml, 310 mmol) was added to a suspension of (9H-fluoren-9-yl) methyl N-[(1s,4s)-4-{[(tert-butoxy)carbonyl]amino}cyclohexyl]carbamate, Intermediate 128 (6.71 g, 15.4 mmol) in dioxane (80 ml). The reaction was left to stir at RT for 20 h.

The reaction mixture was concentrated in vacuo to afford the product as a white solid (6.04 g, 92%).

$^1$H NMR (500 MHz, DMSO-$d_6$) δ 7.95-7.81 (m, 5H), 7.78-7.62 (m, 2H), 7.46-7.40 (m, 2H), 7.36-7.32 (m, 2H), 7.28-7.20 (m, 1H), 4.36-4.16 (m, 3H), 3.54-3.44 (m, 1H), 3.12-2.99 (m, 1H), 1.86-1.41 (m, 8H). Residual solvent estimate: 6.8 wt %

LC/MS (System A): m/z (ESI⁺)=337 [MH⁺], $R_t$=0.90 min, UV purity=94%.

Intermediate 130-Synthesis of (9H-fluoren-9-yl) methyl N-[(1s,4s)-4-{[(2S,3R)-2,3-dihydroxy-3-[(4R,5R)-5-hydroxy-2-phenyl-1,3-dioxan-4-yl]propyl][(2S,3R)-2,3-dihydroxy-3-[(5R)-5-hydroxy-2-phenyl-1,3-dioxan-4-yl]propyl]amino}cyclohexyl] carbamate

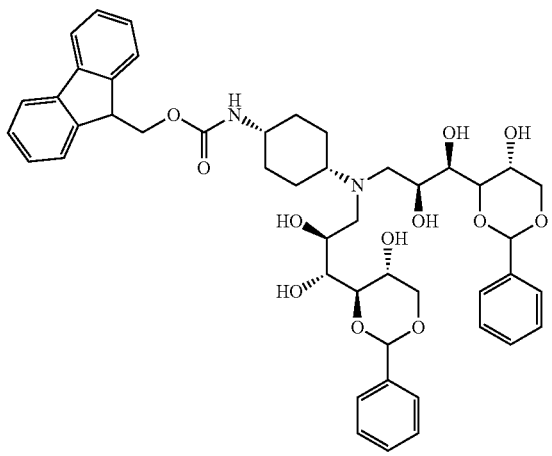

A solution of (9H-fluoren-9-yl)methyl N-[(1s,4s)-4-aminocyclohexyl]carbamate hydrochloride, Intermediate 129 (4.70 g, 12.6 mmol) and 4,6-O-benzylidene-D-glucopyranose (10.1 g, 37.8 mmol) in MeOH (100 ml) was stirred at RT for 0.5 h. NaCNBH3 (3.17 g, 50.4 mmol) was added then the reaction mixture was left to heat at 60° C. for 4.5 h. More 4,6-O-benzylidene-D-glucopyranose (10.1 g, 37.8 mmol) was added then the reaction was left to heat at 60° C. for 20 h. More 4,6-0-benzylidene-D-glucopyranose (10.1 g, 37.8 mmol) was added then the reaction was left to heat at 60° C. for 19 h. The reaction was allowed to cool to RT then added to saturated aqueous NaHCO3 solution (100 ml) and EtOAc (100 ml). The resulting suspension was left to stir at RT for 2 h then filtered through a Celite pad. The pad was rinsed through with EtOAc (50 ml) then the filtrate was transferred to a separating funnel. Saturated aqueous NaHCO3 solution (50 ml) was added then the phases were separated. Water (150 ml) was added to the organic phase then the resultant mixture was left to stir at RT for a further 1 h. The resultant mixture was transferred to a separating funnel then the phases were separated. The organic phase was washed with water (150 ml) and brine (100 ml) then dried over Na₂SO₄ and concentrated in vacuo to afford a golden viscous oil (19.1 g). The crude material was dissolved in refluxing isopropanol (200 ml). The mixture was stirred under reflux for 0.5 h then allowed to cool to RT. The solid was collected by filtration, then rinsed with IPA and dried under vacuum to afford the product as a cream solid (7.68 g). A sample of the solid thus obtained (3.0 g) was purified by flash column chromatography on C18 (120 g). The column was eluted with MeCN:H2O +0.1% formic acid using the following gradient (% MeCN, column volumes): 20%, 2 CV; 20-50%, 10 CV; 50-100%, 2 CV; 100%, 2 CV. The desired fractions were combined and concentrated in vacuo to afford the product as a white solid (1.46 g, 13%)).

$^1$H NMR (500 MHz, CD₃OD) δ 8.35 (s, 1H), 7.85-7.77 (m, 2H), 7.67-7.58 (m, 2H), 7.53-7.43 (m, 4H), 7.41-7.26 (m, 10H), 5.52 (s, 2H), 4.58-4.35 (m, 2H), 4.31-4.23 (m,

2H), 4.23-4.13 (m, 3H), 4.00-3.89 (m, 4H), 3.75 (m, 2H), 3.71-3.65 (m, 1H), 3.62 (m, 2H), 3.44-3.32 (m, 4H), 1.89-1.26 (m, 8H).

LC/MS (System A): m/z (ESI$^+$)=841 [MH$^+$], $R_t$=1.09 min, UV purity=99%.

Intermediate 131-Synthesis of (1R,2S)-3-{[(2S,3R)-2,3-dihydroxy-3-[(4R,5R)-5-hydroxy-2-phenyl-1,3-dioxan-4-yl]propyl][(1s,4s)-4-aminocyclohexyl]amino}-1-[(4R,5R)-5-hydroxy-2-phenyl-1,3-dioxan-4-yl]propane-1,2-diol; bis(formic acid)

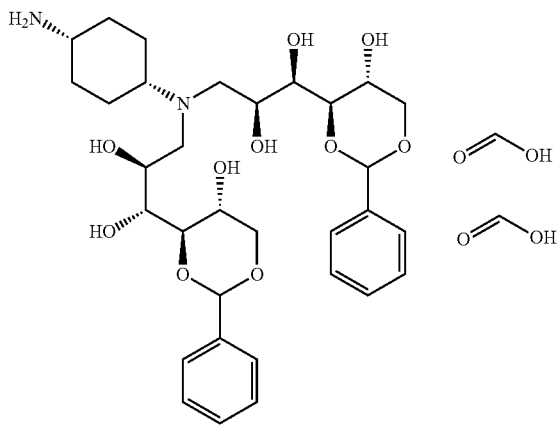

Piperidine (615 uL, 6.23 mmol) was added to a solution of (9H-fluoren-9-yl)methyl N-[(1s,4s)-4-{[(2S,3R)-2,3-dihydroxy-3-[(4R,5R)-5-hydroxy-2-phenyl-1,3-dioxan-4-yl]propyl][(2S,3R)-2,3-dihydroxy-3-[(5R)-5-hydroxy-2-phenyl-1,3-dioxan-4-yl]propyl]amino}cyclohexyl]carbamate, Intermediate 130 (1.46 g, 1.74 mmol) in THF (10 ml). The reaction was left to stir at RT for 21 h then concentrated in vacuo. The residue was suspended in MeOH (10 ml) then filtered. The filtrate was concentrated in vacuo then suspended in MeOH (5 ml) and filtered. The filtrate was purified by flash column chromatography on C18 (60 g). The column was eluted with MeCN:H$_2$O+0.1% formic acid using the following gradient (% MeCN, column volumes): 10%, 2 CV; 10-32%, 7 CV; 32-40%, 1 CV; 12 CV; 40-100%, 2 CV; 100%, 2 CV. The desired fractions were combined then concentrated in vacuo. The residual aqueous solution was lyophilised to afford the product as a white solid (388 mg, 31%). $^1$H NMR (500 MHz, CD$_3$OD) δ 8.40 (s, 2H), 7.51-7.43 (m, 4H), 7.40-7.28 (m, 6H), 5.51 (s, 2H), 4.29-4.20 (m, 2H), 4.08-4.02 (m, 2H), 4.00-3.92 (m, 2H), 3.88 (dd, J=5.0, 2.5 Hz, 2H), 3.72 (dd, J=9.3, 2.5 Hz, 2H), 3.61 (t, J=10.5 Hz, 2H), 3.39-3.34 (m, 1H), 3.07-2.89 (m, 5H), 1.97-1.62 (m, 8H).

LC/MS (System A): m/z (ESI$^+$)=619 [MH$^+$], $R_t$=0.76 min, UV purity=100%.

Intermediate 132-Synthesis of (2R,3R,4R,5S)-6-{[(2S,3R,4R,5R)-2,3,4,5,6-pentahydroxyhexyl][(1s,4s)-4-aminocyclohexyl]amino}hexane-1,2,3,4,5-pentol

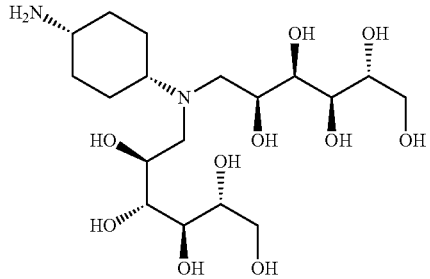 [SMILES: N[C@H]1CC[C@@H](N(C[C@H](O)[C@@H](O)[C@H](O)[C@H](O)CO)C[C@H](O)[C@@H](O)[C@H](O)[C@H](O)CO)CC1]

A solution of (1R,2S)-3-{[(2S,3R)-2,3-dihydroxy-3-[(4R,5R)-5-hydroxy-2-phenyl-1,3-dioxan-4-yl]propyl][(1s,4s)-4-aminocyclohexyl]amino}-1-[(4R,5R)-5-hydroxy-2-phenyl-1,3-dioxan-4-yl]propane-1,2-diol; bis(formic acid), Intermediate 131 (385 mg, 0.622 mmol) in aqueous HCl solution (2 M, 6 ml, 12 mmol) was stirred at RT for 4 h then concentrated in vacuo. The resulting oil was dissolved in water (10 ml) then lyophilised to afford a white foam (323 mg). The material thus obtained was dissolved in water/MeOH then loading on to a pre-wetted SCX cartridge (5 g). The cartridge was eluted with MeOH then the product was released by extensive elution with 7 M ammonia solution in MeOH. The ammonia eluent was concentrated in vacuo. The residue was dissolved in water/MeCN then lyophilised to afford the product as a white solid (212 mg, 77%).

$^1$H NMR (500 MHz, D$_2$O) δ 4.30-4.20 (m, 2H), 3.90-3.62 (m, 12H), 3.57-3.49 (m, 1H), 3.43-3.31 (m, 2H), 2.21-2.09 (m, 3H), 2.06-1.90 (m, 4H), 1.85-1.70 (m, 2H).

LC/MS (System A): m/z (ESI$^+$)=443 [MH$^+$], $R_t$=0.14 min, ELS purity=100%.

Intermediate 133-Synthesis of formic acid; tert-butyl N-(3-{bis[(2S,3R)-2,3-dihydroxy-3-[(4R,5R)-5-hydroxy-2-phenyl-1,3-dioxan-4-yl]propyl]amino}propyl)-N-methylcarbamate

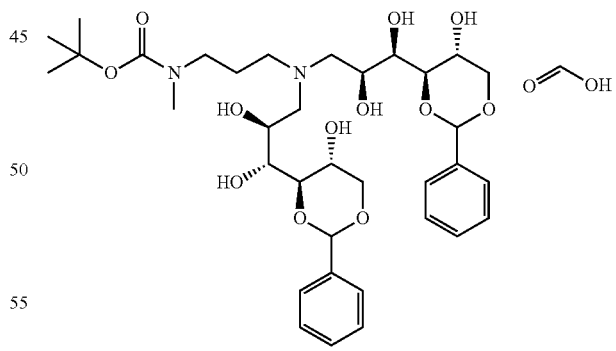

alpha-picoline borane (0.861 g, 8.05 mmol) was added to a suspension of tert-butyl N-(3-aminopropyl)-N-methylcarbamate (0.505 g, 2.68 mmol) and 4,6-O-benzylidene-D-glucopyranose (2.88 g, 10.7 mmol) in MeOH (5 ml). The mixture was heated at 60° C. for 16 h. The reaction mixture was allowed to cool to RT then partitioned between EtOAc (20 ml) and water (20 ml). The phases were separated then the aqueous phase was extracted with EtOAc (20 ml). The combined organic phases were washed with water (20 ml) and 1:1 water:brine (20 ml) then dried over Na$_2$SO$_4$ and concentrated in vacuo. The crude material was purified by flash column chromatography on C18 (60 g). The column was eluted with MeCN:H$_2$O+0.1% formic acid using the following gradient (% MeCN, column volumes): 10%, 2 CV; 10-40%, 10 CV; 40-100%, 2 CV; 100%, 2 CV. The desired fractions were combined and concentrated in vacuo to afford the product as a pale yellow foam (1.19 g, 60%).

$^1$H NMR (500 MHz, CD$_3$OD) δ 8.40 (s, 1H), 7.57-7.44 (m, 4H), 7.44-7.32 (m, 6H), 5.55 (s, 2H), 4.31-4.23 (m, 2H), 4.24-4.15 (m, 2H), 4.00-3.90 (m, 4H), 3.79 (dd, J=9.4, 2.2 Hz, 2H), 3.64 (t, J=10.5 Hz, 2H), 3.41-3.31 (m, 3H), 3.25-3.08 (m, 4H), 2.76-2.64 (m, 3H), 1.88-1.75 (m, 2H), 1.50-1.39 (m, 9H).

LC/MS (System A): m/z (ESI$^+$)=693 [MH$^+$], R$_t$=0.94 min, ELS purity=100%.

Intermediate 134 Synthesis of (2R,3R,4R,5S)-6-{[3-(methylamino)propyl][(2S,3R,4R,5R)-2,3,4,5,6-pentahydroxyhexyl]amino}hexane-1,2,3,4,5-pentol dihydrochloride

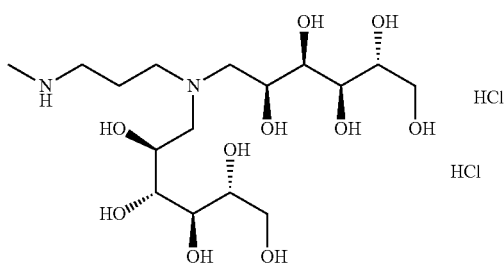 [SMILES: CNCCCN(C[C@H](O)[C@@H](O)[C@H](O)[C@H](O)CO)C[C@H](O)[C@@H](O)[C@H](O)[C@H](O)CO ; Cl ; Cl]

A suspension of formic acid; tert-butyl N-(3-{bis[(2S,3R)-2,3-dihydroxy-3-[(4R,5R)-5-hydroxy-2-phenyl-1,3-dioxan-4-yl]propyl]amino}propyl)-N-methylcarbamate, Intermediate 133 (1.18 g, 1.60 mmol) in aqueous HCl solution (2 M, 30 ml, 60 mmol) and MeOH (1 ml) was stirred at RT for 4 h then concentrated in vacuo. The residue was dissolved in water (30 ml) then lyophilised to afford the product as a cream foam (770 mg, 99%).

$^1$H NMR (500 MHz, CD$_3$OD) δ 4.29-4.20 (m, 2H), 3.96-3.86 (m, 2H), 3.83-3.77 (m, 2H), 3.77-3.65 (m, 6H), 3.63-3.39 (m, 6H), 3.18-3.10 (m, 2H), 2.77 (s, 3H), 2.28-2.18 (m, 2H).

LC/MS (System A): m/z (ESI$^+$)=417 [MH$^+$], R$_t$=0.13 min, ELS purity=100%.

Intermediate 135-Synthesis of formic acid; tert-butyl N-(2-{bis[(2S,3R)-2,3-dihydroxy-3-[(4R,5R)-5-hydroxy-2-phenyl-1,3-dioxan-4-yl]propyl]amino}ethyl)carbamate

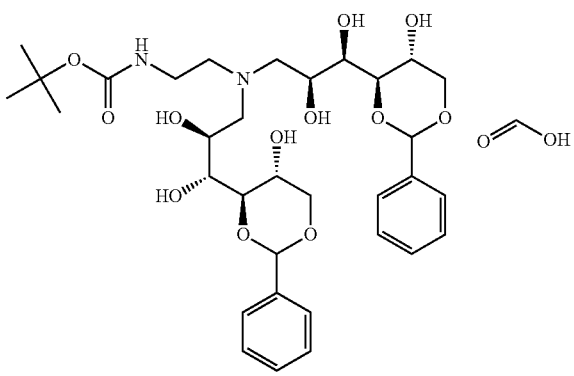

4,6-O-Benzylidene-D-glucopyranose (10.05 g, 37.45 mmol) was added to a solution of tert-butyl N-(2-aminoethyl)carbamate (1.50 g, 9.36 mmol) in MeOH (50 ml). The reaction was stirred at RT for 15 min before then AcOH (2.14 ml, 37.5 mmol) was added. The reaction was stirred at RT for a further 15 min then NaCNBH$_3$ (2.35 g, 37.5 mmol) was added portionwise over 5 min. The reaction was stirred at RT for 16 h then saturated aqueous NaHCO$_3$ solution (50 ml) was added dropwise over 15 min. Further saturated aqueous NaHCO$_3$ solution (50 ml) was added, followed by EtOAc (50 ml). The reaction was stirred at RT for 15 min then transferred to a separating funnel. More EtOAc (100 ml) was added then the phases were separated. The aqueous phase was extracted with EtOAc (150 ml), then the combined organic phases were washed with saturated aqueous NaHCO$_3$ solution (4×200 ml) and brine (50 ml), then dried over Na$_2$SO$_4$, filtered and concentrated in vacuo. The crude material was purified by flash column chromatography on C18 (400 g, Ultra). The column was eluted with MeCN:H$_2$O+0.1% formic acid using the following gradient (% MeCN, column volumes): 10%, 2 CV; 10-49%, 8 CV; 49-54%, 0.5 CV; 54-100%, 1 CV. The desired fractions were combined and concentrated in vacuo then the residual aqueous solution was lyophilised to afford the product as a white solid (2.77 g, 42%).

$^1$H NMR (500 MHz, CD$_3$OD) δ 8.34 (s, 1H), 7.53-7.43 (m, 4H), 7.40-7.26 (m, 6H), 5.52 (s, 2H), 4.25 (dd, J=10.7, 5.4 Hz, 2H), 4.14 (q, J=5.7 Hz, 2H), 3.94 (td, J=10.0, 5.4 Hz, 2H), 3.89 (dd, J=5.0, 2.3 Hz, 2H), 3.75 (dd, J=9.4, 2.2 Hz, 2H), 3.61 (t, J=10.5 Hz, 2H), 3.26-2.99 (m, 8H), 1.42 (s, 9H).

LC/MS (System A): m/z (ESI$^+$)=665 [MH$^+$], R$_t$=0.94 min, UV purity=100%.

Intermediate 136-Synthesis of (2R,3R,4R,5S)-6-[(2-aminoethyl)[(2S,3R,4R,5R)-2,3,4,5,6-pentahydroxyhexyl]amino]hexane-1,2,3,4,5-pentol dihydrochloride

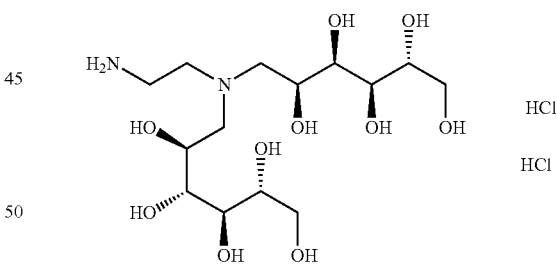

A suspension of formic acid; tert-butyl N-(2-{bis[(2S,3R)-2,3-dihydroxy-3-[(4R,5R)-5-hydroxy-2-phenyl-1,3-dioxan-4-yl]propyl]amino}ethyl)carbamate, Intermediate 135 (1.50 g, 2.11 mmol) in aqueous HCl (2 M, 21 ml, 42 mmol) was stirred at RT for 68 h. The reaction was concentrated in vacuo, then re-dissolved in MeCN/water and concentrated in vacuo. The residue was re-dissolved in MeCN/water then lyophilised to afford the product as a white solid (1.03 g, 99% based on 94% estimated purity).

$^1$H NMR (500 MHz, D$_2$O) δ 4.30 (dt, J=8.9, 4.7 Hz, 2H), 3.88 (dd, J=4.9, 2.2 Hz, 2H), 3.86-3.71 (m, 6H), 3.71-3.66 (m, 4H), 3.61-3.50 (m, 6H).

LC/MS (System A): m/z (ESI$^+$)=389 [MH$^+$], R$_t$=0.14 min, ELS purity=100%.

Intermediate 137-Synthesis of tert-butyl N-[2-(2-{2-[2-({[(9H-fluoren-9-yl)methoxy]carbonyl}amino)ethoxy]ethoxy}ethoxy)ethyl]carbamate

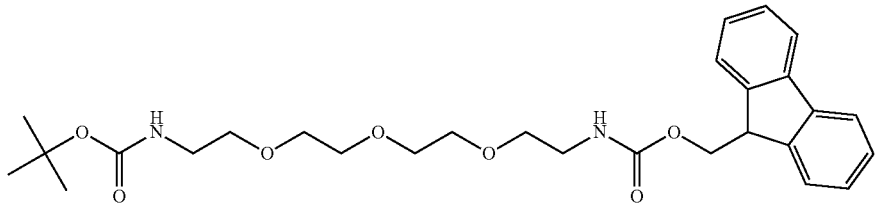 [SMILES: CC(C)(C)OC(=O)NCCOCCOCCOCCNC(=O)OCC1c2ccccc2-c2ccccc21]

NaHCO$_3$ (0.574 g, 6.84 mmol) was added portionwise over 2 min to a stirred solution of tert-butyl N-[2-[2-[2-(2-aminoethoxy)ethoxy]ethoxy]ethyl]carbamate (1.00 g, 3.42 mmol) in MeCN (15 ml) and water (15 ml) RT. A solution of (2,5-dioxopyrrolidin-1-yl) 9H-fluoren-9-ylmethyl carbonate (1.15 g, 3.42 mmol) in MeCN (15 ml) was added dropwise over 30 min. The resulting solution was stirred at RT for 18 h. EtOAc (30 ml) and brine (10 ml) were added then the phases were separated. The aqueous phase was extracted with EtOAc (20 ml). The combined organic extracts were washed with brine (45 ml), dried over MgSO4, then concentrated in vacuo to afford the product as a yellow gum (1.61 g, 76% yield).

$^1$H NMR (500 MHz, DMSO-d$_6$) δ 7.89 (d, J=7.5 Hz, 2H), 7.72-7.61 (m, 2H), 7.41 (t, J=7.4 Hz, 2H), 7.37-7.27 (m, 3H), 6.74 (t, J=5.4 Hz, 1H), 4.29 (d, J=6.9 Hz, 2H), 4.21 (t, J=6.9 Hz, 1H), 3.55-3.44 (m, 8H), 3.40 (t, J=6.0 Hz, 2H), 3.36 (t, J=6.1Hz, 2H), 3.13 (q, J=5.9 Hz, 2H), 3.05 (q, J=6.0 Hz, 2H), 1.36 (s, 9H). LC/MS (System A): m/z (ESI$^+$)=537 [M+Na$^+$], R$_t$=1.28 min, UV purity=83%.

Intermediate 138-Synthesis of (9H-fluoren-9-yl)methyl N-(2-{2-[2-(2-aminoethoxy)ethoxy]ethoxy}ethyl)carbamate hydrochloride

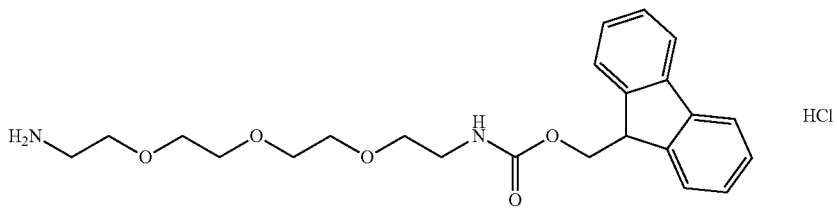 [SMILES: NCCOCCOCCOCCNC(=O)OCC1c2ccccc2-c2ccccc21 ; Cl]

HCl solution in dioxane (4 M, 2 ml, 8 mmol) was added to a stirred solution of tert-butyl N -[2-(2-{2-[2-({[(9H-fluoren-9 -yl)methoxy]carbonyl}amino)ethoxy]ethoxy}ethoxy)ethyl]carbamate, Intermediate 137 (83%, 1.61 g, 2.61 mmol) in MeCN (16 ml). The resulting solution was left to stir at RT for 22 then concentrated in vacuo to afford the product as a yellow gum (1.57 g, quantitative based on 75% estimated purity).

$^1$H NMR (500 MHz, DMSO-d$_6$) δ 7.89 (d, J=7.5 Hz, 2H), 7.83 (s , 3H), 7.69 (d, J=7.4 Hz, 2H), 7.42 (t, J=7.4 Hz, 2H), 7.37-7.29 (m, 3H), 4.30 (d, J=6.9 Hz, 2H), 4.21 (t, J=6.8 Hz, 1H), 3.60-3.57 (m, 2H), 3.56-3.48 (m, 8H), 3.40 (t, J=6.0 Hz, 2H), 3.13 (q, J=5.9 Hz, 2H), 2.98-2.92 (m, 2H). 20 wt % residual solvent.

LC/MS (System A): m/z (ESI$^+$)=415 [MH$^+$], R$_t$=0.89 min, UV purity=92%.

Intermediate 139-Synthesis of (9H-fluoren-9-yl)methyl N-[(14S,15R)-12-[(2S,3R)-2,3-dihydroxy-3-[(4R,5R)-5-hydroxy-2-phenyl-1,3-dioxan-4-yl]propyl]-14,15-dihydroxy-15-[(4R,5R)-5-hydroxy-2-phenyl-1,3-dioxan-4-yl]-3,6,9-trioxa-12-azapentadecan-1-yl]carbamate; formic acid

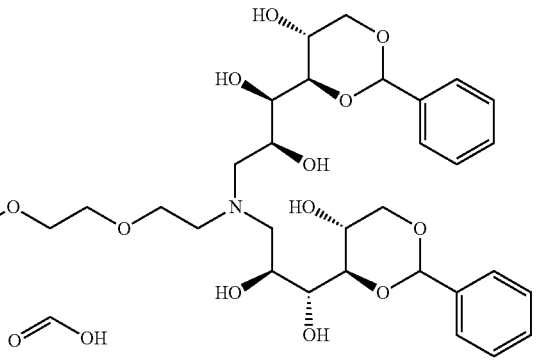

AcOH (737 μL, 12.9 mmol) was added to a solution of (9H-fluoren-9-yl)methyl N-(2-{2-[2-(2-aminoethoxy)ethoxy]ethoxy}ethyl)carbamate hydrochloride, Intermediate 138 (75%, 1.57 g, 3.22 mmol) and 4,6-O-benzylidene-D-glucopyranose (3.46 g, 12.9 mmol) in MeOH (30 ml). The reaction was stirred at RT for 45 min. NaCNBH$_3$ (809 mg, 12.9 mmol) was added portionwise over 50 min. The resultant solution was stirred at RT for 40 h. The reaction mixture was treated with 4,6-O-benzylidene-D-glucopyranose (1.73 g, 6.45 mmol), AcOH (368 μL, 6.43 mmol) and MeOH (10 ml). The reaction was stirred at RT for 1 h then NaCNBH$_3$ (403 mg, 6.41 mmol) was added portionwise over 20 min. MeOH (10 ml) was added then the reaction mixture was stirred at RT for 70 h. Saturated aqueous NaHCO$_3$ solution (100 ml) was added portionwise over 5 min then EtOAc (100 ml) was added. The phases were separated then the aqueous phase was extracted with EtOAc (3×30 ml). The combined organic phases were washed with saturated aqueous NaHCO$_3$ solution (2×50 ml), brine (50 ml), then dried over MgSO$_4$, filtered and concentrated in vacuo to afford a brown gum (3.86 g). A portion (2 g) of the crude material was purified by flash column chromatography on C18 (120 g, Ultra). The column was eluted with MeCN:H$_2$O+0.1% formic acid using the following gradient (% MeCN, column volumes): 10%, 2 CV; 10-31%, 8 CV; 31%, 4.5 CV; 31-35%, 1.5 CV; 35-47%, 1 CV; 47-61%, 1.5 CV; 100% 2 CV. The remaining crude material was purified by flash column chromatography on C18 (120 g, Ultra). The column was eluted with MeCN:H$_2$O+0.1% formic acid using the following gradient (% MeCN, column volumes): 10%, 2 CV; 10-27%, 4 CV; 27%, 0.5 CV; 27-68%, 9 CV; 68%, 0.5 CV; 68-78%, 2 CV; 78-100%, 1.5 CV; 100% 1 CV. The desired fractions from both columns were combined and concentrated in vacuo to afford the product as a light brown resin (1.30 g, 48%).

$^1$H NMR (500 MHz, CD$_3$OD) δ 8.44 (s, 1H), 7.81 (d, J=7.5 Hz, 2H), 7.68-7.59 (m, 2H), 7.52-7.44 (m, 4H), 7.44-7.37 (m, 2H), 7.37-7.30 (m, 8H), 5.52 (s, 2H), 4.36 (d, J=6.8 Hz, 2H), 4.28-4.15 (m, 5H), 3.98-3.88 (m, 4H), 3.75 (dd, J=9.4, 2.3 Hz, 2H), 3.67-3.44 (m, 14H), 3.40-3.33 (m, 4H), 3.31-3.21 (m, 4H).

LC/MS (System A): m/z (ESI$^+$)=919 [MH$^+$], R$_f$=1.02 min, UV purity=93%.

Intermediate 140-Synthesis of (14S,15R)-1-amino-12-[(2S,3R)-2,3-dihydroxy-3-[(4R,5R)-5-hydroxy-2-phenyl-1,3-dioxan-4-yl]propyl]-15-[(4R,5R)-5-hydroxy-2-phenyl-1,3-dioxan-4-yl]-3,6,9-trioxa-12-azapentadecane-14,15-diol; bis(formic acid)

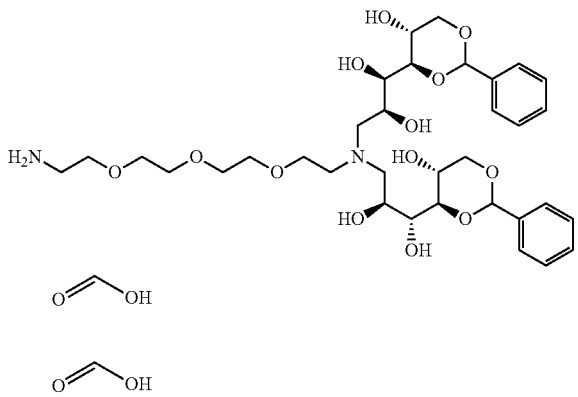

Piperidine (1.34 ml, 13.6 mmol) was added to a stirred solution of (9H-fluoren-9-yl)methyl N-[(14S,15R)-12-[(2S,3R)-2,3-dihydroxy-3-[(4R,5R)-5-hydroxy-2-phenyl-1,3-dioxan-4-yl]propyl]-14,15-dihydroxy-15-[(4R,5R)-5-hydroxy-2-phenyl-1,3-dioxan-4-yl]-3,6,9-trioxa -12-azapentadecan-1-yl]carbamate; formic acid, Intermediate 139 (93%, 1.25 g, 1.20 mmol) in THF (15 ml). The resulting solution was stirred at RT for 6 h then concentrated in vacuo. The residue thus obtained was suspended in Et$_2$O (10 ml) with sonication. The supernatant was decanted off then the process was repeated with more Et$_2$O (10 ml). The residue thus obtained was purified by flash column chromatography on C18 (120 g, Ultra). The column was eluted with MeCN:H$_2$O+0.1% formic acid using the following gradient (% MeCN, column volumes): 10%, 2 CV; 10-13%, 1.5 CV; 13%, 2.5 CV; 13-22%, 5.5 CV; 22-60%, 5.5 CV; 60-83%, 2 CV; 100% 2 CV. The desired fractions were combined and concentrated in vacuo to afford the product as a yellow solid (849 mg, 89%).

$^1$H NMR (500 MHz, CD$_3$OD) δ 8.40 (s, 2H), 7.54-7.43 (m, 4H), 7.41-7.28 (m, 6H), 5.53 (s, 2H), 4.26 (dd, J=10.7, 5.4 Hz, 2H), 4.20-4.12 (m, 2H), 3.97-3.87 (m, 4H), 3.74 (dd, J=9.4, 2.6 Hz, 2H), 3.70-3.54 (m, 14H), 3.29-3.19 (m, 3H), 3.16-3.08 (m, 2H), 3.07-2.99 (m, 1H), 2.98-2.86 (m, 2H).

LC/MS (System A): m/z (ESI$^+$)=697 [MH$^+$], R$_t$=0.74 min, UV purity=100%.

Intermediate 141-Synthesis of (14S,15R,16R,17R)-1-amino-12-[(2S,3R,4R,5R)-2,3,4,5,6-pentahydroxyhexyl]-3,6,9-trioxa-12-azaoctadecane-14,15,16,17,18-pentol dihydrochloride

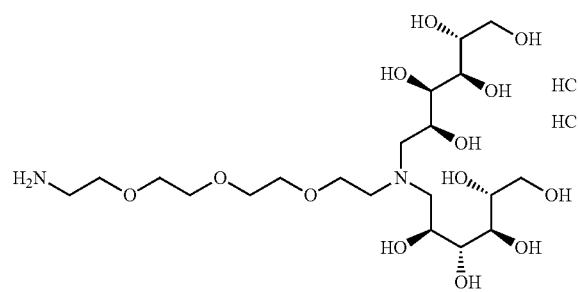

A solution of (14S,15R)-1-amino-12-[(2S,3R)-2,3-dihydroxy-3-[(4R,5R)-5-hydroxy-2-phenyl-1,3-d ioxan-4-yl]propyl]-15-[(4R,5R)-5-hydroxy-2-phenyl-1,3-dioxan-4-yl]-3,6,9-trioxa-12-azapentadecane-14,15-diol; bis(formic acid), Intermediate 140 (845 mg, 1.07 mmol) in aqueous HCl solution (2 M, 10 ml, 20 mmol) was stirred at RT for 5.5 h then concentrated in vacuo. The residue thus obtained was re-dissolved in water (15 ml) then lyophilised to afford a pale yellow gum (660 mg, quantitative based on 96% estimated purity).

$^1$H NMR (500 MHz, D$_2$O) δ 4.30-4.22 (m, 2H), 3.96-3.91 (m, 2H), 3.88-3.82 (m, 4H), 3.81-3.63 (m, 17H), 3.59-3.48 (m, 5H), 3.26-3.20 (m, 2H).

LC/MS (System C): m/z (ESI$^+$)=521 [MH$^+$], R$_t$=0.33 min, ELS purity=100%.

Intermediate 142-Synthesis of tert-butyl N-[2-(4-bromophenyl)ethyl]carbamate

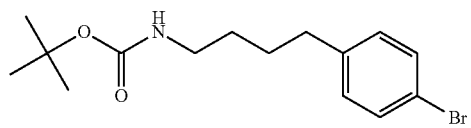 [SMILES: CC(C)(C)OC(=O)NCCCCc1ccc(Br)cc1]

Di-tert-butyl dicarbonate (3.93 g, 18.0 mmol) was added to a cooled (0° C.) stirred solution of 2-(4-bromophenyl)ethanamine (3.00 g, 15.0 mmol) in THF (20 ml). The resulting solution was allowed to warm to RT then stirred at RT for 18 h. The reaction mixture was partitioned between EtOAc (30 ml) and saturated aqueous NaHCO$_3$ solution (50 ml). The phases were separated then the aqueous phase was extracted with EtOAc (15 ml). The combined organic phases were washed with brine (50 ml), dried over MgSO$_4$, then concentrated in vacuo. The crude material was dissolved in the minimum volume of CH$_2$Cl$_2$, pre-adsorbed onto silica, then purified by flash column chromatography on a silica column (25 g). The column was eluted with EtOAc:heptane, using the following gradient (% EtOAc, column volumes): 0%, 1 CV; 0-8%, 2.5 CV; 8-12%, 1 CV; 12%, 3.5 CV; 12-27%, 5.5 CV; 27-30%, 0.5 CV; 30%, 2 CV; 30-90%, 4 CV; 100% 1 CV. The desired fractions were combined and concentrated in vacuo to afford the product as a white solid (3.99 g, 88%).

$^1$H NMR (500 MHz, DMSO-d$_6$) δ 7.50-7.42 (m, 2H), 7.19-7.11 (m, 2H), 6.86 (t, J=5.3 Hz, 1H), 3.12 (q, J=6.6 Hz, 2H), 2.70-2.63 (m, 2H), 1.41-1.26 (m, 9H).

LC/MS (System A): R$_t$=1.27 min, UV purity=99%.

Intermediate 143-Synthesis of tert-butyl N-{2-[4'-(cyanomethyl)-[1,1'-biphenyl]-4-yl]ethyl}carbamate

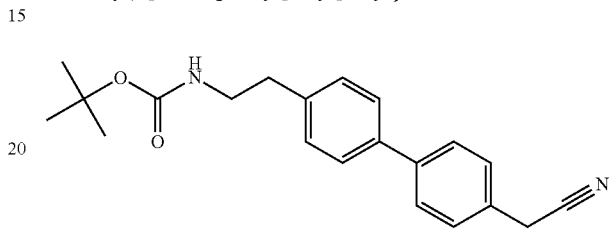

A mixture of tert-butyl N-[2-(4-bromophenyl)ethyl]carbamate, Intermediate 142 (4.09 g, 13.6 mmol), [4-cyanomethyl)phenyl]boronic acid (2.63 g, 16.4 mmol) and K$_2$CO$_3$ (5.65 g, 40.9 mmol) in 1,4-dioxane (105 ml) was degassed by bubbling a stream nitrogen through the mixture for 5 min. Pd(dppf)Cl$_2$.CH$_2$Cl$_2$ (445 mg, 0.545 mmol) was added and degassing was continued for a further 5 min. The reaction mixture was heated at 80° C. for 15 h then at 100° C. for 7 h. The reaction was allowed to cool to RT then retreated with K$_2$CO$_3$ (3.76 g, 27.2 mmol) and degassed for 5 min. Pd(dppf)Cl$_2$.CH$_2$Cl$_2$ (445 mg, 0.545 mmol) was added then the mixture was degassed for a further 5 min. The resultant mixture was heated at 100° C. for 24 h then allowed to cool to RT. The reaction was retreated with K$_2$CO$_3$ (1.88 g, 13.6 mmol) and [4-cyanomethyl)phenyl]boronic acid (0.88 g, 5.5 mmol) then degassed for 10 min. Pd(dppf)Cl$_2$.CH$_2$Cl$_2$ (445 mg, 0.545 mmol) was added then the mixture was degassed for a further 5 min. The reaction was heated at 100° C. for 18 h then allowed to cool to RT. The reaction mixture was filtered then the collected solids were washed with EtOAc (50 ml). The combined filtrate was concentrated in vacuo. The residue was re-dissolved in EtOAc:heptane (1:1) then filtered through a silica pad. The pad was rinsed with EtOAc:heptane (1:1, 200 ml). The filtrate was concentrated in vacuo to afford an off-white solid (3.94 g). The silica pad was rinsed through further with EtOAc (200 ml) to afford a brown solid (1.68 g). The brown solid from the EtOAc filtrate was pre-adsorbed onto silica, then purified by flash column chromatography on a silica column (50 g). The column was eluted with EtOAc:heptane, using the following gradient (% EtOAc, column volumes): 0%, 1 CV; 0-30%, 11 CV; 30%, 20 CV; 30-45%, 4.5 CV; 45%, 7.5 CV; 45-50%, 1 CV; 50%, 15 CV. The desired fractions were combined and concentrated in vacuo to afford an off-white solid (1.00 g, 21%).

$^1$H NMR (500 MHz, DMSO-d$_6$) δ 7.67 (d, J=8.2 Hz, 2H), 7.59 (d, J=8.2 Hz, 2H), 7.42 (d, J=8.2 Hz, 2H), 7.28 (d, J=8.1 Hz, 2H), 6.90 (t, J=5.5 Hz, 1H), 4.07 (s, 2H), 3.17 (q, J=6.5 Hz, 2H), 2.73 (t, J=7.4 Hz, 2H), 1.44-1.29 (m, 9H).

LC/MS (System A): R$_t$=1.27 min, UV purity=97%.

Intermediate 144-Synthesis of tert-butyl N-{2-[4'-(2-aminoethyl)-[1,1'-biphenyl]-4-yl]ethyl}carbamate

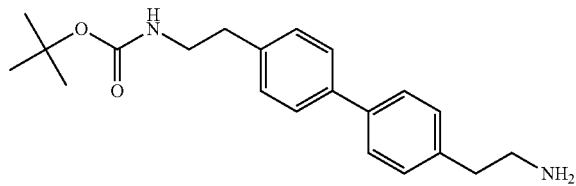 [SMILES: CC(C)(C)OC(=O)NCCc1ccc(-c2ccc(CCN)cc2)cc1]

A mixture of tert-butyl N-{2-[4'-(cyanomethyl)-[1,1'-biphenyl]-4-yl]ethyl}carbamate, Intermediate 143 (570 mg, 1.69 mmol), aqueous ammonia solution (35%, 0.5 ml) and aqueous Raney nickel slurry (50%, 2 ml) in EtOH (15 ml) and DMF (5 ml) was stirred under a hydrogen atmosphere for 18 h. The reaction mixture was filtered through a Celite pad. The pad was rinsed with EtOH (50 ml) and MeOH (100 ml) then the combined filtrate was concentrated in vacuo. The residue was azeotroped with heptane (3×100 ml) then dried in vacuo to afford the product as an off-white solid (515 mg, 84%).

$^1$H NMR (500 MHz, DMSO-$d_6$) δ 7.60-7.50 (m, 4H), 7.31-7.22 (m, 4H), 6.89 (t, J=5.3 Hz, 1H), 3.19-3.13 (m, 2H), 2.78 (t, J=7.2 Hz, 2H), 2.72 (t, J=7.4 Hz, 2H), 2.66 (t, J=7.2 Hz, 2H), 1.43-1.29 (m, 9H).

LC/MS (System A): m/z (ESI$^+$)=341 [MH$^+$], R$_t$=0.93 min, UV purity=94%.

Intermediate 145-Synthesis of tert-butyl N-{2-[4'-(2-{bis[(2S,3R)-2,3-dihydroxy-3-[(4R,5R)-5-hydroxy-2-phenyl-1,3-dioxan-4-yl]propyl]amino}ethyl)-[1,1'-biphenyl]-4-yl]ethyl}carbamate AcOH (0.33 ml, 5.8 mmol) was added to a solution of tert-butyl N-{2-[4'-(2-aminoethyl)-[1,1'-biphenyl]-4-yl]ethyl}carbamate, Intermediate 144 (94%, 515 mg, 1.42 mmol) and 4,6-O-benzylidene-D-glucopyranose (1.58 g, 5.89 mmol) in MeOH (50 ml). The reaction was left to stir at RT for 50 min then NaCNBH$_3$ (370 mg, 5.89 mmol) was added portionwise over 25 min. The resulting solution was stirred at RT for 24 h. Further 4,6-O-benzylidene-D-glucopyranose (790 mg, 2.94 mmol), AcOH (0.17 ml, 3.0 mmol) and MeOH (50 ml) were added then the reaction was left to stir at RT for 40 min. NaCNBH$_3$ (185 mg, 2.94 mmol) was added portionwise over 20 min then the reaction was left to stir at RT for 68 h. Further 4,6-O-benzylidene-D-glucopyranose (790 mg, 2.94 mmol), AcOH (0.17 ml, 3.0 mmol) and MeOH (50 ml) were added then the reaction was left to stir at RT for 30 min. NaCNBH$_3$ (185 mg, 2.94 mmol) was added portionwise over 20 min then the reaction was left to stir at RT for 18 h. Further 4,6-O-benzylidene-D-glucopyranose (790 mg, 2.94 mmol) and MeOH (25 ml) were added then the reaction heated at 40° C. for 18 h. The reaction mixture was allowed to cool to RT then saturated aqueous NaHCO$_3$ solution (40 ml) was added in portions over 15 min. The resultant mixture was stirred at RT for 30 min then the solid was collected by filtration, rinsed with water (10 ml), then dried in vacuo. The crude solid material thus obtained was purified by flash column chromatography on C18 (120 g). The column was eluted with MeCN:H$_2$O+ 0.1% NH$_4$OH using the following gradient (% MeCN, column volumes): 10%, 2 CV; 10-59%, 10 CV; 59%, 2 CV; 59-100%, 8 CV; 100%, 2 CV. The desired fractions were combined and concentrated in vacuo to afford the product as a white solid (932 mg, 78%).

$^1$H NMR (500 MHz, DMSO-$d_6$) δ 7.57-7.49 (m, 2H), 7.46-7.37 (m, 6H), 7.34-7.29 (m, 6H), 7.28-7.23 (m, 2H), 7.09-7.01 (m, 2H), 6.90 (t, J=5.6 Hz, 1H), 5.48 (s, 2H), 5.14 (d, J=5.8 Hz, 2H), 4.50-4.40 (m, 4H), 4.12 (dd, J=10.5, 5.3 Hz, 2H), 3.87-3.75 (m, 4H), 3.75-3.69 (m, 2H), 3.67-3.60 (m, 2H), 3.50 (t, J=10.4 Hz, 2H), 3.21-3.10 (m, 2H), 2.82-2.65 (m, 8H), 2.57 (dd, J=12.9, 8.9 Hz, 2H), 1.43-1.29 (m, 9H).

LC/MS (System B): m/z (ESI$^+$)=845 [MH$^+$], R$_t$=4.80 min, UV purity=100%.

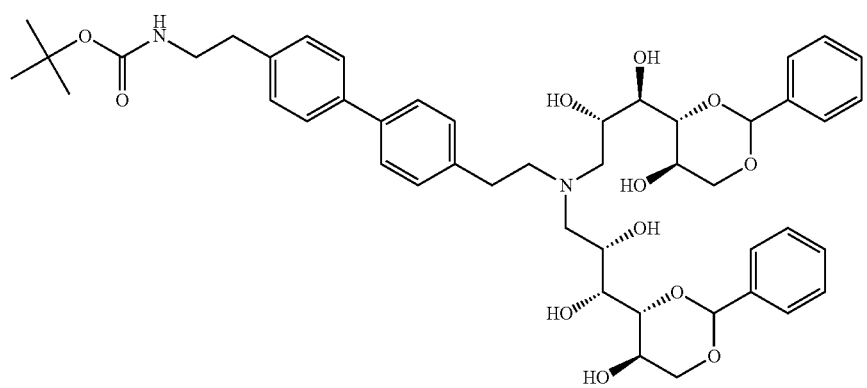

Intermediate 146-Synthesis of (2R,3R,4R,5S)-6-({2-[4'-(2-aminoethyl)-[1,1'-biphenyl]-4-yl]ethyl}[(2S,3R,4R,5R)-2,3,4,5,6-pentahydroxyhexyl]amino)hexane -1,2,3,4,5-pentol dihydrochloride

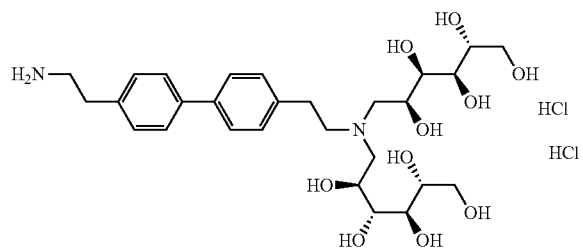 [SMILES: NCCc1ccc(-c2ccc(CCN(C[C@H](O)[C@@H](O)[C@H](O)[C@H](O)CO)C[C@H](O)[C@@H](O)[C@H](O)[C@H](O)CO)cc2)cc1 ; Cl ; Cl]

A suspension of tert-butyl N-{2-[4'-(2-{bis[(2S,3R)-2,3-dihydroxy-3-[(4R,5R)-5-hydroxy-2-phenyl-1,3-dioxan-4-yl]propyl]amino}ethyl)-[1,1'-biphenyl]-4-yl]ethyl}carbamate, Intermediate 145 (932 mg, 1.10 mmol) in aqueous HCl solution (2 M, 8.5 ml, 17 mmol) was stirred at RT for 24 h then further aqueous HCl solution (2 M, 8.5 ml, 17 mmol) was added. The reaction was left to stir at RT for a further 24 h. The reaction mixture was heated at 40° C. for 4 h thenthen concentrated in vacuo. The residue thus obtained was dissolved in water (15 ml) then lyophilised to afford the product as a white resin (753 mg, quantitative based on 94% estimated purity).

$^1$H NMR (500 MHz, D$_2$O) δ 7.77-7.70 (m, 4H), 7.53-7.48 (m, 2H), 7.48-7.43 (m, 2H), 4.30-4.19 (m, 2H), 3.87-3.61 (m, 12H), 3.61-3.45 (m, 4H), 3.33 (t, J=7.4 Hz, 2H), 3.29-3.16 (m, 2H), 3.07 (t, J=7.4 Hz, 2H).

LC/MS (System A): m/z (ESI$^+$)=569 [MH$^+$], R$_t$=0.15 min, ELS purity=100%.

Intermediate 147-Synthesis of (2S)-2-{[(benzyloxy)carbonyl]amino}-4-{[(tert -butoxy)carbonyl]amino}butanoic acid

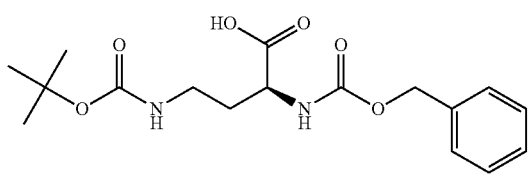 [SMILES: CC(C)(C)OC(=O)NCC[C@H](NC(=O)OCc1ccccc1)C(=O)O]

NaHCO$_3$ (3.13 g, 37.3 mmol) was added to a solution of (2S)-4-amino-2-{[(benzyloxy)carbonyl]amino}butanoic acid (4.70 g, 18.6 mmol) in THF (50 ml) and water (50 ml). The reaction was stirred at RT for 5 min then a solution of di-tert-butyl dicarbonate (4.88 g, 22.4 mmol) in THF (50 ml) was added dropwise over 10 min. The reaction was stirred at RT for 16 h then concentrated in vacuo to remove the majority of the THF. The residual aqueous solution was acidified to pH 2 by dropwise addition of 2 M aqueous HCl solution then extracted with EtOAc (100 ml then 50 ml). The combined organic phases were washed with water (50 ml) and brine (50 ml), then dried over Na$_2$SO$_4$, filtered and concentrated in vacuo to afford the product as a colourless oil (6.65 g, 98%).

$^1$H NMR (500 MHz, DMSO-d$_6$) δ 12.60 (s, 1H), 7.57 (d, J=8.0 Hz, 1H), 7.41-7.24 (m, 5H), 6.87-6.76 (m, 1H), 5.03 (s, 2H), 4.00-3.92 (m, 1H), 3.06-2.90 (m, 2H), 1.92 - 1.77 (m, 1H), 1.71-1.59 (m, 1H), 1.37 (s, 9H).

LC/MS (System A): m/z (ESI$^+$)=375 [M+Na$^+$], R$_t$=1.06 min, UV purity=97%.

Intermediate 148-Synthesis of tert-butyl N-[(3S)-3-{[(benzyloxy)carbonyl]amino}-3-carbamoylpropyl]carbamate

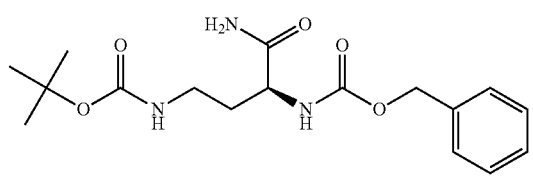 [SMILES: CC(C)(C)OC(=O)NCC[C@H](NC(=O)OCc1ccccc1)C(N)=O]

Isobutyl carbonochloridate (2.94 ml, 22.7 mmol) was added dropwise to a cooled (0°) solution of (2S)-2-{[(benzyloxy)carbonyl]amino}-4-{[(tert-butoxy)carbonyl]amino}butanoic acid, Intermediate 147 (6.15 g, 17.5 mmol) and N-methylmorpholine (2.88 ml, 26.2 mmol) in THF (100 ml). The reaction was allowed to warm to RT then stirred at RT for 17 h. The solution was cooled to 0° C. then ammonia solution in MeOH (7 M, 12 ml, 84 mmol) was added dropwise over 5 min. The reaction mixture was allowed to warm to RT then stirred at RT for 3 h. The resultant suspension was filtered then the filtrate was concentrated in vacuo. The residue was partitioned between EtOAc (200 ml) and saturated aqueous NaHCO$_3$ solution (100 ml). The phases were separated then the organic layer was washed with water (50 ml). The organic phase was concentrated in vacuo to afford an off white solid. The solid thus obtained was suspended in MeCN (50 ml) then filtered. The solid was dried in vacuo to afford the product as a white solid (2.56 g, 40%)

$^1$H NMR (500 MHz, DMSO-d$_6$) δ 7.42-7.24 (m, 7H), 7.08-6.97 (m, 1H), 6.80-6.68 (m, 1H), 5.09-4.92 (m, 2H), 3.98-3.86 (m, 1H), 3.03-2.88 (m, 2H), 1.82-1.68 (m, 1H), 1.67-1.54 (m, 1H), 1.44-1.30 (m, 9H).

LC/MS (System A): m/z (ESI$^+$)=374 [M+Na$^+$], R$_t$=1.52 min, UV purity=97%.

Intermediate 149-Synthesis of tert-butyl N-[(3S)-3-amino-3-carbamoylpropyl]carbamate

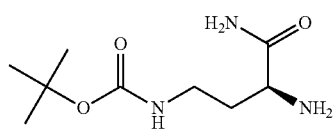

A mixture of tert-butyl N-[(3S)-3-{[(benzyloxy)carbonyl]amino}-3-carbamoylpropyl]carbamate, Intermediate 148 (2.06 g, 5.85 mmol) and 10% Pd/C (50% wet, 0.31 g) (50% wet) in THF (12 ml) and EtOH (12 ml) was stirred under an atmosphere of hydrogen for 18 h. The reaction was filtered through glass fibre filter paper, then concentrated in vacuo to afford the product as a white solid (1.27 g, quantitative). $^1$H NMR (500 MHz, DMSO-d$_6$) δ 7.26 (s, 1H), 6.91 (s, 1H), 6.83-6.69 (m, 1H), 3.11-2.92 (m, 3H), 1.80-1.59 (m, 3H), 1.46-1.32 (m, 10H).

LC/MS (System A): m/z (ESI$^+$)=218 [MH$^+$].

Intermediate 150-Synthesis of tert-butyl N-[(3S)-3-[(3-{[(benzyloxy)carbonyl]amino}propyl)amino]-3-carbamoyl-propyl]carbamate

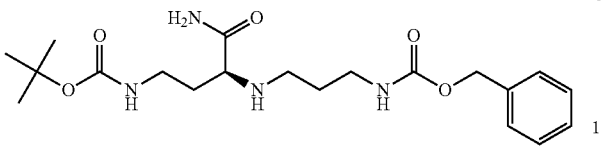

Sodium triacetoxyborohydride (2.37 g, 11.2 mmol) was added portionwise over 5 min to a solution of tert-butyl N-[(3S)-3-amino-3-carbamoylpropyl]carbamate, Intermediate 149 (1.62 g, 7.46 mmol) and benzyl N-(3-oxopropyl)carbamate (1.55 g, 7.46 mmol) in THF (40 ml). The reaction was stirred at RT for 16 h then water (50 ml) was added. The mixture was extracted with EtOAc (4×50 ml). The combined organic phases were washed with saturated aqueous $NaHCO_3$ solution (2×50 ml) and brine (10 ml), then dried over $Na_2SO_4$, filtered and concentrated in vacuo to afford the product as a colourless oil (2.89 g, 85%).

$^1$H NMR (500 MHz, $CD_3OD$) δ 7.39-7.22 (m, 5H), 5.06 (s, 2H), 3.25-3.06 (m, 5H), 2.69-2.45 (m, 2H), 1.85-1.61 (m, 4H), 1.42 (s, 9H).

LC/MS (System A): m/z (ESI$^+$)=409 [MH$^+$], $R_t$=0.87 min, UV purity=90%.

Intermediate 151-Synthesis of tert-butyl N-(3-{[(benzyloxy)carbonyl]amino}propyl)-N-[(1S)-3-{[tert-butoxy)carbonyl]amino}-1-carbamoylpropyl]carbamate

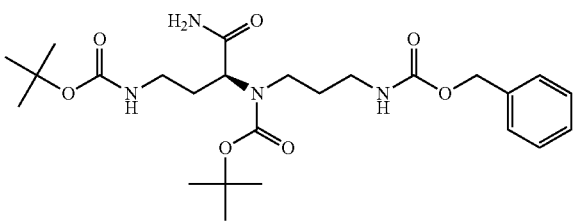 [SMILES: CC(C)(C)OC(=O)NCC[C@@H](C(N)=O)N(CCCNC(=O)OCc1ccccc1)C(=O)OC(C)(C)C]

A solution of di-tert-butyl dicarbonate (1.85 g, 8.49 mmol) in THF (10 ml) was dropwise over 5 min to a solution of tert-butyl N-[(3S)-3-[(3-{[(benzyloxy)carbonyl]amino}propyl)amino]-3-carbamoylpropyl]carbamate, Intermediate 150 (2.89 g, 7.07 mmol)) and triethylamine (1.47 ml, 10.6 mmol) in THF (30 ml). The reaction mixture was left to stir at RT for 16 h then concentrated in vacuo. The resultant oil was partitioned between EtOAc (50 ml) and water (50 ml). The phases were separated then the organic phase was washed with saturated aqueous $NaHCO_3$ solution (50 ml) and brine (20 ml), then dried over $Na_2SO_4$, filtered and concentrated in vacuo. The crude material thus obtained was purified by flash column chromatography on a silica column (50 g). The column was eluted with $CH_2Cl_2$:MeOH, increasing the gradient linearly from 100:0 to 92:8 over 15 CV. The desired fractions were combined and concentrated in vacuo. The material thus obtained was further purified by flash column chromatography on C18 (120 g). The column was eluted with MeCN:$H_2O$+0.1% formic acid using the following gradient (% MeCN, column volumes): 5%, 2 CV; 5-100%, 20 CV; 100%, 2 CV. The desired fractions were combined and concentrated in vacuo to afford the product as an orange oil (0.42 g, 12%).

$^1$H NMR (500 MHz, DMSO-$d_6$) δ 7.42-7.28 (m, 5H), 7.27-6.96 (m, 3H), 6.92-6.61 (m, 1H), 5.08-4.93 (m, 2H), 4.43-3.93 (m, 1H), 3.21-2.78 (m, 6H), 2.03-1.52 (m, 4H), 1.46-1.30 (m, 18H).

LC/MS (System A): m/z (ESI$^+$)=509 [MH$^+$], $R_t$=1.16 min, UV purity=95%.

Intermediate 152-Synthesis of tert-butyl N-(3-aminopropyl)-N-[(1S)-3-{[(tert-butoxy)carbonyl]amino}-1-carbamoylpropyl]carbamate

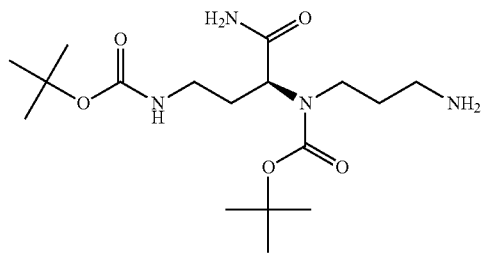 [SMILES: CC(C)(C)OC(=O)NCC[C@@H](C(N)=O)N(CCCN)C(=O)OC(C)(C)C]

A mixture of tert-butyl N-(3-{[(benzyloxy)carbonyl]amino}propyl)-N-[(1S)-3-{[(tert-butoxy)carbonyl]amino}-1-carbamoylpropyl]carbamate, Intermediate 151 (780 mg, 1.47 mmol) and 10% Pd/C (50% wet, 80 mg) in EtOH (20 ml) was stirred under an atmosphere of hydrogen for 40 h at RT. The reaction mixture was filtered through glass fibre filter paper then concentrated in vacuo to afford the product as a white foam (580 mg, quantitative based on 95% estimated purity).

$^1$H NMR (500 MHz, DMSO-$d_6$) δ 7.19 (s, 1H), 7.01 (s, 1H), 6.89-6.66 (m, 1H), 4.40-3.85 (m, 1H), 3.18-2.83 (m, 5H), 2.49-2.37 (m, 2H+solvent), 2.05-1.82 (m, 1H), 1.74-1.30 (m, 22H).

LC/MS (System A): m/z (ESI$^+$)=375 [MH$^+$], $R_t$=0.80 min, UV purity=100%.

Intermediate 153-Synthesis of formic acid; tert-butyl N-(3-{bis[(2S,3R)-2,3-dihydroxy-3-[(4R,5R)-5-hydroxy-2-phenyl-1,3-dioxan-4-yl]propyl]amino}propyl)-N-[(1S)-3-{[(tert-butoxy)carbonyl]amino}-1-carbamoylpropyl]carbamate

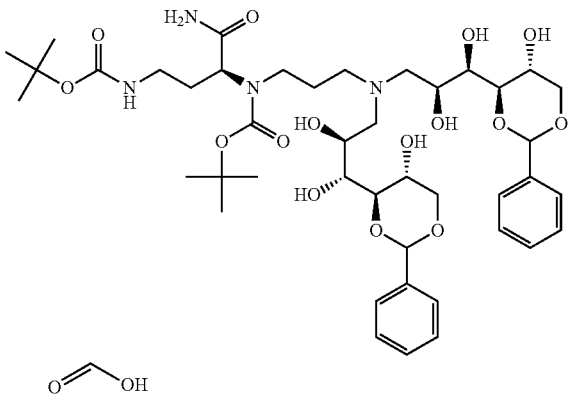

4,6-O-Benzylidene-D-glucopyranose (1.60 g, 5.96 mmol) was added to a solution of tert-butyl N-(3-aminopropyl)-N-[(1S)-3-{[(tert-butoxy)carbonyl]amino}-1-carbamoylpropyl]carbamate, Intermediate 152 (0.558 g, 1.49 mmol) in MeOH (25 ml). The reaction mixture was stirred at RT for 15 min then AcOH (0.341 ml, 5.96 mmol) was added. The reaction mixture was stirred at RT for a further 15 min then NaCNBH$_3$ (0.375 g, 5.96 mmol) was added portion-wise over 5 min. The reaction mixture was stirred at RT for 64 h. The reaction was re-treated with 4,6-O-benzylidene-D-glucopyranose (1.6 g, 5.96 mmol) and stirred for a further 24 h at RT. Saturated aqueous sodium bicarbonate solution (25 ml) was added dropwise over 5 min. EtOAc (20 ml) was added then the resultant mixture was left to stir at RT for 15 min. The phases were separated then the organic phase was washed with saturated aqueous sodium bicarbonate solution (4×50 ml) and brine (25 ml). The organic phase was dried over Na$_2$SO$_4$, filtered and concentrated in vacuo. The crude material was purified by flash column chromatography on C18 (120 g). The column was eluted with MeCN:H$_2$O+0.1% formic acid using the following gradient (% MeCN, column volumes): 10%, 2 CV; 10-46%, 8 CV; 46-52%, 1 CV; 52%, 2 CV; 52-97, 2 CV. The desired fractions were combined and concentrated in vacuo to afford the product as a white solid (690 mg, 50%).

$^1$H NMR (500 MHz, CD$_3$OD) δ 8.39 (s, 1H), 7.54-7.42 (m, 4H), 7.41-7.26 (m, 6H), 5.59-5.47 (m, 2H), 4.33-4.13 (m, 4H), 4.02-3.87 (m, 5H), 3.81-3.70 (m, 2H), 3.67-3.55 (m, 2H), 3.42-3.34 (m, 6H +solvent), 3.20-2.99 (m, 4H), 1.98-1.78 (m, 4H), 1.52-1.33 (m, 18H).

LC/MS (System A): m/z (ESI$^+$)=879 [MH$^+$], R$_t$=0.95 min, UV purity=100%.

Intermediate 154-Synthesis of (2S)-4-amino-2-[(3-{bis[(2S,3R,4R,5R)-2,3,4,5,6-pentahydroxyhexyl]amino}propyl)amino]butanamide trihydrochloride

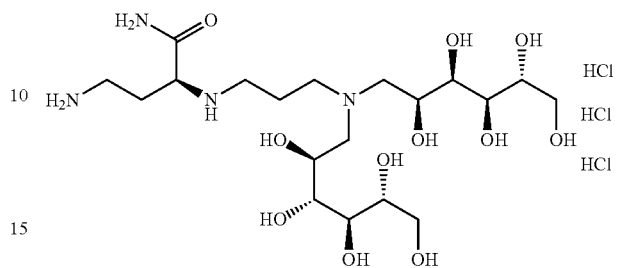

A suspension of formic acid; tert-butyl N-(3-{bis[(2S,3R)-2,3-dihydroxy-3-[(4R,5R)-5-hydroxy-2-phenyl-1,3-dioxan-4-yl]propyl]amino}propyl)-N-[(1S)-3-{[(tert-butoxy)carbonyl]amino}-1-carbamoylpropyl]carbamate, Intermediate 153 (690 mg, 0.746 mmol) in aqueous HCl solution (2.0 M, 7.5 ml, 15 mmol) was stirred at RT for 16 h. The reaction mixture was concentrated in vacuo. The residue was dissolved in MeCN/water then lyophilised to afford the product as a white solid (500 mg, quantitative based on 91% estimated purity).

$^1$H NMR (500 MHz, D$_2$O) δ 4.31-4.21 (m, 2H), 4.15-4.08 (m, 1H), 3.91-3.74 (m, 6H), 3.73-3.61 (m, 4H), 3.58-3.42 (m, 6H), 3.29-3.10 (m, 4H), 2.43-2.20 (m, 4H).

LC/MS (System A): m/z (ESI$^+$)=503 [MH$^+$], R$_t$=0.13 min, ELS purity=100%.

Intermediate 155-Synthesis of 4-[4-(4-aminobutyl)phenyl]-2-[(3-{bis[(2S,3R)-2,3-dihydroxy-3-[(4R,5R)-5-hydroxy-2-phenyl-1,3-dioxan-4-yl]propyl]amino}propyl)amino]butanamide; tetrakis(acetic acid)

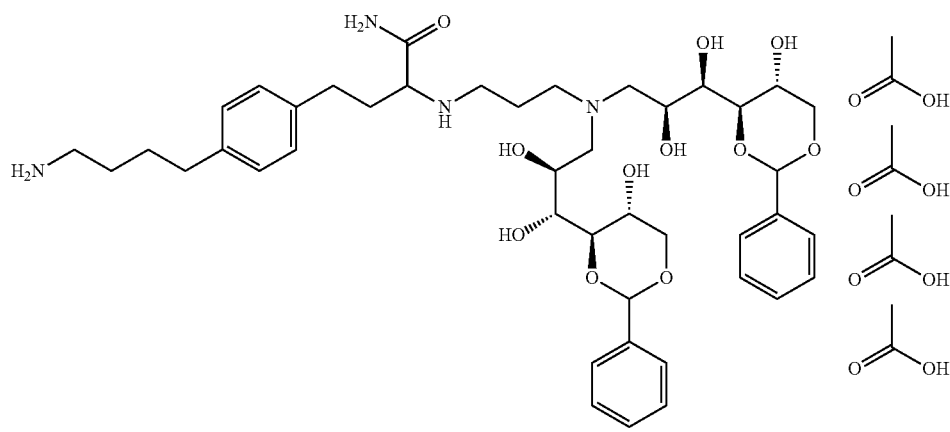

Intermediate 155 was synthesised according to literature procedures (WO2014/099673 A1).

Intermediate 156-Synthesis of 4-[4-(4-aminobutyl)phenyl]-2-[(3-{bis[(2S,3R,4R,5R) 2,3,4,5,6-pentahydroxyhexyl]amino}propyl)amino]butanamide trihydrochloride

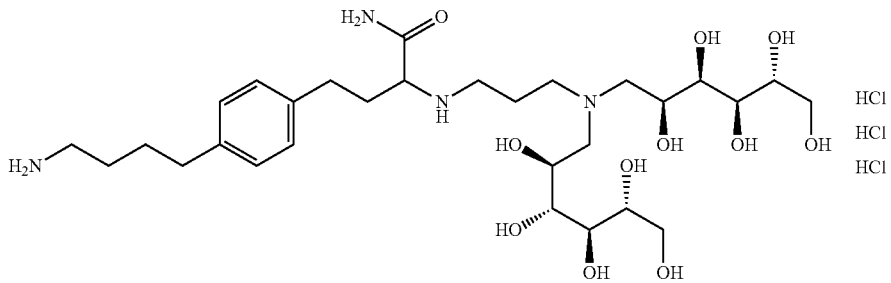 [SMILES: NCCCCc1ccc(CCC(NCCCN(C[C@H](O)[C@@H](O)[C@H](O)[C@H](O)CO)C[C@H](O)[C@@H](O)[C@H](O)[C@H](O)CO)C(N)=O)cc1 ; Cl ; Cl ; Cl]

A solution of 4-[4-(4-aminobutyl)phenyl]-2-[(3-{bis[(2S, 3R)-2,3-dihydroxy-3-[(4R,5R)-5-hydroxy-2-phenyl-1,3-dioxan-4-yl]propyl]amino}propyl)amino]butanamide; tetrakis(acetic acid), Intermediate 155 (96%, 140 mg, 0.13 mmol) in aqueous HCl solution (2 M, 5 ml, 10 mmol) was stirred at RT for 2 h. The reaction mixture was concentrated in vacuo then lyophilised to afford the product as a beige solid (107 mg, quantitative based on 88% estimated purity).

$^1$H NMR (500 MHz, CD$_3$OD) δ 7.22-7.14 (m, 4H), 4.27-4.18 (m, 2H), 4.06-3.99 (m, 1H), 3.91-3.85 (m, 2H), 3.83-3.75 (m, 2H), 3.75-3.63 (m, 6H), 3.63-3.39 (m, 6H), 3.23-3.08 (m, 2H), 2.96-2.88 (m, 2H), 2.76-2.60 (m, 4H), 2.39-2.13 (m, 4H), 1.75-1.62 (m, 4H).

LC/MS (System A): m/z (ESI$^+$)=635 [MH$^+$], R$_t$=0.16min, ELS purity=100%.

Intermediate 157-Synthesis of tert-butyl 2-({[(tert-butoxy)carbonyl]amino}methyl)-1-ethyl-1H-1,3-benzodiazole-6-carboxylate

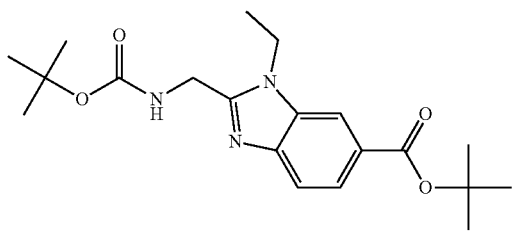 [SMILES: CCn1c(CNC(=O)OC(C)(C)C)nc2ccc(C(=O)OC(C)(C)C)cc21]

N,N-Dimethylformamide di-tert-butyl acetal (3.00 ml, 12.5 mmol) was added to a suspension of 2-({[(tert-butoxy)carbonyl]amino}methyl)-1-ethyl-1H-1,3-benzodiazole-6-carboxylic acid, Intermediate 78 (1.00 g, 3.13 mmol) in toluene (10 ml). The reaction was left to heat at 80° C. for 2 h then allowed to cool to RT. N,N-Dimethylformamide di-tert-butyl acetal (3.00 ml, 12.5 mmol) was added then the reaction was left to heat at 80° C. for 16 h. N,N-Dimethylformamide di-tert-butyl acetal (3.00 ml, 12.5 mmol) was added then the reaction was left to heat at 100° C. for 6 h then allowed to cool to RT. The reaction mixture was diluted with EtOAc (50 ml) then washed with water (2×20 ml), saturated aqueous NaHCO$_3$ solution (2×20 ml) and brine (10 ml) then dried over Na$_2$SO$_4$ and concentrated in vacuo to afford an orange solid (1.6 g). The crude material was purified by flash column chromatography on a silica column (25 g). The column was eluted with EtOAc:heptane, using the following gradient (% EtOAc, column volumes): 0%, 3 CV; 0-53%, 10.5 CV; 53%, 4.5 CV; 53-100%, 9.5 CV. The desired fractions were combined and evaporated to afford the product as an off-white solid (460 mg, 37%).

$^1$H NMR (500 MHz, DMSO-d$_6$) δ 8.08-8.05 (m, 1H), 7.76 (dd, J=8.4, 1.5 Hz, 1H), 7.62 (d, J=8.4 Hz, 1H), 7.51 (t, J=5.4 Hz, 1H), 4.46 (d, J=5.8 Hz, 2H), 4.33 (q, J=7.2 Hz, 2H), 1.57 (s, 9H), 1.45-1.23 (m, 12H).

LC/MS (System A): m/z (ESI$^+$)=376 [MH$^+$], R$_t$=1.14 min, UV purity=94%.

Intermediate 158-Synthesis of 6-[(tert-butoxy)carbonyl]-2-({[(tert-butoxy)carbonyl]amino}methyl)-1,3-diethyl-1H-1,3-benzodiazol-3-ium iodide

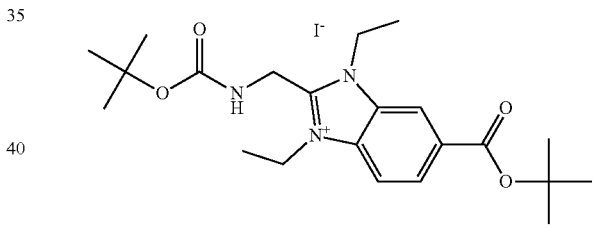

Iodoethane (219 μl, 2.67 mmol) was added to a suspension of tert-butyl 2-({[(tert-butoxy)carbonyl]amino}methyl)-1-ethyl-1H-1,3-benzodiazole-6-carboxylate, Intermediate 157 (250 mg, 0.670 mmol) in MeCN (2.5 ml). The reaction was heated under microwave irradiation for 2 h at 120° C. In a separate vial, iodoethane (175 μl, 2.14 mmol) was added to a suspension of tert-butyl 2-({[(tert-butoxy)carbonyl]amino}methyl)-1-ethyl-1H-1,3-benzodiazole-6-carboxylate, Intermediate 157 (200 mg, 0.532 mmol) in MeCN (2 ml). The resultant mixture was heated under microwave irradiation for 2 h at 120° C. The two reactions were combined then concentrated in vacuo. The crude material was purified by flash column chromatography on a silica column (25 g). The column was eluted with MeOH:CH$_2$Cl$_2$, increasing the gradient linearly from 0:100 to 8:92 over 12 CV. The desired fractions were combined and evaporated to afford a pink foam (550 mg). The material thus obtained was further purified by flash column chromatography on a silica column (25 g). The column was eluted with MeOH:CH$_2$Cl$_2$, increasing the gradient linearly from 0:100 to 5:95 over 14 CV. The desired fractions were combined and evaporated to afford the product as a pink foam (240 mg, 38%).

¹H NMR (500 MHz, DMSO-d₆) δ 8.54 (s, 1H), 8.18 (s, 2H), 8.01 (t, J=5.2 Hz, 1H), 4.81 (d, J=5.3 Hz, 2H), 4.71 (q, J=7.2 Hz, 2H), 4.64 (q, J=7.2 Hz, 2H), 1.61 (s, 9H), 1.51-1.18 (m, 15H).

LC/MS (System C): m/z (ESI⁺)=404 [M⁺], R$_t$=2.56 min, UV purity=100%.

Intermediate 159-Synthesis of 2-(aminomethyl)-6-carboxy-1,3-diethyl-1H-1,3-benzodiazol-3-ium hydrochloride chloride

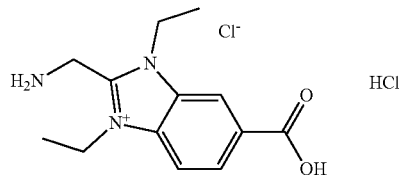 [SMILES: CCn1c(CN)[n+](CC)c2ccc(C(=O)O)cc21 ; [Cl-] ; Cl]

HCl solution in dioxane (4.0 M, 1.1 ml, 4.4 mmol) was added to a solution of 6-[(tert-butoxy)carbonyl]-2-({[(tert-butoxy)carbonyl]amino}methyl)-1,3-diethyl-1H-1,3-benzodiazol-3-ium iodide, Intermediate 158 (465 mg, 0.870 mmol) in MeCN (5 ml). The reaction was left to stir at RT for 16 h. HCl solution in dioxane (4.0 M, 0.20 ml, 0.80 mmol) was added then the reaction was left to stir at RT for 24 h. The reaction mixture was concentrated in vacuo then azeotroped with MeCN (2×10 ml). The residue was suspended in MeCN (5 ml) then filtered and dried in vacuo to afford the product as a dark brown solid (335 mg, quantitative based on 84% estimated purity).

¹H NMR (500 MHz, DMSO-d₆) δ 10.24-8.50 (m, 4H), 8.32-8.21 (m, 2H), 4.88-4.66 (m, 6H), 1.56-1.41 (m, 6H).

LC/MS (System A): m/z (ESI⁺)=248 [M⁺], R$_t$=0.14 min, ELS purity=100%.

Intermediate 160-Synthesis of methyl 3-amino-5-{[2-(trimethylsilyl)ethoxy]methyl}-5H-pyrrolo[2,3-b]pyrazine-2-carboxylate

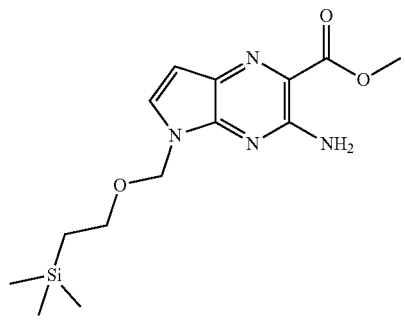

NaH dispersion in mineral oil (60%, 458 mg, 11.5 mmol) was added portionwise over a period of 10 min to a cooled (0° C.) mixture of methyl 3-amino-5H-pyrrolo[2,3-b]pyrazine-2-carboxylate, Intermediate 2 (2.00 g, 10.4 mmol) in DMF (30 ml). The resulting mixture was stirred at 0° C. for 20 min then a solution of 2-(chloromethoxy)ethyl-trimethyl-silane (2.21 ml, 12.5 mmol) in DMF (5 ml) was added dropwise over 3 min. The resulting mixture was stirred at 0° C. for 15 min then water (100 ml) was added. The mixture was extracted with EtOAc (100 ml) then the organic phase was washed with water (2×100 ml) and brine (100 ml) then dried over Na₂SO₄ and concentrated in vacuo. The crude material was purified by flash column chromatography on a silica column (100 g). The column was eluted with EtOAc:heptane, using the following gradient (% EtOAc, column volumes): 0%, 1 CV; 0-60%, 10 CV; 60-100%, 1.5 CV; 100%, 1 CV. The desired fractions were combined and evaporated to afford the product as a yellow solid (1.87 g, 56%).

¹H NMR (500 MHz, DMSO-d₆) δ 7.67 (d, J=3.9 Hz, 1H), 7.24 (s, 2H), 6.53 (d, J=3.9 Hz, 1H), 5.42 (s, 2H), 3.85 (s, 3H), 3.52-3.47 (m, 2H), 0.85-0.79 (m, 2H), -0.07--0.11 (m, 9H).

LC/MS (System A): m/z (ESI⁺)=323 [MH⁺], R$_t$=1.21 min, UV purity=100%.

Intermediate 161-Synthesis of methyl 3-amino-7-bromo-5-{[2-(trimethylsilyl)ethoxy]methyl}-5H-pyrrolo[2,3-b]pyrazine-2-carboxylate

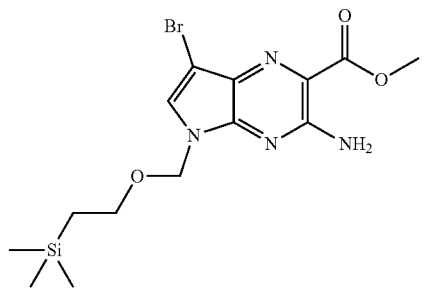

NBS (0.773 g, 4.34 mmol) was added portionwise over 5 min to a cooled (0° C.) solution of methyl 3-amino-5-{[2-(trimethylsilyhethoxy]methyl}-5H-pyrrolo[2,3-b]pyrazine-2-carboxylate, Intermediate 160 (1.56 g, 4.82 mmol) in MeCN (30 ml). The resultant mixture was stirred at 0° C. for 50 min. Additional NBS (0.100 g, 0.562 mmol) was added then the reaction was left to stir at 0° C. for a further 90 min. The reaction mixture was partitioned between EtOAc (100 ml) and water (100 ml). The phases were separated then the organic phases were washed with water (100 ml) and brine (100 ml), then dried over Na₂SO₄ and concentrated in vacuo. The crude material was purified by flash column chromatography on a silica column (100 g). The column was eluted with EtOAc:heptane, using the following gradient (% EtOAc, column volumes): 0%, 1 CV; 0-44%, 7 CV. The desired fractions were combined and evaporated. The material thus obtained was further purified by flash column chromatography on C18 (120 g). The column was eluted with MeCN:H₂O+0.1% formic acid using the following gradient (% MeCN, column volumes): 10%, 2 CV; 10-76%, 18 CV; 76-96%, 2 CV. The desired fractions were combined and concentrated in vacuo to afford the product as a yellow solid (584 mg, 30%).

¹H NMR (500 MHz, DMSO-d₆) δ 7.91 (5, 1H), 7.42 (5, 2H), 5.40 (5, 2H), 3.88 (5, 3H), 3.54-3.48 (m, 2H), 0.86-0.80 (m, 2H), -0.08 (5, 9H).

LC/MS (System A): m/z (ESI⁺)=401 [M(⁷⁹Br)H⁺], 403 [M(⁸¹Br)H⁺], R$_t$=1.33 min, UV purity=100%.

Intermediate 162-Synthesis of methyl 3-amino-7-bromo-5H-pyrrolo[2,3-b]pyrazine -2-carboxylate

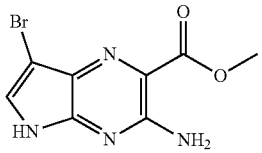

TFA (2.97 ml, 38.9 mmol) was added to a solution of methyl 3-amino-7-bromo-5-{[2-(trimethylsilyhethoxy]methyl}-5H-pyrrolo[2,3-b]pyrazine-2-carboxylate, Intermediate 161 (520 mg, 1.30 mmol) in CH$_2$Cl$_2$ (5 ml). The resulting mixture was stirred at RT for 2.5 h then concentrated in vacuo. The resultant residue was dissolved in CH$_2$Cl$_2$:MeOH:NH$_4$OH (2:1:0.5, 5 ml) then left to stir at RT for 2 h. The reaction mixture was concentrated in vacuo.

The crude material was purified by flash column chromatography on a silica column (100 g). The column was eluted with CH$_2$Cl$_2$:MeOH, using the following gradient (% MeOH, column volumes): 0%, 1 CV; 0-7.5%, 9 CV; 7.5-100% 0.5 CV. The desired fractions were combined and evaporated to afford the product as a yellow/orange solid (309 mg, 83%).

$^1$H NMR (500 MHz, DMSO-d$_6$) δ 11.87 (s, 1H), 7.72 (s, 1H), 7.24 (s, 2H), 3.87 (s, 3H).

LC/MS (System A): m/z (ESI$^+$)=271 [M($^{79}$Br)H$^+$], 273 [M($^{81}$Br)H$^+$], R$_t$=0.89 min, UV purity=94%.

Intermediate 163-Synthesis of lithium(1+) ion 3-amino-7-bromo-5H-pyrrolo[2,3-b]pyrazine-2-carboxylate

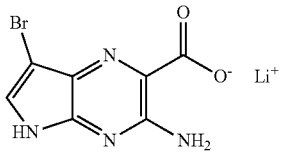 [SMILES: Nc1nc2[nH]cc(Br)c2nc1C(=O)[O-] ; [Li+]]

Aqueous LiOH solution (1.0 M, 2.7 ml, 2.7 mmol) was added to a suspension of methyl 3-amino-7-bromo-5H-pyrrolo[2,3-b]pyrazine-2-carboxylate, Intermediate 162 (361 mg, 1.33 mmol) in MeOH (5 ml). The reaction mixture was stirred at 50° C. for 2.5 h then allowed to cool to RT. The resultant suspension was filtered. The solid collected was rinsed with water then dried under suction to afford a yellow solid (195 mg). The filtrate was concentrated in vacuo then the residue was suspended in water (3 ml). The solid was collected by filtration, combined with the first batch of solid, then dried in vacuo to afford the product as a yellow solid (243 mg, 67%).

$^1$H NMR (500 MHz, DMSO-d$_6$) δ 11.45 (s, 1H), 8.35-6.86 (m, 3H).

LC/MS (System A): m/z (ESI$^+$)=257 [M($^{79}$Br)H$^+$], 259 [M($^{81}$Br)H$^+$], R$_t$=0.82 min, UV purity=96%.

Intermediate 164-Synthesis of 7-bromo-2-(1H-imidazole-1-carbonyl)-5H -pyrrolo[2,3-b]pyrazin-3-amine

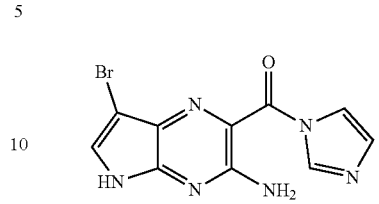

A mixture of lithium(1+) ion 3-amino-7-bromo-5H-pyrrolo[2,3-b]pyrazine-2-carboxylate, Intermediate 163 (243 mg, 0.924 mmol), CDI (300 mg, 1.85 mmol) and imidazole hydrochloride (116 mg, 1.11 mmol) in DMF (3 ml) was stirred at RT for 1 h 15 min. Additional CDI (100 mg, 0.617 mmol) was added then the reaction was left to stir at RT for a further 1 h. The reaction mixture was diluted with water (5 ml) then stirred at RT for 10 min. The resultant suspension was filtered then the collected solid was washed with water (2×5 ml), then dried in vacuo to afford the product as a yellow solid (218 mg, 77%).

$^1$H NMR (500 MHz, DMSO-d$_6$) δ 12.05 (s, 1H), 8.89-8.82 (m, 1H), 8.03-7.99 (m, 1H), 7.86 (s, 1H), 7.58 (s, 2H), 7.13-7.09 (m, 1H).

LC/MS (System A) : m/z (ESI$^+$)=307 [M($^{79}$Br)H$^+$], 309 [M($^{81}$Br)H$^+$], R$_t$=0.81 min, ELS purity=100%.

Intermediate 165-Synthesis of methyl 3-amino-7-iodo-5-{[2-(trimethylsilyl)ethoxy]methyl}-5H-pyrrolo[2,3-b]pyrazine-2-carboxylate

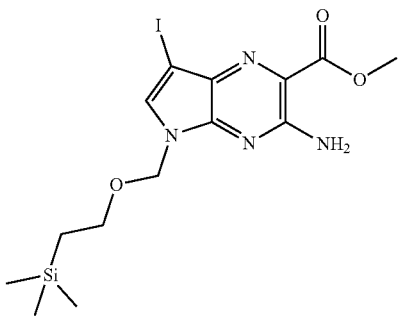

NaH dispersion in mineral oil (60%, 240 mg, 6.00 mmol) was added portionwise over 5 min to a cooled (0° C.) solution of methyl 3-amino-7-iodo-5H-pyrrolo[2,3-b]pyrazine-2-carboxylate, Intermediate 10, (95%, 1.82 g, 5.44 mmol) in DMF (25 ml). The resultant mixture was stirred at 0° C. for 20 min then a solution of 2-(chloromethoxy)ethyltrimethyl -silane (1.01 ml, 5.72 mmol) in DMF (8 ml) was added dropwise over 5 min. The reaction mixture was stirred at 0° C. for 5 min then water (1 ml) was added. The reaction mixture was concentrated in vacuo. The crude material was purified by flash column chromatography on a silica column (340 g). The column was eluted with EtOAc:heptane, using the following gradient (% EtOAc, column volumes): 0%, 1 CV; 0-40%, 6.5 CV. The desired fractions were combined and evaporated to afford the product as a yellow solid (1.85 g, 75%).

¹H NMR (500 MHz, DMSO-d₆) δ 7.98 (s, 1H), 7.47 (s, 2H), 5.48 (s, 2H), 3.97 (s, 3H), 3.62-3.56 (m, 2H), 0.94-0.88 (m, 2H), 0.00 (s, 9H).

LC/MS (System A): m/z (ESI⁺)=449 [MH⁺], $R_t$=1.37 min, UV purity=99%.

Intermediate 166-Synthesis of methyl 3-amino-7-cyano-5-{[2-(trimethylsilyl)ethoxy]methyl}-5H-pyrrolo[2,3-b]pyrazine-2-carboxylate

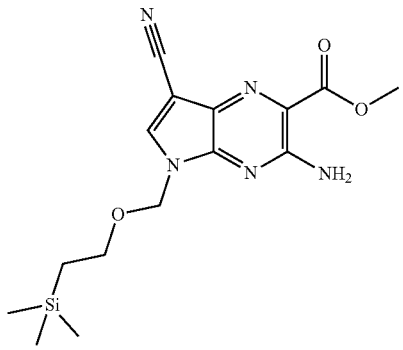

Degassed dioxane (3 ml) and water (3 ml) were added to a flask containing methyl 3-amino-7-iodo-5-{[2-(trimethyl-silyhethoxy]methyl}-5H-pyrrolo[2,3-b]pyrazine-2-carboxylate, Intermediate 165 (316 mg, 0.705 mmol), potassium ferrocyanide (149 mg, 0.353 mmol), Xphos (17 mg, 0.035 mmol), XPhos Pd G3 (30 mg, 0.035 mmol) and KOAc (14 mg, 0.14 mmol). The resulting mixture was heated at 100° C. for 2 h 20 min then allowed to cool to RT. The reaction mixture was partitioned between water (20 ml) and EtOAc (20 ml) then the phases were separated. The organic phase was washed with water (2×20 ml) and brine (20 ml) then dried over Na₂SO₄ and concentrated in vacuo. The crude material was purified by flash column chromatography on a silica column (25 g). The column was eluted with EtOAc:heptane, using the following gradient (% EtOAc, column volumes): 0%, 1 CV; 0-60%, 10 CV; 60-100%, 1.5 CV. The desired fractions were combined and evaporated to afford the product as a yellow solid (183 mg, 72%).

¹H NMR (500 MHz, DMSO-d₆) δ 8.62 (s, 1H), 7.56 (s, 2H), 5.47 (s, 2H), 3.90 (s, 3H), 3.57-3.52 (m, 2H), 0.88-0.79 (m, 2H), -0.08 (s, 9H).

LC/MS (System A): m/z (ESI⁺)=348 [MH⁺], $R_t$=1.25 min, UV purity=97%.

Intermediate 167-Synthesis of tert-butyl 4-[bis[(2S,3R)-2,3-dihydroxy-3-[(4R,5R)-5-hydroxy-2-phenyl-1,3-dioxan-4-yl]propyl]amino]piperidine-1-carboxylate; formic acid;

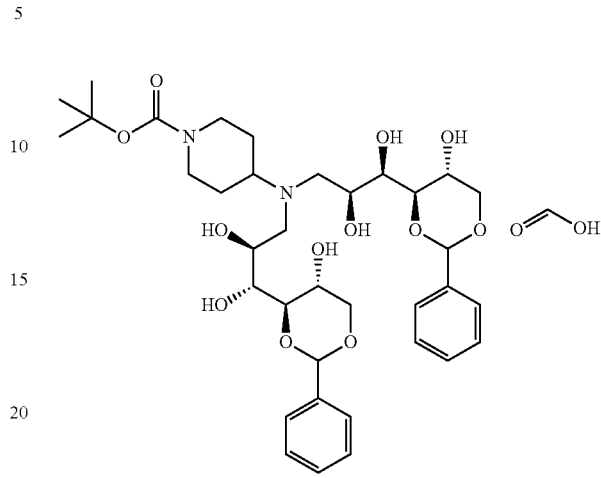

α-Picoline borane complex (0.801 g, 7.49 mmol) was added to a suspension of tert-butyl 4-aminopiperidine-1-carboxylate (0.500 g, 2.50 mmol) and 4,6-O-benzylidene-D-glucopyranose (2.68 g, 9.99 mmol) in MeOH (5 mL). The mixture was heated at 60° C. for 18 h then allowed to cool to RT. The reaction mixture was concentrated in vacuo then the residue was partitioned between EtOAc (15 ml) and water (15 ml). The phases were separated then the organic phase was washed with water (10 ml) and brine (10 ml) then dried over Na2SO4 and concentrated in vacuo.

The crude material was purified by flash column chromatography on C18 (30 g). The column was eluted with MeCN:H2O+0.1% formic acid using the following gradient (% MeCN, column volumes): 10%, 2 CVs; 10-40%, 10 CVs; 40-100%, 2 CVs; 100%, 2 CVs. The desired fractions were combined and concentrated in vacuo then the residual aqueous solution was lyophilised to afford the product as a white solid (1.07 g, 57%).

LC/MS (System B): m/z (ESI⁺)=705 [MH⁺], $R_t$=2.28 min, ELS purity=100%

1H NMR (500 MHz, Methanol-d4) δ 8.42 (s, 1H), 7.54-7.43 (m, 4H), 7.40-7.29 (m, 6H), 5.53 (m, 2H), 4.25 (m, 2H), 4.14-3.89 (m, 8H), 3.76 (m, 2H), 3.61 (m, 2H), 3.27-2.96 (m, 5H), 2.74-2.34 (m, 2H), 1.86-1.74 (m, 2H), 1.60-1.40 (m, 10H), 1.37-1.26 (m, 1H).

Intermediate 112 (method B)-Synthesis of (2R,3R,4R,5S)-6-[[(2S,3R,4R,5R) -2,3,4,5,6-pentahydroxy-hexyl]-(4-piperidyl)amino]hexane-1,2,3,4,5-pentol dihydrochloride;

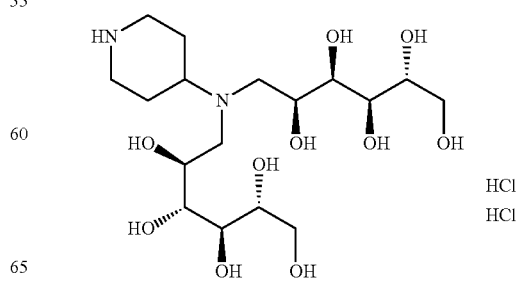

A suspension of tert-butyl 4-[bis[(2S,3R)-2,3-dihydroxy-3-[(4R,5R)-5-hydroxy-2-phenyl -1,3-dioxan-4-yl]propyl]amino]piperidine-1-carboxylate; formic acid (290 mg, 0.38 mmol) in aqueous HCl (2 M, 10 mL, 20 mmol) was stirred at RT for 3 h. The reaction mixture was concentrated in vacuo to afford the product as a yellow hygroscopic solid (225 mg). Yield >100% due to residual water. Purity adjusted to 85% to account for residual water.

LC/MS (System A): m/z (ESI$^+$)=429 [MH$^+$], R$_t$=0.14 min, ELS purity=100%

1H NMR (500 MHz, Deuterium Oxide) δ 4.31-4.20 (m, 2H), 4.09-3.97 (m, 1H), 3.92 -3.74 (m, 6H), 3.74-3.38 (m, 10H), 3.25-3.13 (m, 2H), 2.53-2.33 (m, 2H), 2.24-1.97 (m, 2H).

Intermediate 168-Synthesis of (9H-fluoren-9-yl)methyl 4-{bis[(2S,3R)-2,3-dihydroxy-3-[(4R,5R)-5-hydroxy-2-phenyl-1,3-dioxan-4-yl]propyl]amino}piperidine -1-carboxylate; formic acid

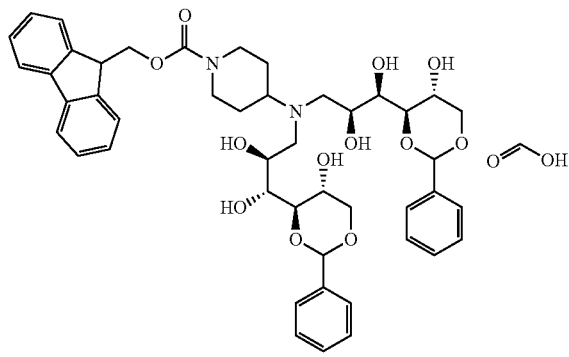

A mixture of 9H-fluoren-9-ylmethyl 4-aminopiperidine-1-carboxylate hydrochloride (7.80 g, 21.7 mmol) and 4,6-O-benzylidene-D-glucopyranose (23.3 g, 86.9 mmol) in MeOH (110 ml) was stirred at RT for 0.5 h. NaCNBH$_3$ (5.46 g, 86.9 mmol) was added then the reaction was heated at 60° C. The reaction was stirred at 60° C. for 18 h. The reaction was recharged with 4,6-O-benzylidene-D-glucopyranose (23.3 g, 86.9 mmol) then left to stir at 60° C. for a further 6 h. The reaction was allowed to cool to RT then added to saturated aqueous NaHCO$_3$ solution (200 ml) and EtOAc (200 ml). The resultant mixture was filtered through a Celite pad then the filtrate was transferred to a separating funnel. The phases were separated then the organic phase was washed with brine:water (1:1, 2×200 ml), brine (100 ml), dried over Na$_2$SO$_4$, filtered and concentrated in vacuo. The residue was suspended in MeCN (200 ml) and tBME (250 ml) the filtered. The solid obtained was suspended in MeOH then filtered. The combined filtrates were concentrated in vacuo. The crude material thus obtained was purified by flash column chromatography on C18 (400 g). The column was eluted with MeCN:water+0.1% formic acid using the following gradient (% MeCN, column volumes): 20%, 1 CV; 20-50%, 10 CV; 50-100%, 2 CV; 100%, 2 CV. The desired fractions were combined and concentrated in vacuo to remove most of the MeCN and some of the water then the residual aqueous solution was lyophilised to afford the product as an off-white solid (12.6 g, 66%).

$^1$H NMR (500 MHz, DMSO-d6) δ 8.16 (s, 1H), 7.90 (d, J=7.4 Hz, 2H), 7.64-7.54 (m, 2H), 7.45-7.27 (m, 14H), 5.46 (s, 2H), 5.23-5.07 (m, 2H), 4.88-4.21 (m, 6H), 4.13 (dd, J=10.5, 5.3 Hz, 2H), 4.02-3.67 (m, 9H), 3.61 (d, J=9.2 Hz, 2H), 3.50 (t, J=10.5 Hz, 2H), 2.64-2.56 (m, 3H), 2.42-2.31 (m, 2H), 1.69-1.51 (m, 2H), 1.31-0.90 (m, 2H).

LC/MS (System A): m/z (ESI$^+$)=827 [MH$^+$], R$_t$=1.08 min, UV purity=100%.

Intermediate 111 (Method B)-Synthesis of (1R,2S)-3-{[(2S,3R)-2,3-dihydroxy-3-[(4R,5R)-5-hydroxy-2-phenyl-1,3-dioxan-4-yl]propyl](piperidin-4-yl)amino}-1-[(4R,5R)-5-hydroxy-2-phenyl-1,3-dioxan-4-yl]propane-1,2-diol

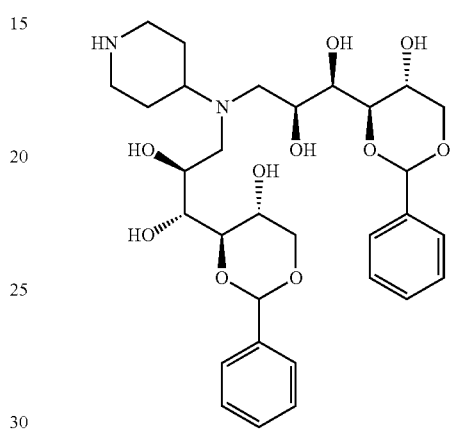

Piperidine (9.01 ml, 91.2 mmol) was added to a solution of (9H-fluoren-9-yl)methyl 4-{bis[(2S,3R)-2,3-dihydroxy-3-[(4R,5R)-5-hydroxy-2-phenyl-1,3-dioxan-4-yl]propyl]amino}piperidine-1-carboxylate; formic acid, Intermediate 112 (12.6 g, 14.4 mmol) in THF (150 ml). The reaction was left to stir at RT for 16 h then concentrated in vacuo. The crude solid material was suspended in MeOH (100 ml) then heated to dissolve. The solution was allowed to cool then concentrated in vacuo until solid was observed. The resultant suspension was stirred at RT for 15 min then filtered. The filtrate was concentrated in vacuo until solid was observed. The resultant suspension was stirred at RT for 15 min then filtered. The filtrate was purified by flash column chromatography on C18 (400 g). The column was eluted with MeCN:H$_2$O+0.1% formic acid using the following gradient (% MeCN, column volumes): 10%, 1 CVs; 10-25%, 6 CVs; 25%, 2 CVs; 25-50%, 1 CV; 50-100%, 1 CVs; 100%, 2 CVs. The desired fractions were combined and concentrated in vacuo to remove the majority of the solvent. The residual solution thus obtained was lyophilised to afford a pale-yellow solid (6.35 g). The solid thus obtained was partitioned between EtOAc (100 ml) and saturated aqueous NaHCO$_3$ solution (100 ml). The phases were separated then the aqueous phase was extracted with CHCl$_3$:IPA (2:1, 100 ml) and n-BuOH (2×100 ml). The combined organic phases were dried over Na$_2$SO$_4$ then concentrated in vacuo. The residue was dissolved in 1:2 MeCN:water then lyophilised to afford the product as a white solid (5.81 g, 67%).

$^1$H NMR (500 MHz, CD$_3$OD) δ 7.48 (dd, J=7.5, 2.0 Hz, 4H), 7.38-7.28 (m, 6H), 5.50 (s, 2H), 4.23 (dd, J=10.6, 5.4 Hz, 2H), 4.00-3.88 (m, 4H), 3.85 (dd, J=5.5, 2.4 Hz, 2H), 3.70 (dd, J=9.3, 2.4 Hz, 2H), 3.60 (t, J=10.5 Hz, 2H), 3.09-3.02 (m, 1H), 3.00-2.91 (m, 1H), 2.78 (dd, J=13.4, 3.7 Hz, 2H), 2.75-2.65 (m, 1H), 2.59 (dd, J=13.4, 8.8 Hz, 2H), 2.54-2.47 (m, 1H), 2.37-2.28 (m, 1H), 1.81-1.70 (m, 2H), 1.55-1.49 (m, 1H), 1.42-1.35 (m, 1H).

LC/MS (System A): m/z (ESI⁺)=605 [MH⁺], R$_f$=0.77 min, UV purity=100%.

SYNTHESIS OF EXAMPLE COMPOUNDS

Example 1-Synthesis of 2-[({3-amino-5H-pyrrolo[2,3-b]pyrazin-2-yl}formamido)methyl]-1-ethyl-3-methyl-1H-1,3-benzodiazol-3-ium formate

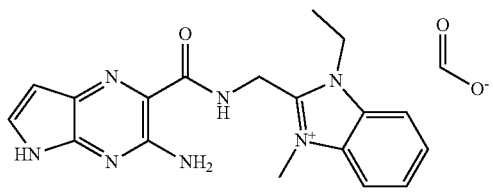

Iodomethane (26 μl, 0.42 mmol) was added to a solution of 3-amino-N-[(1-ethyl-1H-1,3-benzodiazol-2-yl)methyl]-5H-pyrrolo[2,3-b]pyrazine-2-carboxamide, Intermediate 84 (79%, 35 mg, 0.082 mmol) in DMSO (1 ml). The resulting mixture was stirred at RT for 48 h. Additional iodomethane (30 μl, 0.48 mmol) was added and the reaction was stirred at RT for a further 48 h. Additional iodomethane (40 μl, 0.64 mmol) was added and the reaction was stirred at RT for a further 72 h. The reaction mixture was diluted with MeCN to a final volume of 1.5 ml then purified by preparative HPLC (Method A). The desired fractions were combined and concentrated in vacuo to afford the product as a yellow solid (12 mg, 36%).

¹H NMR (500 MHz, DMSO-d₆) δ 11.59 (s, 1H), 9.68 (t, J=5.3 Hz, 1H), 8.47 (s, 1H), 8.10-7.98 (m, 2H), 7.74-7.65 (m, 2H), 7.51 (d, J=3.6 Hz, 1H), 7.19 (s, 2H), 6.41 (d, J=3.7 Hz, 1H), 5.05 (d, J=5.4 Hz, 2H), 4.69 (q, J=7.2 Hz, 2H), 4.16 (s, 3H), 1.39 (t, J=7.2 Hz, 3H).

LC/MS (System C): m/z (ESI⁺)=350 [M⁺], Rt=1.46 min, UV purity=98%.

Example 2-Synthesis of 2-[({3-amino-5H-pyrrolo[2,3-b]pyrazin-2-yl}formamido)methyl]-1-ethyl-6-fluoro-3-methyl-1H-1,3-benzodiazol-3-ium chloride

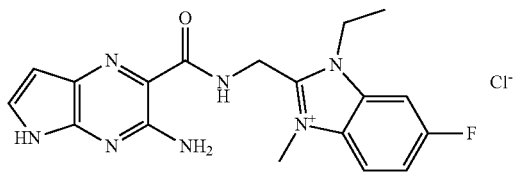 [SMILES: CCn1c(CNC(=O)c2nc3cc[nH]c3nc2N)[n+](C)c2ccc(F)cc21 ; [Cl-]]

A solution of 2-(aminomethyl)-1-ethyl-6-fluoro-3-methyl-1H-1,3-benzodiazol-3-ium hydrochloride iodide, Intermediate 19 (182 mg, 0.489 mmol) and DIPEA (170 μl, 0.98 mmol)) in DMF (1.5 ml) was added to a solution of lithium(1+) ion 3-amino-5H-pyrrolo[2,3-b]pyrazine-2-carboxylate, Intermediate 3 (90 mg, 0.49 mmol), HBTU (204 mg, 0.538 mmol) and DIPEA (170 μl, 0.98 mmol) in DMF (0.5 ml). The reaction was stirred at RT for 72 h then concentrated in vacuo. The crude material thus obtained was purified by flash column chromatography on C18 (12 g). The column was eluted with MeCN:water+0.1% formic acid using the following gradient (% MeCN, column volumes): 5%, 2 CV; 5-69%, 13 CV; 69-100%, 2 CV; 100%, 1 CV. The desired fractions were combined and concentrated in vacuo to afford a green/brown solid (30 mg). The solid thus obtained was dissolved in 2:1 DMSO:MeCN then purified by preparative HPLC (Method A). The desired fractions were combined and concentrated in vacuo to afford the product as a yellow solid (11 mg, 6%).

¹H NMR (500 MHz, DMSO-d₆) δ 11.51 (s, 1H), 9.66 (t, J=5.3 Hz, 1H), 8.12-8.07 (m, 2H), 7.62 (td, J=9.3, 2.4 Hz, 1H), 7.51 (dd, J=3.7, 1.7 Hz, 1H), 7.20 (s, 2H), 6.41 (d, J=3.6 Hz, 1H), 5.02 (d, J=5.4 Hz, 2H), 4.65 (q, J=7.2 Hz, 2H), 4.16 (s, 3H), 1.37 (t, J=7.2 Hz, 3H).

LC/MS (System C): m/z (ESI⁺)=368 [M⁺], Rt=1.48 min, UV purity=99%.

Example 3-Synthesis of 2-[({3-amino-5H-pyrrolo[2,3-b]pyrazin-2-yl}formamido)methyl]-6-chloro-1-ethyl-3-methyl-1H-1,3-benzodiazol-3-ium formate

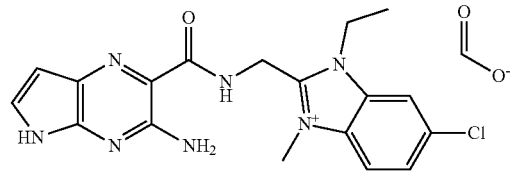

A suspension of lithium(1+) ion 3-amino-5H-pyrrolo[2,3-b]pyrazine-2-carboxylate, Intermediate 3 (90 mg, 0.49 mmol), 2-(aminomethyl)-6-chloro-1-ethyl-3-methyl-1H-1,3-benzodiazol-3-ium iodide, Intermediate 22 (172 g, 0.489 mmol), EDC.HCl (187 mg, 0.978 mmol) and HOAt (66 mg, 0.49 mmol) in DMF (2 ml) was left to stir at RT for 16 h then concentrated in vacuo. The crude material was purified by flash column chromatography on C18 (12 g). The column was eluted with MeCN:water+0.1% formic acid using the following gradient (% MeCN, column volumes): 5%, 6 CV; 10-100%, 20 CV; 100%, 2 CV. The desired fractions were combined and concentrated in vacuo to afford the product as a yellow solid (38 mg, 18%).

¹H NMR (500 MHz, DMSO-d₆) δ 11.65 (s, 1H), 9.67 (t, J=5.3 Hz, 1H), 8.38 (s, 1H), 8.32 (d, J=1.8 Hz, 1H), 8.08 (d, J=8.9 Hz, 1H), 7.76 (dd, J=8.9, 1.8 Hz, 1H), 7.51 (dd, J=3.6, 1.8 Hz, 1H), 7.19 (s, 2H), 6.40 (d, J=3.5 Hz, 1H), 5.03 (d, J=5.3 Hz, 2H), 4.68 (q, J=7.2 Hz, 2H), 4.15 (s, 3H), 1.37 (t, J=7.2 Hz, 3H).

LC/MS (System C): m/z (ESI⁺)=384 [M(³⁵Cl)+], 386 [M(³⁷Cl)+], Rt=1.69 min, UV purity=100%.

Example 4-Synthesis of 2-[({3-amino-5H-pyrrolo[2,3-b]pyrazin-2-yl}formamido)methyl]-1-ethyl-6-methoxy-3-methyl-1H-1,3-benzodiazol-3-ium formate:

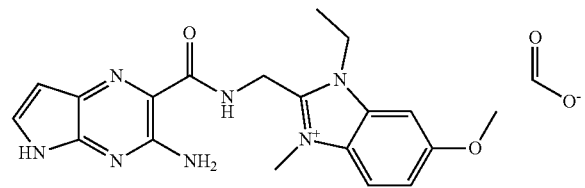

A suspension of 2-(1H-imidazole-1-carbonyl)-5H-pyrrolo[2,3-b]pyrazin-3-amine, Intermediate 4 (230 mg, 1.01 mmol) and 2-(aminomethyl)-1-ethyl-6-methoxy-3-methyl-1H-1,3-benzodiazol-3-ium iodide, Intermediate 25 (350 mg, 1.01 mmol) in DMF (3 ml) was stirred at RT for 16 h. The resultant suspension was filtered under vacuum. The solid thus obtained was washed with MeCN. The combined filtrate was concentrated in vacuo then the crude material was purified by flash column chromatography on C18 (30 g). The column was eluted with MeCN:water+0.1% formic acid using the following gradient (% MeCN, column volumes): 5%, 2 CV; 5-20%, 5 CV; 20% 1 CV; 20-25%, 2 CV; 25-39%, 1 CV; 39-100%, 1 CV; 100%, 1 CV. The desired fractions were combined and concentrated in vacuo to afford the product as a yellow powder (173 mg, 40%).

$^1$H NMR (500 MHz, DMSO-$d_6$) δ 11.56 (s, 1H), 9.65 (t, J=5.3 Hz, 1H), 8.35 (s, 1H), 7.92 (d, J=9.1 Hz, 1H), 7.56 (d, J=2.2 Hz, 1H), 7.50 (dd, J=3.7, 2.4 Hz, 1H), 7.32-7.26 (m, 1H), 7.20 (s, 2H), 6.44-6.36 (m, 1H), 5.00 (d, J=5.4 Hz, 2H), 4.64 (q, J=7.1 Hz, 2H), 4.12 (s, 3H), 3.90 (s, 3H), 1.37 (t, J=7.2 Hz, 3H).

LC/MS (System C): m/z (ESI$^+$)=380 [M$^+$], Rt=1.61 min, UV purity=100%.

Example 5-Synthesis of 2-[({3-amino-5H-pyrrolo[2,3-b]pyrazin-2-yl}formamido)methyl]-1-ethyl-3-methyl-6-(trifluoromethyl)-1H-1,3-benzodiazol-3-ium formate

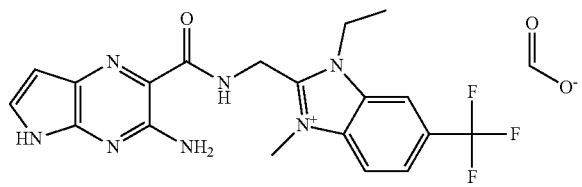

A solution of 2-(1H-imidazole-1-carbonyl)-5H-pyrrolo[2,3-b]pyrazin-3-amine, Intermediate 4 (64 mg, 0.28 mmol) and 2-(aminomethyl)-1-ethyl-6-methoxy-3-methyl-(trifluoromethyl)-1H-1,3-benzodiazol-3-ium hydrochloride iodide, Intermediate 28 (94%, 120 mg, 0.27 mmol) in DMF (1 ml) was stirred at RT for 16 h. The reaction mixture was concentrated in vacuo then purified by flash column chromatography on C18 (12 g). The column was eluted with MeCN:water+0.1% formic acid using the following gradient (% MeCN, column volumes): 5%, 2 CV; 5-24%, 4 CV; 24%, 3 CV; 24-52%, 6 CV; 52-100%, 4 CV; 100% 3 CV. The desired fractions were combined and concentrated in vacuo to afford the product as an orange solid (60 mg, 48%).

$^1$H NMR (500 MHz, DMSO-$d_6$) δ 11.65 (s, 1H), 9.68 (t, J=5.3 Hz, 1H), 8.62 (s, 1H), 8.41 (s, 1H), 8.28 (d, J=8.8 Hz, 1H), 8.06 (dd, J=8.8, 1.1Hz, 1H), 7.51 (dd, J=3.7, 1.8 Hz, 1H), 7.19 (s, 2H), 6.40 (d, J=3.6 Hz, 1H), 5.08 (d, J=5.3 Hz, 2H), 4.79 (q, J=7.1Hz, 2H), 4.20 (s, 3H), 1.39 (t, J=7.2 Hz, 3H).

LC/MS (System C): m/z (ESI$^+$)=418 [M$^+$], Rt=1.84 min, UV purity=100%.

Example 6-Synthesis of 2-[({3-amino-5H-pyrrolo[2,3-b]pyrazin-2-yl}formamido)methyl]-1-ethyl-3-methyl-6-(trifluoromethoxy)-1H-1,3-benzodiazol-3-ium formate

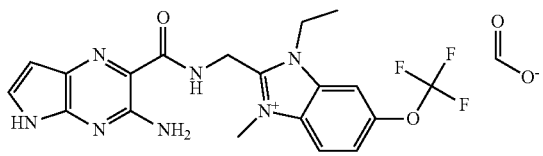

A solution of 2-(1H-imidazole-1-carbonyl)-5H-pyrrolo[2,3-b]pyrazin-3-amine, Intermediate 4 (55 mg, 0.24 mmol) and 2-(aminomethyl)-1-ethyl-3-methyl-6-(trifluoromethoxy)-1H-1,3-benzodiazol-3-ium hydrochloride iodide, Intermediate 32 (87%, 105 mg, 0.209 mmol) in DMF (1 ml) was stirred at RT for 16 h. The reaction mixture was concentrated in vacuo then purified by flash column chromatography on C18 (12 g). The column was eluted with MeCN:water+0.1% formic acid using the following gradient (% MeCN, column volumes): 5%, 2 CV; 5-28%, 5 CV; 28%, 2 CV; 28-43% 3 CV; 43-92%, 2 CV; 100% 3 CV. The desired fractions were combined and concentrated in vacuo. The residue was suspended in MeCN (5 ml) then filtered. The filtrate was concentrated in vacuo then purified by flash column chromatography on C18 (12 g). The column was eluted with MeCN:water+0.1% formic acid using the following gradient (% MeCN, column volumes): 5%, 2 CV; 5-9%, 1 CV; 9% 1 CV; 9-23%, 3 CV; 23%, 4 CV; 23-32% 1 CV; 32-100%, 2 CV, 100% 2 CV. The desired fractions were combined and concentrated in vacuo to afford the product as a brown solid (38 mg, 38%).

$^1$H NMR (500 MHz, DMSO-$d_6$) δ 11.77 (s, 1H), 9.69 (t, J=5.3 Hz, 1H), 8.50 (s, 1H), 8.34-8.26 (m, 1H), 8.19 (d, J=9.1Hz, 1H), 7.79-7.70 (m, 1H), 7.51 (d, J=3.8 Hz, 1H), 7.20 (s, 2H), 6.40 (d, J=3.8 Hz, 1H), 5.05 (d, J=5.3 Hz, 2H), 4.72 (q, J=7.2 Hz, 2H), 4.18 (s, 3H), 1.38 (t, J=7.2 Hz, 3H).

LC/MS (System C): m/z (ESI$^+$)=434 [M$^+$], Rt=1.97 min, UV purity=100%.

Example 7-Synthesis of 2-[({3-amino-5H-pyrrolo[2,3-b]pyrazin-2-yl}formamido)methyl]-1,3-diethyl-6-methoxy-1H-1,3-benzodiazol-3-ium formate

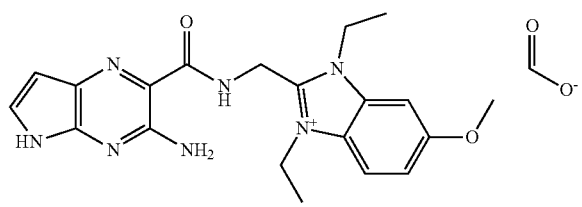

A suspension of lithium(1+) ion 3-amino-5H-pyrrolo[2,3-b]pyrazine-2-carboxylate, Intermediate 3 (40 mg, 0.22 mmol), 2-(aminomethyl)-1,3-diethyl-6-methoxy-1H-1,3-benzodiazol-3-ium iodide, Intermediate 36 (92%, 78 mg, 0.20 mmol), EDC.HCl (83 mg, 0.43 mmol) and HOAt (30 mg, 0.22 mmol) in DMF (1 ml) was stirred at RT for 72 h then concentrated in vacuo. The crude material was purified by flash column chromatography on C18 (12 g). The column was eluted with MeCN:water+0.1% formic acid using the following gradient (% MeCN, column volumes): 5%, 6 CV; 10-100%, 20 CV; 100%, 2 CV. The desired fractions were combined and concentrated in vacuo to afford the product as a green solid (52 mg, 58%).

¹H NMR (500 MHz, DMSO-d₆) δ 11.65 (s, 1H), 9.69 (t, J=5.3 Hz, 1H), 8.40 (s, 1H), 7.99-7.90 (m, 1H), 7.59-7.54 (m, 1H), 7.52-7.48 (m, 1H), 7.32-7.12 (m, 3H), 6.40 (d, J=3.2 Hz, 1H), 5.08-4.98 (m, 2H), 4.65 (q, J=7.1Hz, 4H), 3.90 (s, 3H), 1.39 (td, J=7.1, 1.6 Hz, 6H).

LC/MS (System C): m/z (ESI⁺)=394 [M⁺], Rt=1.75 min, UV purity=98%.

Example 8-Synthesis of 2-[({3-amino-5H-pyrrolo[2,3-b]pyrazin-2-yl}formamido)methyl]-3-benzyl-1-ethyl-6-methoxy-1H-1,3-benzodiazol-3-ium formate

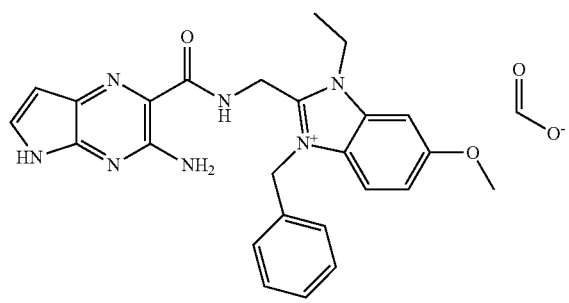

A suspension of lithium(1+) ion 3-amino-5H-pyrrolo[2,3-b]pyrazine-2-carboxylate, Intermediate 3 (90 mg, 0.49 mmol), 2-(aminomethyl)-3-benzyl-1-ethyl-6-methoxy-1H-1,3-benzodiazol-3-ium bromide, Intermediate 38 (56%, 260 mg, 0.39 mmol), EDC.HCl (190 mg, 0.98 mmol) and HOAt (67 mg, 0.49 mmol) in DMF (2 ml) was stirred at RT for 5 h. DMF (2 ml) was added then the reaction was stirred for a further 16 h, then concentrated in vacuo. The crude material was dissolved in 2:1 DMSO:MeCN then purified by preparative HPLC (Method A). The desired fractions were combined and concentrated in vacuo to afford the product as a yellow solid (91 mg, 47%).

¹H NMR (500 MHz, DMSO-d₆) δ 11.55 (s, 1H), 9.59 (t, J=5.4 Hz, 1H), 8.44 (s, 1H), 7.64 (d, J=9.2 Hz, 1H), 7.61 (d, J=2.3 Hz, 1H), 7.49 (dd, J=3.7, 2.3 Hz, 1H), 7.30-7.04 (m, 8H), 6.36 (dd, J=3.7, 1.3 Hz, 1H), 5.91 (s, 2H), 5.13 (d, J=5.4 Hz, 2H), 4.72 (q, J=7.2 Hz, 2H), 3.90 (s, 3H), 1.44 (t, J=7.2 Hz, 3H).

LC/MS (System C): m/z (ESI⁺)=456 [M⁺], Rt=2.13 min, UV purity=100%.

Example 9-Synthesis of 2-[({3-amino-5H-pyrrolo[2,3-b]pyrazin-2-yl}formamido)methyl]-1-ethyl-6-methoxy-3-(2-methoxy-2-oxoethyl)-1H-1,3-benzodiazol-3-ium bromide

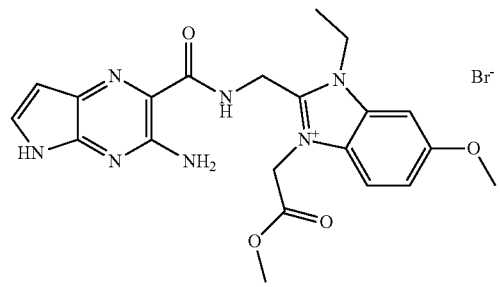 [SMILES: CCn1c(CNC(=O)c2nc3cc[nH]c3nc2N)[n+](CC(=O)OC)c2ccc(OC)cc21 ; [Br-]]

2-(Aminomethyl)-1-ethyl-6-methoxy-3-(2-methoxy-2-oxoethyl)-1H-1,3-benzodiazol-3-ium hydrochloride bromide, Intermediate 41 (65%, 165 mg, 0.272 mmol) was added to a solution of lithium(1+) ion 3-amino-5H-pyrrolo[2,3-b]pyrazine-2-carboxylate, Intermediate 3 (50 mg, 0.27 mmol), DIPEA (189 μl, 1.09 mmol) and HBTU (134 mg, 0.353 mmol) in DMF (1 ml). The resulting mixture was stirred at RT for 1.5 h then concentrated in vacuo.

The crude material was purified by flash column chromatography on C18 (12 g). The column was eluted with MeCN:water+0.1% formic acid using the following gradient (% MeCN, column volumes): 10%, 2 CV; 10-21%, 7 CV; 21%, 1 CV; 21-31%, 7 CV; 31-100%, 6 CV; 100%, 2 CV. The desired fractions were combined and lyophilised to afford a brown solid (16 mg). The solid thus obtained was dissolved in 2:1 CH₂Cl₂/MeOH (5 ml) then stirred with Dowex 1X2 chloride form for 5 min. The resin was removed by filtration then rinsed with 2:1 CH₂Cl₂:MeOH. The filtrate was concentrated in vacuo to afford the product as a yellow/orange solid (10 mg, 7%).

¹H NMR (500 MHz, DMSO-d₆) δ 11.52 (s, 1H), 9.56 (t, J=5.5 Hz, 1H), 7.89 (d, J=9.2 Hz, 1H), 7.63 (d, J=2.3 Hz, 1H), 7.51 (dd, J=3.7, 2.5 Hz, 1H), 7.27 (dd, J=9.1, 2.3 Hz, 1H), 7.17 (s, 2H), 6.41 (dd, J=3.7, 1.6 Hz, 1H), 5.65 (s, 2H), 5.03 (d, J=5.5 Hz, 2H), 4.77 (q, J=7.2 Hz, 2H), 3.92 (s, 3H), 3.37 (s, 3H), 1.47 (t, J=7.2 Hz, 3H).

LC/MS (System C): m/z (ESI⁺)=438 [M⁺], Rt=1.69 min, UV purity=98%.

Example 10-Synthesis of 2-[({3-amino-5H-pyrrolo[2,3-b]pyrazin-2-yl}formamido)methyl]-3-(carboxylatomethyl)-1-ethyl-6-methoxy-1H-1,3-benzodiazol-3-ium

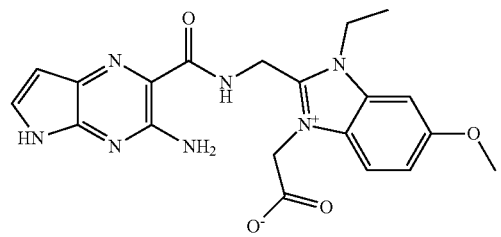 [SMILES: CCn1c(CNC(=O)c2nc3cc[nH]c3nc2N)[n+](CC(=O)[O-])c2ccc(OC)cc21]

1.0 M aqueous LiOH solution (86 μl, 0.086 mmol) was added to a solution of 2-[({3-amino-5H-pyrrolo[2,3-b]

pyrazin-2-yl}formamido)methyl]-1-ethyl-6-methoxy-3-(2-methoxy -2-oxoethyl)-1H-1,3-benzodiazol-3-ium bromide, Example 9 (32 mg, 0.062 mmol) in MeOH (0.5 ml). The resulting solution was stirred at RT for 15 min. The reaction mixture was concentrated under a stream of nitrogen. The residue was suspended in 1:1 DMSO:MeCN then filtered through a syringe filter. The filter was then washed extensively with MeOH. The combined MeOH washings were concentrated to an orange oil. The crude material thus obtained was purified by flash column chromatography on C18 (12 g). The column was eluted with MeCN:water+0.1% formic acid using the following gradient (% MeCN, column volumes): 10%, 2 CV; 10-23%, 6 CV; 23%, 1 CV; 23-29%, 3 CV; 29-100%, 5 CV; 100%, 3 CV. The desired fractions were combined and lyophilised to afford the product as a pale yellow solid (3 mg, 12%).

$^1$H NMR (500 MHz, DMSO-d$_6$) δ 11.47 (s, 1H), 9.53 (t, J=5.7 Hz, 1H), 7.91 (d, J=9.2 Hz, 1H), 7.52 (d, J=2.3 Hz, 1H), 7.48 (dd, J=3.8, 2.1 Hz, 1H), 7.32-7.16 (m, 3H), 6.36 (dd, J=3.8, 1.5 Hz, 1H), 4.97-4.91 (m, 4H), 4.60 (d, J=7.4 Hz, 2H), 3.89 (s, 3H), 1.33 (t, J=7.1 Hz, 3H).

LC/MS (System C): m/z (ESI$^+$)=424 [MH$^+$], Rt=1.56 min, UV purity=100%.

Example 11-Synthesis of 2-[({3-amino-5H-pyrrolo[2,3-b]pyrazin-2-yl}formamido) methyl]-3-(carbamoylmethyl)-1-ethyl-6-methoxy-1H-1,3-benzodiazol-3-ium bromide

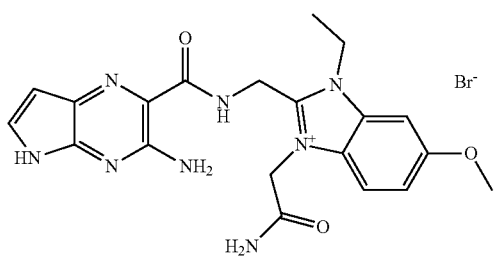 [SMILES: CCn1c(CNC(=O)c2nc3cc[nH]c3nc2N)[n+](CC(N)=O)c2ccc(OC)cc21 ; [Br-]]

2-(Aminomethyl)-3-(carbamoylmethyl)-1-ethyl-6-methoxy-1H-1,3-benzodiazol-3-ium hydrochloride bromide, Intermediate 43 (78%, 265 mg, 0.544 mmol) was added to a solution of lithium(1+) ion 3-amino-5H-pyrrolo[2,3-b]pyrazine-2-carboxylate, Intermediate 3 (60 mg, 0.33 mmol), DIPEA (230 µl, 1.3 mmol) and HBTU (160 mg, 0.42 mmol) in DMF (2 ml). The resulting mixture was stirred at RT for 16 h then concentrated in vacuo to a thick red oil. The crude material thus obtained was purified by flash column chromatography on C18 (30 g). The column was eluted with MeCN:water+0.1% formic acid using the following gradient (% MeCN, column volumes): 10%, 2 CV; 10-34%, 13 CV; 34-100%, 6 CV; 100%, 3 CV. The desired fractions were combined and concentrated in vacuo to afford the product as a pale brown solid (36 mg, 21%).

$^1$H NMR (500 MHz, DMSO-d$_6$) δ 11.50 (s, 1H), 9.56 (t, J=5.5 Hz, 1H), 7.89 (s, 1H), 7.80 (d, J=9.2 Hz, 1H), 7.64-7.57 (m, 2H), 7.50 (dd, J=3.7, 2.4 Hz, 1H), 7.29 (dd, J=9.1, 2.3 Hz, 1H), 7.21 (s, 2H), 6.39 (dd, J=3.7, 1.5 Hz, 1H), 5.40 (s, 2H), 4.99 (d, J=5.5 Hz, 2H), 4.71 (q, J=7.1Hz, 2H), 3.91 (s, 3H), 1.40 (t, J=7.2 Hz, 3H).

LC/MS (System C): m/z (ESI$^+$)=423 [M$^+$], Rt=1.39 min, UV purity=94%.

Example 12-Synthesis of 2-[({3-amino-5H-pyrrolo[2,3-b]pyrazin-2-yl}formamido) methyl]-1-ethyl-6-methoxy-3-[2-(methylsulfanyl)ethyl]-1H-1,3-benzodiazol-3-ium iodide

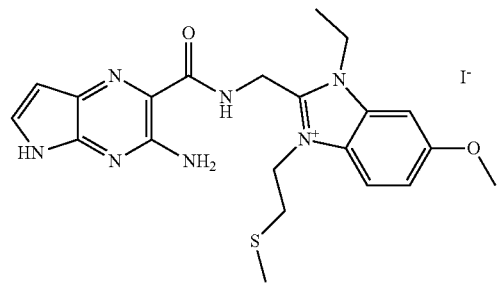 [SMILES: CCn1c(CNC(=O)c2nc3cc[nH]c3nc2N)[n+](CCSC)c2ccc(OC)cc21 ; [I-]]

A solution of 2-(aminomethyl)-1-ethyl-6-methoxy-3-[2-(methylsulfanyl)ethyl]-1H-1,3-benzodiazol-3-ium iodide, Intermediate 45 (80%, 370 mg, 0.73 mmol) in DMF (1 ml) was added to a solution of lithium(1+) ion 3-amino-5H-pyrrolo[2,3-b]pyrazine-2-carboxylate, Intermediate 3 (100 mg, 0.54 mmol), DIPEA (380 µl, 2.2 mmol) and HBTU (270 mg, 0.71 mmol) in DMF (1 ml). The resulting mixture was stirred at RT for 21 h then concentrated in vacuo to a viscous red oil. The crude material was dissolved in 2:1 DMSO:MeCN to a final volume of 1.5 ml then purified by preparative HPLC (Method A). The desired fractions were combined and concentrated in vacuo to a beige solid (47 mg). The material thus obtained was suspended in CH$_2$Cl$_2$ (2 ml). The supernatant was decanted off from the solid via a pipette. The trituration procedure was repeated three more times then the solid was dried under vacuum to afford the product as a brown solid (23 mg, 7%).

$^1$H NMR (500 MHz, DMSO-d$_6$) δ 11.52 (s, 1H), 9.68 (t, J=5.4 Hz, 1H), 7.96 (d, J=9.2 Hz, 1H), 7.57 (d, J=2.3 Hz, 1H), 7.51 (dd, J=3.7, 2.5 Hz, 1H), 7.38-7.11 (m, 3H), 6.40 (dd, J=3.8, 1.7 Hz, 1H), 5.07 (d, J=5.4 Hz, 2H), 4.84 (t, J=7.2 Hz, 2H), 4.67 (q, J=7.1 Hz, 2H), 3.91 (s, 3H), 2.97 (t, J=7.2 Hz, 2H), 2.13 (s, 3H), 1.39 (t, J=7.2 Hz, 3H).

LC/MS (System C): m/z (ESI$^+$)=440 [M$^+$], Rt=1.96 min, UV purity=96%.

Example 13-Synthesis of 2-[({3-amino-5H-pyrrolo[2,3-b]pyrazin-2-yl}formamido) methyl]-1-ethyl-3-(2-hydroxyethyl)-6-methoxy-1H-1,3-benzodiazol-3-ium formate

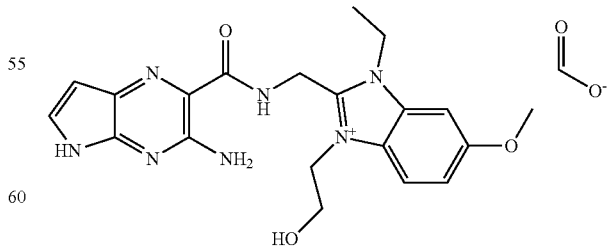

A mixture of 2-(1H-imidazole-1-carbonyl)-5H-pyrrolo[2,3-b]pyrazin-3-amine, Intermediate 4 (92%, 70 mg, 0.28 mmol) and 2-(aminomethyl)-1-ethyl-3-(2-hydroxyethyl)-6-methoxy -1H-1,3-benzodiazol-3-ium hydrochloride bromide, Intermediate 47 (125 mg, 0.341 mmol) in DMF (2 ml) was stirred at RT for 16 h. The reaction mixture was concentrated in vacuo then the resulting solid was suspended in MeCN (5 ml) with sonication. The solid was collected by filtration then washed with MeCN (15 ml) and dried under vacuum to afford a yellow solid (85 mg). The solid thus obtained was dissolved in DMSO then purified by preparative HPLC (Method A, 4 separate injections). The desired fractions were combined and concentrated in vacuo to afford the product as a yellow solid (43 mg, 33%).

$^1$H NMR (500 MHz, DMSO-$d_6$) δ 11.70 (s, 1H), 9.63 (t, J=5.4 Hz, 1H), 8.52 (s, 1H), 7.97 (d, J=9.2 Hz, 1H), 7.55 (d, J=2.3 Hz, 1H), 7.50 (d, J=3.8 Hz, 1H), 7.34-7.04 (m, 3H), 6.39 (d, J=3.8 Hz, 1H), 5.07 (d, J=5.4 Hz, 2H), 4.79 (t, J=4.9 Hz, 2H), 4.65 (q, J=7.1 Hz, 2H), 3.91 (s, 3H), 3.80 (t, J=4.9 Hz, 2H), 1.37 (t, J=7.2 Hz, 3H).

LC/MS (System C): m/z (ESI$^+$)=410 [M$^+$], Rt=1.51 min, UV purity=99%.

Example 14-Synthesis of 2-[({3-amino-5H-pyrrolo[2,3-b]pyrazin-2-yl}formamido) methyl]-1-ethyl-3-{2-[2-(2-hydroxyethoxy)ethoxy]ethyl}-6-methoxy-1H-1,3-benzodiazol-3-ium formate:

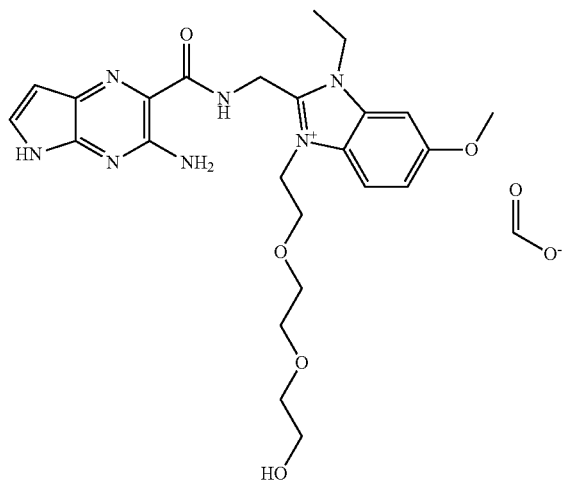

A mixture of 2-(1H-imidazole-1-carbonyl)-5H-pyrrolo[2,3-b]pyrazin-3-amine, Intermediate 4 (92%, 200 mg, 0.806 mmol) and 2-(aminomethyl)-1-ethyl-3-{2-[2-(2-hydroxyethoxy)ethoxy]ethyl}-6-methoxy-1H-1,3-benzodiazol-3-ium iodide, Intermediate 49 (84%, 554 mg, 1.00 mmol) in DMF (5 ml) was stirred at RT for 1.5 h. The reaction mixture was concentrated in vacuo then the crude material was purified by flash column chromatography on C18 (60 g). The column was eluted with MeCN:water+0.1% formic acid using the following gradient (% MeCN, column volumes): 10%, 2 CV; 10-36%, 17 CV; 36-100%, 1 CV; 100%, 3 CV. The desired fractions were combined and concentrated in vacuo to give a brown/yellow oil. The material thus obtained was further purified by preparative HPLC using the following method: Solvent A: Water +0.1% formic acid; Solvent B: MeCN+0.1% formic acid; Column: Waters Sunfire 30 mm×100 mm, 5 µm; Flowrate=40 ml/min; Gradient (time, Solvent B): 0 min, 2%; 2.5 min, 2%; 20.5 min, 15%; 21 min, 100%; 23 min, 100%; 23.5 min, 5%. The desired fractions were combined and concentrated in vacuo to afford the product as a yellow/orange solid (79 mg, 18%).

$^1$H NMR (500 MHz, DMSO-$d_6$) δ 11.60 (s, 1H), 9.61 (t, J=5.4 Hz, 1H), 8.53 (s, 1H), 7.96 (d, J=9.2 Hz, 1H), 7.55 (d, J=2.3 Hz, 1H), 7.51 (d, J=3.8 Hz, 1H), 7.32-7.13 (m, 3H), 6.40 (d, J=3.7 Hz, 1H), 5.06 (d, J=5.5 Hz, 2H), 4.90 (t, J=5.0 Hz, 2H), 4.66 (q, J=7.0 Hz, 2H), 3.91 (s, 3H), 3.82 (d, J=4.9 Hz, 2H), 3.53-3.46 (m, 2H), 3.41-3.38 (m, 4H), 3.38-3.20 (m, 2H+HDO), 1.36 (t, J=7.2 Hz, 3H).

LC/MS (System C): m/z (ESI$^+$)=498 [M$^+$], Rt=1.63 min, UV purity=98%.

Example 15-Synthesis of 2-[({3-amino-5H-pyrrolo[2,3-b]pyrazin-2-yl}formamido)methyl]-1-benzyl-3-methyl-1H-1,3-benzodiazol-3-ium formate

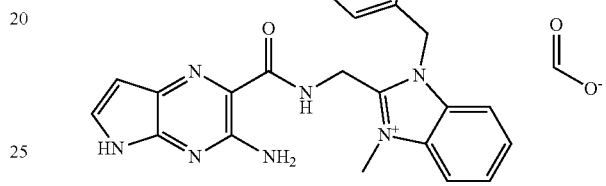

Iodomethane (22 µl, 0.35 mmol) was added to a solution of 3-amino-N-[(1-benzyl-1H -1,3-benzodiazol-2-yhm-ethyl]-5H-pyrrolo[2,3-b]pyrazine-2-carboxamide, Intermediate 85 (35 mg, 0.088 mmol) in DMSO (1 ml). The resulting mixture was stirred at RT for 5 h. Additional iodomethane (40 µl, 0.64 mmol) was added and the reaction mixture was left to stir for a further 16 h at RT. The reaction mixture was diluted with MeCN to a final volume of 1.5 ml then purified by preparative HPLC (Method A). The desired fractions were combined and concentrated in vacuo to afford the product as a yellow solid (9.1 mg, 22%).

$^1$H NMR (500 MHz, DMSO-$d_6$) δ 11.55 (s, 1H), 9.59 (t, J=5.4 Hz, 1H), 8.43 (s, 1H), 8.09 (d, J=8.4 Hz, 1H), 7.76 (d, J=8.3 Hz, 1H), 7.69 (t, J=7.8 Hz, 1H), 7.61 (t, J=7.8 Hz, 1H), 7.49 (dd, J=3.6, 2.4 Hz, 1H), 7.27-7.11 (m, 7H), 6.36 (dd, J=3.7, 1.3 Hz, 1H), 5.96 (s, 2H), 5.14 (d, J=5.4 Hz, 2H), 4.23 (s, 3H).

LC/MS (System C): m/z (ESI$^+$)=412 [M$^+$], Rt=1.82 min, UV purity=98%.

Example 16-Synthesis of 2-[({3-amino-5H-pyrrolo[2,3-b]pyrazin-2-yl}formamido)methyl]-3-benzyl-6-chloro-1-ethyl-1H-1,3-benzodiazol-3-ium bromide

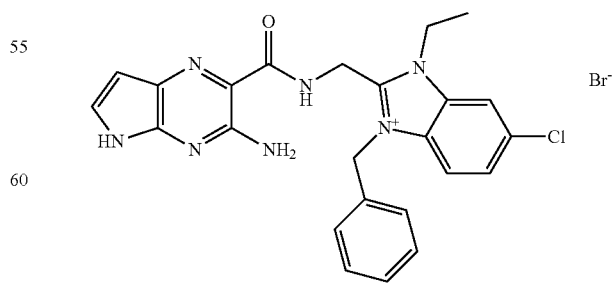

A solution of 2-(1H-imidazole-1-carbonyl)-5H-pyrrolo[2,3-b]pyrazin-3-amine, Intermediate 4 (60 mg, 0.26 mmol)

and 2-(aminomethyl)-3-benzyl-6-chloro-1-ethyl-1H-1,3-benzodiazol-3-ium bromide, Intermediate 51 (85%, 110 mg, 0.25 mmol) in DMF (2 ml) was stirred at RT for 72 h. The resultant suspension was filtered then the solid collected was dried under vacuum. The solid was re-suspended in MeCN (5 ml) then collected by filtration and dried under vacuum to afford a solid (70 mg). The solid was re-suspended in MeOH/MeCN/water (1:1:1, 3 ml) then filtered. The solid thus obtained was dried under vacuum to afford an orange solid (40 mg). The resultant solid was suspended in DMSO: MeCN (2:1, 0.5 ml) then MeOH (0.5 ml) was added. The solid was collected by filtration and dried under vacuum to afford an orange solid (11 mg). The solid this obtained was dissolved MeCN:water (1:1, 1 ml) then lyophilised to afford the product as a yellow solid (9 mg, 7%).

$^1$H NMR (500 MHz, DMSO-d$_6$) δ 11.47 (s, 1H), 9.57 (t, J=5.3 Hz, 1H), 8.38 (d, J=1.8 Hz, 1H), 7.78 (d, J=8.9 Hz, 1H), 7.68 (dd, J=8.9, 1.9 Hz, 1H), 7.48 (dd, J=3.7, 2.5 Hz, 1H), 7.26-7.08 (m, 7H), 6.35 (dd, J=3.8, 1.7 Hz, 1H), 5.95 (s, 2H), 5.15 (d, J=5.3 Hz, 2H), 4.74 (q, J=7.2 Hz, 2H), 1.44 (t, J=7.2 Hz, 3H).

LC/MS (System C): m/z (ESI$^+$)=460 [M($^{35}$Cl)+], 462 [M($^{37}$Cl)+], Rt=2.23 min, UV purity=98%.

Example 17-Synthesis of 2-[({3-am ino-5H-pyrrolo [2,3-b]pyrazin-2-yl}formamido)methyl]-3-benzyl-1-ethyl-6-(trifluoromethyl)-1H-1,3-benzodiazol-3-ium chloride

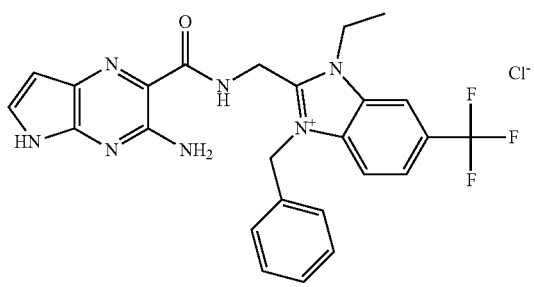 [SMILES: CCn1c(CNC(=O)c2nc3cc[nH]c3nc2N)[n+](Cc2ccccc2)c2ccc(C(F)(F)F)cc21 ; [Cl-]]

A solution of 2-(1H-imidazole-1-carbonyl)-5H-pyrrolo[2,3-b]pyrazin-3-amine, Intermediate 4 (50 mg, 0.22 mmol) and 2-(aminomethyl)-3-benzyl-1-ethyl-6-(trifluoromethyl)-1H-1,3-benzodiazol-3-ium hydrochloride bromide, Intermediate 53 (110 mg, 0.24 mmol) in DMF (1 ml) was stirred at RT for 16 h. The reaction mixture was concentrated in vacuo then dissolved in MeCN:water (1:1, 2 ml). A precipitate formed which was collected by filtration, washed with MeCN:water (1:1) then dried under vacuum to afford the product as an orange solid (45 mg, 39%).

$^1$H NMR (500 MHz, DMSO-d$_6$) δ 11.48 (s, 1H), 9.58 (t, J=5.3 Hz, 1H), 8.69 (s, 1H), 7.98 (s, 2H), 7.48 (dd, J=3.7, 2.5 Hz, 1H), 7.28-7.02 (m, 7H), 6.35 (dd, J=3.8, 1.7 Hz, 1H), 6.01 (s, 2H), 5.20 (d, J=5.3 Hz, 2H), 4.86 (d, J=7.3 Hz, 2H), 1.47 (t, J=7.2 Hz, 3H).

LC/MS (System C): m/z (ESI$^+$)=494 [M$^+$], Rt=2.34 min, UV purity=100%.

Example 18-Synthesis of 2-[({3-amino-5H-pyrrolo [2,3-b]pyrazin-2-yl}formamido)methyl]-3-benzyl-1-[2-oxo-2-(piperidin-1-yl)ethyl]-1H-1,3-benzodiazol-3-ium chloride

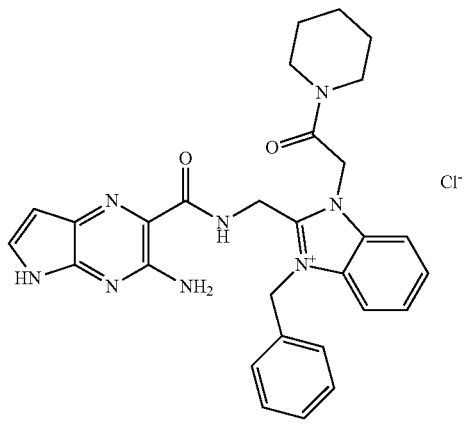 [SMILES: Nc1nc2[nH]ccc2nc1C(=O)NCc1n(CC(=O)N2CCCCC2)c2ccccc2[n+]1Cc1ccccc1 ; [Cl-]]

A solution of 2-(aminomethyl)-1-benzyl-3-[2-oxo-2-(piperidin-1-yl)ethyl]-1H-1,3-benzodiazol-3-ium hydrochloride bromide, Intermediate 57 (76%, 191 mg, 0.303 mmol) in DMF (1 ml) was added to a solution of lithium(1+) ion 3-amino-5H-pyrrolo[2,3-b]pyrazine-2-carboxylate, Intermediate 3 (60 mg, 0.33 mmol), DIPEA (230 μl, 1.3 mmol) and HBTU (160 mg, 0.42 mmol) in DMF (2 ml). The resulting mixture was stirred at RT for 16 h then concentrated in vacuo to a viscous red oil. The crude material was dissolved in 2:1 DMSO:MeCN to a final volume of 1.5 ml then purified by preparative HPLC (Method A). The desired fractions were combined and concentrated in vacuo to afford the product as a pale beige solid (48 mg, 26%).

$^1$H NMR (500 MHz, DMSO-d$_6$) δ 11.46 (s, 1H), 9.45 (t, J=5.6 Hz, 1H), 7.98 (d, J=8.3 Hz, 1H), 7.86 (d, J=7.9 Hz, 1H), 7.70-7.58 (m, 2H), 7.49 (dd, J=3.7, 2.5 Hz, 1H), 7.39-7.00 (m, 7H), 6.36 (dd, J=3.7, 1.7 Hz, 1H), 6.07 (s, 2H), 5.79 (s, 2H), 5.11 (d, J=5.6 Hz, 2H), 3.55-3.49 (m, 2H), 3.17-3.12 (m, 2H), 1.75-1.64 (m, 2H), 1.61-1.48 (m, 2H), 1.25-1.17 (m, 2H).

LC/MS (System C): m/z (ESI$^+$)=523 [M$^+$], Rt=2.21 min, UV purity=99%.

Example 19-Synthesis of 2-[({3-amino-6-methyl-5H-pyrrolo[2,3-b]pyrazin-2-yl}formamido)methyl]-1-ethyl-6-methoxy-3-methyl-1H-1,3-benzodiazol-3-ium formate

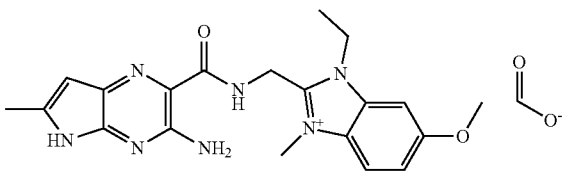

CDI (61 mg, 0.37 mmol) was added to a solution of 3-amino-6-methyl-5H-pyrrolo[2,3-b]pyrazine-2-carboxylic acid, Intermediate 9 (90%, 60 mg, 0.28 mmol) in DMF (2 ml). The reaction mixture was stirred at RT for 1 h. 2-(aminomethyl)-1-ethyl-6-methoxy-3-methyl-1H-1,3-benzodiazol-3-ium iodide, Intermediate 25 (108 mg, 0.312 mmol) was added then the reaction was left to stir for a further 16 h. The reaction mixture was concentrated in vacuo then purified by flash column chromatography on C18 (12 g). The column was eluted with MeCN:water+0.1% formic acid using the following gradient (% MeCN, column volumes): 0%, 3 CV; 0-20%, 14 CV; 20-60% 3 CV; 60-100%, 1 CV, 100% 2 CV. The desired fractions were combined and concentrated in vacuo to afford the product as a yellow solid (35 mg, 28%).

¹H NMR (500 MHz, DMSO-d₆) δ 11.42 (s, 1H), 9.57 (t, J=5.4 Hz, 1H), 8.51 (s, 1H), 7.92 (d, J=9.1Hz, 1H), 7.55 (d, J=2.3 Hz, 1H), 7.28 (dd, J=9.1, 2.3 Hz, 1H), 7.10 (s, 2H), 6.11 (s, 1H), 4.98 (d, J=5.4 Hz, 2H), 4.64 (q, J=7.2 Hz, 2H), 4.11 (s, 3H), 3.90 (s, 3H), 2.37-2.34 (m, 3H), 1.36 (t, J=7.2 Hz, 3H).

LC/MS (System C): m/z (ESI⁺)=394 [M⁺], Rt=1.80 min, UV purity=100%.

Example 20-Synthesis of 2-[({3-amino-7-methyl-5H-pyrrolo[2,3-b]pyrazin-2-yl}formamido)methyl]-6-chloro-1,3-diethyl-1H-1,3-benzodiazol-3-ium formate

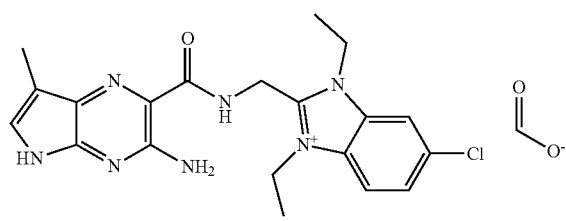

A mixture of 2-(1H-imidazole-1-carbonyl)-7-methyl-5H-pyrrolo[2,3-b]pyrazin-3-amine, Intermediate 13 (95%, 83 mg, 0.33 mmol) and 2-(aminomethyl)-6-chloro-1,3-diethyl-1H -1,3-benzodiazol-3-ium iodide, Intermediate 34 (97%, 140 mg, 0.37 mmol) in DMF (3 ml) was stirred at RT for 64 h. The reaction mixture was concentrated in vacuo then the crude material was purified by flash column chromatography on C18 (30 g). The column was eluted with MeCN:water+ 0.1% formic acid using the following gradient (% MeCN, column volumes): 10%, 2 CV; 10-34%, 16 CV; 34-65%, 4 CV; 65-100%, 2 CV; 100%, 1 CV. The desired fractions were combined and concentrated in vacuo to remove most of the MeCN then lyophilised to afford the product as a yellow solid (44 mg, 25%).

¹H NMR (500 MHz, DMSO-d₆) δ 11.21-11.16 (m, 1H), 9.49 (t, J=5.5 Hz, 1H), 8.49 (s, 1H), 8.34 (d, J=1.8 Hz, 1H), 8.12 (d, J=8.9 Hz, 1H), 7.75 (dd, J=8.9, 1.9 Hz, 1H), 7.26 (dd, J=2.2, 1.2 Hz, 1H), 7.13 (s, 2H), 5.11 (d, J=5.4 Hz, 2H), 4.75-4.67 (m, 4H), 2.24 (d, J=1.1Hz, 3H), 1.43-1.38 (m, 6H).

LC/MS (System C): m/z (ESI⁺)=412 [M(³⁵Cl)⁺], 414 [M(³⁷Cl)⁺], Rt=2.07 min, UV purity=96%.

Example 21-Synthesis of 2-[({3-amino-7-chloro-5H-pyrrolo[2,3-b]pyrazin-2-yl}formamido)methyl]-6-chloro-1,3-diethyl-1H-1,3-benzodiazol-3-ium iodide

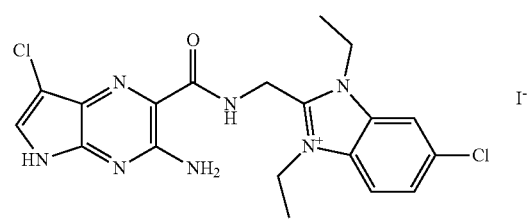 [SMILES: CCn1c(CNC(=O)c2nc3c(Cl)c[nH]c3nc2N)[n+](CC)c2ccc(Cl)cc21 ; [I-]]

A mixture of 7-chloro-2-(1H-imidazole-1-carbonyl)-5H-pyrrolo[2,3-b]pyrazin-3-amine, Intermediate 16 (95%, 160 mg, 0.58 mmol) and 2-(aminomethyl)-6-chloro-1,3-diethyl-1H -1,3-benzodiazol-3-ium iodide, Intermediate 34 (97%, 220 mg, 0.58 mmol) in DMF (4 ml) was stirred at RT for 64 h. The reaction mixture was concentrated in vacuo then the crude material was purified by flash column chromatography on C18 (30 g). The column was eluted with MeCN:water+ 0.1% formic acid using the following gradient (% MeCN, column volumes): 10%, 2 CV; 10-33%, 13 CV; 33-41%, 2 CV; 41-70%, 5 CV; 70%, 3 CV. The desired fractions were combined and concentrated in vacuo to remove most of the MeCN then lyophilised to afford the product as a yellow/orange solid (161 mg, 48%).

¹H NMR (500 MHz, DMSO-d₆) δ 11.80 (s, 1H), 9.51 (t, J=5.3 Hz, 1H), 8.34 (d, J=1.8 Hz, 1H), 8.12 (d, J=8.9 Hz, 1H), 7.75 (dd, J=8.9, 1.9 Hz, 1H), 7.69 (s, 1H), 7.37 (s, 2H), 5.12 (d, J=5.4 Hz, 2H), 4.77-4.61 (m, 4H), 1.44-1.37 (m, 6H).

LC/MS (System C): m/z (ESI⁺)=432 [M(³⁵Cl₂)+], 434 [M(³⁵Cl³⁷Cl)+], 436 [M(³⁷Cl₂)+], Rt=2.14 min, UV purity=97%.

Example 22-Synthesis of 2-[({3-amino-5H-pyrrolo[2,3-b]pyrazin-2-yl}formamido)methyl]-6-(2-{[(tert-butoxy)carbonyl]amino}ethoxy)-1,3-diethyl-1H -1,3-benzodiazol-3-ium formate

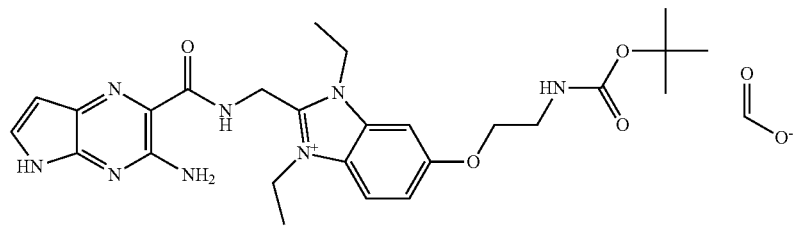

A mixture of 2-(1H-imidazole-1-carbonyl)-5H-pyrrolo[2,3-b]pyrazin-3-amine, Intermediate 4 (98%, 369 mg, 1.59 mmol) and 2-(aminomethyl)-6-(2-{[(tert -butoxy)carbonyl]amino}ethoxy)-1,3-diethyl-1H-1,3-benzodiazol-3-ium iodide, Intermediate 59 (82%, 819 mg, 1.37 mmol) in DMF (8 ml) was stirred at RT for 90 h. The reaction mixture was concentrated in vacuo then the crude material was purified by flash column chromatography on C18 (120 g). The column was eluted with MeCN:water+0.1% formic acid using the following gradient (% MeCN, column volumes): 10%, 2 CV; 10-32%, 11 CV; 32-100%, 3 CV; 100% 2 CV. The desired fractions were combined and concentrated in vacuo to remove most of the MeCN then lyophilised to afford the product as a yellow solid (382 mg, 47%).

$^1$H NMR (500 MHz, DMSO-$d_6$) δ 11.57 (s, 1H), 9.70 (t, J=5.2 Hz, 1H), 8.44 (s, 1H), 7.95 (d, J=9.1Hz, 1H), 7.63 (s, 1H), 7.54-7.49 (m, 1H), 7.31-7.13 (m, 3H), 7.08 (t, J=5.4 Hz, 1H), 6.42 (d, J=3.5 Hz, 1H), 5.04 (d, J=5.3 Hz, 2H), 4.66 (q, J=7.0 Hz, 4H), 4.12 (t, J=5.8 Hz, 2H), 3.36 (m, 2H + HDO), 1.41-1.37 (m, 15H).

LC/MS (System C): m/z (ESI$^+$)=523 [M$^+$], Rt=2.26 min, UV purity=95%.

Example 23-Synthesis of 2-[({3-amino-5H-pyrrolo[2,3-b]pyrazin-2-yl}formamido)methyl]-6-(3-{[(tert-butoxy)carbonyl]amino}propoxy)-1,3-diethyl-1H-1,3-benzodiazol-3-ium formate

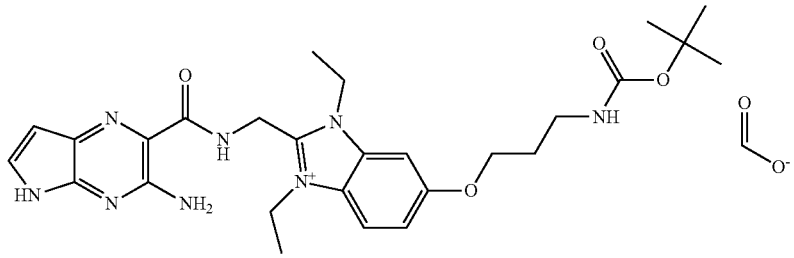

A mixture of 2-(1H-imidazole-1-carbonyl)-5H-pyrrolo[2,3-b]pyrazin-3-amine, Intermediate 4 (98%, 295 mg, 1.27 mmol) and 2-(aminomethyl)-6-(3-{[(tert -butoxy)carbonyl]amino}propoxy)-1,3-diethyl-1H-1,3-benzodiazol-3-ium iodide, Intermediate 64 (91%, 710 mg, 1.28 mmol) in DMF (5 ml) was stirred at RT for 16 h. Additional DMF (3 ml) was added then the reaction was left to stir for a further 72 h. The reaction mixture was concentrated in vacuo then the crude material was purified by flash column chromatography on C18 (60 g). The column was eluted with MeCN:water+0.1% formic acid using the following gradient (% MeCN, column volumes): 10%, 2 CV; 10-34%, 16 CV; 34-100%, 3 CV; 100% 2 CV. The desired fractions were combined and concentrated in vacuo to afford the product as a viscous orange oil (345 mg, 46%).

$^1$H NMR (500 MHz, DMSO-$d_6$) δ 11.53 (s, 1H), 9.69 (t, J=5.4 Hz, 1H), 8.46 (s, 1H), 7.94 (d, J=9.1Hz, 1H), 7.56 (d, J=2.0 Hz, 1H), 7.51 (dd, J=3.6, 1.9 Hz, 1H), 7.26 (dd, J=9.1, 2.2 Hz, 1H), 7.20 (s, 2H), 6.93-6.88 (m, 1H), 6.41 (d, J=3.2 Hz, 1H), 5.03 (s, J=5.4 Hz, 2H), 4.72-4.58 (m, 4H), 4.12 (t, J=6.1Hz, 2H), 3.11 (q, J=6.6 Hz, 2H), 1.89 (p, J=6.4 Hz, 2H), 1.41-1.35 (m, 15H).

LC/MS (System C): m/z (ESI$^+$)=537 [M$^+$], Rt=2.39 min, UV purity=100%.

Example 24-Synthesis of 2-[({3-amino-5H-pyrrolo[2,3-b]pyrazin-2-yl}formamido)methyl]-6-(3-{[(tert-butoxy)carbonyl]amino}propyl)-1,3-diethyl-1H-1,3-benzodiazol-3-ium formate

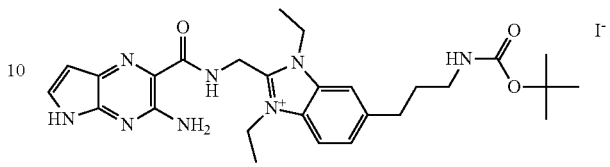

2-(1H-imidazole-1-carbonyl)-5H-pyrrolo[2,3-b]pyrazin-3-amine, Intermediate 4 (252 mg, 1.11 mmol) was added to a solution of 2-(aminomethyl)-6-(3-{[(tert- butoxy)carbonyl]amino}propyl)-1,3-diethyl-1H-1,3-benzodiazol-3-ium iodide, Intermediate 69 (80%, 540 mg, 0.884 mmol) in DMF (12 ml). The resulting solution was stirred at RT for 16 h then for at 30° C. for 2 h. The resultant solution was concentrated in vacuo. The crude material was purified by flash column chromatography on C18 (30 g). The column was eluted with MeCN:water+0.1% formic acid using the following gradient (% MeCN, column volumes): 10%, 2 CV; 10-34%, 16 CV; 34-100%, 3 CV, 100% 2 CV. The desired fractions were combined and concentrated in vacuo to afford the product as a light brown solid (235 mg, 40%).

$^1$H NMR (500 MHz, DMSO-$d_6$) δ 11.55 (s, 1H), 9.70 (t, J=5.3 Hz, 1H), 8.35 (s, 1H), 7.96 (d, J=8.6 Hz, 1H), 7.89 (s, 1H), 7.55-7.50 (m, 2H), 7.19 (s, 2H), 6.89 (t, J=5.3 Hz, 1H), 6.41 (d, J=3.6 Hz, 1H), 5.05 (d, J=5.2 Hz, 2H), 4.66 (dd, J=7.1, 2.5 Hz, 4H), 2.94 (q, J=6.6 Hz, 2H), 2.78 (t, J=7.5 Hz, 2H), 1.79-1.71 (m, 2H), 1.40 (dt, J=7.1, 3.7 Hz, 6H), 1.38 (s, 9H).

LC/MS (System C): m/z (ESI$^+$)=521 [M$^+$], Rt=2.34 min, UV purity=97%.

Example 25-Synthesis of 2-[({3-amino-5H-pyrrolo[2,3-b]pyrazin-2-yl}formamido)methyl]-6-{1-[(tert-butoxy)carbonyl]piperidin-4-yl}-1,3-diethyl-1H-1,3-benzodiazol-3-ium iodide

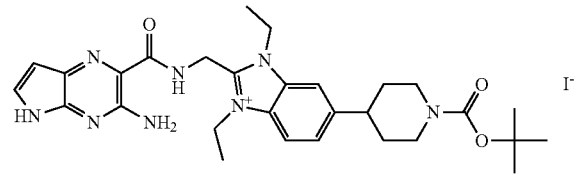 [SMILES: CCn1c(CNC(=O)c2nc3cc[nH]c3nc2N)[n+](CC)c2ccc(C3CCN(C(=O)OC(C)(C)C)CC3)cc21 ; [I-]]

2-(1H-imidazole-1-carbonyl)-5H-pyrrolo[2,3-b]pyrazin-3-amine, Intermediate 4 (251 mg, 1.10 mmol) was added to a solution of 2-(aminomethyl)-6-{1-[(tert -butoxy)carbonyl]piperidin-4-yl}-1,3-diethyl-1H-1,3-benzodiazol-3-ium iodide, Intermediate 73 (72%, 605 mg, 0.847 mmol) in DMF (15 ml). The resulting solution was stirred at RT for 24 h. The reaction mixture was concentrated in vacuo then the crude material was purified by flash column chromatography on C18 (60 g). The column was eluted with MeCN:water+0.1% formic acid using the following gradient (% MeCN, column volumes): 0%, 2 CV; 0-17%, 5 CV; 17-39%, 6 CV; 39%, 2 CV; 39-100%, 4 CV; 100%, 1 CV. The desired fractions were combined and lyophilised to afford the product as a yellow solid (315 mg, 52%).

$^1$H NMR (500 MHz, DMSO-$d_6$) δ 11.56 (s, 1H), 9.70 (t, J=5.2 Hz, 1H), 7.97 (d, J=8.6 Hz, 1H), 7.96 (s, 1H), 7.65-7.57 (m, 1H), 7.51 (dd, J=3.7, 1.7 Hz, 1H), 7.19 (s, 2H), 6.41 (d, J=3.5 Hz, 1H), 5.05 (d, J=5.3 Hz, 2H), 4.73-4.62 (m, 4H), 4.19-4.09 (m, 2H), 3.00-2.90 (m, 1H), 2.85 (br. s, 2H), 1.81 (d, J=12.2 Hz, 2H), 1.65 (qd, J=12.8, 4.3 Hz, 2H), 1.47-1.36 (m, 15H).

LC/MS (System C): m/z (ESI$^+$)=547 [M$^+$], Rt=2.66 min, UV purity=95%.

Example 26-Synthesis of 2-[({3-amino-5H-pyrrolo[2,3-b]pyrazin-2-yl}formamido)methyl]-6-(1-{1-[(tert-butoxy)carbonyl]piperidin-4-yl}-1H-pyrazol-4-yl)-1,3-diethyl-1H-1,3-benzodiazol-3-ium formate

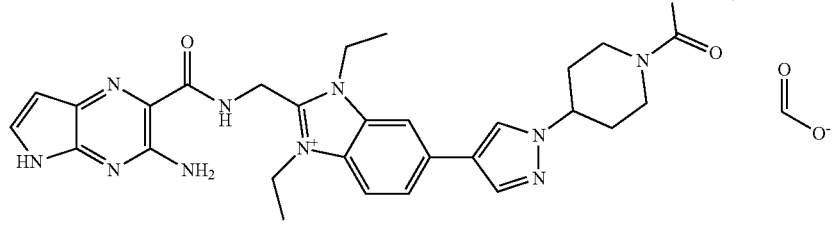

2-(1H-imidazole-1-carbonyl)-5H-pyrrolo[2,3-b]pyrazin-3-amine, Intermediate 4 (312 mg, 1.33 mmol) was added to a solution of 2-(aminomethyl)-6-(1-{1-[(tert -butoxy)carbonyl]piperidin-4-yl}-1H-pyrazol-4-yl)-1,3-diethyl-1H-1,3-benzodiazol-3-ium iodide, Intermediate 76 (83%, 880 mg, 1.26 mmol) in DMF (10 ml). The resulting solution was stirred at RT for 64 h. The reaction mixture was concentrated in vacuo then the crude material was purified by flash column chromatography on C18 (60 g). The column was eluted with MeCN:water+0.1% formic acid using the following gradient (% MeCN, column volumes): 0%, 2 CV; 0-11%, 5 CV; 11-40%, 9 CV; 40%, 2 CV. The desired fractions were combined and concentrated in vacuo to afford the product as a yellow solid (525 mg, 60%).

$^1$H NMR (500 MHz, DMSO-$d_6$) δ 11.58 (s, 1H), 9.72 (t, J=5.3 Hz, 1H), 8.50 (s, 1H), 8.33 (5, 1H), 8.24 (s, 1H), 8.11 (s, 1H), 8.04 (d, J=8.7 Hz, 1H), 7.95-7.89 (m, 1H), 7.52 (dd, J=3.6, 2.3 Hz, 1H), 7.23 (s, 2H), 6.41 (d, J=2.7 Hz, 1H), 5.06 (d, J=5.2 Hz, 2H), 4.68 (q, J=7.0 Hz, 4H), 4.39 (ddt, J=11.4, 7.8, 3.9 Hz, 1H), 4.06 (br. s, 2H), 2.94 (br. s, 2H), 2.11-2.03 (m, 2H), 1.82-1.78 (m, 2H), 1.47-1.38 (m, 15H).

LC/MS (System C): m/z (ESI$^+$)=613 [M$^+$], Rt=2.59 min, UV purity=94%.

Example 27-Synthesis of 2-[({3-amino-5H-pyrrolo[2,3-b]pyrazin-2-yl}formamido)methyl]-6-(2-amino-ethoxy)-1,3-diethyl-1H-1,3-benzodiazol-3-ium hydrochloride chloride

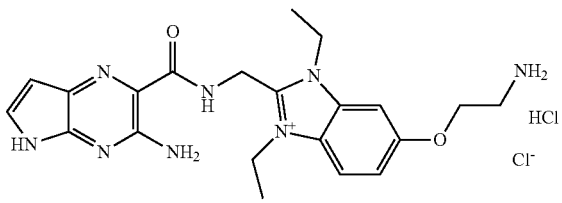 [SMILES: CCn1c(CNC(=O)c2nc3cc[nH]c3nc2N)[n+](CC)c2ccc(OCCN)cc21 ; [Cl-] ; Cl]

HCl solution in dioxane (4.0 M, 140 μl, 0.56 mmol) was added to a solution of 2-[({3-amino-5H-pyrrolo[2,3-b]pyrazin-2-yl}formamido)methyl]-6-(2-{[(tert -butoxy)carbonyl]amino}ethoxy)-1,3-diethyl-1H-1,3-benzodiazol-3-ium formate, Example 22 (95%, 39 mg, 0.065 mmol) in MeCN (1 ml). The resulting mixture was stirred at RT for 50 min then concentrated under a stream of nitrogen. The resulting residue was suspended in MeCN (1 ml). The solid was collected by filtration then washed with MeCN and dried under vacuum to afford the product as an orange solid (20 mg, 64%).

$^1$H NMR (500 MHz, DMSO-$d_6$) δ 11.54 (s, 1H), 9.71 (d, J=5.6 Hz, 1H), 8.13 (s, 3H), 8.00 (d, J=9.2 Hz, 1H), 7.66 (d, J=2.1Hz, 1H), 7.53 (dd, J=3.7, 2.5 Hz, 1H), 7.32 (dd, J=9.1, 2.3 Hz, 1H), 7.21 (s, 2H), 6.42 (dd, J=3.8, 1.7 Hz, 1H), 5.05 (d, J=5.4 Hz, 2H), 4.72-4.56 (m, 5H), 4.40-4.31 (m, 3H), 1.42-1.38 (m, 6H).

LC/MS (System C): m/z (ESI$^+$)=423 [M$^+$], Rt=0.94 min, ELS purity=100%.

Example 28-Synthesis of 2-[({3-amino-5H-pyrrolo[2,3-b]pyrazin-2-yl}formamido)methyl]-6-(3-amino-propoxy)-1,3-diethyl-1H-1,3-benzodiazol-3-ium hydrochloride chloride

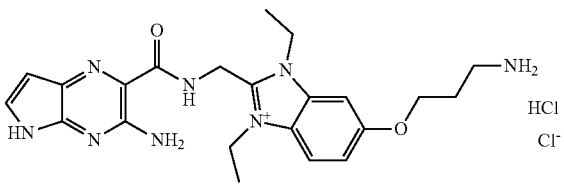 [SMILES: CCn1c(CNC(=O)c2nc3cc[nH]c3nc2N)[n+](CC)c2ccc(OCCCN)cc21 ; Cl ; [Cl-]]

HCl solution in dioxane (4.0 M, 1.6 ml, 6.4 mmol) was added to a solution of 2-[({3-amino-5H-pyrrolo[2,3-b]pyrazin-2-yl}formamido)methyl]-6-(3-{[(tert-butoxy)carbonyl]amino}propoxy)-1,3-diethyl-1H-1,3-benzodiazol-3-ium formate, Example 23 (382 mg, 0.656 mmol) in MeCN (10 ml). The resulting mixture was stirred at RT for 45 min then concentrated in vacuo to afford the product as an orange solid (292 mg, 84%).

$^1$H NMR (500 MHz, DMSO-$d_6$) δ 11.55 (s, 1H), 9.70 (t, J=5.3 Hz, 1H), 8.07 (s, 3H), 7.97 (d, J=9.1Hz, 1H), 7.62 (d, J=2.1Hz, 1H), 7.51 (dd, J=3.7, 2.5 Hz, 1H), 7.29 (m, 3H), 6.41 (dd, J=3.8, 1.7 Hz, 1H), 5.04 (d, J=5.3 Hz, 2H), 4.70-4.63 (m, 4H), 4.24 (t, J=6.2 Hz, 2H), 3.03-2.92 (m, 2H), 2.09 (p, J=6.4 Hz, 2H), 1.39 (t, J=7.2 Hz, 6H).

LC/MS (System C): m/z (ESI$^+$)=437 [M$^+$], Rt=1.02 min, UV purity=96%.

Example 29-Synthesis of 2-[({3-amino-5H-pyrrolo[2,3-b]pyrazin-2-yl}formamido)methyl]-6-(3-aminopropyl)-1,3-diethyl-1H-1,3-benzodiazol-3-ium hydrochloride chloride

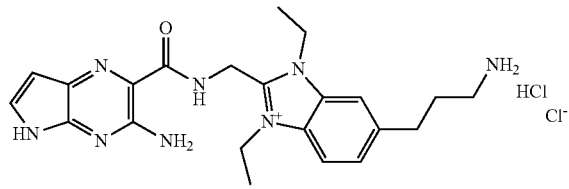 [SMILES: CCn1c(CNC(=O)c2nc3cc[nH]c3nc2N)[n+](CC)c2ccc(CCCN)cc21 ; Cl ; [Cl-]]

HCl solution in dioxane (4.0 M, 31 μl, 0.12 mmol) was added to a solution of 2-[({3-amino-5H-pyrrolo[2,3-b]pyrazin-2-yl}formamido)methyl]-6-(3-{[(tert-butoxy)carbonyl]amino}propyl)-1,3-diethyl-1H-1,3-benzodiazol-3-ium iodide, Example 24 (40 mg, 0.06 mmol) in MeCN (1 ml). The resulting mixture was stirred at RT for 30 min then more HCl solution in dioxane (4.0 M, 15 μl, 0.060 mmol) was added. The reaction mixture was stirred at RT for a further 20 min then concentrated under a stream of nitrogen. The resulting residue was dried under vacuum to afford the product as a yellow solid (27 mg, 84%).

$^1$H NMR (500 MHz, CD$_3$OD) δ 7.92 (d, J=8.6 Hz, 1H), 7.88 (s, 1H), 7.61 (dd, J=8.6, 1.3 Hz, 1H), 7.40 (d, J=3.8 Hz, 1H), 6.45 (d, J=3.8 Hz, 1H), 5.12 (s, 2H), 4.82-4.75 (m, 4H), 3.04-2.96 (m, 4H), 2.08 (p, J=7.8 Hz, 2H), 1.60-1.52 (m, 6H).

LC/MS (System C): m/z (ESI$^+$)=421 [M$^+$], Rt=1.03 min, UV purity=95%.

Example 30-Synthesis of 2-[({3-amino-5H-pyrrolo[2,3-b]pyrazin-2-yl}formamido)methyl]-1,3-diethyl-6-(piperidin-4-yl)-1H-1,3-benzodiazol-3-ium trifluoroacetic acid trifluoroacetate

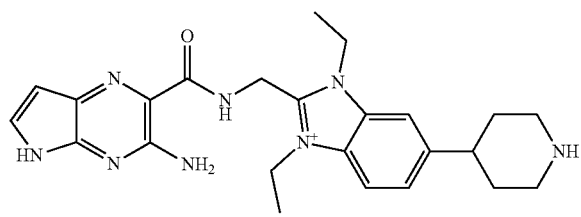

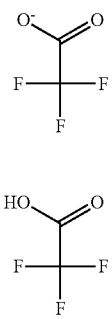

HCl solution in dioxane (4.0 M, 0.27 ml, 1.1 mmol) was added to a solution of 2-[({3-amino-5H-pyrrolo[2,3-b]pyrazin-2-yl}formamido)methyl]-6-{1-[(tert-butoxy)carbonyl]piperidin-4-yl}-1,3-diethyl-1H-1,3-benzodiazol-3-ium iodide, Example 25 (95%, 300 mg, 0.42 mmol) in MeCN (15 ml). The resulting solution was stirred at RT for 16 h then HCl solution in dioxane (4.0 M, 0.27 ml, 1.1 mmol) was added. The reaction was stirred at RT for a further 4 h then concentrated in vacuo then the residue was azeotroped with MeCN (2×30 ml). The resulting solid was suspended in MeCN (30 ml) then filtered, rinsed with MeCN and dried under vacuum to afford the product as a brown solid (90 mg). The remaining material on the filter paper was dissolved in MeOH and combined with the filtrate then concentrated in vacuo to afford a brown viscous oil (125 mg). The oil thus obtained was further purified by preparative HPLC (Method B). The desired fractions were combined and lyophilised to afford a brown solid (35 mg). The material thus obtained was combined with the solid obtained by filtration (90 mg) then the combined material was dissolved in MeCN:water (1:9, 3 ml) and lyophilised to afford a brown solid (125 mg). The material was re-dissolved in MeCN:water (1:9, 3 ml) and lyophilised once more to afford a brown solid (110 mg). The material thus obtained was further purified by flash column chromatography on C18 (12 g). The column was eluted with MeCN:water+0.1% TFA using the following gradient (% MeCN, column volumes): 0%, 2 CV; 0-5%, 2 CV; 5-15%, 3 CV; 15-25%, 3 CV; 25-51%, 3 CV; 51-100%, 2 CV; 100%, 1 CV. The desired fractions were combined and lyophilised to afford a yellow solid (70 mg). The material thus obtained was further purified by HPLC (Method C). The desired fractions were combined and lyophilised to afford an orange solid (63 mg). The material thus obtained was further purified by flash column chromatography on C18 (30 g). The column was eluted with MeCN:water+0.1% TFA using the following gradient (% MeCN, column volumes): 5%, 3 CV; 5-14%, 7 CV; 14%, 4 CV; 14-20%, 5 CV; 20-26%, 1 CV; 26-100%, 2 CV; 100%, 2 CV. The desired fractions were combined and lyophilised to afford the product as a yellow solid (27 mg, 9%).

$^1$H NMR (500 MHz, DMSO-$d_6$) δ 11.54 (s, 1H), 9.72 (t, J=5.3 Hz, 1H), 8.73 (d, J=9.5 Hz, 1H), 8.46 (d, J=10.4 Hz, 1H), 8.04 (d, J=8.7 Hz, 1H), 7.88 (s, 1H), 7.57 (dd, J=8.7, 1.2 Hz, 1H), 7.53 (dd, J=3.7, 2.5Hz, 1H), 7.22 (s, 2H), 6.42 (dd, J=3.8, 1.7 Hz, 1H), 5.07 (d, J=5.3 Hz, 2H), 4.75-4.65 (m, 4H), 3.49-3.40 (m, 2H +HDO), 3.16-2.99 (m, 3H), 2.10-2.01 (m, 2H), 1.90 (qd, J=13.4, 3.8 Hz, 2H), 1.40 (t, 6H).

LC/MS (System C): m/z (ESI$^+$)=447 [M$^+$], Rt=0.98 min, UV purity=100%.

Example 31-Synthesis of 2-[({3-amino-5H-pyrrolo[2,3-b]pyrazin-2-yl}formamido)methyl]-1,3-diethyl-6-[1-(piperidin-4-yl)-1H-pyrazol-4-yl]-1H-1,3-benzodiazol-3-ium hydrochloride iodide

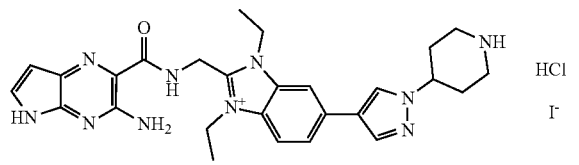 [SMILES: CCn1c(CNC(=O)c2nc3cc[nH]c3nc2N)[n+](CC)c2ccc(-c3cnn(C4CCNCC4)c3)cc21 ; Cl ; [I-]]

HCl solution in dioxane (4.0 M, 420 µl, 1.7 mmol) was added to a solution of 2-[({3-amino-5H-pyrrolo[2,3-b]pyrazin-2-yl}formamido)methyl]-6-(1-{1-[(tert -butoxy)carbonyl]piperidin-4-yl}-1H-pyrazol-4-yl)-1,3-diethyl-1H-1,3-benzodiazol-3-ium formate, Example 26 (94%, 500 mg, 0.71 mmol) in MeCN. The reaction mixture was stirred at RT for 40 h then more HCl solution in dioxane (4.0 M, 200 µl, 0.80 mmol) was added. The reaction mixture was stirred at RT for a further 2 h then concentrated in vacuo. The residue was azeotroped from MeCN then dried under vacuum. The residue thus obtained was re-suspended in MeCN (20 ml) then HCl solution in dioxane (4.0 M, 420 µl, 1.7 mmol) was added. The reaction was stirred at RT for 88 h. The resulting suspension was filtered then the solid was dried under vacuum, re-dissolved in 1:1 MeCN:water (4 ml) then lyophilised to afford the product as a brown solid (450 mg, 90%).

$^1$H NMR (500 MHz, DMSO-$d_6$) δ 11.57 (s, 1H), 9.71 (t, J=5.3 Hz, 1H), 9.40-9.31 (m, 1H), 9.30-9.20 (m, 1H), 8.49 (s, 1H), 8.30 (s, 1H), 8.16 (s, 1H), 8.04 (d, J=8.7 Hz, 1H), 7.97-7.92 (m, 1H), 7.51 (dd, J=3.7, 2.5 Hz, 1H), 6.41 (dd, J=3.7, 1.7 Hz, 1H), 5.07 (d, J=5.2 Hz, 2H), 4.73-4.66 (m, 4H), 4.57-4.50 (m , 1H), 3.38 (d, J=12.3 Hz, 2H), 3.10 (dd, J=10.7 Hz, 2H), 2.31-2.18 (m, 4H), 1.43 (dt, J=12.1, 7.2 Hz, 6H).

LC/MS (System C): m/z (ESI$^+$)=513 [M$^+$], Rt=1.20 min, UV purity=97%.

Example 32-Synthesis of 2-[({3-amino-5H-pyrrolo[2,3-b]pyrazin-2-yl}formamido)methyl]-6-(2-carbamimidamidoethoxy)-1,3-diethyl-1H-1,3-benzodiazol-3-ium formate

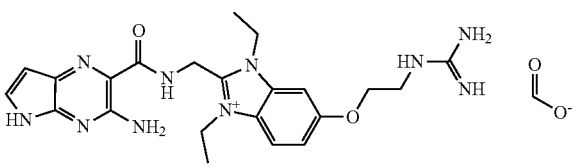

DIPEA (18 µl, 0.10 mmol) was added to a mixture of 2-[({3-amino-5H-pyrrolo[2,3-b]pyrazin-2-yl}formamido)methyl]-6-(2-aminoethoxy)-1,3-diethyl-1H-1,3-benzodiazol-3-ium hydrochloride chloride, Example 27 (18 mg, 0.036 mmol) and 1H-1,2,4-triazole-1-carboximidamide hydrochloride (1:1) (5.5 mg, 0.037 mmol) in DMF (1 ml). The resulting mixture was stirred at RT for 3.5 h. Additional 1H-1,2,4-triazole-1-carboximidamide hydrochloride (1:1) (5.5 mg, 0.037 mmol) was added and the reaction allowed to continue for a further 18 h. The reaction mixture was concentrated in vacuo then the crude material was purified by flash column chromatography on C18 (12 g). The column was eluted with MeCN:water+0.1% formic acid using the following gradient (% MeCN, column volumes): 0%, 2 CV; 0-1%, 1 CV; 1-70%, 6 CV; 70%, 1 CV; 70-100% 3 CV; 100% 2 CV. The desired fractions were combined and concentrated in vacuo to afford an orange solid (17 mg). The material thus obtained was further purified by preparative HPLC (Method A). The desired fractions were combined and concentrated in vacuo to afford the product as a yellow solid (1.7 mg, 9%).

$^1$H NMR (500 MHz, DMSO-$d_6$) δ 11.55 (s, 1H), 9.70 (t, J=5.3 Hz, 1H), 8.59 (s, 1H), 8.44 (s, 1H), 7.97 (d, J=9.1Hz, 1H), 7.75-7.62 (m, 4H), 7.51 (d, J=3.8 Hz, 1H), 7.35-7.09 (m, 3H), 6.41 (d, J=3.8 Hz, 1H), 5.04 (d, J=5.1Hz, 2H), 4.70-4.62 (m, 4H), 4.21 (t, J=5.1Hz, 2H), 3.60-3.54 (m, 2H), 1.43-1.35 (m, 6H).

LC/MS (System C): m/z (ESI$^+$)=465 [M$^+$], Rt=1.07 min, UV purity=100%.

Example 33-Synthesis of 2-[({3-amino-5H-pyrrolo[2,3-b]pyrazin-2-yl}formamido)methyl]-6-(3-carbamimidamidopropyl)-1,3-diethyl-1H-1,3-benzodiazol-3-ium chloride

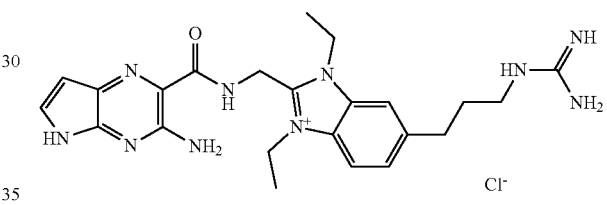

1H-1,2,4-triazole-1-carboximidamide hydrochloride (1:1) (13 mg, 0.090 mmol) was added to a suspension of 2-[({3-amino-5H-pyrrolo[2,3-b]pyrazin-2-yl}formamido)methyl]-6-(3-aminopropyl)-1,3-diethyl-1H-1,3-benzodiazol-3-ium hydrochloride chloride, Example 29 (50 mg, 0.10 mmol) in CH$_2$Cl$_2$ (4 ml). DIPEA (22 µl, 0.13 mmol) was added then the resulting suspension was stirred at RT for 1 h. The reaction was concentrated under a stream of nitrogen then DMF (4 ml) was added. The resulting solution was stirred at RT for 3 h. A further portion of 1H-1,2,4-triazole-1-carboximidamide hydrochloride (1:1) (13 mg, 0.090 mmol) and by DIPEA (22 µl, 0.13 mmol) was added then the reaction mixture was left to stir for a further 16 h. The reaction mixture was concentrated in vacuo then the crude material was purified by flash column chromatography on C18 (12 g). The column was eluted with MeCN:water+0.1% formic acid using the following gradient (% MeCN, column volumes): 0%, 5 CV; 0-42%, 17 CV; 42-65%, 3 CV; 65-100% 1 CV; 100% 1 CV. The desired fractions were combined and concentrated in vacuo. The material thus obtained was further purified by preparative HPLC (Method A). The desired fractions were combined and concentrated in vacuo to afford the product as a yellow solid (10 mg, 19%).

$^1$H NMR (500 MHz, DMSO-$d_6$) δ 11.56 (s, 1H), 9.73 (t, J=5.3 Hz, 1H), 8.82 (s, 1H), 8.42 (s, 1H), 7.98 (d, J=8.5 Hz, 1H), 7.94 (s, 1H), 7.60-7.54 (m, 3H), 7.52 (dd, J=3.7, 2.4 Hz, 1H), 7.21 (s, 2H), 6.44-6.39 (m, 1H), 5.05 (d, J=5.2 Hz, 2H), 4.68 (q, J=6.9 Hz, 4H), 3.10 (d, J=5.8 Hz, 2H), 2.87-2.81 (m, 2H), 1.89-1.81 (m, 2H), 1.40 (td, J=7.2, 4.0 Hz, 6H).

LC/MS (System C): m/z (ESI$^+$)=463 [M$^+$], Rt=1.16 min, UV purity=98%.

Example 34-Synthesis of 2-[({3-amino-5H-pyrrolo[2,3-b]pyrazin-2-yl}formamido)methyl]-6-carboxy-1,3-diethyl-1H-1,3-benzodiazol-3-ium bromide

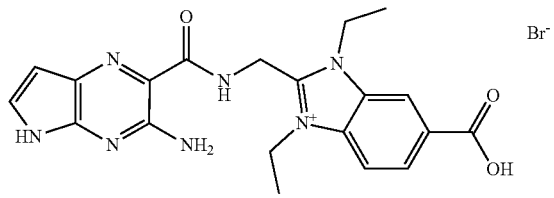 [SMILES: CCn1c(CNC(=O)c2nc3cc[nH]c3nc2N)[n+](CC)c2ccc(C(=O)O)cc21 ; [Br-]]

A suspension of 2-(1H-imidazole-1-carbonyl)-5H-pyrrolo[2,3-b]pyrazin-3-amine, Intermediate 4 (1.26 g, 5.52 mmol) and 2-(aminomethyl)-6-carboxy-1,3-diethyl-1H-1,3-benzodiazol-3-ium hydrobromide bromide, Intermediate 83 (2.26 g, 5.52 mmol) in DMF (11 ml) was stirred at RT for 16 h. The reaction mixture was filtered then the resulting solid was washed with MeCN and dried under vacuum to afford a yellow solid (0.89 g). The filtrate was filtered then the resulting solid was dried under vacuum to afford a yellow solid (0.42 g). The filtrate was concentrated in vacuo then the residue was suspended in MeCN/water (4:1, 5 ml) then filtered and the resulting solid was dried under vacuum to afford a yellow solid (1.15 g). The solids thus obtained were combined as an MeCN suspension then concentrated in vacuo and dried under vacuum to afford the product as a yellow solid (2.46 g, 91%).

$^1$H NMR (500 MHz, DMSO-$d_6$) δ 13.50 (s, 1H), 11.52 (s, 1H), 9.72 (t, J=5.3 Hz, 1H), 8.60 (s, 1H), 8.22 (dd, J=8.7, 1.3 Hz, 1H), 8.17 (d, J=8.7 Hz, 1H), 7.52 (dd, J=3.8, 2.5 Hz, 1H), 7.20 (s, 2H), 6.42 (dd, J=3.8, 1.7 Hz, 1H), 5.10 (d, J=5.3 Hz, 2H), 4.80 (q, J=7.2 Hz, 2H), 4.73 (q, J=7.2 Hz, 2H), 1.42 (t, J=7.2 Hz, 6H).

LC/MS (System C): m/z (ESI$^+$)=408 [M$^+$], Rt=1.39 min, UV purity=100%.

Example 35-Synthesis of 2-[({3-amino-5H-pyrrolo[2,3-b]pyrazin-2-yl}formamido) methyl]-6-[(3-{[(tert-butoxy)carbonyl]amino}propyl)carbamoyl]-1,3-diethyl-1H-1,3- benzodiazol-3-ium formic acid formate tert-Butyl N-(3-aminopropyl)carbamate (89 mg, 0.51 mmol) was added to a solution of 2-[({3-amino-5H-pyrrolo[2,3-b]pyrazin-2-yl}formamido)methyl]-6-carboxy-1,3-diethyl-1H -1,3-benzodiazol-3-ium bromide, Example 34 (250 mg, 0.51 mmol), HBTU (210 mg, 0.56 mmol), and 4-methylmorpholine (0.13 ml, 1.0 mmol) in DMF (2.5 ml). The reaction was stirred at RT for 16 h. The reaction mixture was concentrated in vacuo then the crude material was purified by flash column chromatography on C18 (30 g). The column was eluted with MeCN:water+0.1% formic acid using the following gradient (% MeCN, column volumes): 5%, 2 CV; 5-21%, 3 CV; 21%, 1 CV; 21-29%, 2 CV; 29%, 3 CV; 29-100%, 14 CV. The desired fractions were combined and concentrated in vacuo to afford the product as a yellow solid (205 mg, 60%).

$^1$H NMR (500 MHz, DMSO-$d_6$) δ 11.54 (s, 1H), 9.72 (t, J=5.3 Hz, 1H), 8.73 (t, J=5.5 Hz, 1H), 8.47 (s, 1H), 8.23 (s, 2H), 8.19-8.09 (m, 2H), 7.57-7.47 (m, 1H), 7.20 (s, 2H), 6.84 (t, J=5.6 Hz, 1H), 6.47-6.38 (m, 1H), 5.09 (d, J=5.3 Hz, 2H), 4.81-4.61 (m, 4H), 3.37-3.21 (m, 2H +HDO), 3.09-2.96 (m, 2H), 1.75-1.62 (m, 2H), 1.51-1.31 (m, 15H).

LC/MS (System D): m/z (ESI$^+$)=564 [M$^+$], Rt=2.35 min, UV purity=98%.

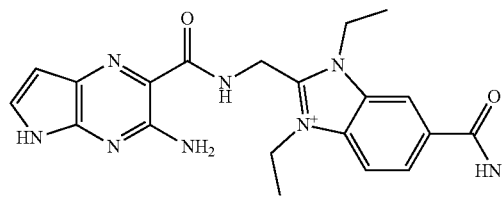 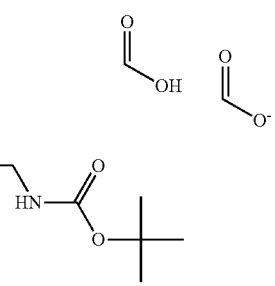

Example 36-Synthesis of 2-[({3-amino-5H-pyrrolo[2,3-b]pyrazin-2-yl}formamido) methyl]-6-({1-[(tert-butoxy)carbonyl]piperidin-4-yl}carbamoyl)-1,3-diethyl-1H-1,3-benzodiazol-3-ium bromide

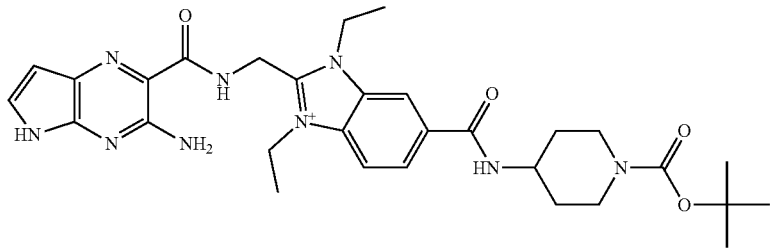

tert-Butyl 4-aminopiperidine-1-carboxylate (82 mg, 0.41 mmol) was added to a solution of 2-[[(3-amino-5H-pyrrolo[2,3-b]pyrazine-2-carbonyl)amino]methyl]-1,3-diethyl -benzimidazol-1-ium-5-carboxylic acid bromide, Example 34 (200 mg, 0.410 mmol), HBTU (171 mg, 0.450 mmol) and 4-methylmorpholine (104 µl, 0.820 mmol) in DMF (2 ml). The reaction was stirred at RT for 64 h then concentrated in vacuo. The crude material was purified by flash column chromatography on C18 (30 g). The column was eluted with MeCN:water+0.1% formic acid using the following gradient (% MeCN, column volumes): 5%, 3 CV; 5-20%, 3 CV; 20%, 4 CV; 20-46%, 5 CV; 46%, 3 CV; 46-56%, 2 CV; 56-94%, 2 CV. The desired fractions were combined and concentrated in vacuo to afford the product as an orange solid (240 mg, 87%).

$^1$H NMR (500 MHz, DMSO-d$_6$) δ 11.53 (s, 1H), 9.72 (t, J=5.3 Hz, 1H), 8.51 (d, J=7.8 Hz, 1H), 8.45 (s, 1H), 8.17-8.11 (m, 2H), 7.55-7.48 (m, 1H), 7.32-7.07 (m, 2H), 6.45-6.39 (m, 1H), 5.10 (d, J=5.3 Hz, 2H), 4.80-4.65 (m, 4H), 4.13-3.86 (m, 3H), 2.97-2.78 (m, 2H), 1.91-1.79 (m, 2H), 1.52-1.36 (m, 17H).

LC/MS (System D): m/z (ESI$^+$)=590 [M$^+$], Rt=2.75 min, UV purity=100%.

Example 37-Synthesis of 2-[({3-amino-5H-pyrrolo[2,3-b]pyrazin-2-yl}formamido) methyl]-6-(4-{[(tert-butoxy)carbonyl]amino}piperidine-1-carbonyl)-1,3-diethyl-1H -1,3-benzodiazol-3-ium bromide

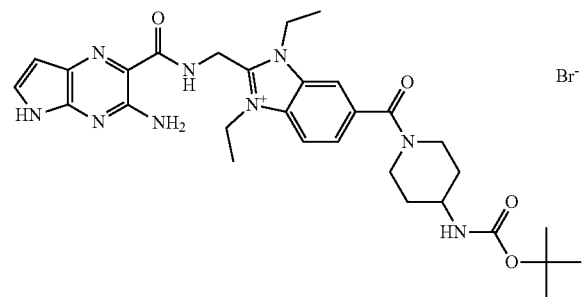 [SMILES: CCn1c(CNC(=O)c2nc3cc[nH]c3nc2N)[n+](CC)c2ccc(C(=O)N3CCC(NC(=O)OC(C)(C)C)CC3)cc21 ; [Br-]]

A solution of 2-[({3-amino-5H-pyrrolo[2,3-b]pyrazin-2-yl}formamido)methyl]-6-carboxy -1,3-diethyl-1H-1,3-benzodiazol-3-ium bromide, Example 34 (200 mg, 0.410 mmol), HBTU (171 mg, 0.451 mmol), and 4-methylmorpholine (104 µl, 0.819 mmol) in DMF (2 ml) was stirred at RT for 5 min. tert-Butyl N-(piperidin-4-yl)carbamate (82 mg, 0.41 mmol) was added then the reaction mixture was stirred at RT for 16 h. The reaction mixture was concentrated in vacuo then the crude material was purified by flash column chromatography on C18 (30 g). The column was eluted with MeCN:water+0.1% TFA using the following gradient (% MeCN, column volumes): 5%, 2 CV; 5-25%, 4 CV; 25%, 1 CV; 25-48%, 5 CV; 48%, 1 CV; 48-57%, 2 CV; 57-100%, 2 CV; 100%, 1 CV. The desired fractions were combined and concentrated in vacuo to afford the product as a yellow solid (135 mg, 48%).

$^1$H NMR (500 MHz, DMSO-d$_6$) δ 11.53 (s, 1H), 9.78-9.65 (m, 1H), 8.52 (d, J=7.7 Hz, 1H), 8.45 (s, 1H), 8.15 (s, 2H), 7.57-7.46 (m, 1H), 7.20 (s, 2H), 6.46-6.36 (m, 1H), 5.16-5.01 (m, 2H), 4.80-4.65 (m, 4H), 4.13-3.86 (m, 3H), 2.89 (s, 2H), 1.90-1.78 (m, 2H), 1.52-1.34 (m, 17H).

LC/MS (System C): m/z (ESI$^+$)=590 [M$^+$], Rt=2.20 min, UV purity=98%.

Example 38-Synthesis of 2-[({3-amino-5H-pyrrolo[2,3-b]pyrazin-2-yl}formamido)methyl]-6-{[2-(4-{[(tert-butoxy)carbonyl]amino}piperidin-1-yl)ethyl]carbamoyl}-1,3-diethyl-1H-1,3-benzodiazol-3-ium formate

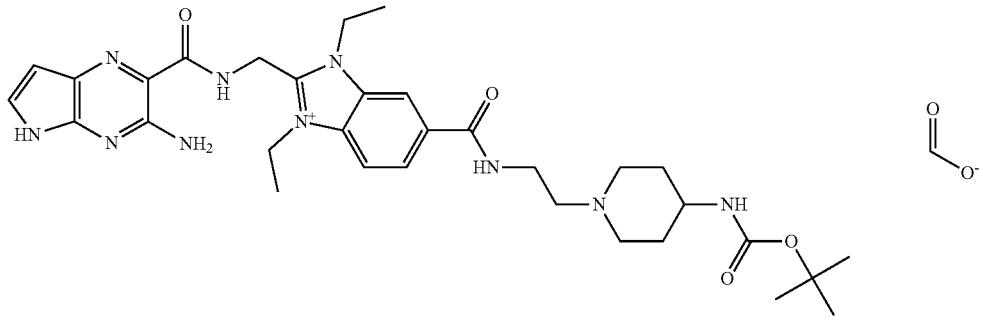

A solution of 2-[({3-amino-5H-pyrrolo[2,3-b]pyrazin-2-yl}formamido)methyl]-6-carboxy-1,3-diethyl-1H-1,3-benzodiazol-3-ium bromide, Example 34 (220 mg, 0.45 mmol), and CDI (100 mg, 0.68 mmol) in DMF (5 ml) was stirred at RT for 0.5 h. Additional CDI (40 mg, 0.25 mmol) was added and the reaction was stirred at RT for a further 0.5 h. A solution of tert-butyl N-[1-(2-aminoethyl)-4-piperidyl]carbamate (139 mg, 0.57 mmol) in DMF (5 ml) was added then the resulting mixture was stirred at RT for 10 min. The reaction mixture was concentrated in vacuo then the crude material was purified by flash column chromatography on C18 (30 g). The column was eluted with MeCN:water+0.1% formic acid using the following gradient (% MeCN, column volumes): 10%, 2 CV; 10-27%, 13 CV; 27-34%, 3 CV; 34-59%, 4 CV; 59-100%, 1 CV; 100%, 2 CV. The desired fractions were combined and concentrated in vacuo to afford the product as a yellow solid (261 mg, 85%).

$^1$H NMR (500 MHz, DMSO-$d_6$) δ 11.54 (s, 1H), 9.72 (t, J=5.3 Hz, 1H), 8.84 (t, J=5.4 Hz, 1H), 8.49 (s, 1H), 8.24 (s, 2H), 8.14 (s, 2H), 7.51 (dd, J=3.7, 2.2 Hz, 1H), 7.20 (s, 2H), 6.45-6.38 (m, 1H), 5.09 (d, J=5.3 Hz, 2H), 4.79-4.65 (m, 4H), 3.82 (d, J=12.4 Hz, 2H), 3.48-3.41 (m, 2H +HDO), 2.84-2.74 (m, 4H), 2.68-2.64 (m, 1H), 1.82-1.74 (m, 2H), 1.47-1.40 (m, 6H), 1.37 (s, 9H), 1.18-1.08 (m, 2H).

LC/MS (System C): m/z (ESI$^+$)=633 [M$^+$], Rt=1.43 min, UV purity=99%.

Example 39-Synthesis of 2-[({3-amino-5H-pyrrolo[2,3-b]pyrazin-2-yl}formamido)methyl]-6-[(3-aminopropyl)carbamoyl]-1,3-diethyl-1H-1,3-benzodiazol-3-ium hydrochloride chloride

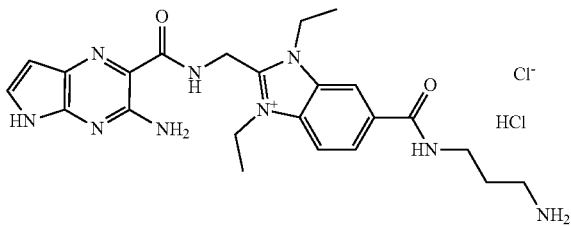 [SMILES: CCn1c(CNC(=O)c2nc3cc[nH]c3nc2N)[n+](CC)c2ccc(C(=O)NCCCN)cc21 ; Cl ; [Cl-]]

HCl solution in dioxane (4.0 M, 0.35 ml, 1.4 mmol) was added to a solution of 2-[({3-amino-5H-pyrrolo[2,3-b]pyrazin-2-yl}formamido)methyl]-6-[(3-{[(tert-butoxy)carbonyl]amino}propyl)carbamoyl]-1,3-diethyl-1H-1,3-benzodiazol-3-ium formic acid formate, Example 35 (180 mg, 0.275 mmol) in MeCN (3 ml). The reaction was stirred at RT for 1 h then concentrated in vacuo. The residue was azeotroped from MeCN (×2) to afford an orange solid. The solid thus obtained was dissolved in 1:1 MeCN:water then lyophilised to afford a yellow solid. The lyophilised solid was suspended in MeCN (1 ml) with sonication. The resulting suspension was left to settle then the supernatant was decanted off with a pipette. The trituration process was repeated once more then the solid was dried under vacuum to afford the product as an orange solid (110 mg, 75%).

$^1$H NMR (500 MHz, DMSO-$d_6$) δ 11.54 (s, 1H), 9.73 (t, J=5.3 Hz, 1H), 9.18-9.08 (m, 1H), 8.63 (s, 1H), 8.23-8.12 (m, 2H), 8.05-7.81 (m, 3H), 7.59-7.46 (m, 1H), 7.46-6.95 (m, 1H), 6.48-6.38 (m, 1H), 5.21-5.02 (m, 2H), 4.87-4.62 (m, 4H), 3.47-3.27 (m, 2H+HDO), 2.98-2.81 (m, 2H), 1.96-1.83 (m, 2H), 1.54-1.36 (m, 6H).

LC/MS (System D): m/z (ESI$^+$)=464 [M$^+$], Rt=1.17 min, UV purity=100%.

Example 40-Synthesis of 2-[({3-amino-5H-pyrrolo[2,3-b]pyrazin-2-yl}formamido)methyl]-1,3-diethyl-6-[(piperidin-4-yl)carbamoyl]-1H-1,3-benzodiazol-3-ium hydrochloride chloride

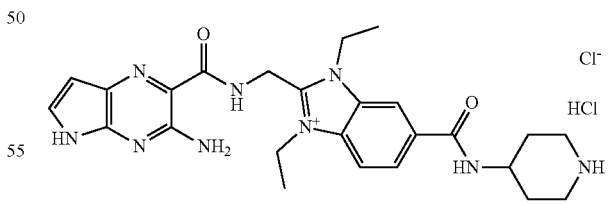

HCl solution in dioxane (4.0 M, 0.37 ml, 1.5 mmol) was added to a solution of 2-[({3-amino-5H-pyrrolo[2,3-b]pyrazin-2-yl}formamido)methyl]-6-({1-[(tert-butoxy)carbonyl]piperidin-4-yl}carbamoyl)-1,3-diethyl-1H-1,3-benzodiazol-3-ium bromide, Example 36 (210 mg, 0.313 mmol) in MeCN (3 ml). The reaction was stirred at RT for 1 h. The reaction mixture was concentrated in vacuo then azeotroped with MeCN (×2). The residue was re-dissolved in MeCN:water then lyophilised. The material thus obtained was suspended in MeCN (1 ml) with sonication. The supernatant was decanted off then the process was repeated with more MeCN (1 ml). The solid thus obtained was dried under vacuum to afford the product as an orange solid (85 mg, 48%).

¹H NMR (500 MHz, DMSO-d₆) δ 11.55 (s, 1H), 9.73 (t, J=5.3 Hz, 1H), 9.00-8.80 (m, 3H), 8.63 (s, 1H), 8.24-8.09 (m, 2H), 7.56-7.47 (m, 1H), 7.47-6.91 (m, 1H), 6.46-6.37 (m, 1H), 5.16-5.04 (m, 2H), 4.82-4.66 (m, 4H), 4.20-4.04 (m, 1H), 3.56-3.19 (m, 2H +HDO), 3.11-2.94 (m, 2H), 2.07-1.96 (m, 2H), 1.94-1.80 (m, 2H), 1.52-1.36 (m, 6H).

LC/MS (System D): m/z (ESI⁺)=490 [M⁺], Rt=1.34 min, UV purity=100%.

Example 41-Synthesis of 2-[({3-amino-5H-pyrrolo [2,3-b]pyrazin-2-yl}formamido)methyl]-6-(4-aminopiperidine-1-carbonyl)-1,3-diethyl-1H-1,3-benzodiazol-3-ium hydrochloride iodide

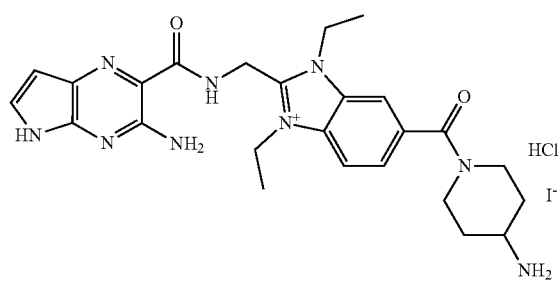 [SMILES: CCn1c(CNC(=O)c2nc3cc[nH]c3nc2N)[n+](CC)c2ccc(C(=O)N3CCC(N)CC3)cc21 ; Cl ; [I-]]

HCl solution in dioxane (4.0 M, 0.25 ml, 1.0 mmol) was added to a solution of 2-[({3-amino-5H-pyrrolo[2,3-b] pyrazin-2-yl}formamido)methyl]-6-(4-{[(tert -butoxy)carbonyl]amino}piperidine-1-carbonyl)-1,3-diethyl-1H-1,3-benzodiazol-3-ium bromide, Example 37 (135 mg, 0.201 mmol) in MeCN (3 ml). The reaction mixture was stirred at RT for 20 min then concentrated in vacuo. The residue was azeotroped from MeCN (×2) then re-dissolved in water and lyophilised to afford the product as an orange solid (123 mg, 99%).

¹H NMR (500 MHz, DMSO-d₆) δ 11.55 (s, 1H), 9.73 (t, J=5.3 Hz, 1H), 8.99-8.76 (m, 3H), 8.62 (s, 1H), 8.25-8.10 (m, 2H), 7.52 (dd, J=3.8, 2.5 Hz, 1H), 7.18 (s, 1H), 6.47-6.37 (m, 1H), 5.10 (d, J=5.3 Hz, 2H), 4.74 (m, 4H), 4.12 (m, 1H), 3.40-3.25 (m, 2H+HDO), 3.14-2.94 (m, 2H), 2.07-1.98 (m, 2H), 1.93-1.80 (m, 2H), 1.43 (m, 6H).

LC/MS (System C): m/z (ESI⁺)=490 [M⁺], Rt=0.98 min, UV purity=97%.

Example 42-Synthesis of 2-[({3-amino-5H-pyrrolo [2,3-b]pyrazin-2-yl}formamido)methyl]-6-{[2-(4-aminopiperidin-1-yl)ethyl]carbamoyl}-1,3-diethyl-1H -1,3-benzodiazol-3-ium trifluoroacetic acid trifluoroacetate

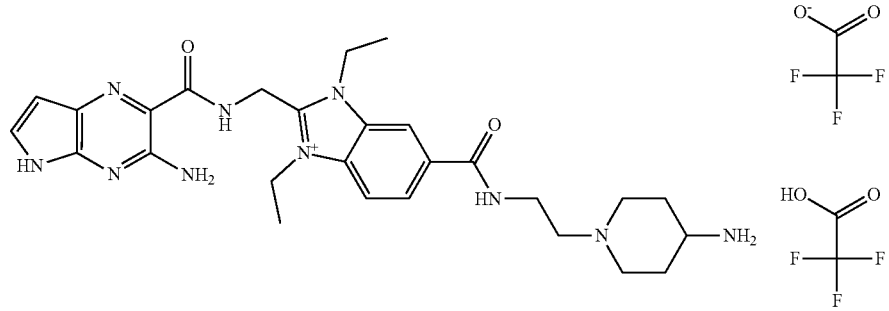 [SMILES: CCn1c(CNC(=O)c2nc3cc[nH]c3nc2N)[n+](CC)c2ccc(C(=O)NCCN3CCC(N)CC3)cc21 ; O=C(O)C(F)(F)F ; O=C([O-])C(F)(F)F]

HCl solution in dioxane (4.0 M, 1.6 ml, 6.4 mmol) was added to a suspension of 2-[({3-amino-5H-pyrrolo[2,3-b] pyrazin-2-yl}formamido)methyl]-6-{[2-(4-{[(tert -butoxy) carbonyl]amino}piperidin-1-yl)ethyl]carbamoyl}-1,3-diethyl-1H-1,3-benzodiazol-3-ium formate Example 38 (99%, 250 mg, 0.36 mmol) in dioxane (4 ml). The resulting mixture was stirred at RT for 30 min then heated to 40° C. for 45 min. MeCN (10 ml) was added then the reaction was heated at 40° C. for 45 min then concentrated in vacuo. The residue was suspended in dioxane (4 ml) then HCl solution in dioxane (4.0 M, 1.6 ml, 6.4 mmol) was added. MeOH was added drop-wise until the suspension became a homogeneous solution. The resulting solution was stirred at RT for 1 h then concentrated in vacuo. The residue was suspended in MeCN (15 ml) with sonication then the solid was left to settle. The supernatant was decanted off with a pipette then the trituration process was repeated (x3). The residual solid was dried under vacuum then purified by flash column chromatography on C18 (30 g). The column was eluted with MeCN:water+0.1% TFA using the following gradient (% MeCN, column volumes): 0%, 2 CV; 0-20%, 20 CV; 20-30%, 2 CV; 30-100%, 2 CV; 100%, 2 CV. The desired fractions were combined and concentrated in vacuo. The residue was re-dissolved in water:MeCN (9:1) then lyophilised to afford the product as an orange solid (190 mg, 68%).

¹H NMR (500 MHz, DMSO-d₆) δ 11.55 (s, 1H), 9.73 (t, J=5.3 Hz, 1H), 9.25-9.11 (m, 3H), 8.95 (d, J=10.0 Hz, 1H), 8.79-8.65 (m, 1H), 8.54 (s, 1H), 8.21-8.15 (m, 2H), 7.80-6.80 (m, 2H), 6.42 (dd, J=3.8, 1.7 Hz, 1H), 5.11 (d, J=5.3 Hz, 2H), 4.77-4.68 (m, 4H), 3.65 (q, J=6.2 Hz, 2H), 3.41 (d, J=12.5 Hz, 3H), 3.25-3.15 (m, 2H), 2.94 (q, J=12.4 Hz, 2H), 2.20 (d, J=12.5 Hz, 2H), 1.81-1.68 (m, 2H), 1.49-1.38 (m, 6H).

LC/MS (System D): m/z (ESI⁺)=533 [M⁺], Rt=1.31 min, UV purity=99%.

Example 43-Synthesis of 2-[({3-amino-5H-pyrrolo[2,3-b]pyrazin-2-yl}formamido)methyl]-5-(2-{bis[(2S,3R,4R,5R)-2,3,4,5,6-pentahydroxyhexyl]amino}ethoxy)-1,3-diethyl-1H-1,3-benzodiazol-3-ium trifluoroacetic acid trifluoroacetate

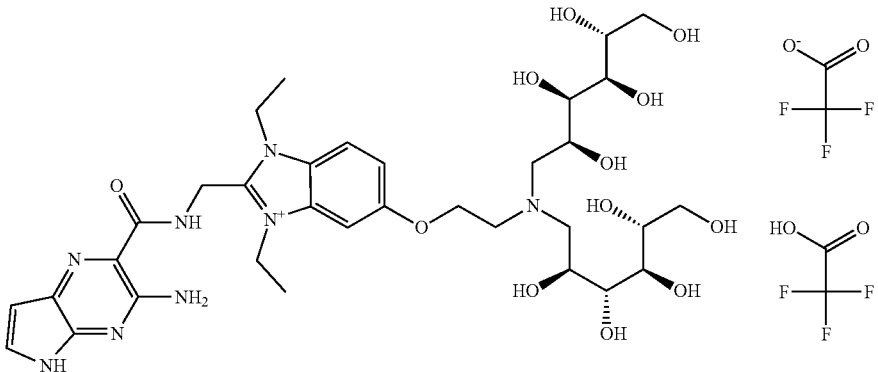 [SMILES: CCn1c(CNC(=O)c2nc3cc[nH]c3nc2N)[n+](CC)c2cc(OCCN(C[C@H](O)[C@@H](O)[C@H](O)[C@H](O)CO)C[C@H](O)[C@@H](O)[C@H](O)[C@H](O)CO)ccc21 ; O=C(O)C(F)(F)F ; O=C([O-])C(F)(F)F]

A solution of 2-(aminomethyl)-5-(2-{bis[(2S,3R,4R,5R)-2,3,4,5,6-pentahydroxyhexyl]amino}ethoxy)-1,3-diethyl-1H-1,3-benzodiazol-3-ium dihydrochloride chloride, Intermediate 89 (70%, 1.53 g, 1.53 mmol), (3-amino-5H-pyrrolo[2,3-b]pyrazin-2-yl)-imidazol-1-yl-methanone, Intermediate 4 (734 mg, 3.22 mmol) and imidazole hydrochloride (336 g, 3.22 mmol) in DMF (14 ml) was stirred at RT for 44 h. Additional (3-amino-5H-pyrrolo[2,3-b]pyrazin-2-yl)-imidazol-1-yl-methanone, Intermediate 4 (150 mg, 0.657 mmol) was added then the reaction was left to stir for a further 72 h at RT. The reaction mixture was diluted with water (30 ml) and filtered. The solid was rinsed through with water (2×10 ml). The filtrate was concentrated in vacuo to a brown/yellow oil. The crude material was purified by flash column chromatography on C18 (60 g). The column was eluted with MeCN:water+0.1% TFA using the following gradient (% MeCN, column volumes): 10%, 2 CV; 10-18%, 15 CV; 18-25%, 2 CV; 25-30%, 1 CV; 30%, 1 CV; 30-36%, 1 CV; 36-40%, 1 CV; 40-100%, 4 CV; 100%, 1 CV. The desired fractions were combined and lyophilised to afford a yellow solid (524 mg). A sample (120 mg) of the material thus obtained was further purified by HPLC (Method D). The desired fractions were combined and lyophilised to afford an orange solid (54 mg). The material thus obtained was further purified by flash column chromatography on C18 (60 g). The column was eluted with MeCN:water+0.1% TFA using the following gradient (% MeCN, column volumes): 0%, 7 CV; 0-20%, 17 CV; 20%, 3 CV; 20-100%, 3 CV; 100%, 1 CV. The desired fractions were combined and lyophilised to afford the product as an orange solid (14 mg, 1%).

$^1$H NMR (500 MHz, CD$_3$OD) δ 7.89 (d, J=9.1Hz, 1H), 7.57 (d, J=1.9 Hz, 1H), 7.43 (dd, J=9.1, 2.1Hz, 1H), 7.39 (d, J=3.8 Hz, 1H), 6.44 (d, J=3.8 Hz, 1H), 5.09 (s, 2H), 4.76 (q, J=7.2 Hz, 4H), 4.57 (s (br), 2H), 4.22 (s (br), 2H), 4.01-3.41 (m, 16H), 1.58-1.51 (m, 6H).

LC/MS (System D): m/z (ESI$^+$)=751 [M$^+$], Rt=1.42 min, UV purity=98%.

Example 44-Synthesis of 2-[({3-amino-5H-pyrrolo[2,3-b]pyrazin-2-yl}formamido)methyl]-5-(3-{bis[(2S,3R,4R,5R)-2,3,4,5,6-pentahydroxyhexyl]amino}propoxy)-1,3-diethyl-1H-1,3-benzodiazol-3-ium trifluoroacetic acid trifluoroacetate A mixture of 2-(aminomethyl)-5-(3-{bis[(2S,3R,4R,5R)-2,3,4,5,6-pentahydroxyhexyl]amino}propoxy)-1,3-diethyl-1H-1,3-benzodiazol-3-ium hydrochloride chloride, Intermediate 93 (80%, 200 mg, 0.24 mmol), 2-(1H-imidazole-1-carbonyl)-5H-pyrrolo[2,3-b]pyrazin-3-amine, Intermediate 4 (95%, 120 mg, 0.50 mmol) and 1H-imidazole hydrochloride (1:1) (52 mg, 0.50 mmol) in DMF (2.5 ml) was stirred at RT for 64 h. The reaction mixture was diluted with water (5 ml) then the solid was collected by filtration and washed with water (2×5 ml). The combined filtrate was concentrated in vacuo to afford the crude product as a yellow/brown oil. The crude material was purified by flash column chromatography on C18 (60 g). The column was eluted with MeCN:water+0.1% TFA using the following gradient (% MeCN, column volumes): 10%, 2 CV; 10-19%, 11 CV; 19-25%, 3 CV; 25-100%, 2 CV; 100%, 1 CV. The desired fractions were combined and lyophilised to afford the product as a yellow solid (40 mg, 15%).

$^1$H NMR (500 MHz, CD$_3$OD) δ 7.88 (d, J=9.2 Hz, 1H), 7.51 (d, J=2.1Hz, 1H), 7.44-7.38 (m, 2H), 6.46 (d, J=3.8 Hz, 1H), 5.10 (s, 2H), 4.78 (q, J=7.3 Hz, 4H), 4.38-4.30 (m, 2H), 4.25 (s (br), 2H), 3.86 (s, 2H), 3.81-3.75 (m, 2H), 3.74-3.51 (m, 10H), 3.50-3.40 (m, 2H), 2.38 (s (br), 2H), 1.56 (t, J=7.1Hz, 6H).

LC/MS (System D): m/z (ESI$^+$)=765 [M$^+$], Rt=1.36 min, UV purity=95%.

Example 45-Synthesis of 2-[({3-amino-5H-pyrrolo[2,3-b]pyrazin-2-yl}formamido)methyl]-5-(3-{bis[(2S,3R,4R,5R)-2,3,4,5,6-pentahydroxyhexyl]amino}propyl)-1,3-diethyl-1H-1,3-benzodiazol-3-ium trifluoroacetic acid trifluoroacetate Step 1: A mixture of 2-[({3-amino-5H-pyrrolo[2,3-b]pyrazin-2-yl}formamido)methyl]-6-(3-aminopropyl)-1,3-diethyl-1H-1,3-benzodiazol-3-ium hydrochloride chloride, Example 29 (350 mg, 0.55 mmol), 4,6-O-benzylidene-D-glucopyranose (571 mg, 2.13 mmol) and AcOH (122 μl, 2.13 mmol) in MeOH (30 ml) was stirred at RT for 0.5 h. NaCNBH$_3$ (134 mg, 2.13 mmol) was added. The resulting mixture was stirred at RT for 16 h. The reaction mixture was re-charged with 4,6-O-benzylidene-D-glucopyranose (591 mg, 2.20 mmol) and NaCNBH$_3$ (138 mg, 2.20 mmol) then left to stir at RT for a further 24 h. The reaction mixture was re-charged with 4,6-O-benzylidene-D-glucopyranose (295 mg, 1.10 mmol) and NaCNBH$_3$ (69 mg, 1.1 mmol) then left to stir at RT for a further 96 h. Saturated aqueous NaHCO$_3$ (30 ml) solution was added dropwise over 5 min then the resultant suspension was sonicated and filtered. The solid collected was washed with water (20 ml) then dried under vacuum. The crude solid thus obtained was purified by flash column chromatography on C18 (60 g). The column was eluted with MeCN:water, sing the following gradient (% MeCN, column volumes): 0%, 2 CV; 0-100%, 12 CV; 100-5%, 2 CV. The column was then further eluted with MeCN:water, +0.1% TFA using the following gradient (% MeCN, column volumes): 0%, 2 CV; 0-50%, 8 CV; 50%, 3 CV; 50-100%, 5 CV. The desired fractions were combined and concentrated in vacuo to afford the protected product as a yellow oil (85 mg). Step 2: 2.0 M aqueous HCl solution (0.53 ml) was added to a solution of the intermediate from Step 1, 2-[({3-amino-5H-pyrrolo[2,3-b]pyrazin-2-yl}formamido)methyl]-5-(3-{bis[(2S,3R)-2,3-dihydroxy-3-[(4R,5R)-5-hydroxy-2-phenyl-1,3-dioxan-4-yl]propyl]amino}propyl)-1,3-diethyl-1H-1,3-benzodiazol-3-ium iodide (80%, 70 mg, 0.053 mmol) in EtOH:water (1:1, 2 ml). The reaction mixture was stirred for 4 h at RT. The reaction mixture was concentrated in vacuo. The crude material was purified by preparative HPLC (Method E). The desired fractions were combined and lyophilised to afford the product as yellow solid (20 mg, 38% over 2 steps).

$^1$H NMR (500 MHz, CD$_3$OD) δ 7.93 (d, J=8.6 Hz, 1H), 7.89 (s, 1H), 7.65 (dd, J=8.6, 0.8 Hz, 1H), 7.41 (d, J=3.8 Hz, 1H), 6.46 (d, J=3.8 Hz, 1H), 5.17-5.09 (m, 2H), 4.82-4.76 (m, 4H), 4.21-4.10 (m, 2H), 3.84 (dd, J=4.5, 1.6 Hz, 2H), 3.79 (dd, J=11.0, 3.4 Hz, 2H), 3.75-3.62 (m, 6H), 3.52-3.37 (m, 4H), 3.10-2.92 (m, 2H), 2.22 (s, 2H), 1.57 (q, J=7.1Hz, 6H), 1.32 (d, J=7.3 Hz, 2H).

LC/MS (System C): m/z (ESI$^+$)=749 [M$^+$], Rt=1.43 min, UV purity=98%.

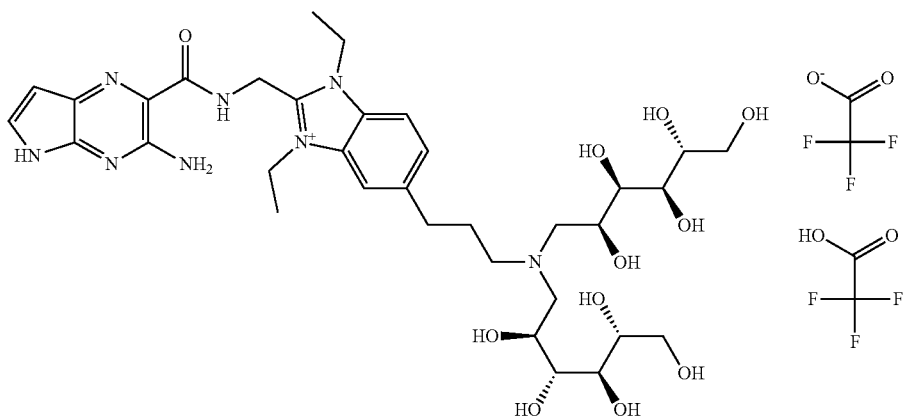 [SMILES: CCn1c(CNC(=O)c2nc3cc[nH]c3nc2N)[n+](CC)c2cc(CCCN(C[C@H](O)[C@@H](O)[C@H](O)[C@H](O)CO)C[C@H](O)[C@@H](O)[C@H](O)[C@H](O)CO)ccc21 ; O=C([O-])C(F)(F)F ; O=C(O)C(F)(F)F]

Example 46-Synthesis of 2-[({3-amino-5H-pyrrolo [2,3-b]pyrazin-2-yl}formamido)methyl]-1,3-diethyl-6-{1-[(2S,3R,4R,5R)-2,3,4,5,6-pentahydroxyhexyl] piperidin-4-yl}-1H-1,3-benzodiazol-3-ium trifluoroacetic acid trifluoroacetate

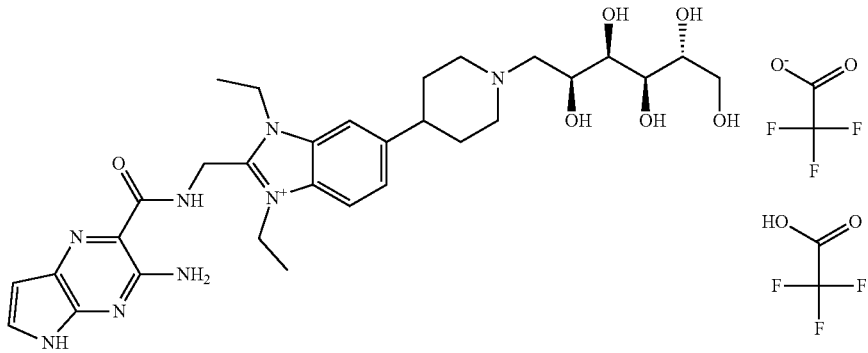 [SMILES: CCn1c(CNC(=O)c2nc3cc[nH]c3nc2N)[n+](CC)c2ccc(C3CCN(C[C@H](O)[C@@H](O)[C@H](O)[C@H](O)CO)CC3)cc21 ; O=C([O-])C(F)(F)F ; O=C(O)C(F)(F)F]

2.0 M aqueous HCl solution (4.7 ml, 9.4 mmol) was added to a solution of 2-[({3-amino -5H-pyrrolo[2,3-b] pyrazin-2-yl}formamido)methyl]-6-{1-[(2S,3R)-2,3-dihydroxy-3-[(4R,5R) -5-hydroxy-2-phenyl-1,3-dioxan-4-yl] propyl]piperidin-4-yl}-1,3-diethyl-1H-1,3-benzodiazol -3-ium iodide, Intermediate 99 (390 mg, 0.470 mmol) in water (3 ml). The resulting solution was sonicated for 5 min then stirred at RT for 1.5 h. The reaction mixture was concentrated in vacuo then purified by flash column chromatography on C18 (30 g). The column was eluted with MeCN:water+0.1% TFA using the following gradient (% MeCN, column volumes): 0%, 2 CV; 0-6%, 4 CV; 6-13%, 4 CV; 13-25%, 8 CV; 25-42%, 2 CV; 42-52%, 1 CV; 52-100%, 1 CV; 100% 2 CV. The desired fractions were combined and lyophilised to afford the product as a yellow solid (120 mg, 30%).

$^1$H NMR (250 MHz, 353 K, 5% $D_2O$ in DMSO-$d_6$) δ 7.97 (d, J=8.7 Hz, 1H), 7.83 (s, 1H), 7.59 (d, J=8.4 Hz, 1H), 7.44 (d, J=3.8 Hz, 1H), 6.40 (d, J=3.8 Hz, 1H), 5.08 (s, 2H), 4.75-4.60 (m, 4H), 4.18-4.10 (m, 1H), 3.77-3.41 (m, 8H), 3.36-3.00 (m, 4H+HDO), 2.11 (s, 4H), 1.44 (dt, J=7.1, 3.5 Hz, 6H).

LC/MS (System C): m/z (ESI$^+$)=611 [M$^+$], Rt=0.91 min, UV purity=100%.

Example 47-Synthesis of 2-[({3-amino-5H-pyrrolo [2,3-b]pyrazin-2-yl}formamido)methyl]-1,3-diethyl-6-(1-{1-[(2S,3R,4R,5R)-2,3,4,5,6-pentahydroxyhexyl]piperidin-4-yl}-1H-pyrazol-4-yl)-1H-1,3-benzodiazol-3-ium trifluoroacetic acid trifluoroacetate

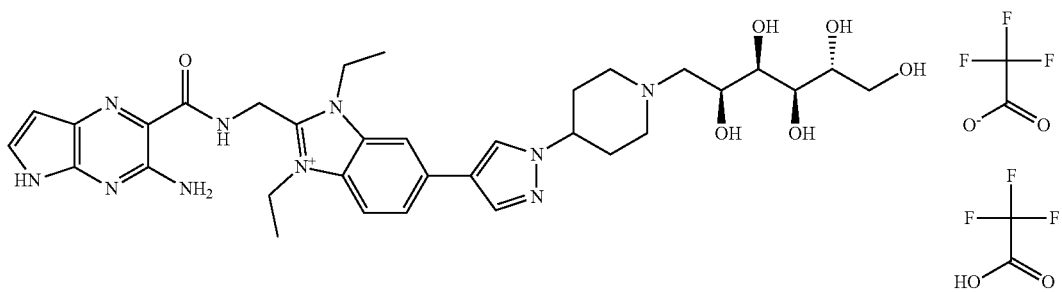 [SMILES: CCn1c(CNC(=O)c2nc3cc[nH]c3nc2N)[n+](CC)c2ccc(-c3cnn(C4CCN(C[C@H](O)[C@@H](O)[C@H](O)[C@H](O)CO)CC4)c3)cc21 ; O=C([O-])C(F)(F)F ; O=C(O)C(F)(F)F]

Step 1: A solution of 2-[({3-amino-5H-pyrrolo[2,3-b]pyrazin-2-yl}formamido)methyl]-1,3-diethyl-6-[1-(piperidin-4-yl)-1H-pyrazol-4-yl]-1H-1,3-benzodiazol-3-ium hydrochloride iodide, Example 31 (360 mg, 0.53 mmol) in MeOH (20 ml), 4,6-O-benzylidene-D-1.5 glucopyranose (417 mg, 1.55 mmol) and AcOH (89 µl, 1.56 mmol) was stirred at RT for 20 min. NaCNBH₃ (98 mg, 1.56 mmol) was added then the resulting mixture was stirred at RT for 48 h. The reaction was recharged with 4,6-O-benzylidene-D-glucopyranose (142 mg, 0.53 mmol) and AcOH (81 µl, 0.53 mmol) then the reaction was stirred at RT for a further 4 h.

Example 48-Synthesis of 2-[({3-amino-5H-pyrrolo[2,3-b]pyrazin-2-yl}formamido)methyl]-6-[(3-{bis[(2S,3R,4R,5R)-2,3,4,5,6-pentahydroxyhexyl]amino}propyl)carbamoyl]-1,3-diethyl-1H-1,3-benzodiazol-3-ium trifluoroacetic acid trifluoroacetate

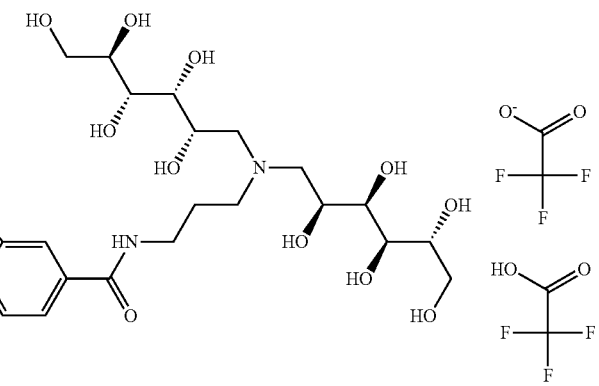

Saturated aqueous NaHCO₃ (40 ml) solution was added dropwise over 5 min then the resultant suspension was filtered. The solid collected was washed with water (40 ml) then dried under vacuum to afford the protected intermediate as a yellow solid. Step 2: Aqueous HCl solution (2.0 M, 10 ml, 20 mmol) was added to a solution of the Intermediate from Step 1, 2-[({3-amino-5H-pyrrolo[2,3-b]pyrazin-2-yl}formamido)methyl]-6-(1-{1-[(2S,3R)-2,3-dihydroxy-3-[(4R,5R)-5-hydroxy-2-phenyl-1,3-dioxan-4-yl]propyl]piperidin-4-yl}-1H-pyrazol-4-yl)-1,3-diethyl-1H-1,3-benzodiazol-3-ium chloride (70%, 275 mg, 0.251 mmol) in water (5 ml). The reaction was stirred at RT for 5 min then THF (5 ml) was added. The reaction mixture was concentrated in vacuo then the crude material was purified by flash column chromatography on C18 (30 g). The column was eluted with MeCN:water using the following gradient (% MeCN, column volumes): 0%, 3 CV; 2-10%, 2 CV; 10-21%, 3 CV; 21-42%, 1 CV; 42-50%, 1 CV. The column was then eluted with MeCN:water+0.1% formic acid using the following gradient (% MeCN, column volumes): 0%, 2 CV; 0-10%, 4 CV; 10-29%, 1 CV; 29-57%, 1 CV; 29-57%, 1 CV; 100%, 2 CV. The desired fractions were combined and concentrated in vacuo to afford a black gum (280 mg). The material thus obtained was further purified by preparative HPLC (Method E). The desired fractions were combined then lyophilised to afford the product as a yellow solid (18 mg, 8%).

¹H NMR (500 MHz, DMSO-d₆) δ 11.53 (s, 1H), 9.72 (t, J=5.3 Hz, 1H), 9.23 (s, 1H), 8.57-8.43 (m, 1H), 8.45 (s, 0.75 H), 8.25 (s, 1H), 8.18 (d, J=12.1Hz, 1H), 8.06 (dd, J=8.7, 4.8 Hz, 1H), 7.94 (dd, J=8.6, 1.2 Hz, 1H), 7.52 (dd, J=3.7, 2.5 Hz, 1H), 7.22 (s, 2H), 6.42 (dd, J=3.8, 1.7 Hz, 1H), 5.50 (s, 1H), 5.07 (d, J=5.2 Hz, 2H), 4.81 (d, J=45.4 Hz, 1H), 4.69 (q, J=6.8 Hz, 4H), 4.61 (s, 2H), 4.54-4.38 (m, 2H), 4.09-3.95 (m, 1H), 3.73-3.57 (m, 4H), 3.56-3.39 (m, 4H), 3.28-3.13 (m, 5H), 2.34-2.20 (m, 2H), 1.43 (dt, J=10.8, 7.2 Hz, 6H).

LC/MS (System C): m/z (ESI⁺)=677 [M⁺], Rt=1.20 min, UV purity=100%.

A solution of 2-[({3-amino-5H-pyrrolo[2,3-b]pyrazin-2-yl}formamido)methyl]-6-carboxy-1,3-diethyl-1H-1,3-benzodiazol-3-ium bromide, Example 34 (200 mg, 0.410 mmol) and CDI (100 mg, 0.614 mmol) in DMF (2 ml) was stirred at RT for 4 h. The resulting solution was added to (2R,3R,4R,5S)-6-[(3-aminopropyl)[(2S,3R,4R,5R)-2,3,4,5,6-pentahydroxyhexyl]amino]hexane-1,2,3,4,5-pentol dihydrochloride, Intermediate 104 (234 mg, 0.490 mmol) and rinsed into the reaction flask with DMF (2×1 ml). The resulting solution was stirred at RT for 18 h. The reaction mixture was concentrated in vacuo then the crude material was purified by flash column chromatography on C18 (30 g). The column was eluted with MeCN:water+0.1% TFA using the following gradient (% MeCN, column volumes): 5%, 2 CV; 5-25%, 11 CV; 25%, 2 CV; 25-34%, 1 CV; 34-100%, 2 CV; 100%, 1 CV. The desired fractions were combined and lyophilised to afford the product as a yellow solid (160 mg, 38%).

δ (ppm): ¹H NMR (500 MHz, CD₃OD) δ 8.47 (s, 1H), 8.18 (dd, J=8.8, 1.4 Hz, 1H), 8.08 (d, J=8.8 Hz, 1H), 7.39 (d, J=3.8 Hz, 1H), 6.44 (d, J=3.8 Hz, 1H), 5.19-5.10 (m, 2H), 4.94-4.74 (m, 4H+HDO), 4.26-4.15 (m, 2H), 3.88-3.81 (m, 2H), 3.81-3.73 (m, 2H), 3.73-3.38 (m, 14H), 2.24-2.10 (m, 2H), 1.67-1.51 (m, 6H).

LC/MS (System D): m/z (ESI⁺)=792 [M⁺], Rt=1.24 min, UV purity=100%.

Example 49-Synthesis of 2-[({3-amino-5H-pyrrolo[2,3-b]pyrazin-2-yl}formamido)methyl]-1,3-diethyl-6-({1-[(2S,3R,4R,5R)-2,3,4,5,6-pentahydroxyhexyl]piperidin-4-yl}carbamoyl)-1H-1,3-benzodiazol-3-ium trifluoroacetic acid trifluoroacetate

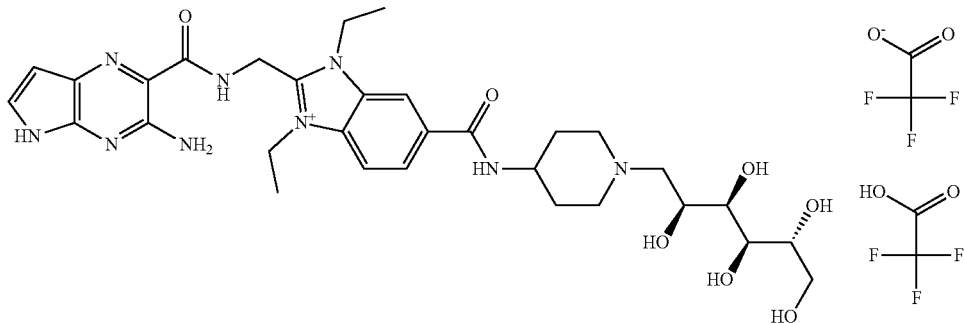 [SMILES: CCn1c(CNC(=O)c2nc3cc[nH]c3nc2N)[n+](CC)c2ccc(C(=O)NC3CCN(C[C@H](O)[C@@H](O)[C@H](O)[C@H](O)CO)CC3)cc21 ; O=C([O-])C(F)(F)F ; O=C(O)C(F)(F)F]

A mixture of 2-[({3-amino-5H-pyrrolo[2,3-b]pyrazin-2-yl}formamido) methyl]-6-carboxy -1,3-diethyl-1H-1,3-benzodiazol-3-ium bromide, Example 34 (150 mg, 0.31 mmol) and CDI (75 mg, 0.46 mmol) in DMF (8 ml) was stirred for 1 h at RT then (2R,3R,4R,5S)-6-(4-aminopiperidin-1-yl) hexane-1,2,3,4,5-pentol dihydrochloride, Intermediate 109 (140 mg, 0.42 mmol) was added. The reaction was left to stir at RT for 64 h then concentrated in vacuo. The crude material was purified by flash column chromatography on C18 (30 g). The column was eluted with MeCN:water+0.1% TFA using the following gradient (% MeCN, column volumes): 0%, 2 CV; 0-8%, 6 CV; 8-9%, 1 CV; 9-20%, 5 CV; 20-25%, 2 CV; 25-44%, 3 CV; 44-51%, 1 CV; 51-100%, 1 CV; 100%, 1 CV. The desired fractions were combined and lyophilised to afford the product as a yellow solid (46 mg, 17%).

$^1$H NMR (500 MHz, 5% $D_2O$ in DMSO-$d_6$) δ 8.37 (s, 1H), 8.08 (s, 2H), 7.46 (d, J=3.8 Hz, 1H), 6.43 (d, J=3.8 Hz, 1H), 5.06 (s, 2H), 4.75-4.61 (m, 4H), 4.19-3.97 (m, 2H), 3.68-3.30 (m, 8H), 3.20-2.99 (m, 3H) (m, 3H), 2.19-1.74 (m, 4H), 1.40 (dt, J=15.9, 7.4 Hz, 6H).

LC/MS (System D): m/z (ESI$^+$)=654 [M$^+$], Rt=1.38 min, UV purity=100%.

Example 50-Synthesis of 2-[({3-amino-5H-pyrrolo[2,3-13]pyrazin-2-yl}formamido) methyl]-6-(4-{bis[(2S,3R,4R,5R)-2,3,4,5,6-pentahydroxyhexyl]amino}piperidine-1-carbonyl)-1,3-diethyl-1H-1,3-benzodiazol-3-ium trifluoroacetic acid trifluoroacetate

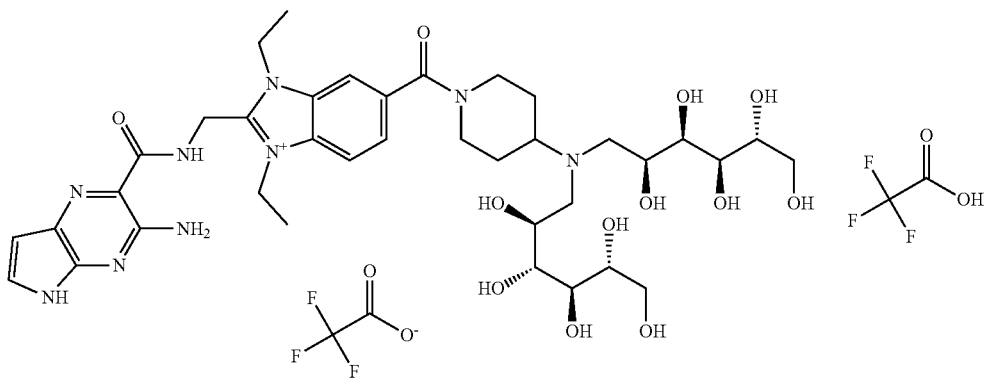 [SMILES: CCn1c(CNC(=O)c2nc3cc[nH]c3nc2N)[n+](CC)c2ccc(C(=O)N3CCC(N(C[C@H](O)[C@@H](O)[C@H](O)[C@H](O)CO)C[C@H](O)[C@@H](O)[C@H](O)[C@H](O)CO)CC3)cc21 ; O=C([O-])C(F)(F)F ; O=C(O)C(F)(F)F]

A solution of 2-[({3-amino-5H-pyrrolo[2,3-b]pyrazin-2-yl}formamido)methyl]-6-carboxy -1,3-diethyl-1H-1,3-benzodiazol-3-ium bromide, Example 34 (210 mg, 0.43 mmol) and CDI (105 mg, 0.65 mmol) in DMF (2 ml) was stirred at RT for 1.5 h. The reaction mixture was added to (2R,3R,4R,5S)-6-{[(2S,3R,4R,5R)-2,3,4,5,6-pentahydroxyhexyl](piperidin -4-yhamino}hexane-1,2,3,4,5-pentol dihydrochloride, Intermediate 112 (260 mg, 0.52 mmol). The reaction mixture was left to stir at RT for 16 h then concentrated in vacuo. The crude material was purified by flash column chromatography on C18 (30 g). The column was eluted with MeCN:water+0.1% TFA using the following gradient (% MeCN, column volumes): 5%, 2 CV; 5-12%, 6 CV; 12%, 3 CV; 12-20%, 6 CV; 20-51%, 3 CV; 25-93%, 2 CV. The desired fractions were combined and lyophilised to afford the product as a yellow solid (114 mg, 25%).

$^1$H NMR (500 MHz, DMSO-d$_6$) δ 11.54 (s, 1H), 9.74 (t, J=5.3 Hz, 1H), 8.34-8.07 (m, 3H), 7.73 (d, J=9.3 Hz, 1H), 7.57-7.48 (m, 1H), 7.32-7.06 (m, 2H), 6.46-6.38 (m, 1H), 5.64-5.44 (m, 2H), 5.14-5.02 (m, 2H), 4.94-4.33 (m, 12H), 4.12-3.93 (m, 2H), 3.90-3.78 (m, 1H), 3.77-3.69 (m, 2H), 3.33 (15H +HDO), 2.95-2.74 (m, 1H), 2.27-1.55 (m, 4H), 1.49-1.36 (m, 6H).

LC/MS (System D): m/z (ESI+)=818 [M$^+$], Rt=1.33 min, UV purity=100%.

Example 51—Synthesis of 2-[({3-amino-5H-pyrrolo[2,3-b]pyrazin-2-yl}formamido) methyl]-6-{[2-(4-{bis[(2S,3R,4R,5R)-2,3,4,5,6-pentahydroxyhexyl]amino}piperidin-1-yl)ethyl]carbamoyl}-1,3-diethyl-1H-1,3-benzodiazol-3-ium trifluoroacetic acid trifluoroacetate A solution of 2-[({3-amino-5H-pyrrolo[2,3-b]pyrazin-2-yl}formamido)methyl]-6-carboxy -1,3-diethyl-1H-1,3-benzodiazol-3-ium bromide, Example 34 (210 mg, 0.43 mmol) and CDI (98 mg, 0.60 mmol) in DMF (5 ml) was stirred at RT for 45 min. The resultant solution was added to (2R,3R,4R,5S)-6-{[1-(2-aminoethyl)piperidin-4-yl][(2S,3R,4R,5R) -2,3,4,5,6-pentahydroxyhexyl]amino}hexane-1,2,3,4,5-pentol trihydrochloride, Intermediate 116 (88%, 500 mg, 0.76 mmol) and rinsed into the flask with DMF (0.5 ml). The resultant reaction mixture was stirred at RT for 64 h. The reaction mixture was concentrated in vacuo then purified by flash column chromatography on C18 (30 g). The column was eluted with MeCN:water+0.1% TFA using the following gradient (% MeCN, column volumes): 0%, 2 CV; 0-20%, 20 CV; 20%, 2 CV; 20-100%, 2 CV; 100% 2 CV. The desired fractions were combined and lyophilised to afford the product as a yellow solid (216 mg, 46%).

$^1$H NMR (500 MHz, CD$_3$OD) δ 8.52 (s, 1H), 8.24 (d, J=8.7 Hz, 1H), 8.12 (d, J=8.8 Hz, 1H), 7.43 (d, J=3.8 Hz, 1H), 6.48 (d, J=3.8 Hz, 1H), 5.19 (s, 2H), 4.93-4.84 (m, 4H+HDO), 4.22 (s, 2H), 4.10-3.63 (m, 16H), 3.55-3.38 (m, 5H), 3.22-3.05 (m, 2H), 2.50-2.09 (m, 4H), 1.68-1.56 (m, 6H).

LC/MS (System D): m/z (ESI+)=431.5 [(M$^+$)], Rt=1.31 min, UV purity=100%.

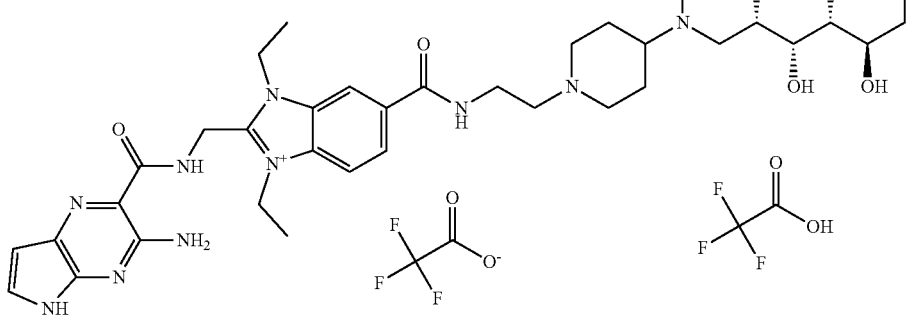

Example 52—Synthesis of 2-[({3-amino-5H-pyrrolo[2,3-b]pyrazin-2-yl}formamido)methyl]-5-[4-({bis[(2S,3R,4R,5R)-2,3,4,5,6-pentahydroxyhexyl]amino}methyl)piperidine-1-carbonyl]-1,3-diethyl-1H-1,3-benzodiazol-3-ium trifluoroacetic acid trifluoroacetate

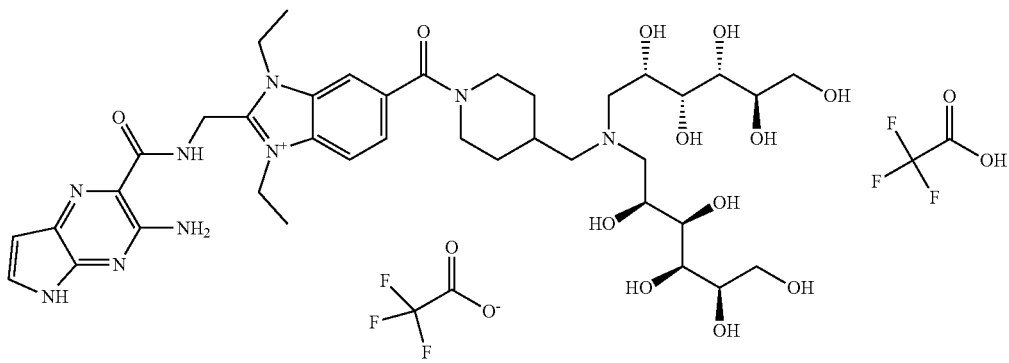 [SMILES: CCn1c(CNC(=O)c2nc3cc[nH]c3nc2N)[n+](CC)c2ccc(C(=O)N3CCC(CN(C[C@H](O)[C@@H](O)[C@H](O)[C@H](O)CO)C[C@H](O)[C@@H](O)[C@H](O)[C@H](O)CO)CC3)cc21 ; O=C([O-])C(F)(F)F ; O=C(O)C(F)(F)F]

A solution of 2-[({3-amino-5H-pyrrolo[2,3-b]pyrazin-2-yl}formamido)methyl]-6-carboxy -1,3-diethyl-1H-1,3-benzodiazol-3-ium bromide, Example 34 (196 mg, 0.402 mmol) and CDI (98 mg, 0.60 mmol) in DMF (1.5 ml) was stirred at RT for 3.5 h. (2R,3R,4R,5S)-6-{[(2S,3R,4R,5R)-2,3,4,5,6-Pentahydroxyhexyl][(piperidin-4-yl)methyl]amino}hexane -1,2,3,4,5-pentol dihydrochloride, Intermediate 121 (93%, 248 mg, 0.448 mmol) was added then the reaction was left to stir at RT for 16 h. The reaction mixture was purified by flash column chromatography on C18 (30 g). The column was eluted with MeCN:H$_2$O+0.1% TFA using the following gradient (% MeCN, column volumes): 5%, 1.5 CV; 5-25%, 10.5 CV; 25%, 2 CV; 25-34%, 1 CV; 34-100%, 2 CV; 100% 2 CV. The desired fractions were combined and lyophilised to afford the product as a yellow solid (72 mg, 17%).

$^1$H NMR (500 MHz, DMSO-d$_6$) δ 11.55 (s, 1H), 9.75 (t, J=5.3 Hz, 1H), 8.20-8.09 (m, 2H), 7.83 (s, 1H), 7.73-7.62 (m, 1H), 7.58-7.48 (m, 1H), 7.21 (s, 2H), 6.48-6.38 (m, 1H), 5.73-5.48 (m, 2H), 5.18-5.01 (m, 2H), 4.97-4.40 (m, 13H), 4.09-3.87 (m, 2H), 3.77-3.66 (m, 2H), 3.65-3.06 (m, 16H), 2.97-2.73 (m, 1H), 2.27-2.08 (m, 1H), 2.04-1.52 (m, 2H), 1.52-1.36 (m, 6H), 1.35-1.13 (m, 2H).

LC/MS (System D): m/z (ESI$^+$)=832 [M$^+$], R$_t$=1.33 min, UV purity=99%.

Example 53—Synthesis of 2-[({3-amino-5H-pyrrolo[2,3-b]pyrazin-2 -yl}formamido)methyl]-6-[(3R)-3-{bis[(2S,3R,4R,5R)-2,3,4,5,6 -pentahydroxyhexyl]amino}pyrrolidine-1-carbonyl]-1,3-diethyl-1H-1,3-benzodiazol -3-ium trifluoroacetic acid trifluoroacetate

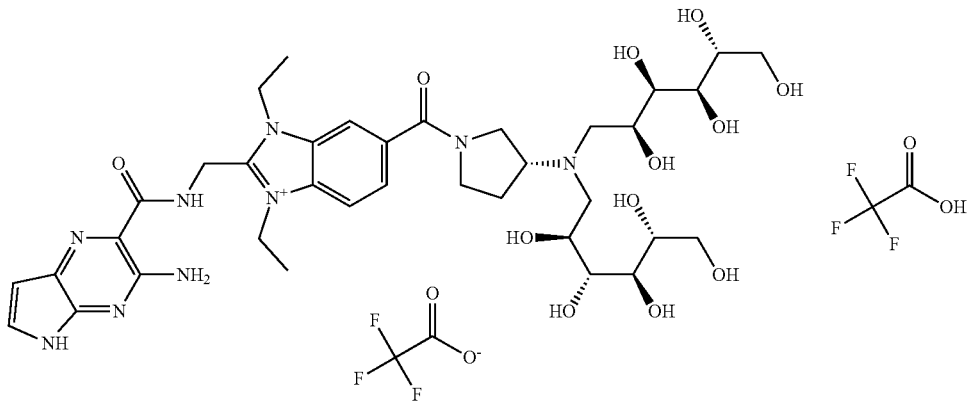 [SMILES: CCn1c(CNC(=O)c2nc3cc[nH]c3nc2N)[n+](CC)c2ccc(C(=O)N3CC[C@@H](N(C[C@H](O)[C@@H](O)[C@H](O)[C@H](O)CO)C[C@H](O)[C@@H](O)[C@H](O)[C@H](O)CO)C3)cc21 ; O=C([O-])C(F)(F)F ; O=C(O)C(F)(F)F]

A suspension of 2-[({3-amino-5H-pyrrolo[2,3-b]pyrazin-2-yl}formamido)methyl]-6-carboxy -1,3-diethyl-1H-1,3-benzodiazol-3-ium bromide, Example 34 (200 mg, 0.410 mmol) and CDI (100 mg, 0.61 mmol) in DMF (2 ml) was stirred at RT for 1 h. (2R,3R,4R,5S)-6-{[(2S,3R,4R,5R)-2,3,4,5,6-pentahydroxyhexyl][(3R)-pyrrolidin-3-yl]amino}hexane -1,2,3,4,5-pentol dihydrochloride, Intermediate 123 (83%, 289 mg, 0.492 mmol) was added then the reaction was left to stir at RT for 64 h. The reaction mixture was concentrated under a stream of nitrogen, then the crude material was purified by flash column chromatography on C18 (12 g). The column was eluted with MeCN:H$_2$O+TFA using the following gradient (% MeCN, column volumes): 2%, 2 CV; 2-25%, 15 CV; 25-100%, 2 CV. The desired fractions were combined and concentrated in vacuo then lyophilised to afford a yellow solid (140 mg). The material thus obtained was further purified by flash column chromatography on C18 (12 g). The column was eluted with MeCN:H₂O+TFA using the following gradient (% MeCN, column volumes): 2%, 1 CV; 2-20%, 10 CV; 20-100%, 2 CV. The desired fractions were combined and concentrated in vacuo then lyophilised to afford a yellow solid (65 mg, 15%).

$^1$H NMR (500 MHz, DMSO-d$_6$) δ 11.54 (s, 1H), 9.74 (t, J=4.7 Hz, 1H), 9.33-8.80 (m, 1H), 8.29-8.21 (m, 1H), 8.20-8.11 (m, 1H), 7.85-7.76 (m, 1H), 7.53 (dd, J=3.7, 2.6 Hz, 1H), 7.39-7.05 (m, 2H), 6.42 (dd, J=3.8, 1.8 Hz, 1H), 5.62-5.21 (m, 2H), 5.09 (d, J=4.9 Hz, 2H), 4.94-3.45 (m, 33H), 2.34-2.04 (m, 2H), 1.46-1.35 (m, 6H).

LC/MS (System D): m/z (ESI$^+$)=804 [M$^+$], R$_t$=1.27 min, UV purity=98%.

Example 54—Synthesis of 2-[({3-amino-5H-pyrrolo[2,3-b]pyrazin-2-yl}formamido)methyl]-6-[(3S)-3-{bis[(2S,3R,4R,5R)-2,3,4,5,6-pentahydroxyhexyl]amino}pyrrolidine-1-carbonyl]-1,3-diethyl-1H-1,3-benzodiazol-3-ium trifluoroacetic acid trifluoroacetate column was eluted with MeCN:H₂O+TFA using the following gradient (% MeCN, column volumes): 2%, 2 CV; 2-20%, 10 CV; 20-100%, 2 CV. The desired fractions were combined and concentrated in vacuo then lyophilised to afford a yellow solid (140 mg). The material thus obtained was further purified by flash column chromatography on C18 (12 g). The column was eluted with MeCN:H₂O+TFA using the following gradient (% MeCN, column volumes): 2%, 1 CV; 2-20%, 10 CV; 20-100%, 2 CV. The desired fractions were combined and concentrated in vacuo then lyophilised to afford a yellow solid (232 mg, 54%).

$^1$H NMR (500 MHz, DMSO-d$_6$+D₂O) δ 9.79-9.68 (m, 1H), 8.18-8.11 (m, 1H), 8.11-8.04 (m, 1H), 7.76 (d, J=8.8 Hz, 1H), 7.46 (d, J=3.8 Hz, 1H), 6.43 (d, J=3.8 Hz, 1H), 5.12-4.97 (m, 2H), 4.77-4.59 (m, 4H), 4.41-4.19 (m, 1H),

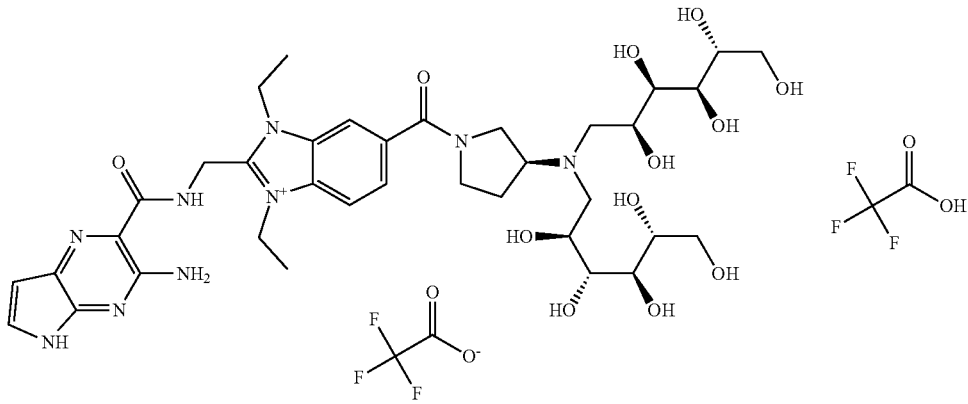 [SMILES: CCn1c(CNC(=O)c2nc3cc[nH]c3nc2N)[n+](CC)c2ccc(C(=O)N3CC[C@H](N(C[C@H](O)[C@@H](O)[C@H](O)[C@H](O)CO)C[C@H](O)[C@@H](O)[C@H](O)[C@H](O)CO)C3)cc21 ; O=C([O-])C(F)(F)F ; O=C(O)C(F)(F)F]

A suspension of 2-[({3-amino-5H-pyrrolo[2,3-b]pyrazin-2-yl}formamido)methyl]-6-carboxy-1,3-diethyl-1H-1,3-benzodiazol-3-ium bromide, Example 34 (200 mg, 0.410 mmol) and CDI (100 mg, 0.61 mmol) in DMF (2 ml) was stirred at RT for 1 h. (2R,3R,4R,5S)-6-{[(2S,3R,4R,5R)-2,3,4,5,6-Pentahydroxyhexyl][(3S)-pyrrolidin-3-yl]amino}hexane-1,2,3,4,5-pentol dihydrochloride, Intermediate 125 (240 mg, 0.492 mmol) was added then the reaction was left to stir at RT for 16 h. The reaction mixture was concentrated under a stream of nitrogen, then the crude material was purified by flash column chromatography on C18 (30 g). The 4.13-3.95 (m, 2H), 3.79-3.20 (m, 17H), 2.47-2.34 (m, 2H), 2.29-2.12 (m, 1H), 1.45-1.32 (m, 6H).

LC/MS (System D): m/z (ESI$^+$)=804 [M$^+$], R$_t$=1.27 min, UV purity=99%.

Example 55—Synthesis of 2-[({3-amino-5H-pyrrolo[2,3-b]pyrazin-2-yl}formamido)methyl]-1,3-diethyl-6-{[(1r,4r)-4-{bis[(2S,3R,4R,5R)-2,3,4,5,6-pentahydroxyhexyl]amino}cyclohexyl]carbamoyl}-1H-1,3-benzodiazol-3-ium trifluoroacetic acid trifluoroacetate

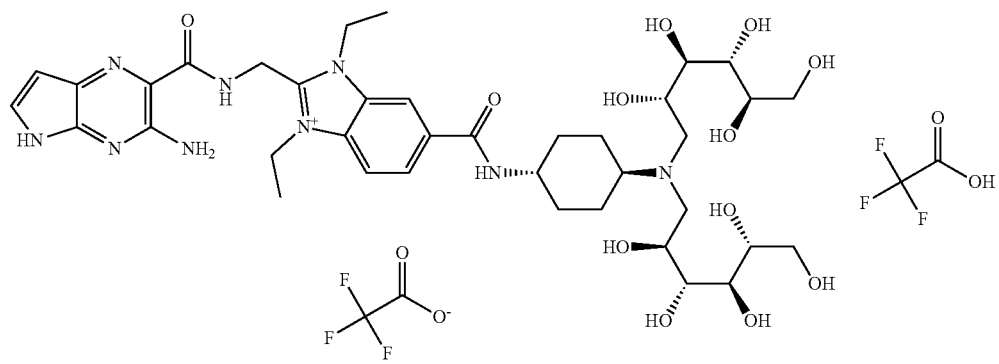 [SMILES: CCn1c(CNC(=O)c2nc3cc[nH]c3nc2N)[n+](CC)c2ccc(C(=O)N[C@H]3CC[C@H](N(C[C@H](O)[C@@H](O)[C@H](O)[C@H](O)CO)C[C@H](O)[C@@H](O)[C@H](O)[C@H](O)CO)CC3)cc21 ; O=C([O-])C(F)(F)F ; O=C(O)C(F)(F)F]

A suspension of 2-[({3-amino-5H-pyrrolo[2,3-b]pyrazin-2-yl}formamido)methyl]-6-carboxy -1,3-diethyl-1H-1,3-benzodiazol-3-ium bromide, Example 34 (400 mg, 0.819 mmol) and CDI (199 mg, 1.23 mmol) in DMF (4 ml) was stirred at RT for 1 h. (2R,3R,4R,5S)-6-{[(2S,3R,4R,5R)-2,3,4,5,6-Pentahydroxyhexyl][(1r,4r)-4-aminocyclohexyl]amino}hexane -1,2,3,4,5-pentol dihydrochloride, Intermediate 127 (90%, 550 mg, 0.960 mmol) was added then the reaction was left to stir at RT for 16 h. The reaction mixture was concentrated under a stream of nitrogen, then the crude material was purified by flash column chromatography on C18 (30 g). The column was eluted with MeCN:H$_2$O+TFA using the following gradient (% MeCN, column volumes):

Example 56—Synthesis of 2-[({3-amino-5H-pyrrolo[2,3-b]pyrazin-2-yl}formamido)methyl]-1,3-diethyl-6-{[(1s,4s)-4-{bis[(2S,3R,4R,5R)-2,3,4,5,6-pentahydroxyhexyl]amino}cyclohexyl]carbamoyl}-1H-1,3-benzodiazol-3-ium trifluoroacetic acid trifluoroacetate

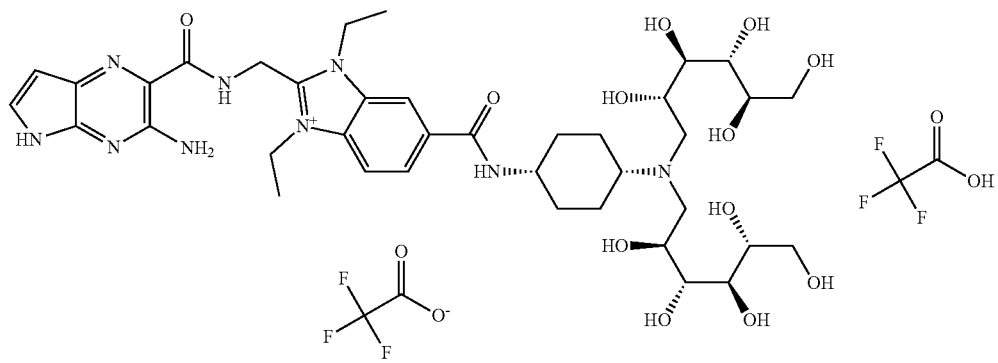 [SMILES: CCn1c(CNC(=O)c2nc3cc[nH]c3nc2N)[n+](CC)c2ccc(C(=O)N[C@H]3CC[C@@H](N(C[C@H](O)[C@@H](O)[C@H](O)[C@H](O)CO)C[C@H](O)[C@@H](O)[C@H](O)[C@H](O)CO)CC3)cc21 ; O=C([O-])C(F)(F)F ; O=C(O)C(F)(F)F]

2%, 2 CV; 2-25%, 15 CV; 25-100%, 2 CV. The desired fractions were combined and concentrated in vacuo to afford a yellow/orange solid (292 mg). The material thus obtained was dissolved in water (3 ml) then an aliquot (1 ml) was purified by column chromatography on C4 (12 g). The column was eluted with MeCN:H$_2$O+TFA using the following gradient (% MeCN, column volumes): 5%, 2 CV; 5-22%, 10 CV; 22-100%, 2 CV, 100%, 2 CV. A second aliquot (1 ml) was purified by column chromatography on a cyano column (13 g). The column was eluted with MeCN: H$_2$O+TFA using the following gradient (% MeCN, column volumes): 2%, 2 CV; 2-4%, 2 CV; 4-8%, 2 CV; 8-100%, 2 CV, 100%, 2 CV. An further aliquot (1 ml) was purified by column chromatography on C18 (12 g). The column was eluted with MeCN:H$_2$O+TFA using the following gradient (% MeCN, column volumes): 2%, 2 CV; 2-15%, 11 CV; 15-20%, 1 CV; 20-100%, 2 CV, 100%, 2 CV. The desired fractions from the three columns were combined and concentrated in vacuo then lyophilised to afford two batches of yellow solid (77 mg and 163 mg). Both batches of solid thus obtained were further purified by column chromatography on C18 (12 g). The column was eluted with MeCN:H$_2$O+TFA using the following gradient (% MeCN, column volumes): 2%, 2 CV; 2-15%, 10 CV; 15-100%, 2 CV, 100%, 2 CV. The desired fractions from both columns were combined and concentrated in vacuo then lyophilised to afford a yellow solid (53 mg). The material thus obtained was further purified by HPLC purification under the following conditions: stationary phase: XSelect CSH C18 30×100 mm, 5 µm; detection UV 220 nm; mobile phase A: water+0.1% TFA; B: MeCN+0.1% TFA; gradient: 1-15% solvent B over 18 min; flowrate: 42 ml/min. The desired fractions were combined and concentrated in vacuo then lyophilised to afford the product as a yellow solid (26 mg, 3.0%).

$^1$H NMR (500 MHz, DMSO-d$_6$+D$_2$O) δ 9.73 (t, J=5.4 Hz, 1H), 8.65-8.54 (m, 1H), 8.40 (s, 1H), 8.10 (s, 2H), 7.49 (d, J=3.8 Hz, 1H), 6.42 (d, J=3.8 Hz, 1H), 5.07 (d, J=4.5 Hz, 2H), 4.79-4.62 (m, 4H), 4.29-3.76 (m, 6H), 3.56-3.10 (m, 11H), 2.23-1.56 (m, 7H), 1.50-1.32 (m, 8H).

LC/MS (System D): m/z (ESI$^+$)=832 [M$^+$], R$_t$=1.38 min, UV purity=99%.

A suspension of 2-[({3-amino-5H-pyrrolo[2,3-b]pyrazin-2-yl}formamido)methyl]-6-carboxy -1,3-diethyl-1H-1,3-benzodiazol-3-ium bromide, Example 34 (185 mg, 0.379 mmol) and CDI (92 mg, 0.57 mmol) in DMF (1.5 ml) was stirred at RT for 2 h. The reaction mixture was added to 2R,3R,4R,5S)-6-{[(2S,3R,4R,5R)-2,3,4,5,6-Pentahydroxyhexyl][(1s,4s)-4-aminocyclohexyl]amino}hexane-1,2,3,4,5-pentol, Intermediate 132 (210 mg, 0.475 mmol) and rinsed in DMF (1 ml). The reaction was left to stir at RT for 16 h. The reaction mixture was concentrated in vacuo then the crude material was purified by flash column chromatography on C18 (30 g). The column was eluted with MeCN:H$_2$O+TFA using the following gradient (% MeCN, column volumes): 2%, 2 CV; 2-20%, 15 CV; 20-100%, 2 CV; 100%, 2 CV. The desired fractions were combined and lyophilised to afford a yellow solid (42 mg). A sample (31 mg) of the material thus obtained was further purified by flash column chromatography on C18 (12 g). The column was eluted with MeCN:H$_2$O+TFA using the following gradient (% MeCN, column volumes): 2%, 2 CV; 2-20%, 10 CV; 20-100%, 2 CV; 100%, 2 CV. The desired fractions were combined and concentrated in vacuo then lyophilised to afford the product as a yellow solid (30 mg, 7.4%).

$^1$H NMR (500 MHz, DMSO-d$_6$) δ 11.59-11.50 (m, 1H), 9.74 (t, J=5.3 Hz, 1H), 8.40 (s, 1H), 8.16-8.11 (m, 1H), 7.93-7.84 (m, 1H), 7.53 (dd, J=3.7, 2.6 Hz, 1H), 7.35-7.02 (m, 2H), 6.45-6.40 (m, 1H), 5.77-5.47 (m, 2H), 5.19-5.07 (m, 2H), 5.01-3.68 (m, 25H), 3.26-3.12 (m, 4H), 2.14-1.36 (m, 16H).

LC/MS (System D): m/z (ESI$^+$)=832 [M$^+$], R$_t$=1.38 min, UV purity=99%.

Example 57—Synthesis of 2-[({3-amino-5H-pyrrolo[2,3-b]pyrazin-2-yl}formamido)methyl]-6-[(3-{bis[(2S,3R,4R,5R)-2,3,4,5,6-pentahydroxyhexyl]amino}propyl)(methyl)carbamoyl]-1,3-diethyl-1H-1,3-benzodiazol-3-ium trifluoroacetic acid trifluoroacetate

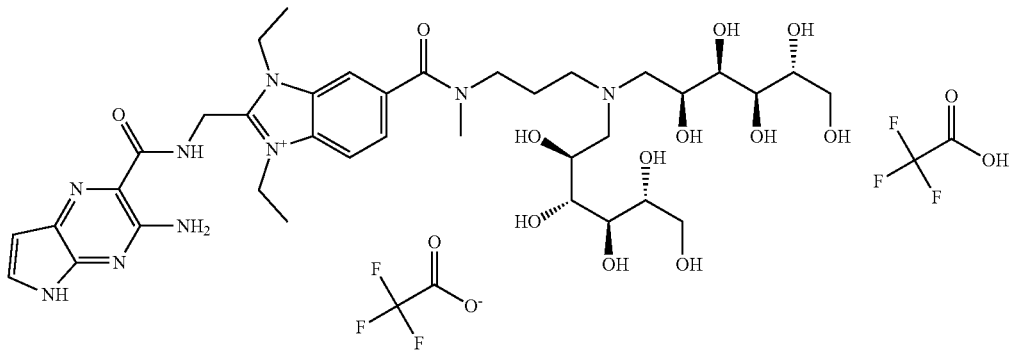 [SMILES: CCn1c(CNC(=O)c2nc3cc[nH]c3nc2N)[n+](CC)c2ccc(C(=O)N(C)CCCN(C[C@H](O)[C@@H](O)[C@H](O)[C@H](O)CO)C[C@H](O)[C@@H](O)[C@H](O)[C@H](O)CO)cc21 ; O=C([O-])C(F)(F)F ; O=C(O)C(F)(F)F]

A suspension of 2-[({3-amino-5H-pyrrolo[2,3-b]pyrazin-2-yl}formamido) methyl]-6-carboxy -1,3-diethyl-1H-1,3-benzodiazol-3-ium bromide, Example 34 (200 mg, 0.410 mmol) and CDI (100 mg, 0.61 mmol) in DMF (2 ml) was stirred at RT for 1 h. (2R,3R,4R,5S)-6-{[3-(Methylamino)propyl][(2S,3R,4R,5R)-2,3,4,5,6-pentahydroxyhexyl]amino}hexane -1,2,3,4,5-pentol dihydrochloride, Intermediate 134 (241 mg, 0.492 mmol) was added then the reaction was left to stir at RT for 16 h. The reaction mixture was concentrated under a stream of nitrogen, then the crude material was purified by flash column chromatography on C18 (30 g). The column was eluted with MeCN:H$_2$O+TFA using the following gradient (% MeCN, column volumes): 2%, 2 CV; 2-20%, 10 CV; 20-100%, 2 CV; 100%, 2 CV. The desired fractions were combined and concentrated in vacuo then lyophilised to afford the product as a yellow solid (35 mg, 8.0%).

$^1$H NMR (500 MHz, DMSO-d$_6$+D$_2$O) δ 9.79-9.71 (m, 1H), 8.13-8.05 (m, 2H), 7.74-7.59 (m, 1H), 7.49 (d, J=3.8 Hz, 1H), 6.43 (d, J=3.8 Hz, 1H), 5.13-4.98 (m, 2H), 4.80-4.63 (m, 4H), 4.09-3.81 (m, 2H), 3.66-3.14 (m, 17H), 3.05-2.85 (m, 3H), 2.58-2.54 (m, 1H), 2.13-1.83 (m, 2H), 1.47-1.33 (m, 6H).

LC/MS (System D): m/z (ESI$^+$)=806 [M$^+$], R$_t$=1.30 min, UV purity=97%.

Example 58—Synthesis of 2-[({3-amino-5H-pyrrolo[2,3-b]pyrazin-2-yl}formamido)methyl]-6-[(2-{bis[(2S,3R,4R,5R)-2,3,4,5,6-pentahydroxyhexyl]amino}ethyl)carbamoyl]-1,3-diethyl-1H-1,3-benzodiazol-3-ium trifluoroacetic acid trifluoroacetate

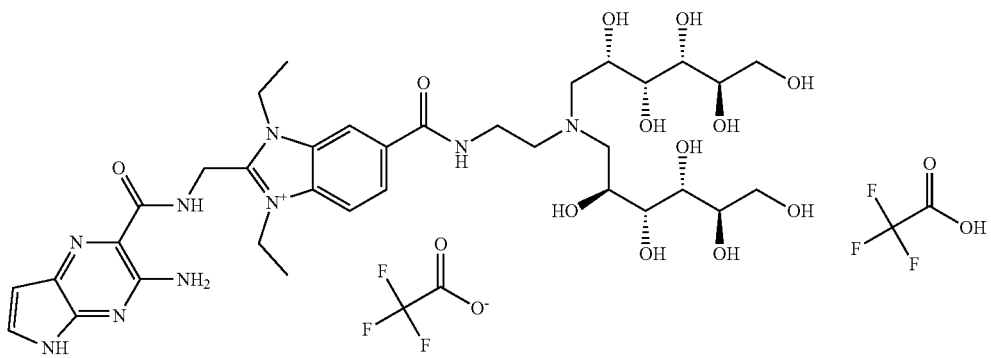 [SMILES: CCn1c(CNC(=O)c2nc3cc[nH]c3nc2N)[n+](CC)c2ccc(C(=O)NCCN(C[C@H](O)[C@@H](O)[C@H](O)[C@H](O)CO)C[C@H](O)[C@@H](O)[C@H](O)[C@H](O)CO)cc21 ; O=C([O-])C(F)(F)F ; O=C(O)C(F)(F)F]

A suspension of 2-[({3-amino-5H-pyrrolo[2,3-b]pyrazin-2-yl}formamido)methyl]-6-carboxy -1,3-diethyl-1H-1,3-benzodiazol-3-ium bromide, Example 34 (200 mg, 0.410 mmol) and CDI (100 mg, 0.61 mmol) in DMF (3 ml) was stirred at RT for 1.5 h. The resultant solution was added to (2R,3R,4R,5S)-6-[(2-aminoethyl)[(2S,3R,4R,5R)-2,3,4,5,6-pentahydroxyhexyl]amino]hexane-1,2,3,4,5-pentol dihydrochloride, Intermediate 136 (94%, 227 mg, 0.462 mmol) and rinsed into the flask with DMF (1.5 ml). The reaction was stirred at RT for 16 h then concentrated in vacuo, then the crude material was purified by flash column chromatography on C18 (30 g). The column was eluted with MeCN:H$_2$O+TFA using the following gradient (% MeCN, column volumes): 5%, 2 CV; 5-25%, 10.5 CV; 25%, 2 CV; 25-34%, 1 CV; 34-100%, 2 CV; 100%, 2 CV. The desired fractions were combined and concentrated in vacuo then lyophilised to afford the product as a yellow solid (101 mg, 24%).

$^1$H NMR (500 MHz, CD$_3$OD) δ 8.51-8.43 (m, 1H), 8.19 (dd, J=8.7, 1.3 Hz, 1H), 8.09 (d, J=8.8 Hz, 1H), 7.39 (d, J=3.8 Hz, 1H), 6.45 (d, J=3.8 Hz, 1H), 5.19-5.08 (m, 2H), 4.86-4.75 (m, 4H), 4.29-4.19 (m, 2H), 3.99-3.47 (m, 18H), 1.67-1.49 (m, 6H).

LC/MS (System D): m/z (ESI$^+$)=778 [M$^+$], R$_t$=1.32 min, UV purity=98%.

Example 59—Synthesis of 2-[({3-amino-5H-pyrrolo[2,3-b]pyrazin-2-yl}formamido)methyl]-1,3-diethyl-5-{[(14S,15R,16R,17R)-14,15,16,17,18-pentahydroxy-12-[(2S,3R,4R,5R)-2,3,4,5,6-pentahydroxyhexyl]-3,6,9-trioxa-12-azaoctadecan-1-yl]carbamoyl}-1H-1,3-benzodiazol-3-ium trifluoroacetic acid trifluoroacetate

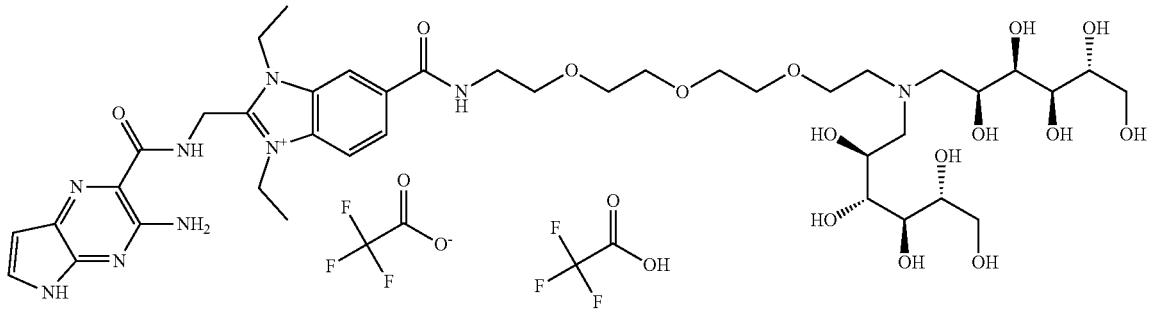 [SMILES: CCn1c(CNC(=O)c2nc3cc[nH]c3nc2N)[n+](CC)c2ccc(C(=O)NCCOCCOCCOCCN(C[C@H](O)[C@@H](O)[C@H](O)[C@H](O)CO)C[C@H](O)[C@@H](O)[C@H](O)[C@H](O)CO)cc21 ; O=C([O-])C(F)(F)F ; O=C(O)C(F)(F)F]

CDI (99 mg, 0.61 mmol) was added to a suspension of 2-[({3-amino-5H-pyrrolo[2,3-b]pyrazin-2-yl}formamido)methyl]-6-carboxy-1,3-diethyl-1H-1,3-benzodiazol-3-ium bromide, Example 34 (217 mg, 0.444 mmol) in DMF (1.5 ml). The reaction was left to stir at RT for 4 h then added to (14S,15R,16R,17R)-1-amino-12-[(2S,3R,4R,5R)-2,3,4,5,6-pentahydroxyhexyl]-3,6,9-trioxa-12-azaoctadecane-14,15,16,17,18-pentol dihydrochloride, Intermediate 141 (96%, 289 mg, 0.467 mmol) and rinsed in with DMF (1 ml). The reaction was stirred at RT for 16 h. The crude material was purified by flash column chromatography on C18 (30 g). The column was eluted with MeCN:H$_2$O+TFA using the following gradient (% MeCN, column volumes): 2%, 2 CV; 2-6%, 3 CV; 6%, 1 CV; 6-13%, 6 CV; 13%, 5 CV; 13-20%, 5 CV; 20%, 2 CV; 20-100%, 2 CV; 100%, 1 CV. The desired fractions were combined and lyophilised to afford a yellow solid (101 mg). The material thus obtained was further purified by flash column chromatography on C18 (12 g). The column was eluted with MeCN:H$_2$O+TFA using the following gradient (% MeCN, column volumes): 2%, 1.5 CV; 2-10%, 3 CV; 10-12%, 1 CV; 12%, 6 CV. The desired fractions were combined and lyophilised to afford the product as a yellow solid (77 mg, 15%).

$^1$H NMR (500 MHz, DMSO-d$_6$) δ 11.58-11.46 (m, 1H), 9.73 (t, J=5.2 Hz, 1H), 8.85 (t, J=5.6 Hz, 1H), 8.50 (s, 1H), 8.29-8.03 (m, 3H), 7.52 (dd, J=3.7, 2.6 Hz, 1H), 7.33-7.12 (m, 2H), 6.42 (dd, J=3.8, 1.7 Hz, 1H), 5.50-5.28 (m, 1H), 5.10 (d, J=5.2 Hz, 2H), 4.90-4.62 (m, 5H), 4.61-4.34 (m, 5H), 4.03-3.90 (m, 2H), 3.81-3.33 (m, 33H), 1.50-1.34 (m, 6H).

LC/MS (System D): m/z (ESI$^+$)=910 [M$^+$], R$_t$=1.50 min, UV purity=99%.

Example 60—Synthesis of 2-[({3-amino-5H-pyrrolo[2,3-b]pyrazin-2-yl}formamido)methyl]-6-({2-[4'-(2-{bis[(2S,3R,4R,5R)-2,3,4,5,6pentahydroxyhexyl]amino}ethyl)-[1,1-biphenyl]-4-yl]ethyl}carbamoyl)-1,3-diethyl -1H-1,3-benzodiazol-3-ium trifluoroacetic acid trifluoroacetate

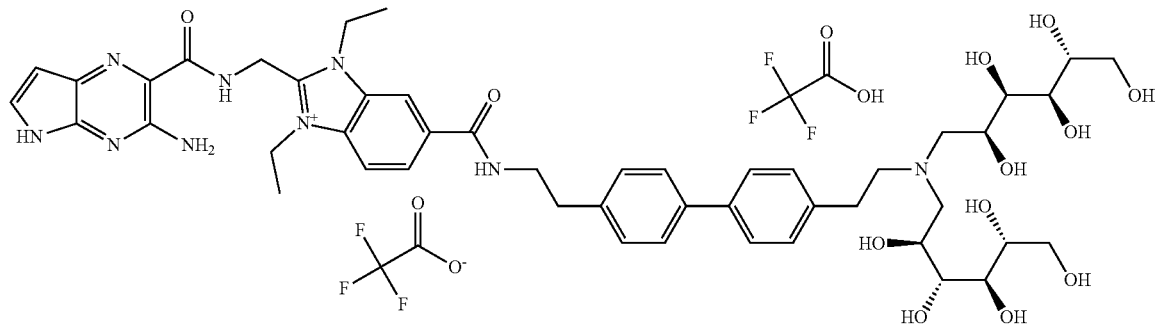 [SMILES: CCn1c(CNC(=O)c2nc3cc[nH]c3nc2N)[n+](CC)c2ccc(C(=O)NCCc3ccc(-c4ccc(CCN(C[C@H](O)[C@@H](O)[C@H](O)[C@H](O)CO)C[C@H](O)[C@@H](O)[C@H](O)[C@H](O)CO)cc4)cc3)cc21 ; O=C([O-])C(F)(F)F ; O=C(O)C(F)(F)F]

CDI (93 mg, 0.57 mmol) was added to a suspension of 2-[({3-amino-5H-pyrrolo[2,3 -b]pyrazin-2-yl}formamido)methyl]-6-carboxy-1,3-diethyl-1H-1,3-benzodiazol-3-ium bromide, Example 34 (187 mg, 0.38 mmol) in DMF (1.5 ml). The reaction was left to stir at RT for 5 h then (2R,3R,4R,5S)-6-({2-[4'-(2-aminoethyl)-[1,1'-biphenyl]-4 -yl]ethyl}[(2S,3R,4R,5R)-2,3,4,5,6-pentahydroxyhexyl]amino)hexane-1,2,3,4,5-pentol dihydrochloride, Intermediate 146 (94%, 459 mg, 0.672 mmol) and DMF (0.5 ml) were added. The reaction was left to stir at RT for a further 17 h. The crude material was purified by flash column chromatography on C18 (30 g). The column was eluted with MeCN:H$_2$O+TFA using the following gradient (% MeCN, column volumes): 2%, 2 CV; 2-9%, 6 CV; 9%, 3 CV; 9-16%, 6 CV; 16-17%, 1 CV; 17%, 16 CV. The desired fractions were combined and lyophilised to afford the product as a yellow solid (156 mg, 33%).

$^1$H NMR (500 MHz, DMSO-d$_6$) δ 11.61-11.47 (m, 1H), 9.73 (t, J=5.4 Hz, 1H), 8.92 (t, J =5.4 Hz, 1H), 8.82-8.65 (m, 1H), 8.49 (s, 1H), 8.22-8.09 (m, 2H), 7.66-7.58 (m, 4H), 7.52 (dd, J=3.7, 2.5 Hz, 1H), 7.41-7.03 (m, 6H), 6.42 (dd, J=3.8, 1.8 Hz, 1H), 5.70-5.30 (m, 2H), 5.17-5.00 (m, 3H), 4.77-4.67 (m, 5H), 4.14-4.00 (m, 4H), 3.75-3.25 (m, 22H+ HDO), 3.10-3.01 (m, 2H), 2.94 (t, J=7.3 Hz, 2H), 1.49-1.38 (m, 6H).

LC/MS (System D): m/z (ESI$^+$)=480 [(M+H)$^{2+}$], R$_f$=1.50 min, UV purity=99%.

Example 61—Synthesis of 2-[({3-amino-5H-pyrrolo[2,3-b]pyrazin-2-yl}formamido)methyl]-6-{[(3S)-3-[(3-{bis[(2S,3R,4R,5R)-2,3,4,5,6-pentahydroxyhexyl]amino}propyl)amino]-3-carbamoylpropyl]carbamoyl}-1,3-diethyl-1H-1,3-benzodiazol-3-ium bis(trifluoroacetic acid) trifluoroacetate

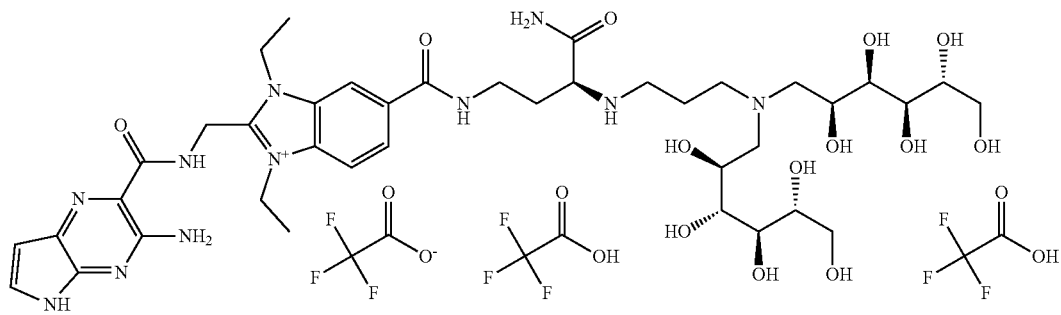 [SMILES: CCn1c(CNC(=O)c2nc3cc[nH]c3nc2N)[n+](CC)c2ccc(C(=O)NCC[C@H](NCCCN(C[C@H](O)[C@@H](O)[C@H](O)[C@H](O)CO)C[C@H](O)[C@@H](O)[C@H](O)[C@H](O)CO)C(N)=O)cc21 ; O=C([O-])C(F)(F)F ; O=C(O)C(F)(F)F ; O=C(O)C(F)(F)F]

A suspension of 2-[({3-amino-5H-pyrrolo[2,3-b]pyrazin-2-yl}formamido)methyl]-6-carboxy -1,3-diethyl-1H-1,3-benzodiazol-3-ium bromide, Example 34 (200 mg, 0.410 mmol) and CDI (100 mg, 0.614 mmol) in DMF (2 ml) was stirred at RT for 1.5 h then added to (2S)-4-amino-2-[(3-{bis[(2S,3R,4R,5R)-2,3,4,5,6-pentahydroxyhexyl]amino} propylamino] butanamide trihydrochloride, Intermediate 154 (91%, 323 mg, 0.480 mmol) and rinsed in with DMF (1 ml). The reaction was stirred at RT for 16 h then concentrated in vacuo. The crude material was purified by flash column chromatography on C18 (30 g). The column was eluted with MeCN:H$_2$O+TFA using the following gradient (% MeCN, column volumes): 5%, 2 CV; 5-25%, 10.5 CV; 25%, 2 CV; 25-34%, 1 CV; 34-100%, 1 CV; 100%, 2 CV. The desired fractions were combined, concentrated in vacuo then lyophilised to afford the product as a yellow solid (95 mg, 18%).

$^1$H NMR (500 MHz, CD$_3$OD) δ 8.53-8.45 (m, 1H), 8.21 (dd, J=8.8, 1.4 Hz, 1H), 8.10 (d, J=8.8 Hz, 1H), 7.40 (d, J=3.8 Hz, 1H), 6.45 (d, J=3.8 Hz, 1H), 5.15 (s, 2H), 4.86-4.77 (m, 4H), 4.26-4.17 (m, 2H), 4.02-3.97 (m, 1H), 3.89-3.84 (m, 2H), 3.80-3.74 (m, 2H), 3.73-3.38 (m, 14H), 3.24-3.11 (m, 2H), 2.33-2.21 (m, 4H), 1.65-1.53 (m, 6H).

LC/MS (System D): m/z (ESI$^+$)=447 [(M+H)$^{2+}$], R$_t$=1.32 min, UV purity=95%.

Example 62—Synthesis of 2-[({3-amino-5H-pyrrolo[2,3-b]pyrazin-2-yl}formamido)methyl]-6-{[4-(4-{3-[(3-{bis[(2S,3R,4R,5R)-2,3,4,5,6-pentahydroxyhexyl]amino}propyl)amino]-3-carbamoylpropyl}phenyl)butyl]carbamoyl}-1,3-diethyl-1H-1,3-benzodiazol-3-ium bis(trifluoroacetic acid) trifluoroacetate

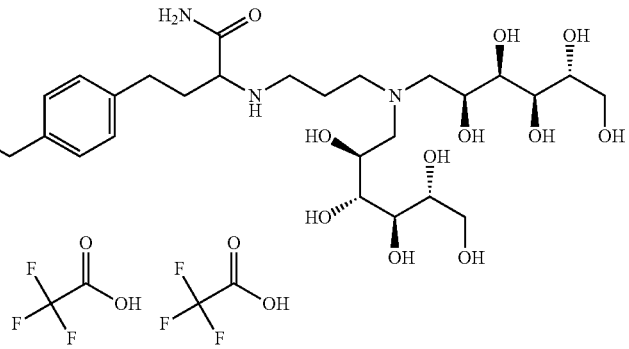

CDI (30 mg, 0.19 mmol) was added to a suspension of 2-[({3-amino-5H-pyrrolo[2,3-b]pyrazin-2-yl}formamido) methyl]-6-carboxy-1,3-diethyl-1H-1,3-benzodiazol-3-ium bromide, Example 34(61 mg, 0.12 mmol) in DMF (1 ml). The reaction was left to stir at RT for 1.5 h then more CDI (4 mg, 0.02 mmol) was added. The reaction was left to stir at RT for a further 1 h then added to a suspension of 4-[4-(4-aminobutyl)phenyl]-2-[(3-{bis[(2S,3R,4R,5R)-2,3,4,5,6-pentahydroxyhexyl]amino}propyl)amino]butanamide trihydrochloride, Intermediate 156 (88%, 106 mg, 0.125 mmol) in DMF (1 ml). Further DMF (1 ml) was used to rinse the reaction mixture into the flask. The reaction was left to stir at RT for 16 h then concentrated in vacuo. The crude material was purified by flash column chromatography on C18 (12 g). The column was eluted with MeCN:H$_2$O+TFA using the following gradient (% MeCN, column volumes): 2%, 4 CV; 2-20%, 30 CV; 20-100%, 4 CV; 100%, 4 CV. The desired fractions were combined then lyophilised to afford the product as a yellow solid (11 mg, 6.2%).

$^1$H NMR (500 MHz, D$_2$O) δ 8.28-8.24 (m, 1H), 8.04-7.96 (m, 2H), 7.54 (d, J=3.9 Hz, 1H), 7.28 (d, J=8.1 Hz, 2H), 7.23 (d, J=8.1 Hz, 2H), 6.56 (d, J=3.9 Hz, 1H), 5.23 (s, 2H), 4.77-4.71 (m, 4H), 4.29-4.22 (m, 2H), 4.04-3.97 (m, 1H), 3.89-3.83 (m, 2H), 3.87-3.80 (m, 2H), 3.82-3.74 (m, 2H), 3.71-3.63 (m, 4H), 3.54-3.28 (m, 8H), 3.24-3.09 (m, 2H), 2.78-2.63 (m, 4H), 2.33-2.14 (m, 4H), 1.77-1.64 (m, 4H), 1.57-1.48 (m, 6H).

LC/MS (System D): m/z (ESI$^+$)=513 [(M+H)$^{2+}$], R$_t$=1.32 min, UV purity=95%.

Example 63—Synthesis of 2-[({3-amino-7-chloro-5H-pyrrolo[2,3-b]pyrazin-2-yl}formamido)methyl]-6-carboxy-1,3-diethyl-1H-1,3-benzodiazol-3-ium chloride

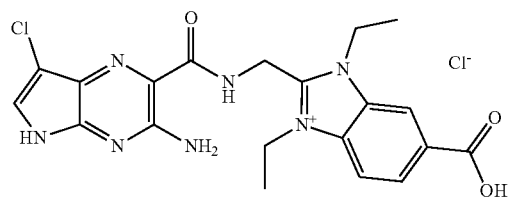 [SMILES: CCn1c(CNC(=O)c2nc3c(Cl)c[nH]c3nc2N)[n+](CC)c2ccc(C(=O)O)cc21 ; [Cl-]]

A suspension of 2-(aminomethyl)-6-carboxy-1,3-diethyl-1H-1,3-benzodiazol-3-ium hydrochloride chloride, Intermediate 159 (84%, 257 mg, 0.674 mmol) and 7-chloro-2-(1H-imidazole-1-carbonyl)-5H-pyrrolo[2,3-b]pyrazin-3-amine, Intermediate 16 (85%, 248 mg, 0.803 mmol) in DMF (2.5 ml) was stirred at RT for 20 h. Further 2-(aminomethyl)-6-carboxy-1,3-diethyl-1H-1,3-benzodiazol-3-ium hydrochloride chloride, Intermediate 159 (84%, 60 mg, 0.16 mmol) was added then the reaction was left to stir at RT for 6 h. The reaction mixture was concentrated in vacuo then the crude material was purified by flash column chromatography on C18 (12 g). The column was eluted with MeCN:H$_2$O+ formic acid using the following gradient (% MeCN, column volumes): 10%, 1.5 CV; 10-26%, 15 CV; 26-100%, 6 CV; 100%, 1 CV. The desired fractions were combined then lyophilised to afford the product as a yellow/green solid (98 mg, 25%).

$^1$H NMR (500 MHz, DMSO-d$_6$) δ 11.89 (s, 1H), 9.54 (t, J=5.4 Hz, 1H), 8.40-8.36 (m, 1H), 8.22-8.16 (m, 1H), 7.92 (d, J=8.6 Hz, 1H), 7.68 (s, 1H), 7.39 (s, 2H), 5.13 (d, J=5.4 Hz, 2H), 4.77-4.62 (m, 4H), 1.46-1.35 (m, 6H).

LC/MS (System C): m/z (ESI$^+$)=442 [M($^{35}$Cl)$^+$], 444 [M($^{37}$Cl)$^+$], R$_t$=1.61 min, UV purity=99%.

Example 64—Synthesis of 2-[({3-amino-7-bromo-5H-pyrrolo[2,3-b]pyrazin-2 -yl}formamido)methyl]-6-carboxy-1,3-diethyl-1H-1,3-benzodiazol-3-ium bromide

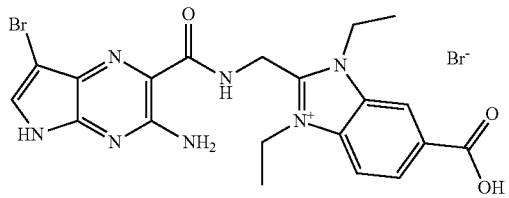

2-(aminomethyl)-6-carboxy-1,3-diethyl-1H-1,3-benzodiazol-3-ium hydrobromide bromide, Intermediate 83 (388 mg, 0.950 mmol) was added to a mixture of 7-bromo-2-(1H-imidazole-1-carbonyl)-5H-pyrrolo[2,3-b]pyrazin-3-amine, Intermediate 164 (243 mg, 0.791 mmol) in DMF (2.5 ml). The resultant mixture was stirred at RT for 19 h. The reaction mixture was concentrated in vacuo then the crude material was purified by flash column chromatography on C18 (30 g). The column was eluted with MeCN:H$_2$O+ formic acid using the following gradient (% MeCN, column volumes): 5%, 1.5 CV; 5-27%, 12 CV; 27-50%, 3 CV; 50-83%, 1.5 CV; 83-100%, 0.5 CV; 100%, 1 CV. The desired fractions were combined then concentrated in vacuo to afford the product as a yellow/orange solid (391 mg, 87%).

$^1$H NMR (500 MHz, DMSO-d$_6$) δ 11.91 (s, 1H), 9.49 (t, J=5.4 Hz, 1H), 8.49-8.42 (m, 1H), 8.20 (dd, J=8.6, 1.2 Hz, 1H), 8.01 (d, J=8.6 Hz, 1H), 7.72 (s, 1H), 7.37 (s, 2H), 5.15 (d, J=5.4 Hz, 2H), 4.76 (q, J=7.2 Hz, 2H), 4.70 (q, J=7.1 Hz, 2H), 1.45-1.40 (m, 6H).

LC/MS (System C): m/z (ESI$^+$)=486 [M($^{79}$Br)$^+$], 488 [M($^{81}$Br)$^+$], R$_t$=1.67 min, UV purity=100%.

Example 65—Synthesis of 2-[({3-amino-7-chloro-5H-pyrrolo[2,3-b]pyrazin-2-yl}formamido)methyl]-6-(4-{bis[(2S,3R,4R,5R)-2,3,4,5,6-pentahydroxyhexyl]amino}piperidine-1-carbonyl)-1,3-diethyl-1H-1,3-benzodiazol-3-ium trifluoroacetic acid trifluoroacetate A mixture of 2-[({3-amino-7-chloro-5H-pyrrolo[2,3-b]pyrazin-2-yl}formamido)methyl]-6-carboxy-1,3-diethyl-1H-1,3-benzodiazol-3-ium chloride, Example 63 (92 mg, 0.19 mmol) and CDI (47 mg, 0.29 mmol) in DMF (2 ml) was stirred at RT for 1.5 h. Additional CDI (40 mg, 0.25 mmol) and DMF (1 ml) were added then the reaction was stirred at RT for 15 min. The reaction mixture was then added to (2R,3R,4R,5S)-6-{[(2S,3R,4R,5R)-2,3,4,5,6-pentahydroxyhexyl](piperidin-4-yl)amino}hexane-1,2,3,4,5-pentol dihydrochloride, Intermediate 112 (145 mg, 0.289 mmol) and rinsed in with DMF (0.5 ml). The resultant mixture was stirred at RT for 18 h. The reaction mixture was concentrated in vacuo then the crude material was purified by flash column chromatography on C18 (30 g). The column was eluted with MeCN:H$_2$O+TFA using the following gradient (% MeCN, column volumes): 5%, 1.5 CV; 5-32%, 28 CV; 52-100%, 2 CV; 100%, 2 CV. The desired fractions were combined then lyophilised to afford a yellow/brown solid (29 mg). The material thus obtained was further purified by flash column chromatography on C18 (12 g). The column was eluted with MeCN:H$_2$O+TFA using the following gradient (% MeCN, column volumes): 0%, 1.5 CV; 0-23%, 13 CV; 23-40%, 5 CV. The desired fractions were combined then lyophilised to afford a yellow/orange solid (16 mg, 7.6%).

$^1$H NMR (500 MHz, CD$_3$OD) δ 8.18-8.15 (m, 1H), 8.11 (d, J=8.6 Hz, 1H), 7.82-7.77 (m, 1H), 7.43 (s, 1H), 5.20 (s, 2H), 4.86-4.81 (m, 4H +HDO), 4.37-3.36 (m, 20H), 3.08 -2.92 (m, 1H), 2.40-1.66 (m, 4H), 1.64-1.55 (m, 6H).

LC/MS (System C): m/z (ESI$^+$)=852 [M($^{35}$Cl)$^+$], 854 [M($^{37}$Cl)$^+$], R$_t$=0.99 min, UV purity=99%.

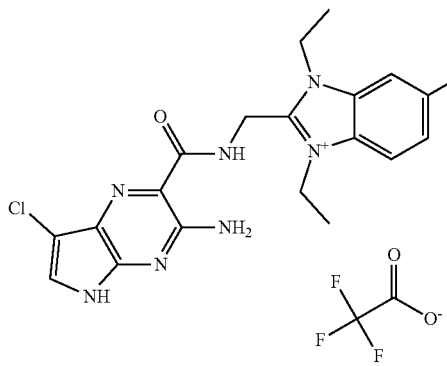
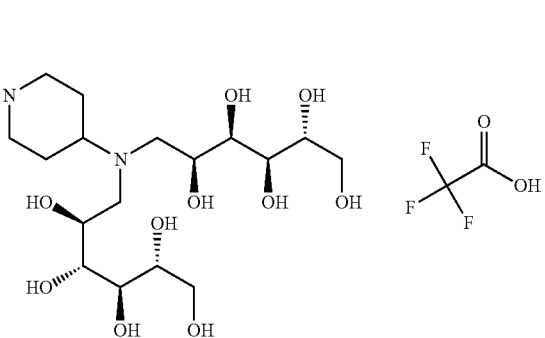

Example 66—Synthesis of 2-[({3-amino-7-bromo-5H-pyrrolo[2,3-b]pyrazin-2yl}formamido)methyl]-6-(4-{bis[(2S,3R,4R,5R)-2,3,4,5,6-pentahydroxyhexyl]amino}piperidine-1-carbonyl)-1,3-diethyl-1H-1,3-benzodiazol-3-ium trifluoroacetic acid trifluoroacetate

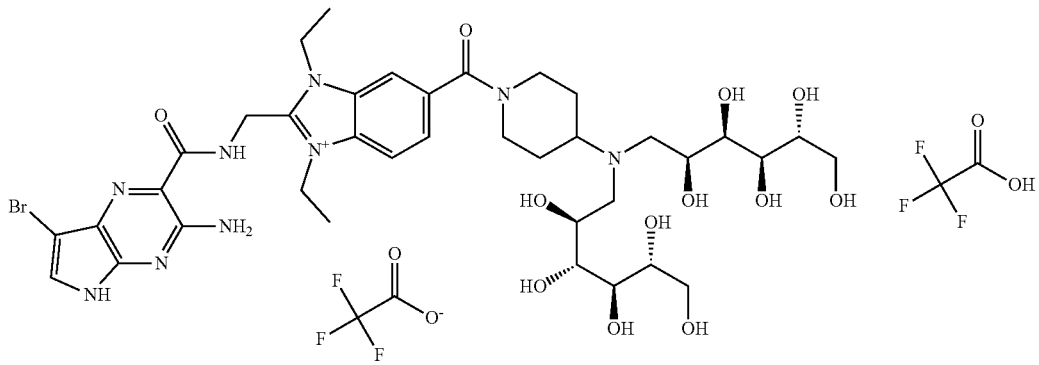 [SMILES: CCn1c(CNC(=O)c2nc3c(Cl)c[nH]c3nc2N)[n+](CC)c2ccc(C(=O)N3CCC(N(C[C@H](O)[C@@H](O)[C@H](O)[C@H](O)CO)C[C@H](O)[C@@H](O)[C@H](O)[C@H](O)CO)CC3)cc21 ; O=C([O-])C(F)(F)F ; O=C(O)C(F)(F)F]

A mixture of 2-[({3-amino-7-bromo-5H-pyrrolo[2,3-b]pyrazin-2-yl}formamido) methyl]-6-carboxy-1,3-diethyl-1H-1,3-benzodiazol-3-ium bromide, Example 64 (190 mg, 0.335 mmol) and CDI (81 mg, 0.50 mmol) in DMF (2 ml) was stirred at RT for 2 h. Additional CDI (60 mg, 0.37 mmol) was added then the reaction was left to stir at RT for 0.5 h. The reaction mixture was added to (2R,3R,4R,5S)-6-{[(2S,3R,4R,5R)-2,3,4,5,6-pentahydroxyhexyl](piperidin-4-yl)amino}hexane-1,2,3,4,5-pentol dihydrochloride, Intermediate 112 (90%, 224 mg, 0.402 mmol) and rinsed in with DMF (1 ml). The resultant mixture was left to stir at RT for 18 h. The reaction mixture was concentrated in vacuo then the crude material was purified in 2 batches by flash column chromatography on C18 (30 g). The column was eluted with MeCN:H$_2$O+TFA using the following gradient (% MeCN, column volumes): 2%, 1.5 CV; 2-22%, 15 CV; 22-45%, 6 CV; 45-100%, 2 CV. The desired fractions from both columns were combined then lyophilised to afford the product as a yellow solid (36 mg, 10%).

$^1$H NMR (500 MHz, DMSO-d$_6$) δ 11.90 (d, J=2.4 Hz, 1H), 9.51 (t, J=5.3 Hz, 1H), 8.31-8.09 (m, 3H), 7.76-7.71 (m, 2H), 7.37 (s, 2H), 5.69-5.43 (m, 2H), 5.16 (d, J=5.3 Hz, 2H), 4.93-4.37 (m, 14H), 4.10-3.91 (m, 2H), 3.87-3.76 (m, 1H), 3.75-3.56 (m, 6H), 3.53-3.40 (m, 8H), 3.20-3.14 (m, 1H), 2.91-2.76 (m, 1H), 2.26-1.55 (m, 4H), 1.47-1.41 (m, 6H).

LC/MS (System C): m/z (ESI$^+$)=896 [M($^{79}$Br)$^+$], 898 [M($^{81}$Br)$^+$], R$_t$=1.02 min, UV purity=100%.

Example 67—Synthesis of 2-[({3-amino-7-cyano-5H-pyrrolo[2,3-b]pyrazin-2-yl}formamido)methyl]-1,3-diethyl-6-methoxy-1H-1,3-benzodiazol-3-ium formate

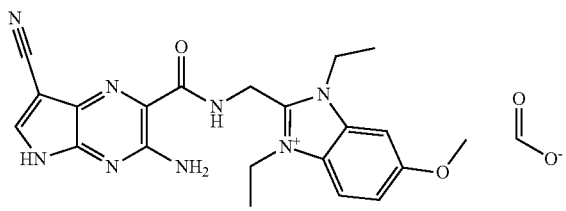

TFA (991 µl, 13.0 mmol) was added to a solution of 3-amino-7-cyano-5-{[2-(trimethylsilyl)ethoxy]methyl}-5H-pyrrolo[2,3-b]pyrazine-2-carboxylate, Intermediate 166 (150 mg, 0.43 mmol) in CH$_2$Cl$_2$ (2 ml). The resultant mixture was stirred at RT for 4.5 h. The reaction mixture was concentrated in vacuo, azeotroped with toluene (2×5 ml), then dried in vacuo to afford a red/orange solid (114 mg). A portion (83 mg) of the solid thus obtained was dissolved in MeOH (3 ml). Aqueous NaOH solution (5.0 M, 0.67 ml, 3.4 mmol) was added then the resulting mixture was heated at 60° C. for 1 h then at 80° C. for 1.5 h. The reaction mixture was allowed to cool to RT then filtered. The collected solid was washed with water then dried in vacuo to afford a brown solid (60 mg). The solid thus obtained was dissolved in DMF (1 ml) then CDI (78 mg, 0.48 mmol) and imidazole hydrochloride (25 mg, 0.24 mmol) were added. The reaction was stirred at RT for 10 min. Water (3 ml) was added then the reaction was stirred at RT for 5 min. The solid was collected by filtration, washed with water, then dried in vacuo to afford a brown solid (39 mg). The solid thus obtained was dissolved in DMF (1 ml) then 2-(aminomethyl)-1,3-diethyl-6-methoxy-1H-1,3-benzodiazol-3-ium iodide, Intermediate 36 (45 mg, 0.13 mmol) was added. The resultant mixture was stirred at RT for 2.5 h then concentrated in vacuo. The crude material was purified by flash column chromatography on C18 (12 g). The column was eluted with MeCN:H$_2$O+0.1% TFA using the following gradient (% MeCN, column volumes): 2%, 2 CV; 2-37%, 18 CV; 37-48%, 1 CV; 48-89%, 3 CV; 89-100%, 1 CV; 100% 2 CV. The desired fractions were combined and lyophilised. The material thus obtained was further purified by preparative HPLC (Method A). The desired fractions were combined and lyophilised to afford the product as a yellow solid (3.5 mg, 1.7%).

$^1$H NMR (500 MHz, DMSO-d$_6$) δ 9.41 (t, J=5.0 Hz, 1H), 8.34 (s, 1H), 8.23 (s, 1H), 7.89 (d, J=9.1 Hz, 1H), 7.51 (d, J=2.3 Hz, 1H), 7.21 (dd, J=9.1, 2.3 Hz, 1H), 7.09 (s, 2H), 5.01 (d, J=5.4 Hz, 2H), 4.66-4.56 (m, 4H), 3.84 (s, 3H), 1.38-1.28 (m, 6H). LC/MS (System C): m/z (ESI$^+$)=419 [M$^+$], R$_t$=1.85 min, UV purity=99%.

C. BIOLOGICAL EXAMPLES

Example 68—Short Circuit Current Assay to Determine ENaC Blocker Potency in Human Bronchial Epithelial Cells Cell Culture Human bronchial epithelial cells (HBECs) (Lonza, UK) were cultured using a modification of the method described by Coote et al, (2008). Cells were seeded into plastic T-75 flasks and grown in Bronchial Epithelial Cell Growth Medium (BEGM) (Lonza, UK) supplemented with bovine pituitary extract (52 ng/mL), hydrocortisone (0.5 μg/mL), human recombinant Epidermal Growth Factor (0.5 ng/mL), epinephrine (0.5 ng/mL), transferrin (10 ng/mL), insulin (5 ng/mL), retinoic acid (0.1 ng/mL), triiodothyronine (6.5 ng/mL), gentamycin (50 μg/mL) and amphotericin-B (50 ng/mL). Medium was changed every 48 hours until cells were 90% confluent. Cells were then passaged and seeded ($8.25 \times 10^5$ cells/insert) onto polycarbonate Snapwell™ inserts (Costar, UK) in differentiation media containing 50% DMEM in BGEM with the same supplements as above but without triiodothyronine and a final retinoic acid concentration of 50 nM (all-trans retinoic acid; Sigma-Aldrich, UK). Cells were maintained submerged for the first 7 days in culture after which time they were exposed to an apical air interface for the remainder of the culture period. From the first day of establishment of an ALI, HBEC were fed with a DMEM:HAMS F-12 (1:1) media containing 2% Ultroser G (Pall BioSepra, France) with gentamycin (50 μg/mL) and amphotericin B (50 ng/mL). Cells were used for short-circuit current assay between days 14-21 after the establishment of the ALI. At all stages of culture, cells were maintained at 37° C. in 5% $CO_2$ in an air incubator.

Short-Circuit Current (ISC) Measurements

Snapwell inserts were mounted in Costar Vertical Diffusion Chambers (Costar, UK) and were bathed with continuously gassed Ringer solution (5% $CO_2$ in $O_2$; pH 7.4) maintained at 37° C. containing (in mM): 120 NaCl, 25 $NaHCO_3$, 3.3 $KH_2PO_4$, 0.8 $K_2HPO_4$, 1.2 $CaCl_2$, 1.2 $MgCl_2$ and 10 glucose. The solution osmolarity was always between 280-300 mOsm/kg $H_2O$ for all physiological salt solutions used. Cells were voltage clamped to 0 mV (model EVC4000, WPI). Transepithelial resistance (RT) was measured by applying a 2 mV pulse at 30 s intervals and calculating RT by Ohm's law. Data were recorded using a PowerLab workstation (ADInstruments, UK).

ENaC blocker compounds were added to the apical chamber from a 1000-fold stock solution (prepared in DMSO) to achieve a cumulative concentration response in terms of the inhibition of the basal ISC. At the completion of the concentration response, a supra -maximal concentration of amiloride (10 μM) was added. The concentration of test compound that induced a 50% inhibition of the total amiloride-sensitive ISC ($IC_{50}$) was calculated using Graph-Pad Prism v6.05. The results are presented in Table 2, from which it can be seen that the compounds of the present invention have ENaC inhibiting activity.

TABLE 2

| Example No. | Averages•ENaC $IC_{50}$ (nM) Avg |
| --- | --- |
| 1 | 33 |
| 2 | 43 |
| 3 | 19 |
| 4 | 8 |
| 5 | 9 |
| 6 | 5 |
| 7 | 3 |
| 8 | 9 |
| 9 | 48 |
| 10 | 199 |
| 11 | 22 |
| 12 | 5 |
| 13 | 4 |
| 14 | 11 |
| 15 | 198 |
| 16 | 10 |
| 17 | 15 |
| 18 | 5450 |
| 19 | 8 |
| 20 | 4 |
| 21 | 2 |
| 22 | 8 |
| 23 | 4 |
| 24 | 6 |
| 25 | 2 |
| 26 | 1 |
| 27 | 14 |
| 28 | 7 |
| 29 | 5 |
| 30 | 6 |
| 31 | 1 |
| 32 | 3 |
| 33 | 3 |
| 34 | 160 |
| 35 | 5 |
| 36 | 3 |
| 37 | NR |
| 38 | 9 |
| 39 | 15 |
| 40 | 7 |
| 41 | 11 |
| 42 | 10 |
| 43 | 51 |
| 44 | 21 |
| 45 | 14 |
| 46 | 8 |
| 47 | 5 |
| 48 | 18 |
| 49 | 7 |
| 50 | 35 |
| 51 | 38 |
| 52 | 69 |
| 53 | 202 |
| 54 | 49 |
| 55 | 78 |
| 56 | 15 |
| 57 | 36 |
| 58 | 78 |
| 59 | 171 |
| 60 | 22 |
| 61 | 43 |
| 62 | 24 |
| 63 | 133 |
| 64 | 244 |
| 65 | 49 |
| 66 | 199 |
| 67 | 54 |

NR—not recorded

Example 69—Bronchoalveolar Lavage (BAL) Procedure

A 0.1 mg/mL solution of ENaC inhibitor in 5% dextrose was administered intratracheally to a rat weighing 225-250 g. A volume of 1 mL/Kg was used. After 6 hours, lungs were lavaged with 3×4 mL of sterile saline. A 1 mL aliquot was subsequently snap frozen. Lungs were excised, weighed and snap frozen. Compound levels in the BAL and lung tissue were subsequently determined using LC/MS/MS bioanalysis.

The results are presented in Table 3 and demonstrate that significant amounts of the compounds of the invention persisted in the lungs 6 hours after administration.

TABLE 3

| Example No. | BAL@ 6 hours (ng/mL) |
| --- | --- |
| 50 | 260 |
| 52 | 302 |
| 54 | 139 |
| 55 | 284 |
| 56 | 283 |
| 57 | 283 |
| 58 | 256 |
| 59 | 197 |
| 60 | 176 |
| 61 | 167 |
| 62 | 140 |

Example 70—Sheep Mucociliary Clearance (MCC)

MCC was measured in conscious sheep as previously described (Coote et al., 2009; Hirsh et al., 2008). Briefly, adult ewes (25-45 kg) were restrained in an upright position in specialized body harness in modified carts. The head of the animal was immobilized, and after local anesthesia of the nasal passage was induced with 2% lidocaine, the animals were nasally intubated with a standard endotracheal tube (7.5 mm diameter, Mallinckrodt, St. Louis, Mo.). Test compounds and vehicle were delivered as nebulized aqueous solution via the endotracheal tube as a volume of 3 mL. All aerosols were generated using a Raindrop Nebulizer (Nellcor Puritan Bennett, Carlsbad, Calif.) which produces a droplet with a mass median aerodynamic diameter (MMAD) of approximately 1.1 μm. The output of the nebulizer was connected to a T-piece, with one end attached to a respirator (Harvard Apparatus Inc., Holliston, Mass.). The system was activated for 1 second at the onset of the inspiratory cycle of the respirator, which was set at an inspiratory/expiratory ratio of 1:1 and a rate of 20 breaths min-1. Aerosolized technetium labeled sulfur colloid (99mTc-SC) was used to measure the effects of the various doses of test compounds or control on MCC. Approximately 20 millicurie of 99mTc-SC in a total volume of 2 mL of sterile saline was placed in the nebulizer. A tidal volume of 500 mL was used to deliver the 99mTc-SC for 3 minutes. A gamma camera (Dyna Cam, Picker Corp., Nothford, Conn.) integrated with a computer was used to record and analyze the clearance of 99mTc-SC over 2 hours. After 99mTc-SC nebulization, the animals were immediately extubated and positioned in their natural upright position underneath the gamma camera so that the field of image was perpendicular to the animals' spinal cord. After acquisition of a baseline image, serial images were obtained over a 2 hour period at 5 minute intervals for the first hour and then every 15 minutes for the next hour. All images were obtained and stored in the computer for analysis. An 'area of interest' was traced over the image corresponding to the right lung of the animals, and counts were recorded. The left lung was excluded from analysis because its corresponding image is superimposed over the stomach and counts could be affected by swallowed radiolabeled mucus. The counts were corrected for decay and expressed as a percentage of radioactivity cleared relative to the baseline image (% cleared). Differences in clearance of 99mTc-SC were compared at both 60 and 120 min after radioaerosol administration.

Figure 2:
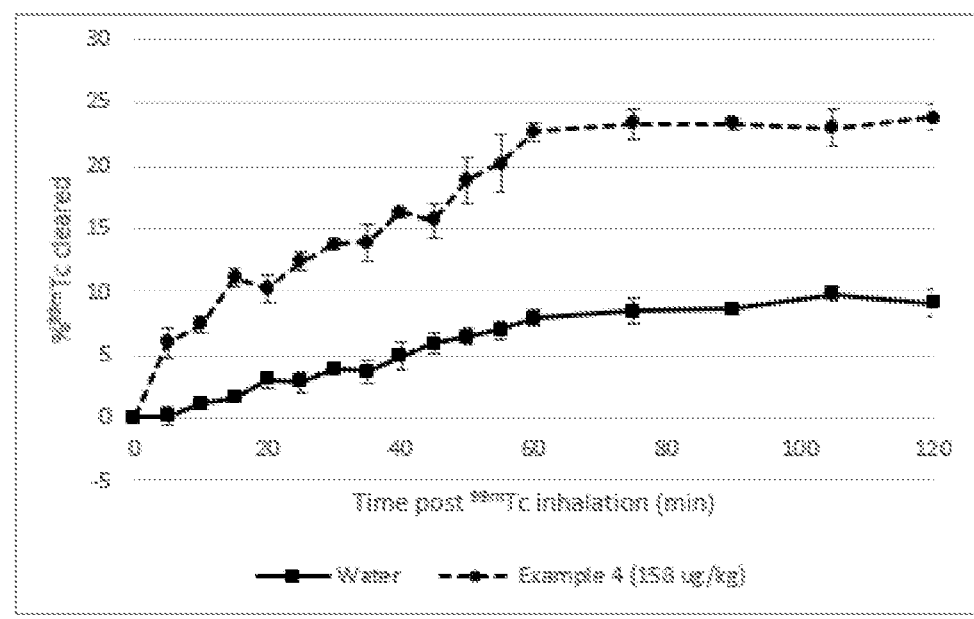
FIG. 2 is a plot showing the results of the sheep MCC experiment of Example 70 showing clearance of 99mTc-SC from the lungs of sheep treated with the compound of Example 4 at doses of 158 μg/kg (●) compared with water (■).
Figure 3:
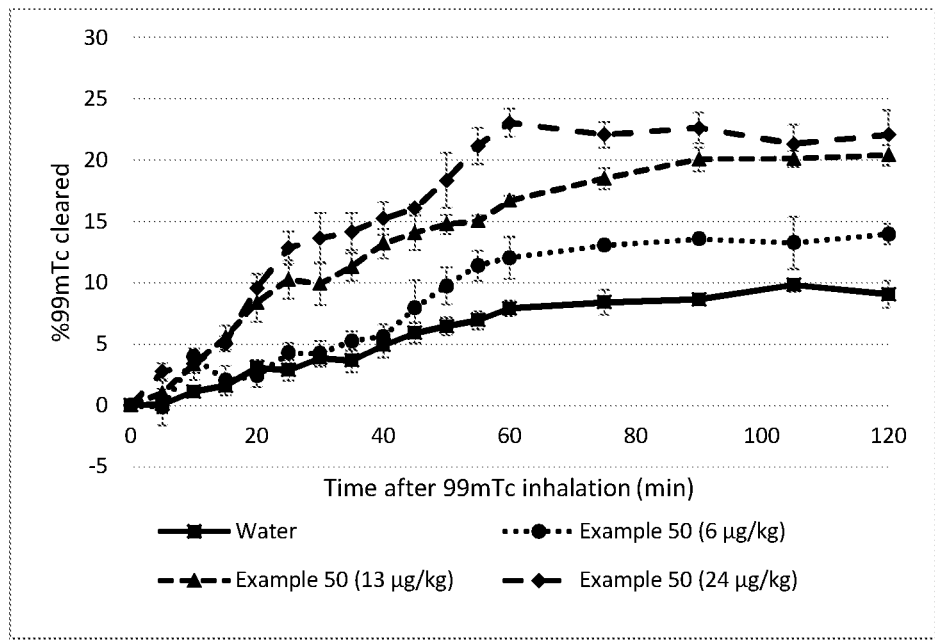
FIG. 3 is a series of two plots showing the results of the sheep MCC experiment of Example 70 showing clearance of 99mTc-SC from the lungs of sheep treated with the compound of Example 50; A-Compound 50 at doses of 6 μg/kg (●) 13 μg/kg (▲) and 24 μg/kg (♦) and water (■); B-Repeat doses of Compound 50 at 3 μg/kg BiD (●)and 13 μg/kg (▲) and water (■).
Figure 3:
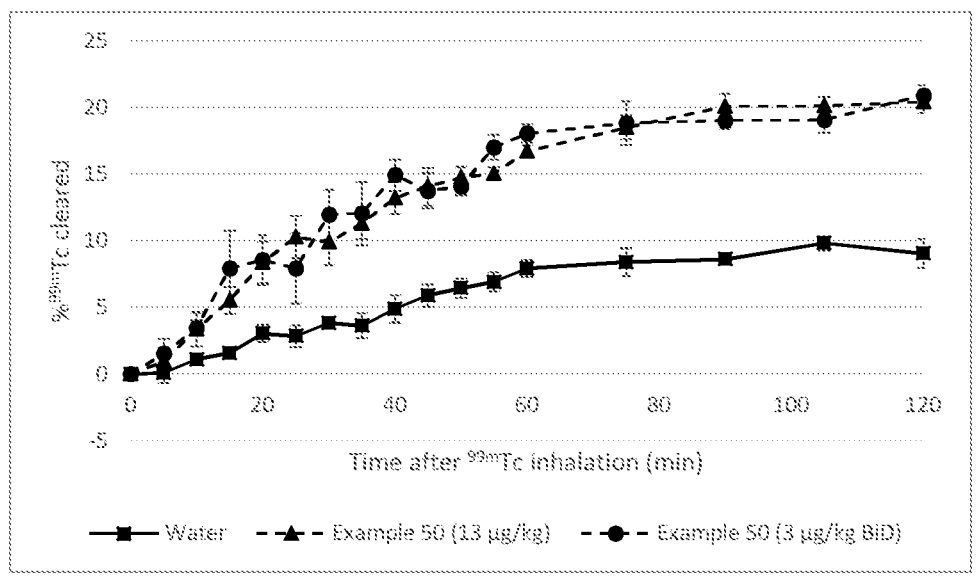
Figure 4:
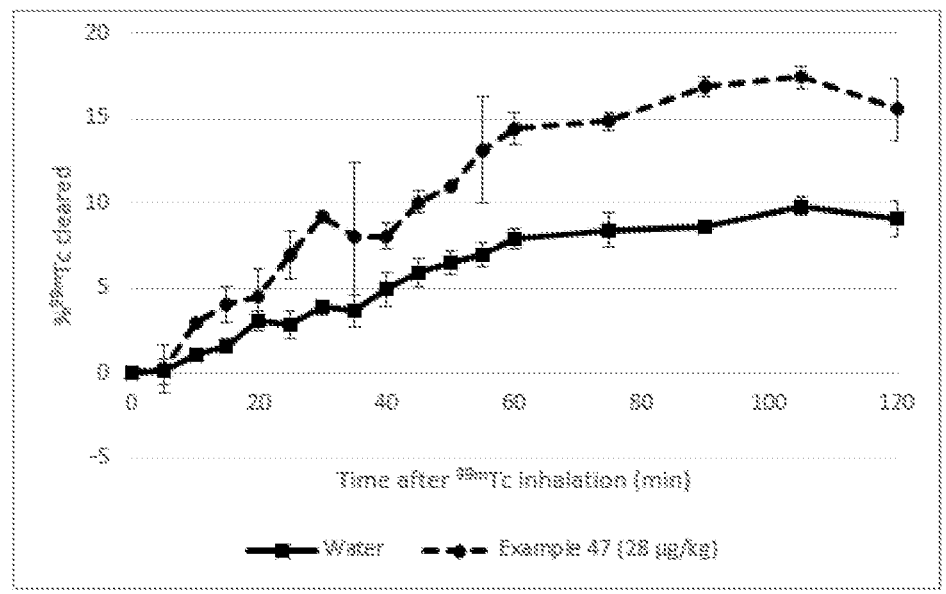
FIG. 4 is a plot showing the results of the sheep MCC experiment of Example 70 showing clearance of 99mTc-SC from the lungs of sheep treated with the compound of Example 47 at a dose of 28 μg/kg (●) compared with water (■).
Figure 5:
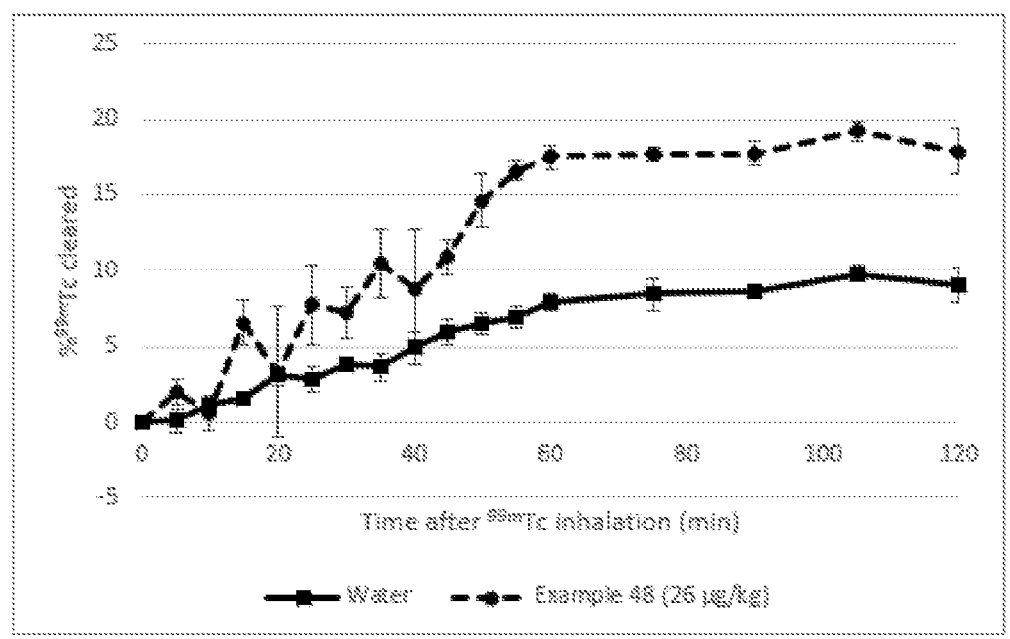
FIG. 5 is a plot showing the results of the sheep MCC experiment of Example 70 showing clearance of 99mTc-SC from the lungs of sheep treated with the compound of Example 48 at a dose of 26 μg/kg (●) compared with water (■).
Figure 6:
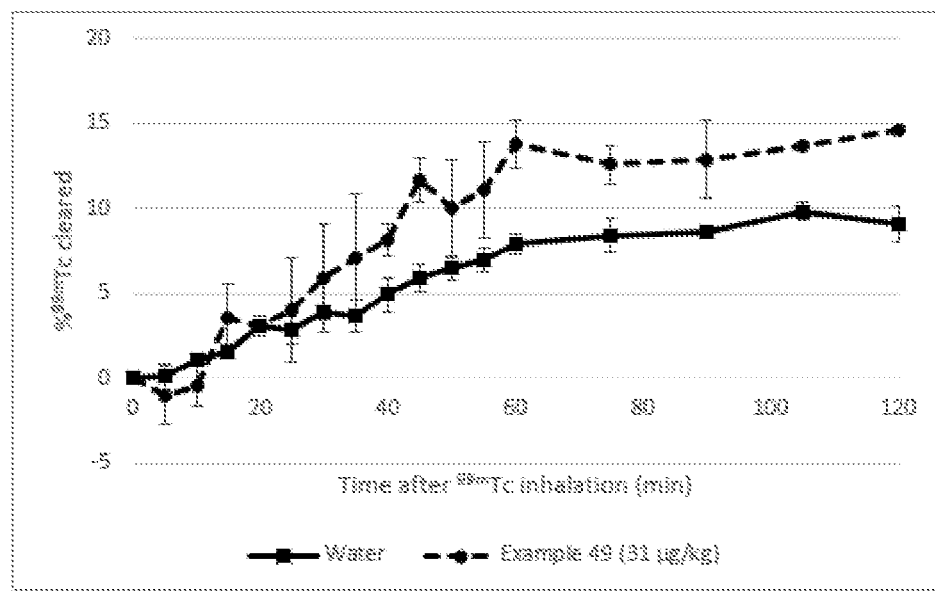
FIG. 6 is a plot showing the results of the sheep MCC experiment of Example 70 showing clearance of 99mTc-SC from the lungs of sheep treated with the compound of Example 49 at a dose of 31 μg/kg (●) compared with water (■).
Figure 7:
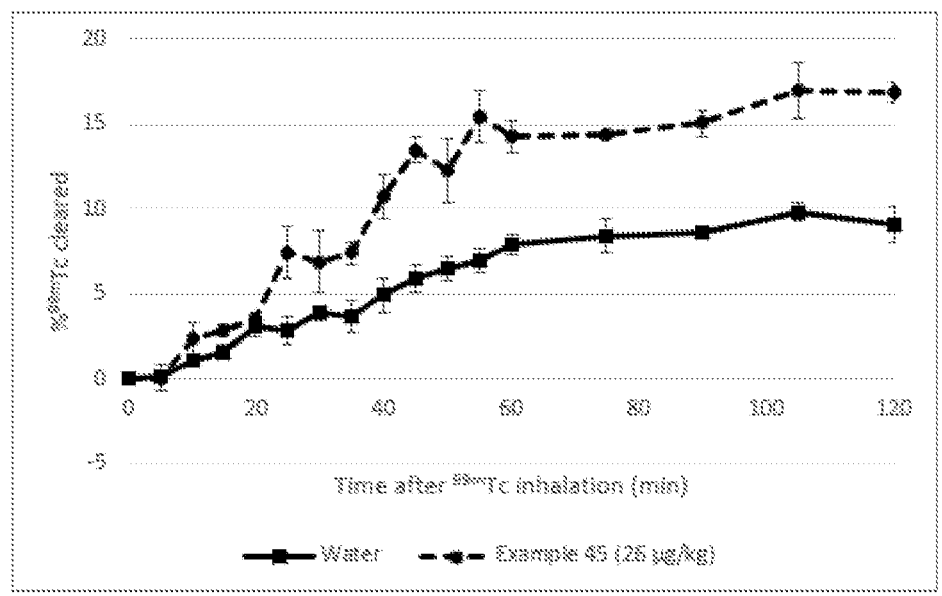
FIG. 7 is a plot showing the results of the sheep MCC experiment of Example 70 showing clearance of 99mTc-SC from the lungs of sheep treated with the compound of Example 45 at a dose of 26 μg/kg (●) compared with water (■).
Figure 8:
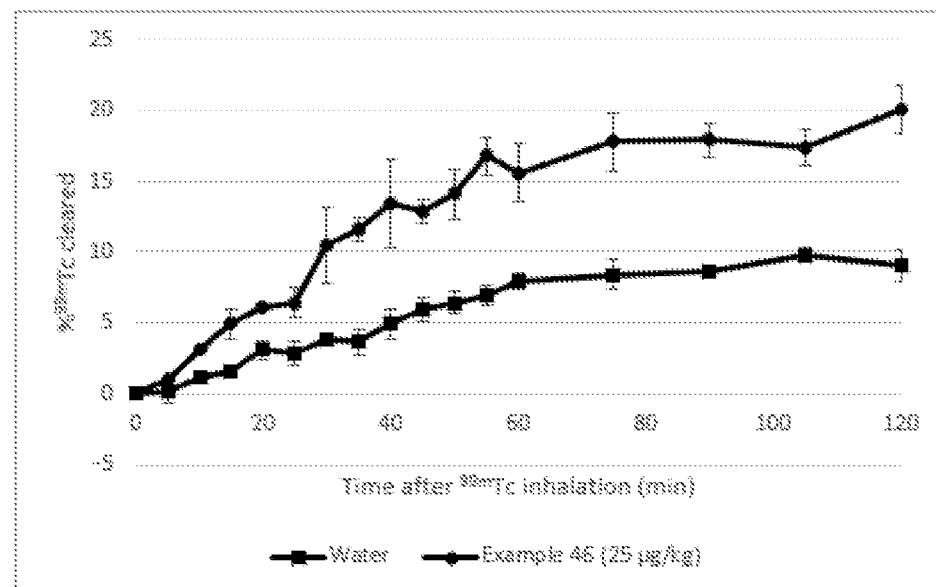
FIG. 8 is a plot showing the results of the sheep MCC experiment of Example 70 showing clearance of 99mTc-SC from the lungs of sheep treated with the compound of Example 46 at a dose of 25 μg/kg (●) compared with water (■).
Figure 9:
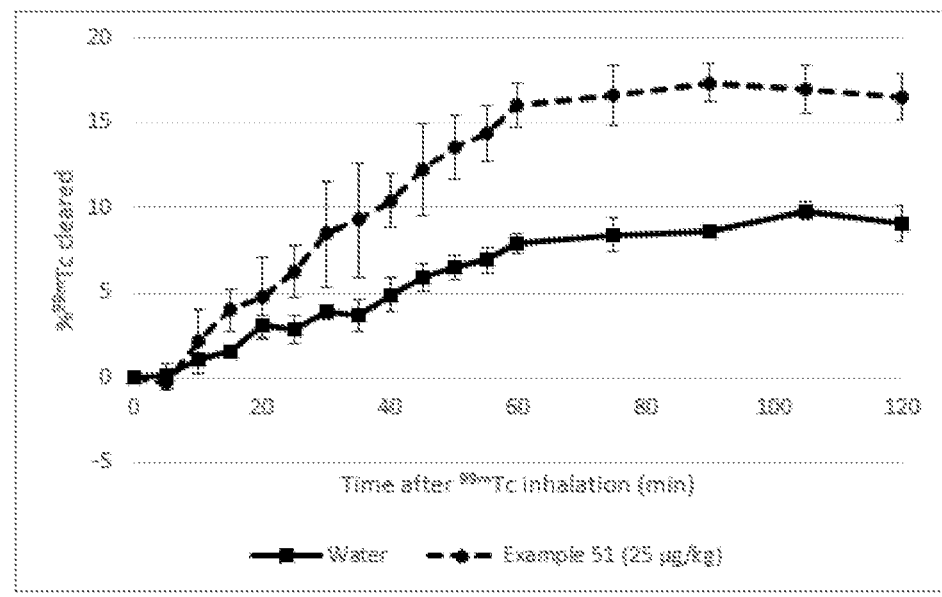
FIG. 9 is a plot showing the results of the sheep MCC experiment of Example 70 showing clearance of 99mTc-SC from the lungs of sheep treated with the compound of Example 51 at a dose of 25 μg/kg (●) compared with water (■).
Figure 10:
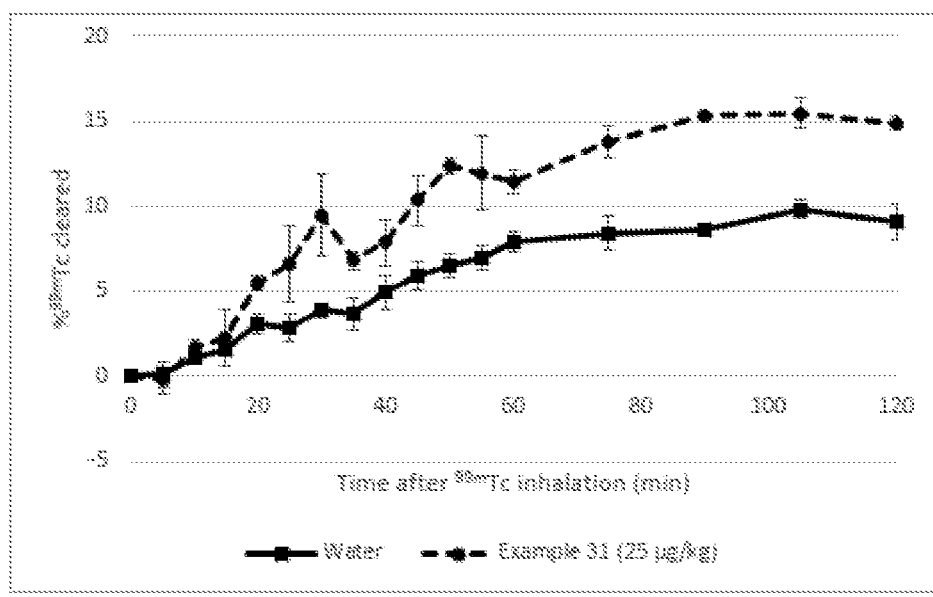
FIG. 10 is a plot showing the results of the sheep MCC experiment of Example 70 showing clearance of 99mTc-SC from the lungs of sheep treated with the compound of Example 31 at a dose of 25 μg/kg (●) compared with water (■).
Figure 11:
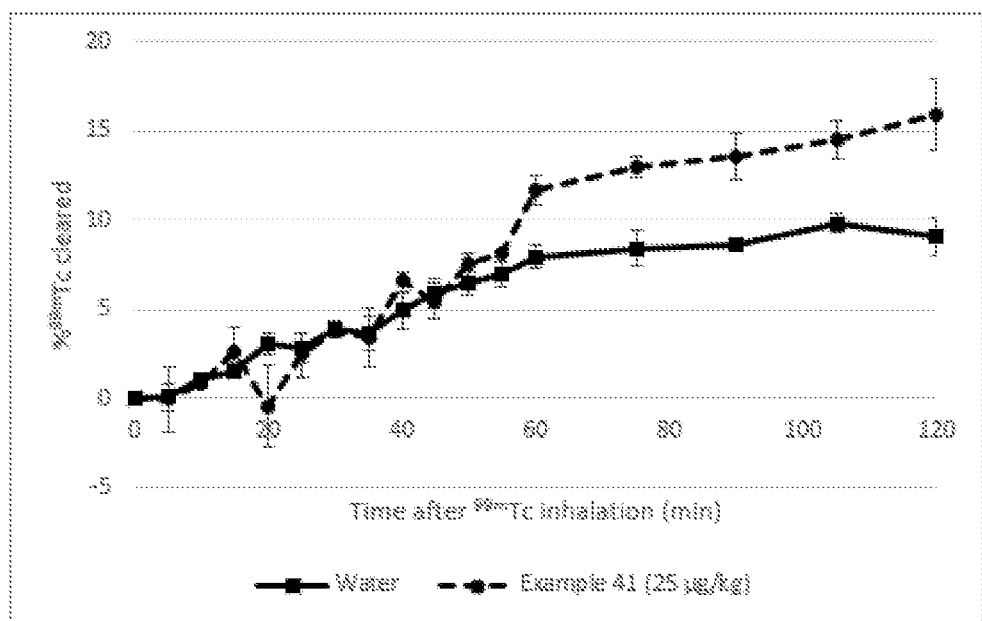
FIG. 11 is a plot showing the results of the sheep MCC experiment of Example 70 showing clearance of 99mTc-SC from the lungs of sheep treated with the compound of Example 41 at a dose of 25 μg/kg (●) compared with water (■).
Figure 12:
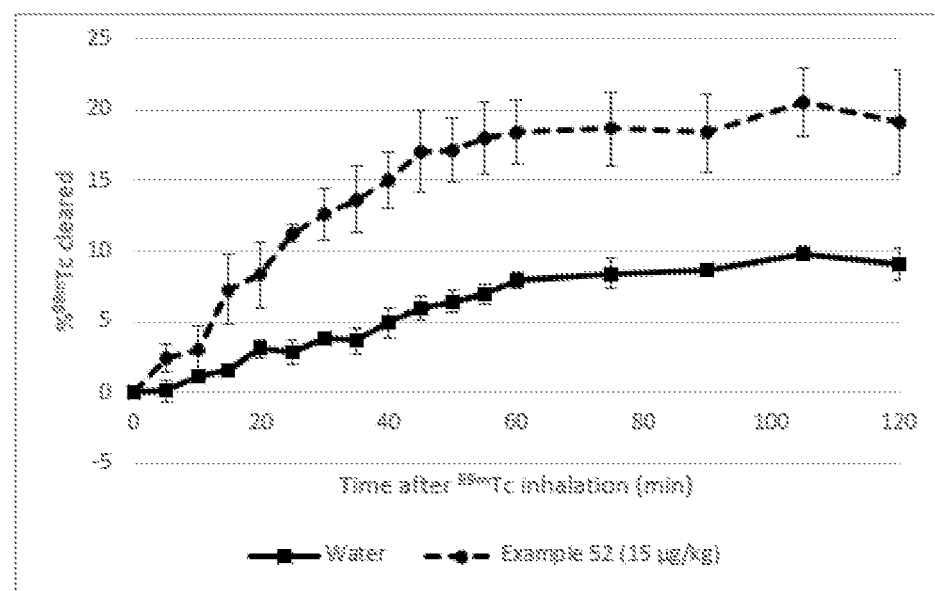
FIG. 12 is a plot showing the results of the sheep MCC experiment of Example 70 showing clearance of 99mTc-SC from the lungs of sheep treated with the compound of Example 52 at a dose of 15 μg/kg (●) compared with water (■).
Figure 13:
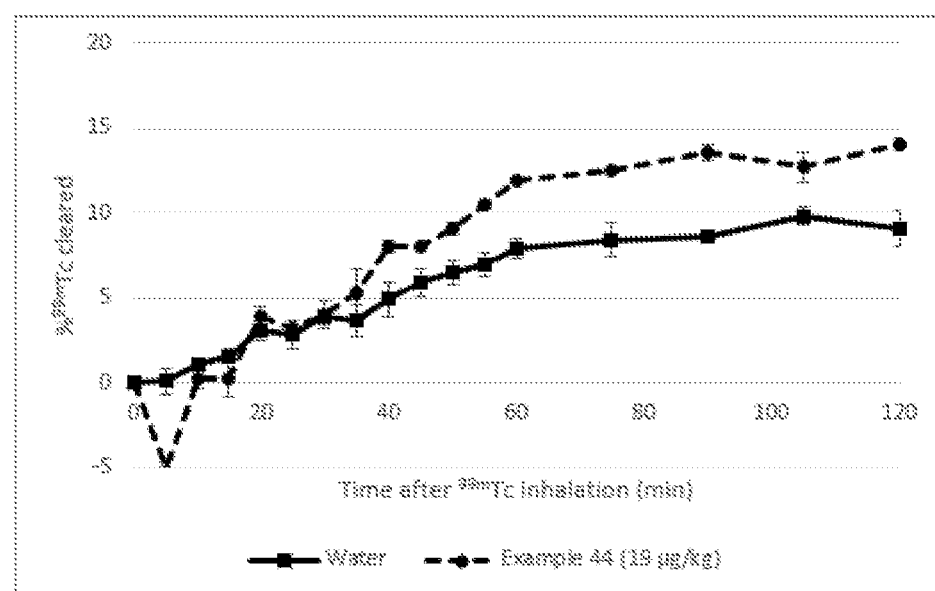
FIG. 13 is a plot showing the results of the sheep MCC experiment of Example 70 showing clearance of 99mTc-SC from the lungs of sheep treated with the compound of Example 44 at a dose of 19 μg/kg (●) compared with water (■).

The results are presented in FIGS. 1-13, all of which show that, for all of the compounds tested, the amount of 99mTc-SC cleared over a 120 minute period, 4 hours after administration of test compound was significantly increased compared with the amount cleared when the sheep was treated with water. Repeat dosing was carried out for the compound of Example 50. In this case, the compound was administered at a dose of 3 μg/kg twice daily (BiD) at 12 hour intervals for a total of 7 doses (i.e. over 3.5 days).

Measurement of the amount of 99mTc-SC cleared over a 120 minute period was begun 4 hours after administration of the final dose of the test compound. The results are presented in FIG. 3B, which compares a single 13 μg/kg dose, 3 μg/kg BiD dosing and a single dose of water.

The sheep mucociliary clearance model described above is a model for studying the clearance of mucus and is therefore a model for the effectiveness of test compounds in diseases and conditions characterised by a build-up of mucus in the lungs, for example cystic fibrosis, chronic bronchitis, bronchiectasis, severe asthma and primary ciliary dyskinesia. Therefore, the results presented in FIGS. 1-13 indicate that the compounds tested are likely to be of use in the treatment of conditions of this type, as well as other diseases and conditions mediated by ENaC.

The inventors have also compared in this model certain compounds of the present invention with compounds in which the pyrrolopyrazine moiety is replaced with the conventional 6-chloro-3,5-diaminopyrazine moiety which occurs in the majority of prior art compounds as discussed above, but which are otherwise structurally identical. They were able to show that in the sheep MCC model the tested compounds of general formula (I) showed a significant increase in mucociliary clearance compared with the corresponding 6-chloro-3,5-diaminopyrazine compounds. This indicates that compounds of the present invention have superior activity in vivo compared with prior art compounds.

REFERENCES

App E M, King M, Helfesrieder R, Köhler D and Matthys H. Acute and long-term amiloride inhalation in cystic fibrosis lung disease. A rational approach to cystic fibrosis therapy. Am Rev Respir Dis., 1990, 141(3):605-12.

Botero-Velez M, Curtis J J and Warnock D G. Brief report: Liddle's syndrome revisited—a disorder of sodium reabsorption in the distal tubule. N Engl J Med., 1994, 330(3):178-81.

Boucher R C. Evidence for airway surface dehydration as the initiating event in CF airway disease. J Intern Med., 2007, 261(1):5-16.

Bowler I M, Kelman B, Worthington D, Littlewood J M, Watson A, Conway S P, Smye S W, James S L and Sheldon T A. Nebulised amiloride in respiratory exacerbations of cystic fibrosis: a randomised controlled trial. Arch Dis Child., 1995, 73(5):427-30.

Chang S S, Grunder S, Hanukoglu A, Rosier A, Mathew P M, Hanukoglu I, Schild L, Lu Y, Shimkets R A, Nelson-Williams C, Rossier B C and Lifton R P. Mutations in subunits of the epithelial sodium channel cause salt wasting with hyperkalaemic acidosis, pseudohypoaldosteronism type 1. Nat Genet., 1996, 12(3):248-53.

Coote K, Atherton-Watson HC, Sugar R, Young A, MacKenzie-Beevor A, Gosling M, Bhalay G, Bloomfield G, Dunstan A, Bridges R J, Sabater J R, Abraham W M, Tully D, Pacoma R, Schumacher A, Harris J, Danahay H. Camostat attenuates airway epithelial sodium channel function in vivo through the inhibition of a channel-activating protease. J Pharmacol Exp Ther. 2009 May; 329(2):764-74.

Coote K J, Atherton H, Young A, Sugar R, Burrows R, Smith N J, Schlaeppi J M, Groot -Kormelink P J, Gosling M, Danahay H. The guinea-pig tracheal potertial difference as an in vivo model for the study of epithelial sodium channel function in the airways. Br J Pharmacol. 2008 December; 155(7):1025-33.

Fajac I, Hubert D, Guillemot D, Honore I, Bienvenu T, Volter F, Dall'Ava-Santucci J and Dusser D J. Nasal airway ion transport is linked to the cystic fibrosis phenotype in adult patients. Thorax, 2004, 59(11):971-6.

Frateschi S, Charles R-P, Hummler E. The Epithelial Sodium Channel ENaC and its Regulators in the Epidermal Permeability Barrier Function. The Open Dermatology Journal, 2010, 4: 27-35.

Graham A, Hasani A, Alton E W, Martin G P, Marriott C, Hodson M E, Clarke S W and Geddes D M. No added benefit from nebulized amiloride in patients with cystic fibrosis. Eur Respir J., 1993, 6(9):1243-8.

Hirsh A J, Zhang J, Zamurs A, Fleegle J, Thelin W R, Caldwell R A, Sabater J R, Abraham W M, Donowitz M, Cha B, Johnson K B, St George J A, Johnson M R, Boucher R C. Pharmacological properties of N-(3,5-diamino-6-chloropyrazine-2-carbonyl)-N'-4-[4-(2,3-dihydroxpropoxy)phenyl]butyl-guanidine methanesulfonate (552-02), a novel epithelial sodium channel blocker with potertial clinical efficacy for cystic fibrosis lung disease. J Pharmacol Exp Ther. 2008 April; 325(1):77-88.

Kellenberger S and Schild L. Epithelial sodium channel/ degenerin family of ion channels: a variety of functions for a shared structure. Physiol Rev., 2002 82(3):735-67.

Kerem E, Bistritzer T, Hanukoglu A, Hofmann T, Zhou Z, Bennett W, MacLaughlin E, Barker P, Nash M, Quittell L, Boucher R and Knowles M R. Pulmonary epithelial sodium -channel dysfunction and excess airway liquid in pseudohypoaldosteronism. N Engl J Med., 1999, 341(3):156-62.

Knowles M R, Stutts M J, Spock A, Fischer N, Gatzy J T and Boucher R C. Abnormal ion permeation through cystic fibrosis respiratory epithelium. Science, 1983, 221(4615): 1067-70.

Knowles M R, Church N L, Waltner W E, Yankaskas J R, Gilligan P, King M, Edwards L J, Helms R W and Boucher R C. A pilot study of aerosolized amiloride for the treatment of lung disease in cystic fibrosis. N Engl J Med., 1990, 322(17):1189-94.

Leal T, Fajac I, Wallace H L, Lebecque P, Lebacq J, Hubert D, Dall'Ava J, Dusser D, Ganesan A P, Knoop C, Cumps J, Wallemacq P and Southern K W. Airway ion transport impacts on disease presentation and severity in cystic fibrosis. Clin Biochem., 2008, 41(10-11):764-72.

Matsui H, Grubb B R, Tarran R, Randell S H, Gatzy J T, Davis C W and Boucher R C. Evidence for periciliary liquid layer depletion, not abnormal ion composition, in the pathogenesis of cystic fibrosis airways disease. Cell, 1998, 95(7): 1005-15.

Middleton P G, Geddes D M and Alton E W. Effect of amiloride and saline on nasal mucociliary clearance and potertial difference in cystic fibrosis and normal subjects. Thorax, 1993, 48(8):812-6.

Noone P G, Regnis J A, Liu X, Brouwer K L, Robinson M, Edwards L and Knowles M R. Airway deposition and clearance and systemic pharmacokinetics of amiloride following aerosolization with an ultrasonic nebulizer to normal airways. Chest, 1997, 112(5):1283-90.

Perazella M A. Drug-induced hyperkalemia: old culprits and new offenders. Am J Med., 2000, 109(4):307-14.

Pons G, Marchand M C, d'Athis P, Sauvage E, Foucard C, Chaumet-Riffaud P, Sautegeau A, Navarro J and Lenoir G. French multicenter randomized double-blind placebo-controlled trial on nebulized amiloride in cystic fibrosis patients. The Amiloride -AFLM Collaborative Study Group. Pediatr Pulmonol., 2000, 30(1):25-31.

Thelin W R, Johnson M R, Hirsh A J, Kublin C L, Zoukhri D. Effect of Topically Applied Epithelial Sodium Channel Inhibitors on Tear Production in Normal Mice and in Mice with Induced Tear Deficiency. J Ocul Pharmacol Ther, 2012, 28(4):433-438.

The invention claimed is:
1. A compound of formula (I):

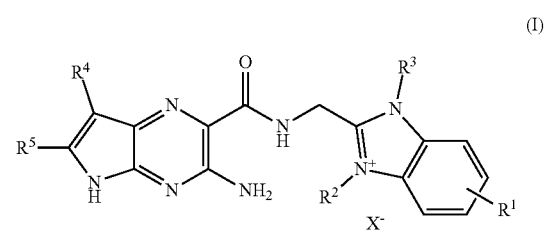

or a pharmaceutically acceptable salt, stereoisomer or tautomer thereof, wherein:

$R^1$ is H, halo, $L^1R^{10}$, $R^{12}$, $OR^{12}SO_2R^{12}$, $C(O)OR^{12}$, $C(O)NR^{12}R^{13}$, $C(=NR^9)NR^{12}R^{13}$, $Q^1OR^{12}$, $Q^1SO_2R^{12}$, $Q^1C(O)OR^{12}$, $Q^1C(O)NR^{12}R^{13}$, $Q^1C(=NR^7)NR^{12}R^{13}$, $Q^1Q^2OR^{12}$, $Q^1SO_2R^{12}$, $Q^1Q^2C(O)OR^{12}$, $Q^1Q^2C(O)NR^{12}R^{13}$, or $Q^1Q^2C(=NR^9)NR^{12}R^{13}$;

each of $R^2$ and $R^3$ is independently $C_{1-10}$ alkyl, optionally substituted with one or more substituents independently selected from the group consisting of halo, $C(O)N(R^7)R^8$, $C(O)OR^7$, $N(R^7)R^8$, $OR^7$, SH, $N(R^7)R^8$, cycloalkyl, heterocyclyl, aryl, and heteroaryl, wherein one or more —$CH_2$— groups are optionally and independently replaced by —O—, —S— or —$NR^7$—, provided that adjacent —$CH_2$— groups are not so replaced;

$R^4$ is H, halo, cyano, $C_{1-6}$ alkyl, $C(O)N(R^{16})R^{17}$, or $C(O)OR^{16}$;

wherein $C_{1-6}$ alkyl is optionally substituted with one or more substituents independently selected from the group consisting of halo, $N(R^7)R^8$, and $OR^7$;

$R^5$ is H or methyl;

$L^1$ is —$Z^1$—, —$Q^1$—, —$Z^1Q^1$—, —$Q^1Z^1$—, —$Z^1Q^1Z^2$—, —$Q^1Q^2$—, —$Q^1Q^2Z^1$—, —$Q^1Q^2Z^1Q^3Z^2$—, —$Z^1Q^1OQ^2OQ^3$—;

—$OZ^1$—, —$OQ^1$—, —$OZ^1Q^1$—, —$OQ^1Z^1$—, —$OZ^1Q^1Z^2$—, —$OQ^1Q^2$—, —$OQ^1Q^2Z^1$—, —$OQ^1Q^2Z^1Q^3Z^2$—, —$OZ^1Q^1OQ^2OQ^3$—;

—$Z^1N(R^7)Z^2$—, —$Q^1Z^1N(R^7)Z^2$—, —$Z^1N(R^7)Z^2Q^1$—, —$Q^1Z^1N(R^7)Z^2Q^2Z^3$—;

—$Z^1O(CH_2CH_2O)_nZ^2$—, —$Z^1O(CH_2CH_2O)_nQ^1$—, —$Z^1O(CH_2CH_2O)_nZ^2Q^1$, —$Z^1O(CH_2CH_2O)_nQ^1Z^2$—, —$Q^1Z^1O(CH_2CH_2O)_nZ^2$—, —$Q^1Z^1O(CH_2CH_2O)_nQ^1$—, —$Q^1Z^1O(CH_2CH_2O)_nZ^2Q^1$, —$Z^1O(CH_2CH_2O)_nQ^1Z^3$—;

—$C(O)Z^1$—, —$C(O)Q^1$—, —$C(O)Z^1Q^1$—, —$C(O)Z^1Q^1Z^2$—, —$C(O)Q^1Z^1$—, —$C(O)Q^1Q^2$—, —$C(O)Q^1Q^2Z^1$—, —$C(O)Q^1N(R^7)C(O)Z^1$—, —$C(O)Q^1N(R^7)C(O)Z^1$—, —$C(O)Q^1N(R^7)C(O)Z^1Q^2Q^3$—, —$C(O)Q^1N(R^7)C(O)Z^1Q^2Z^2$—, —$C(O)Z^1Q^1OQ^2OQ^3$—;

—C(O)N(R⁷)Z¹—, —C(O)N(R⁷)Q¹—, —C(O)N(R⁷)Z¹Q¹—, —C(O)N(R⁷)Z¹Q¹Z²—, —C(O)N(R⁷)Q¹Z¹—, —C(O)N(R⁷)Q¹Q²—, —C(O)N(R⁷)Q¹Q²Z¹—, —C(O)N(R⁷)Z¹Q¹Q²Z²—, —C(O)N(R⁷)Z¹O(CH₂CH₂O)ₙZ²—, —C(O)N(R⁷)Z¹O(CH₂O)ₙZ²—, —C(O)N(R⁷)Z¹Q¹Z²N(R⁸)Z³—, —C(O)N(R⁷)Z¹N(R⁸)Z²—, —C(O)N(R⁷)Q¹Z¹N(R⁸)Z²—, —C(O)N(R⁷)Z¹Q¹OQ²OQ³—, —C(O)N(R⁷)Z¹Q¹OQ²OQ³Z²—;

—Z¹C(O)N(R⁷)Z²—, —Z¹C(O)N(R⁷)Q¹—, —Z¹C(O)N(R⁷)Z²Q¹—, —Z¹C(O)N(R⁷)Q¹Z²—, —Z¹C(O)N(R⁷)Q¹Q²—, —Z¹C(O)Q¹—, —Z¹C(O)Q¹Z²—, —Z¹C(O)Q¹Q²—, —Z¹C(O)N(R⁷)Q¹Q²Z²—;

—C(O)OZ¹—, —C(O)OQ¹—, —C(O)OZ¹Q¹—, —C(O)OZ¹Q¹Z²—, —C(O)OQ¹Z¹—, —C(O)OQ¹Q²—, —C(O)OQ¹Q²Z¹—;

—Q¹C(O)Q²—, Q¹C(O)Z¹—, —Q¹C(O)Q²Z¹—, Q¹C(O)Q²Q³—, Q¹C(O)Z¹Q²—, Q¹C(O)Q²Q³Z¹—; —C(=NR⁹)N(R⁷)Z¹—, —C(=NR⁹)N(R⁷)Q¹—, —C(=NR⁹)N(R⁷)Z¹Q¹—, —C(=NR⁹)N(R⁷)Z¹Q¹Z²—, —C(=NR⁹)N(R⁷)Q¹Z¹—, —C(=NR⁹)N(R⁷)Q¹Q²—, or C(=NR⁹)N(R⁷)Q¹Q²Z¹—;

R¹⁰ is H, C(O)OR⁷, N(R⁷)R⁸, N(R⁷)C(=NR⁹)N(R⁸)₂, N(R⁷)—C(O)OR⁸, or OR⁷; or R¹⁰ is N(R⁷)—C(O)—C₁₋₃ alkylene-N (R⁸)₃⁺ or N(R⁸)₃⁺;

each of R¹² and R¹³ is independently H, C₁₋₆ alkyl, C₂₋₆ alkenyl, C₂₋₆ alkynyl, C₃₋₈ cycloalkyl or 3- to 8-membered heterocyclyl, wherein each C₁₋₆ alkyl, C₂₋₆ alkenyl and C₂₋₆ alkynyl is optionally and independently substituted with one or more substituents independently selected from the group consisting of halo, C(O)N(R⁷)R⁸, C(O)OR⁷, N(R⁷)R⁸, and OR⁷, and further wherein each C₃₋₈ cycloalkyl and 3- to 8-membered heterocyclyl is optionally and independently substituted with one or more substituents independently selected from the group consisting of oxo, halo, C(O)N(R⁷)R⁸, C(O)OR⁷, N(R⁷)R⁸, and OR⁷;

each of R⁷ and R⁸ is independently H or C₁₋₁₂ alkyl, wherein the C₁₋₁₂ alkyl is optionally substituted with one or more substituents independently selected from the group consisting of halo and OH; or R⁷ and R⁸, together with any nitrogen atom to which they are attached, form a 5- or 6-membered heterocyclic ring optionally containing one or more additional heteroatoms selected from the group consisting of nitrogen, oxygen, and sulfur; or two R⁸, together with any nitrogen atom to which they are attached, form a 5- or 6-membered heterocyclic ring optionally containing one or more additional heteroatoms selected from the group consisting of nitrogen, oxygen, and sulfur;

R⁹ is H or C₁₋₆ alkyl;

each of Q¹, Q² and Q³ is independently carbocyclyl, heterocyclyl, aryl, or heteroaryl, wherein each aryl and heteroaryl is optionally and independently substituted with one or more substituents independently selected from the group consisting of halo, C₁₋₄ alkyl, C₁₋₄ haloalkyl, C(O)NR¹⁵R¹⁶, C(O)OR¹⁵, NR¹⁵R¹⁶, and OH, and further wherein each carbocycyl and heterocyclyl is optionally and independently substituted with one or more substituents independently selected from the group consisting of oxo, halo, C₁₋₄ alkyl, C₁₋₄ haloalkyl, C(O)NR¹⁵R¹⁶, C(O)OR¹⁵, NR¹⁵R¹⁶, and OH;

each of Z¹, Z² and Z³ is independently C₁₋₁₂ alkylene, C₂₋₁₂ alkenylene, or C₂₋₁₂ alkynylene, wherein each C₁₋₁₂ alkylene, C₂₋₁₂ alkenylene and C₂₋₁₂ alkynylene is optionally substituted by one or more substituents independently selected from the group consisting of halo, C(O)NR¹⁵R¹⁶, C(O)OR¹⁵, NR¹⁵R¹⁶, and OH;

R¹⁵ is H or C₁₋₆ alkyl;
R¹⁶ is H or C₁₋₆ alkyl;
R¹⁷ is H or C₁₋₆ alkyl; or

R¹⁵ and R¹⁶ together with the nitrogen atom to which they are attached form a 5- or 6-membered heterocyclic ring optionally containing one or more additional heteroatoms selected from the group consisting of nitrogen, oxygen, and sulfur; or R¹⁶ and R¹⁷ together with the nitrogen atom to which they are attached form a 5- or 6-membered heterocyclic ring optionally containing one or more additional heteroatoms selected from the group consisting of nitrogen, oxygen, and sulfur;

n is 1, 2, 3, 4, 5 or 6; and

X⁻ is an anion;

provided that when R¹⁰ is N(R⁷)—C(O)—C₁₋₃ alkylene-N (R⁸)₃⁺ or N(R⁸)₃⁺, the compound of formula (I) has an additional X⁻.

2. The compound according to claim 1, wherein the compound is of formula (IA) or formula (IB):

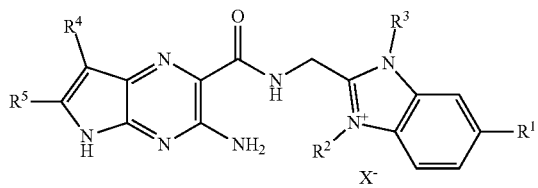

(IA)

or

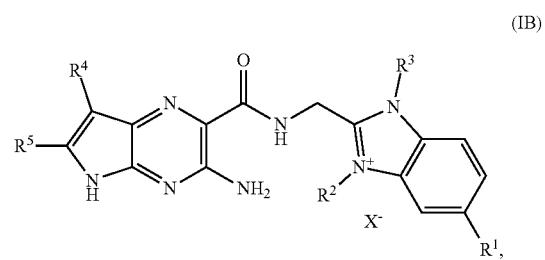

(IB)

or a pharmaceutically acceptable salt, stereoisomer or tautomer thereof.

3. The compound according to claim 1, or a pharmaceutically acceptable salt, stereoisomer or tautomer thereof, wherein R¹ is H, halo, R¹², C(O)OR¹², or OR¹².

4. The compound according to claim 1, or a pharmaceutically acceptable salt, stereoisomer, or tautomer thereof, wherein R¹ is L¹R¹⁰.

5. The compound according to claim 4, or a pharmaceutically acceptable salt, stereoisomer or tautomer thereof, wherein L¹ is —Z¹—, —Q¹—, —Q¹Z¹—, —Q¹Q²—, —Q¹Q²Z¹—, —OZ¹—, —C(O)Q¹—, —C(O)Q¹Z¹—, —C(O)N(R⁷)Z¹—, C(O)N(R⁷)Q¹—, —C(O)N(R⁷)Z¹Q¹—, —C(O)N(R⁷)Q¹Z¹—, —C(O)N(R⁷)Z¹Q¹Q²Z²—, —C(O)N(R⁷)Z¹O(CH₂CH₂O)ₙZ²— or —C(O)N(R⁷)Z¹Q¹Z²N(R⁸)Z³—.

6. The compound according to claim 4, or a pharmaceutically acceptable salt, stereoisomer or tautomer thereof, wherein:

$R^{10}$ is H, C(O)OR$^7$, N(R$^7$)R$^8$, N(R$^7$)C(=NR$^9$)N(R$^8$)$_2$, N(R$^7$)C(O)OR$^8$, or OR$^7$; or $R^{10}$ is N(R$^7$)C(O)—C$_{1-3}$ alkylene-N(R$^8$)$_3$$^+$ or N(R$^8$)$_3$$^+$.

7. The compound according to claim 4, or a pharmaceutically acceptable salt, stereoisomer or tautomer thereof, wherein:
   a) L$^1$ is —OZ$^1$—;
      Z$^1$ is C$_{1-4}$ alkylene; and
      R$^{10}$ is H; or
   b) L$^1$ is —Q$^1$— or —C(O)N(R$^7$)Q$^1$—;
      Q$^1$ is a nitrogen-containing heterocyclyl, wherein the heterocyclyl is linked to R$^{10}$ via a ring nitrogen atom; and
      R$^{10}$ is H; or
   c) L$^1$ is —Q$^1$Q$^2$—;
      Q$^2$ is a nitrogen-containing heterocyclyl, wherein the heterocyclyl is linked to R$^{10}$ via a ring nitrogen atom; and
      R$^{10}$ is H; or
   d) L$^1$ is —Z$^1$—, Q$^1$, —Q$^1$Z$^1$—, —Q$^1$Q$^2$—, —Q$^1$Q$^2$Z$^1$—, —OZ$^1$—, —OQ$^1$Z$^1$—, —OQ$^1$Q$^2$Z$^1$—, —C(O)Z$^1$—, —C(O)Q$^1$Z$^1$—, —C(O)Q$^1$Q$^2$Z$^1$—, —C(O)N(R$^7$)Z$^1$—, —C(O)N(R$^7$)Q$^1$Z$^1$—, —C(O)N(R$^7$)Q$^1$Q$^2$Z$^1$—, —C(O)OZ$^1$—, —C(O)OQ$^1$Z$^1$—, —C(O)OQ$^1$Q$^2$—, —C(O)OQ$^1$Q$^2$Z$^1$—, —C(=NR$^9$)N(R$^7$)Z$^1$—, —C(=NR$^9$)N(R$^7$)Q$^1$Z$^1$—, or —C(=NR$^9$)N(R$^7$)Q$^1$Q$^2$Z$^1$—; and
      R$^{10}$ is H; or
   e) L$^1$ is —Q$^1$Z$^1$—, —Z$^1$Q$^1$Z$^2$—, —Q$^1$Q$^2$Z$^1$—, —OQ$^1$Z$^1$—, —OZ$^1$Q$^1$Z$^2$—, —OQ$^1$Q$^2$Z$^1$—, —Z$^1$O(CH$_2$CH$_2$O)$_n$Q$^1$Z$^2$—, —Q$^1$Z$^1$O(CH$_2$CH$_2$O)$_n$Z$^2$—, —Z$^1$O(CH$_2$CH$_2$O)$_n$Z$^2$Q$^1$Z$^3$—, —C(O)Z$^1$Q$^1$Z$^2$—, —C(O)Q$^1$Z$^1$—, —C(O)Q$^1$Q$^2$Z$^1$—, —C(O)Q$^1$N(R$^7$)C(O)Z$^1$Q$^2$Z$^2$—, —C(O)N(R$^7$)Z$^1$Q$^1$Z$^2$—, —C(O)N(R$^7$)Q$^1$Z$^1$—, —C(O)N(R$^7$)Q$^1$Q$^2$Z$^1$—, —C(O)N(R$^7$)Z$^1$Q$^1$Q$^2$Z$^2$—, —C(O)N(R$^7$)Z$^1$Q$^1$OQ$^2$OQ$^3$Z$^2$—, —Z$^1$C(O)N(R$^7$)Q$^1$Z$^2$—, Z$^1$C(O)Q$^1$Z$^2$—, —Z$^1$C(O)Q$^1$Z$^2$—, Z$^1$C(O)N(R$^7$)$^7$Q$^1$Q$^2$Z$^2$—, —C(O)OZ$^1$Q$^1$Z$^2$—, —C(O)OQ$^1$Z$^1$—, —C(O)OQ$^1$Q$^2$Z$^1$—, —Q$^1$C(O)Q$^2$Z$^1$—, Q$^1$C(O)Q$^2$Q$^3$Z$^1$—, —C(=NR$^9$)N(R$^7$)Z$^1$Q$^1$Z$^2$—, —C(=NR$^9$)N(R$^7$)Q$^1$Z$^1$—, or —C(=NR$^9$)N(R$^7$)Q$^1$Q$^2$Z$^1$—;
      each of Q$^1$, Q$^2$ and Q$^3$ is independently a nitrogen-containing heterocyclyl, wherein the heterocyclyl is linked to each of Z$^1$, Z$^2$, and/or Z$^3$ via a ring nitrogen atom; and
      R$^{10}$ is H; or
   f) L$^1$ is —CH$_2$[CH(OH)]$_4$—CH(OH)—; and
      R$^{10}$ is H.

8. The compound according to claim 6, or a pharmaceutically acceptable salt, stereoisomer or tautomer thereof, wherein:
   a) L$^1$ is —Q$^1$— or —C(O)N(R$^7$)Q$^1$—;
      Q$^1$ is carbocyclyl; and
      R$^{10}$ is C(O)OR$^7$; or
   b) L$^1$ is —Q$^1$— or —C(O)N(R$^7$)Q$^1$—;
      Q$^1$ is heterocyclyl, wherein the heterocyclyl is linked to R$^{10}$ via a ring nitrogen atom; and
      R$^{10}$ is C(O)OR$^7$; or
   c) L$^1$ is —Q$^1$Q$^2$—;
      Q$^2$ is carbocyclyl; and
      R$^{10}$ is C(O)OR$^7$; or
   d) L$^1$ is —Q$^1$Q$^2$—;
      Q$^2$ is heterocyclyl, wher3ein the heterocyclyl is linked to R$^{10}$ via a ring carbon atom; and
      R$^{10}$ is C(O)OR$^7$; or
   e) L$^1$ is —Z$^1$—, —OZ$^1$—, —C(O)N(R$^7$)Z$^1$—, —C(O)N(R$^7$)Z$^1$Q$^1$Q$^2$Z$^2$—, or —C(O)N(R$^7$)Z$^1$Q$^1$Z$^2$N(R$^8$)Z$^3$—, or —C(O)Q$^1$Z$^1$—; and
      R$^{10}$ is N(R$^7$)R$^8$, N(R$^7$)C(=NR$^9$)N(R$^8$)$_2$, or N(R$^7$)C(O)OR$^8$; or
   f) L$^1$ is —C(O)N(R$^7$)Q$^1$—, —C(O)N(R$^7$)Z$^1$Q$^1$—, or —C(O)Q$^1$—;
      Q$^1$ is heterocyclyl; and
      R$^{10}$ is N(R$^7$)R$^8$, N(R$^7$)C(=NR$^9$)N(R$^8$)$_2$, or N(R$^7$)C(O)OR$^8$; or
   g) L$^1$ is —C(O)N(R$^7$)Q$^1$—, —C(O)N(R$^7$)Z$^1$Q$^1$—, or —C(O)Q$^1$—;
      Q$^1$ is heterocyclyl, wherein the heterocyclyl is linked to R$^{10}$ via a ring carbon atom; and
      R$^{10}$ is N(R$^7$)R$^8$, N(R$^7$)C(=NR$^9$)N(R$^8$)$_2$, or N(R$^7$)C(O)OR$^8$.

9. The compound according to claim 8, or a pharmaceutically acceptable salt, stereoisomer or tautomer thereof, wherein
   a) R$^{10}$ is N(R$^7$)R$^8$; and
      R$^7$ is CH$_2$[CH(OH)]$_4$—CH$_2$OH; or
   b) R$^{10}$ is N(R$^7$)R$^8$; and
      R$^8$ is CH$_2$[CH(OH)]$_4$—CH$_2$OH; or
   c) R$^{10}$ is N(R$^7$)R$^8$;
      R$^7$ is CH$_2$[CH(OH)]$_4$—CH$_2$OH; and
      R$^8$ is CH$_2$[CH(OH)]$_4$—CH$_2$OH.

10. The compound according to claim 9, or a pharmaceutically acceptable salt, stereoisomer, or tautomer thereof, wherein R$^{10}$ is N{CH$_2$[CH(OH)]$_4$—CH$_2$OH}$_2$.

11. The compound according to claim 8, or a pharmaceutically acceptable salt, stereoisomer or tautomer thereof, wherein:
    R$^{10}$ is N(R$^7$)C(=NR$^9$)N(R$^8$)$_2$;
    R$^7$ is H or C$_{1-4}$ alkyl;
    at least one R$^8$ is CH$_2$[CH(OH)]$_4$—CH$_2$OH; and
    R$^9$ is H or C$_{1-4}$ alkyl.

12. The compound according to claim 1, or a pharmaceutically acceptable salt, stereoisomer or tautomer thereof, wherein each of R$^2$ and R$^3$ is independently unsubstituted C$_{1-4}$ alkyl.

13. The compound according to claim 1, or a pharmaceutically acceptable salt, stereoisomer or tautomer thereof, wherein
    a) R$^4$ is H; and
       R$^5$ is H; or
    b) R$^4$ is H; or
    c) R$^5$ is H.

14. The compound according to claim 1, wherein the compound has a cation selected from the group consisting of:
    2-[({3-amino-5H-pyrrolo[2,3-b]pyrazin-2-yl}formamido)methyl]-1-ethyl-3-methyl-1H-1,3-benzodiazol-3-ium;
    2-[({3-amino-5H-pyrrolo[2,3-b]pyrazin-2-yl}formamido)methyl]-1-ethyl-6-fluoro-3-methyl-1H-1,3-benzodiazol-3-ium;
    2-[({3-amino-5H-pyrrolo[2,3-b]pyrazin-2-yl}formamido)methyl]-6-chloro-1-ethyl-3-methyl-1H-1,3-benzodiazol-3-ium;
    2-[({3-amino-5H-pyrrolo[2,3-b]pyrazin-2-yl}formamido)methyl]-1-ethyl-6-methoxy-3-methyl-1H-1,3-benzodiazol-3-ium;
    2-[({3-amino-5H-pyrrolo[2,3-b]pyrazin-2-yl}formamido)methyl]-1-ethyl-3-methyl-6-(trifluoromethyl)-1H-1,3-benzodiazol-3-ium;

2-[({3-amino-5H-pyrrolo[2,3-b]pyrazin-2-yl}formamido)methyl]-1-ethyl-3-methyl-6-(trifluoromethoxy)-1H-1,3-benzodiazol-3-ium;

2-[({3-amino-5H-pyrrolo[2,3-b]pyrazin-2-yl}formamido)methyl]-1,3-diethyl-6-methoxy-1H-1,3-benzodiazol-3-ium;

2-[({3-amino-5H-pyrrolo[2,3-b]pyrazin-2-yl}formamido)methyl]-3-benzyl-1-ethyl-6-methoxy-1H-1,3-benzodiazol-3-ium;

2-[({3-amino-5H-pyrrolo[2,3-b]pyrazin-2-yl}formamido)methyl]-1-ethyl-6-methoxy-3-(2-methoxy-2-oxoethyl)-1H-1,3-benzodiazol-3-ium;

2-[({3-amino-5H-pyrrolo[2,3-b]pyrazin-2-yl}formamido)methyl]-3-(carboxylatomethyl)-1-ethyl-6-methoxy-1H-1,3-benzodiazol-3-ium 2-[({3-amino-5H-pyrrolo[2,3-b]pyrazin-2-yl}formamido)methyl]-3-(carbamoylmethyl)-1-ethyl-6-methoxy-1H-1,3-benzodiazol-3-ium;

2-[({3-amino-5H-pyrrolo[2,3-b]pyrazin-2-yl}formamido)methyl]-1-ethyl-6-methoxy-3-[2-(methylsulfanyl)ethyl]-1H-1,3-benzodiazol-3-ium;

2-[({3-amino-5H-pyrrolo[2,3-b]pyrazin-2-yl}formamido)methyl]-1-ethyl-3-(2-hydroxyethyl)-6-methoxy-1H-1,3-benzodiazol-3-ium;

2-[({3-amino-5H-pyrrolo[2,3-b]pyrazin-2-yl}formamido)methyl]-1-ethyl-3-{2-[2-(2-hydroxyethoxy)ethoxy]ethyl}-6-methoxy-1H-1,3-benzodiazol-3-ium;

2-[({3-amino-5H-pyrrolo[2,3-b]pyrazin-2-yl}formamido)methyl]-1-benzyl-3-methyl-1H-1,3-benzodiazol-3-ium;

2-[({3-amino-5H-pyrrolo[2,3-b]pyrazin-2-yl}formamido)methyl]-3-benzyl-6-chloro-1-ethyl-1H-1,3-benzodiazol-3-ium;

2-[({3-amino-5H-pyrrolo[2,3-b]pyrazin-2-yl}formamido)methyl]-3-benzyl-1-ethyl-6-(trifluoromethyl)-1H-1,3-benzodiazol-3-ium;

2-[({3-amino-5H-pyrrolo[2,3-b]pyrazin-2-yl}formamido)methyl]-3-benzyl-1-[2-oxo-2-(piperidin-1-yl)ethyl]-1H-1,3-benzodiazol-3-ium;

2-[({3-amino-6-methyl-5H-pyrrolo[2,3-b]pyrazin-2-yl}formamido)methyl]-1-ethyl-6-methoxy-3-methyl-1H-1,3-benzodiazol-3-ium;

2-[({3-amino-7-methyl-5H-pyrrolo[2,3-b]pyrazin-2-yl}formamido) methyl]-6-chloro-1,3-diethyl-1H-1,3-benzodiazol-3-ium;

2-[({3-amino-7-chloro-5H-pyrrolo[2,3-b]pyrazin-2-yl}formamido)methyl]-6-chloro-1,3-diethyl-1H-1,3-benzodiazol-3-ium;

2-[({3-amino-5H-pyrrolo[2,3-b]pyrazin-2-yl}formamido)methyl]-6-(2-{[(tert-butoxy)carbonyl]amino}ethoxy)-1,3-diethyl-1H-1,3-benzodiazol-3-ium;

2-[({3-amino-5H-pyrrolo[2,3-b]pyrazin-2-yl}formamido)methyl]-6-(3-{[(tert-butoxy)carbonyl]amino}propoxy)-1,3-diethyl-1H-1,3-benzodiazol-3-ium;

2-[({3-amino-5H-pyrrolo[2,3-b]pyrazin-2-yl}formamido)methyl]-6-(3-{[(tert-butoxy)carbonyl]amino}propyl)-1,3-diethyl-1H-1,3-benzodiazol-3-ium;

2-[({3-amino-5H-pyrrolo[2,3-b]pyrazin-2-yl}formamido)methyl]-6-{1-[(tert-butoxy)carbonyl]piperidin-4-yl}-1,3-diethyl-1H-1,3-benzodiazol-3-ium;

2-[({3-amino-5H-pyrrolo[2,3-b]pyrazin-2-yl}formamido)methyl]-6-(1-{1-[(tert-butoxy)carbonyl]piperidin-4-yl}-1H-pyrazol-4-yl)-1,3-diethyl-1H-1,3-benzodiazol-3-ium;

2-[({3-amino-5H-pyrrolo[2,3-b]pyrazin-2-yl}formamido)methyl]-6-(2-aminoethoxy)-1,3-diethyl-1H-1,3-benzodiazol-3-ium;

2-[({3-amino-5H-pyrrolo[2,3-b]pyrazin-2-yl}formamido)methyl]-6-(3-aminopropoxy)-1,3-diethyl-1H-1,3-benzodiazol-3-ium;

2-[({3-amino-5H-pyrrolo[2,3-b]pyrazin-2-yl}formamido)methyl]-6-(3-aminopropyl)-1,3-diethyl-1H-1,3-benzodiazol-3-ium;

2-[({3-amino-5H-pyrrolo[2,3-b]pyrazin-2-yl}formamido)methyl]-1,3-diethyl-6-(piperidin-4-yl)-1H-1,3-benzodiazol-3-ium;

2-[({3-amino-5H-pyrrolo[2,3-b]pyrazin-2-yl}formamido)methyl]-1,3-diethyl-6-[1-(piperidin-4-yl)-1H-pyrazol-4-yl]-1H-1,3-benzodiazol-3-ium;

2-[({3-amino-5H-pyrrolo[2,3-b]pyrazin-2-yl}formamido)methyl]-6-(2-carbamimidamidoethoxy)-1,3-diethyl-1H-1,3-benzodiazol-3-ium;

2-[({3-amino-5H-pyrrolo[2,3-b]pyrazin-2-yl}formamido)methyl]-6-(3-carbamimidamidopropyl)-1,3-diethyl-1H-1,3-benzodiazol-3-ium;

2-[({3-amino-5H-pyrrolo[2,3-b]pyrazin-2-yl}formamido)methyl]-6-carboxy-1,3-diethyl-1H-1,3-benzodiazol-3-ium;

2-[({3-amino-5H-pyrrolo[2,3-b]pyrazin-2-yl}formamido) methyl]-6-[(3-{[(tert-butoxy)carbonyl]amino}propyl)carbamoyl]-1,3-diethyl-1H-1,3-benzodiazol-3-ium formic acid;

2-[({3-amino-5H-pyrrolo[2,3-b]pyrazin-2-yl}formamido) methyl]-6-({1-[(tert-butoxy)carbonyl]piperidin-4-yl}carbamoyl)-1,3-diethyl-1H-1,3-benzodiazol-3-ium;

2-[({3-amino-5H-pyrrolo[2,3-b]pyrazin-2-yl}formamido) methyl]-6-(4-{[(tert-butoxy)carbonyl]amino}piperidine-1-carbonyl)-1,3-diethyl-1H-1,3-benzodiazol-3-ium;

2-[({3-amino-5H-pyrrolo[2,3-b]pyrazin-2-yl}formamido)methyl]-6-{[2-(4-{[(tert-butoxy)carbonyl]amino}piperidin-1-yl)ethyl]carbamoyl}-1,3-diethyl-1H-1,3-benzodiazol-3-ium;

2-[({3-amino-5H-pyrrolo[2,3-b]pyrazin-2-yl}formamido)methyl]-6-[(3-aminopropyl)carbamoyl]-1,3-diethyl-1H-1,3-benzodiazol-3-ium;

2-[({3-amino-5H-pyrrolo[2,3-b]pyrazin-2-yl}formamido)methyl]-1,3-diethyl-6-[(piperidin-4-yl)carbamoyl]-1H-1,3-benzodiazol-3-ium;

2-[({3-amino-5H-pyrrolo[2,3-b]pyrazin-2-yl}formamido)methyl]-6-(4-aminopiperidine-1-carbonyl)-1,3-diethyl-1H-1,3-benzodiazol-3-ium;

2-[({3-amino-5H-pyrrolo[2,3-b]pyrazin-2-yl}formamido)methyl]-6-{[2-(4-aminopiperidin-1-yl)ethyl]carbamoyl}-1,3-diethyl-1H-1,3-benzodiazol-3-ium;

2-[({3-amino-5H-pyrrolo[2,3-b]pyrazin-2-yl}formamido)methyl]-5-(2-{bis[(2S,3R,4R,5R)-2,3,4,5,6-pentahydroxyhexyl]amino}ethoxy)-1,3-diethyl-1H-1,3-benzodiazol-3-ium;

2-[({3-amino-5H-pyrrolo[2,3-b]pyrazin-2-yl}formamido)methyl]-5-(3-{bis[(2S,3R,4R,5R)-2,3,4,5,6-pentahydroxyhexyl]amino}propoxy)-1,3-diethyl-1H-1,3-benzodiazol-3-ium;

2-[({3-amino-5H-pyrrolo[2,3-b]pyrazin-2-yl}formamido)methyl]-5-(3-{bis[(2S,3R,4R,5R)-2,3, 4,5,6-pentahydroxyhexyl]amino}propyl)-1,3-diethyl-1H -1,3-benzodiazol-3-ium;

2-[({3-amino-5H-pyrrolo[2,3-b]pyrazin-2-yl}formamido)methyl]-1,3-diethyl-6-{1-[(2S,3R,4R,5R)-2,3,4,5,6-pentahydroxyhexyl]piperidin-4-yl}-1H-1,3-benzodiazol -3-ium;

2-[({3-amino-5H-pyrrolo[2,3-b]pyrazin-2-yl}formamido)methyl]-1,3-diethyl-6-(1-{1-[(2S,3R,4R,5R)-2,3,4,5,6-pentahydroxyhexyl]piperidin-4-yl}-1H-pyrazol-4-yl)-1H -1,3-benzodiazol-3-ium;

2-[({3-amino-5H-pyrrolo[2,3-b]pyrazin-2-yl}formamido)methyl]-6-[(3-{bis[(2S,3R,4R,5R)-2,3,4,5,6-pentahydroxyhexyl]amino}propyl)carbamoyl]-1,3-diethyl-1H-1,3-benzodiazol-3-ium;

2-[({3-amino-5H-pyrrolo[2,3-b]pyrazin-2-yl}formamido)methyl]-1,3-diethyl-6-({1-[(2S,3R,4R,5R)-2,3,4,5,6-pentahydroxyhexyl]piperidin-4-yl}carbamoyl)-1H-1,3-benzodiazol-3-ium;

2-[({3-amino-5H-pyrrolo[2,3-b]pyrazin-2-yl}formamido)methyl]-6-(4-{bis[(2S,3R,4R,5R)-2,3,4,5,6-pentahydroxyhexyl]amino}piperidine-1-carbonyl) -1,3-diethyl-1H-1,3-benzodiazol-3-ium;

2-[({3-amino-5H-pyrrolo[2,3-b]pyrazin-2-yl}formamido)methyl]-6-{[2-(4-{bis[(2S,3R,4R,5R)-2,3,4,5,6-pentahydroxyhexyl]amino}piperidin-1-yl)ethyl]carbamoyl}-1,3-diethyl-1H-1,3-benzodiazol-3-ium;

2-[({3-amino-5H-pyrrolo[2,3-b]pyrazin-2-yl}formamido)methyl]-5-[4-({bis[(2S,3R,4R,5R)-2,3,4,5,6-pentahydroxyhexyl]amino}methyl)piperidine-1-carbonyl]-1,3-diethyl-1H-1,3-benzodiazol-3-ium;

2-[({3-amino-5H-pyrrolo[2,3-b]pyrazin-2-yl}formamido)methyl]-6-[(3R)-3-{bis[(2S,3R,4R,5R)-2,3,4,5,6-pentahydroxyhexyl]amino}pyrrolidine-1-carbonyl]-1,3-diethyl-1H-1,3-benzodiazol-3-ium;

2-[({3-amino-5H-pyrrolo[2,3-b]pyrazin-2-yl}formamido)methyl]-6-[(3S)-3-{bis[(2S,3R,4R,5R)-2,3,4,5,6-pentahydroxyhexyl]amino}pyrrolidine-1-carbonyl]-1,3-diethyl-1H-1,3-benzodiazol-3-ium;

2-[({3-amino-5H-pyrrolo[2,3-b]pyrazin-2-yl}formamido)methyl]-1,3-diethyl-6-{[(1r,4r)-4-{bis[(2S,3R,4R,5R)-2,3,4,5,6-pentahydroxyhexyl]amino}cyclohexyl]carbamoyl}-1H-1,3-benzodiazol-3-ium;

2-[({3-amino-5H-pyrrolo[2,3-b]pyrazin-2-yl}formamido)methyl]-1,3-diethyl-6-{[(1s,4s)-4-{bis[(2S,3R,4R,5R)-2,3,4,5,6-pentahydroxyhexyl]amino}cyclohexyl]carbamoyl}-1H-1,3-benzodiazol-3-ium;

2-[({3-amino-5H-pyrrolo[2,3-b]pyrazin-2-yl}formamido)methyl]-6-[(3-{bis[(2S,3R,4R,5R)-2,3,4,5,6-pentahydroxyhexyl]amino}propyl)(methyl)carbamoyl]-1,3-diethyl-1H-1,3-benzodiazol-3-ium;

2-[({3-amino-5H-pyrrolo[2,3-b]pyrazin-2-yl}formamido)methyl]-6-[(2-{bis[(2S,3R,4R,5R)-2,3,4,5,6-pentahydroxyhexyl]amino}ethyl)carbamoyl]-1,3-diethyl-1H-1,3-benzodiazol-3-ium;

2-[({3-amino-5H-pyrrolo[2,3-b]pyrazin-2-yl}formamido)methyl]-1,3-diethyl-5-{[(14S,15R,16R,17R)-14,15,16,17,18-pentahydroxy-12-[(2S,3R,4R,5R)-2,3,4,5,6-pentahydroxyhexyl]-3,6,9-trioxa-12-azaoctadecan-1-yl]carbamoyl}-1H-1,3-benzodiazol-3-ium;

2-[({3-amino-5H-pyrrolo[2,3-b]pyrazin-2-yl}formamido)methyl]-6-({2-[4'-(2-{bis[(2S,3R,4R,5R)-2,3,4,5,6-pentahydroxyhexyl]amino}ethyl)-[1,1'-biphenyl]-4-yl]ethyl}carbamoyl)-1,3-diethyl-1H-1,3-benzodiazol-3-ium;

2-[({3-amino-5H-pyrrolo[2,3-b]pyrazin-2-yl}formamido) methyl]-6-{[(3S)-3-[(3-{bis[(2S,3R,4R,5R)-2,3,4,5,6-pentahydroxyhexyl]amino}propyl)amino]-3-carbamoylpropyl]carbamoyl}-1,3-diethyl-1H-1,3-benzodiazol-3-ium;

2-[({3-amino-5H-pyrrolo[2,3-b]pyrazin-2-yl}formamido)methyl]-6-{[4-(4-{3-[(3-{bis[(2S,3R,4R,5R)-2,3,4,5,6-pentahydroxyhexyl]amino}propyl)amino]-3-carbamoylpropyl}phenyl)butyl]carbamoyl}-1,3-diethyl-1H-1,3-benzodiazol-3-ium;

2-[({3-amino-7-chloro-5H-pyrrolo[2,3-b]pyrazin-2-yl}formamido)methyl]-6-carboxy -1,3-diethyl-1H-1,3-benzodiazol-3-ium;

2-[({3-amino-7-bromo-5H-pyrrolo[2,3-b]pyrazin-2-yl}formamido)methyl]-6carboxy-1,3-diethyl-1H-1,3-benzodiazol-3-ium;

2-[({3-amino-7-chloro-5H-pyrrolo[2,3-b]pyrazin-2-yl}formamido)methyl]-6-(4-{bis[(2S,3R,4R,5R)-2,3,4,5,6-pentahydroxyhexyl]amino}piperidine-1-carbonyl) -1,3-diethyl-1H-1,3-benzodiazol-3-ium;

2-[({3-amino-7-bromo-5H-pyrrolo[2,3-b]pyrazin-2-yl}formamido)methyl]-6-(4-{bis[(2S,3R,4R,5R)-2,3,4,5,6-pentahydroxyhexyl]amino}piperidine-1-carbonyl) -1,3-diethyl-1H-1,3-benzodiazol-3-ium;

2-[({3-amino-7-cyano-5H-pyrrolo[2,3-b]pyrazin-2-yl}formamido)methyl]-1,3-diethyl-6-methoxy-1H-1,3-benzodiazol-3-ium.

15. A pharmaceutical composition comprising a compound according to claim 1, or a pharmaceutically acceptable salt, stereoisomer or tautomer thereof, and a pharmaceutically acceptable excipient.

16. The pharmaceutical composition according to claim 15, wherein the pharmaceutical composition is formulated for nasal, bronchial, or buccal administration.

17. The pharmaceutical composition according to claim 15, wherein the pharmaceutical composition further comprises an additional active agent selected from the group consisting of a β2 adrenoreceptor agonist, an antihistamine, dornase alfa, a corticosteroid, a leukotriene antagonist, a conductance regulator repairing agent, a transmembrane member 16A modulator, and an antibiotic.

18. The pharmaceutical composition according to claim 16, wherein the pharmaceutical composition is formulated as a dry powder for nasal or bronchial administration; or as an aerosol or a spray for nasal, bronchial, or buccal administration.

19. A product comprising
a compound according to claim 1, or a pharmaceutically acceptable salt, stereoisomer, or tautomer thereof; and
an additional active agent selected from the group consisting of a β2 adrenoreceptor agonist, an antihistamine, dornase alfa, a corticosteroid, a leukotriene antagonist, a conductance regulator repairing agent, a transmembrane member 16A modulator, and an antibiotic.

20. The compound according to claim 14, wherein the compound has the cation 2-[({3 -amino-5H-pyrrolo[2,3 -b]pyrazin-2-yl} formamido)methyl]-6-(4-{bis[(2S,3R,4R,5R) -2,3,4,5,6-pentahydroxyhexyl]amino}piperidine-1-carbonyl)-1,3-diethyl-1H-1,3-benzodiazol-3-ium.

21. The compound according to claim 14, wherein the compound has the cation 2-[({3-amino-5H-pyrrolo[2,3-b]pyrazin-2-yl}formamido)methyl]-5-[4-({bis[(2S,3R,4R,5R)

-2,3,4,5,6-pentahydroxyhexyl]amino}methyl)piperidine-1-carbonyl]-1,3-diethyl-1H-1,3-benzodiazol-3-ium.

\* \* \* \* \*

UNITED STATES PATENT AND TRADEMARK OFFICE
CERTIFICATE OF CORRECTION

PATENT NO. : 10,941,149 B2  
APPLICATION NO. : 16/462794  
DATED : March 9, 2021  
INVENTOR(S) : Clive McCarthy et al.

Page 1 of 3

It is certified that error appears in the above-identified patent and that said Letters Patent is hereby corrected as shown below:

In the Claims

In Claim 1, Column 218, delete Lines 26-42, and insert the following:
    -- $R^1$ is H, halo, $R^{12}$, $C(=NR^9)NR^{12}R^{13}$, $C(O)NR^{12}R^{13}$, $C(O)OR^{12}$, $OR^{12}$, $S(O)_2R^{12}$, $Q^1R^{12}$, $Q^1C(=NR^7)NR^{12}R^{13}$, $Q^1C(O)NR^{12}R^{13}$, $Q^1C(O)OR^{12}$, $Q^1OR^{12}$, $Q^1S(O)_2R^{12}$, $Q^1Q^2C(=NR^9)NR^{12}R^{13}$, $Q^1Q^2C(O)NR^{12}R^{13}$, $Q^1Q^2C(O)OR^{12}$, $Q^1Q^2OR^{12}$, or $L^1R^{10}$;
    $R^2$ is $C_{1-10}$ alkyl, optionally substituted with one or more substituents independently selected from the group consisting of halo, $C(O)N(R^7)R^8$, $C(O)OR^7$, $N(R^7)R^8$, $OR^7$, SH, cycloalkyl, heterocyclyl, aryl, and heteroaryl, wherein one or more -$CH_2$- groups are optionally and independently replaced by -$NR^7$-, -O-, or -S-, provided that adjacent -$CH_2$- groups are not so replaced;
    $R^3$ is $C_{1-10}$ alkyl, optionally substituted with one or more substituents independently selected from the group consisting of halo, $C(O)N(R^7)R^8$, $C(O)OR^7$, $N(R^7)R^8$, $OR^7$, SH, cycloalkyl, heterocyclyl, aryl, and heteroaryl, wherein one or more -$CH_2$- groups are optionally and independently replaced by -$NR^7$-, -O-, or -S-, provided that adjacent -$CH_2$- groups are not so replaced; --.

In Claim 1, Column 219, delete Lines 26-41, and insert the following:
    -- $R^{12}$ is H, $C_{1-6}$ alkyl, $C_{2-6}$ alkenyl, $C_{2-6}$ alkynyl, $C_{3-8}$ cycloalkyl or 3- to 8-membered heterocyclyl, wherein each $C_{1-6}$ alkyl, $C_{2-6}$ alkenyl and $C_{2-6}$ alkynyl is optionally and independently substituted with one or more substituents independently selected from the group consisting of halo, $C(O)N(R^7)R^8$, $C(O)OR^7$, $N(R^7)R^8$, and $OR^7$, and further wherein each $C_{3-8}$ cycloalkyl and 3- to 8-membered heterocyclyl is optionally and independently substituted with one or more substituents independently selected from the group consisting of oxo, halo, $C(O)N(R^7)R^8$, $C(O)OR^7$, $N(R^7)R^8$, and $OR^7$;
    $R^{13}$ is H, $C_{1-6}$ alkyl, $C_{2-6}$ alkenyl, $C_{2-6}$ alkynyl, $C_{3-8}$ cycloalkyl or 3- to 8-membered heterocyclyl, wherein each $C_{1-6}$ alkyl, $C_{2-6}$ alkenyl and $C_{2-6}$ alkynyl is optionally and independently substituted with one or more substituents independently selected from the group consisting of halo, $C(O)N(R^7)R^8$, $C(O)OR^7$, $N(R^7)R^8$, and $OR^7$, and further wherein each $C_{3-8}$ cycloalkyl and 3- to 8-membered heterocyclyl is optionally and Signed and Sealed this  
Twenty-sixth Day of October, 2021

Drew Hirshfeld  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 10,941,149 B2 independently substituted with one or more substituents independently selected from the group consisting of oxo, halo, $C(O)N(R^7)R^8$, $C(O)OR^7$, $N(R^7)R^8$, and $OR^7$;

$R^7$ is H or $C_{1-12}$ alkyl, wherein the $C_{1-12}$ alkyl is optionally substituted with one or more substituents independently selected from the group consisting of halo and OH;

$R^8$ is H or $C_{1-12}$ alkyl, wherein the $C_{1-12}$ alkyl is optionally substituted with one or more substituents independently selected from the group consisting of halo and OH;
or --.

In Claim 1, delete Column 219, Line 53 to Column 220, Line 3, and insert the following:

-- $Q^1$ is carbocyclyl, heterocyclyl, aryl, or heteroaryl, wherein each aryl and heteroaryl is optionally and independently substituted with one or more substituents independently selected from the group consisting of halo, $C_{1-4}$ alkyl, $C_{1-4}$ haloalkyl, $C(O)NR^{15}R^{16}$, $C(O)OR^{15}$, $NR^{15}R^{16}$, and OH, and further wherein each carbocyclyl and heterocyclyl is optionally and independently substituted with one or more substituents independently selected from the group consisting of oxo, halo, $C_{1-4}$ alkyl, $C_{1-4}$ haloalkyl, $C(O)NR^{15}R^{16}$, $C(O)OR^{15}$, $NR^{15}R^{16}$, and OH;

$Q^2$ is carbocyclyl, heterocyclyl, aryl, or heteroaryl, wherein each aryl and heteroaryl is optionally and independently substituted with one or more substituents independently selected from the group consisting of halo, $C_{1-4}$ alkyl, $C_{1-4}$ haloalkyl, $C(O)NR^{15}R^{16}$, $C(O)OR^{15}$, $NR^{15}R^{16}$, and OH, and further wherein each carbocyclyl and heterocyclyl is optionally and independently substituted with one or more substituents independently selected from the group consisting of oxo, halo, $C_{1-4}$ alkyl, $C_{1-4}$ haloalkyl, $C(O)NR^{15}R^{16}$, $C(O)OR^{15}$, $NR^{15}R^{16}$, and OH;

$Q^3$ is carbocyclyl, heterocyclyl, aryl, or heteroaryl, wherein each aryl and heteroaryl is optionally and independently substituted with one or more substituents independently selected from the group consisting of halo, $C_{1-4}$ alkyl, $C_{1-4}$ haloalkyl, $C(O)NR^{15}R^{16}$, $C(O)OR^{15}$, $NR^{15}R^{16}$, and OH, and further wherein each carbocyclyl and heterocyclyl is optionally and independently substituted with one or more substituents independently selected from the group consisting of oxo, halo, $C_{1-4}$ alkyl, $C_{1-4}$ haloalkyl, $C(O)NR^{15}R^{16}$, $C(O)OR^{15}$, $NR^{15}R^{16}$, and OH;

$Z^1$ is $C_{1-12}$ alkylene, $C_{2-12}$ alkenylene, or $C_{2-12}$ alkynylene, wherein the $C_{1-12}$ alkylene, $C_{2-12}$ alkenylene and $C_{2-12}$ alkynylene is optionally substituted by one or more substituents independently selected from the group consisting of halo, $C(O)NR^{15}R^{16}$, $C(O)OR^{15}$, $NR^{15}R^{16}$, and OH;

$Z^2$ is $C_{1-12}$ alkylene, $C_{2-12}$ alkenylene, or $C_{2-12}$ alkynylene, wherein the $C_{1-12}$ alkylene, $C_{2-12}$ alkenylene and $C_{2-12}$ alkynylene is optionally substituted by one or more substituents independently selected from the group consisting of halo, $C(O)NR^{15}R^{16}$, $C(O)OR^{15}$, $NR^{15}R^{16}$, and OH;

$Z^3$ is $C_{1-12}$ alkylene, $C_{2-12}$ alkenylene, or $C_{2-12}$ alkynylene, wherein each $C_{1-12}$ alkylene, $C_{2-12}$ alkenylene and $C_{2-12}$ alkynylene is optionally substituted by one or more substituents independently selected from the group consisting of halo, $C(O)NR^{15}R^{16}$, $C(O)OR^{15}$, $NR^{15}R^{16}$, and OH; --.

In Claim 8, Column 221, Line 65, replace "wher3ein" with -- wherein --.

In Claim 8, Column 222, delete Lines 1-18, and insert the following:
-- e) $L^1$ is $-Z^1-$, $-OZ^1-$, $-C(O)Q^1Z^1-$, $-C(O)N(R^7)Z^1-$, $-C(O)N(R^7)Z^1Q^1Q^2Z^2-$,
$-C(O)N(R^7)Z^1O(CH_2CH_2O)_nZ^2-$, or $-C(O)N(R^7)Z^1Q^1Z^2N(R^8)Z^3-$; and
$R^{10}$ is $N(R^7)R^8$, $N(R^7)C(=NR^9)N(R^8)_2$, or $N(R^7)C(O)OR^8$; or
f) $L^1$ is $-C(O)Q^1-$, $-C(O)N(R^7)Q^1-$, or $-C(O)N(R^7)Z^1Q^1-$;
$Q^1$ is carbocyclyl; and
$R^{10}$ is $N(R^7)R^8$, $N(R^7)C(=NR^9)N(R^8)_2$, or $N(R^7)C(O)OR^8$; or g) $L^1$ is $-C(O)Q^1-$, $-C(O)N(R^7)Q^1-$,
or $-C(O)N(R^7)Z^1Q^1-$;
$Q^1$ is heterocyclyl, wherein the heterocyclyl is linked to $R^{10}$ via a ring carbon atom; and
$R^{10}$ is $N(R^7)R^8$, $N(R^7)C(=NR^9)N(R^8)_2$, or $N(R^7)C(O)OR^8$. --.

In Claim 11, Column 222, Line 37, replace "$CH_2[CH(OH)]_4$   $CH_2OH$" with
-- $CH_2[CH(OH)]_4-CH_2OH$ --.

In Claim 12, Column 222, delete Lines 41-42, and insert the following:
-- wherein:
$R^2$ is unsubstituted $C_{1-4}$ alkyl; and
$R^3$ is unsubstituted $C_{1-4}$ alkyl. --.

In Claim 14, Column 223, Line 46, replace "7-methyl-SH-pyrrolo" with -- 7-methyl-5H-pyrrolo --.

In Claim 17, Column 226, Lines 43-44, replace "a conductance regulator repairing agent" with -- a cystic fibrosis transmembrane conductance regulator repairing agent --.

In Claim 19, Column 226, Line 57, replace "a conductance regulator repairing agent" with -- a cystic fibrosis transmembrane conductance regulator repairing agent --.